US008901118B2

(12) United States Patent
Zhang et al.

(10) Patent No.: US 8,901,118 B2
(45) Date of Patent: Dec. 2, 2014

(54) COMPOUNDS AND METHODS FOR KINASE MODULATION, AND INDICATIONS THEREFOR

(75) Inventors: Jiazhong Zhang, Foster City, CA (US); Prabha N. Ibrahim, Mountain View, CA (US); Wayne Spevak, Berkeley, CA (US); Jianming Tsai, Vallejo, CA (US); Todd Ewing, Walnut Creek, CA (US); Ying Zhang, Fremont, CA (US); Chao Zhang, Morago, CA (US)

(73) Assignee: Plexxikon Inc., Berkeley, CA (US)

( * ) Notice: Subject to any disclaimer, the term of this patent is extended or adjusted under 35 U.S.C. 154(b) by 391 days.

(21) Appl. No.: 13/090,969

(22) Filed: Apr. 20, 2011

(65) Prior Publication Data

US 2011/0263595 A1  Oct. 27, 2011

Related U.S. Application Data

(60) Provisional application No. 61/326,626, filed on Apr. 21, 2010.

(51) Int. Cl.
| C07D 487/04 | (2006.01) |
| A61K 31/519 | (2006.01) |
| C07D 471/04 | (2006.01) |
| A61P 19/02 | (2006.01) |
| A61P 19/10 | (2006.01) |
| A61P 25/28 | (2006.01) |
| A61P 29/00 | (2006.01) |
| A61K 31/437 | (2006.01) |

(52) U.S. Cl.
CPC ............ *C07D 487/04* (2013.01); *C07D 471/04* (2013.01)
USPC ..................... 514/234.2; 514/265.1; 514/275; 514/300; 544/117; 544/280; 544/331; 546/113

(58) Field of Classification Search
CPC ...................................................... C07D 487/04
USPC ........................................ 544/280; 514/265.1
See application file for complete search history.

(56) References Cited

U.S. PATENT DOCUMENTS

| 2006/0058324 A1 | 3/2006 | Capraro et al. |
| 2007/0161666 A1 | 7/2007 | Blumenkopf et al. |
| 2007/0225306 A1 | 9/2007 | Choi et al. |
| 2009/0076046 A1 | 3/2009 | Zhang et al. |

FOREIGN PATENT DOCUMENTS

| WO | WO 03/062236 | 7/2003 |
| WO | WO 2004/074278 | 9/2004 |
| WO | WO 2005/005426 | 1/2005 |
| WO | WO 2007/013896 | 2/2007 |
| WO | WO 2008/076779 | 6/2008 |
| WO | WO 2009/115084 | 9/2009 |
| WO | WO 2010/020905 | 2/2010 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
International Search Report dated Dec. 19, 2011 in International PCT Application No. PCT/US2011/033192.
Bayindir et al., Cellular mesoblastic nephroma (infantile renal fibrosarcoma): institutional review of clinical, diagnostic imaging, and pathologic features of a distinctive neoplasm of infancy, Pediatr. Radiol., 39(10):1066-74 (2009).
Bjorntrop, Neuroendocrine Perturbations as a Cause of Insulin Resistence, Diabetes Metab. Res. Rev., 15: 427-441 (1999).

(Continued)

*Primary Examiner* — Susanna Moore
(74) *Attorney, Agent, or Firm* — Sheppard Mullin Richter & Hampton LLP

(57) ABSTRACT

Compounds and salts thereof, formulations thereof, conjugates thereof, derivatives thereof, forms thereof and uses thereof are described, wherein the compounds have formula I:

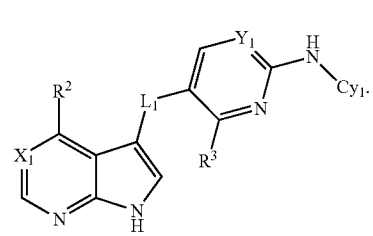

In certain aspects and embodiments, the described compounds or salts thereof, formulations thereof, conjugates thereof, derivatives thereof, forms thereof are active on one or more of Fms, Kit, Flt3, TrkA, TrkB and TrkC kinase protein. Also described are methods of use thereof to treat diseases and conditions, including diseases and conditions associated with activity of one or more of Fms, Kit, Flt3, TrkA, TrkB and TrkC, including rheumatoid arthiritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, global ischemia, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, breast cancer, prostate cancer, pancreatic cancer, lung cancer, ovarian cancer, gliomas, glioblastoma, neurofibromatosis, osteolytic bone metastases, brain metasteses, gastrointestinal stromal tumors, and giant cell tumors.

46 Claims, No Drawings

(56) References Cited

OTHER PUBLICATIONS

Broudy, Stem Cell Factor and Hematopoiesis, Blood, 90:1345-1364 (1997).
Bouzas-Rodriguez et al., Neurotrophin-3 production promotes human neuroblastoma cell survival by inhibiting TrkC-induced apoptosis, J. Clin. Invest., 120(3):850-8 (2010).
Clohisy et al, Review of Cellular Mechanisms of Tumor Osteolysis, Clin. Orthop., 373: 104-14 2000).
Coulie et al, Recombinant Human Neurotrophic Factors Accelerate Colonic Transit and Relieve Constipation in Humans, Gastroenterology 119:41-50 (2000).
Douma et al, Suppression of anoikis and induction of metastasis by the neurotrophic receptor TrkB, Nature 430:1034-9 (2004).
Feng et al, Tyrosines 559 and 807 in the Cytoplasmic Tail of the Macrophage Colony-Stimulating Factor Receptor Play Distinct Roles in Osteoclast Differentiation and Function, Endocrinology, 143: 4868-74 (2002).
Flanagan & Lader, Update on the biologic effects of macrophage colony-stimulating factor, Curr Opin Hematol., 5:181-5 (1998).
Gallego et al., Increased opioid dependence in a mouse model of panic disorder, Front Behav. Neurosci., 3:60 (2010).
Halvorson et al, A Blocking Antibody to Nerve Growth Factor Attenuates Skeletal Pain Induced by Prostate Tumor Cells Growing in Bone, Cancer Res. 65:9426-35 (2005).
Hasegawa and Wang, Visualizing Mechanosensory Endings of TrkC-Expressing Neurons in HS3ST-2-hPLAP Mice, J Comp. Neurol., 511(4):543-556 (2008).
Isbel et al., Local macrophage proliferation correlates with increased renal M-CSF expression in human glomerulonephritis, Nephrol Dial Transplant, 16: 1638-1647 (2001).
Kassel et al., Local increase in the number of mast cells and expression of nerve growth factor in the bronchus of asthmatic patients after repeated inhalation of allergen at low-dose, Clin Exp Allergy, 31:1432-40 (2001).
Kodama et al., Congenital Osteoclast Deficiency in Osteopetrotic (op/op) Mice Is Cured by Injections of Macrophage Colony-stimulating Factor, J. Exp. Med., 173: 269-72 (1991).
Kubo et al., Resequencing and copy number analysis of the human tyrosine kinase gene family in poorly differentiated gastric cancer, Carcinogenesis, 30(11):1857-64 (2009).
Kubo et al., Resequencing Analysis of the Human Tyrosine Kinase Gene Family in Pancreatic Cancer, Pancreas, 38(7):e200-e206, (2009).
Lambros et al., Genomic profile of a secretory breast cancer with an ETV6-NTRK3 duplication, J. Clin. Pathol., 62(7):604-12 (2009).
Le Meur et al., Macrophage accumulation at a site of renal inflammation is dependent on the M-CSF/c-fms pathway, J. Leukocyte Biology., 72:530-537 (2002).
Levis et al., A FLT3 tyrosine kinase inhibitor is selectively cytotoxic to acute myeloid leukemia blasts harboring FLT3 internal tandem duplication mutations, Blood, 98:885-887 (2001).
Libby, Nature, Inflammation in atherosclerosis, 420:868-874 (2002).
Loveland, et al., Stem cell factor and c-kit in the mammalian testis: lessons originating from Mother Nature's gene knockouts, J. Endocrinol, 153:337-344 (1997).
Lyman, et al., c-kit Ligand and Flt3 Ligand: Stem/Progenitor Cell Factors With Overlapping Yet Distinct Activities, Blood, 91:1101-1134 (1998).
Marchetti et al., Frequent Mutations in the Neurotrophic Tyrosine Receptor Kinase Gene Family in Large Cell Neuroendocrine Carcinoma of the Lung, Hum. Mutat., 29(5):609-16 (2008).
Motoyoshi, Biological activities and clinical application of M-CSF, Int J Hematol., 67:109-22 (1998).
Nakagawara et al., Expression and Function of TRK-B and BDNF in Human Neuroblastomas, Mol Cell Biol. 14:759-767 (1994).
Nassentein et al., The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthma, J Exp Med 198:455-467 (2003).
Ochs et al., A phase I/II trial of recombinant methionyl human brain derived neurotrophic factor administered by intrathecal infusion to patients with amyotrophic lateral sclerosis Amyotroph Lateral Scler Other Motor Neuron Disord. 1:201-6 (2000).
Petty et al., The Effect of Systemically Administered Recombinant Human Nerve Growth Factor in Healthy Human Subjects, Ann Neurol. 36: 244-6 (1994).
Pignon, C-kit mutations and mast cell disorders A model of activating mutations of growth factor receptors, Hermatol Cell Ther, 39:114-116 (1997).
Qiao, et. al., Role of Macrophage Colony-Stimulating Factor in Atherosclerosis, Am. J. Path.,150:1687-1699 (1997).
Rajavashisth, et al., Heterozygous Osteopetrotic (op) Mutation Reduces Atherosclerosis in LDL Receptor-deficient Mice, J. Clin. Invest., 101:2702-2710 (1998).
Ridge et al., FMS mutations in myelodysplastic, leukemic, and normal subjects, Proc. Nat. Acad. Sci., 87:1377-1380 (1990).
Robinson et al., Stimulation of bine marrow colony growth in vitro by human urine. Blood., 33(3):396-99 (1969).
Rodan and Martin, Therapeutic Approaches to Bone Diseases, Science, 289:1508 (2000).
Rosnet et al., Isolation and Chromosomal Localization of a Novel FMS-like Tyrosine Kinase Gene, Genomics, 9: 380-385 (1991).
Sclabas et al., Overexpression of Tropomysin-Related Kinase B in Metastatic Human Pancreatic Cancer Cells, Clin. Cancer. Res, V11:440-449 (2005).
Shibata et al., Alveolar macrophage deficiency in osteopetrotic mice deficient in macrophage colony-stimulating factor is spontaneously corrected with age and associated with matrix metalloproteinase expression and emphysema, Blood, 98: pp. 2845-2852 (2001).
Small et al., STK-1, the human homolog of Flk-2/Flt-3, is selectively expressed in CD34$^+$ human bone marrow cells and is involved in the proliferation of early progenitor/stem cells, Proc. Nat. Acad. Sci., 91: 459-463 (1994).
Specchia et al., Constitutive expression of IL-1β, M-CSF and c-fms during the myeloid blastic phase of chronic myelogenous leukaemia, Br J Haematol., Mar; 80(3):310-6 (1992).
Teitelbaum, Bone Resorption by Osteoclasts, Science, 289:1504 (2000).
Tsujimura, Role of c-kit receptor tyrosine kinase in the development, survival and neoplastic transformation of mast cells, Pathol Int, 46:933-938 (1996).
Viskochil, It takes two to tango: mast cell and Schwann cell interactions in neurofibromas, J Clin Invest., 112:1791-1793 (2003).
Vliagoftis, et al., The protooncogene c-kit and c-kit ligand in human disease, Clin Immunol, 100:435-440 (1997).
Wild et al., Antibodies to Nerve Growth Factor Reverse Established Tactile Allodynia in Rodent Models of Neuropathic Pain without Tolerance, J. Pharmacol. Exp. Ther., 322:282-287 (2007).
Yang et al., Identification of Brain-Derived Neurotrophic Factor as a Novel Functional Protein in Hepatocellular Carcinoma, Cancer. Res, 65:219-225 (2005).
Yang et al., Neurofibromin-deficient Schwann cells secrete a potent migratory stimulus for $Nf1^{+/-}$ mast cells, J Clin Invest., 112:1851-1861 (2003).
Supplementary European Search Report for EP Application No. 11772612, dated Sep. 20, 2013.

* cited by examiner

COMPOUNDS AND METHODS FOR KINASE MODULATION, AND INDICATIONS THEREFOR

CROSS-REFERENCE TO RELATED PATENT APPLICATION

This application claims the benefit of U.S. Provisional Application 61/326,626, filed Apr. 21, 2010, which is incorporated herein by reference in its entirety, including drawings.

FIELD OF THE INVENTION

Disclosed are novel compounds and uses thereof. In certain embodiments disclosed compounds are kinase inhibitors.

SUMMARY OF THE INVENTION

In certain aspects and embodiments disclosed herein, compounds are provided, as well as various salts thereof, formulations thereof, conjugates thereof, derivatives thereof, forms thereof and uses thereof. In certain embodiments, the compounds are active on one or more protein kinases, including Fms, Kit, Flt3, TrkA, TrkB and/or TrkC, including any mutations thereof. In certain embodiments, compounds are active on Fms kinase. In certain embodiments, compounds are active on Fms and Kit kinase. In certain embodiments, compounds are selectively active on Fms kinase relative to Kit kinase. In certain embodiments, compounds are active on Fms kinase and Flt3 kinase. In certain embodiments, compounds are active on Fms kinase and one or more of TrkA, TrkB and TrkC kinase.

Also contemplated in accordance with the present invention are methods for the use of the compounds in treating diseases and conditions associated with regulation of the activity of one or more of Fms, Kit, Flt3, TrkA, TrkB and TrkC, including any mutations thereof. Thus, the use of compounds for therapeutic methods involving modulation of protein kinases are provided. In certain embodiments, the compounds are used for therapeutic methods involving the treatment of a variety of indications, including, but not limited to, rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, global ischemia, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, breast cancer, prostate cancer, pancreatic cancer, lung cancer, ovarian cancer, gliomas, glioblastoma, neurofibromatosis, osteolytic bone metastases, brain metasteses, gastrointestinal stromal tumors, and giant cell tumors. In some embodiments, compounds are of Formula I as described below.

In a first aspect, compounds having the structure according to the following Formula I are provided:

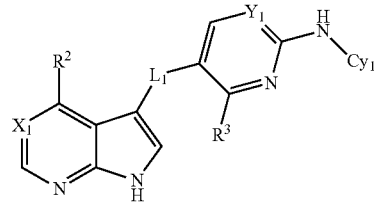

Formula I or a salt, a prodrug, a solvate, a tautomer or a stereoisomer thereof, wherein:
$X_1$ is —N=, —C(H)=, or —C($R^1$)=;
$Y_1$ is —N= and $R^3$ is hydrogen; or $Y_1$ is —C(H)= and $R^3$ is fluoro or chloro;
$L_1$ is —C($H_2$)— or —C(O)—;
$Cy_1$ is cycloalkyl optionally substituted with one or more $R^4$, phenyl optionally substituted with one or more $R^5$, or 5 or 6 membered heteroaryl optionally substituted on an available carbon atom with one or more $R^6$ and optionally substituted on an available nitrogen atom with $R^7$;
when $X_1$ is —C($R^1$)=, $R^2$ is hydrogen;
when $X_1$ is —N= or —C(H)=, $R^2$ is selected from the group consisting of hydrogen, cycloalkyl, lower alkyl optionally substituted with one or more $R^8$, —N($R^{9a}$)($R^{9b}$), and —O—$R^9$;
$R^1$ is fluoro, chloro, or lower alkyl optionally substituted with one or more fluoro;
each $R^4$ is independently selected from the group consisting of fluoro, —OH, lower alkyl optionally substituted with one or more fluoro, and lower alkoxy optionally substituted with one or more fluoro;
each $R^5$ is independently selected from the group consisting of fluoro, chloro, —O—$R^{10}$, —S—$R^{11}$, —S($O_2$)—$R^{12}$, and lower alkyl optionally substituted with one or more $R^{13}$;
each $R^6$ is independently selected from the group consisting of fluoro, chloro, bromo, cycloalkyl, lower alkyl optionally substituted with one or more fluoro, and lower alkoxy optionally substituted with one or more fluoro; or two $R^6$ bound to adjacent carbon atoms of the heteroaryl ring, taken together, form a fused cycloalkyl ring;
$R^7$ is cycloalkyl, lower alkoxy or lower alkyl optionally substituted with one or more fluoro;
$R^8$ is fluoro or lower alkoxy optionally substituted with one or more fluoro;
$R^{9a}$ is H and $R^{9b}$ is selected from the group consisting of (i) H, lower alkyl, lower alkyl substituted with one or more fluoro, lower alkyl substituted with lower alkoxy or lower alkyl substituted with hydroxyl and (ii) cycloalkyl, cycloalkylalkyl, heterocycloalkyl, heterocycloalkylalkyl, arylalkyl, heteroarylalkyl, each of which is optionally substituted with one to three members selected from lower alkyl, haloalkyl, lower alkoxy or fluoro; or
$R^{9a}$ and $R^{9b}$ together with the nitrogen to which they are attached form a 5- or 6-membered ring having from 0 to 1 additional heteroatom selected from O, N or S, each of which is optionally substituted with one to three members selected from lower alkyl, haloalkyl, lower alkoxy or fluoro;
$R^9$ is lower alkyl, lower alkyl substituted with one or more fluoro, or lower alkyl substituted with lower alkoxy;

each $R^{10}$, $R^{11}$ and $R^{12}$ are independently lower alkyl optionally substituted with one or more fluoro; and each $R^{13}$ is independently selected from the group consisting of fluoro, —OH, and lower alkoxy optionally substituted with one or more fluoro.

In some embodiments of compounds of Formula I, $R^3$ is fluoro. In certain embodiments, the salt is a pharmaceutically acceptable salt.

In some embodiments, the invention provides compounds of Formula I or any of the subformulas as described herein, or a pharmaceutically acceptable salt, a solvate, a tautomer or a stereoisomer thereof. In other embodiments of the invention, there are provided compounds of Formula I or any of the subformulas as described herein, or a pharmaceutically acceptable salt or a solvate thereof. In some embodiments, the solvate is a hydrate.

In some embodiments of compounds of Formula I, $X_1$ is —N= and $R^2$ is selected from the group consisting of cycloalkyl, lower alkyl optionally substituted with one or more $R^8$, for example, 1 to 3 $R^8$, and —O—$R^9$. In one embodiment, $X_1$ is —N= and $R^2$ is selected from the group consisting of cycloalkyl, lower alkyl, lower alkoxy, and lower alkoxy substituted with lower alkoxy. In one embodiment, $X_1$ is —N= and $R^2$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $X_1$ is —N= and $R^2$ is selected from the group consisting of methyl, cyclopropyl, cyclobutyl, cyclopentyl, cyclohexyl, methoxy, ethoxy, and 2-methoxy-ethoxy.

In some embodiments of compounds of Formula I, $X_1$ is —C(H)= or —C($R^1$)= and $R^1$ is fluoro, chloro, or lower alkyl optionally substituted with one or more fluoro. In one embodiment, $X_1$ is —C(H)= or —C($R^1$)= and $R^1$ is chloro or lower alkyl. In one embodiment, $X_1$ is —C(H)= or —C($R^1$)= and $R^1$ is chloro or $C_{1-3}$ alkyl. In one embodiment, $X_1$ is —C(H)= or —C($R^1$)= and $R^1$ is chloro or methyl.

In some embodiments of compounds of Formula I, further to any of the above embodiments of Formula I, $Cy_1$ is cycloalkyl optionally substituted with one or more $R^4$, phenyl optionally substituted with one or more $R^5$, or 5 or 6 membered heteroaryl optionally substituted on an available carbon atom with one or more $R^6$ and optionally substituted on an available nitrogen atom with $R^7$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula I, further to any of the above embodiments of Formula I, $Cy_1$ is cycloalkyl optionally substituted with one or more $R^4$, phenyl optionally substituted with one or more $R^5$, or 5 or 6 membered heteroaryl optionally substituted on an available carbon atom with one or more $R^6$ and optionally substituted on an available nitrogen atom with $R^7$, wherein cycloalkyl is cyclohexyl, or cycloheptyl, and heteroaryl is pyridin-3-yl or pyrazol-4-yl.

In some embodiments of compounds of Formula I, further to any of the above embodiments of Formula I, $L_1$ is —C($H_2$)—. In some embodiments of compounds of Formula I, further to any of the above embodiments of Formula I, $L_1$ is —C(O)—.

In some embodiments of compounds of Formula I, further to any of the above embodiments of Formula I, $Y_1$ is —N= and $R^3$ is hydrogen. In some embodiments of compounds of Formula I, further to any of the above embodiments of Formula I, $Y_1$ is —C(H)= and $R^3$ is fluoro.

In some embodiments (A) of compounds of Formula I, $X_1$ is N and all the other variables are as defined herein. Within embodiments (A), in certain instances, $L_1$ is $CH_2$, $Y_1$ is CH and $R^3$ is F. In other instances, $L_1$ is $CH_2$, $Y_1$ is N and $R^3$ is F. In yet other instances, $L_1$ is —C(=O)—, $Y_1$ is CH and $R^3$ is F. In still other instances, $L_1$ is —C(=O)—, $Y_1$ is N and $R^3$ is F.

In some embodiments (B) of compounds of Formula I, $X_1$ is —C($R^1$)=, $R^1$ and all the other variables are as defined herein. Within embodiments (B), in certain instances, $L_1$ is $CH_2$, $Y_1$ is CH and $R^3$ is F. In other instances, $L_1$ is —C(=O)—, $Y_1$ is CH and $R^3$ is F. In yet other instances, $L_1$ is —$CH_2$—, $Y_1$ is N and $R^3$ is F. In still other instances, $L_1$ is —C(=O)—, $Y_1$ is N and $R^3$ is F.

In some embodiments (C) of compounds of Formula I, $X_1$ is N, $R^2$ is —N($R^{9a}$)($R^{9b}$), and all the other variables are as defined herein.

In some embodiments of compounds of Formula I, $Cy_1$ is cycloalkyl optionally substituted with one or more $R^4$. In certain instances, $Cy_1$ is cyclopropyl, cyclobutyl, cyclopentyl, cyclohexyl, cyclopentyl, each of which is optionally substituted with from 1 to 3 $R^4$. All the other variables are as defined herein.

In some embodiments of compounds of Formula I, $Cy_1$ is phenyl optionally substituted with one or more $R^5$ and all the other variables are as defined herein.

In some embodiments of compounds of Formula I, wherein $Cy_1$ is 5 or 6-membered heteroaryl optionally substituted on an available carbon atom with one or more $R^6$ and optionally substituted on an available nitrogen atom with $R^7$. In certain instances, $Cy_1$ is 3-pyridyl, 2-pyrrolyl, 3-pyrrolyl or 4-pyrazolyl, optionally substituted on an available carbon atom with from 1 to 3 $R^6$ and optionally substituted on an available nitrogen atom with $R^7$. In some embodiments, each $R^6$ is independently selected from the group consisting of fluoro, chloro, bromo, cycloalkyl, lower alkyl optionally substituted with from one to three fluoro, and lower alkoxy optionally substituted with one to three fluoro; or two $R^6$ bound to adjacent carbon atoms of the heteroaryl ring form a fused cycloalkyl ring. All the other variables are as defined herein.

In some embodiments of compounds of Formula I, $R^{9a}$ is H and $R^{9b}$ is selected from H, lower alkyl, lower alkyl substituted with hydroxy, lower alkyl substituted with lower alkoxy, lower alkyl substituted with 1 to 3 fluoro groups, cycloalkyl optionally substituted with lower alkyl or one to three fluoro, cycloalkylalkyl optionally substituted with lower alkyl or one to three fluoro substituents, heterocycloalkyl optionally substituted with lower alkyl, heterocycloalkylalkyl, arylalkyl optionally substituted with from 1 to 3 members selected from lower alkyl, fluoro or haloalkyl and heteroarylalkyl optionally substituted with from one to three members selected from alkyl, fluoro or haloalkyl. In certain instances, $R^{9a}$ is H and $R^{9b}$ is selected from (i) H, methyl, ethyl, t-butyl, propyl, isopropyl, 2-butyl, n-butyl, 2-hydroxy-2-methylpropyl, 2-methoxyethyl, 3-methoxypropyl, 2,2,2-trifluoroethyl, or 4-methoxybutyl and (ii) cyclopropyl, cyclobutyl, cyclopentyl, cylohexyl, cyclopropylmethyl, cyclobutylmethyl, cyclopentylmethyl, cyclohexymethyl, benzyl, 1-methylbenzyl, 4,4-difluorocyclohexyl, 2-tetrahydrofuranylmethyl, 4-piperadinyl, 3-pyridyl, 2-pyridyl or 4-pyridyl, each of which is optionally substituted with from 1 to 3 members selected from lower alkyl, lower alkoxy, fluoro or $CF_3$. All the other variables are as defined herein.

In some embodiments of compounds of Formula I, —N($R^{9a}$)($R^{9b}$) is 1-piperadinyl, 4-morpholinyl, 1-piperazinyl or 1-pyrrolidinyl, each of which is optionally substituted with one to three members selected from lower alkyl, haloalkyl, lower alkoxy or fluoro. All the other variables are as defined herein.

In a second aspect, compounds of Formula I having the structure according to the following Formula Ia are provided:

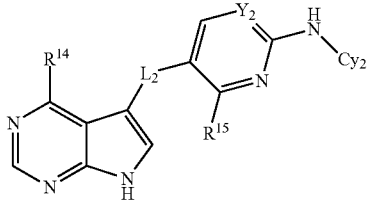

Formula Ia or a salt, a prodrug, a solvate, a tautomer or a stereoisomer thereof,
wherein:
$Y_2$ is —N= and $R^{15}$ is hydrogen; or $Y_2$ is —C(H)= and $R^{15}$ is fluoro or chloro;
$L_2$ is —C(H$_2$)— or —C(O)—;
$Cy_2$ is cycloalkyl optionally substituted with one or more $R^{16}$, phenyl optionally substituted with one or more $R^{17}$, or 5 or 6 membered heteroaryl optionally substituted on an available carbon atom with one or more $R^{18}$ and optionally substituted on an available nitrogen atom with $R^{19}$;
$R^{14}$ is selected from the group consisting of cycloalkyl, lower alkyl optionally substituted with one or more $R^{20}$ and —O—$R^{21}$;
each $R^{16}$ is independently selected from the group consisting of fluoro, —OH, lower alkyl optionally substituted with one or more fluoro, and lower alkoxy optionally substituted with one or more fluoro;
each $R^{17}$ is independently selected from the group consisting of fluoro, chloro, —O—$R^{22}$, —S—$R^{23}$, —S(O$_2$)—$R^{24}$, and lower alkyl optionally substituted with one or more $R^{25}$;
each $R^{18}$ is independently selected from the group consisting of fluoro, chloro, bromo, cycloalkyl, lower alkyl optionally substituted with one or more fluoro, and lower alkoxy optionally substituted with one or more fluoro; or two $R^{18}$ bound to adjacent carbon atoms of the heteroaryl ring, taken together, form a fused cycloalkyl ring;
$R^{19}$ is cycloalkyl, lower alkoxy, or lower alkyl optionally substituted with one or more fluoro;
$R^{20}$ is fluoro or lower alkoxy optionally substituted with one or more fluoro;
$R^{21}$ is lower alkyl, lower alkyl substituted with one or more fluoro, or lower alkyl substituted with lower alkoxy;
each $R^{22}$, $R^{23}$ and $R^{24}$ are independently lower alkyl optionally substituted with one or more fluoro; and
each $R^{25}$ is independently selected from the group consisting of fluoro, —OH, and lower alkoxy optionally substituted with one or more fluoro.

In some embodiments of compounds of Formula Ia, $R^{14}$ is selected from the group consisting of cycloalkyl, lower alkyl, lower alkoxy, and lower alkoxy substituted with lower alkoxy. In one embodiment, $R^{14}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{14}$ is selected from the group consisting of methyl, cyclopropyl, methoxy, ethoxy, and 2-methoxy-ethoxy.

In some embodiments of compounds of Formula Ia, further to any of the above embodiments of Formula Ia, $Cy_2$ is cycloalkyl optionally substituted with one or more $R^{16}$, phenyl optionally substituted with one or more $R^{17}$, or 5 or 6 membered heteroaryl optionally substituted on an available carbon atom with one or more $R^{18}$ and optionally substituted on an available nitrogen atom with $R^{19}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ia, further to any of the above embodiments of Formula Ia, $Cy_2$ is cycloalkyl optionally substituted with one or more $R^{16}$, phenyl optionally substituted with one or more $R^{17}$, or 5 or 6 membered heteroaryl optionally substituted on an available carbon atom with one or more $R^{18}$ and optionally substituted on an available nitrogen atom with $R^{19}$, wherein cycloalkyl is cyclohexyl, or cycloheptyl, and heteroaryl is pyridin-3-yl or pyrazol-4-yl.

In some embodiments of compounds of Formula Ia, further to any of the above embodiments of Formula Ia, $L_2$ is —C(H$_2$)—. In some embodiments of compounds of Formula Ia, further to any of the above embodiments of Formula Ia, $L_2$ is —C(O)—.

In some embodiments of compounds of Formula Ia, further to any of the above embodiments of Formula Ia, $Y_2$ is —N= and $R^{15}$ is hydrogen. In some embodiments of compounds of Formula Ia, further to any of the above embodiments of Formula Ia, $Y_2$ is —C(H)= and $R^{15}$ is fluoro.

In a third aspect, compounds of Formula I having the structure according to the following Formula Ib are provided:

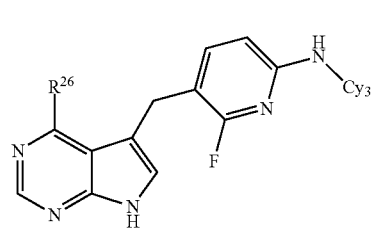

Formula Ib or a salt, a prodrug, a solvate, a tautomer or a stereoisomer thereof,
wherein:
$Cy_3$ is cycloalkyl optionally substituted with one or more $R^{27}$, phenyl optionally substituted with one or more $R^{28}$, or 5 or 6 membered heteroaryl optionally substituted on an available carbon atom with one or more $R^{29}$ and optionally substituted on an available nitrogen atom with $R^{30}$;
$R^{26}$ is selected from the group consisting of cycloalkyl, lower alkyl optionally substituted with one or more $R^{31}$, and —O—$R^{32}$;
each $R^{27}$ is independently selected from the group consisting of fluoro, —OH, lower alkyl optionally substituted with one or more fluoro, and lower alkoxy optionally substituted with one or more fluoro;
each $R^{28}$ is independently selected from the group consisting of fluoro, chloro, —O—$R^{33}$, —S—$R^{34}$, —S(O$_2$)—$R^{35}$, and lower alkyl optionally substituted with one or more $R^{36}$;
each $R^{29}$ is independently selected from the group consisting of fluoro, chloro, bromo, cycloalkyl, lower alkyl optionally substituted with one or more fluoro, and lower alkoxy optionally substituted with one or more fluoro; or two $R^{29}$ bound to adjacent carbon atoms of the heteroaryl ring, taken together, form a fused cycloalkyl ring;

$R^{30}$ is cycloalkyl or lower alkyl optionally substituted with one or more fluoro;

$R^{31}$ is fluoro or lower alkoxy optionally substituted with one or more fluoro;

$R^{32}$ is lower alkyl, lower alkyl substituted with one or more fluoro, or lower alkyl substituted with lower alkoxy;

each $R^{33}$, $R^{34}$ and $R^{35}$ are independently lower alkyl optionally substituted with one or more fluoro; and each $R^{36}$ is independently selected from the group consisting of fluoro, —OH, and lower alkoxy optionally substituted with one or more fluoro.

In some embodiments of compounds of Formula Ib, $R^{26}$ is selected from the group consisting of cycloalkyl, lower alkyl, lower alkoxy, and lower alkoxy substituted with lower alkoxy. In one embodiment, $R^{26}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{26}$ is selected from the group consisting of methyl, cyclopropyl, methoxy, ethoxy, and 2-methoxy-ethoxy.

In some embodiments of compounds of Formula Ib, further to any of the above embodiments of Formula Ib, $Cy_3$ is cycloalkyl optionally substituted with one or more $R^{27}$, phenyl optionally substituted with one or more $R^{28}$, or 5 or 6 membered heteroaryl optionally substituted on an available carbon atom with one or more $R^{29}$ and optionally substituted on an available nitrogen atom with $R^{30}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ib, further to any of the above embodiments of Formula Ib, $Cy_3$ is cycloalkyl optionally substituted with one or more $R^{27}$, phenyl optionally substituted with one or more $R^{28}$, or 5 or 6 membered heteroaryl optionally substituted on an available carbon atom with one or more $R^{29}$ and optionally substituted on an available nitrogen atom with $R^{30}$, wherein cycloalkyl is cyclohexyl, or cycloheptyl, and heteroaryl is pyridin-3-yl or pyrazol-4-yl.

In a fourth aspect, compounds of Formula I having the structure according to the following Formula Ic are provided:

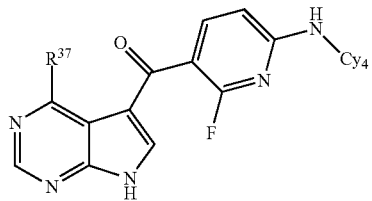

Formula Ic or a salt, a prodrug, a solvate, a tautomer or a stereoisomer thereof, wherein:

$Cy_4$ is cycloalkyl optionally substituted with one or more $R^{38}$, phenyl optionally substituted with one or more $R^{39}$, or 5 or 6 membered heteroaryl optionally substituted on an available carbon atom with one or more $R^{40}$ and optionally substituted on an available nitrogen atom with $R^{41}$;

$R^{37}$ is selected from the group consisting of cycloalkyl, lower alkyl optionally substituted with one or more $R^{42}$, and —O—$R^{43}$;

each $R^{38}$ is independently selected from the group consisting of fluoro, —OH, lower alkyl optionally substituted with one or more fluoro, and lower alkoxy optionally substituted with one or more fluoro;

each $R^{39}$ is independently selected from the group consisting of fluoro, chloro, —O—$R^{44}$, —S—$R^{45}$, —S(O$_2$)—$R^{46}$, and lower alkyl optionally substituted with one or more $R^{47}$;

each $R^{40}$ is independently selected from the group consisting of fluoro, chloro, bromo, cycloalkyl, lower alkyl optionally substituted with one or more fluoro, and lower alkoxy optionally substituted with one or more fluoro; or two $R^{40}$ bound to adjacent carbon atoms of the heteroaryl ring, taken together, form a fused cycloalkyl ring;

$R^{41}$ is cycloalkyl or lower alkyl optionally substituted with one or more fluoro;

$R^{42}$ is fluoro or lower alkoxy optionally substituted with one or more fluoro;

$R^{43}$ is lower alkyl, lower alkyl substituted with one or more fluoro, or lower alkyl substituted with lower alkoxy;

each $R^{44}$, $R^{45}$ and $R^{46}$ are independently lower alkyl optionally substituted with one or more fluoro; and each $R^{47}$ is independently selected from the group consisting of fluoro, —OH, and lower alkoxy optionally substituted with one or more fluoro.

In some embodiments of compounds of Formula Ic, $R^{37}$ is selected from the group consisting of cycloalkyl, lower alkyl, lower alkoxy, and lower alkoxy substituted with lower alkoxy. In one embodiment, $R^{37}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{37}$ is selected from the group consisting of methyl, cyclopropyl, methoxy, ethoxy, and 2-methoxy-ethoxy.

In some embodiments of compounds of Formula Ic, further to any of the above embodiments of Formula Ic, $Cy_4$ is cycloalkyl optionally substituted with one or more $R^{38}$, phenyl optionally substituted with one or more $R^{39}$, or 5 or 6 membered heteroaryl optionally substituted on an available carbon atom with one or more $R^{40}$ and optionally substituted on an available nitrogen atom with $R^{41}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ic, further to any of the above embodiments of Formula Ic, $Cy_4$ is cycloalkyl optionally substituted with one or more $R^{38}$, phenyl optionally substituted with one or more $R^{39}$, or 5 or 6 membered heteroaryl optionally substituted on an available carbon atom with one or more $R^{40}$ and optionally substituted on an available nitrogen atom with $R^{41}$, wherein cycloalkyl is cyclohexyl, or cycloheptyl, and heteroaryl is pyridin-3-yl or pyrazol-4-yl.

In a fifth aspect, compounds of Formula I having the structure according to the following Formula Id are provided:

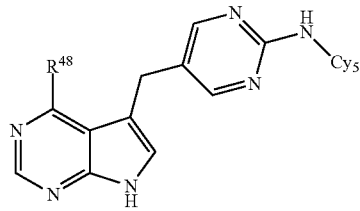

Formula Id or a salt, a prodrug, a solvate, a tautomer or a stereoisomer thereof, wherein:

$Cy_5$ is cycloalkyl optionally substituted with one or more $R^{49}$, phenyl optionally substituted with one or more $R^{50}$, or 5 or 6 membered heteroaryl optionally substituted on an available carbon atom with one or more $R^{51}$ and optionally substituted on an available nitrogen atom with $R^{52}$;

$R^{48}$ is selected from the group consisting of cycloalkyl, lower alkyl optionally substituted with one or more $R^{53}$, and —O—$R^{54}$;

each $R^{49}$ is independently selected from the group consisting of fluoro, —OH, lower alkyl optionally substituted with one or more fluoro, and lower alkoxy optionally substituted with one or more fluoro;

each $R^{50}$ is independently selected from the group consisting of fluoro, chloro, —O—$R^{55}$, —S—$R^{56}$, —S(O$_2$)—$R^{57}$, and lower alkyl optionally substituted with one or more $R^{58}$;

each $R^{51}$ is independently selected from the group consisting of fluoro, chloro, bromo, cycloalkyl, lower alkyl optionally substituted with one or more fluoro, and lower alkoxy optionally substituted with one or more fluoro; or two $R^{51}$ bound to adjacent carbon atoms of the heteroaryl ring, taken together, form a fused cycloalkyl ring;

$R^{52}$ is cycloalkyl or lower alkyl optionally substituted with one or more fluoro;

$R^{53}$ is fluoro or lower alkoxy optionally substituted with one or more fluoro;

$R^{54}$ is lower alkyl, lower alkyl substituted with one or more fluoro, or lower alkyl substituted with lower alkoxy;

each $R^{55}$, $R^{56}$ and $R^{57}$ are independently lower alkyl optionally substituted with one or more fluoro; and each $R^{58}$ is independently selected from the group consisting of fluoro, —OH, and lower alkoxy optionally substituted with one or more fluoro.

In some embodiments of compounds of Formula Id, $R^{48}$ is selected from the group consisting of cycloalkyl, lower alkyl, lower alkoxy, and lower alkoxy substituted with lower alkoxy. In one embodiment, $R^{48}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{48}$ is selected from the group consisting of methyl, cyclopropyl, methoxy, ethoxy, and 2-methoxy-ethoxy.

In some embodiments of compounds of Formula Id, further to any of the above embodiments of Formula Id, Cy$_5$ is cycloalkyl optionally substituted with one or more $R^{49}$, phenyl optionally substituted with one or more $R^{50}$, or 5 or 6 membered heteroaryl optionally substituted on an available carbon atom with one or more $R^{51}$ and optionally substituted on an available nitrogen atom with $R^{52}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Id, further to any of the above embodiments of Formula Id, Cy$_5$ is cycloalkyl optionally substituted with one or more $R^{49}$, phenyl optionally substituted with one or more $R^{50}$, or 5 or 6 membered heteroaryl optionally substituted on an available carbon atom with one or more $R^{51}$ and optionally substituted on an available nitrogen atom with $R^{52}$, wherein cycloalkyl is cyclohexyl, or cycloheptyl, and heteroaryl is pyridin-3-yl or pyrazol-4-yl.

In a sixth aspect, compounds of Formula I having the structure according to the following Formula Ie are provided:

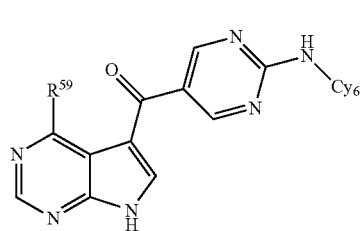

Formula Ie or a salt, a prodrug, a solvate, a tautomer or a stereoisomer thereof, wherein:

Cy$_6$ is cycloalkyl optionally substituted with one or more $R^{60}$, phenyl optionally substituted with one or more $R^{61}$, or 5 or 6 membered heteroaryl optionally substituted on an available carbon atom with one or more $R^{62}$ and optionally substituted on an available nitrogen atom with $R^{63}$;

$R^{59}$ is selected from the group consisting of cycloalkyl, lower alkyl optionally substituted with one or more $R^{64}$, and —O—$R^{65}$;

each $R^{60}$ is independently selected from the group consisting of fluoro, —OH, lower alkyl optionally substituted with one or more fluoro, and lower alkoxy optionally substituted with one or more fluoro;

each $R^{61}$ is independently selected from the group consisting of fluoro, chloro, —O—$R^{66}$, —S—$R^{67}$, —S(O$_2$)—$R^{68}$, and lower alkyl optionally substituted with one or more $R^{69}$;

each $R^{62}$ is independently selected from the group consisting of fluoro, chloro, bromo, cycloalkyl, lower alkyl optionally substituted with one or more fluoro, and lower alkoxy optionally substituted with one or more fluoro; or two $R^{62}$ bound to adjacent carbon atoms of the heteroaryl ring, taken together, form a fused cycloalkyl ring;

$R^{63}$ is cycloalkyl or lower alkyl optionally substituted with one or more fluoro;

$R^{64}$ is fluoro or lower alkoxy optionally substituted with one or more fluoro;

$R^{65}$ is lower alkyl, lower alkyl substituted with one or more fluoro, or lower alkyl substituted with lower alkoxy;

each $R^{66}$, $R^{67}$ and $R^{68}$ are independently lower alkyl optionally substituted with one or more fluoro; and each $R^{69}$ is independently selected from the group consisting of fluoro, —OH, and lower alkoxy optionally substituted with one or more fluoro.

In some embodiments of compounds of Formula Ie, $R^{59}$ is selected from the group consisting of cycloalkyl, lower alkyl, lower alkoxy, and lower alkoxy substituted with lower alkoxy. In one embodiment, $R^{59}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{59}$ is selected from the group consisting of methyl, cyclopropyl, methoxy, ethoxy, and 2-methoxy-ethoxy.

In some embodiments of compounds of Formula Ie, further to any of the above embodiments of Formula Ie, Cy$_6$ is cycloalkyl optionally substituted with one or more $R^{60}$, phenyl optionally substituted with one or more $R^{61}$, or 5 or 6 membered heteroaryl optionally substituted on an available carbon atom with one or more $R^{62}$ and optionally substituted on an available nitrogen atom with $R^{63}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ie, further to any of the above embodiments of Formula Ie, $Cy_6$ is cycloalkyl optionally substituted with one or more $R^{60}$, phenyl optionally substituted with one or more $R^{61}$, or 5 or 6 membered heteroaryl optionally substituted on an available carbon atom with one or more $R^{62}$ and optionally substituted on an available nitrogen atom with $R^{63}$, wherein cycloalkyl is cyclohexyl, or cycloheptyl, and heteroaryl is pyridin-3-yl or pyrazol-4-yl.

In a seventh aspect, compounds of Formula I having the structure according to the following Formula If are provided:

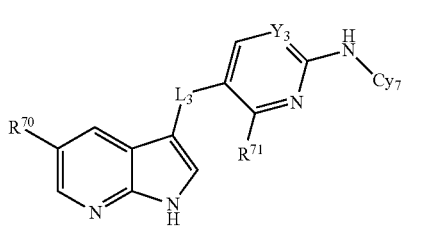

Formula If or a salt, a prodrug, a solvate, a tautomer or a stereoisomer thereof,
wherein:
$Y_3$ is —N═ and $R^{71}$ is hydrogen; or $Y_3$ is —C(H)═ and $R^{71}$ is fluoro;
$L_3$ is —C(H$_2$)— or —C(O)—;
$Cy_7$ is cycloalkyl optionally substituted with one or more $R^{72}$, phenyl optionally substituted with one or more $R^{73}$, or 5 or 6 membered heteroaryl optionally substituted on an available carbon atom with one or more $R^{74}$ and optionally substituted on an available nitrogen atom with $R^{75}$;
$R^{70}$ is hydrogen, fluoro, chloro, or lower alkyl optionally substituted with one or more fluoro;
each $R^{72}$ is independently selected from the group consisting of fluoro, —OH, lower alkyl optionally substituted with one or more fluoro, and lower alkoxy optionally substituted with one or more fluoro;
each $R^{73}$ is independently selected from the group consisting of fluoro, chloro, —O—$R^{76}$, —S—$R^{77}$, —S(O$_2$)—$R^{78}$, and lower alkyl optionally substituted with one or more $R^{79}$;
each $R^{74}$ is independently selected from the group consisting of fluoro, chloro, bromo, cycloalkyl, lower alkyl optionally substituted with one or more fluoro, and lower alkoxy optionally substituted with one or more fluoro; or two $R^{74}$ bound to adjacent carbon atoms of the heteroaryl ring, taken together, form a fused cycloalkyl ring;
$R^{75}$ is cycloalkyl or lower alkyl optionally substituted with one or more fluoro;
each $R^{76}$, $R^{77}$ and $R^{78}$ are independently lower alkyl optionally substituted with one or more fluoro; and
each $R^{79}$ is independently selected from the group consisting of fluoro, —OH, and lower alkoxy optionally substituted with one or more fluoro.

In some embodiments of compounds of Formula If, $R^{70}$ is hydrogen, chloro or lower alkyl. In one embodiment, $R^{70}$ is hydrogen, chloro or $C_{1-3}$ alkyl. In one embodiment, $R^{70}$ is hydrogen, chloro or methyl.

In some embodiments of compounds of Formula If, further to any of the above embodiments of Formula If, $Cy_7$ is cycloalkyl optionally substituted with one or more $R^{72}$, phenyl optionally substituted with one or more $R^{73}$, or 5 or 6 membered heteroaryl optionally substituted on an available carbon atom with one or more $R^{74}$ and optionally substituted on an available nitrogen atom with $R^{75}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula If, further to any of the above embodiments of Formula If, $Cy_7$ is cycloalkyl optionally substituted with one or more $R^{72}$, phenyl optionally substituted with one or more $R^{73}$, or 5 or 6 membered heteroaryl optionally substituted on an available carbon atom with one or more $R^{74}$ and optionally substituted on an available nitrogen atom with $R^{75}$, wherein cycloalkyl is cyclohexyl, or cycloheptyl, and heteroaryl is pyridin-3-yl or pyrazol-4-yl.

In some embodiments of compounds of Formula If, further to any of the above embodiments of Formula If, $L_3$ is —C(H$_2$)—. In some embodiments of compounds of Formula If, further to any of the above embodiments of Formula If, $L_3$ is —C(O)—.

In some embodiments of compounds of Formula If, further to any of the above embodiments of Formula If, $Y_3$ is —N═ and $R^{71}$ is hydrogen. In some embodiments of compounds of Formula If, further to any of the above embodiments of Formula If, $Y_3$ is —C(H)═ and $R^{71}$ is fluoro.

In an eighth aspect, compounds of Formula I having the structure according to the following Formula Ig are provided:

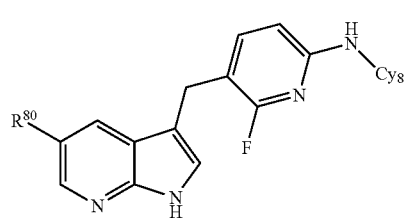

Formula Ig or a salt, a prodrug, a solvate, a tautomer or a stereoisomer thereof,
wherein:
$Cy_8$ is cycloalkyl optionally substituted with one or more $R^{81}$, phenyl optionally substituted with one or more $R^{82}$, or 5 or 6 membered heteroaryl optionally substituted on an available carbon atom with one or more $R^{83}$ and optionally substituted on an available nitrogen atom with $R^{84}$;
$R^{80}$ is hydrogen, fluoro, chloro, or lower alkyl optionally substituted with one or more fluoro;
each $R^{81}$ is independently selected from the group consisting of fluoro, —OH, lower alkyl optionally substituted with one or more fluoro, and lower alkoxy optionally substituted with one or more fluoro;
each $R^{82}$ is independently selected from the group consisting of fluoro, chloro, —O—$R^{85}$, —S—$R^{86}$, —S(O$_2$)—$R^{87}$, and lower alkyl optionally substituted with one or more $R^{88}$;
each $R^{83}$ is independently selected from the group consisting of fluoro, chloro, bromo, cycloalkyl, lower alkyl optionally substituted with one or more fluoro, and lower alkoxy optionally substituted with one or more fluoro; or two $R^{83}$ bound to adjacent carbon atoms of the heteroaryl ring, taken together, form a fused cycloalkyl ring;
$R^{84}$ is cycloalkyl or lower alkyl optionally substituted with one or more fluoro;

each $R^{85}$, $R^{86}$ and $R^{87}$ are independently lower alkyl optionally substituted with one or more fluoro; and each $R^{88}$ is independently selected from the group consisting of fluoro, —OH, and lower alkoxy optionally substituted with one or more fluoro.

In some embodiments of compounds of Formula Ig, $R^{80}$ is hydrogen, chloro or lower alkyl. In one embodiment, $R^{80}$ is hydrogen, chloro or $C_{1-3}$ alkyl. In one embodiment, $R^{80}$ is hydrogen, chloro or methyl.

In some embodiments of compounds of Formula Ig, further to any of the above embodiments of Formula Ig, $Cy_8$ is cycloalkyl optionally substituted with one or more $R^{81}$, phenyl optionally substituted with one or more $R^{82}$, or 5 or 6 membered heteroaryl optionally substituted on an available carbon atom with one or more $R^{83}$ and optionally substituted on an available nitrogen atom with $R^{84}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ig, further to any of the above embodiments of Formula Ig, $Cy_8$ is cycloalkyl optionally substituted with one or more $R^{81}$, phenyl optionally substituted with one or more $R^{82}$, or 5 or 6 membered heteroaryl optionally substituted on an available carbon atom with one or more $R^{83}$ and optionally substituted on an available nitrogen atom with $R^{84}$, wherein cycloalkyl is cyclohexyl, or cycloheptyl, and heteroaryl is pyridin-3-yl or pyrazol-4-yl.

In a ninth aspect, compounds of Formula I having the structure according to the following Formula Ih are provided:

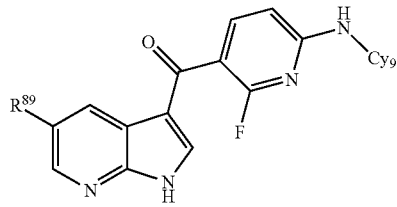

Formula Ih or a salt, a prodrug, a solvate, a tautomer or a stereoisomer thereof,
wherein:
$Cy_9$ is cycloalkyl optionally substituted with one or more $R^{90}$, phenyl optionally substituted with one or more $R^{91}$, or 5 or 6 membered heteroaryl optionally substituted on an available carbon atom with one or more $R^{92}$ and optionally substituted on an available nitrogen atom with $R^{93}$;

$R^{89}$ is hydrogen, fluoro, chloro, or lower alkyl optionally substituted with one or more fluoro;

each $R^{90}$ is independently selected from the group consisting of fluoro, —OH, lower alkyl optionally substituted with one or more fluoro, and lower alkoxy optionally substituted with one or more fluoro;

each $R^{91}$ is independently selected from the group consisting of fluoro, chloro, —O—$R^{94}$, —S—$R^{95}$, —S($O_2$)—$R^{96}$, and lower alkyl optionally substituted with one or more $R^{97}$;

each $R^{92}$ is independently selected from the group consisting of fluoro, chloro, bromo, cycloalkyl, lower alkyl optionally substituted with one or more fluoro, and lower alkoxy optionally substituted with one or more fluoro; or two $R^{92}$ bound to adjacent carbon atoms of the heteroaryl ring, taken together, form a fused cycloalkyl ring;

$R^{93}$ is cycloalkyl or lower alkyl optionally substituted with one or more fluoro;

each $R^{94}$, $R^{95}$ and $R^{96}$ are independently lower alkyl optionally substituted with one or more fluoro; and each $R^{97}$ is independently selected from the group consisting of fluoro, —OH, and lower alkoxy optionally substituted with one or more fluoro.

In some embodiments of compounds of Formula Ih, $R^{89}$ is hydrogen, chloro or lower alkyl. In one embodiment, $R^{89}$ is hydrogen, chloro or $C_{1-3}$ alkyl. In one embodiment, $R^{89}$ is hydrogen, chloro or methyl.

In some embodiments of compounds of Formula Ih, further to any of the above embodiments of Formula Ih, $Cy_9$ is cycloalkyl optionally substituted with one or more $R^{90}$, phenyl optionally substituted with one or more $R^{91}$, or 5 or 6 membered heteroaryl optionally substituted on an available carbon atom with one or more $R^{92}$ and optionally substituted on an available nitrogen atom with $R^{93}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ih, further to any of the above embodiments of Formula Ih, $Cy_9$ is cycloalkyl optionally substituted with one or more $R^{90}$, phenyl optionally substituted with one or more $R^{91}$, or 5 or 6 membered heteroaryl optionally substituted on an available carbon atom with one or more $R^{92}$ and optionally substituted on an available nitrogen atom with $R^{93}$, wherein cycloalkyl is cyclohexyl, or cycloheptyl, and heteroaryl is pyridin-3-yl or pyrazol-4-yl.

In a tenth aspect, compounds of Formula I having the structure according to the following Formula Ii are provided:

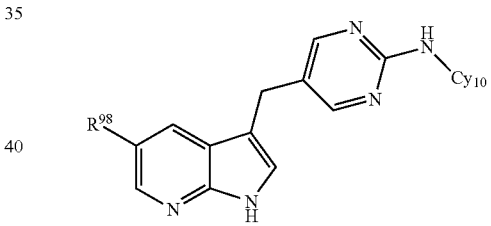

Formula Ii or a salt, a prodrug, a solvate, a tautomer or a stereoisomer thereof,
wherein:
$Cy_{10}$ is cycloalkyl optionally substituted with one or more $R^{99}$, phenyl optionally substituted with one or more $R^{100}$, or 5 or 6 membered heteroaryl optionally substituted on an available carbon atom with one or more $R^{101}$ and optionally substituted on an available nitrogen atom with $R^{102}$;

$R^{98}$ is hydrogen, fluoro, chloro, or lower alkyl optionally substituted with one or more fluoro;

each $R^{99}$ is independently selected from the group consisting of fluoro, —OH, lower alkyl optionally substituted with one or more fluoro, and lower alkoxy optionally substituted with one or more fluoro;

each $R^{100}$ is independently selected from the group consisting of fluoro, chloro, —O—$R^{103}$, —S—$R^{104}$, —S($O_2$)—$R^{105}$, and lower alkyl optionally substituted with one or more $R^{106}$;

each $R^{101}$ is independently selected from the group consisting of fluoro, chloro, bromo, cycloalkyl, lower alkyl optionally substituted with one or more fluoro, and lower alkoxy optionally substituted with one or more fluoro; or two $R^{101}$ bound to adjacent carbon atoms of the heteroaryl ring, taken together, form a fused cycloalkyl ring;

$R^{102}$ is cycloalkyl or lower alkyl optionally substituted with one or more fluoro;

each $R^{102}$, $R^{104}$ and $R^{105}$ are independently lower alkyl optionally substituted with one or more fluoro; and each $R^{106}$ is independently selected from the group consisting of fluoro, —OH, and lower alkoxy optionally substituted with one or more fluoro.

In some embodiments of compounds of Formula Ii, $R^{98}$ is hydrogen, chloro or lower alkyl. In one embodiment, $R^{98}$ is hydrogen, chloro or $C_{1-3}$ alkyl. In one embodiment, $R^{98}$ is hydrogen, chloro or methyl.

In some embodiments of compounds of Formula II, further to any of the above embodiments of Formula Ii, $Cy_{10}$ is cycloalkyl optionally substituted with one or more $R^{99}$, phenyl optionally substituted with one or more $R^{100}$, or 5 or 6 membered heteroaryl optionally substituted on an available carbon atom with one or more $R^{101}$ and optionally substituted on an available nitrogen atom with $R^{102}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ii, further to any of the above embodiments of Formula Ii, $Cy_{10}$ is cycloalkyl optionally substituted with one or more $R^{99}$, phenyl optionally substituted with one or more $R^{100}$, or 5 or 6 membered heteroaryl optionally substituted on an available carbon atom with one or more $R^{101}$ and optionally substituted on an available nitrogen atom with $R^{102}$, wherein cycloalkyl is cyclohexyl, or cycloheptyl, and heteroaryl is pyridin-3-yl or pyrazol-4-yl.

In an eleventh aspect, compounds of Formula I having the structure according to the following Formula Ij are provided:

Formula Ij

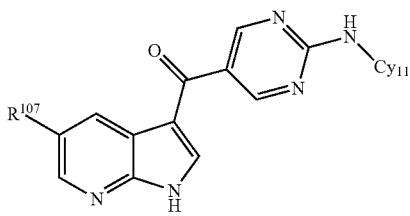

or a salt, a prodrug, a solvate, a tautomer or a stereoisomer thereof, wherein:

$Cy_{11}$ is cycloalkyl optionally substituted with one or more $R^{108}$, phenyl optionally substituted with one or more $R^{109}$, or 5 or 6 membered heteroaryl optionally substituted on an available carbon atom with one or more $R^{110}$ and optionally substituted on an available nitrogen atom with $R^{111}$;

$R^{107}$ is hydrogen, fluoro, chloro, or lower alkyl optionally substituted with one or more fluoro;

each $R^{108}$ is independently selected from the group consisting of fluoro, —OH, lower alkyl optionally substituted with one or more fluoro, and lower alkoxy optionally substituted with one or more fluoro;

each $R^{109}$ is independently selected from the group consisting of fluoro, chloro, —O—$R^{112}$, —S—$R^{113}$, —S($O_2$)—$R^{114}$, and lower alkyl optionally substituted with one or more $R^{115}$;

each $R^{110}$ is independently selected from the group consisting of fluoro, chloro, bromo, cycloalkyl, lower alkyl optionally substituted with one or more fluoro, and lower alkoxy optionally substituted with one or more fluoro; or two $R^{110}$ bound to adjacent carbon atoms of the heteroaryl ring, taken together, form a fused cycloalkyl ring;

$R^{111}$ is cycloalkyl or lower alkyl optionally substituted with one or more fluoro;

each $R^{112}$, $R^{113}$ and $R^{114}$ are independently lower alkyl optionally substituted with one or more fluoro; and each $R^{115}$ is independently selected from the group consisting of fluoro, —OH, and lower alkoxy optionally substituted with one or more fluoro.

In some embodiments of compounds of Formula Ij, $R^{107}$ is hydrogen, chloro or lower alkyl. In one embodiment, $R^{107}$ is hydrogen, chloro or $C_{1-3}$ alkyl. In one embodiment, $R^{107}$ is hydrogen, chloro or methyl.

In some embodiments of compounds of Formula Ij, further to any of the above embodiments of Formula Ij, $Cy_{11}$ is cycloalkyl optionally substituted with one or more $R^{108}$, phenyl optionally substituted with one or more $R^{109}$, or 5 or 6 membered heteroaryl optionally substituted on an available carbon atom with one or more $R^{110}$ and optionally substituted on an available nitrogen atom with $R^{111}$, wherein cycloalkyl is cyclopropyl, cyclobutyl, cyclopentyl, cyclohexyl, or cycloheptyl, and heteroaryl is pyridinyl or pyrazolyl.

In some embodiments of compounds of Formula Ij, further to any of the above embodiments of Formula Ij, $Cy_{11}$ is cycloalkyl optionally substituted with one or more $R^{108}$, phenyl optionally substituted with one or more $R^{109}$, or 5 or 6 membered heteroaryl optionally substituted on an available carbon atom with one or more $R^{110}$ and optionally substituted on an available nitrogen atom with $R^{111}$, wherein cycloalkyl is cyclohexyl, or cycloheptyl, and heteroaryl is pyridin-3-yl or pyrazol-4-yl.

In a twelfth aspect, compounds of Formula I having the structure according to the following Formula Ik are provided:

Formula Ik

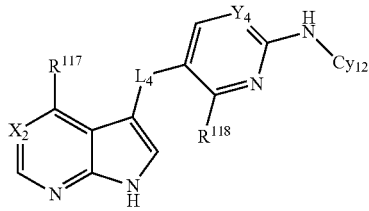

or a salt, a prodrug, a solvate, a tautomer or a stereoisomer thereof, wherein:

$X_2$ is —N=, —C(H)=, or —C($R^{116}$)=;

$Y_4$ is —N= and $R^{118}$ is hydrogen; or $Y_4$ is —C(H)= and $R^{118}$ is fluoro;

$L_4$ is —C($H_2$)— or —C(O)—;

$Cy_{12}$ is cycloalkyl optionally substituted with one or more $R^{119}$;

when $X_2$ is —C($R^{116}$)=, $R^{117}$ is hydrogen;

when $X_2$ is —N= or —C(H)=, $R^{117}$ is selected from the group consisting of hydrogen, cycloalkyl, lower alkyl optionally substituted with one or more $R^{120}$, and —O—$R^{121}$;

$R^{116}$ is fluoro, chloro, or lower alkyl optionally substituted with one or more fluoro;

each $R^{119}$ is independently selected from the group consisting of fluoro, —OH, lower alkyl optionally substituted with one or more fluoro, and lower alkoxy optionally substituted with one or more fluoro;

$R^{120}$ is fluoro or lower alkoxy optionally substituted with one or more fluoro; and $R^{121}$ is lower alkyl, lower alkyl substituted with one or more fluoro, or lower alkyl substituted with lower alkoxy.

In some embodiments of compounds of Formula Ik, $X_2$ is —N═ and $R^{117}$ is selected from the group consisting of hydrogen, cycloalkyl, lower alkyl optionally substituted with one or more $R^{120}$, and —O—$R^{121}$. In one embodiment, $X_2$ is —N═ and $R^{117}$ is selected from the group consisting of cycloalkyl, lower alkyl, lower alkoxy, and lower alkoxy substituted with lower alkoxy. In one embodiment, $X_2$ is —N═ and $R^{117}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $X_2$ is —N═ and $R^{117}$ is selected from the group consisting of methyl, cyclopropyl, methoxy, ethoxy, and 2-methoxy-ethoxy.

In some embodiments of compounds of Formula Ik, $X_2$ is —C(H)═ or —C($R^{116}$)═ and $R^{116}$ is fluoro, chloro, or lower alkyl optionally substituted with one or more fluoro. In one embodiment, $X_2$ is —C(H)═ or —C($R^{116}$)═ and $R^{116}$ is chloro or lower alkyl. In one embodiment, $X_2$ is —C(H)═ or —C($R^{116}$)═ and $R^{116}$ is chloro or $C_{1-3}$ alkyl. In one embodiment, $X_2$ is —C(H)═ or —C($R^{116}$)═ and $R^{116}$ is chloro or methyl.

In some embodiments of compounds of Formula Ik, further to any of the above embodiments of Formula Ik, $Cy_{12}$ is cyclopentyl optionally substituted with 1 or 2 $R^{119}$, cyclohexyl optionally substituted with 1 or 2 $R^{119}$, or cycloheptyl optionally substituted with 1 or 2 $R^{119}$.

In some embodiments of compounds of Formula Ik, further to any of the above embodiments of Formula Ik, $Cy_{12}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Ik, further to any of the above embodiments of Formula Ik, $Cy_{12}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Ik, further to any of the above embodiments of Formula Ik, $Cy_{12}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Ik, further to any of the above embodiments of Formula Ik, $Cy_{12}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In some embodiments of compounds of Formula Ik, further to any of the above embodiments of Formula Ik, $L_4$ is —C($H_2$)—. In some embodiments of compounds of Formula Ik, further to any of the above embodiments of Formula Ik, $L_4$ is —C(O)—.

In some embodiments of compounds of Formula Ik, further to any of the above embodiments of Formula Ik, $Y_4$ is —N═ and $R^{118}$ is hydrogen. In some embodiments of compounds of Formula Ik, further to any of the above embodiments of Formula Ik, $Y_4$ is —C(H)═ and $R^{118}$ is fluoro.

In a thirteenth aspect, compounds of Formula I having the structure according to the following Formula Im are provided:

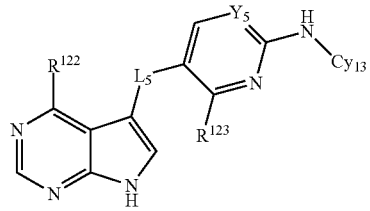

Formula Im or a salt, a prodrug, a solvate, a tautomer or a stereoisomer thereof, wherein:

$Y_5$ is —N═ and $R^{123}$ is hydrogen; or $Y_5$ is —C(H)═ and $R^{123}$ is fluoro;

$L_5$ is —C($H_2$)— or —C(O)—;

$Cy_{13}$ is cycloalkyl optionally substituted with one or more $R^{124}$;

$R^{122}$ is selected from the group consisting of cycloalkyl, lower alkyl optionally substituted with one or more $R^{125}$, and —O—$R^{126}$;

each $R^{124}$ is independently selected from the group consisting of fluoro, —OH, lower alkyl optionally substituted with one or more fluoro, and lower alkoxy optionally substituted with one or more fluoro;

$R^{125}$ is fluoro or lower alkoxy optionally substituted with one or more fluoro; and $R^{126}$ is lower alkyl, lower alkyl substituted with one or more fluoro, or lower alkyl substituted with lower alkoxy.

In some embodiments of compounds of Formula Im, $R^{122}$ is selected from the group consisting of cycloalkyl, lower alkyl, lower alkoxy, and lower alkoxy substituted with lower alkoxy. In one embodiment $R^{122}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment $R^{122}$ is selected from the group consisting of methyl, cyclopropyl, methoxy, ethoxy, and 2-methoxy-ethoxy.

In some embodiments of compounds of Formula Im, further to any of the above embodiments of Formula Im, $Cy_{13}$ is cyclopentyl optionally substituted with 1 or 2 $R^{124}$, cyclohexyl optionally substituted with 1 or 2 $R^{124}$, or cycloheptyl optionally substituted with 1 or 2 $R^{124}$.

In some embodiments of compounds of Formula Im, further to any of the above embodiments of Formula Im, $Cy_{13}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Im, further to any of the above embodiments of Formula Im, $Cy_{13}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Im, further to any of the above embodiments of Formula Im, $Cy_{13}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Im, further to any of the above embodiments of Formula Im, $Cy_{13}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In some embodiments of compounds of Formula Im, further to any of the above embodiments of Formula Im, $L_5$ is —C(H_2)—. In some embodiments of compounds of Formula Im, further to any of the above embodiments of Formula Im, $L_5$ is —C(O)—.

In some embodiments of compounds of Formula Im, further to any of the above embodiments of Formula Im, $Y_5$ is —N= and $R^{123}$ is hydrogen. In some embodiments of compounds of Formula Im, further to any of the above embodiments of Formula Im, $Y_5$ is —C(H)= and $R^{123}$ is fluoro.

In a fourteenth aspect, compounds of Formula I having the structure according to the following Formula In are provided:

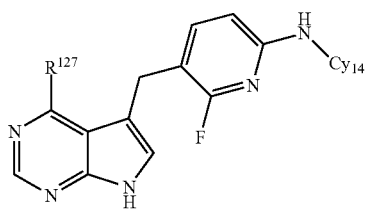

Formula In or a salt, a prodrug, a solvate, a tautomer or a stereoisomer thereof,
wherein:
$Cy_{14}$ is cycloalkyl optionally substituted with one or more $R^{128}$;
$R^{127}$ is selected from the group consisting of cycloalkyl, lower alkyl optionally substituted with one or more $R^{129}$, and —O—$R^{130}$;
each $R^{128}$ is independently selected from the group consisting of fluoro, —OH, lower alkyl optionally substituted with one or more fluoro, and lower alkoxy optionally substituted with one or more fluoro;
$R^{129}$ is fluoro or lower alkoxy optionally substituted with one or more fluoro; and
$R^{130}$ is lower alkyl, lower alkyl substituted with one or more fluoro, or lower alkyl substituted with lower alkoxy.

In some embodiments of compounds of Formula In, $R^{127}$ is selected from the group consisting of cycloalkyl, lower alkyl, lower alkoxy, and lower alkoxy substituted with lower alkoxy. In one embodiment $R^{127}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment $R^{127}$ is selected from the group consisting of methyl, cyclopropyl, methoxy, ethoxy, and 2-methoxy-ethoxy.

In some embodiments of compounds of Formula In, further to any of the above embodiments of Formula In, $Cy_{14}$ is cyclopentyl optionally substituted with 1 or 2 $R^{128}$, cyclohexyl optionally substituted with 1 or 2 $R^{128}$, or cycloheptyl optionally substituted with 1 or 2 $R^{128}$.

In some embodiments of compounds of Formula In, further to any of the above embodiments of Formula In, $Cy_{14}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula In, further to any of the above embodiments of Formula In, $Cy_{14}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula In, further to any of the above embodiments of Formula In, $Cy_{14}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula In, further to any of the above embodiments of Formula In, $Cy_{14}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In a fifteenth aspect, compounds of Formula I having the structure according to the following Formula Io are provided:

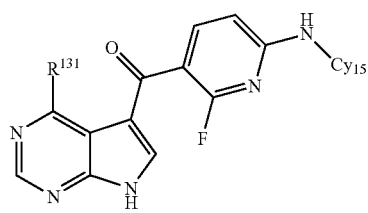

Formula Io or a salt, a prodrug, a solvate, a tautomer or a stereoisomer thereof,
wherein:
$Cy_{15}$ is cycloalkyl optionally substituted with one or more $R^{132}$;
$R^{131}$ is selected from the group consisting of cycloalkyl, lower alkyl optionally substituted with one or more $R^{133}$, and —O—$R^{134}$;
each $R^{132}$ is independently selected from the group consisting of fluoro, —OH, lower alkyl optionally substituted with one or more fluoro, and lower alkoxy optionally substituted with one or more fluoro;
$R^{133}$ is fluoro or lower alkoxy optionally substituted with one or more fluoro; and
$R^{134}$ is lower alkyl, lower alkyl substituted with one or more fluoro, or lower alkyl substituted with lower alkoxy.

In some embodiments of compounds of Formula Io, $R^{131}$ is selected from the group consisting of cycloalkyl, lower alkyl, lower alkoxy, and lower alkoxy substituted with lower alkoxy. In one embodiment $R^{131}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment $R^{131}$ is selected from the group consisting of methyl, cyclopropyl, methoxy, ethoxy, and 2-methoxy-ethoxy.

In some embodiments of compounds of Formula Io, further to any of the above embodiments of Formula Io, $Cy_{15}$ is cyclopentyl optionally substituted with 1 or 2 $R^{132}$, cyclohexyl optionally substituted with 1 or 2 $R^{132}$, or cycloheptyl optionally substituted with 1 or 2 $R^{132}$.

In some embodiments of compounds of Formula Io, further to any of the above embodiments of Formula Io, $Cy_{15}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Io, further to any of the above embodiments of Formula Io, $Cy_{15}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Io, further to any of the above embodiments of Formula Io, $Cy_{15}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Io, further to any of the above embodiments of Formula Io, $Cy_{15}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In a sixteenth aspect, compounds of Formula I having the structure according to the following Formula Ip are provided:

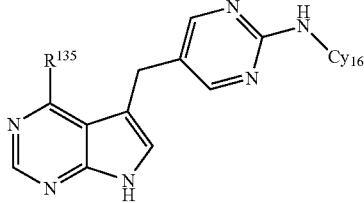

Formula Ip or a salt, a prodrug, a solvate, a tautomer or a stereoisomer thereof,
wherein:
$Cy_{16}$ is cycloalkyl optionally substituted with one or more $R^{136}$;
$R^{135}$ is selected from the group consisting of cycloalkyl, lower alkyl optionally substituted with one or more $R^{137}$, and —O—$R^{138}$;
each $R^{136}$ is independently selected from the group consisting of fluoro, —OH, lower alkyl optionally substituted with one or more fluoro, and lower alkoxy optionally substituted with one or more fluoro;
$R^{137}$ is fluoro or lower alkoxy optionally substituted with one or more fluoro; and
$R^{138}$ is lower alkyl, lower alkyl substituted with one or more fluoro, or lower alkyl substituted with lower alkoxy.

In some embodiments of compounds of Formula Ip, $R^{135}$ is selected from the group consisting of cycloalkyl, lower alkyl, lower alkoxy, and lower alkoxy substituted with lower alkoxy. In one embodiment $R^{135}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment $R^{135}$ is selected from the group consisting of methyl, cyclopropyl, methoxy, ethoxy, and 2-methoxy-ethoxy.

In some embodiments of compounds of Formula Ip, further to any of the above embodiments of Formula Ip, $Cy_{16}$ is cyclopentyl optionally substituted with 1 or 2 $R^{136}$, cyclohexyl optionally substituted with 1 or 2 $R^{136}$, or cycloheptyl optionally substituted with 1 or 2 $R^{136}$.

In some embodiments of compounds of Formula Ip, further to any of the above embodiments of Formula Ip, $Cy_{16}$ is cyclopentyl optionally substituted with 1 or 2 fluoro, or 1 or 2 lower alkyl, or 1 or 2—OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Ip, further to any of the above embodiments of Formula Ip, $Cy_{16}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Ip, further to any of the above embodiments of Formula Ip, $Cy_{16}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Ip, further to any of the above embodiments of Formula Ip, $Cy_{16}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In a seventeenth aspect, compounds of Formula I having the structure according to the following Formula Iq are provided:

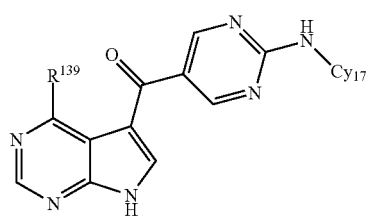

Formula Iq or a salt, a prodrug, a solvate, a tautomer or a stereoisomer thereof,
wherein:
$Cy_{16}$ is cycloalkyl optionally substituted with one or more $R^{140}$;
$R^{139}$ is selected from the group consisting of cycloalkyl, lower alkyl optionally substituted with one or more $R^{141}$, and —O—$R^{142}$;
each $R^{140}$ is independently selected from the group consisting of fluoro, —OH, lower alkyl optionally substituted with one or more fluoro, and lower alkoxy optionally substituted with one or more fluoro;
$R^{141}$ is fluoro or lower alkoxy optionally substituted with one or more fluoro; and
$R^{142}$ is lower alkyl, lower alkyl substituted with one or more fluoro, or lower alkyl substituted with lower alkoxy.

In some embodiments of compounds of Formula Iq, $R^{139}$ is selected from the group consisting of cycloalkyl, lower alkyl, lower alkoxy, and lower alkoxy substituted with lower alkyl. In one embodiment $R^{139}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment $R^{139}$ is selected from the group consisting of methyl, cyclopropyl, methoxy, ethoxy, and 2-methoxy-ethoxy.

In some embodiments of compounds of Formula Iq, further to any of the above embodiments of Formula Iq, $Cy_{17}$ is cyclopentyl optionally substituted with 1 or 2 $R^{140}$, cyclohexyl optionally substituted with 1 or 2 $R^{140}$, or cycloheptyl optionally substituted with 1 or 2 $R^{140}$.

In some embodiments of compounds of Formula Iq, further to any of the above embodiments of Formula Iq, $Cy_{17}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Iq, further to any of the above embodiments of Formula Iq, $Cy_{17}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Iq, further to any of the above embodiments of Formula Iq, $Cy_{17}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Iq, further to any of the above embodiments of Formula Iq, $Cy_{17}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In an eighteenth aspect, compounds of Formula I having the structure according to the following Formula Ir are provided:

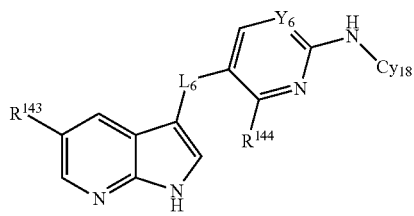

Formula Ir or a salt, a prodrug, a solvate, a tautomer or a stereoisomer thereof,
wherein:
$Y_6$ is —N═ and $R^{144}$ is hydrogen; or $Y_6$ is —C(H)═ and $R^{144}$ is fluoro;
$L_6$ is —C(H$_2$)— or —C(O)—;
$Cy_{18}$ is cycloalkyl optionally substituted with one or more $R^{145}$;
$R^{143}$ is hydrogen, fluoro, chloro, or lower alkyl optionally substituted with one or more fluoro; and
each $R^{145}$ is independently selected from the group consisting of fluoro, —OH, lower alkyl optionally substituted with one or more fluoro, and lower alkoxy optionally substituted with one or more fluoro.

In some embodiments of compounds of Formula Ir, $R^{143}$ is hydrogen, chloro or lower alkyl. In one embodiment, $R^{143}$ is hydrogen, chloro or $C_{1-3}$ alkyl. In one embodiment, $R^{143}$ is hydrogen, chloro or methyl.

In some embodiments of compounds of Formula Ir, further to any of the above embodiments of Formula Ir, $Cy_{18}$ is cyclopentyl optionally substituted with 1 or 2 $R^{145}$, cyclohexyl optionally substituted with 1 or 2 $R^{145}$, or cycloheptyl optionally substituted with 1 or 2 $R^{145}$.

In some embodiments of compounds of Formula Ir, further to any of the above embodiments of Formula Ir, $Cy_{18}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Ir, further to any of the above embodiments of Formula Ir, $Cy_{18}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Ir, further to any of the above embodiments of Formula Ir, $Cy_{18}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Ir, further to any of the above embodiments of Formula Ir, $Cy_{18}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In some embodiments of compounds of Formula Ir, further to any of the above embodiments of Formula Ir, $L_6$ is —C(H$_2$)—. In some embodiments of compounds of Formula Ir, further to any of the above embodiments of Formula Ir, $L_6$ is —C(O)—.

In some embodiments of compounds of Formula Ir, further to any of the above embodiments of Formula Ir, $Y_6$ is —N═ and $R^{144}$ is hydrogen. In some embodiments of compounds of Formula Ir, further to any of the above embodiments of Formula Ir, $Y_6$ is —C(H)═ and $R^{144}$ is fluoro.

In a nineteenth aspect, compounds of Formula I having the structure according to the following Formula Is are provided:

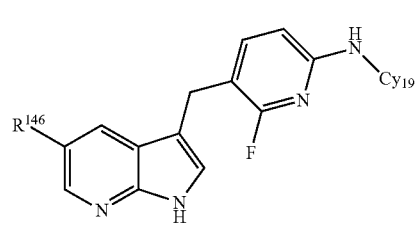

Formula Is or a salt, a prodrug, a solvate, a tautomer or a stereoisomer thereof,
wherein:
$Cy_{19}$ is cycloalkyl optionally substituted with one or more $R^{147}$;

$R^{146}$ is hydrogen, fluoro, chloro, or lower alkyl optionally substituted with one or more fluoro; and each $R^{147}$ is independently selected from the group consisting of fluoro, —OH, lower alkyl optionally substituted with one or more fluoro, and lower alkoxy optionally substituted with one or more fluoro.

In some embodiments of compounds of Formula Is, $R^{146}$ is hydrogen, chloro or lower alkyl. In one embodiment, $R^{146}$ is hydrogen, chloro or $C_{1-3}$ alkyl. In one embodiment, $R^{146}$ is hydrogen, chloro or methyl.

In some embodiments of compounds of Formula Is, further to any of the above embodiments of Formula Is, $Cy_{19}$ is cyclopentyl optionally substituted with 1 or 2 $R^{147}$, cyclohexyl optionally substituted with 1 or 2 $R^{147}$, or cycloheptyl optionally substituted with 1 or 2 $R^{147}$.

In some embodiments of compounds of Formula Is, further to any of the above embodiments of Formula Is, $Cy_{19}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Is, further to any of the above embodiments of Formula Is, $Cy_{19}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Is, further to any of the above embodiments of Formula Is, $Cy_{19}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Is, further to any of the above embodiments of Formula Is, $Cy_{19}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In a twentieth aspect, compounds of Formula I having the structure according to the following Formula It are provided:

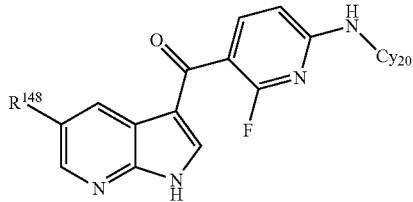

Formula It or a salt, a prodrug, a solvate, a tautomer or a stereoisomer thereof,
wherein:
$Cy_{20}$ is cycloalkyl optionally substituted with one or more $R^{149}$;
$R^{148}$ is hydrogen, fluoro, chloro, or lower alkyl optionally substituted with one or more fluoro; and
each $R^{149}$ is independently selected from the group consisting of fluoro, —OH, lower alkyl optionally substituted with one or more fluoro, and lower alkoxy optionally substituted with one or more fluoro.

In some embodiments of compounds of Formula It, $R^{148}$ is hydrogen, chloro or lower alkyl. In one embodiment, $R^{148}$ is hydrogen, chloro or $C_{1-3}$ alkyl. In one embodiment, $R^{148}$ is hydrogen, chloro or methyl.

In some embodiments of compounds of Formula It, further to any of the above embodiments of Formula It, $Cy_{20}$ is cyclopentyl optionally substituted with 1 or 2 $R^{149}$, cyclohexyl optionally substituted with 1 or 2 $R^{149}$, or cycloheptyl optionally substituted with 1 or 2 $R^{149}$.

In some embodiments of compounds of Formula It, further to any of the above embodiments of Formula It, $Cy_{20}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula It, further to any of the above embodiments of Formula It, $Cy_{20}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula It, further to any of the above embodiments of Formula It, $Cy_{20}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula It, further to any of the above embodiments of Formula It, $Cy_{20}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In a twenty-first aspect, compounds of Formula I having the structure according to the following Formula Iu are provided:

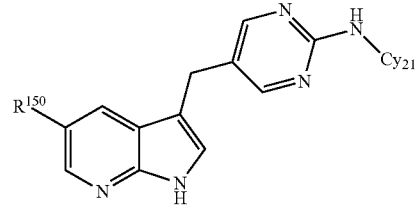

Formula Iu or a salt, a prodrug, a solvate, a tautomer or a stereoisomer thereof,
wherein:
$Cy_{21}$ is cycloalkyl optionally substituted with one or more $R^{151}$;
$R^{150}$ is hydrogen, fluoro, chloro, or lower alkyl optionally substituted with one or more fluoro; and
each $R^{151}$ is independently selected from the group consisting of fluoro, —OH, lower alkyl optionally substituted with one or more fluoro, and lower alkoxy optionally substituted with one or more fluoro.

In some embodiments of compounds of Formula Iu, $R^{150}$ is hydrogen, chloro or lower alkyl. In one embodiment, $R^{150}$ is hydrogen, chloro or $C_{1-3}$ alkyl. In one embodiment, $R^{150}$ is hydrogen, chloro or methyl.

In some embodiments of compounds of Formula Iu, further to any of the above embodiments of Formula Iu, $Cy_{21}$ is cyclopentyl optionally substituted with 1 or 2 $R^{151}$, cyclohexyl optionally substituted with 1 or 2 $R^{151}$, or cycloheptyl optionally substituted with 1 or 2 $R^{151}$.

In some embodiments of compounds of Formula Iu, further to any of the above embodiments of Formula Iu, $Cy_{21}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Iu, further to any of the above embodiments of Formula Iu, $Cy_{21}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Iu, further to any of the above embodiments of Formula Iu, $Cy_{21}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Iu, further to any of the above embodiments of Formula Iu, $Cy_{21}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In a twenty-second aspect, compounds of Formula I having the structure according to the following Formula Iv are provided:

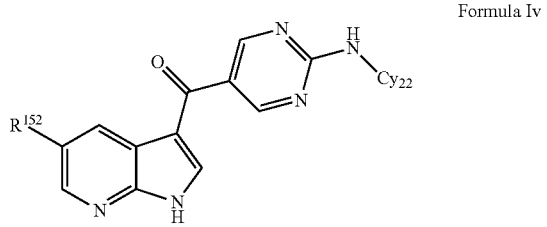

Formula Iv or a salt, a prodrug, a solvate, a tautomer or a stereoisomer thereof,
wherein:
$Cy_{22}$ is cycloalkyl optionally substituted with one or more $R^{153}$;
$R^{152}$ is hydrogen, fluoro, chloro, or lower alkyl optionally substituted with one or more fluoro; and
each $R^{153}$ is independently selected from the group consisting of fluoro, —OH, lower alkyl optionally substituted with one or more fluoro, and lower alkoxy optionally substituted with one or more fluoro.

In some embodiments of compounds of Formula Iv, $R^{152}$ is hydrogen, chloro or lower alkyl. In one embodiment, $R^{152}$ is hydrogen, chloro or $C_{1-3}$ alkyl. In one embodiment, $R^{152}$ is hydrogen, chloro or methyl.

In some embodiments of compounds of Formula Iv, further to any of the above embodiments of Formula Iv, $Cy_{22}$ is cyclopentyl optionally substituted with 1 or 2 $R^{153}$, cyclohexyl optionally substituted with 1 or 2 $R^{153}$, or cycloheptyl optionally substituted with 1 or 2 $R^{153}$.

In some embodiments of compounds of Formula Iv, further to any of the above embodiments of Formula Iv, $Cy_{22}$ is cyclopentyl optionally substituted with 1 or 2 fluoro, or 1 or 2 lower alkyl, or 1 or 2 —OH, or 1 or 2 lower alkoxy; cyclohexyl optionally substituted with 1 or 2 fluoro, or 1 or 2 lower alkyl, or 1 or 2 —OH, or 1 or 2 lower alkoxy; or cycloheptyl optionally substituted with 1 or 2 fluoro, or 1 or 2 lower alkyl, or 1 or 2 —OH, or 1 or 2 lower alkoxy.

In some embodiments of compounds of Formula Iv, further to any of the above embodiments of Formula Iv, $Cy_{22}$ is cyclopentyl, cyclopentyl substituted with 1 or 2 fluoro, cyclopentyl substituted with 1 or 2 lower alkyl, cyclopentyl substituted with 1 or 2 —OH, or cyclopentyl substituted with 1 or 2 lower alkoxy.

In some embodiments of compounds of Formula Iv, further to any of the above embodiments of Formula Iv, $Cy_{22}$ is cyclohexyl, cyclohexyl substituted with 1 or 2 fluoro, cyclohexyl substituted with 1 or 2 lower alkyl, cyclohexyl substituted with 1 or 2 —OH, or cyclohexyl substituted with 1 or 2 lower alkoxy.

In some embodiments of compounds of Formula Iv, further to any of the above embodiments of Formula Iv, $Cy_{22}$ is cycloheptyl, cycloheptyl substituted with 1 or 2 fluoro, cycloheptyl substituted with 1 or 2 lower alkyl, cycloheptyl substituted with 1 or 2 —OH, or cycloheptyl substituted with 1 or 2 lower alkoxy.

In a twenty-third aspect, compounds of Formula I having the structure according to the following Formula Iw are provided:

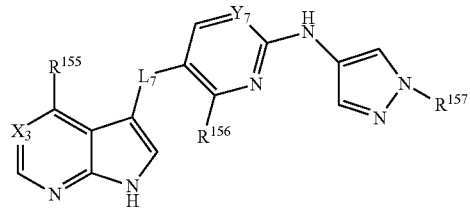

Formula Iw or a salt, a prodrug, a solvate, a tautomer or a stereoisomer thereof,
wherein:
$X_3$ is —N═, —C(H)═, or —C($R^{154}$)═;
$Y_7$ is —N═ and $R^{156}$ is hydrogen; or $Y_7$ is —C(H)═ and $R^{156}$ is fluoro;
$L_7$ is —C($H_2$)— or —C(O)—;
when $X_3$ is —C($R^{154}$)═, $R^{155}$ is hydrogen;
when $X_3$ is —N═ or —C(H)═, $R^{155}$ is selected from the group consisting of hydrogen, cycloalkyl, lower alkyl optionally substituted with one or more $R^{158}$, and —O—$R^{159}$;
$R^{154}$ is fluoro, chloro, or lower alkyl optionally substituted with one or more fluoro;
$R^{157}$ is cycloalkyl or lower alkyl optionally substituted with one or more fluoro;
$R^{158}$ is fluoro or lower alkoxy optionally substituted with one or more fluoro; and
$R^{159}$ is lower alkyl, lower alkyl substituted with one or more fluoro, or lower alkyl substituted with lower alkoxy.

In some embodiments of compounds of Formula Iw, $X_3$ is —N═ and $R^{155}$ is selected from the group consisting of hydrogen, cycloalkyl, lower alkyl optionally substituted with one or more $R^{158}$, and —O—$R^{159}$. In one embodiment, $X_3$ is —N═ and $R^{155}$ is selected from the group consisting of cycloalkyl, lower alkyl, lower alkoxy, and lower alkoxy substituted with lower alkoxy. In one embodiment, $X_3$ is —N═ and $R^{155}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $X_3$ is —N═ and $R^{155}$ is selected from the group consisting of methyl, cyclopropyl, methoxy, ethoxy, and 2-methoxy-ethoxy.

In some embodiments of compounds of Formula Iw, $X_3$ is —C(H)═ or —C($R^{154}$)═ and $R^{154}$ is fluoro, chloro, or lower alkyl optionally substituted with one or more fluoro. In one embodiment, $X_3$ is —C(H)═ or —C($R^{154}$)═ and $R^{154}$ is chloro or lower alkyl. In one embodiment, $X_3$ is —C(H)═ or —C($R^{154}$)═ and $R^{154}$ is chloro or $C_{1-3}$ alkyl. In one embodiment, $X_3$ is —C(H)═ or —C($R^{154}$)═ and $R^{154}$ is chloro or methyl.

In some embodiments of compounds of Formula Iw, further to any of the above embodiments of Formula Iw, $R^{157}$ is cycloalkyl or lower alkyl.

In some embodiments of compounds of Formula Iw, further to any of the above embodiments of Formula Iw, $R^{157}$ is $C_{3-6}$ cycloalkyl or lower alkyl.

In some embodiments of compounds of Formula Iw, further to any of the above embodiments of Formula Iw, $R^{157}$ is cyclopropyl or lower alkyl.

In some embodiments of compounds of Formula Iw, further to any of the above embodiments of Formula Iw, $R^{157}$ is lower alkyl.

In some embodiments of compounds of Formula Iw, further to any of the above embodiments of Formula Iw, $R^{157}$ is $C_{1-3}$ alkyl.

In some embodiments of compounds of Formula Iw, further to any of the above embodiments of Formula Iw, $R^{157}$ is ethyl.

In some embodiments of compounds of Formula Iw, further to any of the above embodiments of Formula Iw, $L_7$ is —C($H_2$)—. In some embodiments of compounds of Formula Iw, further to any of the above embodiments of Formula Iw, $L_7$ is —C(O)—.

In some embodiments of compounds of Formula Iw, further to any of the above embodiments of Formula Iw, $Y_7$ is —N═ and $R^{156}$ is hydrogen. In some embodiments of compounds of Formula Iw, further to any of the above embodiments of Formula Iw, $Y_7$ is —C(H)═ and $R^{156}$ is fluoro.

In a twenty-fourth aspect, compounds of Formula I having the structure according to the following Formula Ix are provided:

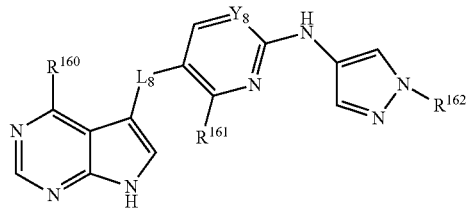

Formula Ix or a salt, a prodrug, a solvate, a tautomer or a stereoisomer thereof,
wherein:
$Y_8$ is —N═ and $R^{161}$ is hydrogen; or $Y_8$ is —C(H)═ and $R^{161}$ is fluoro;
$L_8$ is —C($H_2$)— or —C(O)—;

$R^{160}$ is selected from the group consisting of hydrogen, cycloalkyl, lower alkyl optionally substituted with one or more $R^{163}$, and —O—$R^{164}$;
$R^{162}$ is cycloalkyl or lower alkyl optionally substituted with one or more fluoro;
$R^{163}$ is fluoro or lower alkoxy optionally substituted with one or more fluoro; and
$R^{164}$ is lower alkyl, lower alkyl substituted with one or more fluoro, or lower alkyl substituted with lower alkoxy.

In some embodiments of compounds of Formula Ix, $R^{160}$ is selected from the group consisting of cycloalkyl, lower alkyl, lower alkoxy, and lower alkoxy substituted with lower alkoxy. In one embodiment, $R^{160}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{160}$ is selected from the group consisting of methyl, cyclopropyl, methoxy, ethoxy, and 2-methoxy-ethoxy.

In some embodiments of compounds of Formula Ix, further to any of the above embodiments of Formula Ix, $R^{162}$ is cycloalkyl or lower alkyl.

In some embodiments of compounds of Formula Ix, further to any of the above embodiments of Formula Ix, $R^{162}$ is $C_{3-6}$ cycloalkyl or lower alkyl.

In some embodiments of compounds of Formula Ix, further to any of the above embodiments of Formula Ix, $R^{162}$ is cyclopropyl or lower alkyl.

In some embodiments of compounds of Formula Ix, further to any of the above embodiments of Formula Ix, $R^{162}$ is lower alkyl.

In some embodiments of compounds of Formula Ix, further to any of the above embodiments of Formula Ix, $R^{162}$ is $C_{1-3}$ alkyl.

In some embodiments of compounds of Formula Ix, further to any of the above embodiments of Formula Ix, $R^{162}$ is ethyl.

In some embodiments of compounds of Formula Ix, further to any of the above embodiments of Formula Ix, $L_g$ is —C($H_2$)—. In some embodiments of compounds of Formula Ix, further to any of the above embodiments of Formula Ix, $L_g$ is —C(O)—.

In some embodiments of compounds of Formula Ix, further to any of the above embodiments of Formula Ix, $Y_8$ is —N═ and $R^{161}$ is hydrogen. In some embodiments of compounds of Formula Ix, further to any of the above embodiments of Formula Ix, $Y_8$ is —C(H)═ and $R^{161}$ is fluoro.

In a twenty-fifth aspect, compounds of Formula I having the structure according to the following Formula Iy are provided:

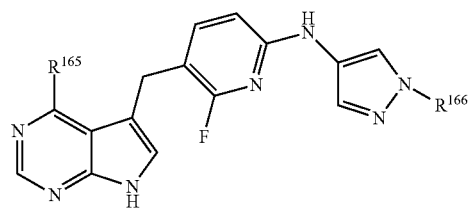

Formula Iy or a salt, a prodrug, a solvate, a tautomer or a stereoisomer thereof,
wherein:
$R^{165}$ is selected from the group consisting of hydrogen, cycloalkyl, lower alkyl optionally substituted with one or more $R^{167}$, and —O—$R^{168}$;

$R^{166}$ is cycloalkyl or lower alkyl optionally substituted with one or more fluoro;

$R^{167}$ is fluoro or lower alkoxy optionally substituted with one or more fluoro; and $R^{168}$ is lower alkyl, lower alkyl substituted with one or more fluoro, or lower alkyl substituted with lower alkoxy.

In some embodiments of compounds of Formula Iy, $R^{165}$ is selected from the group consisting of cycloalkyl, lower alkyl, lower alkoxy, and lower alkoxy substituted with lower alkoxy. In one embodiment, $R^{165}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{165}$ is selected from the group consisting of methyl, cyclopropyl, methoxy, ethoxy, and 2-methoxy-ethoxy.

In some embodiments of compounds of Formula Iy, further to any of the above embodiments of Formula Iy, $R^{166}$ is cycloalkyl or lower alkyl.

In some embodiments of compounds of Formula Iy, further to any of the above embodiments of Formula Iy, $R^{166}$ is $C_{3-6}$ cycloalkyl or lower alkyl.

In some embodiments of compounds of Formula Iy, further to any of the above embodiments of Formula Iy, $R^{166}$ is cyclopropyl or lower alkyl.

In some embodiments of compounds of Formula Iy, further to any of the above embodiments of Formula Iy, $R^{166}$ is lower alkyl.

In some embodiments of compounds of Formula Iy, further to any of the above embodiments of Formula Iy, $R^{166}$ is $C_{1-3}$ alkyl.

In some embodiments of compounds of Formula Iy, further to any of the above embodiments of Formula Iy, $R^{166}$ is ethyl.

In a twenty-sixth aspect, compounds of Formula I having the structure according to the following Formula Iz are provided:

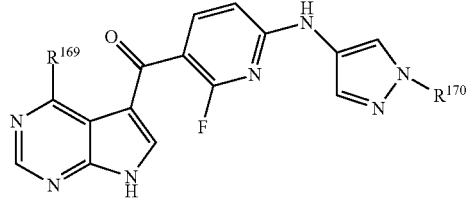

Formula Iz or a salt, a prodrug, a solvate, a tautomer or a stereoisomer thereof, wherein:

$R^{169}$ is selected from the group consisting of hydrogen, cycloalkyl, lower alkyl optionally substituted with one or more $R^{171}$, and —O—$R^{172}$;

$R^{170}$ is cycloalkyl or lower alkyl optionally substituted with one or more fluoro;

$R^{171}$ is fluoro or lower alkoxy optionally substituted with one or more fluoro; and $R^{172}$ is lower alkyl, lower alkyl substituted with one or more fluoro, or lower alkyl substituted with lower alkoxy.

In some embodiments of compounds of Formula Iz, $R^{169}$ is selected from the group consisting of cycloalkyl, lower alkyl, lower alkoxy, and lower alkoxy substituted with lower alkoxy. In one embodiment, $R^{169}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{169}$ is selected from the group consisting of methyl, cyclopropyl, methoxy, ethoxy, and 2-methoxy-ethoxy.

In some embodiments of compounds of Formula Iz, further to any of the above embodiments of Formula Iz, $R^{170}$ is cycloalkyl or lower alkyl.

In some embodiments of compounds of Formula Iz, further to any of the above embodiments of Formula Iz, $R^{170}$ is $C_{3-6}$ cycloalkyl or lower alkyl.

In some embodiments of compounds of Formula Iz, further to any of the above embodiments of Formula Iz, $R^{170}$ is cyclopropyl or lower alkyl.

In some embodiments of compounds of Formula Iz, further to any of the above embodiments of Formula Iz, $R^{170}$ is lower alkyl.

In some embodiments of compounds of Formula Iz, further to any of the above embodiments of Formula Iz, $R^{170}$ is $C_{1-3}$ alkyl.

In some embodiments of compounds of Formula Iz, further to any of the above embodiments of Formula Iz, $R^{170}$ is ethyl.

In a twenty-seventh aspect, compounds of Formula I having the structure according to the following Formula Iaa are provided:

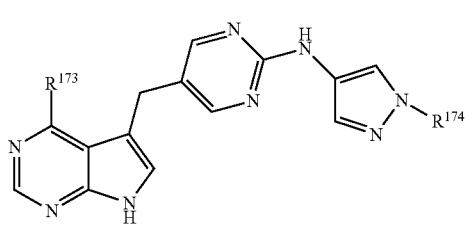

Formula Iaa or a salt, a prodrug, a solvate, a tautomer or a stereoisomer thereof, wherein:

$R^{173}$ is selected from the group consisting of hydrogen, cycloalkyl, lower alkyl optionally substituted with one or more $R^{175}$, and —O—$R^{176}$;

$R^{174}$ is cycloalkyl or lower alkyl optionally substituted with one or more fluoro;

$R^{175}$ is fluoro or lower alkoxy optionally substituted with one or more fluoro; and $R^{176}$ is lower alkyl, lower alkyl substituted with one or more fluoro, or lower alkyl substituted with lower alkoxy.

In some embodiments of compounds of Formula Iaa, $R^{173}$ is selected from the group consisting of cycloalkyl, lower alkyl, lower alkoxy, and lower alkoxy substituted with lower alkoxy. In one embodiment, $R^{173}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{173}$ is selected from the group consisting of methyl, cyclopropyl, methoxy, ethoxy, and 2-methoxy-ethoxy.

In some embodiments of compounds of Formula Iaa, further to any of the above embodiments of Formula Iaa, $R^{174}$ is cycloalkyl or lower alkyl.

In some embodiments of compounds of Formula Iaa, further to any of the above embodiments of Formula Iaa, $R^{174}$ is $C_{3-6}$ cycloalkyl or lower alkyl.

In some embodiments of compounds of Formula Iaa, further to any of the above embodiments of Formula Iaa, $R^{174}$ is cyclopropyl or lower alkyl.

In some embodiments of compounds of Formula Iaa, further to any of the above embodiments of Formula Iaa, $R^{174}$ is lower alkyl.

In some embodiments of compounds of Formula Iaa, further to any of the above embodiments of Formula Iaa, $R^{174}$ is $C_{1-3}$ alkyl.

In some embodiments of compounds of Formula Iaa, further to any of the above embodiments of Formula Iaa, $R^{174}$ is ethyl.

In a twenty-eighth aspect, compounds of Formula I having the structure according to the following Formula Ibb are provided:

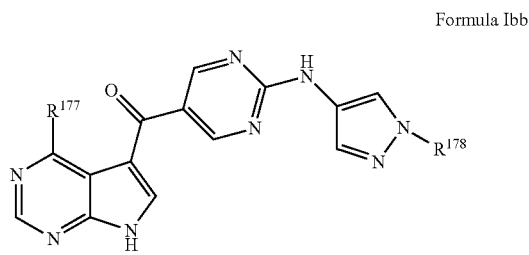

Formula Ibb or a salt, a prodrug, a solvate, a tautomer or a stereoisomer thereof,
wherein:
$R^{177}$ is selected from the group consisting of hydrogen, cycloalkyl, lower alkyl optionally substituted with one or more $R^{179}$, and —O—$R^{180}$;
$R^{178}$ is cycloalkyl or lower alkyl optionally substituted with one or more fluoro;
$R^{179}$ is fluoro or lower alkoxy optionally substituted with one or more fluoro; and
$R^{180}$ is lower alkyl, lower alkyl substituted with one or more fluoro, or lower alkyl substituted with lower alkoxy.

In some embodiments of compounds of Formula Ibb, $R^{177}$ is selected from the group consisting of cycloalkyl, lower alkyl, lower alkoxy, and lower alkoxy substituted with lower alkoxy. In one embodiment, $R^{177}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{177}$ is selected from the group consisting of methyl, cyclopropyl, methoxy, ethoxy, and 2-methoxy-ethoxy.

In some embodiments of compounds of Formula Ibb, further to any of the above embodiments of Formula Ibb, $R^{178}$ is cycloalkyl or lower alkyl.

In some embodiments of compounds of Formula Ibb, further to any of the above embodiments of Formula Ibb, $R^{178}$ is $C_{3-6}$ cycloalkyl or lower alkyl.

In some embodiments of compounds of Formula Ibb, further to any of the above embodiments of Formula Ibb, $R^{178}$ is cyclopropyl or lower alkyl.

In some embodiments of compounds of Formula Ibb, further to any of the above embodiments of Formula Ibb, $R^{178}$ is lower alkyl.

In some embodiments of compounds of Formula Ibb, further to any of the above embodiments of Formula Ibb, $R^{178}$ is $C_{1-3}$ alkyl.

In some embodiments of compounds of Formula Ibb, further to any of the above embodiments of Formula Ibb, $R^{178}$ is ethyl.

In a twenty-ninth aspect, compounds of Formula I having the structure according to the following Formula Icc are provided:

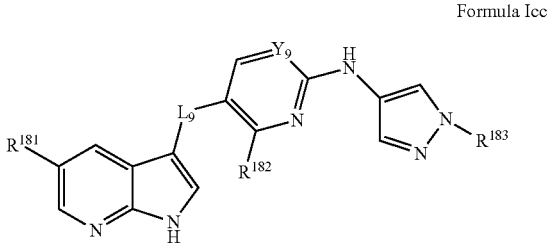

Formula Icc or a salt, a prodrug, a solvate, a tautomer or a stereoisomer thereof,
wherein:
$Y_9$ is —N= and $R^{182}$ is hydrogen; or $Y_9$ is —C(H)= and $R^{182}$ is fluoro;
$L_9$ is —C($H_2$)— or —C(O)—;
$R^{181}$ is hydrogen, fluoro, chloro, or lower alkyl optionally substituted with one or more fluoro; and
$R^{183}$ is cycloalkyl or lower alkyl optionally substituted with one or more fluoro.

In some embodiments of compounds of Formula Icc, $R^{181}$ is hydrogen, chloro or lower alkyl. In one embodiment, $R^{181}$ is hydrogen, chloro or $C_{1-3}$ alkyl. In one embodiment, $R^{181}$ is hydrogen, chloro or methyl.

In some embodiments of compounds of Formula Icc, further to any of the above embodiments of Formula Icc, $R^{183}$ is cycloalkyl or lower alkyl.

In some embodiments of compounds of Formula Icc, further to any of the above embodiments of Formula Icc, $R^{183}$ is $C_{3-6}$ cycloalkyl or lower alkyl.

In some embodiments of compounds of Formula Icc, further to any of the above embodiments of Formula Icc, $R^{183}$ is cyclopropyl or lower alkyl.

In some embodiments of compounds of Formula Icc, further to any of the above embodiments of Formula Icc, $R^{183}$ is lower alkyl.

In some embodiments of compounds of Formula Icc, further to any of the above embodiments of Formula Icc, $R^{183}$ is $C_{1-3}$ alkyl.

In some embodiments of compounds of Formula Icc, further to any of the above embodiments of Formula Icc, $R^{183}$ is ethyl.

In some embodiments of compounds of Formula Icc, further to any of the above embodiments of Formula Icc, $L_9$ is —C($H_2$)—. In some embodiments of compounds of Formula Icc, further to any of the above embodiments of Formula Icc, $L_9$ is —C(O)—.

In some embodiments of compounds of Formula Icc, further to any of the above embodiments of Formula Icc, $Y_9$ is —N= and $R^{182}$ is hydrogen. In some embodiments of compounds of Formula Icc, further to any of the above embodiments of Formula Icc, $Y_9$ is —C(H)= and $R^{182}$ is fluoro.

In a thirtieth aspect, compounds of Formula I having the structure according to the following Formula Idd are provided:

Formula Idd

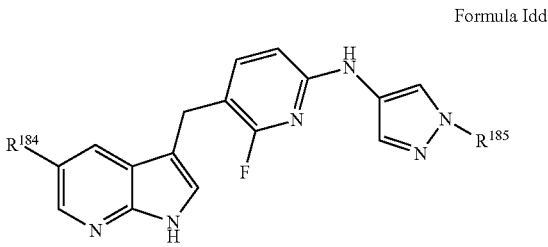

or a salt, a prodrug, a solvate, a tautomer or a stereoisomer thereof,
wherein:
$R^{184}$ is hydrogen, fluoro, chloro, or lower alkyl optionally substituted with one or more fluoro; and
$R^{185}$ is cycloalkyl or lower alkyl optionally substituted with one or more fluoro.

In some embodiments of compounds of Formula Idd, $R^{184}$ is hydrogen, chloro or lower alkyl. In one embodiment, $R^{184}$ is hydrogen, chloro or $C_{1-3}$ alkyl. In one embodiment, $R^{184}$ is hydrogen, chloro or methyl.

In some embodiments of compounds of Formula Idd, further to any of the above embodiments of Formula Idd, $R^{185}$ is cycloalkyl or lower alkyl.

In some embodiments of compounds of Formula Idd, further to any of the above embodiments of Formula Idd, $R^{185}$ is $C_{3-6}$ cycloalkyl or lower alkyl.

In some embodiments of compounds of Formula Idd, further to any of the above embodiments of Formula Idd, $R^{185}$ is cyclopropyl or lower alkyl.

In some embodiments of compounds of Formula Idd, further to any of the above embodiments of Formula Idd, $R^{185}$ is lower alkyl.

In some embodiments of compounds of Formula Idd, further to any of the above embodiments of Formula Idd, $R^{185}$ is $C_{1-3}$ alkyl.

In some embodiments of compounds of Formula Idd, further to any of the above embodiments of Formula Idd, $R^{185}$ is ethyl.

In a thirty-first aspect, compounds of Formula I having the structure according to the following Formula Iee are provided:

Formula Iee

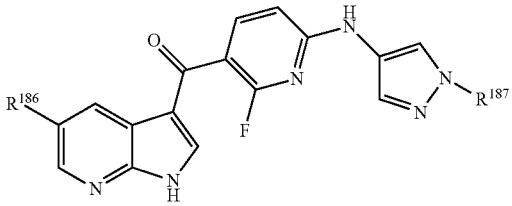

or a salt, a prodrug, a solvate, a tautomer or a stereoisomer thereof,
wherein:
$R^{186}$ is hydrogen, fluoro, chloro, or lower alkyl optionally substituted with one or more fluoro; and
$R^{187}$ is cycloalkyl or lower alkyl optionally substituted with one or more fluoro.

In some embodiments of compounds of Formula Iee, $R^{186}$ is hydrogen, chloro or lower alkyl. In one embodiment, $R^{186}$ is hydrogen, chloro or $C_{1-3}$ alkyl. In one embodiment, $R^{186}$ is hydrogen, chloro or methyl.

In some embodiments of compounds of Formula Iee, further to any of the above embodiments of Formula Iee, $R^{187}$ is cycloalkyl or lower alkyl.

In some embodiments of compounds of Formula Iee, further to any of the above embodiments of Formula Iee, $R^{187}$ is $C_{3-6}$ cycloalkyl or lower alkyl.

In some embodiments of compounds of Formula Iee, further to any of the above embodiments of Formula Iee, $R^{187}$ is cyclopropyl or lower alkyl.

In some embodiments of compounds of Formula Iee, further to any of the above embodiments of Formula Iee, $R^{187}$ is lower alkyl.

In some embodiments of compounds of Formula Iee, further to any of the above embodiments of Formula Iee, $R^{187}$ is $C_{1-3}$ alkyl.

In some embodiments of compounds of Formula Iee, further to any of the above embodiments of Formula Iee, $R^{187}$ is ethyl.

In a thirty-second aspect, compounds of Formula I having the structure according to the following Formula Iff are provided:

Formula Iff

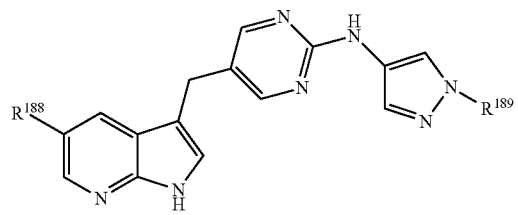

or a salt, a prodrug, a solvate, a tautomer or a stereoisomer thereof,
wherein:
$R^{188}$ is hydrogen, fluoro, chloro, or lower alkyl optionally substituted with one or more fluoro; and
$R^{189}$ is cycloalkyl or lower alkyl optionally substituted with one or more fluoro.

In some embodiments of compounds of Formula Iff, $R^{188}$ is hydrogen, chloro or lower alkyl. In one embodiment, $R^{188}$ is hydrogen, chloro or $C_{1-3}$ alkyl. In one embodiment, $R^{188}$ is hydrogen, chloro or methyl.

In some embodiments of compounds of Formula Iff, further to any of the above embodiments of Formula Iff, $R^{189}$ is cycloalkyl or lower alkyl.

In some embodiments of compounds of Formula Iff, further to any of the above embodiments of Formula Iff, $R^{189}$ is $C_{3-6}$ cycloalkyl or lower alkyl.

In some embodiments of compounds of Formula Iff, further to any of the above embodiments of Formula Iff, $R^{189}$ is cyclopropyl or lower alkyl.

In some embodiments of compounds of Formula Iff, further to any of the above embodiments of Formula Iff, $R^{189}$ is lower alkyl.

In some embodiments of compounds of Formula Iff, further to any of the above embodiments of Formula Iff, $R^{189}$ is $C_{1-3}$ alkyl.

In some embodiments of compounds of Formula Iff, further to any of the above embodiments of Formula Iff, $R^{189}$ is ethyl.

In a thirty-third aspect, compounds of Formula I having the structure according to the following Formula Igg are provided:

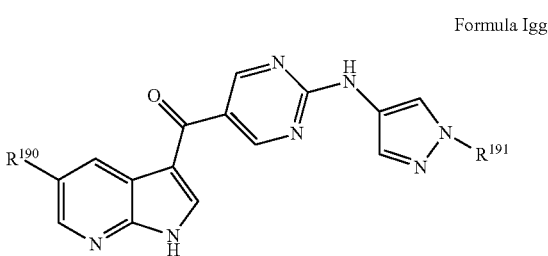

Formula Igg or a salt, a prodrug, a solvate, a tautomer or a stereoisomer thereof,
wherein:
$R^{190}$ is hydrogen, fluoro, chloro, or lower alkyl optionally substituted with one or more fluoro; and
$R^{191}$ is cycloalkyl or lower alkyl optionally substituted with one or more fluoro.

In some embodiments of compounds of Formula Igg, $R^{190}$ is hydrogen, chloro or lower alkyl. In one embodiment, $R^{190}$ is hydrogen, chloro or $C_{1-3}$ alkyl. In one embodiment, $R^{190}$ is hydrogen, chloro or methyl.

In some embodiments of compounds of Formula Igg, further to any of the above embodiments of Formula Igg, $R^{191}$ is cycloalkyl or lower alkyl.

In some embodiments of compounds of Formula Igg, further to any of the above embodiments of Formula Igg, $R^{191}$ is $C_{3-6}$ cycloalkyl or lower alkyl.

In some embodiments of compounds of Formula Igg, further to any of the above embodiments of Formula Igg, $R^{191}$ is cyclopropyl or lower alkyl.

In some embodiments of compounds of Formula Igg, further to any of the above embodiments of Formula Igg, $R^{191}$ is lower alkyl.

In some embodiments of compounds of Formula Igg, further to any of the above embodiments of Formula Igg, $R^{191}$ is $C_{1-3}$ alkyl.

In some embodiments of compounds of Formula Igg, further to any of the above embodiments of Formula Igg, $R^{191}$ is ethyl.

In a thirty-fourth aspect, compounds of Formula I having the structure according to the following Formula Ihh are provided:

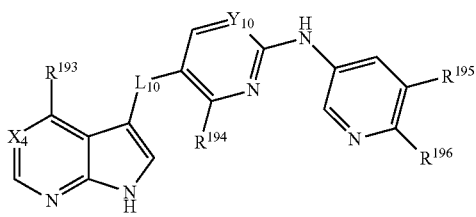

Formula Ihh or a salt, a prodrug, a solvate, a tautomer or a stereoisomer thereof,
wherein:
$X_4$ is —N=, —C(H)=, or —C($R^{192}$)=;
$Y_{10}$ is —N= and $R^{194}$ is hydrogen; or $Y_{10}$ is —C(H)= and $R^{194}$ is fluoro;
$L_{10}$ is —C(H$_2$)— or —C(O)—;
when $X_4$ is —C($R^{192}$)=, $R^{193}$ is hydrogen;
when $X_4$ is —N= or —C(H)=, $R^{193}$ is selected from the group consisting of hydrogen, cycloalkyl, lower alkyl optionally substituted with one or more $R^{197}$, and —O—$R^{198}$;

$R^{192}$ is fluoro, chloro, or lower alkyl optionally substituted with one or more fluoro;
$R^{195}$ is hydrogen and $R^{196}$ is hydrogen, fluoro, chloro, bromo, cycloalkyl, lower alkyl optionally substituted with one or more fluoro, or lower alkoxy optionally substituted with one or more fluoro; or
$R^{196}$ is hydrogen and $R^{195}$ is fluoro, chloro, bromo, cycloalkyl, lower alkyl optionally substituted with one or more fluoro, or lower alkoxy optionally substituted with one or more fluoro;
$R^{197}$ is fluoro or lower alkoxy optionally substituted with one or more fluoro; and
$R^{198}$ is lower alkyl, lower alkyl substituted with one or more fluoro, or lower alkyl substituted with lower alkoxy.

In some embodiments of compounds of Formula Ihh, $X_4$ is —N= and $R^{193}$ is selected from the group consisting of hydrogen, cycloalkyl, lower alkyl optionally substituted with one or more $R^{197}$, and —O—$R^{198}$. In one embodiment, $X_4$ is —N= and $R^{193}$ is selected from the group consisting of cycloalkyl, lower alkyl, lower alkoxy, and lower alkoxy substituted with lower alkoxy. In one embodiment, $X_4$ is —N= and $R^{193}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $X_4$ is —N= and $R^{193}$ is selected from the group consisting of methyl, cyclopropyl, methoxy, ethoxy, and 2-methoxy-ethoxy.

In some embodiments of compounds of Formula Ihh, $X_4$ is —C(H)= or —C($R^{192}$)= and $R^{192}$ is fluoro, chloro, or lower alkyl optionally substituted with one or more fluoro. In one embodiment, $X_4$ is —C(H)= or —C($R^{192}$)= and $R^{192}$ is chloro or lower alkyl. In one embodiment, $X_4$ is —C(H)= or —C($R^{192}$)= and $R^{192}$ is chloro or $C_{1-3}$ alkyl. In one embodiment, $X_4$ is —C(H)= or —C($R^{192}$)= and $R^{192}$ is chloro or methyl.

In some embodiments of compounds of Formula Ihh, further to any of the above embodiments of Formula Ihh, $R^{196}$ is hydrogen and $R^{195}$ is fluoro, chloro, bromo, cycloalkyl, lower alkyl optionally substituted with one or more fluoro, or lower alkoxy optionally substituted with one or more fluoro. In some embodiments of compounds of Formula Ihh, further to any of the above embodiments of Formula Ihh, $R^{196}$ is hydrogen and $R^{195}$ is lower alkyl optionally substituted with one or more fluoro. In some embodiments of compounds of Formula Ihh, further to any of the above embodiments of Formula Ihh, $R^{196}$ is hydrogen and $R^{195}$ is lower alkyl. In some embodiments of compounds of Formula Ihh, further to any of the above embodiments of Formula Ihh, $R^{196}$ is hydrogen and $R^{195}$ is $C_{1-3}$ alkyl. In some embodiments of compounds of Formula Ihh, further to any of the above embodiments of Formula Ihh, $R^{196}$ is hydrogen and $R^{195}$ is methyl.

In some embodiments of compounds of Formula Ihh, further to any of the above embodiments of Formula Ihh, $R^{195}$ is hydrogen and $R^{196}$ is fluoro, chloro, bromo, cycloalkyl, lower alkyl optionally substituted with one or more fluoro, or lower alkoxy optionally substituted with one or more fluoro. In some embodiments of compounds of Formula Ihh, further to any of the above embodiments of Formula Ihh, $R^{195}$ is hydrogen and $R^{196}$ is fluoro, chloro, bromo. In some embodiments of compounds of Formula Ihh, further to any of the above embodiments of Formula Ihh, $R^{195}$ is hydrogen and $R^{196}$ is cycloalkyl, lower alkyl optionally substituted with one or more fluoro, or lower alkoxy optionally substituted with one or more fluoro.

In some embodiments of compounds of Formula Ihh, further to any of the above embodiments of Formula Ihh, $R^{195}$ is hydrogen and $R^{196}$ is cycloalkyl or lower alkyl optionally substituted with one or more fluoro. In some embodiments of compounds of Formula Ihh, further to any of the above embodiments of Formula Ihh, $R^{195}$ is hydrogen and $R^{196}$ is cycloalkyl or $C_{1-3}$ alkyl optionally substituted with 1, 2, or 3 fluoro. In some embodiments of compounds of Formula Ihh, further to any of the above embodiments of Formula Ihh, $R^{195}$ is hydrogen and $R^{196}$ is cyclopropyl or $C_{1-3}$ alkyl optionally substituted with 1, 2, or 3 fluoro. In some embodiments of compounds of Formula Ihh, further to any of the above embodiments of Formula Ihh, $R^{195}$ is hydrogen and $R^{196}$ is cyclopropyl, trifluoromethyl, methyl or ethyl.

In some embodiments of compounds of Formula Ihh, further to any of the above embodiments of Formula Ihh, $R^{195}$ is hydrogen and $R^{196}$ is cycloalkyl. In some embodiments of compounds of Formula Ihh, further to any of the above embodiments of Formula Ihh, $R^{195}$ is hydrogen and $R^{196}$ is cyclopropyl.

In some embodiments of compounds of Formula Ihh, further to any of the above embodiments of Formula Ihh, $R^{195}$ is hydrogen and $R^{196}$ is lower alkyl optionally substituted with one or more fluoro. In some embodiments of compounds of Formula Ihh, further to any of the above embodiments of Formula Ihh, $R^{195}$ is hydrogen and $R^{196}$ is $C_{1-3}$ alkyl optionally substituted with 1, 2, or 3 fluoro. In some embodiments of compounds of Formula Ihh, further to any of the above embodiments of Formula Ihh, $R^{195}$ is hydrogen and $R^{196}$ is trifluoromethyl, methyl or ethyl. In some embodiments of compounds of Formula Ihh, further to any of the above embodiments of Formula Ihh, $R^{195}$ is hydrogen and $R^{196}$ is trifluoromethyl. In some embodiments of compounds of Formula Ihh, further to any of the above embodiments of Formula Ihh, $R^{195}$ is hydrogen and $R^{196}$ is methyl. In some embodiments of compounds of Formula Ihh, further to any of the above embodiments of Formula Ihh, $R^{195}$ is hydrogen and $R^{196}$ is ethyl.

In some embodiments of compounds of Formula Ihh, further to any of the above embodiments of Formula Ihh, $R^{195}$ is hydrogen and $R^{196}$ is lower alkoxy optionally substituted with one or more fluoro. In some embodiments of compounds of Formula Ihh, further to any of the above embodiments of Formula Ihh, $R^{195}$ is hydrogen and $R^{196}$ is lower alkoxy. In some embodiments of compounds of Formula Ihh, further to any of the above embodiments of Formula Ihh, $R^{195}$ is hydrogen and $R^{196}$ is $C_{1-3}$ alkoxy. In some embodiments of compounds of Formula Ihh, further to any of the above embodiments of Formula Ihh, $R^{195}$ is hydrogen and $R^{196}$ is methoxy or ethoxy. In some embodiments of compounds of Formula Ihh, further to any of the above embodiments of Formula Ihh, $R^{195}$ is hydrogen and $R^{196}$ is methoxy. In some embodiments of compounds of Formula Ihh, further to any of the above embodiments of Formula Ihh, $R^{195}$ is hydrogen and $R^{196}$ is ethoxy.

In some embodiments of compounds of Formula Ihh, further to any of the above embodiments of Formula Ihh, $L_{10}$ is —C($H_2$)—. In some embodiments of compounds of Formula Ihh, further to any of the above embodiments of Formula Ihh, $L_{10}$ is —C(O)—.

In some embodiments of compounds of Formula Ihh, further to any of the above embodiments of Formula Ihh, $Y_{10}$ is —N= and $R^{194}$ is hydrogen. In some embodiments of compounds of Formula Ihh, further to any of the above embodiments of Formula Ihh, $Y_{10}$ is —C(H)= and $R^{194}$ is fluoro.

In a thirty-fifth aspect, compounds of Formula I having the structure according to the following Formula Iii are provided:

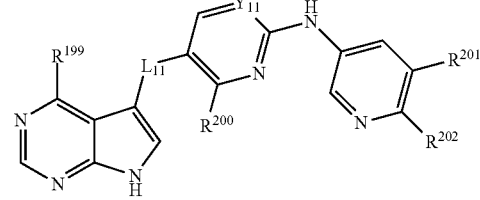

Formula Iii or a salt, a prodrug, a solvate, a tautomer or a stereoisomer thereof, wherein:
$Y_{11}$ is —N= and $R^{200}$ is hydrogen; or $Y_{11}$ is —C(H)= and $R^{200}$ is fluoro;
$L_{11}$ is —C($H_2$)— or —C(O)—;
$R^{199}$ is selected from the group consisting of hydrogen, cycloalkyl, lower alkyl optionally substituted with one or more $R^{203}$, and —O—$R^{204}$;
$R^{201}$ is hydrogen and $R^{202}$ is hydrogen, fluoro, chloro, bromo, cycloalkyl, lower alkyl optionally substituted with one or more fluoro, or lower alkoxy optionally substituted with one or more fluoro; or
$R^{202}$ is hydrogen and $R^{201}$ is fluoro, chloro, bromo, cycloalkyl, lower alkyl optionally substituted with one or more fluoro, or lower alkoxy optionally substituted with one or more fluoro;
$R^{203}$ is fluoro or lower alkoxy optionally substituted with one or more fluoro; and
$R^{204}$ is lower alkyl, lower alkyl substituted with one or more fluoro, or lower alkyl substituted with lower alkoxy.

In some embodiments of compounds of Formula Iii, $R^{199}$ is selected from the group consisting of cycloalkyl, lower alkyl, lower alkoxy, and lower alkoxy substituted with lower alkoxy. In one embodiment, $R^{199}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{199}$ is selected from the group consisting of methyl, cyclopropyl, methoxy, ethoxy, and 2-methoxy-ethoxy.

In some embodiments of compounds of Formula Iii, further to any of the above embodiments of Formula Iii, $R^{202}$ is hydrogen and $R^{201}$ is fluoro, chloro, bromo, cycloalkyl, lower alkyl optionally substituted with one or more fluoro, or lower alkoxy optionally substituted with one or more fluoro. In some embodiments of compounds of Formula Iii, further to any of the above embodiments of Formula Iii, $R^{202}$ is hydrogen and $R^{201}$ is lower alkyl optionally substituted with one or more fluoro. In some embodiments of compounds of Formula Iii, further to any of the above embodiments of Formula Iii, $R^{202}$ is hydrogen and $R^{201}$ is lower alkyl. In some embodiments of compounds of Formula Iii, further to any of the above embodiments of Formula Iii, $R^{202}$ is hydrogen and $R^{201}$ is $C_{1-3}$ alkyl. In some embodiments of compounds of Formula Iii, further to any of the above embodiments of Formula Iii, $R^{202}$ is hydrogen and $R^{201}$ is methyl.

In some embodiments of compounds of Formula Iii, further to any of the above embodiments of Formula Iii, $R^{201}$ is hydrogen and $R^{202}$ is fluoro, chloro, bromo, cycloalkyl, lower alkyl optionally substituted with one or more fluoro, or lower alkoxy optionally substituted with one or more fluoro. In some embodiments of compounds of Formula Iii, further to any of the above embodiments of Formula Iii, $R^{201}$ is hydrogen and $R^{202}$ is fluoro, chloro, bromo. In some embodiments of compounds of Formula Iii, further to any of the above embodiments of Formula Iii, $R^{201}$ is hydrogen and $R^{202}$ is cycloalkyl, lower alkyl optionally substituted with one or more fluoro, or lower alkoxy optionally substituted with one or more fluoro.

In some embodiments of compounds of Formula Iii, further to any of the above embodiments of Formula Iii, $R^{201}$ is hydrogen and $R^{202}$ is cycloalkyl or lower alkyl optionally substituted with one or more fluoro. In some embodiments of compounds of Formula Iii, further to any of the above embodiments of Formula Iii, $R^{201}$ is hydrogen and $R^{202}$ is cycloalkyl or $C_{1-3}$ alkyl optionally substituted with 1, 2, or 3 fluoro. In some embodiments of compounds of Formula Iii, further to any of the above embodiments of Formula Iii, $R^{201}$ is hydrogen and $R^{202}$ is cyclopropyl or $C_{1-3}$ alkyl optionally substituted with 1, 2, or 3 fluoro. In some embodiments of compounds of Formula Iii, further to any of the above embodiments of Formula Iii, $R^{201}$ is hydrogen and $R^{202}$ is cyclopropyl, trifluoromethyl, methyl or ethyl.

In some embodiments of compounds of Formula Iii, further to any of the above embodiments of Formula Iii, $R^{201}$ is hydrogen and $R^{202}$ is cycloalkyl. In some embodiments of compounds of Formula Iii, further to any of the above embodiments of Formula Iii, $R^{201}$ is hydrogen and $R^{202}$ is cyclopropyl.

In some embodiments of compounds of Formula Iii, further to any of the above embodiments of Formula Iii, $R^{201}$ is hydrogen and $R^{202}$ is lower alkyl optionally substituted with one or more fluoro. In some embodiments of compounds of Formula Iii, further to any of the above embodiments of Formula Iii, $R^{201}$ is hydrogen and $R^{202}$ is $C_{1-3}$ alkyl optionally substituted with 1, 2, or 3 fluoro. In some embodiments of compounds of Formula Iii, further to any of the above embodiments of Formula Iii, $R^{201}$ is hydrogen and $R^{202}$ is trifluoromethyl, methyl or ethyl. In some embodiments of compounds of Formula Iii, further to any of the above embodiments of Formula Iii, $R^{201}$ is hydrogen and $R^{202}$ is trifluoromethyl. In some embodiments of compounds of Formula Iii, further to any of the above embodiments of Formula Iii, $R^{201}$ is hydrogen and $R^{202}$ is methyl. In some embodiments of compounds of Formula Iii, further to any of the above embodiments of Formula Iii, $R^{201}$ is hydrogen and $R^{202}$ is ethyl.

In some embodiments of compounds of Formula Iii, further to any of the above embodiments of Formula Iii, $R^{201}$ is hydrogen and $R^{202}$ is lower alkoxy optionally substituted with one or more fluoro. In some embodiments of compounds of Formula Iii, further to any of the above embodiments of Formula Iii, $R^{201}$ is hydrogen and $R^{202}$ is lower alkoxy. In some embodiments of compounds of Formula Iii, further to any of the above embodiments of Formula Iii, $R^{201}$ is hydrogen and $R^{202}$ is $C_{1-3}$ alkoxy. In some embodiments of compounds of Formula Iii, further to any of the above embodiments of Formula Iii, $R^{201}$ is hydrogen and $R^{202}$ is methoxy or ethoxy. In some embodiments of compounds of Formula Iii, further to any of the above embodiments of Formula Iii, $R^{201}$ is hydrogen and $R^{202}$ is methoxy. In some embodiments of compounds of Formula Iii, further to any of the above embodiments of Formula Iii, $R^{201}$ is hydrogen and $R^{202}$ is ethoxy.

In some embodiments of compounds of Formula Iii, further to any of the above embodiments of Formula Iii, $L_{11}$ is —C(H$_2$)—. In some embodiments of compounds of Formula Iii, further to any of the above embodiments of Formula Iii, $L_{11}$ is —C(O)—.

In some embodiments of compounds of Formula Iii, further to any of the above embodiments of Formula Iii, $Y_{11}$ is —N═ and $R^{200}$ is hydrogen. In some embodiments of compounds of Formula Iii, further to any of the above embodiments of Formula Iii, $Y_{11}$ is —C(H)═ and $R^{200}$ is fluoro.

In a thirty-sixth aspect, compounds of Formula I having the structure according to the following Formula Ijj are provided:

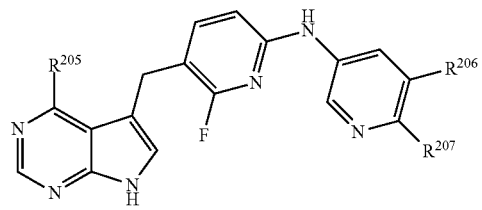

Formula Ijj or a salt, a prodrug, a solvate, a tautomer or a stereoisomer thereof, wherein:

$R^{205}$ is selected from the group consisting of hydrogen, cycloalkyl, lower alkyl optionally substituted with one or more $R^{208}$, and —O—$R^{209}$;

$R^{206}$ is hydrogen and $R^{207}$ is hydrogen, fluoro, chloro, bromo, cycloalkyl, lower alkyl optionally substituted with one or more fluoro, or lower alkoxy optionally substituted with one or more fluoro; or $R^{207}$ is hydrogen and $R^{206}$ is fluoro, chloro, bromo, cycloalkyl, lower alkyl optionally substituted with one or more fluoro, or lower alkoxy optionally substituted with one or more fluoro;

$R^{208}$ is fluoro or lower alkoxy optionally substituted with one or more fluoro; and $R^{209}$ is lower alkyl, lower alkyl substituted with one or more fluoro, or lower alkyl substituted with lower alkoxy.

In some embodiments of compounds of Formula Ijj, $R^{205}$ is selected from the group consisting of cycloalkyl, lower alkyl, lower alkoxy, and lower alkoxy substituted with lower alkoxy. In one embodiment, $R^{205}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{205}$ is selected from the group consisting of methyl, cyclopropyl, methoxy, ethoxy, and 2-methoxy-ethoxy.

In some embodiments of compounds of Formula Ijj, further to any of the above embodiments of Formula Ijj, $R^{207}$ is hydrogen and $R^{206}$ is fluoro, chloro, bromo, cycloalkyl, lower alkyl optionally substituted with one or more fluoro, or lower alkoxy optionally substituted with one or more fluoro. In some embodiments of compounds of Formula Ijj, further to any of the above embodiments of Formula Ijj, $R^{207}$ is hydrogen and $R^{206}$ is lower alkyl optionally substituted with one or more fluoro. In some embodiments of compounds of Formula Ijj, further to any of the above embodiments of Formula Ijj, $R^{207}$ is hydrogen and $R^{206}$ is lower alkyl. In some embodiments of compounds of Formula Ijj, further to any of the above embodiments of Formula Ijj, $R^{207}$ is hydrogen and $R^{206}$ is $C_{1-3}$ alkyl. In some embodiments of compounds of Formula Ijj, further to any of the above embodiments of Formula Ijj, $R^{207}$ is hydrogen and $R^{206}$ is methyl.

In some embodiments of compounds of Formula Ijj, further to any of the above embodiments of Formula Ijj, $R^{206}$ is hydrogen and $R^{207}$ is fluoro, chloro, bromo, cycloalkyl, lower alkyl optionally substituted with one or more fluoro, or lower alkoxy optionally substituted with one or more fluoro. In some embodiments of compounds of Formula Ijj, further to any of the above embodiments of Formula Ijj, $R^{206}$ is hydrogen and $R^{207}$ is fluoro, chloro, bromo. In some embodiments of compounds of Formula Ijj, further to any of the above embodiments of Formula Ijj, $R^{206}$ is hydrogen and $R^{207}$ is cycloalkyl, lower alkyl optionally substituted with one or more fluoro, or lower alkoxy optionally substituted with one or more fluoro.

In some embodiments of compounds of Formula Ijj, further to any of the above embodiments of Formula Ijj, $R^{206}$ is hydrogen and $R^{207}$ is cycloalkyl or lower alkyl optionally substituted with one or more fluoro. In some embodiments of compounds of Formula Ijj, further to any of the above embodiments of Formula Ijj, $R^{206}$ is hydrogen and $R^{207}$ is cycloalkyl or $C_{1-3}$ alkyl optionally substituted with 1, 2, or 3 fluoro. In some embodiments of compounds of Formula Ijj, further to any of the above embodiments of Formula Ijj, $R^{206}$ is hydrogen and $R^{207}$ is cyclopropyl or $C_{1-3}$ alkyl optionally substituted with 1, 2, or 3 fluoro. In some embodiments of compounds of Formula Ijj, further to any of the above embodiments of Formula Ijj, $R^{206}$ is hydrogen and $R^{207}$ is cyclopropyl, trifluoromethyl, methyl or ethyl.

In some embodiments of compounds of Formula Ijj, further to any of the above embodiments of Formula Ijj, $R^{206}$ is hydrogen and $R^{207}$ is cycloalkyl. In some embodiments of compounds of Formula Ijj, further to any of the above embodiments of Formula Ijj, $R^{206}$ is hydrogen and $R^{207}$ is cyclopropyl.

In some embodiments of compounds of Formula Ijj, further to any of the above embodiments of Formula Ijj, $R^{206}$ is hydrogen and $R^{207}$ is lower alkyl optionally substituted with one or more fluoro. In some embodiments of compounds of Formula Ijj, further to any of the above embodiments of Formula Ijj, $R^{206}$ is hydrogen and $R^{207}$ is $C_{1-3}$ alkyl optionally substituted with 1, 2, or 3 fluoro. In some embodiments of compounds of Formula Ijj, further to any of the above embodiments of Formula Ijj, $R^{206}$ is hydrogen and $R^{207}$ is trifluoromethyl, methyl or ethyl. In some embodiments of compounds of Formula Ijj, further to any of the above embodiments of Formula Ijj, $R^{206}$ is hydrogen and $R^{207}$ is trifluoromethyl. In some embodiments of compounds of Formula Ijj, further to any of the above embodiments of Formula Ijj, $R^{206}$ is hydrogen and $R^{207}$ is methyl. In some embodiments of compounds of Formula Ijj, further to any of the above embodiments of Formula Ijj, $R^{206}$ is hydrogen and $R^{207}$ is ethyl.

In some embodiments of compounds of Formula Ijj, further to any of the above embodiments of Formula Ijj, $R^{206}$ is hydrogen and $R^{207}$ is lower alkoxy optionally substituted with one or more fluoro. In some embodiments of compounds of Formula Ijj, further to any of the above embodiments of Formula Ijj, $R^{206}$ is hydrogen and $R^{207}$ is lower alkoxy. In some embodiments of compounds of Formula Ijj, further to any of the above embodiments of Formula Ijj, $R^{206}$ is hydrogen and $R^{207}$ is $C_{1-3}$ alkoxy. In some embodiments of compounds of Formula Ijj, further to any of the above embodiments of Formula Ijj, $R^{206}$ is hydrogen and $R^{207}$ is methoxy or ethoxy. In some embodiments of compounds of Formula Ijj, further to any of the above embodiments of Formula Ijj, $R^{206}$ is hydrogen and $R^{207}$ is methoxy. In some embodiments of compounds of Formula Ijj, further to any of the above embodiments of Formula Ijj, $R^{206}$ is hydrogen and $R^{207}$ is ethoxy.

In a thirty-seventh aspect, compounds of Formula I having the structure according to the following Formula Ikk are provided:

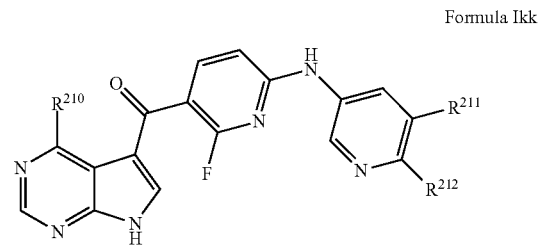

Formula Ikk or a salt, a prodrug, a solvate, a tautomer or a stereoisomer thereof,
wherein:
$R^{210}$ is selected from the group consisting of hydrogen, cycloalkyl, lower alkyl optionally substituted with one or more $R^{213}$, and —O—$R^{214}$;
$R^{211}$ is hydrogen and $R^{212}$ is hydrogen, fluoro, chloro, bromo, cycloalkyl, lower alkyl optionally substituted with one or more fluoro, or lower alkoxy optionally substituted with one or more fluoro; or
$R^{212}$ is hydrogen and $R^{211}$ is fluoro, chloro, bromo, cycloalkyl, lower alkyl optionally substituted with one or more fluoro, or lower alkoxy optionally substituted with one or more fluoro;
$R^{213}$ is fluoro or lower alkoxy optionally substituted with one or more fluoro; and
$R^{214}$ is lower alkyl, lower alkyl substituted with one or more fluoro, or lower alkyl substituted with lower alkoxy.

In some embodiments of compounds of Formula Ikk, $R^{210}$ is selected from the group consisting of cycloalkyl, lower alkyl, lower alkoxy, and lower alkoxy substituted with lower alkoxy. In one embodiment, $R^{210}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{210}$ is selected from the group consisting of methyl, cyclopropyl, methoxy, ethoxy, and 2-methoxy-ethoxy.

In some embodiments of compounds of Formula Ikk, further to any of the above embodiments of Formula Ikk, $R^{212}$ is hydrogen and $R^{211}$ is fluoro, chloro, bromo, cycloalkyl, lower alkyl optionally substituted with one or more fluoro, or lower alkoxy optionally substituted with one or more fluoro. In some embodiments of compounds of Formula Ikk, further to any of the above embodiments of Formula Ikk, $R^{212}$ is hydrogen and $R^{211}$ is lower alkyl optionally substituted with one or more fluoro. In some embodiments of compounds of Formula Ikk, further to any of the above embodiments of Formula Ikk, $R^{212}$ is hydrogen and $R^{211}$ is lower alkyl. In some embodiments of compounds of Formula Ikk, further to any of the above embodiments of Formula Ikk, $R^{212}$ is hydrogen and $R^{211}$ is $C_{1-3}$ alkyl. In some embodiments of compounds of Formula Ikk, further to any of the above embodiments of Formula Ikk, $R^{212}$ is hydrogen and $R^{211}$ is methyl.

In some embodiments of compounds of Formula Ikk, further to any of the above embodiments of Formula Ikk, $R^{211}$ is hydrogen and $R^{212}$ is fluoro, chloro, bromo, cycloalkyl, lower alkyl optionally substituted with one or more fluoro, or lower alkoxy optionally substituted with one or more fluoro. In some embodiments of compounds of Formula Ikk, further to any of the above embodiments of Formula Ikk, $R^{211}$ is hydrogen and $R^{212}$ is fluoro, chloro, bromo. In some embodiments of compounds of Formula Ikk, further to any of the above embodiments of Formula Ikk, $R^{211}$ is hydrogen and $R^{212}$ is cycloalkyl, lower alkyl optionally substituted with one or more fluoro, or lower alkoxy optionally substituted with one or more fluoro.

In some embodiments of compounds of Formula Ikk, further to any of the above embodiments of Formula Ikk, $R^{211}$ is hydrogen and $R^{212}$ is cycloalkyl or lower alkyl optionally substituted with one or more fluoro. In some embodiments of compounds of Formula Ikk, further to any of the above embodiments of Formula Ikk, $R^{211}$ is hydrogen and $R^{212}$ is cycloalkyl or $C_{1-3}$ alkyl optionally substituted with 1, 2, or 3 fluoro. In some embodiments of compounds of Formula Ikk, further to any of the above embodiments of Formula Ikk, $R^{211}$ is hydrogen and $R^{212}$ is cyclopropyl or $C_{1-3}$ alkyl optionally substituted with 1, 2, or 3 fluoro. In some embodiments of compounds of Formula Ikk, further to any of the above embodiments of Formula Ikk, $R^{211}$ is hydrogen and $R^{212}$ is cyclopropyl, trifluoromethyl, methyl or ethyl.

In some embodiments of compounds of Formula Ikk, further to any of the above embodiments of Formula Ikk, $R^{211}$ is hydrogen and $R^{212}$ is cycloalkyl. In some embodiments of compounds of Formula Ikk, further to any of the above embodiments of Formula Ikk, $R^{211}$ is hydrogen and $R^{212}$ is cyclopropyl.

In some embodiments of compounds of Formula Ikk, further to any of the above embodiments of Formula Ikk, $R^{211}$ is hydrogen and $R^{212}$ is lower alkyl optionally substituted with one or more fluoro. In some embodiments of compounds of Formula Ikk, further to any of the above embodiments of Formula Ikk, $R^{211}$ is hydrogen and $R^{212}$ is $C_{1-3}$ alkyl optionally substituted with 1, 2, or 3 fluoro. In some embodiments of compounds of Formula Ikk, further to any of the above embodiments of Formula Ikk, $R^{211}$ is hydrogen and $R^{212}$ is trifluoromethyl, methyl or ethyl. In some embodiments of compounds of Formula Ikk, further to any of the above embodiments of Formula Ikk, $R^{211}$ is hydrogen and $R^{212}$ is trifluoromethyl. In some embodiments of compounds of Formula Ikk, further to any of the above embodiments of Formula Ikk, $R^{211}$ is hydrogen and $R^{212}$ is methyl. In some embodiments of compounds of Formula Ikk, further to any of the above embodiments of Formula Ikk, $R^{211}$ is hydrogen and $R^{212}$ is ethyl.

In some embodiments of compounds of Formula Ikk, further to any of the above embodiments of Formula Ikk, $R^{211}$ is hydrogen and $R^{212}$ is lower alkoxy optionally substituted with one or more fluoro. In some embodiments of compounds of Formula Ikk, further to any of the above embodiments of Formula Ikk, $R^{211}$ is hydrogen and $R^{212}$ is lower alkoxy. In some embodiments of compounds of Formula Ikk, further to any of the above embodiments of Formula Ikk, $R^{211}$ is hydrogen and $R^{212}$ is $C_{1-3}$ alkoxy. In some embodiments of compounds of Formula Ikk, further to any of the above embodiments of Formula Ikk, $R^{211}$ is hydrogen and $R^{212}$ is methoxy or ethoxy. In some embodiments of compounds of Formula Ikk, further to any of the above embodiments of Formula Ikk, $R^{211}$ is hydrogen and $R^{212}$ is methoxy. In some embodiments of compounds of Formula Ikk, further to any of the above embodiments of Formula Ikk, $R^{211}$ is hydrogen and $R^{212}$ is ethoxy.

In a thirty-eighth aspect, compounds of Formula I having the structure according to the following Formula Imm are provided:

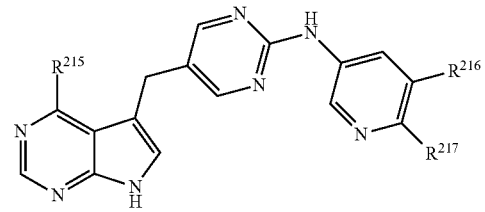

Formula Imm or a salt, a prodrug, a solvate, a tautomer or a stereoisomer thereof,
wherein:
$R^{215}$ is selected from the group consisting of hydrogen, cycloalkyl, lower alkyl optionally substituted with one or more $R^{218}$, and —O—$R^{219}$;
$R^{216}$ is hydrogen and $R^{217}$ is hydrogen, fluoro, chloro, bromo, cycloalkyl, lower alkyl optionally substituted with one or more fluoro, or lower alkoxy optionally substituted with one or more fluoro; or
$R^{217}$ is hydrogen and $R^{216}$ is fluoro, chloro, bromo, cycloalkyl, lower alkyl optionally substituted with one or more fluoro, or lower alkoxy optionally substituted with one or more fluoro;
$R^{218}$ is fluoro or lower alkoxy optionally substituted with one or more fluoro; and
$R^{219}$ is lower alkyl, lower alkyl substituted with one or more fluoro, or lower alkyl substituted with lower alkoxy.

In some embodiments of compounds of Formula Imm, $R^{215}$ is selected from the group consisting of cycloalkyl, lower alkyl, lower alkoxy, and lower alkoxy substituted with lower alkoxy. In one embodiment, $R^{215}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{215}$ is selected from the group consisting of methyl, cyclopropyl, methoxy, ethoxy, and 2-methoxy-ethoxy.

In some embodiments of compounds of Formula Imm, further to any of the above embodiments of Formula Imm, $R^{217}$ is hydrogen and $R^{216}$ is fluoro, chloro, bromo, cycloalkyl, lower alkyl optionally substituted with one or more fluoro, or lower alkoxy optionally substituted with one or more fluoro. In some embodiments of compounds of Formula Imm, further to any of the above embodiments of Formula I mm, $R^{217}$ is hydrogen and $R^{216}$ is lower alkyl optionally substituted with one or more fluoro. In some embodiments of compounds of Formula Imm, further to any of the above embodiments of Formula Imm, $R^{217}$ is hydrogen and $R^{216}$ is lower alkyl. In some embodiments of compounds of Formula Imm, further to any of the above embodiments of Formula Imm, $R^{217}$ is hydrogen and $R^{216}$ is $C_{1-3}$ alkyl. In some embodiments of compounds of Formula Imm, further to any of the above embodiments of Formula Imm, $R^{217}$ is hydrogen and $R^{216}$ is methyl.

In some embodiments of compounds of Formula Imm, further to any of the above embodiments of Formula Imm, $R^{216}$ is hydrogen and $R^{217}$ is fluoro, chloro, bromo, cycloalkyl, lower alkyl optionally substituted with one or more fluoro, or lower alkoxy optionally substituted with one or more fluoro. In some embodiments of compounds of Formula Imm, further to any of the above embodiments of Formula I mm, $R^{216}$ is hydrogen and $R^{217}$ is fluoro, chloro, bromo. In some embodiments of compounds of Formula I mm, further to any of the above embodiments of Formula Imm, $R^{216}$ is hydrogen and $R^{217}$ is cycloalkyl, lower alkyl optionally substituted with one or more fluoro, or lower alkoxy optionally substituted with one or more fluoro.

In some embodiments of compounds of Formula Imm, further to any of the above embodiments of Formula Imm, $R^{216}$ is hydrogen and $R^{217}$ is cycloalkyl or lower alkyl optionally substituted with one or more fluoro. In some embodiments of compounds of Formula Imm, further to any of the above embodiments of Formula Imm, $R^{216}$ is hydrogen and $R^{217}$ is cycloalkyl or $C_{1-3}$ alkyl optionally substituted with 1, 2, or 3 fluoro. In some embodiments of compounds of Formula Imm, further to any of the above embodiments of Formula Imm, $R^{216}$ is hydrogen and $R^{217}$ is cyclopropyl or $C_{1-3}$ alkyl optionally substituted with 1, 2, or 3 fluoro. In some embodiments of compounds of Formula Imm, further to any of the above embodiments of Formula Imm, $R^{216}$ is hydrogen and $R^{217}$ is cyclopropyl, trifluoromethyl, methyl or ethyl.

In some embodiments of compounds of Formula Imm, further to any of the above embodiments of Formula Imm, $R^{216}$ is hydrogen and $R^{217}$ is cycloalkyl. In some embodiments of compounds of Formula Imm, further to any of the above embodiments of Formula Imm, $R^{216}$ is hydrogen and $R^{217}$ is cyclopropyl.

In some embodiments of compounds of Formula Imm, further to any of the above embodiments of Formula Imm, $R^{216}$ is hydrogen and $R^{217}$ is lower alkyl optionally substituted with one or more fluoro. In some embodiments of compounds of Formula Imm, further to any of the above embodiments of Formula Imm, $R^{216}$ is hydrogen and $R^{217}$ is $C_{1-3}$ alkyl optionally substituted with 1, 2, or 3 fluoro. In some embodiments of compounds of Formula Imm, further to any of the above embodiments of Formula Imm, $R^{216}$ is hydrogen and $R^{217}$ is trifluoromethyl, methyl or ethyl. In some embodiments of compounds of Formula Imm, further to any of the above embodiments of Formula Imm, $R^{216}$ is hydrogen and $R^{217}$ is trifluoromethyl. In some embodiments of compounds of Formula Imm, further to any of the above embodiments of Formula Imm, $R^{216}$ is hydrogen and $R^{217}$ is methyl. In some embodiments of compounds of Formula Imm, further to any of the above embodiments of Formula Imm, $R^{216}$ is hydrogen and $R^{217}$ is ethyl.

In some embodiments of compounds of Formula Imm, further to any of the above embodiments of Formula Imm, $R^{216}$ is hydrogen and $R^{217}$ is lower alkoxy optionally substituted with one or more fluoro. In some embodiments of compounds of Formula Imm, further to any of the above embodiments of Formula Imm, $R^{216}$ is hydrogen and $R^{217}$ is lower alkoxy. In some embodiments of compounds of Formula Imm, further to any of the above embodiments of Formula Imm, $R^{216}$ is hydrogen and $R^{217}$ is $C_{1-3}$ alkoxy. In some embodiments of compounds of Formula Imm, further to any of the above embodiments of Formula Imm, $R^{216}$ is hydrogen and $R^{217}$ is methoxy or ethoxy. In some embodiments of compounds of Formula Imm, further to any of the above embodiments of Formula Imm, $R^{216}$ is hydrogen and $R^{217}$ is methoxy. In some embodiments of compounds of Formula Imm, further to any of the above embodiments of Formula Imm, $R^{216}$ is hydrogen and $R^{217}$ is ethoxy.

In a thirty-ninth aspect, compounds of Formula I having the structure according to the following Formula Inn are provided:

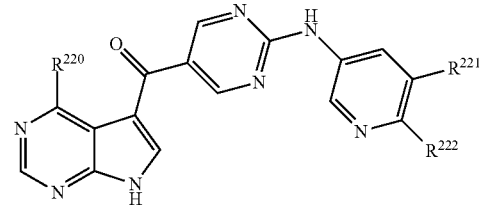

Formula Inn or a salt, a prodrug, a solvate, a tautomer or a stereoisomer thereof,
wherein:
$R^{220}$ is selected from the group consisting of hydrogen, cycloalkyl, lower alkyl optionally substituted with one or more $R^{223}$, and —O—$R^{224}$;
$R^{221}$ is hydrogen and $R^{222}$ is hydrogen, fluoro, chloro, bromo, cycloalkyl, lower alkyl optionally substituted with one or more fluoro, or lower alkoxy optionally substituted with one or more fluoro; or
$R^{222}$ is hydrogen and $R^{221}$ is fluoro, chloro, bromo, cycloalkyl, lower alkyl optionally substituted with one or more fluoro, or lower alkoxy optionally substituted with one or more fluoro;
$R^{223}$ is fluoro or lower alkoxy optionally substituted with one or more fluoro; and
$R^{224}$ is lower alkyl, lower alkyl substituted with one or more fluoro, or lower alkyl substituted with lower alkoxy.

In some embodiments of compounds of Formula Inn, $R^{220}$ is selected from the group consisting of cycloalkyl, lower alkyl, lower alkoxy, and lower alkoxy substituted with lower alkoxy. In one embodiment, $R^{220}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{220}$ is selected from the group consisting of methyl, cyclopropyl, methoxy, ethoxy, and 2-methoxy-ethoxy.

In some embodiments of compounds of Formula Inn, further to any of the above embodiments of Formula Inn, $R^{222}$ is hydrogen and $R^{221}$ is fluoro, chloro, bromo, cycloalkyl, lower alkyl optionally substituted with one or more fluoro, or lower alkoxy optionally substituted with one or more fluoro. In some embodiments of compounds of Formula Inn, further to any of the above embodiments of Formula Inn, $R^{222}$ is hydrogen and $R^{221}$ is lower alkyl optionally substituted with one or more fluoro. In some embodiments of compounds of Formula Inn, further to any of the above embodiments of Formula Inn, $R^{222}$ is hydrogen and $R^{221}$ is lower alkyl. In some embodiments of compounds of Formula Inn, further to any of the above embodiments of Formula Inn, $R^{222}$ is hydrogen and $R^{221}$ is $C_{1-3}$ alkyl. In some embodiments of compounds of Formula Inn, further to any of the above embodiments of Formula Inn, $R^{222}$ is hydrogen and $R^{221}$ is methyl.

In some embodiments of compounds of Formula Inn, further to any of the above embodiments of Formula Inn, $R^{221}$ is hydrogen and $R^{222}$ is fluoro, chloro, bromo, cycloalkyl, lower alkyl optionally substituted with one or more fluoro, or lower alkoxy optionally substituted with one or more fluoro. In some embodiments of compounds of Formula Inn, further to any of the above embodiments of Formula Inn, $R^{221}$ is hydrogen and $R^{222}$ is fluoro, chloro, bromo. In some embodiments of compounds of Formula Inn, further to any of the above embodiments of Formula Inn, $R^{221}$ is hydrogen and $R^{222}$ is cycloalkyl, lower alkyl optionally substituted with one or more fluoro, or lower alkoxy optionally substituted with one or more fluoro.

In some embodiments of compounds of Formula Inn, further to any of the above embodiments of Formula Inn, $R^{221}$ is hydrogen and $R^{222}$ is cycloalkyl or lower alkyl optionally substituted with one or more fluoro. In some embodiments of compounds of Formula Inn, further to any of the above embodiments of Formula Inn, $R^{221}$ is hydrogen and $R^{222}$ is cycloalkyl or $C_{1-3}$ alkyl optionally substituted with 1, 2, or 3 fluoro. In some embodiments of compounds of Formula Inn, further to any of the above embodiments of Formula Inn, $R^{221}$ is hydrogen and $R^{222}$ is cyclopropyl or $C_{1-3}$ alkyl optionally substituted with 1, 2, or 3 fluoro. In some embodiments of compounds of Formula Inn, further to any of the above embodiments of Formula Inn, $R^{221}$ is hydrogen and $R^{222}$ is cyclopropyl, trifluoromethyl, methyl or ethyl.

In some embodiments of compounds of Formula Inn, further to any of the above embodiments of Formula Inn, $R^{221}$ is hydrogen and $R^{222}$ is cycloalkyl. In some embodiments of compounds of Formula Inn, further to any of the above embodiments of Formula Inn, $R^{221}$ is hydrogen and $R^{222}$ is cyclopropyl.

In some embodiments of compounds of Formula Inn, further to any of the above embodiments of Formula Inn, $R^{221}$ is hydrogen and $R^{222}$ is lower alkyl optionally substituted with one or more fluoro. In some embodiments of compounds of Formula Inn, further to any of the above embodiments of Formula Inn, $R^{221}$ is hydrogen and $R^{222}$ is $C_{1-3}$ alkyl optionally substituted with 1, 2, or 3 fluoro. In some embodiments of compounds of Formula Inn, further to any of the above embodiments of Formula Inn, $R^{221}$ is hydrogen and $R^{222}$ is trifluoromethyl, methyl or ethyl. In some embodiments of compounds of Formula Inn, further to any of the above embodiments of Formula Inn, $R^{221}$ is hydrogen and $R^{222}$ is trifluoromethyl. In some embodiments of compounds of Formula Inn, further to any of the above embodiments of Formula Inn, $R^{221}$ is hydrogen and $R^{222}$ is methyl. In some embodiments of compounds of Formula Inn, further to any of the above embodiments of Formula Inn, $R^{221}$ is hydrogen and $R^{222}$ is ethyl.

In some embodiments of compounds of Formula Inn, further to any of the above embodiments of Formula Inn, $R^{221}$ is hydrogen and $R^{222}$ is lower alkoxy optionally substituted with one or more fluoro. In some embodiments of compounds of Formula Inn, further to any of the above embodiments of Formula Inn, $R^{221}$ is hydrogen and $R^{222}$ is lower alkoxy. In some embodiments of compounds of Formula Inn, further to any of the above embodiments of Formula Inn, $R^{221}$ is hydrogen and $R^{222}$ is $C_{1-3}$ alkoxy. In some embodiments of compounds of Formula Inn, further to any of the above embodiments of Formula Inn, $R^{221}$ is hydrogen and $R^{222}$ is methoxy or ethoxy. In some embodiments of compounds of Formula Inn, further to any of the above embodiments of Formula Inn, $R^{221}$ is hydrogen and $R^{222}$ is methoxy. In some embodiments of compounds of Formula Inn, further to any of the above embodiments of Formula Inn, $R^{221}$ is hydrogen and $R^{222}$ is ethoxy.

In a fortieth aspect, compounds of Formula I having the structure according to the following Formula Ioo are provided:

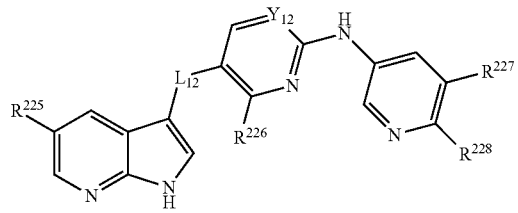

Formula Ioo or a salt, a prodrug, a solvate, a tautomer or a stereoisomer thereof,
wherein:
$Y_{12}$ is —N═ and $R^{226}$ is hydrogen; or $Y_{12}$ is —C(H)═ and $R^{226}$ is fluoro;
$L_{12}$ is —C(H$_2$)— or —C(O)—;
$R^{225}$ is hydrogen, fluoro, chloro, or lower alkyl optionally substituted with one or more fluoro;
$R^{227}$ is hydrogen and $R^{228}$ is hydrogen, fluoro, chloro, bromo, cycloalkyl, lower alkyl optionally substituted with one or more fluoro, or lower alkoxy optionally substituted with one or more fluoro; or
$R^{228}$ is hydrogen and $R^{227}$ is fluoro, chloro, bromo, cycloalkyl, lower alkyl optionally substituted with one or more fluoro, or lower alkoxy optionally substituted with one or more fluoro.

In some embodiments of compounds of Formula Ioo, $R^{225}$ is hydrogen, chloro or lower alkyl. In one embodiment, $R^{225}$ is hydrogen, chloro or $C_{1-3}$ alkyl. In one embodiment, $R^{225}$ is hydrogen, chloro or methyl.

In some embodiments of compounds of Formula Ioo, further to any of the above embodiments of Formula Ioo, $R^{228}$ is hydrogen and $R^{227}$ is fluoro, chloro, bromo, cycloalkyl, lower alkyl optionally substituted with one or more fluoro, or lower alkoxy optionally substituted with one or more fluoro. In some embodiments of compounds of Formula Ioo, further to any of the above embodiments of Formula Ioo, $R^{228}$ is hydrogen and $R^{227}$ is lower alkyl optionally substituted with one or more fluoro. In some embodiments of compounds of Formula Ioo, further to any of the above embodiments of Formula Ioo, $R^{228}$ is hydrogen and $R^{227}$ is lower alkyl. In some embodiments of compounds of Formula Ioo, further to any of the above embodiments of Formula Ioo, $R^{228}$ is hydrogen and $R^{227}$ is $C_{1-3}$ alkyl. In some embodiments of compounds of Formula Ioo, further to any of the above embodiments of Formula Ioo, $R^{228}$ is hydrogen and $R^{227}$ is methyl.

In some embodiments of compounds of Formula Ioo, further to any of the above embodiments of Formula Ioo, $R^{227}$ is hydrogen and $R^{228}$ is fluoro, chloro, bromo, cycloalkyl, lower alkyl optionally substituted with one or more fluoro, or lower alkoxy optionally substituted with one or more fluoro. In some embodiments of compounds of Formula Ioo, further to any of the above embodiments of Formula Ioo, $R^{227}$ is hydrogen and $R^{228}$ is fluoro, chloro, bromo. In some embodiments of compounds of Formula Ioo, further to any of the above embodiments of Formula Ioo, $R^{227}$ is hydrogen and $R^{228}$ is cycloalkyl, lower alkyl optionally substituted with one or more fluoro, or lower alkoxy optionally substituted with one or more fluoro.

In some embodiments of compounds of Formula Ioo, further to any of the above embodiments of Formula Ioo, $R^{227}$ is hydrogen and $R^{228}$ is cycloalkyl or lower alkyl optionally substituted with one or more fluoro. In some embodiments of compounds of Formula Ioo, further to any of the above embodiments of Formula Ioo, $R^{227}$ is hydrogen and $R^{228}$ is cycloalkyl or $C_{1-3}$ alkyl optionally substituted with 1, 2, or 3 fluoro. In some embodiments of compounds of Formula Ioo, further to any of the above embodiments of Formula Ioo, $R^{227}$ is hydrogen and $R^{228}$ is cyclopropyl or $C_{1-3}$ alkyl optionally substituted with 1, 2, or 3 fluoro. In some embodiments of compounds of Formula Ioo, further to any of the above embodiments of Formula Ioo, $R^{227}$ is hydrogen and $R^{228}$ is cyclopropyl, trifluoromethyl, methyl or ethyl.

In some embodiments of compounds of Formula Ioo, further to any of the above embodiments of Formula Ioo, $R^{227}$ is hydrogen and $R^{228}$ is cycloalkyl. In some embodiments of compounds of Formula Ioo, further to any of the above embodiments of Formula Ioo, $R^{227}$ is hydrogen and $R^{228}$ is cyclopropyl.

In some embodiments of compounds of Formula Ioo, further to any of the above embodiments of Formula Ioo, $R^{227}$ is hydrogen and $R^{228}$ is lower alkyl optionally substituted with one or more fluoro. In some embodiments of compounds of Formula Ioo, further to any of the above embodiments of Formula Ioo, $R^{227}$ is hydrogen and $R^{228}$ is $C_{1-3}$ alkyl optionally substituted with 1, 2, or 3 fluoro. In some embodiments of compounds of Formula Ioo, further to any of the above embodiments of Formula Ioo, $R^{227}$ is hydrogen and $R^{228}$ is trifluoromethyl, methyl or ethyl. In some embodiments of compounds of Formula Ioo, further to any of the above embodiments of Formula Ioo, $R^{227}$ is hydrogen and $R^{228}$ is trifluoromethyl. In some embodiments of compounds of Formula Ioo, further to any of the above embodiments of Formula Ioo, $R^{227}$ is hydrogen and $R^{228}$ is methyl. In some embodiments of compounds of Formula Ioo, further to any of the above embodiments of Formula Ioo, $R^{227}$ is hydrogen and $R^{228}$ is ethyl.

In some embodiments of compounds of Formula Ioo, further to any of the above embodiments of Formula Ioo, $R^{227}$ is hydrogen and $R^{228}$ is lower alkoxy optionally substituted with one or more fluoro. In some embodiments of compounds of Formula Ioo, further to any of the above embodiments of Formula Ioo, $R^{227}$ is hydrogen and $R^{228}$ is lower alkoxy. In some embodiments of compounds of Formula Ioo, further to any of the above embodiments of Formula Ioo, $R^{227}$ is hydrogen and $R^{228}$ is $C_{1-3}$ alkoxy. In some embodiments of compounds of Formula Ioo, further to any of the above embodiments of Formula Ioo, $R^{227}$ is hydrogen and $R^{228}$ is methoxy or ethoxy. In some embodiments of compounds of Formula Ioo, further to any of the above embodiments of Formula Ioo, $R^{227}$ is hydrogen and $R^{228}$ is methoxy. In some embodiments of compounds of Formula Ioo, further to any of the above embodiments of Formula Ioo, $R^{227}$ is hydrogen and $R^{228}$ is ethoxy.

In some embodiments of compounds of Formula Ioo, further to any of the above embodiments of Formula Ioo, $L_{12}$ is —C(H$_2$)—. In some embodiments of compounds of Formula Ioo, further to any of the above embodiments of Formula Ioo, $L_{12}$ is —C(O)—.

In some embodiments of compounds of Formula Ioo, further to any of the above embodiments of Formula Ioo, $Y_{12}$ is —N= and $R^{226}$ is hydrogen. In some embodiments of compounds of Formula Ioo, further to any of the above embodiments of Formula Ioo, $Y_{12}$ is —C(H)= and $R^{226}$ is fluoro.

In a forty-first aspect, compounds of Formula I having the structure according to the following Formula Ipp are provided:

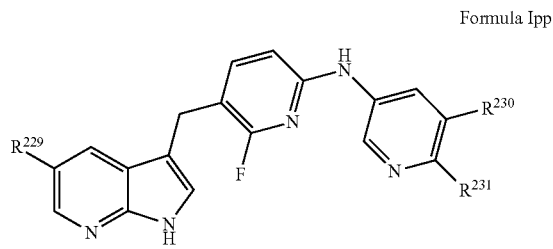

Formula Ipp or a salt, a prodrug, a solvate, a tautomer or a stereoisomer thereof, wherein:
$R^{229}$ is hydrogen, fluoro, chloro, or lower alkyl optionally substituted with one or more fluoro;
$R^{230}$ is hydrogen and $R^{231}$ is hydrogen, fluoro, chloro, bromo, cycloalkyl, lower alkyl optionally substituted with one or more fluoro, or lower alkoxy optionally substituted with one or more fluoro; or
$R^{231}$ is hydrogen and $R^{230}$ is fluoro, chloro, bromo, cycloalkyl, lower alkyl optionally substituted with one or more fluoro, or lower alkoxy optionally substituted with one or more fluoro.

In some embodiments of compounds of Formula Ipp, $R^{229}$ is hydrogen, chloro or lower alkyl. In one embodiment, $R^{229}$ is hydrogen, chloro or $C_{1-3}$ alkyl. In one embodiment, $R^{229}$ is hydrogen, chloro or methyl.

In some embodiments of compounds of Formula Ipp, further to any of the above embodiments of Formula Ipp, $R^{231}$ is hydrogen and $R^{230}$ is fluoro, chloro, bromo, cycloalkyl, lower alkyl optionally substituted with one or more fluoro, or lower alkoxy optionally substituted with one or more fluoro. In some embodiments of compounds of Formula Ipp, further to any of the above embodiments of Formula Ipp, $R^{231}$ is hydrogen and $R^{230}$ is lower alkyl optionally substituted with one or more fluoro. In some embodiments of compounds of Formula Ipp, further to any of the above embodiments of Formula Ipp, $R^{231}$ is hydrogen and $R^{230}$ is lower alkyl. In some embodiments of compounds of Formula Ipp, further to any of the above embodiments of Formula Ipp, $R^{231}$ is hydrogen and $R^{230}$ is $C_{1-3}$ alkyl. In some embodiments of compounds of Formula Ipp, further to any of the above embodiments of Formula Ipp, $R^{231}$ is hydrogen and $R^{230}$ is methyl.

In some embodiments of compounds of Formula Ipp, further to any of the above embodiments of Formula Ipp, $R^{230}$ is hydrogen and $R^{231}$ is fluoro, chloro, bromo, cycloalkyl, lower alkyl optionally substituted with one or more fluoro, or lower alkoxy optionally substituted with one or more fluoro. In some embodiments of compounds of Formula Ipp, further to any of the above embodiments of Formula Ipp, $R^{230}$ is hydrogen and $R^{231}$ is fluoro, chloro, bromo. In some embodiments of compounds of Formula Ipp, further to any of the above embodiments of Formula Ipp, $R^{230}$ is hydrogen and $R^{231}$ is cycloalkyl, lower alkyl optionally substituted with one or more fluoro, or lower alkoxy optionally substituted with one or more fluoro.

In some embodiments of compounds of Formula Ipp, further to any of the above embodiments of Formula Ipp, $R^{230}$ is hydrogen and $R^{231}$ is cycloalkyl or lower alkyl optionally substituted with one or more fluoro. In some embodiments of compounds of Formula Ipp, further to any of the above embodiments of Formula Ipp, $R^{230}$ is hydrogen and $R^{231}$ is cycloalkyl or $C_{1-3}$ alkyl optionally substituted with 1, 2, or 3 fluoro. In some embodiments of compounds of Formula Ipp, further to any of the above embodiments of Formula Ipp, $R^{230}$ is hydrogen and $R^{231}$ is cyclopropyl or $C_{1-3}$ alkyl optionally substituted with 1, 2, or 3 fluoro. In some embodiments of compounds of Formula Ipp, further to any of the above embodiments of Formula Ipp, $R^{230}$ is hydrogen and $R^{231}$ is cyclopropyl, trifluoromethyl, methyl or ethyl.

In some embodiments of compounds of Formula Ipp, further to any of the above embodiments of Formula Ipp, $R^{230}$ is hydrogen and $R^{231}$ is cycloalkyl. In some embodiments of compounds of Formula Ipp, further to any of the above embodiments of Formula Ipp, $R^{230}$ is hydrogen and $R^{231}$ is cyclopropyl.

In some embodiments of compounds of Formula Ipp, further to any of the above embodiments of Formula Ipp, $R^{230}$ is hydrogen and $R^{231}$ is lower alkyl optionally substituted with one or more fluoro. In some embodiments of compounds of Formula Ipp, further to any of the above embodiments of Formula Ipp, $R^{230}$ is hydrogen and $R^{231}$ is $C_{1-3}$ alkyl optionally substituted with 1, 2, or 3 fluoro. In some embodiments of compounds of Formula Ipp, further to any of the above embodiments of Formula Ipp, $R^{230}$ is hydrogen and $R^{231}$ is trifluoromethyl, methyl or ethyl. In some embodiments of compounds of Formula Ipp, further to any of the above embodiments of Formula Ipp, $R^{230}$ is hydrogen and $R^{231}$ is trifluoromethyl. In some embodiments of compounds of Formula Ipp, further to any of the above embodiments of Formula Ipp, $R^{230}$ is hydrogen and $R^{231}$ is methyl. In some embodiments of compounds of Formula Ipp, further to any of the above embodiments of Formula Ipp, $R^{230}$ is hydrogen and $R^{231}$ is ethyl.

In some embodiments of compounds of Formula Ipp, further to any of the above embodiments of Formula Ipp, $R^{230}$ is hydrogen and $R^{231}$ is lower alkoxy optionally substituted with one or more fluoro. In some embodiments of compounds of Formula Ipp, further to any of the above embodiments of Formula Ipp, $R^{230}$ is hydrogen and $R^{231}$ is lower alkoxy. In some embodiments of compounds of Formula Ipp, further to any of the above embodiments of Formula Ipp, $R^{230}$ is hydrogen and $R^{231}$ is $C_{1-3}$ alkoxy. In some embodiments of compounds of Formula Ipp, further to any of the above embodiments of Formula Ipp, $R^{230}$ is hydrogen and $R^{231}$ is methoxy or ethoxy. In some embodiments of compounds of Formula Ipp, further to any of the above embodiments of Formula Ipp, $R^{230}$ is hydrogen and $R^{231}$ is methoxy. In some embodiments of compounds of Formula Ipp, further to any of the above embodiments of Formula Ipp, $R^{230}$ is hydrogen and $R^{231}$ is ethoxy.

In a forty-second aspect, compounds of Formula I having the structure according to the following Formula Iqq are provided:

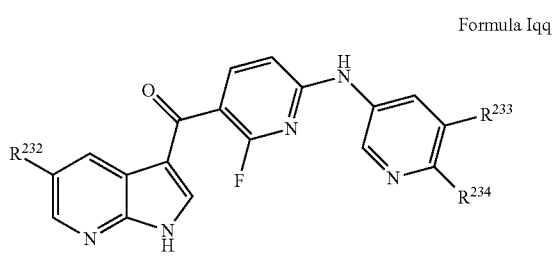

Formula Iqq or a salt, a prodrug, a solvate, a tautomer or a stereoisomer thereof,
wherein:
$R^{232}$ is hydrogen, fluoro, chloro, or lower alkyl optionally substituted with one or more fluoro;

$R^{233}$ is hydrogen and $R^{234}$ is hydrogen, fluoro, chloro, bromo, cycloalkyl, lower alkyl optionally substituted with one or more fluoro, or lower alkoxy optionally substituted with one or more fluoro; or
$R^{234}$ is hydrogen and $R^{233}$ is fluoro, chloro, bromo, cycloalkyl, lower alkyl optionally substituted with one or more fluoro, or lower alkoxy optionally substituted with one or more fluoro.

In some embodiments of compounds of Formula Iqq, $R^{232}$ is hydrogen, chloro or lower alkyl. In one embodiment, $R^{232}$ is hydrogen, chloro or $C_{1-3}$ alkyl. In one embodiment, $R^{232}$ is hydrogen, chloro or methyl.

In some embodiments of compounds of Formula Iqq, further to any of the above embodiments of Formula Iqq, $R^{234}$ is hydrogen and $R^{233}$ is fluoro, chloro, bromo, cycloalkyl, lower alkyl optionally substituted with one or more fluoro, or lower alkoxy optionally substituted with one or more fluoro. In some embodiments of compounds of Formula Iqq, further to any of the above embodiments of Formula Iqq, $R^{234}$ is hydrogen and $R^{233}$ is lower alkyl optionally substituted with one or more fluoro. In some embodiments of compounds of Formula Iqq, further to any of the above embodiments of Formula Iqq, $R^{234}$ is hydrogen and $R^{233}$ is lower alkyl. In some embodiments of compounds of Formula Iqq, further to any of the above embodiments of Formula Iqq, $R^{234}$ is hydrogen and $R^{233}$ is $C_{1-3}$ alkyl. In some embodiments of compounds of Formula Iqq, further to any of the above embodiments of Formula Iqq, $R^{234}$ is hydrogen and $R^{233}$ is methyl.

In some embodiments of compounds of Formula Iqq, further to any of the above embodiments of Formula Iqq, $R^{233}$ is hydrogen and $R^{234}$ is fluoro, chloro, bromo, cycloalkyl, lower alkyl optionally substituted with one or more fluoro, or lower alkoxy optionally substituted with one or more fluoro. In some embodiments of compounds of Formula Iqq, further to any of the above embodiments of Formula Iqq, $R^{233}$ is hydrogen and $R^{234}$ is fluoro, chloro, bromo. In some embodiments of compounds of Formula Iqq, further to any of the above embodiments of Formula Iqq, $R^{233}$ is hydrogen and $R^{234}$ is cycloalkyl, lower alkyl optionally substituted with one or more fluoro, or lower alkoxy optionally substituted with one or more fluoro.

In some embodiments of compounds of Formula Iqq, further to any of the above embodiments of Formula Iqq, $R^{233}$ is hydrogen and $R^{234}$ is cycloalkyl or lower alkyl optionally substituted with one or more fluoro. In some embodiments of compounds of Formula Iqq, further to any of the above embodiments of Formula Iqq, $R^{233}$ is hydrogen and $R^{234}$ is cycloalkyl or $C_{1-3}$ alkyl optionally substituted with 1, 2, or 3 fluoro. In some embodiments of compounds of Formula Iqq, further to any of the above embodiments of Formula Iqq, $R^{233}$ is hydrogen and $R^{234}$ is cyclopropyl or $C_{1-3}$ alkyl optionally substituted with 1, 2, or 3 fluoro. In some embodiments of compounds of Formula Iqq, further to any of the above embodiments of Formula Iqq, $R^{233}$ is hydrogen and $R^{234}$ is cyclopropyl, trifluoromethyl, methyl or ethyl.

In some embodiments of compounds of Formula Iqq, further to any of the above embodiments of Formula Iqq, $R^{233}$ is hydrogen and $R^{234}$ is cycloalkyl. In some embodiments of compounds of Formula Iqq, further to any of the above embodiments of Formula Iqq, $R^{233}$ is hydrogen and $R^{234}$ is cyclopropyl.

In some embodiments of compounds of Formula Iqq, further to any of the above embodiments of Formula Iqq, $R^{233}$ is hydrogen and $R^{234}$ is lower alkyl optionally substituted with one or more fluoro. In some embodiments of compounds of Formula Iqq, further to any of the above embodiments of Formula Iqq, $R^{233}$ is hydrogen and $R^{234}$ is $C_{1-3}$ alkyl optionally substituted with 1, 2, or 3 fluoro. In some embodiments of compounds of Formula Iqq, further to any of the above embodiments of Formula Iqq, $R^{233}$ is hydrogen and $R^{234}$ is trifluoromethyl, methyl or ethyl. In some embodiments of compounds of Formula Iqq, further to any of the above embodiments of Formula Iqq, $R^{233}$ is hydrogen and $R^{234}$ is trifluoromethyl. In some embodiments of compounds of Formula Iqq, further to any of the above embodiments of Formula Iqq, $R^{233}$ is hydrogen and $R^{234}$ is methyl. In some embodiments of compounds of Formula Iqq, further to any of the above embodiments of Formula Iqq, $R^{233}$ is hydrogen and $R^{234}$ is ethyl.

In some embodiments of compounds of Formula Iqq, further to any of the above embodiments of Formula Iqq, $R^{233}$ is hydrogen and $R^{234}$ is lower alkoxy optionally substituted with one or more fluoro. In some embodiments of compounds of Formula Iqq, further to any of the above embodiments of Formula Iqq, $R^{233}$ is hydrogen and $R^{234}$ is lower alkoxy. In some embodiments of compounds of Formula Iqq, further to any of the above embodiments of Formula Iqq, $R^{233}$ is hydrogen and $R^{234}$ is $C_{1-3}$ alkoxy. In some embodiments of compounds of Formula Iqq, further to any of the above embodiments of Formula Iqq, $R^{233}$ is hydrogen and $R^{234}$ is methoxy or ethoxy. In some embodiments of compounds of Formula Iqq, further to any of the above embodiments of Formula Iqq, $R^{233}$ is hydrogen and $R^{234}$ is methoxy. In some embodiments of compounds of Formula Iqq, further to any of the above embodiments of Formula Iqq, $R^{233}$ is hydrogen and $R^{234}$ is ethoxy.

In a forty-third aspect, compounds of Formula I having the structure according to the following Formula Irr are provided:

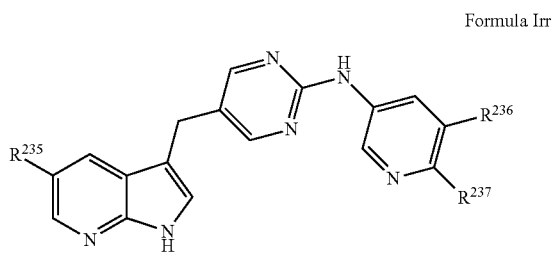

Formula Irr or a salt, a prodrug, a solvate, a tautomer or a stereoisomer thereof,
wherein:
$R^{235}$ is hydrogen, fluoro, chloro, or lower alkyl optionally substituted with one or more fluoro;
$R^{236}$ is hydrogen and $R^{237}$ is hydrogen, fluoro, chloro, bromo, cycloalkyl, lower alkyl optionally substituted with one or more fluoro, or lower alkoxy optionally substituted with one or more fluoro; or
$R^{237}$ is hydrogen and $R^{236}$ is fluoro, chloro, bromo, cycloalkyl, lower alkyl optionally substituted with one or more fluoro, or lower alkoxy optionally substituted with one or more fluoro.

In some embodiments of compounds of Formula Irr, $R^{235}$ is hydrogen, chloro or lower alkyl. In one embodiment, $R^{235}$ is hydrogen, chloro or $C_{1-3}$ alkyl. In one embodiment, $R^{235}$ is hydrogen, chloro or methyl.

In some embodiments of compounds of Formula Irr, further to any of the above embodiments of Formula Irr, $R^{237}$ is hydrogen and $R^{236}$ is fluoro, chloro, bromo, cycloalkyl, lower alkyl optionally substituted with one or more fluoro, or lower alkoxy optionally substituted with one or more fluoro. In some embodiments of compounds of Formula Irr, further to any of the above embodiments of Formula Irr, $R^{237}$ is hydrogen and $R^{236}$ is lower alkyl optionally substituted with one or more fluoro. In some embodiments of compounds of Formula Irr, further to any of the above embodiments of Formula Irr, $R^{237}$ is hydrogen and $R^{236}$ is lower alkyl. In some embodiments of compounds of Formula Irr, further to any of the above embodiments of Formula Irr, $R^{237}$ is hydrogen and $R^{236}$ is $C_{1-3}$ alkyl. In some embodiments of compounds of Formula Irr, further to any of the above embodiments of Formula Irr, $R^{237}$ is hydrogen and $R^{236}$ is methyl.

In some embodiments of compounds of Formula Irr, further to any of the above embodiments of Formula Irr, $R^{236}$ is hydrogen and $R^{237}$ is fluoro, chloro, bromo, cycloalkyl, lower alkyl optionally substituted with one or more fluoro, or lower alkoxy optionally substituted with one or more fluoro. In some embodiments of compounds of Formula Irr, further to any of the above embodiments of Formula Irr, $R^{236}$ is hydrogen and $R^{237}$ is fluoro, chloro, bromo. In some embodiments of compounds of Formula Irr, further to any of the above embodiments of Formula Irr, $R^{236}$ is hydrogen and $R^{237}$ is cycloalkyl, lower alkyl optionally substituted with one or more fluoro, or lower alkoxy optionally substituted with one or more fluoro.

In some embodiments of compounds of Formula Irr, further to any of the above embodiments of Formula Irr, $R^{236}$ is hydrogen and $R^{237}$ is cycloalkyl or lower alkyl optionally substituted with one or more fluoro. In some embodiments of compounds of Formula Irr, further to any of the above embodiments of Formula Irr, $R^{236}$ is hydrogen and $R^{237}$ is cycloalkyl or $C_{1-3}$ alkyl optionally substituted with 1, 2, or 3 fluoro. In some embodiments of compounds of Formula Irr, further to any of the above embodiments of Formula Irr, $R^{236}$ is hydrogen and $R^{237}$ is cyclopropyl or $C_{1-3}$ alkyl optionally substituted with 1, 2, or 3 fluoro. In some embodiments of compounds of Formula Irr, further to any of the above embodiments of Formula Irr, $R^{236}$ is hydrogen and $R^{237}$ is cyclopropyl, trifluoromethyl, methyl or ethyl.

In some embodiments of compounds of Formula Irr, further to any of the above embodiments of Formula Irr, $R^{236}$ is hydrogen and $R^{237}$ is cycloalkyl. In some embodiments of compounds of Formula Irr, further to any of the above embodiments of Formula Irr, $R^{236}$ is hydrogen and $R^{237}$ is cyclopropyl.

In some embodiments of compounds of Formula Irr, further to any of the above embodiments of Formula Irr, $R^{236}$ is hydrogen and $R^{237}$ is lower alkyl optionally substituted with one or more fluoro. In some embodiments of compounds of Formula Irr, further to any of the above embodiments of Formula Irr, $R^{236}$ is hydrogen and $R^{237}$ is $C_{1-3}$ alkyl optionally substituted with 1, 2, or 3 fluoro. In some embodiments of compounds of Formula Irr, further to any of the above embodiments of Formula Irr, $R^{236}$ is hydrogen and $R^{237}$ is trifluoromethyl, methyl or ethyl. In some embodiments of compounds of Formula Irr, further to any of the above embodiments of Formula Irr, $R^{236}$ is hydrogen and $R^{237}$ is trifluoromethyl. In some embodiments of compounds of Formula Irr, further to any of the above embodiments of Formula Irr, $R^{236}$ is hydrogen and $R^{237}$ is methyl. In some embodiments of compounds of Formula Irr, further to any of the above embodiments of Formula Irr, $R^{236}$ is hydrogen and $R^{237}$ is ethyl.

In some embodiments of compounds of Formula Irr, further to any of the above embodiments of Formula Irr, $R^{236}$ is hydrogen and $R^{237}$ is lower alkoxy optionally substituted with one or more fluoro. In some embodiments of compounds of Formula Irr, further to any of the above embodiments of Formula Irr, $R^{236}$ is hydrogen and $R^{237}$ is lower alkoxy. In some embodiments of compounds of Formula Irr, further to any of the above embodiments of Formula Irr, $R^{236}$ is hydrogen and $R^{237}$ is $C_{1-3}$ alkoxy. In some embodiments of compounds of Formula Irr, further to any of the above embodiments of Formula Irr, $R^{236}$ is hydrogen and $R^{237}$ is methoxy or ethoxy. In some embodiments of compounds of Formula Irr, further to any of the above embodiments of Formula Irr, $R^{236}$ is hydrogen and $R^{237}$ is methoxy. In some embodiments of compounds of Formula Irr, further to any of the above embodiments of Formula Irr, $R^{236}$ is hydrogen and $R^{237}$ is ethoxy.

In a forty-fourth aspect, compounds of Formula I having the structure according to the following Formula Iss are provided:

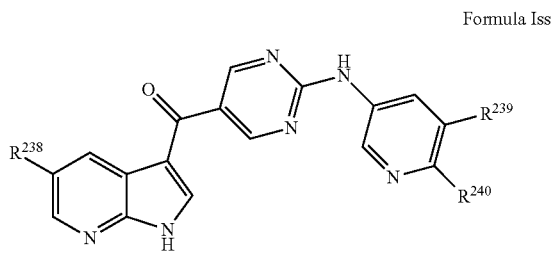

Formula Iss or a salt, a prodrug, a solvate, a tautomer or a stereoisomer thereof,
wherein:
$R^{238}$ is hydrogen, fluoro, chloro, or lower alkyl optionally substituted with one or more fluoro;
$R^{239}$ is hydrogen and $R^{240}$ is hydrogen, fluoro, chloro, bromo, cycloalkyl, lower alkyl optionally substituted with one or more fluoro, or lower alkoxy optionally substituted with one or more fluoro; or
$R^{240}$ is hydrogen and $R^{239}$ is fluoro, chloro, bromo, cycloalkyl, lower alkyl optionally substituted with one or more fluoro, or lower alkoxy optionally substituted with one or more fluoro.

In some embodiments of compounds of Formula Iss, $R^{238}$ is hydrogen, chloro or lower alkyl. In one embodiment, $R^{238}$ is hydrogen, chloro or $C_{1-3}$ alkyl. In one embodiment, $R^{238}$ is hydrogen, chloro or methyl.

In some embodiments of compounds of Formula Iss, further to any of the above embodiments of Formula Iss, $R^{240}$ is hydrogen and $R^{239}$ is fluoro, chloro, bromo, cycloalkyl, lower alkyl optionally substituted with one or more fluoro, or lower alkoxy optionally substituted with one or more fluoro. In some embodiments of compounds of Formula Iss, further to any of the above embodiments of Formula Iss, $R^{240}$ is hydrogen and $R^{239}$ is lower alkyl optionally substituted with one or more fluoro. In some embodiments of compounds of Formula Iss, further to any of the above embodiments of Formula Iss, $R^{240}$ is hydrogen and $R^{239}$ is lower alkyl. In some embodiments of compounds of Formula Iss, further to any of the above embodiments of Formula Iss, $R^{240}$ is hydrogen and $R^{239}$ is $C_{1-3}$ alkyl. In some embodiments of Formula Iss, further to any of the above embodiments of Formula Iss, $R^{240}$ is hydrogen and $R^{239}$ is methyl.

In some embodiments of compounds of Formula Iss, further to any of the above embodiments of Formula Iss, $R^{239}$ is hydrogen and $R^{240}$ is fluoro, chloro, bromo, cycloalkyl, lower alkyl optionally substituted with one or more fluoro, or lower alkoxy optionally substituted with one or more fluoro. In some embodiments of compounds of Formula Iss, further to any of the above embodiments of Formula Iss, $R^{239}$ is hydrogen and $R^{240}$ is fluoro, chloro, bromo. In some embodiments of compounds of Formula Iss, further to any of the above embodiments of Formula Iss, $R^{239}$ is hydrogen and $R^{240}$ is cycloalkyl, lower alkyl optionally substituted with one or more fluoro, or lower alkoxy optionally substituted with one or more fluoro.

In some embodiments of compounds of Formula Iss, further to any of the above embodiments of Formula Iss, $R^{239}$ is hydrogen and $R^{240}$ is cycloalkyl or lower alkyl optionally substituted with one or more fluoro. In some embodiments of compounds of Formula Iss, further to any of the above embodiments of Formula Iss, $R^{239}$ is hydrogen and $R^{240}$ is cycloalkyl or $C_{1-3}$ alkyl optionally substituted with 1, 2, or 3 fluoro. In some embodiments of compounds of Formula Iss, further to any of the above embodiments of Formula Iss, $R^{239}$ is hydrogen and $R^{240}$ is cyclopropyl or $C_{1-3}$ alkyl optionally substituted with 1, 2, or 3 fluoro. In some embodiments of compounds of Formula Iss, further to any of the above embodiments of Formula Iss, $R^{239}$ is hydrogen and $R^{240}$ is cyclopropyl, trifluoromethyl, methyl or ethyl.

In some embodiments of compounds of Formula Iss, further to any of the above embodiments of Formula Iss, $R^{239}$ is hydrogen and $R^{240}$ is cycloalkyl. In some embodiments of compounds of Formula Iss, further to any of the above embodiments of Formula Iss, $R^{239}$ is hydrogen and $R^{240}$ is cyclopropyl.

In some embodiments of compounds of Formula Iss, further to any of the above embodiments of Formula Iss, $R^{239}$ is hydrogen and $R^{240}$ is lower alkyl optionally substituted with one or more fluoro. In some embodiments of compounds of Formula Iss, further to any of the above embodiments of Formula Iss, $R^{239}$ is hydrogen and $R^{240}$ is $C_{1-3}$ alkyl optionally substituted with 1, 2, or 3 fluoro. In some embodiments of compounds of Formula Iss, further to any of the above embodiments of Formula Iss, $R^{239}$ is hydrogen and $R^{240}$ is trifluoromethyl, methyl or ethyl. In some embodiments of compounds of Formula Iss, further to any of the above embodiments of Formula Iss, $R^{239}$ is hydrogen and $R^{240}$ is trifluoromethyl. In some embodiments of compounds of Formula Iss, further to any of the above embodiments of Formula Iss, $R^{239}$ is hydrogen and $R^{240}$ is methyl. In some embodiments of compounds of Formula Iss, further to any of the above embodiments of Formula Iss, $R^{239}$ is hydrogen and $R^{240}$ is ethyl.

In some embodiments of compounds of Formula Iss, further to any of the above embodiments of Formula Iss, $R^{239}$ is hydrogen and $R^{240}$ is lower alkoxy optionally substituted with one or more fluoro. In some embodiments of compounds of Formula Iss, further to any of the above embodiments of Formula Iss, $R^{239}$ is hydrogen and $R^{240}$ is lower alkoxy. In some embodiments of compounds of Formula Iss, further to any of the above embodiments of Formula Iss, $R^{239}$ is hydrogen and $R^{240}$ is $C_{1-3}$ alkoxy. In some embodiments of compounds of Formula Iss, further to any of the above embodiments of Formula Iss, $R^{239}$ is hydrogen and $R^{240}$ is methoxy or ethoxy. In some embodiments of compounds of Formula Iss, further to any of the above embodiments of Formula Iss, $R^{239}$ is hydrogen and $R^{240}$ is methoxy. In some embodiments of compounds of Formula Iss, further to any of the above embodiments of Formula Iss, $R^{239}$ is hydrogen and $R^{240}$ is ethoxy.

In a forty-fifth aspect, compounds of Formula I having the structure according to the following Formula Itt are provided:

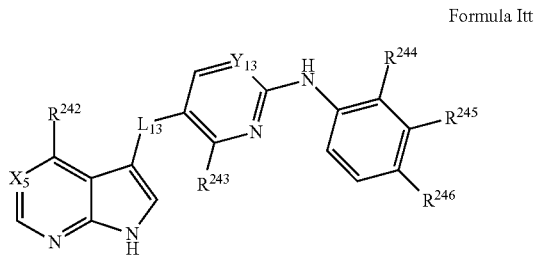

Formula Itt or a salt, a prodrug, a solvate, a tautomer or a stereoisomer thereof,
wherein:
$X_5$ is —N═, —C(H)═, or —C($R^{241}$)═;
$Y_{13}$ is —N═ and $R^{243}$ is hydrogen; or $Y_{13}$ is —C(H)═ and $R^{243}$ is fluoro;
$L_{13}$ is —C($H_2$)— or —C(O)—;
when $X_5$ is —C($R^{241}$)═, $R^{242}$ is hydrogen;
when $X_5$ is —N═ or —C(H)═, $R^{242}$ is selected from the group consisting of hydrogen, cycloalkyl, lower alkyl optionally substituted with one or more $R^{247}$, and —O—$R^{248}$;
$R^{241}$ is fluoro, chloro, or lower alkyl optionally substituted with one or more fluoro;
$R^{244}$ and $R^{245}$ are hydrogen and $R^{246}$ is selected from the group consisting of fluoro, chloro, —O—$R^{249}$, —S—$R^{250}$, —S($O_2$)—$R^{251}$, and lower alkyl optionally substituted with one or more $R^{252}$; or
$R^{244}$ and $R^{246}$ are hydrogen and $R^{245}$ is fluoro, chloro, lower alkyl optionally substituted with one or more fluoro, or lower alkoxy optionally substituted with one or more fluoro; or
$R^{245}$ and $R^{246}$ are hydrogen and $R^{244}$ is fluoro, chloro, lower alkyl optionally substituted with one or more fluoro, or lower alkoxy optionally substituted with one or more fluoro; or
$R^{244}$ is hydrogen, $R^{245}$ is fluoro, chloro, lower alkyl optionally substituted with one or more fluoro, or lower alkoxy optionally substituted with one or more fluoro and $R^{246}$ is fluoro, chloro, lower alkyl optionally substituted with one or more fluoro, or lower alkoxy optionally substituted with one or more fluoro;
$R^{247}$ is fluoro or lower alkoxy optionally substituted with one or more fluoro;
$R^{248}$ is lower alkyl, lower alkyl substituted with one or more fluoro, or lower alkyl substituted with lower alkoxy;
$R^{249}$, $R^{250}$ and $R^{251}$ are lower alkyl optionally substituted with one or more fluoro; and
$R^{252}$ is fluoro, —OH, or lower alkoxy optionally substituted with one or more fluoro.

In some embodiments of compounds of Formula Itt, $X_5$ is —N═ and $R^{242}$ is selected from the group consisting of hydrogen, cycloalkyl, lower alkyl optionally substituted with one or more $R^{247}$, and —O—$R^{248}$. In one embodiment, $X_5$ is —N═ and $R^{242}$ is selected from the group consisting of cycloalkyl, lower alkyl, lower alkoxy, and lower alkoxy substituted with lower alkoxy. In one embodiment, $X_5$ is —N═ and $R^{242}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $X_5$ is —N═ and $R^{242}$ is selected from the group consisting of methyl, cyclopropyl, methoxy, ethoxy, and 2-methoxy-ethoxy.

In some embodiments of compounds of Formula Itt, $X_5$ is —C(H)═ or —C($R^{241}$)═ and $R^{241}$ is fluoro, chloro, or lower alkyl optionally substituted with one or more fluoro. In one embodiment, $X_5$ is —C(H)═ or —C($R^{241}$)═ and $R^{241}$ is chloro or lower alkyl. In one embodiment, $X_5$ is —C(H)═ or —C($R^{241}$)═ and $R^{241}$ is chloro or $C_{1-3}$ alkyl. In one embodiment, $X_5$ is —C(H)═ or —C($R^{241}$)═ and $R^{241}$ is chloro or methyl.

In some embodiments of compounds of Formula Itt, further to any of the above embodiments of Formula Itt, $R^{244}$ and $R^{245}$ are hydrogen and $R^{246}$ is selected from the group consisting of fluoro, chloro, —O—$R^{249}$, —S—$R^{250}$, —S($O_2$)—$R^{251}$, and lower alkyl optionally substituted with one or more $R^{252}$. In some embodiments of compounds of Formula Itt, further to any of the above embodiments of Formula Itt, $R^{244}$ and $R^{245}$ are hydrogen and $R^{246}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Itt, further to any of the above embodiments of Formula Itt, $R^{244}$ and $R^{245}$ are hydrogen and $R^{246}$ is selected from the group consisting of fluoro, chloro, lower alkoxy, lower alkylthio, lower alkylsulfonyl, and lower alkyl.

In some embodiments of compounds of Formula Itt, further to any of the above embodiments of Formula Itt, $R^{244}$ and $R^{246}$ are hydrogen and $R^{245}$ is fluoro, chloro, lower alkyl optionally substituted with one or more fluoro, or lower alkoxy optionally substituted with one or more fluoro. In some embodiments of compounds of Formula Itt, further to any of the above embodiments of Formula Itt, $R^{244}$ and $R^{246}$ are hydrogen and $R^{245}$ is fluoro, chloro, lower alkyl or lower alkoxy.

In some embodiments of compounds of Formula Itt, further to any of the above embodiments of Formula Itt, $R^{245}$ and $R^{246}$ are hydrogen and $R^{244}$ is fluoro, chloro, lower alkyl optionally substituted with one or more fluoro, or lower alkoxy optionally substituted with one or more fluoro. In some embodiments of compounds of Formula Itt, further to any of the above embodiments of Formula Itt, $R^{245}$ and $R^{246}$ are hydrogen and $R^{244}$ is fluoro, chloro, lower alkyl or lower alkoxy.

In some embodiments of compounds of Formula Itt, further to any of the above embodiments of Formula Itt, $R^{244}$ is hydrogen, $R^{245}$ is fluoro, chloro, lower alkyl optionally substituted with one or more fluoro, or lower alkoxy optionally substituted with one or more fluoro and $R^{246}$ is fluoro, chloro, lower alkyl optionally substituted with one or more fluoro, or lower alkoxy optionally substituted with one or more fluoro. In some embodiments of compounds of Formula Itt, further to any of the above embodiments of Formula Itt, $R^{244}$ is hydrogen, $R^{245}$ is fluoro, chloro, lower alkyl or lower alkoxy and $R^{246}$ is fluoro, chloro, lower alkyl or lower alkoxy. In some embodiments of compounds of Formula Itt, further to any of the above embodiments of Formula Itt, $R^{244}$ is hydrogen, $R^{245}$ is fluoro, chloro, or lower alkoxy and $R^{246}$ is fluoro, chloro, or lower alkoxy.

In some embodiments of compounds of Formula Itt, further to any of the above embodiments of Formula Itt, $L_{13}$ is —C($H_2$)—. In some embodiments of compounds of Formula Itt, further to any of the above embodiments of Formula Itt, $L_{13}$ is —C(O)—.

In some embodiments of compounds of Formula Itt, further to any of the above embodiments of Formula Itt, $Y_{13}$ is —N═ and $R^{243}$ is hydrogen. In some embodiments of compounds of Formula Itt, further to any of the above embodiments of Formula Itt, $Y_{13}$ is —C(H)═ and $R^{243}$ is fluoro.

In a forty-sixth aspect, compounds of Formula I having the structure according to the following Formula Iuu are provided:

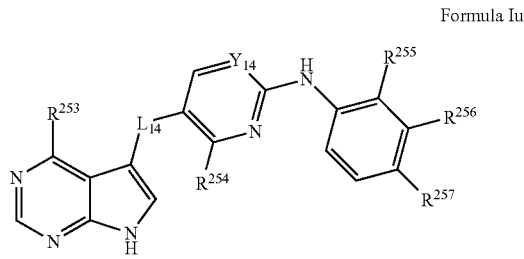

Formula Iuu or a salt, a prodrug, a solvate, a tautomer or a stereoisomer thereof,
wherein:
$Y_{14}$ is —N= and $R^{254}$ is hydrogen; or $Y_{14}$ is —C(H)= and $R^{254}$ is fluoro;
$L_{14}$ is —C(H$_2$)— or —C(O)—;
$R^{253}$ is selected from the group consisting of hydrogen, cycloalkyl, lower alkyl optionally substituted with one or more $R^{258}$, and —O—$R^{259}$;
$R^{255}$ and $R^{256}$ are hydrogen and $R^{257}$ is selected from the group consisting of fluoro, chloro, —O—$R^{260}$, —S—$R^{261}$, —S(O$_2$)—$R^{262}$, and lower alkyl optionally substituted with one or more $R^{263}$; or
$R^{255}$ and $R^{257}$ are hydrogen and $R^{256}$ is fluoro, chloro, lower alkyl optionally substituted with one or more fluoro, or lower alkoxy optionally substituted with one or more fluoro; or
$R^{256}$ and $R^{257}$ are hydrogen and $R^{255}$ is fluoro, chloro, lower alkyl optionally substituted with one or more fluoro, or lower alkoxy optionally substituted with one or more fluoro; or
$R^{255}$ is hydrogen, $R^{256}$ is fluoro, chloro, lower alkyl optionally substituted with one or more fluoro, or lower alkoxy optionally substituted with one or more fluoro and $R^{257}$ is fluoro, chloro, lower alkyl optionally substituted with one or more fluoro, or lower alkoxy optionally substituted with one or more fluoro;
$R^{258}$ is fluoro or lower alkoxy optionally substituted with one or more fluoro;
$R^{259}$ is lower alkyl, lower alkyl substituted with one or more fluoro, or lower alkyl substituted with lower alkoxy;
$R^{260}$, $R^{261}$ and $R^{262}$ are lower alkyl optionally substituted with one or more fluoro; and
$R^{263}$ is fluoro, —OH, or lower alkoxy optionally substituted with one or more fluoro.

In some embodiments of compounds of Formula Iuu, $R^{253}$ is selected from the group consisting of cycloalkyl, lower alkyl, lower alkoxy, and lower alkoxy substituted with lower alkoxy. In one embodiment, $R^{253}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{253}$ is selected from the group consisting of methyl, cyclopropyl, methoxy, ethoxy, and 2-methoxy-ethoxy.

In some embodiments of compounds of Formula Iuu, further to any of the above embodiments of Formula Iuu, $R^{255}$ and $R^{256}$ are hydrogen and $R^{257}$ is selected from the group consisting of fluoro, chloro, —O—$R^{260}$, —S—$R^{261}$, —S(O$_2$)—$R^{262}$, and lower alkyl optionally substituted with one or more $R^{263}$. In some embodiments of compounds of Formula Iuu, further to any of the above embodiments of Formula Iuu, $R^{255}$ and $R^{256}$ are hydrogen and $R^{257}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Iuu, further to any of the above embodiments of Formula Iuu, $R^{255}$ and $R^{256}$ are hydrogen and $R^{257}$ is selected from the group consisting of fluoro, chloro, lower alkoxy, lower alkylthio, lower alkylsulfonyl, and lower alkyl.

In some embodiments of compounds of Formula Iuu, further to any of the above embodiments of Formula Iuu, $R^{255}$ and $R^{257}$ are hydrogen and $R^{256}$ is fluoro, chloro, lower alkyl optionally substituted with one or more fluoro, or lower alkoxy optionally substituted with one or more fluoro. In some embodiments of compounds of Formula Iuu, further to any of the above embodiments of Formula Iuu, $R^{255}$ and $R^{257}$ are hydrogen and $R^{256}$ is fluoro, chloro, lower alkyl or lower alkoxy.

In some embodiments of compounds of Formula Iuu, further to any of the above embodiments of Formula Iuu, $R^{256}$ and $R^{257}$ are hydrogen and $R^{255}$ is fluoro, chloro, lower alkyl optionally substituted with one or more fluoro, or lower alkoxy optionally substituted with one or more fluoro. In some embodiments of compounds of Formula Iuu, further to any of the above embodiments of Formula Iuu, $R^{256}$ and $R^{257}$ are hydrogen and $R^{255}$ is fluoro, chloro, lower alkyl or lower alkoxy.

In some embodiments of compounds of Formula Iuu, further to any of the above embodiments of Formula Iuu, $R^{255}$ is hydrogen, $R^{256}$ is fluoro, chloro, lower alkyl optionally substituted with one or more fluoro, or lower alkoxy optionally substituted with one or more fluoro and $R^{257}$ is fluoro, chloro, lower alkyl optionally substituted with one or more fluoro, or lower alkoxy optionally substituted with one or more fluoro. In some embodiments of compounds of Formula Iuu, further to any of the above embodiments of Formula Iuu, $R^{255}$ is hydrogen, $R^{256}$ is fluoro, chloro, lower alkyl or lower alkoxy and $R^{257}$ is fluoro, chloro, lower alkyl or lower alkoxy. In some embodiments of compounds of Formula Iuu, further to any of the above embodiments of Formula Iuu, $R^{255}$ is hydrogen, $R^{256}$ is fluoro, chloro, or lower alkoxy and $R^{257}$ is fluoro, chloro, or lower alkoxy.

In some embodiments of compounds of Formula Iuu, further to any of the above embodiments of Formula Iuu, $L_{14}$ is —C(H$_2$)—. In some embodiments of compounds of Formula Iuu, further to any of the above embodiments of Formula Iuu, $L_{14}$ is —C(O)—.

In some embodiments of compounds of Formula Iuu, further to any of the above embodiments of Formula Iuu, $Y_{14}$ is —N= and $R^{254}$ is hydrogen. In some embodiments of compounds of Formula Iuu, further to any of the above embodiments of Formula Iuu, $Y_{14}$ is —C(H)= and $R^{254}$ is fluoro.

In a forty-seventh aspect, compounds of Formula I having the structure according to the following Formula Ivv are provided:

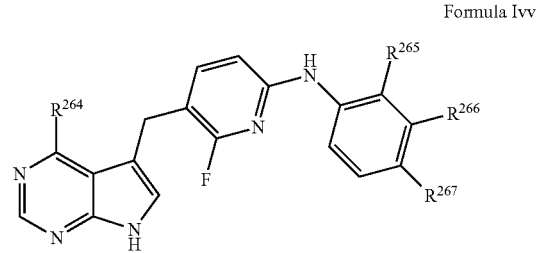

Formula Ivv or a salt, a prodrug, a solvate, a tautomer or a stereoisomer thereof, wherein:
- $R^{264}$ is selected from the group consisting of hydrogen, cycloalkyl, lower alkyl optionally substituted with one or more $R^{268}$, and —O—$R^{269}$;
- $R^{265}$ and $R^{266}$ are hydrogen and $R^{267}$ is selected from the group consisting of fluoro, chloro, —O—$R^{270}$, —S—$R^{271}$, —S(O$_2$)—$R^{272}$, and lower alkyl optionally substituted with one or more $R^{273}$; or
- $R^{265}$ and $R^{267}$ are hydrogen and $R^{266}$ is fluoro, chloro, lower alkyl optionally substituted with one or more fluoro, or lower alkoxy optionally substituted with one or more fluoro; or
- $R^{266}$ and $R^{267}$ are hydrogen and $R^{265}$ is fluoro, chloro, lower alkyl optionally substituted with one or more fluoro, or lower alkoxy optionally substituted with one or more fluoro; or
- $R^{265}$ is hydrogen, $R^{266}$ is fluoro, chloro, lower alkyl optionally substituted with one or more fluoro, or lower alkoxy optionally substituted with one or more fluoro and $R^{267}$ is fluoro, chloro, lower alkyl optionally substituted with one or more fluoro, or lower alkoxy optionally substituted with one or more fluoro;
- $R^{268}$ is fluoro or lower alkoxy optionally substituted with one or more fluoro;
- $R^{269}$ is lower alkyl, lower alkyl substituted with one or more fluoro, or lower alkyl substituted with lower alkoxy;
- $R^{270}$, $R^{271}$ and $R^{272}$ are lower alkyl optionally substituted with one or more fluoro; and
- $R^{273}$ is fluoro, —OH, or lower alkoxy optionally substituted with one or more fluoro.

In some embodiments of compounds of Formula Ivv, $R^{264}$ is selected from the group consisting of cycloalkyl, lower alkyl, lower alkoxy, and lower alkoxy substituted with lower alkoxy. In one embodiment, $R^{264}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{264}$ is selected from the group consisting of methyl, cyclopropyl, methoxy, ethoxy, and 2-methoxy-ethoxy.

In some embodiments of compounds of Formula Ivv, further to any of the above embodiments of Formula Ivv, $R^{265}$ and $R^{266}$ are hydrogen and $R^{267}$ is selected from the group consisting of fluoro, chloro, —O—$R^{270}$, —S—$R^{271}$, —S(O$_2$)—$R^{272}$, and lower alkyl optionally substituted with one or more $R^{273}$. In some embodiments of compounds of Formula Ivv, further to any of the above embodiments of Formula Ivv, $R^{265}$ and $R^{266}$ are hydrogen and $R^{267}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Ivv, further to any of the above embodiments of Formula Ivv, $R^{265}$ and $R^{266}$ are hydrogen and $R^{267}$ is selected from the group consisting of fluoro, chloro, lower alkoxy, lower alkylthio, lower alkylsulfonyl, and lower alkyl.

In some embodiments of compounds of Formula Ivv, further to any of the above embodiments of Formula Ivv, $R^{265}$ and $R^{267}$ are hydrogen and $R^{266}$ is fluoro, chloro, lower alkyl optionally substituted with one or more fluoro, or lower alkoxy optionally substituted with one or more fluoro. In some embodiments of compounds of Formula Ivv, further to any of the above embodiments of Formula Ivv, $R^{266}$ and $R^{267}$ are hydrogen and $R^{265}$ is fluoro, chloro, lower alkyl or lower alkoxy.

In some embodiments of compounds of Formula Ivv, further to any of the above embodiments of Formula Ivv, $R^{266}$ and $R^{267}$ are hydrogen and $R^{265}$ is fluoro, chloro, lower alkyl or lower alkoxy.

In some embodiments of compounds of Formula Ivv, further to any of the above embodiments of Formula Ivv, $R^{265}$ is hydrogen, $R^{266}$ is fluoro, chloro, lower alkyl optionally substituted with one or more fluoro, or lower alkoxy optionally substituted with one or more fluoro and $R^{267}$ is fluoro, chloro, lower alkyl optionally substituted with one or more fluoro, or lower alkoxy optionally substituted with one or more fluoro. In some embodiments of compounds of Formula Ivv, further to any of the above embodiments of Formula Ivv, $R^{265}$ is hydrogen, $R^{266}$ is fluoro, chloro, lower alkyl or lower alkoxy and $R^{267}$ is fluoro, chloro, lower alkyl or lower alkoxy. In some embodiments of compounds of Formula Ivv, further to any of the above embodiments of Formula Ivv, $R^{265}$ is hydrogen, $R^{266}$ is fluoro, chloro, or lower alkoxy and $R^{267}$ is fluoro, chloro, or lower alkoxy.

In a forty-eighth aspect, compounds of Formula I having the structure according to the following Formula Iww are provided:

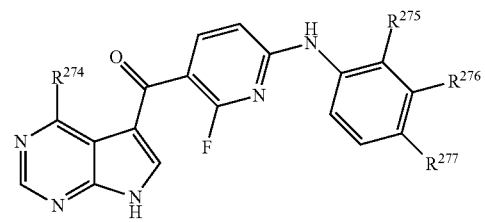

Formula Iww or a salt, a prodrug, a solvate, a tautomer or a stereoisomer thereof,
wherein:
- $R^{274}$ is selected from the group consisting of hydrogen, cycloalkyl, lower alkyl optionally substituted with one or more $R^{278}$, and —O—$R^{279}$;
- $R^{275}$ and $R^{276}$ are hydrogen and $R^{277}$ is selected from the group consisting of fluoro, chloro, —O—$R^{280}$, —S—$R^{281}$, —S(O$_2$)—$R^{282}$, and lower alkyl optionally substituted with one or more $R^{283}$; or
- $R^{275}$ and $R^{277}$ are hydrogen and $R^{276}$ is fluoro, chloro, lower alkyl optionally substituted with one or more fluoro, or lower alkoxy optionally substituted with one or more fluoro; or
- $R^{276}$ and $R^{277}$ are hydrogen and $R^{275}$ is fluoro, chloro, lower alkyl optionally substituted with one or more fluoro, or lower alkoxy optionally substituted with one or more fluoro; or
- $R^{275}$ is hydrogen, $R^{276}$ is fluoro, chloro, lower alkyl optionally substituted with one or more fluoro, or lower alkoxy optionally substituted with one or more fluoro and $R^{277}$ is fluoro, chloro, lower alkyl optionally substituted with one or more fluoro, or lower alkoxy optionally substituted with one or more fluoro;
- $R^{278}$ is fluoro or lower alkoxy optionally substituted with one or more fluoro;
- $R^{279}$ is lower alkyl, lower alkyl substituted with one or more fluoro, or lower alkyl substituted with lower alkoxy;

$R^{280}$, $R^{281}$ and $R^{282}$ are lower alkyl optionally substituted with one or more fluoro; and $R^{283}$ is fluoro, —OH, or lower alkoxy optionally substituted with one or more fluoro.

In some embodiments of compounds of Formula Iww, $R^{274}$ is selected from the group consisting of cycloalkyl, lower alkyl, lower alkoxy, and lower alkoxy substituted with lower alkyl. In one embodiment, $R^{274}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{274}$ is selected from the group consisting of methyl, cyclopropyl, methoxy, ethoxy, and 2-methoxy-ethoxy.

In some embodiments of compounds of Formula Iww, further to any of the above embodiments of Formula Iww, $R^{275}$ and $R^{276}$ are hydrogen and $R^{277}$ is selected from the group consisting of fluoro, chloro, —O—$R^{280}$, —S—$R^{281}$, —S(O$_2$)—$R^{282}$, and lower alkyl optionally substituted with one or more $R^{283}$. In some embodiments of compounds of Formula Iww, further to any of the above embodiments of Formula Iww, $R^{275}$ and $R^{276}$ are hydrogen and $R^{277}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Iww, further to any of the above embodiments of Formula Iww, $R^{275}$ and $R^{276}$ are hydrogen and $R^{277}$ is selected from the group consisting of fluoro, chloro, lower alkoxy, lower alkylthio, lower alkylsulfonyl, and lower alkyl.

In some embodiments of compounds of Formula Iww, further to any of the above embodiments of Formula Iww, $R^{275}$ and $R^{277}$ are hydrogen and $R^{276}$ is fluoro, chloro, lower alkyl optionally substituted with one or more fluoro, or lower alkoxy optionally substituted with one or more fluoro. In some embodiments of compounds of Formula Iww, further to any of the above embodiments of Formula Iww, $R^{275}$ and $R^{277}$ are hydrogen and $R^{276}$ is fluoro, chloro, lower alkyl or lower alkoxy.

In some embodiments of compounds of Formula Iww, further to any of the above embodiments of Formula Iww, $R^{276}$ and $R^{277}$ are hydrogen and $R^{275}$ is fluoro, chloro, lower alkyl optionally substituted with one or more fluoro, or lower alkoxy optionally substituted with one or more fluoro. In some embodiments of compounds of Formula Iww, further to any of the above embodiments of Formula Iww, $R^{276}$ and $R^{277}$ are hydrogen and $R^{275}$ is fluoro, chloro, lower alkyl or lower alkoxy.

In some embodiments of compounds of Formula Iww, further to any of the above embodiments of Formula Iww, $R^{275}$ is hydrogen, $R^{276}$ is fluoro, chloro, lower alkyl optionally substituted with one or more fluoro, or lower alkoxy optionally substituted with one or more fluoro and $R^{277}$ is fluoro, chloro, lower alkyl optionally substituted with one or more fluoro, or lower alkoxy optionally substituted with one or more fluoro. In some embodiments of compounds of Formula Iww, further to any of the above embodiments of Formula Iww, $R^{275}$ is hydrogen, $R^{276}$ is fluoro, chloro, lower alkyl or lower alkoxy and $R^{277}$ is fluoro, chloro, lower alkyl or lower alkoxy.

In a forty-ninth aspect, compounds of Formula I having the structure according to the following Formula Ixx are provided:

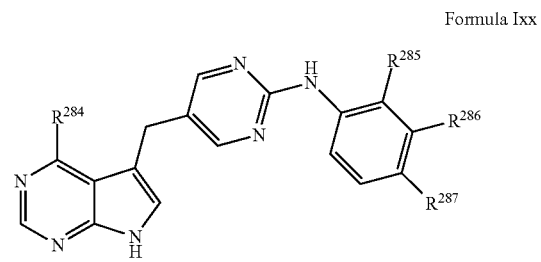

Formula Ixx or a salt, a prodrug, a solvate, a tautomer or a stereoisomer thereof,
wherein:
$R^{284}$ is selected from the group consisting of hydrogen, cycloalkyl, lower alkyl optionally substituted with one or more $R^{288}$, and —O—$R^{289}$;

$R^{285}$ and $R^{286}$ are hydrogen and $R^{287}$ is selected from the group consisting of fluoro, chloro, —O—$R^{290}$, —S—$R^{291}$, —S(O$_2$)—$R^{292}$, and lower alkyl optionally substituted with one or more $R^{293}$; or $R^{285}$ and $R^{287}$ are hydrogen and $R^{286}$ is fluoro, chloro, lower alkyl optionally substituted with one or more fluoro, or lower alkoxy optionally substituted with one or more fluoro; or $R^{286}$ and $R^{287}$ are hydrogen and $R^{285}$ is fluoro, chloro, lower alkyl optionally substituted with one or more fluoro, or lower alkoxy optionally substituted with one or more fluoro; or $R^{285}$ is hydrogen, $R^{286}$ is fluoro, chloro, lower alkyl optionally substituted with one or more fluoro, or lower alkoxy optionally substituted with one or more fluoro and $R^{287}$ is fluoro, chloro, lower alkyl optionally substituted with one or more fluoro, or lower alkoxy optionally substituted with one or more fluoro;

$R^{288}$ is fluoro or lower alkoxy optionally substituted with one or more fluoro;

$R^{289}$ is lower alkyl, lower alkyl substituted with one or more fluoro, or lower alkyl substituted with lower alkoxy;

$R^{290}$, $R^{291}$ and $R^{292}$ are lower alkyl optionally substituted with one or more fluoro; and $R^{293}$ is fluoro, —OH, or lower alkoxy optionally substituted with one or more fluoro.

In some embodiments of compounds of Formula Ixx, $R^{284}$ is selected from the group consisting of cycloalkyl, lower alkyl, lower alkoxy, and lower alkoxy substituted with lower alkoxy. In one embodiment, $R^{284}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{284}$ is selected from the group consisting of methyl, cyclopropyl, methoxy, ethoxy, and 2-methoxy-ethoxy.

In some embodiments of compounds of Formula Ixx, further to any of the above embodiments of Formula Ixx, $R^{285}$ and $R^{286}$ are hydrogen and $R^{287}$ is selected from the group consisting of fluoro, chloro, —O—$R^{290}$, —S—$R^{291}$, —S(O$_2$)—$R^{292}$, and lower alkyl optionally substituted with one or more $R^{293}$. In some embodiments of compounds of Formula Ixx, further to any of the above embodiments of Formula Ixx, $R^{285}$ and $R^{286}$ are hydrogen and $R^{287}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Ixx, further to any of the above embodiments of Formula Ixx, $R^{285}$ and $R^{286}$ are hydrogen and $R^{287}$ is selected from the group consisting of fluoro, chloro, lower alkoxy, lower alkylthio, lower alkylsulfonyl, and lower alkyl.

In some embodiments of compounds of Formula Ixx, further to any of the above embodiments of Formula Ixx, $R^{285}$ and $R^{287}$ are hydrogen and $R^{286}$ is fluoro, chloro, lower alkyl optionally substituted with one or more fluoro, or lower alkoxy optionally substituted with one or more fluoro. In some embodiments of compounds of Formula Ixx, further to any of the above embodiments of Formula Ixx, $R^{285}$ and $R^{287}$ are hydrogen and $R^{286}$ is fluoro, chloro, lower alkyl or lower alkoxy.

In some embodiments of compounds of Formula Ixx, further to any of the above embodiments of Formula Ixx, $R^{286}$ and $R^{287}$ are hydrogen and $R^{285}$ is fluoro, chloro, lower alkyl optionally substituted with one or more fluoro, or lower alkoxy optionally substituted with one or more fluoro. In some embodiments of compounds of Formula Ixx, further to any of the above embodiments of Formula Ixx, $R^{286}$ and $R^{287}$ are hydrogen and $R^{285}$ is fluoro, chloro, lower alkyl or lower alkoxy.

In some embodiments of compounds of Formula Ixx, further to any of the above embodiments of Formula Ixx, $R^{285}$ is hydrogen, $R^{286}$ is fluoro, chloro, lower alkyl optionally substituted with one or more fluoro, or lower alkoxy optionally substituted with one or more fluoro and $R^{287}$ is fluoro, chloro, lower alkyl optionally substituted with one or more fluoro, or lower alkoxy optionally substituted with one or more fluoro. In some embodiments of compounds of Formula Ixx, further to any of the above embodiments of Formula Ixx, $R^{285}$ is hydrogen, $R^{286}$ is fluoro, chloro, lower alkyl or lower alkoxy and $R^{287}$ is fluoro, chloro, lower alkyl or lower alkoxy. In some embodiments of compounds of Formula Ixx, further to any of the above embodiments of Formula Ixx, $R^{285}$ is hydrogen, $R^{286}$ is fluoro, chloro, or lower alkoxy and $R^{287}$ is fluoro, chloro, or lower alkoxy.

In a fiftieth aspect, compounds of Formula I having the structure according to the following Formula Iyy are provided:

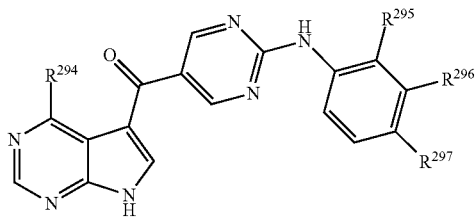

Formula Iyy or a salt, a prodrug, a solvate, a tautomer or a stereoisomer thereof,
wherein:
$R^{294}$ is selected from the group consisting of hydrogen, cycloalkyl, lower alkyl optionally substituted with one or more $R^{298}$, and —O—$R^{299}$;
$R^{295}$ and $R^{296}$ are hydrogen and $R^{297}$ is selected from the group consisting of fluoro, chloro, —O—$R^{300}$, —S—$R^{301}$, —S(O$_2$)—$R^{302}$, and lower alkyl optionally substituted with one or more $R^{303}$; or
$R^{295}$ and $R^{297}$ are hydrogen and $R^{296}$ is fluoro, chloro, lower alkyl optionally substituted with one or more fluoro, or lower alkoxy optionally substituted with one or more fluoro; or $R^{296}$ and $R^{297}$ are hydrogen and $R^{295}$ is fluoro, chloro, lower alkyl optionally substituted with one or more fluoro, or lower alkoxy optionally substituted with one or more fluoro; or
$R^{295}$ is hydrogen, $R^{296}$ is fluoro, chloro, lower alkyl optionally substituted with one or more fluoro, or lower alkoxy optionally substituted with one or more fluoro and $R^{297}$ is fluoro, chloro, lower alkyl optionally substituted with one or more fluoro, or lower alkoxy optionally substituted with one or more fluoro;
$R^{298}$ is fluoro or lower alkoxy optionally substituted with one or more fluoro;
$R^{299}$ is lower alkyl, lower alkyl substituted with one or more fluoro, or lower alkyl substituted with lower alkoxy;
$R^{300}$, $R^{301}$ and $R^{302}$ are lower alkyl optionally substituted with one or more fluoro; and
$R^{303}$ is fluoro, —OH, or lower alkoxy optionally substituted with one or more fluoro.

In some embodiments of compounds of Formula Iyy, $R^{294}$ is selected from the group consisting of cycloalkyl, lower alkyl, lower alkoxy, and lower alkoxy substituted with lower alkoxy. In one embodiment, $R^{294}$ is selected from the group consisting of $C_{3-6}$ cycloalkyl, $C_{1-3}$ alkyl, $C_{1-3}$ alkoxy, and $C_{1-3}$ alkoxy substituted with $C_{1-3}$ alkoxy. In one embodiment, $R^{294}$ is selected from the group consisting of methyl, cyclopropyl, methoxy, ethoxy, and 2-methoxy-ethoxy.

In some embodiments of compounds of Formula Iyy, further to any of the above embodiments of Formula Iyy, $R^{295}$ and $R^{296}$ are hydrogen and $R^{297}$ is selected from the group consisting of fluoro, chloro, —O—$R^{300}$, —S—$R^{301}$, —S(O$_2$)—$R^{302}$, and lower alkyl optionally substituted with one or more $R^{303}$. In some embodiments of compounds of Formula Iyy, further to any of the above embodiments of Formula Iyy, $R^{295}$ and $R^{296}$ are hydrogen and $R^{297}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Iyy, further to any of the above embodiments of Formula Iyy, $R^{295}$ and $R^{296}$ are hydrogen and $R^{297}$ is selected from the group consisting of fluoro, chloro, lower alkoxy, lower alkylthio, lower alkylsulfonyl, and lower alkyl.

In some embodiments of compounds of Formula Iyy, further to any of the above embodiments of Formula Iyy, $R^{295}$ and $R^{297}$ are hydrogen and $R^{296}$ is fluoro, chloro, lower alkyl optionally substituted with one or more fluoro, or lower alkoxy optionally substituted with one or more fluoro. In some embodiments of compounds of Formula Iyy, further to any of the above embodiments of Formula Iyy, $R^{295}$ and $R^{297}$ are hydrogen and $R^{296}$ is fluoro, chloro, lower alkyl or lower alkoxy.

In some embodiments of compounds of Formula Iyy, further to any of the above embodiments of Formula Iyy, $R^{296}$ and $R^{297}$ are hydrogen and $R^{295}$ is fluoro, chloro, lower alkyl optionally substituted with one or more fluoro, or lower alkoxy optionally substituted with one or more fluoro. In some embodiments of compounds of Formula Iyy, further to any of the above embodiments of Formula Iyy, $R^{296}$ and $R^{297}$ are hydrogen and $R^{295}$ is fluoro, chloro, lower alkyl or lower alkoxy.

In some embodiments of compounds of Formula Iyy, further to any of the above embodiments of Formula Iyy, $R^{295}$ is hydrogen, $R^{296}$ is fluoro, chloro, lower alkyl optionally substituted with one or more fluoro, or lower alkoxy optionally substituted with one or more fluoro and $R^{297}$ is fluoro, chloro, lower alkyl optionally substituted with one or more fluoro, or lower alkoxy optionally substituted with one or more fluoro. In some embodiments of compounds of Formula Iyy, further to any of the above embodiments of Formula Iyy, $R^{295}$ is hydrogen, $R^{296}$ is fluoro, chloro, lower alkyl or lower alkoxy and $R^{297}$ is fluoro, chloro, lower alkyl or lower alkoxy. In some embodiments of compounds of Formula Iyy, further to any of the above embodiments of Formula Iyy, $R^{295}$ is hydrogen, $R^{296}$ is fluoro, chloro, or lower alkoxy and $R^{297}$ is fluoro, chloro, or lower alkoxy.

In a fifty-first aspect, compounds of Formula I having the structure according to the following Formula Izz are provided:

Formula Izz

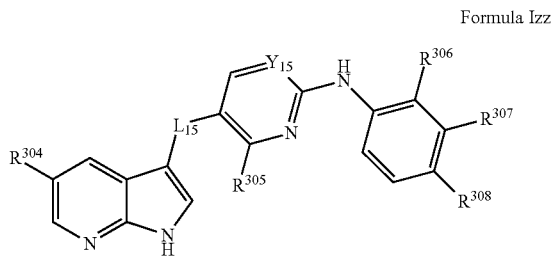

or a salt, a prodrug, a solvate, a tautomer or a stereoisomer thereof,
wherein:
$Y_{15}$ is —N═ and $R^{305}$ is hydrogen; or $Y_{15}$ is —C(H)═ and $R^{305}$ is fluoro;
$L_{15}$ is —C(H$_2$)— or —C(O)—;
$R^{304}$ is hydrogen, fluoro, chloro, or lower alkyl optionally substituted with one or more fluoro;
$R^{306}$ and $R^{307}$ are hydrogen and $R^{308}$ is selected from the group consisting of fluoro, chloro, —O—$R^{309}$, —S—$R^{310}$, —S(O$_2$)—$R^{311}$, and lower alkyl optionally substituted with one or more $R^{312}$; or
$R^{306}$ and $R^{308}$ are hydrogen and $R^{307}$ is fluoro, chloro, lower alkyl optionally substituted with one or more fluoro, or lower alkoxy optionally substituted with one or more fluoro; or
$R^{307}$ and $R^{308}$ are hydrogen and $R^{306}$ is fluoro, chloro, lower alkyl optionally substituted with one or more fluoro, or lower alkoxy optionally substituted with one or more fluoro; or
$R^{306}$ is hydrogen, $R^{307}$ is fluoro, chloro, lower alkyl optionally substituted with one or more fluoro, or lower alkoxy optionally substituted with one or more fluoro and $R^{308}$ is fluoro, chloro, lower alkyl optionally substituted with one or more fluoro, or lower alkoxy optionally substituted with one or more fluoro;
$R^{309}$, $R^{310}$ and $R^{311}$ are lower alkyl optionally substituted with one or more fluoro; and
$R^{312}$ is fluoro, —OH, or lower alkoxy optionally substituted with one or more fluoro.

In some embodiments of compounds of Formula Izz, $R^{304}$ is hydrogen, chloro or lower alkyl. In one embodiment, $R^{304}$ is chloro or $C_{1-3}$ alkyl. In one embodiment, $R^{304}$ is chloro or methyl.

In some embodiments of compounds of Formula Izz, further to any of the above embodiments of Formula Izz, $R^{306}$ and $R^{307}$ are hydrogen and $R^{308}$ is selected from the group consisting of fluoro, chloro, —O—$R^{309}$, —S—$R^{310}$, —S(O$_2$)—$R^{311}$, and lower alkyl optionally substituted with one or more $R^{312}$. In some embodiments of compounds of Formula Izz, further to any of the above embodiments of Formula Izz, $R^{306}$ and $R^{307}$ are hydrogen and $R^{308}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Izz, further to any of the above embodiments of Formula Izz, $R^{306}$ and $R^{307}$ are hydrogen and $R^{308}$ is selected from the group consisting of fluoro, chloro, lower alkoxy, lower alkylthio, lower alkylsulfonyl, and lower alkyl.

In some embodiments of compounds of Formula Izz, further to any of the above embodiments of Formula Izz, $R^{306}$ and $R^{308}$ are hydrogen and $R^{307}$ is fluoro, chloro, lower alkyl optionally substituted with one or more fluoro, or lower alkoxy optionally substituted with one or more fluoro. In some embodiments of compounds of Formula Izz, further to any of the above embodiments of Formula Izz, $R^{306}$ and $R^{308}$ are hydrogen and $R^{307}$ is fluoro, chloro, lower alkyl or lower alkoxy.

In some embodiments of compounds of Formula Izz, further to any of the above embodiments of Formula Izz, $R^{307}$ and $R^{308}$ are hydrogen and $R^{306}$ is fluoro, chloro, lower alkyl optionally substituted with one or more fluoro, or lower alkoxy optionally substituted with one or more fluoro. In some embodiments of compounds of Formula Izz, further to any of the above embodiments of Formula Izz, $R^{307}$ and $R^{308}$ are hydrogen and $R^{306}$ is fluoro, chloro, lower alkyl or lower alkoxy.

In some embodiments of compounds of Formula Izz, further to any of the above embodiments of Formula Izz, $R^{306}$ is hydrogen, $R^{307}$ is fluoro, chloro, lower alkyl optionally substituted with one or more fluoro, or lower alkoxy optionally substituted with one or more fluoro and $R^{308}$ is fluoro, chloro, lower alkyl optionally substituted with one or more fluoro, or lower alkoxy optionally substituted with one or more fluoro. In some embodiments of compounds of Formula Izz, further to any of the above embodiments of Formula Izz, $R^{306}$ is hydrogen, $R^{307}$ is fluoro, chloro, lower alkyl or lower alkoxy and $R^{308}$ is fluoro, chloro, lower alkyl or lower alkoxy. In some embodiments of compounds of Formula Izz, further to any of the above embodiments of Formula Izz, $R^{306}$ is hydrogen, $R^{307}$ is fluoro, chloro, or lower alkoxy and $R^{308}$ is fluoro, chloro, or lower alkoxy.

In some embodiments of compounds of Formula Izz, further to any of the above embodiments of Formula Izz, $L_{15}$ is —C(H$_2$)—. In some embodiments of compounds of Formula Izz, further to any of the above embodiments of Formula Izz, $L_{15}$ is —C(O)—.

In some embodiments of compounds of Formula Izz, further to any of the above embodiments of Formula Izz, $Y_{15}$ is —N═ and $R^{305}$ is hydrogen. In some embodiments of compounds of Formula Izz, further to any of the above embodiments of Formula Izz, $Y_{15}$ is —C(H)═ and $R^{305}$ is fluoro.

In a fifty-second aspect, compounds of Formula I having the structure according to the following Formula Iab are provided:

Formula Iab

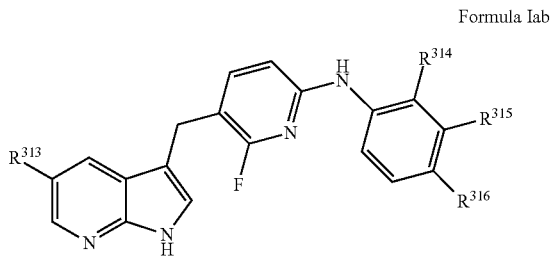

or a salt, a prodrug, a solvate, a tautomer or a stereoisomer thereof, wherein:
$R^{313}$ is hydrogen, fluoro, chloro, or lower alkyl optionally substituted with one or more fluoro;
$R^{314}$ and $R^{315}$ are hydrogen and $R^{316}$ is selected from the group consisting of fluoro, chloro, —O—$R^{317}$, —S—$R^{318}$, —S(O$_2$)—$R^{319}$, and lower alkyl optionally substituted with one or more $R^{320}$; or
$R^{314}$ and $R^{316}$ are hydrogen and $R^{315}$ is fluoro, chloro, lower alkyl optionally substituted with one or more fluoro, or lower alkoxy optionally substituted with one or more fluoro; or
$R^{315}$ and $R^{316}$ are hydrogen and $R^{314}$ is fluoro, chloro, lower alkyl optionally substituted with one or more fluoro, or lower alkoxy optionally substituted with one or more fluoro; or
$R^{314}$ is hydrogen, $R^{315}$ is fluoro, chloro, lower alkyl optionally substituted with one or more fluoro, or lower alkoxy optionally substituted with one or more fluoro and $R^{316}$ is fluoro, chloro, lower alkyl optionally substituted with one or more fluoro, or lower alkoxy optionally substituted with one or more fluoro;
$R^{317}$, $R^{318}$ and $R^{319}$ are lower alkyl optionally substituted with one or more fluoro; and
$R^{320}$ is fluoro, —OH, or lower alkoxy optionally substituted with one or more fluoro.

In some embodiments of compounds of Formula Iab, $R^{313}$ is hydrogen, chloro or lower alkyl. In one embodiment, $R^{313}$ is chloro or $C_{1-3}$ alkyl. In one embodiment, $R^{313}$ is chloro or methyl.

In some embodiments of compounds of Formula Iab, further to any of the above embodiments of Formula Iab, $R^{314}$ and $R^{315}$ are hydrogen and $R^{316}$ is selected from the group consisting of fluoro, chloro, —O—$R^{317}$, —S—$R^{318}$, —S(O$_2$)—$R^{319}$, and lower alkyl optionally substituted with one or more $R^{320}$. In some embodiments of compounds of Formula Iab, further to any of the above embodiments of Formula Iab, $R^{314}$ and $R^{315}$ are hydrogen and $R^{316}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Iab, further to any of the above embodiments of Formula Iab, $R^{314}$ and $R^{315}$ are hydrogen and $R^{316}$ is selected from the group consisting of fluoro, chloro, lower alkoxy, lower alkylthio, lower alkylsulfonyl, and lower alkyl.

In some embodiments of compounds of Formula Iab, further to any of the above embodiments of Formula Iab, $R^{314}$ and $R^{316}$ are hydrogen and $R^{315}$ is fluoro, chloro, lower alkyl optionally substituted with one or more fluoro, or lower alkoxy optionally substituted with one or more fluoro. In some embodiments of compounds of Formula Iab, further to any of the above embodiments of Formula Iab, $R^{314}$ and $R^{316}$ are hydrogen and $R^{315}$ is fluoro, chloro, lower alkyl or lower alkoxy.

In some embodiments of compounds of Formula Iab, further to any of the above embodiments of Formula Iab, $R^{315}$ and $R^{316}$ are hydrogen and $R^{314}$ is fluoro, chloro, lower alkyl optionally substituted with one or more fluoro, or lower alkoxy optionally substituted with one or more fluoro. In some embodiments of compounds of Formula Iab, further to any of the above embodiments of Formula Iab, $R^{315}$ and $R^{316}$ are hydrogen and $R^{314}$ is fluoro, chloro, lower alkyl or lower alkoxy.

In some embodiments of compounds of Formula Iab, further to any of the above embodiments of Formula Iab, $R^{314}$ is hydrogen, $R^{315}$ is fluoro, chloro, lower alkyl optionally substituted with one or more fluoro, or lower alkoxy optionally substituted with one or more fluoro and $R^{316}$ is fluoro, chloro, lower alkyl optionally substituted with one or more fluoro, or lower alkoxy optionally substituted with one or more fluoro. In some embodiments of compounds of Formula Iab, further to any of the above embodiments of Formula Iab, $R^{314}$ is hydrogen, $R^{315}$ is fluoro, chloro, lower alkyl or lower alkoxy and $R^{316}$ is fluoro, chloro, lower alkyl or lower alkoxy. In some embodiments of compounds of Formula Iab, further to any of the above embodiments of Formula Iab, $R^{314}$ is hydrogen, $R^{315}$ is fluoro, chloro, or lower alkoxy and $R^{316}$ is fluoro, chloro, or lower alkoxy.

In a fifty-third aspect, compounds of Formula I having the structure according to the following Formula Iac are provided:

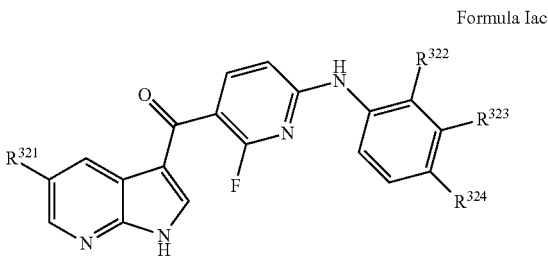

Formula Iac or a salt, a prodrug, a solvate, a tautomer or a stereoisomer thereof,
wherein:
$R^{321}$ is hydrogen, fluoro, chloro, or lower alkyl optionally substituted with one or more fluoro;
$R^{322}$ and $R^{323}$ are hydrogen and $R^{324}$ is selected from the group consisting of fluoro, chloro, —O—$R^{325}$, —S—$R^{326}$, —S(O$_2$)—$R^{327}$, and lower alkyl optionally substituted with one or more $R^{328}$; or
$R^{322}$ and $R^{324}$ are hydrogen and $R^{323}$ is fluoro, chloro, lower alkyl optionally substituted with one or more fluoro, or lower alkoxy optionally substituted with one or more fluoro; or
$R^{323}$ and $R^{324}$ are hydrogen and $R^{322}$ is fluoro, chloro, lower alkyl optionally substituted with one or more fluoro, or lower alkoxy optionally substituted with one or more fluoro; or
$R^{322}$ is hydrogen, $R^{323}$ is fluoro, chloro, lower alkyl optionally substituted with one or more fluoro, or lower alkoxy optionally substituted with one or more fluoro and $R^{324}$ is fluoro, chloro, lower alkyl optionally substituted with one or more fluoro, or lower alkoxy optionally substituted with one or more fluoro;
$R^{325}$, $R^{326}$ and $R^{327}$ are lower alkyl optionally substituted with one or more fluoro; and
$R^{328}$ is fluoro, —OH, or lower alkoxy optionally substituted with one or more fluoro.

In some embodiments of compounds of Formula Iac, $R^{321}$ is hydrogen, chloro or lower alkyl. In one embodiment, $R^{321}$ is chloro or $C_{1-3}$ alkyl. In one embodiment, $R^{321}$ is chloro or methyl.

In some embodiments of compounds of Formula Iac, further to any of the above embodiments of Formula Iac, $R^{322}$ and $R^{323}$ are hydrogen and $R^{324}$ is selected from the group consisting of fluoro, chloro, —O—$R^{325}$, —S—$R^{326}$, —S(O$_2$)—$R^{327}$, and lower alkyl optionally substituted with one or more $R^{328}$. In some embodiments of compounds of Formula Iac, further to any of the above embodiments of Formula Iac, $R^{322}$ and $R^{323}$ are hydrogen and $R^{324}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Iac, further to any of the above embodiments of Formula Iac, $R^{322}$ and $R^{323}$ are hydrogen and $R^{324}$ is selected from the group consisting of fluoro, chloro, lower alkoxy, lower alkylthio, lower alkylsulfonyl, and lower alkyl.

In some embodiments of compounds of Formula Iac, further to any of the above embodiments of Formula Iac, $R^{322}$ and $R^{324}$ are hydrogen and $R^{323}$ is fluoro, chloro, lower alkyl optionally substituted with one or more fluoro, or lower alkoxy optionally substituted with one or more fluoro. In some embodiments of compounds of Formula Iac, further to any of the above embodiments of Formula Iac, $R^{322}$ and $R^{324}$ are hydrogen and $R^{323}$ is fluoro, chloro, lower alkyl or lower alkoxy.

In some embodiments of compounds of Formula Iac, further to any of the above embodiments of Formula Iac, $R^{323}$ and $R^{324}$ are hydrogen and $R^{322}$ is fluoro, chloro, lower alkyl optionally substituted with one or more fluoro, or lower alkoxy optionally substituted with one or more fluoro. In some embodiments of compounds of Formula Iac, further to any of the above embodiments of Formula Iac, $R^{323}$ and $R^{324}$ are hydrogen and $R^{322}$ is fluoro, chloro, lower alkyl or lower alkoxy.

In some embodiments of compounds of Formula Iac, further to any of the above embodiments of Formula Iac, $R^{322}$ is hydrogen, $R^{323}$ is fluoro, chloro, lower alkyl optionally substituted with one or more fluoro, or lower alkoxy optionally substituted with one or more fluoro and $R^{324}$ is fluoro, chloro, lower alkyl optionally substituted with one or more fluoro, or lower alkoxy optionally substituted with one or more fluoro. In some embodiments of compounds of Formula Iac, further to any of the above embodiments of Formula Iac, $R^{322}$ is hydrogen, $R^{323}$ is fluoro, chloro, lower alkyl or lower alkoxy and $R^{324}$ is fluoro, chloro, lower alkyl or lower alkoxy. In some embodiments of compounds of Formula Iac, further to any of the above embodiments of Formula Iac, $R^{322}$ is hydrogen, $R^{323}$ is fluoro, chloro, or lower alkoxy and $R^{324}$ is fluoro, chloro, or lower alkoxy.

In a fifty-fourth aspect, compounds of Formula I having the structure according to the following Formula Iad are provided:

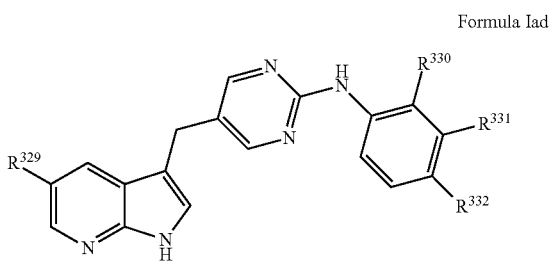

Formula Iad or a salt, a prodrug, a solvate, a tautomer or a stereoisomer thereof,
wherein:
$R^{329}$ is hydrogen, fluoro, chloro, or lower alkyl optionally substituted with one or more fluoro;
$R^{330}$ and $R^{331}$ are hydrogen and $R^{332}$ is selected from the group consisting of fluoro, chloro, —O—$R^{333}$, —S—$R^{334}$, —S($O_2$)—$R^{335}$, and lower alkyl optionally substituted with one or more $R^{336}$; or $R^{330}$ and $R^{332}$ are hydrogen and $R^{331}$ is fluoro, chloro, lower alkyl optionally substituted with one or more fluoro, or lower alkoxy optionally substituted with one or more fluoro; or
$R^{331}$ and $R^{332}$ are hydrogen and $R^{330}$ is fluoro, chloro, lower alkyl optionally substituted with one or more fluoro, or lower alkoxy optionally substituted with one or more fluoro; or
$R^{330}$ is hydrogen, $R^{331}$ is fluoro, chloro, lower alkyl optionally substituted with one or more fluoro, or lower alkoxy optionally substituted with one or more fluoro and $R^{332}$ is fluoro, chloro, lower alkyl optionally substituted with one or more fluoro, or lower alkoxy optionally substituted with one or more fluoro;
$R^{333}$, $R^{334}$ and $R^{335}$ are lower alkyl optionally substituted with one or more fluoro; and
$R^{336}$ is fluoro, —OH, or lower alkoxy optionally substituted with one or more fluoro.

In some embodiments of compounds of Formula Iad, $R^{329}$ is hydrogen, chloro or lower alkyl. In one embodiment, $R^{329}$ is chloro or $C_{1-3}$ alkyl. In one embodiment, $R^{329}$ is chloro or methyl.

In some embodiments of compounds of Formula Iad, further to any of the above embodiments of Formula Iad, $R^{330}$ and $R^{331}$ are hydrogen and $R^{332}$ is selected from the group consisting of fluoro, chloro, —O—$R^{333}$, —S—$R^{334}$, —S($O_2$)—$R^{335}$, and lower alkyl optionally substituted with one or more $R^{336}$. In some embodiments of compounds of Formula Iad, further to any of the above embodiments of Formula Iad, $R^{330}$ and $R^{331}$ are hydrogen and $R^{332}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Iad, further to any of the above embodiments of Formula Iad, $R^{330}$ and $R^{331}$ are hydrogen and $R^{332}$ is selected from the group consisting of fluoro, chloro, lower alkoxy, lower alkylthio, lower alkylsulfonyl, and lower alkyl.

In some embodiments of compounds of Formula Iad, further to any of the above embodiments of Formula Iad, $R^{330}$ and $R^{332}$ are hydrogen and $R^{331}$ is fluoro, chloro, lower alkyl optionally substituted with one or more fluoro, or lower alkoxy optionally substituted with one or more fluoro. In some embodiments of compounds of Formula Iad, further to any of the above embodiments of Formula Iad, $R^{330}$ and $R^{332}$ are hydrogen and $R^{331}$ is fluoro, chloro, lower alkyl or lower alkoxy.

In some embodiments of compounds of Formula Iad, further to any of the above embodiments of Formula Iad, $R^{331}$ and $R^{332}$ are hydrogen and $R^{330}$ is fluoro, chloro, lower alkyl optionally substituted with one or more fluoro, or lower alkoxy optionally substituted with one or more fluoro. In some embodiments of compounds of Formula Iad, further to any of the above embodiments of Formula Iad, $R^{331}$ and $R^{332}$ are hydrogen and $R^{330}$ is fluoro, chloro, lower alkyl or lower alkoxy.

In some embodiments of compounds of Formula Iad, further to any of the above embodiments of Formula Iad, $R^{330}$ is hydrogen, $R^{331}$ is fluoro, chloro, lower alkyl optionally substituted with one or more fluoro, or lower alkoxy optionally substituted with one or more fluoro and $R^{332}$ is fluoro, chloro, lower alkyl optionally substituted with one or more fluoro, or lower alkoxy optionally substituted with one or more fluoro. In some embodiments of compounds of Formula Iad, further to any of the above embodiments of Formula Iad, $R^{330}$ is hydrogen, $R^{331}$ is fluoro, chloro, lower alkyl or lower alkoxy and $R^{332}$ is fluoro, chloro, lower alkyl or lower alkoxy. In some embodiments of compounds of Formula Iad, further to any of the above embodiments of Formula Iad, $R^{330}$ is hydrogen, $R^{331}$ is fluoro, chloro, or lower alkoxy and $R^{332}$ is fluoro, chloro, or lower alkoxy.

In a fifty-fifth aspect, compounds of Formula I having the structure according to the following Formula Iae are provided:

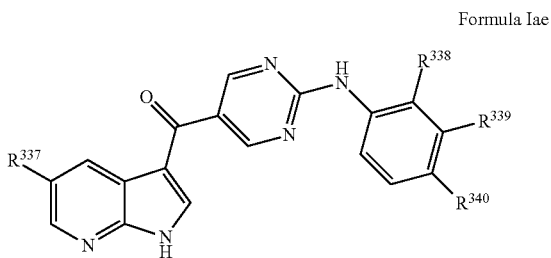

Formula Iae or a salt, a prodrug, a solvate, a tautomer or a stereoisomer thereof,
wherein:
$R^{337}$ is hydrogen, fluoro, chloro, or lower alkyl optionally substituted with one or more fluoro;
$R^{338}$ and $R^{339}$ are hydrogen and $R^{340}$ is selected from the group consisting of fluoro, chloro, —O—$R^{341}$, —S—$R^{342}$, —S($O_2$)—$R^{343}$, and lower alkyl optionally substituted with one or more $R^{344}$; or
$R^{338}$ and $R^{340}$ are hydrogen and $R^{339}$ is fluoro, chloro, lower alkyl optionally substituted with one or more fluoro, or lower alkoxy optionally substituted with one or more fluoro; or
$R^{339}$ and $R^{340}$ are hydrogen and $R^{338}$ is fluoro, chloro, lower alkyl optionally substituted with one or more fluoro, or lower alkoxy optionally substituted with one or more fluoro; or
$R^{338}$ is hydrogen, $R^{339}$ is fluoro, chloro, lower alkyl optionally substituted with one or more fluoro, or lower alkoxy optionally substituted with one or more fluoro and $R^{340}$ is fluoro, chloro, lower alkyl optionally substituted with one or more fluoro, or lower alkoxy optionally substituted with one or more fluoro;
$R^{341}$, $R^{342}$ and $R^{343}$ are lower alkyl optionally substituted with one or more fluoro; and
$R^{344}$ is fluoro, —OH, or lower alkoxy optionally substituted with one or more fluoro.

In some embodiments of compounds of Formula Iae, $R^{337}$ is hydrogen, chloro or lower alkyl. In one embodiment, $R^{337}$ is chloro or $C_{1-3}$ alkyl. In one embodiment, $R^{337}$ is chloro or methyl.

In some embodiments of compounds of Formula Iae, further to any of the above embodiments of Formula Iae, $R^{338}$ and $R^{339}$ are hydrogen and $R^{340}$ is selected from the group consisting of fluoro, chloro, —O—$R^{341}$, —S—$R^{342}$, —S($O_2$)—$R^{343}$, and lower alkyl optionally substituted with one or more $R^{344}$. In some embodiments of compounds of Formula Iae, further to any of the above embodiments of Formula Iae, $R^{338}$ and $R^{339}$ are hydrogen and $R^{340}$ is selected from the group consisting of fluoro, chloro, lower alkoxy, lower alkylthio, lower alkylsulfonyl, and lower alkyl optionally substituted with one or more fluoro or —OH. In some embodiments of compounds of Formula Iae, further to any of the above embodiments of Formula Iae, $R^{338}$ and $R^{339}$ are hydrogen and $R^{340}$ is selected from the group consisting of fluoro, chloro, lower alkoxy, lower alkylthio, lower alkylsulfonyl, and lower alkyl.

In some embodiments of compounds of Formula Iae, further to any of the above embodiments of Formula Iae, $R^{338}$ and $R^{340}$ are hydrogen and $R^{339}$ is fluoro, chloro, lower alkyl optionally substituted with one or more fluoro, or lower alkoxy optionally substituted with one or more fluoro. In some embodiments of compounds of Formula Iae, further to any of the above embodiments of Formula Iae, $R^{338}$ and $R^{340}$ are hydrogen and $R^{339}$ is fluoro, chloro, lower alkyl or lower alkoxy.

In some embodiments of compounds of Formula Iae, further to any of the above embodiments of Formula Iae, $R^{339}$ and $R^{340}$ are hydrogen and $R^{338}$ is fluoro, chloro, lower alkyl optionally substituted with one or more fluoro, or lower alkoxy optionally substituted with one or more fluoro. In some embodiments of compounds of Formula Iae, further to any of the above embodiments of Formula Iae, $R^{339}$ and $R^{340}$ are hydrogen and $R^{338}$ is fluoro, chloro, lower alkyl or lower alkoxy.

In some embodiments of compounds of Formula Iae, further to any of the above embodiments of Formula Iae, $R^{338}$ is hydrogen, $R^{339}$ is fluoro, chloro, lower alkyl optionally substituted with one or more fluoro, or lower alkoxy optionally substituted with one or more fluoro and $R^{340}$ is fluoro, chloro, lower alkyl optionally substituted with one or more fluoro, or lower alkoxy optionally substituted with one or more fluoro. In some embodiments of compounds of Formula Iae, further to any of the above embodiments of Formula Iae, $R^{338}$ is hydrogen, $R^{339}$ is fluoro, chloro, lower alkyl or lower alkoxy and $R^{340}$ is fluoro, chloro, lower alkyl or lower alkoxy. In some embodiments of compounds of Formula Iae, further to any of the above embodiments of Formula Iae, $R^{338}$ is hydrogen, $R^{339}$ is fluoro, chloro, or lower alkoxy and $R^{340}$ is fluoro, chloro, or lower alkoxy.

In one embodiment of compounds of Formula I, the compound is selected from the group consisting of those set forth in Table 1.

TABLE 1

[5-(5-Chloro-1H-pyrrolo[2,3-b]pyridin-3-ylmethyl)-pyrimidin-2-yl]-cyclohexyl-amine (P-3001),
[5-(5-Chloro-1H-pyrrolo[2,3-b]pyridin-3-ylmethyl)-pyrimidin-2-yl]-cyclopentyl-amine (P-3003),
[5-(5-Chloro-1H-pyrrolo[2,3-b]pyridin-3-ylmethyl)-pyrimidin-2-yl]-(4,4-difluoro-cyclohexyl)-amine (P-3004),
[5-(5-Chloro-1H-pyrrolo[2,3-b]pyridin-3-ylmethyl)-pyrimidin-2-yl]-cyclopropyl-amine (P-3005),
[5-(5-Chloro-1H-pyrrolo[2,3-b]pyridin-3-ylmethyl)-pyrimidin-2-yl]-cycloheptyl-amine (P-3006),
[5-(5-Chloro-1H-pyrrolo[2,3-b]pyridin-3-ylmethyl)-pyrimidin-2-yl]-cyclobutyl-amine (P-3007),
Cyclohexyl-[6-fluoro-5-(5-methyl-1H-pyrrolo[2,3-b]pyridin-3-ylmethyl)-pyridin-2-yl]-amine (P-3008),
[5-(5-Chloro-1H-pyrrolo[2,3-b]pyridin-3-ylmethyl)-pyrimidin-2-yl]-(4-methyl-cyclohexyl)-amine (P-3009),
(4-Fluoro-phenyl)-[5-(5-methyl-1H-pyrrolo[2,3-b]pyridin-3-ylmethyl)-pyrimidin-2-yl]-amine (P-3010),
(4-Chloro-phenyl)-[5-(5-chloro-1H-pyrrolo[2,3-b]pyridin-3-ylmethyl)-pyrimidin-2-yl]-amine (P-3011),
[5-(5-Chloro-1H-pyrrolo[2,3-b]pyridin-3-ylmethyl)-pyrimidin-2-yl]-(4-fluoro-phenyl)-amine (P-3012),
[5-(5-Chloro-1H-pyrrolo[2,3-b]pyridin-3-ylmethyl)-6-fluoro-pyridin-2-yl]-(4,4-difluoro-cyclohexyl)-amine (P-3013), TABLE 1-continued

[5-(5-Chloro-1H-pyrrolo[2,3-b]pyridin-3-ylmethyl)-pyrimidin-2-yl]-(2-fluoro-phenyl)-amine (P-3014),
(2-Chloro-phenyl)-[5-(5-chloro-1H-pyrrolo[2,3-b]pyridin-3-ylmethyl)-pyrimidin-2-yl]-amine (P-3015),
[5-(5-Chloro-1H-pyrrolo[2,3-b]pyridin-3-ylmethyl)-pyrimidin-2-yl]-(2-methoxy-phenyl)-amine (P-3016),
[5-(5-Chloro-1H-pyrrolo[2,3-b]pyridin-3-ylmethyl)-pyrimidin-2-yl]-(3-fluoro-phenyl)-amine (P-3017),
[5-(5-Methyl-1H-pyrrolo[2,3-b]pyridin-3-ylmethyl)-pyrimidin-2-yl]-(6-trifluoromethyl-pyridin-3-yl)-amine (P-3018),
[6-Fluoro-5-(5-methyl-1H-pyrrolo[2,3-b]pyridin-3-ylmethyl)-pyridin-2-yl]-(6-methoxy-pyridin-3-yl)-amine (P-3019),
(6-Methoxy-pyridin-3-yl)-[5-(5-methyl-1H-pyrrolo[2,3-b]pyridin-3-ylmethyl)-pyrimidin-2-yl]-amine (P-3020),
(4-Methoxy-phenyl)-[5-(5-methyl-1H-pyrrolo[2,3-b]pyridin-3-ylmethyl)-pyrimidin-2-yl]-amine (P-3021),
(4-Fluoro-3-methoxy-phenyl)-[5-(5-methyl-1H-pyrrolo[2,3-b]pyridin-3-ylmethyl)-pyrimidin-2-yl]-amine (P-3022),
(3-Fluoro-4-methoxy-phenyl)-[5-(5-methyl-1H-pyrrolo[2,3-b]pyridin-3-ylmethyl)-pyrimidin-2-yl]-amine (P-3023),
[5-(5-Methyl-1H-pyrrolo[2,3-b]pyridin-3-ylmethyl)-pyrimidin-2-yl]-(4-propoxy-phenyl)-amine (P-3024),
(4-Ethyl-phenyl)-[5-(5-methyl-1H-pyrrolo[2,3-b]pyridin-3-ylmethyl)-pyrimidin-2-yl]-amine (P-3025),
(4-Ethoxy-phenyl)-[5-(5-methyl-1H-pyrrolo[2,3-b]pyridin-3-ylmethyl)-pyrimidin-2-yl]-amine (P-3026),
(6-Ethoxy-pyridin-3-yl)-[5-(5-methyl-1H-pyrrolo[2,3-b]pyridin-3-ylmethyl)-pyrimidin-2-yl]-amine (P-3027),
[5-(4-Fluoro-phenyl)-2H-pyrazol-3-yl]-[5-(5-methyl-1H-pyrrolo[2,3-b]pyridin-3-ylmethyl)-pyrimidin-2-yl]-amine (P-3028),
(5-tert-Butyl-2H-pyrazol-3-yl)-[5-(5-methyl-1H-pyrrolo[2,3-b]pyridin-3-ylmethyl)-pyrimidin-2-yl]-amine (P-3029),
(4-tert-Butyl-phenyl)-[5-(5-methyl-1H-pyrrolo[2,3-b]pyridin-3-ylmethyl)-pyrimidin-2-yl]-amine (P-3030),
1,1,1,3,3,3-Hexafluoro-2-{4-[5-(5-methyl-1H-pyrrolo[2,3-b]pyridin-3-ylmethyl)-pyrimidin-2-ylamino]-phenyl}-propan-2-ol (P-3031),
(5-Cyclopropyl-2H-pyrazol-3-yl)-[5-(5-methyl-1H-pyrrolo[2,3-b]pyridin-3-ylmethyl)-pyrimidin-2-yl]-amine (P-3032),
[5-(5-Methyl-1H-pyrrolo[2,3-b]pyridin-3-ylmethyl)-pyrimidin-2-yl]-(4-methylsulfanyl-phenyl)-amine (P-3033),
(4-Methanesulfonyl-phenyl)-[5-(5-methyl-1H-pyrrolo[2,3-b]pyridin-3-ylmethyl)-pyrimidin-2-yl]-amine (P-3034),
(1-Ethyl-1H-pyrazol-3-yl)-[5-(5-methyl-1H-pyrrolo[2,3-b]pyridin-3-ylmethyl)-pyrimidin-2-yl]-amine (P-3035),
(1-Ethyl-1H-pyrazol-4-yl)-[5-(5-methyl-1H-pyrrolo[2,3-b]pyridin-3-ylmethyl)-pyrimidin-2-yl]-amine (P-3036),
[5-(5-Methyl-1H-pyrrolo[2,3-b]pyridin-3-ylmethyl)-pyrimidin-2-yl]-(5-trifluoromethyl-2H-pyrazol-3-yl)-amine (P-3037),
(5-Isopropoxy-2H-pyrazol-3-yl)-[5-(5-methyl-1H-pyrrolo[2,3-b]pyridin-3-ylmethyl)-pyrimidin-2-yl]-amine (P-3038),
(6-Ethoxy-pyridin-3-yl)-[6-fluoro-5-(5-methyl-1H-pyrrolo[2,3-b]pyridin-3-ylmethyl)-pyridin-2-yl]-amine (P-3039),
[2-Fluoro-6-(6-methoxy-pyridin-3-ylamino)-pyridin-3-yl]-(5-methyl-1H-pyrrolo[2,3-b]pyridin-3-yl)-methanone (P-3040),
[6-Fluoro-5-(5-methyl-1H-pyrrolo[2,3-b]pyridin-3-ylmethyl)-pyridin-2-yl]-(6-methyl-pyridin-3-yl)-amine (P-3041),
[5-(5-Chloro-1H-pyrrolo[2,3-b]pyridin-3-ylmethyl)-6-fluoro-pyridin-2-yl]-(6-methyl-pyridin-3-yl)-amine (P-3042),
[2-Fluoro-6-(6-methyl-pyridin-3-ylamino)-pyridin-3-yl]-(5-methyl-1H-pyrrolo[2,3-b]pyridin-3-yl)-methanone (P-3043),
(5-Chloro-1H-pyrrolo[2,3-b]pyridin-3-yl)-[2-fluoro-6-(6-methyl-pyridin-3-ylamino)-pyridin-3-yl]-methanone (P-3044),
[6-(6-Ethoxy-pyridin-3-ylamino)-2-fluoro-pyridin-3-yl]-(5-methyl-1H-pyrrolo[2,3-b]pyridin-3-yl)-methanone (P-3045),
(6-Ethyl-pyridin-3-yl)-[6-fluoro-5-(5-methyl-1H-pyrrolo[2,3-b]pyridin-3-ylmethyl)-pyridin-2-yl]-amine (P-3048),
[6-(6-Ethyl-pyridin-3-ylamino)-2-fluoro-pyridin-3-yl]-(5-methyl-1H-pyrrolo[2,3-b]pyridin-3-yl)-methanone (P-3049),
(6-Cyclopropyl-pyridin-3-yl)-[6-fluoro-5-(5-methyl-1H-pyrrolo[2,3-b]pyridin-3-ylmethyl)-pyridin-2-yl]-amine (P-3050),
[6-(6-Cyclopropyl-pyridin-3-ylamino)-2-fluoro-pyridin-3-yl]-(5-methyl-1H-pyrrolo[2,3-b]pyridin-3-yl)-methanone (P-3051),
[6-(6-Cyclopropyl-pyridin-3-ylamino)-2-fluoro-pyridin-3-yl]-(1H-pyrrolo[2,3-b]pyridin-3-yl)-methanone (P-3052),
(6-Cyclopropyl-pyridin-3-yl)-[6-fluoro-5-(1H-pyrrolo[2,3-b]pyridin-3-ylmethyl)-pyridin-2-yl]-amine (P-3053),
[6-Fluoro-5-(4-methoxy-7H-pyrrolo[2,3-d]pyrimidin-5-ylmethyl)-pyridin-2-yl]-(6-methoxy-pyridin-3-yl)-amine (P-4001),
[6-Fluoro-5-(4-methyl-7H-pyrrolo[2,3-d]pyrimidin-5-ylmethyl)-pyridin-2-yl]-(6-methoxy-pyridin-3-yl)-amine (P-4002),
(6-Chloro-pyridin-3-yl)-[6-fluoro-5-(4-methoxy-7H-pyrrolo[2,3-d]pyrimidin-5-ylmethyl)-pyridin-2-yl]-amine (P-4003),
(6-Cyclopropyl-pyridin-3-yl)-[6-fluoro-5-(4-methoxy-7H-pyrrolo[2,3-d]pyrimidin-5-ylmethyl)-pyridin-2-yl]-amine (P-4004),
(6-Ethoxy-pyridin-3-yl)-[6-fluoro-5-(4-methoxy-7H-pyrrolo[2,3-d]pyrimidin-5-ylmethyl)-pyridin-2-yl]-amine (P-4005), TABLE 1-continued (6-Ethoxy-pyridin-3-yl)-[6-fluoro-5-(4-methyl-7H-pyrrolo[2,3-d]pyrimidin-5-ylmethyl)-pyridin-2-yl]-amine (P-4006),
(6-Ethyl-pyridin-3-yl)-[6-fluoro-5-(4-methoxy-7H-pyrrolo[2,3-d]pyrimidin-5-ylmethyl)-pyridin-2-yl]-amine (P-4007),
(6-Ethoxy-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4008),
(6-Ethyl-pyridin-3-yl)-[6-fluoro-5-(4-methyl-7H-pyrrolo[2,3-d]pyrimidin-5-ylmethyl)-pyridin-2-yl]-amine (P-4009),
[6-Fluoro-5-(4-methoxy-7H-pyrrolo[2,3-d]pyrimidin-5-ylmethyl)-pyridin-2-yl]-(6-methyl-pyridin-3-yl)-amine (P-4010),
(1-Ethyl-1H-pyrazol-4-yl)-[6-fluoro-5-(4-methoxy-7H-pyrrolo[2,3-d]pyrimidin-5-ylmethyl)-pyridin-2-yl]-amine (P-4011),
[5-(4-Ethoxy-7H-pyrrolo[2,3-d]pyrimidin-5-ylmethyl)-6-fluoro-pyridin-2-yl]-(1-ethyl-1H-pyrazol-4-yl)-amine (P-4012),
(1-Ethyl-1H-pyrazol-4-yl)-[6-fluoro-5-(4-methyl-7H-pyrrolo[2,3-d]pyrimidin-5-ylmethyl)-pyridin-2-yl]-amine (P-4013),
(1-Ethyl-1H-pyrazol-4-yl)-{6-fluoro-5-[4-(2-methoxy-ethoxy)-7H-pyrrolo[2,3-d]pyrimidin-5-ylmethyl]-pyridin-2-yl}-amine (P-4014),
{6-Fluoro-5-[4-(2-methoxy-ethoxy)-7H-pyrrolo[2,3-d]pyrimidin-5-ylmethyl]-pyridin-2-yl}-(6-methyl-pyridin-3-yl)-amine (P-4015),
(6-Ethyl-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4016),
[5-(4-Ethoxy-7H-pyrrolo[2,3-d]pyrimidin-5-ylmethyl)-6-fluoro-pyridin-2-yl]-(6-methyl-pyridin-3-yl)-amine (P-4017),
[5-(4-Ethoxy-7H-pyrrolo[2,3-d]pyrimidin-5-ylmethyl)-6-fluoro-pyridin-2-yl]-(6-methoxy-pyridin-3-yl)-amine (P-4018),
{6-Fluoro-5-[4-(2-methoxy-ethoxy)-7H-pyrrolo[2,3-d]pyrimidin-5-ylmethyl]-pyridin-2-yl}-(6-methoxy-pyridin-3-yl)-amine (P-4019),
(6-Bromo-pyridin-3-yl)-[5-(4-ethoxy-7H-pyrrolo[2,3-d]pyrimidin-5-ylmethyl)-6-fluoro-pyridin-2-yl]-amine (P-4020),
[5-(4-Ethoxy-7H-pyrrolo[2,3-d]pyrimidin-5-ylmethyl)-6-fluoro-pyridin-2-yl]-pyridin-3-yl-amine (P-4021),
(4-Cyclopropyl-7H-pyrrolo[2,3-d]pyrimidin-5-yl)-[2-fluoro-6-(6-methoxy-pyridin-3-ylamino)-pyridin-3-yl]-methanone (P-4022),
[5-(4-Cyclopropyl-7H-pyrrolo[2,3-d]pyrimidin-5-ylmethyl)-6-fluoro-pyridin-2-yl]-(6-methoxy-pyridin-3-yl)-amine (P-4023),
[6-(6-Ethoxy-pyridin-3-ylamino)-2-fluoro-pyridin-3-yl]-(4-methoxy-7H-pyrrolo[2,3-d]pyrimidin-5-yl)-methanone (P-4024),
(4-Ethoxy-7H-pyrrolo[2,3-d]pyrimidin-5-yl)-[2-fluoro-6-(6-methoxy-pyridin-3-ylamino)-pyridin-3-yl]-methanone (P-4025),
[5-(4-Cyclopropyl-7H-pyrrolo[2,3-d]pyrimidin-5-ylmethyl)-6-fluoro-pyridin-2-yl]-(6-ethoxy-pyridin-3-yl)-amine (P-4026),
(4-Cyclopropyl-7H-pyrrolo[2,3-d]pyrimidin-5-yl)-[6-(6-ethoxy-pyridin-3-ylamino)-2-fluoro-pyridin-3-yl]-methanone (P-4027),
[5-(4-Cyclopropyl-7H-pyrrolo[2,3-d]pyrimidin-5-ylmethyl)-6-fluoro-pyridin-2-yl]-(6-ethyl-pyridin-3-yl)-amine (P-4028),
(4-Cyclopropyl-7H-pyrrolo[2,3-d]pyrimidin-5-yl)-[6-(6-ethyl-pyridin-3-ylamino)-2-fluoro-pyridin-3-yl]-methanone (P-4029),
[5-(4-Cyclopropyl-7H-pyrrolo[2,3-d]pyrimidin-5-ylmethyl)-6-fluoro-pyridin-2-yl]-(6-methyl-pyridin-3-yl)-amine (P-4030),
(4-Cyclopropyl-7H-pyrrolo[2,3-d]pyrimidin-5-yl)-[2-fluoro-6-(6-methyl-pyridin-3-ylamino)-pyridin-3-yl]-methanone (P-4031),
[6-(6-Ethoxy-pyridin-3-ylamino)-2-fluoro-pyridin-3-yl]-(4-methyl-7H-pyrrolo[2,3-d]pyrimidin-5-yl)-methanone (P-4032),
[5-(4-Cyclopropyl-7H-pyrrolo[2,3-d]pyrimidin-5-ylmethyl)-6-fluoro-pyridin-2-yl]-(1-ethyl-1H-pyrazol-4-yl)-amine (P-4036),
(4-Cyclopropyl-7H-pyrrolo[2,3-d]pyrimidin-5-yl)-[6-(1-ethyl-1H-pyrazol-4-ylamino)-2-fluoro-pyridin-3-yl]-methanone (P-4037),
[5-(4-Cyclopropyl-7H-pyrrolo[2,3-d]pyrimidin-5-ylmethyl)-6-fluoro-pyridin-2-yl]-(5-methyl-pyridin-3-yl)-amine (P-4038),
(4-Cyclopropyl-7H-pyrrolo[2,3-d]pyrimidin-5-yl)-[2-fluoro-6-(5-methyl-pyridin-3-ylamino)-pyridin-3-yl]-methanone (P-4039),
[6-(6-Cyclopropyl-pyridin-3-ylamino)-2-fluoro-pyridin-3-yl]-(4-cyclopropyl-7H-pyrrolo[2,3-d]pyrimidin-5-yl)-methanone (P-4040),
(6-Cyclopropyl-pyridin-3-yl)-[5-(4-cyclopropyl-7H-pyrrolo[2,3-d]pyrimidin-5-ylmethyl)-6-fluoro-pyridin-2-yl]-amine (P-4041),
[5-(4-Cyclopropyl-7H-pyrrolo[2,3-d]pyrimidin-5-ylmethyl)-6-fluoro-pyridin-2-yl]-(6,7-dihydro-5H-[1]pyrindin-3-yl)-amine (P-4042),
(4-Cyclopropyl-7H-pyrrolo[2,3-d]pyrimidin-5-yl)-[6-(6,7-dihydro-5H-[1]pyrindin-3-ylamino)-2-fluoro-pyridin-3-yl]-methanone (P-4043),
(6-Cyclopropyl-pyridin-3-yl)-[6-fluoro-5-(4-methyl-7H-pyrrolo[2,3-d]pyrimidin-5-ylmethyl)-pyridin-2-yl]-amine (P-4044),
[6-(6-Cyclopropyl-pyridin-3-ylamino)-2-fluoro-pyridin-3-yl]-(4-methyl-7H-pyrrolo[2,3-d]pyrimidin-5-yl)-methanone (P-4045),
(4-amino-7H-pyrrolo[2,3-d]pyrimidin-5-yl)-[2-chloro-6-[(4,4-difluorocyclohexyl)amino]-3-pyridyl]methanone (P-4046),
[2-chloro-6-[(4,4-difluorocyclohexyl)amino]-3-pyridyl]-[4-(2-methylprop-1-enylamino)-7H-pyrrolo[2,3-d]pyrimidin-5-yl]methanone (P-4047),
(4-amino-7H-pyrrolo[2,3-d]pyrimidin-5-yl)-[6-[(6-cyclopropyl-3-pyridyl)amino]-2-fluoro-3-pyridyl]methanone (P-4048), TABLE 1-continued

[6-[(6-cyclopropyl-3-pyridyl)amino]-2-fluoro-3-pyridyl]-[4-[(2-hydroxy-2-methyl-propyl)amino]-7H-pyrrolo[2,3-d]pyrimidin-5-yl]methanone (P-4049),
[2-chloro-6-[(4,4-difluorocyclohexyl)amino]-3-pyridyl]-[4-(ethylamino)-7H-pyrrolo[2,3-d]pyrimidin-5-yl]methanone (P-4050),
[6-[(4,4-difluorocyclohexyl)amino]-5-fluoro-3-pyridyl]-[4-(ethylamino)-7H-pyrrolo[2,3-d]pyrimidin-5-yl]methanone (P-4051),
[6-[(4,4-difluorocyclohexyl)amino]-5-fluoro-3-pyridyl]-[4-(2,2,2-trifluoroethylamino)-7H-pyrrolo[2,3-d]pyrimidin-5-yl]methanone (P-4052),
[4-(cyclopropylamino)-7H-pyrrolo[2,3-d]pyrimidin-5-yl]-[6-[(4,4-difluorocyclohexyl)amino]-5-fluoro-3-pyridyl]methanone (P-4053),
[6-[(4,4-difluorocyclohexyl)amino]-5-fluoro-3-pyridyl]-[4-(methylamino)-7H-pyrrolo[2,3-d]pyrimidin-5-yl]methanone (P-4054),
[4-[(tert-butylamino)-7H-pyrrolo[2,3-d]pyrimidin-5-yl]-[2-fluoro-6-[(6-methoxy-3-pyridyl)amino]-3-pyridyl]methanone (P-4055),
[4-[(4,4-difluorocyclohexyl)amino]-7H-pyrrolo[2,3-d]pyrimidin-5-yl]-[2-fluoro-6-[(6-methoxy-3-pyridyl)amino]-3-pyridyl]methanone (P-4056),
[2-chloro-6-[(4,4-difluorocyclohexyl)amino]-3-pyridyl]-[4-(2,2,2-trifluoroethylamino)-7H-pyrrolo[2,3-d]pyrimidin-5-yl]methanone (P-4057),
[2-chloro-6-[(4,4-difluorocyclohexyl)amino]-3-pyridyl]-[4-(methylamino)-7H-pyrrolo[2,3-d]pyrimidin-5-yl]methanone (P-4058),
[2-chloro-6-[(4,4-difluorocyclohexyl)amino]-3-pyridyl]-[4-(cyclopropylamino)-7H-pyrrolo[2,3-d]pyrimidin-5-yl]methanone (P-4059),
[6-[(6-cyclopropyl-3-pyridyl)amino]-2-fluoro-3-pyridyl]-[4-(ethylamino)-7H-pyrrolo[2,3-d]pyrimidin-5-yl]methanone (P-4060),
[6-[(4,4-difluorocyclohexyl)amino]-2-fluoro-3-pyridyl]-[4-(2,2,2-trifluoroethylamino)-7H-pyrrolo[2,3-d]pyrimidin-5-yl]methanone (P-4061),
[4-(cyclopropylamino)-7H-pyrrolo[2,3-d]pyrimidin-5-yl]-[6-[(4,4-difluorocyclohexyl)amino]-2-fluoro-3-pyridyl]methanone (P-4062),
[6-[(4,4-difluorocyclohexyl)amino]-2-fluoro-3-pyridyl]-[4-(methylamino)-7H-pyrrolo[2,3-d]pyrimidin-5-yl]methanone (P-4063),
[6-[(6-ethyl-3-pyridyl)amino]-2-fluoro-3-pyridyl]-[4-[(2-hydroxy-2-methyl-propyl)amino]-7H-pyrrolo[2,3-d]pyrimidin-5-yl]methanone (P-4064),
(4-amino-7H-pyrrolo[2,3-d]pyrimidin-5-yl)-[6-[(6-ethyl-3-pyridyl)amino]-2-fluoro-3-pyridyl]methanone (P-4065),
[2-fluoro-6-[(6-methoxy-3-pyridyl)amino]-3-pyridyl]-[4-(isopropylamino)-7H-pyrrolo[2,3-d]pyrimidin-5-yl]methanone (P-4066),
[4-(cyclopropylmethylamino)-7H-pyrrolo[2,3-d]pyrimidin-5-yl]-[2-fluoro-6-[(6-methoxy-3-pyridyl)amino]-3-pyridyl]methanone (P-4067),
[2-fluoro-6-[(6-methoxy-3-pyridyl)amino]-3-pyridyl]-[4-(propylamino)-7H-pyrrolo[2,3-d]pyrimidin-5-yl]methanone (P-4068),
[2-fluoro-6-[(6-methoxy-3-pyridyl)amino]-3-pyridyl]-[4-(1-piperidyl)-7H-pyrrolo[2,3-d]pyrimidin-5-yl]methanone (P-4069),
[2-fluoro-6-[(6-methoxy-3-pyridyl)amino]-3-pyridyl]-(4-morpholino-7H-pyrrolo[2,3-d]pyrimidin-5-yl)methanone (P-4070),
[2-fluoro-6-[(6-methoxy-3-pyridyl)amino]-3-pyridyl]-[4-[[6-(trifluoromethyl)-3-pyridyl]methylamino]-7H-pyrrolo[2,3-d]pyrimidin-5-yl]methanone (P-4071),
[2-fluoro-6-[(6-methoxy-3-pyridyl)amino]-3-pyridyl]-[4-[[(1S)-1-(4-fluorophenyl)ethyl]amino]-7H-pyrrolo[2,3-d]pyrimidin-5-yl]methanone (P-4072),
[2-fluoro-6-[(6-methoxy-3-pyridyl)amino]-3-pyridyl]-[4-(tetrahydrofuran-2-ylmethylamino)-7H-pyrrolo[2,3-d]pyrimidin-5-yl]methanone (P-4073),
[4-[(1-ethyl-4-piperidyl)amino]-7H-pyrrolo[2,3-d]pyrimidin-5-yl]-[2-fluoro-6-[(6-methoxy-3-pyridyl)amino]-3-pyridyl]methanone (P-4074),
[4-(cyclopentylamino)-7H-pyrrolo[2,3-d]pyrimidin-5-yl]-[2-fluoro-6-[(6-methoxy-3-pyridyl)amino]-3-pyridyl]methanone (P-4075),
[4-(cyclobutylamino)-7H-pyrrolo[2,3-d]pyrimidin-5-yl]-[2-fluoro-6-[(6-methoxy-3-pyridyl)amino]-3-pyridyl]methanone (P-4076),
[4-(1-ethylpropylamino)-7H-pyrrolo[2,3-d]pyrimidin-5-yl]-[2-fluoro-6-[(6-methoxy-3-pyridyl)amino]-3-pyridyl]methanone (P-4077),
[2-fluoro-6-[(6-methoxy-3-pyridyl)amino]-3-pyridyl]-[4-(sec-butylamino)-7H-pyrrolo[2,3-d]pyrimidin-5-yl]methanone (P-4078),
[2-fluoro-6-[(6-methoxy-3-pyridyl)amino]-3-pyridyl]-[4-(3-methoxypropylamino)-7H-pyrrolo[2,3-d]pyrimidin-5-yl]methanone (P-4079),
[4-(butylamino)-7H-pyrrolo[2,3-d]pyrimidin-5-yl]-[2-fluoro-6-[(6-methoxy-3-pyridyl)amino]-3-pyridyl]methanone (P-4080),
[4-(ethylamino)-7H-pyrrolo[2,3-d]pyrimidin-5-yl]-[2-fluoro-6-[(6-methoxy-3-pyridyl)amino]-3-pyridyl]methanone (P-4081),
[4-(cyclohexylamino)-7H-pyrrolo[2,3-d]pyrimidin-5-yl]-[2-fluoro-6-[(6-methoxy-3-pyridyl)amino]-3-pyridyl]methanone (P-4082),
[2-fluoro-6-[(6-methoxy-3-pyridyl)amino]-3-pyridyl]-[4-(methylamino)-7H-pyrrolo[2,3-d]pyrimidin-5-yl]methanone (P-4083),
[2-fluoro-6-[(6-methoxy-3-pyridyl)amino]-3-pyridyl]-[4-(2,2,2-trifluoroethylamino)-7H-pyrrolo[2,3-d]pyrimidin-5-yl]methanone (P-4084),
[2-methoxy-6-[(6-methoxy-3-pyridyl)amino]-3-pyridyl]-[4-(methylamino)-7H-pyrrolo[2,3-d]pyrimidin-5-yl]methanone (P-4085),
[6-[(6-ethyl-3-pyridyl)amino]-2-fluoro-3-pyridyl]-[4-[(6-methyl-3-pyridyl)amino]-7H-pyrrolo[2,3-d]pyrimidin-5-yl]methanone (P-4086),
[6-[(4,4-difluorocyclohexyl)amino]-3-pyridyl]-[4-(2,2,2-trifluoroethylamino)-7H-pyrrolo[2,3-d]pyrimidin-5-yl]methanone (P-4087),
[4-(cyclopropylamino)-7H-pyrrolo[2,3-d]pyrimidin-5-yl]-[6-[(4,4-difluorocyclohexyl)amino]-3-pyridyl]methanone (P-4088), TABLE 1-continued

[6-[(4,4-difluorocyclohexyl)amino]-3-pyridyl]-[4-(methylamino)-7H-pyrrolo[2,3-d]pyrimidin-5-yl]methanone (P-4089),
[6-[(6-cyclopropyl-3-pyridyl)amino]-2-fluoro-3-pyridyl]-[4-(2,2,2-trifluoroethylamino)-7H-pyrrolo[2,3-d]pyrimidin-5-yl]methanone (P-4090),
[4-(cyclopropylamino)-7H-pyrrolo[2,3-d]pyrimidin-5-yl]-[2-fluoro-6-[[6-(trifluoromethyl)-3-pyridyl]amino]-3-pyridyl]methanone (P-4091),
[2-fluoro-6-[[6-(trifluoromethyl)-3-pyridyl]amino]-3-pyridyl]-[4-(methylamino)-7H-pyrrolo[2,3-d]pyrimidin-5-yl]methanone (P-4092),
[4-(cyclopropylamino)-7H-pyrrolo[2,3-d]pyrimidin-5-yl]-[6-[(6-cyclopropyl-3-pyridyl)amino]-2-fluoro-3-pyridyl]methanone (P-4093),
[6-[(6-cyclopropyl-3-pyridyl)amino]-2-fluoro-3-pyridyl]-[4-(methylamino)-7H-pyrrolo[2,3-d]pyrimidin-5-yl]methanone (P-4094),
[4-(cyclobutylamino)-7H-pyrrolo[2,3-d]pyrimidin-5-yl]-[6-[(6-ethyl-3-pyridyl)amino]-2-fluoro-3-pyridyl]methanone (P-4095),
[4-[(4,4-difluorocyclohexyl)amino]-7H-pyrrolo[2,3-d]pyrimidin-5-yl]-[6-[(6-ethyl-3-pyridyl)amino]-2-fluoro-3-pyridyl]methanone (P-4096),
[6-[(6-ethyl-3-pyridyl)amino]-2-fluoro-3-pyridyl]-[4-[[(1S)-1-(4-fluorophenyl)ethyl]amino]-7H-pyrrolo[2,3-d]pyrimidin-5-yl]methanone (P-4097),
[6-[(6-ethyl-3-pyridyl)amino]-2-fluoro-3-pyridyl]-[4-(3-methoxypropylamino)-7H-pyrrolo[2,3-d]pyrimidin-5-yl]methanone (P-4098),
[4-(cyclopentylamino)-7H-pyrrolo[2,3-d]pyrimidin-5-yl]-[6-[(6-ethyl-3-pyridyl)amino]-2-fluoro-3-pyridyl]methanone (P-4099),
[4-(butylamino)-7H-pyrrolo[2,3-d]pyrimidin-5-yl]-[6-[(6-ethyl-3-pyridyl)amino]-2-fluoro-3-pyridyl]methanone (P-4100),
[6-(cyclohexylamino)-2-fluoro-3-pyridyl]-[4-(isopropylamino)-7H-pyrrolo[2,3-d]pyrimidin-5-yl]methanone (P-4101),
[6-(cyclohexylamino)-2-fluoro-3-pyridyl]-[4-(methylamino)-7H-pyrrolo[2,3-d]pyrimidin-5-yl]methanone (P-4102),
[2-fluoro-6-[(5-methoxy-3-pyridyl)amino]-3-pyridyl]-[4-(2,2,2-trifluoroethylamino)-7H-pyrrolo[2,3-d]pyrimidin-5-yl]methanone (P-4103),
[4-(cyclohexylamino)-7H-pyrrolo[2,3-d]pyrimidin-5-yl]-[2-fluoro-6-[(5-methoxy-3-pyridyl)amino]-3-pyridyl]methanone (P-4104),
[2-fluoro-6-[(5-methoxy-3-pyridyl)amino]-3-pyridyl]-[4-(propylamino)-7H-pyrrolo[2,3-d]pyrimidin-5-yl]methanone (P-4105),
[2-fluoro-6-[(5-methoxy-3-pyridyl)amino]-3-pyridyl]-[4-(isopropylamino)-7H-pyrrolo[2,3-d]pyrimidin-5-yl]methanone (P-4106),
[4-(cyclopropylamino)-7H-pyrrolo[2,3-d]pyrimidin-5-yl]-[2-fluoro-6-[(5-methoxy-3-pyridyl)amino]-3-pyridyl]methanone (P-4107),
[2-fluoro-6-[(5-methoxy-3-pyridyl)amino]-3-pyridyl]-[4-(methylamino)-7H-pyrrolo[2,3-d]pyrimidin-5-yl]methanone (P-4108),
[2-chloro-6-(cyclohexylamino)-3-pyridyl]-[4-(isopropylamino)-7H-pyrrolo[2,3-d]pyrimidin-5-yl]methanone (P-4109),
[2-chloro-6-(cyclohexylamino)-3-pyridyl]-[4-(methylamino)-7H-pyrrolo[2,3-d]pyrimidin-5-yl]methanone (P-4110),
[4-(cyclohexylamino)-7H-pyrrolo[2,3-d]pyrimidin-5-yl]-[2-fluoro-6-[(6-methyl-3-pyridyl)amino]-3-pyridyl]methanone (P-4111),
[2-fluoro-6-[(6-methyl-3-pyridyl)amino]-3-pyridyl]-[4-(2,2,2-trifluoroethylamino)-7H-pyrrolo[2,3-d]pyrimidin-5-yl]methanone (P-4112),
[4-(cyclopropylmethylamino)-7H-pyrrolo[2,3-d]pyrimidin-5-yl]-[2-fluoro-6-[(6-methyl-3-pyridyl)amino]-3-pyridyl]methanone (P-4113),
[2-fluoro-6-[(6-methyl-3-pyridyl)amino]-3-pyridyl]-[4-(propylamino)-7H-pyrrolo[2,3-d]pyrimidin-5-yl]methanone (P-4114),
[2-fluoro-6-[(6-methyl-3-pyridyl)amino]-3-pyridyl]-[4-(methylamino)-7H-pyrrolo[2,3-d]pyrimidin-5-yl]methanone (P-4115),
[6-[(6-ethyl-3-pyridyl)amino]-2-fluoro-3-pyridyl]-[4-(tetrahydropyran-4-ylamino)-7H-pyrrolo[2,3-d]pyrimidin-5-yl]methanone (P-4116),
[6-[(6-ethyl-3-pyridyl)amino]-2-fluoro-3-pyridyl]-[4-(isopropylamino)-7H-pyrrolo[2,3-d]pyrimidin-5-yl]methanone (P-4117),
[4-(cyclopropylmethylamino)-7H-pyrrolo[2,3-d]pyrimidin-5-yl]-[6-[(6-ethyl-3-pyridyl)amino]-2-fluoro-3-pyridyl]methanone (P-4118),
[6-[(6-ethyl-3-pyridyl)amino]-2-fluoro-3-pyridyl]-[4-(2-methoxyethylamino)-7H-pyrrolo[2,3-d]pyrimidin-5-yl]methanone (P-4119),
[6-[(6-ethyl-3-pyridyl)amino]-2-fluoro-3-pyridyl]-[4-(2,2,2-trifluoroethylamino)-7H-pyrrolo[2,3-d]pyrimidin-5-yl]methanone (P-4120),
[6-[(6-ethyl-3-pyridyl)amino]-2-fluoro-3-pyridyl]-[4-(isobutylamino)-7H-pyrrolo[2,3-d]pyrimidin-5-yl]methanone (P-4121),
[6-[(6-ethyl-3-pyridyl)amino]-2-fluoro-3-pyridyl]-[4-(propylamino)-7H-pyrrolo[2,3-d]pyrimidin-5-yl]methanone (P-4122),
[4-(ethylamino)-7H-pyrrolo[2,3-d]pyrimidin-5-yl]-[6-[(6-ethyl-3-pyridyl)amino]-2-fluoro-3-pyridyl]methanone (P-4123),
[6-[(6-ethyl-3-pyridyl)amino]-2-fluoro-3-pyridyl]-[4-(methylamino)-7H-pyrrolo[2,3-d]pyrimidin-5-yl]methanone (P-4124),
[4-(cyclopropylamino)-7H-pyrrolo[2,3-d]pyrimidin-5-yl]-[6-[(6-ethyl-3-pyridyl)amino]-2-fluoro-3-pyridyl]methanone (P-4125),
[4-(cyclopropylamino)-7H-pyrrolo[2,3-d]pyrimidin-5-yl]-[2-fluoro-6-[(6-methoxy-3-pyridyl)amino]-3-pyridyl]methanone (P-4126),
N-cyclopropyl-5-[[6-[(4,4-difluorocyclohexyl)amino]-5-fluoro-3-pyridyl]methyl]-7H-pyrrolo[2,3-d]pyrimidin-4-amine (P-4127),
5-[[6-[(4,4-difluorocyclohexyl)amino]-2-fluoro-3-pyridyl]methyl]-N-(2,2,2-trifluoroethyl)-7H-pyrrolo[2,3-d]pyrimidin-4-amine (P-4128), TABLE 1-continued N-cyclopropyl-5-[[6-[(4,4-difluorocyclohexyl)amino]-2-fluoro-3-pyridyl]methyl]-7H-pyrrolo[2,3-d]pyrimidin-4-amine (P-4129),
5-[[6-[(6-cyclopropyl-3-pyridyl)amino]-2-fluoro-3-pyridyl]methyl]-N-(2,2,2-trifluoroethyl)-7H-pyrrolo[2,3-d]pyrimidin-4-amine (P-4130),
5-[[6-(cyclohexylamino)-2-fluoro-3-pyridyl]methyl]-N-cyclopropyl-7H-pyrrolo[2,3-d]pyrimidin-4-amine (P-4131),
[2-fluoro-6-[(6-methoxy-3-pyridyl)amino]-3-pyridyl]-[4-[[(1R)-1-(4-fluorophenyl)ethyl]amino]-7H-pyrrolo[2,3-d]pyrimidin-5-yl]methanone (P-4132),
[6-[(6-ethyl-3-pyridyl)amino]-2-fluoro-3-pyridyl]-[4-[[(1R)-1-(4-fluorophenyl)ethyl]amino]-7H-pyrrolo[2,3-d]pyrimidin-5-yl]methanone (P-4133),
[2-fluoro-6-[(4-fluorocyclohexyl)amino]-3-pyridyl]-[4-(methylamino)-7H-pyrrolo[2,3-d]pyrimidin-5-yl]methanone (P-4134),
[4-(ethylamino)-7H-pyrrolo[2,3-d]pyrimidin-5-yl]-[2-fluoro-6-[(4-fluorocyclohexyl)amino]-3-pyridyl]methanone (P-4135),
[2-fluoro-6-[(4-fluorocyclohexyl)amino]-3-pyridyl]-[4-(isopropylamino)-7H-pyrrolo[2,3-d]pyrimidin-5-yl]methanone (P-4136),
[4-(cyclopropylamino)-7H-pyrrolo[2,3-d]pyrimidin-5-yl]-[2-fluoro-6-[(4-fluorocyclohexyl)amino]-3-pyridyl]methanone (P-4137),
[2-fluoro-6-[(4-fluorocyclohexyl)amino]-3-pyridyl]-[4-(2,2,2-trifluoroethylamino)-7H-pyrrolo[2,3-d]pyrimidin-5-yl]methanone (P-4138),
[4-[[(1R)-1-cyclopropylethyl]amino]-7H-pyrrolo[2,3-d]pyrimidin-5-yl]-[2-fluoro-6-[(4-fluorocyclohexyl)amino]-3-pyridyl]methanone (P-4139),
[4-[[(1S)-1-cyclopropylethyl]amino]-7H-pyrrolo[2,3-d]pyrimidin-5-yl]-[2-fluoro-6-[(4-fluorocyclohexyl)amino]-3-pyridyl]methanone (P-4140),
[2-fluoro-6-[(4-fluorocyclohexyl)amino]-3-pyridyl]-[4-(methoxymethylamino)-7H-pyrrolo[2,3-d]pyrimidin-5-yl]methanone (P-4141),
[2-fluoro-6-[(4-fluorocyclohexyl)amino]-3-pyridyl]-[4-(3-methoxypropylamino)-7H-pyrrolo[2,3-d]pyrimidin-5-yl]methanone (P-4142),
[2-fluoro-6-[(4-fluorocyclohexyl)amino]-3-pyridyl]-[4-(tetrahydropyran-4-ylamino)-7H-pyrrolo[2,3-d]pyrimidin-5-yl]methanone (P-4143),
[4-(cyclobutylamino)-7H-pyrrolo[2,3-d]pyrimidin-5-yl]-[2-fluoro-6-[(4-fluorocyclohexyl)amino]-3-pyridyl]methanone (P-4144),
[6-[(3,3-difluorocyclobutyl)amino]-2-fluoro-3-pyridyl]-[4-(methylamino)-7H-pyrrolo[2,3-d]pyrimidin-5-yl]methanone (P-4145),
[6-[(3,3-difluorocyclobutyl)amino]-2-fluoro-3-pyridyl]-[4-(ethylamino)-7H-pyrrolo[2,3-d]pyrimidin-5-yl]methanone (P-4146),
[6-[(3,3-difluorocyclobutyl)amino]-2-fluoro-3-pyridyl]-[4-(propylamino)-7H-pyrrolo[2,3-d]pyrimidin-5-yl]methanone (P-4147),
[6-[(3,3-difluorocyclobutyl)amino]-2-fluoro-3-pyridyl]-[4-(isopropylamino)-7H-pyrrolo[2,3-d]pyrimidin-5-yl]methanone (P-4148),
[6-[(3,3-difluorocyclobutyl)amino]-2-fluoro-3-pyridyl]-[4-(2,2,2-trifluoroethylamino)-7H-pyrrolo[2,3-d]pyrimidin-5-yl]methanone (P-4149),
[4-[[(1R)-1-cyclopropylethyl]amino]-7H-pyrrolo[2,3-d]pyrimidin-5-yl]-[6-[(3,3-difluorocyclobutyl)amino]-2-fluoro-3-pyridyl]methanone (P-4150),
[4-[[(1S)-1-cyclopropylethyl]amino]-7H-pyrrolo[2,3-d]pyrimidin-5-yl]-[6-[(3,3-difluorocyclobutyl)amino]-2-fluoro-3-pyridyl]methanone (P-4151),
[6-[(3,3-difluorocyclobutyl)amino]-2-fluoro-3-pyridyl]-[4-(methoxymethylamino)-7H-pyrrolo[2,3-d]pyrimidin-5-yl]methanone (P-4152),
[6-[(3,3-15difluorocyclobutyl)amino]-2-fluoro-3-pyridyl]-[4-(tetrahydropyran-4-ylamino)-7H-pyrrolo[2,3-d]pyrimidin-5-yl]methanone (P-4153),
[4-(cyclobutylamino)-7H-pyrrolo[2,3-d]pyrimidin-5-yl]-[6-[(3,3-difluorocyclobutyl)amino]-2-fluoro-3-pyridyl]methanone (P-4154),
[6-[(3,3-difluorocyclobutyl)amino]-2-fluoro-3-pyridyl]-[4-(3-methoxypropylamino)-7H-pyrrolo[2,3-d]pyrimidin-5-yl]methanone (P-4155),
[6-[(4,4-difluorocyclohexyl)amino]-2-fluoro-3-pyridyl]-[4-(3-methoxypropylamino)-7H-pyrrolo[2,3-d]pyrimidin-5-yl]methanone (P-4156),
[6-[(4,4-difluorocyclohexyl)amino]-2-fluoro-3-pyridyl]-[4-(2-methoxyethylamino)-7H-pyrrolo[2,3-d]pyrimidin-5-yl]methanone (P-4157),
[4-(cyclobutylamino)-7H-pyrrolo[2,3-d]pyrimidin-5-yl]-[6-[(4,4-difluorocyclohexyl)amino]-2-fluoro-3-pyridyl]methanone (P-4158),
[6-[(4,4-difluorocyclohexyl)amino]-2-fluoro-3-pyridyl]-[4-(tetrahydropyran-4-ylamino)-7H-pyrrolo[2,3-d]pyrimidin-5-yl]methanone (P-4159),
[4-[[(1R)-1-cyclopropylethyl]amino]-7H-pyrrolo[2,3-d]pyrimidin-5-yl]-[6-[(4,4-difluorocyclohexyl)amino]-2-fluoro-3-pyridyl]methanone (P-4160),
[4-[[(1S)-1-cyclopropylethyl]amino]-7H-pyrrolo[2,3-d]pyrimidin-5-yl]-[6-[(4,4-difluorocyclohexyl)amino]-2-fluoro-3-pyridyl]methanone (P-4161),
[6-[(4,4-difluorocyclohexyl)amino]-2-fluoro-3-pyridyl]-[4-(ethylamino)-7H-pyrrolo[2,3-d]pyrimidin-5-yl]methanone (P-4162),
[4-(cyclobutylamino)-7H-pyrrolo[2,3-d]pyrimidin-5-yl]-[6-[(4,4-difluorocyclohexyl)amino]-5-fluoro-3-pyridyl]methanone (P-4163),
[6-[(4,4-difluorocyclohexyl)amino]-5-fluoro-3-pyridyl]-[4-(methoxymethylamino)-7H-pyrrolo[2,3-d]pyrimidin-5-yl]methanone (P-4164),
[6-[(4,4-difluorocyclohexyl)amino]-5-fluoro-3-pyridyl]-[4-(3-methoxypropylamino)-7H-pyrrolo[2,3-d]pyrimidin-5-yl]methanone (P-4165),
[6-[(4,4-difluorocyclohexyl)amino]-5-fluoro-3-pyridyl]-[4-(tetrahydropyran-4-ylamino)-7H-pyrrolo[2,3-d]pyrimidin-5-yl]methanone (P-4166),
[4-[[(1R)-1-cyclopropylethyl]amino]-7H-pyrrolo[2,3-d]pyrimidin-5-yl]-[6-[(4,4-difluorocyclohexyl)amino]-5-fluoro-3-pyridyl]methanone (P-4167),
[4-[[(1S)-1-cyclopropylethyl]amino]-7H-pyrrolo[2,3-d]pyrimidin-5-yl]-[6-[(4,4-difluorocyclohexyl)amino]-5-fluoro-3-pyridyl]methanone (P-4168), TABLE 1-continued

[6-[(6-cyclopropyl-3-pyridyl)amino]-2-fluoro-3-pyridyl]-[4-[[(1S)-1-methylpropyl]amino]-7H-pyrrolo[2,3-d]pyrimidin-5-yl]methanone (P-4169),
[6-[(6-cyclopropyl-3-pyridyl)amino]-2-fluoro-3-pyridyl]-[4-[(3-hydroxy-1-methyl-propyl)amino]-7H-pyrrolo[2,3-d]pyrimidin-5-yl]methanone (P-4170),
[6-[(6-cyclopropyl-3-pyridyl)amino]-2-fluoro-3-pyridyl]-[4-[[(1R)-1-(hydroxymethyl)propyl]amino]-7H-pyrrolo[2,3-d]pyrimidin-5-yl]methanone (P-4171),
4-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-2-one (P-4172),
[6-[(6-cyclopropyl-3-pyridyl)amino]-2-fluoro-3-pyridyl]-[4-[[(1R)-2-hydroxy-1-methyl-ethyl]amino]-7H-pyrrolo[2,3-d]pyrimidin-5-yl]methanone (P-4173),
[6-[(6-cyclopropyl-3-pyridyl)amino]-2-fluoro-3-pyridyl]-[4-[[(1R,3R)-3-hydroxycyclohexyl]amino]-7H-pyrrolo[2,3-d]pyrimidin-5-yl]methanone (P-4174),
[6-[(6-cyclopropyl-3-pyridyl)amino]-2-fluoro-3-pyridyl]-[4-[[(1R,2R)-2-hydroxycyclopentyl]amino]-7H-pyrrolo[2,3-d]pyrimidin-5-yl]methanone (P-4175),
1-[3-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-1-yl]ethanone (P-4176),
(2R)-2-[[5-[6-[(6-cyclopropyl-3-pyridyl)amino]-2-fluoro-pyridine-3-carbonyl]-7H-pyrrolo[2,3-d]pyrimidin-4-yl]amino]cyclohexanone (P-4177),
[6-[(6-cyclopropyl-3-pyridyl)amino]-2-fluoro-3-pyridyl]-[4-[(1,1-dioxothiolan-3-yl)amino]-7H-pyrrolo[2,3-d]pyrimidin-5-yl]methanone (P-4178),
[6-[(6-cyclopropyl-3-pyridyl)amino]-2-fluoro-3-pyridyl]-[4-[[(1R,2R)-2-hydroxycyclohexyl]amino]-7H-pyrrolo[2,3-d]pyrimidin-5-yl]methanone (P-4179),
[6-[(6-cyclopropyl-3-pyridyl)amino]-2-fluoro-3-pyridyl]-[4-[[(1R)-2-methoxy-1-methyl-ethyl]amino]-7H-pyrrolo[2,3-d]pyrimidin-5-yl]methanone (P-4180),
4-[[5-[6-[(6-cyclopropyl-3-pyridyl)amino]-2-fluoro-pyridine-3-carbonyl]-7H-pyrrolo[2,3-d]pyrimidin-4-yl]amino]piperidin-2-one (P-4181),
[6-[(6-cyclopropyl-3-pyridyl)amino]-2-fluoro-3-pyridyl]-[4-[[(1R)-2,2,2-trifluoro-1-methyl-ethyl]amino]-7H-pyrrolo[2,3-d]pyrimidin-5-yl]methanone (P-4182),
4-[[5-[6-[(6-cyclopropyl-3-pyridyl)amino]-2-fluoro-pyridine-3-carbonyl]-7H-pyrrolo[2,3-d]pyrimidin-4-yl]amino]-1-methyl-piperidin-2-one (P-4183),
[6-[(6-cyclopropyl-3-pyridyl)amino]-2-fluoro-3-pyridyl]-[4-[(1,1-dioxothian-3-yl)amino]-7H-pyrrolo[2,3-d]pyrimidin-5-yl]methanone (P-4184),
1-cyclopropyl-4-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-2-one (P-4185),
[6-[(4,4-difluorocyclohexyl)amino]-2-fluoro-3-pyridyl]-[4-[[(1S)-1-methylpropyl]amino]-7H-pyrrolo[2,3-d]pyrimidin-5-yl]methanone (P-4186),
[6-[(4,4-difluorocyclohexyl)amino]-2-fluoro-3-pyridyl]-[4-[(3-hydroxy-1-methyl-propyl)amino]-7H-pyrrolo[2,3-d]pyrimidin-5-yl]methanone (P-4187),
[6-[(4,4-difluorocyclohexyl)amino]-2-fluoro-3-pyridyl]-[4-[[(1R)-1-(hydroxymethyl)propyl]amino]-7H-pyrrolo[2,3-d]pyrimidin-5-yl]methanone (P-4188),
4-[[5-[6-[(4,4-difluorocyclohexyl)amino]-2-fluoro-pyridine-3-carbonyl]-7H-pyrrolo[2,3-d]pyrimidin-4-yl]amino]pyrrolidin-2-one (P-4189),
[6-[(4,4-difluorocyclohexyl)amino]-2-fluoro-3-pyridyl]-[4-[[(1R)-2-hydroxy-1-methyl-ethyl]amino]-7H-pyrrolo[2,3-d]pyrimidin-5-yl]methanone (P-4190),
[6-[(4,4-difluorocyclohexyl)amino]-2-fluoro-3-pyridyl]-[4-[[(1R,3R)-3-hydroxycyclohexyl]amino]-7H-pyrrolo[2,3-d]pyrimidin-5-yl]methanone (P-4191),
[6-[(4,4-difluorocyclohexyl)amino]-2-fluoro-3-pyridyl]-[4-[[(1R,2R)-2-hydroxycyclopentyl]amino]-7H-pyrrolo[2,3-d]pyrimidin-5-yl]methanone (P-4192),
1-[3-[[5-[6-[(4,4-difluorocyclohexyl)amino]-2-fluoro-pyridine-3-carbonyl]-7H-pyrrolo[2,3-d]pyrimidin-4-yl]amino]pyrrolidin-1-yl]ethanone (P-4193),
(2R)-2-[[5-[6-[(4,4-difluorocyclohexyl)amino]-2-fluoro-pyridine-3-carbonyl]-7H-pyrrolo[2,3-d]pyrimidin-4-yl]amino]cyclohexanone (P-4194),
[6-[(4,4-difluorocyclohexyl)amino]-2-fluoro-3-pyridyl]-[4-[(1,1-dioxothiolan-3-yl)amino]-7H-pyrrolo[2,3-d]pyrimidin-5-yl]methanone (P-4195),
[6-[(4,4-difluorocyclohexyl)amino]-2-fluoro-3-pyridyl]-[4-[[(1R,2R)-2-hydroxycyclohexyl]amino]-7H-pyrrolo[2,3-d]pyrimidin-5-yl]methanone (P-4196),
[6-[(4,4-difluorocyclohexyl)amino]-2-fluoro-3-pyridyl]-[4-[[(1R)-2-methoxy-1-methyl-ethyl]amino]-7H-pyrrolo[2,3-d]pyrimidin-5-yl]methanone (P-4197),
4-[[5-[6-[(4,4-difluorocyclohexyl)amino]-2-fluoro-pyridine-3-carbonyl]-7H-pyrrolo[2,3-d]pyrimidin-4-yl]amino]piperidin-2-one (P-4198),
[6-[(4,4-difluorocyclohexyl)amino]-2-fluoro-3-pyridyl]-[4-[[(1R)-2,2,2-trifluoro-1-methyl-ethyl]amino]-7H-pyrrolo[2,3-d]pyrimidin-5-yl]methanone (P-4199),
4-[[5-[6-[(4,4-difluorocyclohexyl)amino]-2-fluoro-pyridine-3-carbonyl]-7H-pyrrolo[2,3-d]pyrimidin-4-yl]amino]-1-methyl-piperidin-2-one (P-4200),
[6-[(4,4-difluorocyclohexyl)amino]-2-fluoro-3-pyridyl]-[4-[(1,1-dioxothian-3-yl)amino]-7H-pyrrolo[2,3-d]pyrimidin-5-yl]methanone (P-4201),
1-cyclopropyl-4-[[5-[6-[(4,4-difluorocyclohexyl)amino]-2-fluoro-pyridine-3-carbonyl]-7H-pyrrolo[2,3-d]pyrimidin-4-yl]amino]pyrrolidin-2-one (P-4202); and
any salt, prodrug, solvate, tautomer, or stereoisomer thereof. In some embodiments, the salt is a pharmaceutically acceptable salt.

In one embodiment of compounds of Formula I, the compound is selected from the group consisting of:

[5-(5-Chloro-1H-pyrrolo[2,3-b]pyridin-3-ylmethyl)-pyrimidin-2-yl]-cyclohexyl-amine (P-3001),

[5-(5-Chloro-1H-pyrrolo[2,3-b]pyridin-3-ylmethyl)-pyrimidin-2-yl]-cyclopentyl-amine (P-3003),

[5-(5-Chloro-1H-pyrrolo[2,3-b]pyridin-3-ylmethyl)-pyrimidin-2-yl]-(4,4-difluoro-cyclohexyl)-amine (P-3004),

[5-(5-Chloro-1H-pyrrolo[2,3-b]pyridin-3-ylmethyl)-pyrimidin-2-yl]-cyclopropyl-amine (P-3005),

[5-(5-Chloro-1H-pyrrolo[2,3-b]pyridin-3-ylmethyl)-pyrimidin-2-yl]-cycloheptyl-amine (P-3006),

[5-(5-Chloro-1H-pyrrolo[2,3-b]pyridin-3-ylmethyl)-pyrimidin-2-yl]-cyclobutyl-amine (P-3007),
Cyclohexyl-[6-fluoro-5-(5-methyl-1H-pyrrolo[2,3-b]pyridin-3-ylmethyl)-pyridin-2-yl]-amine (P-3008),
[5-(5-Chloro-1H-pyrrolo[2,3-b]pyridin-3-ylmethyl)-pyrimidin-2-yl]-(4-methyl-cyclohexyl)-amine (P-3009),
[5-(5-Chloro-1H-pyrrolo[2,3-b]pyridin-3-ylmethyl)-6-fluoro-pyridin-2-yl]-(4,4-difluoro-cyclohexyl)-amine (P-3013), and any salt, prodrug, solvate, tautomer, or stereoisomer thereof. In some embodiments, the salt is a pharmaceutically acceptable salt.

In one embodiment of compounds of Formula I, the compound is selected from the group consisting of:
[5-(5-Chloro-1H-pyrrolo[2,3-b]pyridin-3-ylmethyl)-pyrimidin-2-yl]-(4,4-difluoro-cyclohexyl)-amine (P-3004),
[5-(5-Chloro-1H-pyrrolo[2,3-b]pyridin-3-ylmethyl)-pyrimidin-2-yl]-cycloheptyl-amine (P-3006),
[5-(5-Chloro-1H-pyrrolo[2,3-b]pyridin-3-ylmethyl)-6-fluoro-pyridin-2-yl]-(4,4-difluoro-cyclohexyl)-amine (P-3013), and any salt, prodrug, solvate, tautomer, or stereoisomer thereof. In some embodiments, the salt is a pharmaceutically acceptable salt.

In one embodiment of compounds of Formula I, the compound is selected from the group consisting of:
(1-Ethyl-1H-pyrazol-3-yl)-[5-(5-methyl-1H-pyrrolo[2,3-b]pyridin-3-ylmethyl)-pyrimidin-2-yl]-amine (P-3035),
(1-Ethyl-1H-pyrazol-4-yl)-[5-(5-methyl-1H-pyrrolo[2,3-b]pyridin-3-ylmethyl)-pyrimidin-2-yl]-amine (P-3036),
(1-Ethyl-1H-pyrazol-4-yl)-[6-fluoro-5-(4-methoxy-7H-pyrrolo[2,3-d]pyrimidin-5-ylmethyl)-pyridin-2-yl]-amine (P-4011),
[5-(4-Ethoxy-7H-pyrrolo[2,3-d]pyrimidin-5-ylmethyl)-6-fluoro-pyridin-2-yl]-(1-ethyl-1H-pyrazol-4-yl)-amine (P-4012),
(1-Ethyl-1H-pyrazol-4-yl)-[6-fluoro-5-(4-methyl-7H-pyrrolo[2,3-d]pyrimidin-5-ylmethyl)-pyridin-2-yl]-amine (P-4013),
(1-Ethyl-1H-pyrazol-4-yl)-{6-fluoro-5-[4-(2-methoxy-ethoxy)-7H-pyrrolo[2,3-d]pyrimidin-5-ylmethyl]-pyridin-2-yl}-amine (P-4014),
[5-(4-Cyclopropyl-7H-pyrrolo[2,3-d]pyrimidin-5-ylmethyl)-6-fluoro-pyridin-2-yl]-(1-ethyl-1H-pyrazol-4-yl)-amine (P-4036),
(4-Cyclopropyl-7H-pyrrolo[2,3-d]pyrimidin-5-yl)-[6-(1-ethyl-1H-pyrazol-4-ylamino)-2-fluoro-pyridin-3-yl]-methanone (P-4037), and any salt, prodrug, solvate, tautomer, or stereoisomer thereof. In some embodiments, the salt is a pharmaceutically acceptable salt.

In one embodiment of compounds of Formula I, the compound is selected from the group consisting of:
(4-Fluoro-phenyl)-[5-(5-methyl-1H-pyrrolo[2,3-b]pyridin-3-ylmethyl)-pyrimidin-2-yl]-amine (P-3010),
(4-Chloro-phenyl)-[5-(5-chloro-1H-pyrrolo[2,3-b]pyridin-3-ylmethyl)-pyrimidin-2-yl]-amine (P-3011),
[5-(5-Chloro-1H-pyrrolo[2,3-b]pyridin-3-ylmethyl)-pyrimidin-2-yl]-(4-fluoro-phenyl)-amine (P-3012),
[5-(5-Chloro-1H-pyrrolo[2,3-b]pyridin-3-ylmethyl)-pyrimidin-2-yl]-(2-fluoro-phenyl)-amine (P-3014),
(2-Chloro-phenyl)-[5-(5-chloro-1H-pyrrolo[2,3-b]pyridin-3-ylmethyl)-pyrimidin-2-yl]-amine (P-3015),
[5-(5-Chloro-1H-pyrrolo[2,3-b]pyridin-3-ylmethyl)-pyrimidin-2-yl]-(2-methoxy-phenyl)-amine (P-3016),
[5-(5-Chloro-1H-pyrrolo[2,3-b]pyridin-3-ylmethyl)-pyrimidin-2-yl]-(3-fluoro-phenyl)-amine (P-3017),
(4-Methoxy-phenyl)-[5-(5-methyl-1H-pyrrolo[2,3-b]pyridin-3-ylmethyl)-pyrimidin-2-yl]-amine (P-3021),
(4-Fluoro-3-methoxy-phenyl)-[5-(5-methyl-1H-pyrrolo[2,3-b]pyridin-3-ylmethyl)-pyrimidin-2-yl]-amine (P-3022),
(3-Fluoro-4-methoxy-phenyl)-[5-(5-methyl-1H-pyrrolo[2,3-b]pyridin-3-ylmethyl)-pyrimidin-2-yl]-amine (P-3023),
[5-(5-Methyl-1H-pyrrolo[2,3-b]pyridin-3-ylmethyl)-pyrimidin-2-yl]-(4-propoxy-phenyl)-amine (P-3024),
(4-Ethyl-phenyl)-[5-(5-methyl-1H-pyrrolo[2,3-b]pyridin-3-ylmethyl)-pyrimidin-2-yl]-amine (P-3025),
(4-Ethoxy-phenyl)-[5-(5-methyl-1H-pyrrolo[2,3-b]pyridin-3-ylmethyl)-pyrimidin-2-yl]-amine (P-3026),
(4-tert-Butyl-phenyl)-[5-(5-methyl-1H-pyrrolo[2,3-b]pyridin-3-ylmethyl)-pyrimidin-2-yl]-amine (P-3030),
1,1,1,3,3,3-Hexafluoro-2-{4-[5-(5-methyl-1H-pyrrolo[2,3-b]pyridin-3-ylmethyl)-pyrimidin-2-ylamino]-phenyl}-propan-2-ol (P-3031),
[5-(5-Methyl-1H-pyrrolo[2,3-b]pyridin-3-ylmethyl)-pyrimidin-2-yl]-(4-methylsulfanyl-phenyl)-amine (P-3033),
(4-Methanesulfonyl-phenyl)-[5-(5-methyl-1H-pyrrolo[2,3-b]pyridin-3-ylmethyl)-pyrimidin-2-yl]-amine (P-3034), and any salt, prodrug, solvate, tautomer, or stereoisomer thereof. In some embodiments, the salt is a pharmaceutically acceptable salt.

In one embodiment of compounds of Formula I, the compound is selected from the group consisting of:
(4-Fluoro-phenyl)-[5-(5-methyl-1H-pyrrolo[2,3-b]pyridin-3-ylmethyl)-pyrimidin-2-yl]-amine (P-3010),
(4-Chloro-phenyl)-[5-(5-chloro-1H-pyrrolo[2,3-b]pyridin-3-ylmethyl)-pyrimidin-2-yl]-amine (P-3011),
[5-(5-Chloro-1H-pyrrolo[2,3-b]pyridin-3-ylmethyl)-pyrimidin-2-yl]-(4-fluoro-phenyl)-amine (P-3012),
[5-(5-Chloro-1H-pyrrolo[2,3-b]pyridin-3-ylmethyl)-pyrimidin-2-yl]-(2-fluoro-phenyl)-amine (P-3014),
(4-Methoxy-phenyl)-[5-(5-methyl-1H-pyrrolo[2,3-b]pyridin-3-ylmethyl)-pyrimidin-2-yl]-amine (P-3021),
(4-Ethyl-phenyl)-[5-(5-methyl-1H-pyrrolo[2,3-b]pyridin-3-ylmethyl)-pyrimidin-2-yl]-amine (P-3025),
(4-Ethoxy-phenyl)-[5-(5-methyl-1H-pyrrolo[2,3-b]pyridin-3-ylmethyl)-pyrimidin-2-yl]-amine (P-3026),
(4-tert-Butyl-phenyl)-[5-(5-methyl-1H-pyrrolo[2,3-b]pyridin-3-ylmethyl)-pyrimidin-2-yl]-amine (P-3030),
1,1,1,3,3,3-Hexafluoro-2-{4-[5-(5-methyl-1H-pyrrolo[2,3-b]pyridin-3-ylmethyl)-pyrimidin-2-ylamino]-phenyl}-propan-2-ol (P-3031),
[5-(5-Methyl-1H-pyrrolo[2,3-b]pyridin-3-ylmethyl)-pyrimidin-2-yl]-(4-methylsulfanyl-phenyl)-amine (P-3033), and any salt, prodrug, solvate, tautomer, or stereoisomer thereof. In some embodiments, the salt is a pharmaceutically acceptable salt.

In one embodiment of compounds of Formula I, the compound is selected from the group consisting of:
[5-(5-Methyl-1H-pyrrolo[2,3-b]pyridin-3-ylmethyl)-pyrimidin-2-yl]-(6-trifluoromethyl-pyridin-3-yl)-amine (P-3018),
[6-Fluoro-5-(5-methyl-1H-pyrrolo[2,3-b]pyridin-3-ylmethyl)-pyridin-2-yl]-(6-methoxy-pyridin-3-yl)-amine (P-3019),
(6-Methoxy-pyridin-3-yl)-[5-(5-methyl-1H-pyrrolo[2,3-b]pyridin-3-ylmethyl)-pyrimidin-2-yl]-amine (P-3020),
(6-Ethoxy-pyridin-3-yl)-[5-(5-methyl-1H-pyrrolo[2,3-b]pyridin-3-ylmethyl)-pyrimidin-2-yl]-amine (P-3027),
(6-Ethoxy-pyridin-3-yl)-[6-fluoro-5-(5-methyl-1H-pyrrolo[2,3-b]pyridin-3-ylmethyl)-pyridin-2-yl]-amine (P-3039),

[2-Fluoro-6-(6-methoxy-pyridin-3-ylamino)-pyridin-3-yl]-(5-methyl-1H-pyrrolo[2,3-b]pyridin-3-yl)-methanone (P-3040),

[6-(6-Ethoxy-pyridin-3-ylamino)-2-fluoro-pyridin-3-yl]-(5-methyl-1H-pyrrolo[2,3-b]pyridin-3-yl)-methanone (P-3045),

[6-Fluoro-5-(4-methoxy-7H-pyrrolo[2,3-d]pyrimidin-5-ylmethyl)-pyridin-2-yl]-(6-methoxy-pyridin-3-yl)-amine (P-4001),

[6-Fluoro-5-(4-methyl-7H-pyrrolo[2,3-d]pyrimidin-5-ylmethyl)-pyridin-2-yl]-(6-methoxy-pyridin-3-yl)-amine (P-4002), (6-Ethoxy-pyridin-3-yl)-[6-fluoro-5-(4-methoxy-7H-pyrrolo[2,3-d]pyrimidin-5-ylmethyl)-pyridin-2-yl]-amine (P-4005), (6-Ethoxy-pyridin-3-yl)-[6-fluoro-5-(4-methyl-7H-pyrrolo[2,3-d]pyrimidin-5-ylmethyl)-pyridin-2-yl]-amine (P-4006), (6-Ethoxy-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4008),

[5-(4-Ethoxy-7H-pyrrolo[2,3-d]pyrimidin-5-ylmethyl)-6-fluoro-pyridin-2-yl]-(6-methoxy-pyridin-3-yl)-amine (P-4018), {6-Fluoro-5-[4-(2-methoxy-ethoxy)-7H-pyrrolo[2,3-d]pyrimidin-5-ylmethyl]-pyridin-2-yl}-(6-methoxy-pyridin-3-yl)-amine (P-4019), (4-Cyclopropyl-7H-pyrrolo[2,3-d]pyrimidin-5-yl)-[2-fluoro-6-(6-methoxy-pyridin-3-ylamino)-pyridin-3-yl]-methanone (P-4022),

[5-(4-Cyclopropyl-7H-pyrrolo[2,3-d]pyrimidin-5-ylmethyl)-6-fluoro-pyridin-2-yl]-(6-methoxy-pyridin-3-yl)-amine (P-4023),

[6-(6-Ethoxy-pyridin-3-ylamino)-2-fluoro-pyridin-3-yl]-(4-methoxy-7H-pyrrolo[2,3-d]pyrimidin-5-yl)-methanone (P-4024), (4-Ethoxy-7H-pyrrolo[2,3-d]pyrimidin-5-yl)-[2-fluoro-6-(6-methoxy-pyridin-3-ylamino)-pyridin-3-yl]-methanone (P-4025),

[5-(4-Cyclopropyl-7H-pyrrolo[2,3-d]pyrimidin-5-ylmethyl)-6-fluoro-pyridin-2-yl]-(6-ethoxy-pyridin-3-yl)-amine (P-4026), (4-Cyclopropyl-7H-pyrrolo[2,3-d]pyrimidin-5-yl)-[6-(6-ethoxy-pyridin-3-ylamino)-2-fluoro-pyridin-3-yl]-methanone (P-4027),

[6-(6-Ethoxy-pyridin-3-ylamino)-2-fluoro-pyridin-3-yl]-(4-methyl-7H-pyrrolo[2,3-d]pyrimidin-5-yl)-methanone (P-4032), and any salt, prodrug, solvate, tautomer, or stereoisomer thereof. In some embodiments, the salt is a pharmaceutically acceptable salt.

In one embodiment of compounds of Formula I, the compound is selected from the group consisting of:

[5-(5-Methyl-1H-pyrrolo[2,3-b]pyridin-3-ylmethyl)-pyrimidin-2-yl]-(6-trifluoromethyl-pyridin-3-yl)-amine (P-3018),

[6-Fluoro-5-(5-methyl-1H-pyrrolo[2,3-b]pyridin-3-ylmethyl)-pyridin-2-yl]-(6-methoxy-pyridin-3-yl)-amine (P-3019), (6-Methoxy-pyridin-3-yl)-[5-(5-methyl-1H-pyrrolo[2,3-b]pyridin-3-ylmethyl)-pyrimidin-2-yl]-amine (P-3020), (6-Ethoxy-pyridin-3-yl)-[5-(5-methyl-1H-pyrrolo[2,3-b]pyridin-3-ylmethyl)-pyrimidin-2-yl]-amine (P-3027), (6-Ethoxy-pyridin-3-yl)[6-fluoro-5-(5-methyl-1H-pyrrolo[2,3-b]pyridin-3-ylmethyl)-pyridin-2-yl]-amine (P-3039),

[2-Fluoro-6-(6-methoxy-pyridin-3-ylamino)-pyridin-3-yl]-(5-methyl-1H-pyrrolo[2,3-b]pyridin-3-yl)-methanone (P-3040),

[6-(6-Ethoxy-pyridin-3-ylamino)-2-fluoro-pyridin-3-yl]-(5-methyl-1H-pyrrolo[2,3-b]pyridin-3-yl)-methanone (P-3045),

[6-Fluoro-5-(4-methoxy-7H-pyrrolo[2,3-d]pyrimidin-5-ylmethyl)-pyridin-2-yl]-(6-methoxy-pyridin-3-yl)-amine (P-4001), (6-Ethoxy-pyridin-3-yl)-[6-fluoro-5-(4-methoxy-7H-pyrrolo[2,3-d]pyrimidin-5-ylmethyl)-pyridin-2-yl]-amine (P-4005), (6-Ethoxy-pyridin-3-yl)-[6-fluoro-5-(4-methyl-7H-pyrrolo[2,3-d]pyrimidin-5-ylmethyl)-pyridin-2-yl]-amine (P-4006), (6-Ethoxy-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4008),

[5-(4-Ethoxy-7H-pyrrolo[2,3-d]pyrimidin-5-ylmethyl)-6-fluoro-pyridin-2-yl]-(6-methoxy-pyridin-3-yl)-amine (P-4018), {6-Fluoro-5-[4-(2-methoxy-ethoxy)-7H-pyrrolo[2,3-d]pyrimidin-5-ylmethyl]-pyridin-2-yl}-(6-methoxy-pyridin-3-yl)-amine (P-4019), (4-Cyclopropyl-7H-pyrrolo[2,3-d]pyrimidin-5-yl)-[2-fluoro-6-(6-methoxy-pyridin-3-ylamino)-pyridin-3-yl]-methanone (P-4022),

[5-(4-Cyclopropyl-7H-pyrrolo[2,3-d]pyrimidin-5-ylmethyl)-6-fluoro-pyridin-2-yl]-(6-methoxy-pyridin-3-yl)-amine (P-4023),

[5-(4-Cyclopropyl-7H-pyrrolo[2,3-d]pyrimidin-5-ylmethyl)-6-fluoro-pyridin-2-yl]-(6-ethoxy-pyridin-3-yl)-amine (P-4026), (4-Cyclopropyl-7H-pyrrolo[2,3-d]pyrimidin-5-yl)-[6-(6-ethoxy-pyridin-3-ylamino)-2-fluoro-pyridin-3-yl]-methanone (P-4027),

[6-(6-Ethoxy-pyridin-3-ylamino)-2-fluoro-pyridin-3-yl]-(4-methyl-7H-pyrrolo[2,3-d]pyrimidin-5-yl)-methanone (P-4032), and any salt, prodrug, solvate, tautomer, or stereoisomer thereof. In some embodiments, the salt is a pharmaceutically acceptable salt.

In one embodiment of compounds of Formula I, the compound is selected from the group consisting of:

[6-Fluoro-5-(5-methyl-1H-pyrrolo[2,3-b]pyridin-3-ylmethyl)-pyridin-2-yl]-(6-methyl-pyridin-3-yl)-amine (P-3041),

[5-(5-Chloro-1H-pyrrolo[2,3-b]pyridin-3-ylmethyl)-6-fluoro-pyridin-2-yl]-(6-methyl-pyridin-3-yl)-amine (P-3042),

[2-Fluoro-6-(6-methyl-pyridin-3-ylamino)-pyridin-3-yl]-(5-methyl-1H-pyrrolo[2,3-b]pyridin-3-yl)-methanone (P-3043), (5-Chloro-1H-pyrrolo[2,3-b]pyridin-3-yl)-[2-fluoro-6-(6-methyl-pyridin-3-ylamino)-pyridin-3-yl]-methanone (P-3044), (6-Ethyl-pyridin-3-yl)-[6-fluoro-5-(5-methyl-1H-pyrrolo[2,3-b]pyridin-3-ylmethyl)-pyridin-2-yl]-amine (P-3048),

[6-(6-Ethyl-pyridin-3-ylamino)-2-fluoro-pyridin-3-yl]-(5-methyl-1H-pyrrolo[2,3-b]pyridin-3-yl)-methanone (P-3049), (6-Cyclopropyl-pyridin-3-yl)-[6-fluoro-5-(5-methyl-1H-pyrrolo[2,3-b]pyridin-3-ylmethyl)-pyridin-2-yl]-amine (P-3050),

[6-(6-Cyclopropyl-pyridin-3-ylamino)-2-fluoro-pyridin-3-yl]-(5-methyl-1H-pyrrolo[2,3-b]pyridin-3-yl)-methanone (P-3051),

[6-(6-Cyclopropyl-pyridin-3-ylamino)-2-fluoro-pyridin-3-yl]-(1H-pyrrolo[2,3-b]pyridin-3-yl)-methanone (P-3052),
(6-Cyclopropyl-pyridin-3-yl)-[6-fluoro-5-(1H-pyrrolo[2,3-b]pyridin-3-ylmethyl)-pyridin-2-yl]-amine (P-3053),
(6-Cyclopropyl-pyridin-3-yl)-[6-fluoro-5-(4-methoxy-7H-pyrrolo[2,3-d]pyrimidin-5-ylmethyl)-pyridin-2-yl]-amine (P-4004),
(6-Ethyl-pyridin-3-yl)-[6-fluoro-5-(4-methoxy-7H-pyrrolo[2,3-d]pyrimidin-5-ylmethyl)-pyridin-2-yl]-amine (P-4007),
(6-Ethyl-pyridin-3-yl)-[6-fluoro-5-(4-methyl-7H-pyrrolo[2,3-d]pyrimidin-5-ylmethyl)-pyridin-2-yl]-amine (P-4009),
[6-Fluoro-5-(4-methoxy-7H-pyrrolo[2,3-d]pyrimidin-5-ylmethyl)-pyridin-2-yl]-(6-methyl-pyridin-3-yl)-amine (P-4010),
{6-Fluoro-5-[4-(2-methoxy-ethoxy)-7H-pyrrolo[2,3-d]pyrimidin-5-ylmethyl]-pyridin-2-yl}-(6-methyl-pyridin-3-yl)-amine (P-4015),
(6-Ethyl-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4016),
[5-(4-Ethoxy-7H-pyrrolo[2,3-d]pyrimidin-5-ylmethyl)-6-fluoro-pyridin-2-yl]-(6-methyl-pyridin-3-yl)-amine (P-4017),
[5-(4-Cyclopropyl-7H-pyrrolo[2,3-d]pyrimidin-5-ylmethyl)-6-fluoro-pyridin-2-yl]-(6-ethyl-pyridin-3-yl)-amine (P-4028),
(4-Cyclopropyl-7H-pyrrolo[2,3-d]pyrimidin-5-yl)-[6-(6-ethyl-pyridin-3-ylamino)-2-fluoro-pyridin-3-yl]-methanone (P-4029),
[5-(4-Cyclopropyl-7H-pyrrolo[2,3-d]pyrimidin-5-ylmethyl)-6-fluoro-pyridin-2-yl]-(6-methyl-pyridin-3-yl)-amine (P-4030),
(4-Cyclopropyl-7H-pyrrolo[2,3-d]pyrimidin-5-yl)-[2-fluoro-6-(6-methyl-pyridin-3-ylamino)-pyridin-3-yl]-methanone (P-4031),
[6-(6-Cyclopropyl-pyridin-3-ylamino)-2-fluoro-pyridin-3-yl]-(4-cyclopropyl-7H-pyrrolo[2,3-d]pyrimidin-5-yl)-methanone (P-4040),
(6-Cyclopropyl-pyridin-3-yl)-[5-(4-cyclopropyl-7H-pyrrolo[2,3-d]pyrimidin-5-ylmethyl)-6-fluoro-pyridin-2-yl]-amine (P-4041),
[5-(4-Cyclopropyl-7H-pyrrolo[2,3-d]pyrimidin-5-ylmethyl)-6-fluoro-pyridin-2-yl]-(6,7-dihydro-5H-[1]pyrindin-3-yl)-amine (P-4042),
(4-Cyclopropyl-7H-pyrrolo[2,3-d]pyrimidin-5-yl)-[6-(6,7-dihydro-5H-[1]pyrindin-3-ylamino)-2-fluoro-pyridin-3-yl]-methanone (P-4043),
(6-Cyclopropyl-pyridin-3-yl)-[6-fluoro-5-(4-methyl-7H-pyrrolo[2,3-d]pyrimidin-5-ylmethyl)-pyridin-2-yl]-amine (P-4044),
[6-(6-Cyclopropyl-pyridin-3-ylamino)-2-fluoro-pyridin-3-yl]-(4-methyl-7H-pyrrolo[2,3-d]pyrimidin-5-yl)-methanone (P-4045), and
any salt, prodrug, solvate, tautomer, or stereoisomer thereof. In some embodiments, the salt is a pharmaceutically acceptable salt.

In one embodiment of compounds of Formula I, the compound is selected from the group consisting of:
[6-Fluoro-5-(5-methyl-1H-pyrrolo[2,3-b]pyridin-3-ylmethyl)-pyridin-2-yl]-(6-methyl-pyridin-3-yl)-amine (P-3041),
[5-(5-Chloro-1H-pyrrolo[2,3-b]pyridin-3-ylmethyl)-6-fluoro-pyridin-2-yl]-(6-methyl-pyridin-3-yl)-amine (P-3042),
[2-Fluoro-6-(6-methyl-pyridin-3-ylamino)-pyridin-3-yl]-(5-methyl-1H-pyrrolo[2,3-b]pyridin-3-yl)-methanone (P-3043),
(5-Chloro-1H-pyrrolo[2,3-b]pyridin-3-yl)-[2-fluoro-6-(6-methyl-pyridin-3-ylamino)-pyridin-3-yl]-methanone (P-3044),
(6-Ethyl-pyridin-3-yl)-[6-fluoro-5-(5-methyl-1H-pyrrolo[2,3-b]pyridin-3-ylmethyl)-pyridin-2-yl]-amine (P-3048),
[6-(6-Ethyl-pyridin-3-ylamino)-2-fluoro-pyridin-3-yl]-(5-methyl-1H-pyrrolo[2,3-b]pyridin-3-yl)-methanone (P-3049),
(6-Cyclopropyl-pyridin-3-yl)-[6-fluoro-5-(5-methyl-1H-pyrrolo[2,3-b]pyridin-3-ylmethyl)-pyridin-2-yl]-amine (P-3050),
[6-(6-Cyclopropyl-pyridin-3-ylamino)-2-fluoro-pyridin-3-yl]-(5-methyl-1H-pyrrolo[2,3-b]pyridin-3-yl)-methanone (P-3051),
[6-(6-Cyclopropyl-pyridin-3-ylamino)-2-fluoro-pyridin-3-yl]-(1H-pyrrolo[2,3-b]pyridin-3-yl)-methanone (P-3052),
(6-Cyclopropyl-pyridin-3-yl)-[6-fluoro-5-(1H-pyrrolo[2,3-b]pyridin-3-ylmethyl)-pyridin-2-yl]-amine (P-3053),
(6-Cyclopropyl-pyridin-3-yl)-[6-fluoro-5-(4-methoxy-7H-pyrrolo[2,3-d]pyrimidin-5-ylmethyl)-pyridin-2-yl]-amine (P-4004),
(6-Ethyl-pyridin-3-yl)-[6-fluoro-5-(4-methoxy-7H-pyrrolo[2,3-d]pyrimidin-5-ylmethyl)-pyridin-2-yl]-amine (P-4007),
(6-Ethyl-pyridin-3-yl)-[6-fluoro-5-(4-methyl-7H-pyrrolo[2,3-d]pyrimidin-5-ylmethyl)-pyridin-2-yl]-amine (P-4009),
[6-Fluoro-5-(4-methoxy-7H-pyrrolo[2,3-d]pyrimidin-5-ylmethyl)-pyridin-2-yl]-(6-methyl-pyridin-3-yl)-amine (P-4010),
(6-Ethyl-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4016),
[5-(4-Ethoxy-7H-pyrrolo[2,3-d]pyrimidin-5-ylmethyl)-6-fluoro-pyridin-2-yl]-(6-methyl-pyridin-3-yl)-amine (P-4017),
[5-(4-Cyclopropyl-7H-pyrrolo[2,3-d]pyrimidin-5-ylmethyl)-6-fluoro-pyridin-2-yl]-(6-ethyl-pyridin-3-yl)-amine (P-4028),
(4-Cyclopropyl-7H-pyrrolo[2,3-d]pyrimidin-5-yl)-[6-(6-ethyl-pyridin-3-ylamino)-2-fluoro-pyridin-3-yl]-methanone (P-4029),
[5-(4-Cyclopropyl-7H-pyrrolo[2,3-d]pyrimidin-5-ylmethyl)-6-fluoro-pyridin-2-yl]-(6-methyl-pyridin-3-yl)-amine (P-4030),
(4-Cyclopropyl-7H-pyrrolo[2,3-d]pyrimidin-5-yl)-[2-fluoro-6-(6-methyl-pyridin-3-ylamino)-pyridin-3-yl]-methanone (P-4031),
[6-(6-Cyclopropyl-pyridin-3-ylamino)-2-fluoro-pyridin-3-yl]-(4-cyclopropyl-7H-pyrrolo[2,3-d]pyrimidin-5-yl)-methanone (P-4040),
(6-Cyclopropyl-pyridin-3-yl)-[5-(4-cyclopropyl-7H-pyrrolo[2,3-d]pyrimidin-5-ylmethyl)-6-fluoro-pyridin-2-yl]-amine (P-4041), and
any salt, prodrug, solvate, tautomer, or stereoisomer thereof. In some embodiments, the salt is a pharmaceutically acceptable salt.

In one embodiment of compounds of Formula I, the compound is selected from the group consisting of:
(6-Chloro-pyridin-3-yl)-[6-fluoro-5-(4-methoxy-7H-pyrrolo[2,3-d]pyrimidin-5-ylmethyl)-pyridin-2-yl]-amine (P-4003),
(6-Bromo-pyridin-3-yl)-[5-(4-ethoxy-7H-pyrrolo[2,3-d]pyrimidin-5-ylmethyl)-6-fluoro-pyridin-2-yl]-amine (P-4020),

[5-(4-Ethoxy-7H-pyrrolo[2,3-d]pyrimidin-5-ylmethyl)-6-fluoro-pyridin-2-yl]-pyridin-3-yl-amine (P-4021),
[5-(4-Cyclopropyl-7H-pyrrolo[2,3-d]pyrimidin-5-ylmethyl)-6-fluoro-pyridin-2-yl]-(5-methyl-pyridin-3-yl)-amine (P-4038),
(4-Cyclopropyl-7H-pyrrolo[2,3-d]pyrimidin-5-yl)-[2-fluoro-6-(5-methyl-pyridin-3-ylamino)-pyridin-3-yl]-methanone (P-4039), and any salt, prodrug, solvate, tautomer, or stereoisomer thereof. In some embodiments, the salt is a pharmaceutically acceptable salt.

In one embodiment of compounds of Formula I, the compound is selected from the group consisting of:
[6-Fluoro-5-(5-methyl-1H-pyrrolo[2,3-b]pyridin-3-ylmethyl)-pyridin-2-yl]-(6-methoxy-pyridin-3-yl)-amine (P-3019),
(6-Methoxy-pyridin-3-yl)-[5-(5-methyl-1H-pyrrolo[2,3-b]pyridin-3-ylmethyl)-pyrimidin-2-yl]-amine (P-3020),
(4-Methoxy-phenyl)-[5-(5-methyl-1H-pyrrolo[2,3-b]pyridin-3-ylmethyl)-pyrimidin-2-yl]-amine (P-3021),
[2-Fluoro-6-(6-methyl-pyridin-3-ylamino)-pyridin-3-yl]-(5-methyl-1H-pyrrolo[2,3-b]pyridin-3-yl)-methanone (P-3043),
(5-Chloro-1H-pyrrolo[2,3-b]pyridin-3-yl)-[2-fluoro-6-(6-methyl-pyridin-3-ylamino)-pyridin-3-yl]-methanone (P-3044),
[6-(6-Ethoxy-pyridin-3-ylamino)-2-fluoro-pyridin-3-yl]-(5-methyl-1H-pyrrolo[2,3-b]pyridin-3-yl)-methanone (P-3045),
(6-Ethyl-pyridin-3-yl)-[6-fluoro-5-(5-methyl-1H-pyrrolo[2,3-b]pyridin-3-ylmethyl)-pyridin-2-yl]-amine (P-3048),
[6-(6-Ethyl-pyridin-3-ylamino)-2-fluoro-pyridin-3-yl]-(5-methyl-1H-pyrrolo[2,3-b]pyridin-3-yl)-methanone (P-3049),
(6-Ethoxy-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4008),
(6-Ethyl-pyridin-3-yl)-[6-fluoro-5-(4-methyl-7H-pyrrolo[2,3-d]pyrimidin-5-ylmethyl)-pyridin-2-yl]-amine (P-4009),
(6-Ethyl-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4016),
[5-(4-Ethoxy-7H-pyrrolo[2,3-d]pyrimidin-5-ylmethyl)-6-fluoro-pyridin-2-yl]-(6-methoxy-pyridin-3-yl)-amine (P-4018),
{6-Fluoro-5-[4-(2-methoxy-ethoxy)-7H-pyrrolo[2,3-d]pyrimidin-5-ylmethyl]-pyridin-2-yl}-(6-methoxy-pyridin-3-yl)-amine (P-4019),
(6-Bromo-pyridin-3-yl)-[5-(4-ethoxy-7H-pyrrolo[2,3-d]pyrimidin-5-ylmethyl)-6-fluoro-pyridin-2-yl]-amine (P-4020),
[5-(4-Cyclopropyl-7H-pyrrolo[2,3-d]pyrimidin-5-ylmethyl)-6-fluoro-pyridin-2-yl]-(6-methoxy-pyridin-3-yl)-amine (P-4023),
[5-(4-Cyclopropyl-7H-pyrrolo[2,3-d]pyrimidin-5-ylmethyl)-6-fluoro-pyridin-2-yl]-(6-ethoxy-pyridin-3-yl)-amine (P-4026),
[5-(4-Cyclopropyl-7H-pyrrolo[2,3-d]pyrimidin-5-ylmethyl)-6-fluoro-pyridin-2-yl]-(6-ethyl-pyridin-3-yl)-amine (P-4028),
(4-Cyclopropyl-7H-pyrrolo[2,3-d]pyrimidin-5-yl)-[6-(6-ethyl-pyridin-3-ylamino)-2-fluoro-pyridin-3-yl]-methanone (P-4029),
[5-(4-Cyclopropyl-7H-pyrrolo[2,3-d]pyrimidin-5-ylmethyl)-6-fluoro-pyridin-2-yl]-(6-methyl-pyridin-3-yl)-amine (P-4030), and any salt, prodrug, solvate, tautomer, or stereoisomer thereof. In some embodiments, the salt is a pharmaceutically acceptable salt.

In one embodiment of compounds of Formula I, the compound is selected from the group consisting of:
[6-Fluoro-5-(5-methyl-1H-pyrrolo[2,3-b]pyridin-3-ylmethyl)-pyridin-2-yl]-(6-methoxy-pyridin-3-yl)-amine (P-3019),
(6-Methoxy-pyridin-3-yl)-[5-(5-methyl-1H-pyrrolo[2,3-b]pyridin-3-ylmethyl)-pyrimidin-2-yl]-amine (P-3020),
(4-Methoxy-phenyl)-[5-(5-methyl-1H-pyrrolo[2,3-b]pyridin-3-ylmethyl)-pyrimidin-2-yl]-amine (P-3021),
(6-Ethyl-pyridin-3-yl)-[6-fluoro-5-(5-methyl-1H-pyrrolo[2,3-b]pyridin-3-ylmethyl)-pyridin-2-yl]-amine (P-3048),
(6-Ethyl-pyridin-3-yl)-[6-fluoro-5-(4-methyl-7H-pyrrolo[2,3-d]pyrimidin-5-ylmethyl)-pyridin-2-yl]-amine (P-4009),
(6-Ethyl-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4016),
[5-(4-Ethoxy-7H-pyrrolo[2,3-d]pyrimidin-5-ylmethyl)-6-fluoro-pyridin-2-yl]-(6-methoxy-pyridin-3-yl)-amine (P-4018),
(6-Bromo-pyridin-3-yl)-[5-(4-ethoxy-7H-pyrrolo[2,3-d]pyrimidin-5-ylmethyl)-6-fluoro-pyridin-2-yl]-amine (P-4020),
[5-(4-Cyclopropyl-7H-pyrrolo[2,3-d]pyrimidin-5-ylmethyl)-6-fluoro-pyridin-2-yl]-(6-ethoxy-pyridin-3-yl)-amine (P-4026),
[5-(4-Cyclopropyl-7H-pyrrolo[2,3-d]pyrimidin-5-ylmethyl)-6-fluoro-pyridin-2-yl]-(6-ethyl-pyridin-3-yl)-amine (P-4028),
(4-Cyclopropyl-7H-pyrrolo[2,3-d]pyrimidin-5-yl)-[6-(6-ethyl-pyridin-3-ylamino)-2-fluoro-pyridin-3-yl]-methanone (P-4029), and any salt, prodrug, solvate, tautomer, or stereoisomer thereof. In some embodiments, the salt is a pharmaceutically acceptable salt.

In one embodiment of compounds of Formula I, the compound is selected from the group consisting of:
[2-Fluoro-6-(6-methyl-pyridin-3-ylamino)-pyridin-3-yl]-(5-methyl-1H-pyrrolo[2,3-b]pyridin-3-yl)-methanone (P-3043),
(5-Chloro-1H-pyrrolo[2,3-b]pyridin-3-yl)-[2-fluoro-6-(6-methyl-pyridin-3-ylamino)-pyridin-3-yl]-methanone (P-3044),
[6-(6-Ethoxy-pyridin-3-ylamino)-2-fluoro-pyridin-3-yl]-(5-methyl-1H-pyrrolo[2,3-b]pyridin-3-yl)-methanone (P-3045),
[6-(6-Ethyl-pyridin-3-ylamino)-2-fluoro-pyridin-3-yl]-(5-methyl-1H-pyrrolo[2,3-b]pyridin-3-yl)-methanone (P-3049),
(6-Ethoxy-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4008),
{6-Fluoro-5-[4-(2-methoxy-ethoxy)-7H-pyrrolo[2,3-d]pyrimidin-5-ylmethyl]-pyridin-2-yl}-(6-methoxy-pyridin-3-yl)-amine (P-4019),
[5-(4-Cyclopropyl-7H-pyrrolo[2,3-d]pyrimidin-5-ylmethyl)-6-fluoro-pyridin-2-yl]-(6-methoxy-pyridin-3-yl)-amine (P-4023),
[5-(4-Cyclopropyl-7H-pyrrolo[2,3-d]pyrimidin-5-ylmethyl)-6-fluoro-pyridin-2-yl]-(6-methyl-pyridin-3-yl)-amine (P-4030), and any salt, prodrug, solvate, tautomer, or stereoisomer thereof. In some embodiments, the salt is a pharmaceutically acceptable salt.

In one embodiment of compounds of Formula I, the compound is selected from the group consisting of:

[5-(5-Chloro-1H-pyrrolo[2,3-b]pyridin-3-ylmethyl)-pyrimidin-2-yl]-(4,4-difluoro-cyclohexyl)-amine (P-3004),
[5-(5-Chloro-1H-pyrrolo[2,3-b]pyridin-3-ylmethyl)-6-fluoro-pyridin-2-yl]-(4,4-difluoro-cyclohexyl)-amine (P-3013),
[6-Fluoro-5-(5-methyl-1H-pyrrolo[2,3-b]pyridin-3-ylmethyl)-pyridin-2-yl]-(6-methyl-pyridin-3-yl)-amine (P-3041),
[5-(5-Chloro-1H-pyrrolo[2,3-b]pyridin-3-ylmethyl)-6-fluoro-pyridin-2-yl]-(6-methyl-pyridin-3-yl)-amine (P-3042),
[6-Fluoro-5-(4-methoxy-7H-pyrrolo[2,3-d]pyrimidin-5-ylmethyl)-pyridin-2-yl]-(6-methyl-pyridin-3-yl)-amine (P-4010),
(1-Ethyl-1H-pyrazol-4-yl)-[6-fluoro-5-(4-methoxy-7H-pyrrolo[2,3-d]pyrimidin-5-ylmethyl)-pyridin-2-yl]amine (P-4011),
[5-(4-Ethoxy-7H-pyrrolo[2,3-d]pyrimidin-5-ylmethyl)-6-fluoro-pyridin-2-yl]-(1-ethyl-1H-pyrazol-4-yl)-amine (P-4012),
(1-Ethyl-1H-pyrazol-4-yl)-[6-fluoro-5-(4-methyl-7H-pyrrolo[2,3-d]pyrimidin-5-ylmethyl)-pyridin-2-yl]-amine (P-4013),
[5-(4-Cyclopropyl-7H-pyrrolo[2,3-d]pyrimidin-5-ylmethyl)-6-fluoro-pyridin-2-yl]-(1-ethyl-1H-pyrazol-4-yl)-amine (P-4036), and any salt, prodrug, solvate, tautomer, or stereoisomer thereof. In some embodiments, the salt is a pharmaceutically acceptable salt.

In one embodiment of compounds of Formula I, the compound is selected from the group consisting of:

[5-(5-Chloro-1H-pyrrolo[2,3-b]pyridin-3-ylmethyl)-pyrimidin-2-yl]-cycloheptyl-amine (P-3006),
(4-Fluoro-phenyl)-[5-(5-methyl-1H-pyrrolo[2,3-b]pyridin-3-ylmethyl)-pyrimidin-2-yl]-amine (P-3010),
(4-Chloro-phenyl)-[5-(5-chloro-1H-pyrrolo[2,3-b]pyridin-3-ylmethyl)-pyrimidin-2-yl]-amine (P-3011),
[5-(5-Chloro-1H-pyrrolo[2,3-b]pyridin-3-ylmethyl)-pyrimidin-2-yl]-(4-fluoro-phenyl)-amine (P-3012),
[5-(5-Chloro-1H-pyrrolo[2,3-b]pyridin-3-ylmethyl)-pyrimidin-2-yl]-(2-fluoro-phenyl)-amine (P-3014),
[5-(5-Methyl-1H-pyrrolo[2,3-b]pyridin-3-ylmethyl)-pyrimidin-2-yl]-(6-trifluoromethyl-pyridin-3-yl)-amine (P-3018),
(4-Ethoxy-phenyl)-[5-(5-methyl-1H-pyrrolo[2,3-b]pyridin-3-ylmethyl)-pyrimidin-2-yl]-amine (P-3026),
(6-Ethoxy-pyridin-3-yl)-[5-(5-methyl-1H-pyrrolo[2,3-b]pyridin-3-ylmethyl)-pyrimidin-2-yl]-amine (P-3027),
(1-Ethyl-1H-pyrazol-4-yl)-[5-(5-methyl-1H-pyrrolo[2,3-b]pyridin-3-ylmethyl)-pyrimidin-2-yl]-amine (P-3036),
(6-Ethoxy-pyridin-3-yl)-[6-fluoro-5-(5-methyl-1H-pyrrolo[2,3-b]pyridin-3-ylmethyl)-pyridin-2-yl]-amine (P-3039),
(1-Ethyl-1H-pyrazol-4-yl)-{6-fluoro-5-[4-(2-methoxyethoxy)-7H-pyrrolo[2,3-d]pyrimidin-5-ylmethyl]-pyridin-2-yl}-amine (P-4014),
[5-(4-Ethoxy-7H-pyrrolo[2,3-d]pyrimidin-5-ylmethyl)-6-fluoro-pyridin-2-yl]-(6-methyl-pyridin-3-yl)-amine (P-4017), and any salt, prodrug, solvate, tautomer, or stereoisomer thereof. In some embodiments, the salt is a pharmaceutically acceptable salt. In some embodiments, the invention provides a compound as set forth in Table 7 and any salt, solvate, prodrug, stereoisomer, or tautomer thereof. In some embodiments, the salt is a pharmaceutically acceptable salt.

In reference to compounds herein, unless clearly indicated to the contrary, specification of a compound or group of compounds includes salts of such compound(s) (including pharmaceutically acceptable salts), formulations of such compound(s) (including pharmaceutically acceptable formulations), conjugates thereof, derivatives thereof, forms thereof, prodrugs thereof, and all stereoisomers thereof. In reference to compositions, kits, methods of use, etc. of compounds of Formula I described herein, it is understood (unless indicated otherwise) that a compound of Formula I includes all sub-embodiments thereof (Including any sub-generic Formulae Ia through Iae).

In a fifty-sixth aspect, a compound of Formula I is an inhibitor of Fms kinase and has an $IC_{50}$ of less than 500 nm, less than 100 nM, less than 50 nM, less than 20 nM, less than 10 nM, less than 5 nM, or less than 1 nM as determined in a generally accepted Fms kinase activity assay. In some embodiments, the compound is selective relative to other protein kinases, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the compound is selective relative to Kit protein kinase, such that the ratio of $IC_{50}$ for Kit kinase assessed comparably, divided by the $IC_{50}$ for Fms kinase is >20, also >30, also >40, also >50, also >60, also >70, also >80, also >90, also >100.

In fifty-seventh aspect, a compound of Formula I is a Fms selective inhibitor, i.e. will selectively inhibit Fms kinase relative to Kit kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100. In some embodiments, the compound is also selective relative to protein kinases other than Kit, such that the ratio of $IC_{50}$ for another kinase assessed comparably, divided by the $IC_{50}$ for Fms kinase is >20, also >30, also >40, also >50, also >60, also >70, also >80, also >90, also >100, wherein the other protein kinase includes, but is not limited to Flt-3, CSK, Insulin receptor kinase, AMPK, PDGFR or VEGFR. In one embodiment, the Fms selective inhibitor does not effectively cross the blood brain barrier. In one embodiment, the Fms selective inhibitor does effectively cross the blood brain barrier.

In a fifty-eighth aspect, a compound of Formula I is a dual Fms/Kit inhibitor, i.e. will be approximately equipotent with respect to inhibition of Fms kinase and Kit kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the ratio of $IC_{50}$ for Kit kinase divided by the $IC_{50}$ for Fms kinase is in the range of 20 to 0.05, also 10 to 0.1, also 5 to 0.2. In some embodiments, the compound is selective relative to other protein kinases, such that the ratio of $IC_{50}$ for another kinase assessed comparably, divided by the $IC_{50}$ for Fms kinase (and/or Kit kinase) is >20, also >30, also >40, also >50, also >60, also >70, also >80, also >90, also >100, wherein the other protein kinase includes, but is not limited to CSK, Insulin receptor kinase, AMPK, PDGFR or VEGFR.

In a fifty-ninth aspect, a compound of Formula I is a dual Fms/Flt-3 inhibitor, i.e. will be approximately equipotent with respect to inhibition of Fms kinase and Flt-3 kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the ratio of $IC_{50}$ for Flt-3 kinase divided by the $IC_{50}$ for Fms kinase is in the range of 20 to 0.05, also 10 to 0.1, also 5 to 0.2. In some embodiments, the compound is selective relative to other protein kinases, such that the ratio of $IC_{50}$ for another kinase assessed comparably, divided by the $IC_{50}$ for Fms kinase (and/or Flt3 kinase) is >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the dual Fms/Flt-3 inhibitor is selective with respect to Kit. In some embodiments, the dual Fms/Flt-3 inhibitor also inhibits Kit.

In a sixtieth aspect, a compound of Formula I is a dual Fms/Trk inhibitor, i.e. will be approximately equipotent with respect to inhibition of Fms kinase and Trk kinase. In some embodiments the compound will have an $IC_{50}$ of less than 500 nm, less than 100 nM, less than 50 nM, less than 20 nM, less than 10 nM, less than 5 nM, or less than 1 nM as determined in a generally accepted Fms kinase activity assay and will have an $IC_{50}$ of less than 500 nm, less than 100 nM, less than 50 nM, less than 20 nM, less than 10 nM, less than 5 nM, or less than 1 nM as determined in a comparable generally accepted Trk kinase activity assay (including any one or more of TrkA, TrkB, and TrkC), wherein the ratio of $IC_{50}$ for Trk kinase (at least one of TrkA, TrkB, and TrkC) divided by the $IC_{50}$ for Fms kinase is in the range of 20 to 0.05, also 10 to 0.1, also 5 to 0.2. In some embodiments, the compound is selective relative to other protein kinases, such that the ratio of $IC_{50}$ for another kinase assessed comparably, divided by the $IC_{50}$ for Fms kinase (and/or Trk kinase) is >20, also >30, also >40, also >50, also >60, also >70, also >80, also >90, also >100, wherein the other protein kinase includes, but is not limited to CSK, Insulin receptor kinase, AMPK, PDGFR or VEGFR. In some embodiments, the dual Fms/Trk inhibitor is selective with respect to Kit. In some embodiments, the dual Fms/Trk inhibitor also inhibits Kit.

Further to any of the above mentioned aspects and embodiments, a compound of Formula I will also inhibit the effects of a mutation of the kinase, including, but not limited to, a mutation that is related to a disease state, such as a cancer.

In a sixty-first aspect, compositions are provided that include a therapeutically effective amount of any one or more compound(s) of Formula I and at least one pharmaceutically acceptable carrier, excipient, and/or diluent, including combinations of any two or more compounds of Formula I. The composition can further include a plurality of different pharmacologically active compounds, which can include a plurality of compounds of Formula I. In certain embodiments, the composition can include any one or more compound(s) of Formula I along with one or more compounds that are therapeutically effective for the same disease indication. In one aspect, the composition includes any one or more compound(s) of Formula I along with one or more compounds that are therapeutically effective for the same disease indication, wherein the compounds have a synergistic effect on the disease indication. In one embodiment, the composition includes any one or more compound(s) of Formula I effective in treating a cancer and one or more other compounds that are effective in treating the same cancer, further wherein the compounds are synergistically effective in treating the cancer.

In a sixty-second aspect, methods are provided for treating a disease or condition related to any one or more of Fms protein kinase, Kit protein kinase, Flt3 protein kinase, and Trk protein kinase in an animal subject in need thereof, wherein the method involves administering to the subject an effective amount of any one or more compound(s) of Formula I or a composition comprising any one or more compound(s) of Formula I. In certain embodiments, the method involves administering to the subject an effective amount of a compound of Formula I or a composition comprising a compound of Formula I in combination with one or more other therapies for the disease or condition.

In a sixty-third aspect, methods are provided for treating a disease or condition related to Fms protein kinase in an animal subject in need thereof, wherein the method involves administering to the subject an effective amount of any one or more compound(s) of Formula I or a composition comprising any one or more compound(s) of Formula I. In certain embodiments, the method involves administering to the subject an effective amount of a compound of Formula I or a composition comprising a compound of Formula I in combination with one or more other therapies for the disease or condition.

In a sixty-fourth aspect, methods are provided for treating a disease or condition related to Trk protein kinase in an animal subject in need thereof, wherein the method involves administering to the subject an effective amount of any one or more compound(s) of Formula I or a composition comprising any one or more compound(s) of Formula I. In certain embodiments, the method involves administering to the subject an effective amount of a compound of Formula I or a composition comprising a compound of Formula I in combination with one or more other therapies for the disease or condition.

In a sixty-fifth aspect, methods are provided for treating a disease or condition related to Kit protein kinase in an animal subject in need thereof, wherein the method involves administering to the subject an effective amount of any one or more compound(s) of Formula I or a composition comprising any one or more compound(s) of Formula I. In certain embodiments, the method involves administering to the subject an effective amount of a compound of Formula I or a composition comprising a compound of Formula I in combination with one or more other therapies for the disease or condition.

In a sixty-sixth aspect, methods are provided for treating a disease or condition related to Flt3 protein kinase in an animal subject in need thereof, wherein the method involves administering to the subject an effective amount of any one or more compound(s) of Formula I or a composition comprising any one or more compound(s) of Formula I. In certain embodiments, the method involves administering to the subject an effective amount of a compound of Formula I or a composition comprising a compound of Formula I in combination with one or more other therapies for the disease or condition.

In a sixty-seventh aspect, methods are provided for treating a disease or condition related to Fms protein kinase and Kit protein kinase in an animal subject in need thereof, wherein the method involves administering to the subject an effective amount of any one or more dual Fms/Kit inhibitor(s) of Formula I or a composition comprising any one or more dual Fms/Kit inhibitor(s) of Formula I. In certain embodiments, the method involves administering to the subject an effective amount of a dual Fms/Kit inhibitor of Formula I or a composition comprising a dual Fms/Kit inhibitor of Formula I in combination with one or more other therapies for the disease or condition.

In a sixty-eighth aspect, methods are provided for treating a disease or condition related to Fms protein kinase and Flt-3 protein kinase in an animal subject in need thereof, wherein the method involves administering to the subject an effective amount of any one or more dual Fms/Flt-3 inhibitor(s) of Formula I or a composition comprising any one or more dual Fms/Flt-3 inhibitor(s) of Formula I. In certain embodiments, the method involves administering to the subject an effective amount of a dual Fms/Flt-3 inhibitor of Formula I or a composition comprising a dual Fms/Flt-3 inhibitor of Formula I in combination with one or more other therapies for the disease or condition.

In a sixty-ninth aspect, methods are provided for treating a disease or condition related to Fms protein kinase and Trk protein kinase in an animal subject in need thereof, wherein the method involves administering to the subject an effective amount of any one or more dual Fms/Trk inhibitor(s) of Formula I or a composition comprising any one or more dual Fms/Trk inhibitor(s) of Formula I. In certain embodiments, the method involves administering to the subject an effective amount of a dual Fms/Trk inhibitor of Formula I or a composition comprising a dual Fms/Trk inhibitor of Formula I in combination with one or more other therapies for the disease or condition.

In a seventieth aspect, the invention provides a method of treating a cancer in a subject in need thereof by administering to the subject an effective amount of any one or more compound(s) of Formula I or a composition comprising any one or more compound(s) of Formula I, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, γ-ray, or electron, proton, neutron, or a particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), surgery, or bone marrow and stem cell transplantation.

In a seventy-first aspect, the invention provides a method of treating a cancer in a subject in need thereof by administering to the subject an effective amount of any one or more compound(s) of Formula I or a composition comprising any one or more compound(s) of Formula I, in combination with one or more suitable chemotherapeutic agents. In one embodiment, the one or more suitable chemotherapeutic agents is selected from an alkylating agent, including, but not limited to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, and uramustine; an antibiotic, including, but not limited to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limited to, aminopterin, azacitidine, azathioprine, capecitabine, cladribine, clofarabine, cytarabine, decitabine, floxuridine, fludarabine, 5-fluorouracil, 2'-F-ara-deoxyuridine, gemcitabine, hydroxyurea, mercaptopurine, methotrexate, nelarabine, pemetrexed, pralatrexate, azathioprine, raltitrexed, tegafur-uracil, thioguanine, trimethoprim, trimetrexate, and vidarabine; an immunotherapy, including, but not limited to, alemtuzumab, bevacizumab, cetuximab, denileukin diftitox, galiximab, gemtuzumab, ofatumumab, panitumumab, pertuzumab, rituximab, tositumomab, trastuzumab, and 90Y ibritumomab tiuxetan, ipilimumab, and tremelimumab; a hormone or hormone antagonist, including, but not limited to, anastrozole, androgens, bicalutamide, buserelin, Degarelix, diethylstilbestrol, exemestane, flutamide, fulvestrant, goserelin, idoxifene, letrozole, leuprolide, megestrol, nilutamide, raloxifene, tamoxifen, 4-hydroxytamoxifen, toremifene, and triptorelin; a taxane, including, but not limited to, DJ-927, docetaxel, TPI 287, larotaxel, ortataxel, paclitaxel, DHA-paclitaxel, and tesetaxel; a retinoid, including, but not limited to, alitretinoin, bexarotene, fenretinide, isotretinoin, and tretinoin; an alkaloid, including, but not limited to, demecolcine, homoharringtonine, vinblastine, vincristine, vindesine, vinflunine, and vinorelbine; an antiangiogenic agent, including, but not limited to, AE-941 (GW786034, Neovastat), ABT-510, 2-methoxyestradiol, lenalidomide, and thalidomide; a topoisomerase inhibitor, including, but not limited to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not limited to, axitinib (AG 013736), dasatinib (BMS 354825), erlotinib, gefitinib, flavopiridol, imatinib mesylate, lapatinib, motesanib diphosphate (AMG 706), nilotinib (AMN107), pazopanib, seliciclib, sorafenib, sunitinib malate, AEE-788, BMS-599626, UCN-01 (7-hydroxystaurosporine), PLX4032, vatalanib, mTOR inhibitors (e.g. temsirolimus, everolimus, deforolimus, rapamycin), PI3K inhibitors (e.g. BEZ235, GDC-0941, XL147, XL765, CAL-101, PX-866, BGT226, GSK1059615), Cdk4 inhibitors (e.g. PD-332991, AG-024322), Akt inhibitors (e.g. GSK2110183, SR13668), MEK inhibitors (e.g. PD0325901, AZD8330, GSK1120212, R04987655, RDEA119, XL518); a targeted signal transduction inhibitor including, but not limited to bortezomib, and geldanamycin; a biological response modifier, including, but not limited to, imiquimod, interferon-α, and interleukin-2; and other chemotherapeutics, including, but not limited to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, COX-2 inhibitors (e.g. celecoxib, rofecoxib, valdecoxib, lumiracoxib, etoricoxib), Hsp90 inhibitors (e.g. tanespimycin) and farnesyltransferase inhibitors (e.g. tipifarnib).

In a seventy-second aspect, the invention provides kits that include any one or more compound(s) of Formula I or a composition comprising any one or more compound(s) of Formula I. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the invention kit includes written instructions for use and/or other indication that the compound or composition is suitable or approved for administration to a mammal, e.g., a human, for a protein kinase-mediated disease or condition; and the compound or composition is packaged in unit dose or single dose form, e.g., single dose pills, capsules, or the like.

In aspects and embodiments involving treatment or prophylaxis of a disease or condition with any one or more compound(s) of Formula I or a composition comprising any one or more compound(s) of Formula I, the invention provides methods for treating a disease or condition related to Kit in an animal subject in need thereof (e.g. a mammal such as a human, other primates, sports animals, animals of commercial interest such as cattle, farm animals such as horses, or pets such as dogs and cats), e.g., a disease or condition characterized by abnormal Kit activity (e.g. kinase activity). In some embodiments invention methods may involve administering to the subject suffering from or at risk of a disease or condition related to Kit an effective amount of any one or more compound(s) of Formula I or a composition comprising any one or more compound(s) of Formula I. In one embodiment, the disease related to Kit is selected from the group consisting of malignancies, including, but not limited to, mast cell tumors, small cell lung cancer, non-small cell lung cancer (NSCLC), testicular cancer, pancreatic cancer, breast cancer, prostate cancer, merkel cell carcinoma, carcinomas of the female genital tract, sarcomas of neuroectodermal origin, colorectal carcinoma, carcinoma in situ, gastrointestinal stromal tumors (GISTs), multiple myeloma, tumor angiogenesis, brain metastases, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

In aspects and embodiments involving treatment or prophylaxis of a disease or condition with any one or more compound(s) of Formula I or a composition comprising any one or more compound(s) of Formula I, the invention provides methods for treating a disease or condition related to Fms in an animal subject in need thereof (e.g. a mammal such as a human, other primates, sports animals, animals of commercial interest such as cattle, farm animals such as horses, or pets such as dogs and cats), e.g., a disease or condition characterized by abnormal Fms activity (e.g. kinase activity). In some embodiments, invention methods may involve administering to the subject suffering from or at risk of a disease or condition related to Fms an effective amount of any one or more compound(s) of Formula I or a composition comprising any one or more compound(s) of Formula I. In one embodiment, the disease related to Fms is selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosus (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, glioma, other tumors of the central nervous system, brain metasteses, osteolytic bone metastases, metastasis of tumors to other tissues, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); global ischemia, and surgical indications, including but not limited to (cardiopulmonary) bypass surgery, vascular surgery, and vascular grafts.

In aspects and embodiments involving treatment or prophylaxis of a disease or condition with the any one or more compound(s) of Formula I or a composition comprising any one or more compound(s) of Formula I, the invention provides methods for treating a disease or condition related to Flt-3 in an animal subject in need thereof (e.g. a mammal such as a human, other primates, sports animals, animals of commercial interest such as cattle, farm animals such as horses, or pets such as dogs and cats), e.g., a disease or condition characterized by abnormal Flt-3 activity (e.g. kinase activity). In some embodiments, invention methods may involve administering to the subject suffering from or at risk of a disease or condition related to Flt-3 an effective amount of any one or more compound(s) of Formula I or a composition comprising any one or more compound(s) of Formula I. In one embodiment, the disease related to Flt-3 is selected from the group consisting of malignancies, including, but not limited to, glioma, glioblastoma, brain metastases, lung cancer, breast cancer, colorectal cancer, prostate cancer, gastric cancer, esophageal cancer, pancreatic cancer, ovarian cancer, non-Hodgkin's lymphoma, Hodgkin's lymphoma, multiple myeloma, acute lymphocytic leukemia, acute myeloid leukemia, acute myeloid leukemia with trilineage myelodysplasia, acute promyelocytic leukemia, chronic lymphocytic leukemia, chronic myeloid leukemia, chronic neutrophilic leukemia, acute undifferentiated leukemia, anaplastic large-cell lymphoma, prolymphocyte leukemia, juvenile myelomonocytic leukemia, adult T-cell acute lymphocytic leukemia, T-cell type acute lymphocytic leukemia, B-cell type acute lymphocytic leukemia, mixed lineage leukemia, multiple myeloma, chronic myelocytic leukemia, acute lymphoblastic leukemia, acute myeloblastic leukemia, chronic myelomonocytic leukemia; other diseases including psoriasis, atopic dermatitis, axonal degeneration, acute transverse myelitis, amyotrophic lateral sclerosis, infantile spinal muscular atrophy, juvenile spinal muscular atrophy, Creutzfeldt-Jakob disease, subacute sclerosing panencephalitis, organ rejection, bone marrow transplant rejection, non-myeloablative bone marrow transplant rejection, ankylosing spondylitis, aplastic anemia, Behcet's disease, graft-versus-host disease, Graves' disease, autoimmune hemolytic anemia, Wegener's granulomatosis, hyper IgE syndrome, idiopathic thrombocytopenia purpura, Myasthenia gravis, type 1 diabetes mellitus, rheumatoid arthritis, Crohn's disease, multiple sclerosis, systemic lupus erythematosus, myelodysplastic syndrome, thrombocythemia, essential thrombocytosis, angiogenic myeloid metaplasia, myelofibrosis, myelofibrosis with myeloid metaplasia, chronic idiopathic myelofibrosis, polycythemia vera, anemia, leukopenia, neutropenia, thrombocytopenia, granulocytopenia, and pancytopenia.

In aspects and embodiments involving treatment or prophylaxis of a disease or condition with the any one or more compound(s) of Formula I or a composition comprising any one or more compound(s) of Formula I, the invention provides methods for treating a disease or condition related to Trk in an animal subject in need thereof (e.g. a mammal such as a human, other primates, sports animals, animals of commercial interest such as cattle, farm animals such as horses, or pets such as dogs and cats), e.g., a disease or condition characterized by abnormal Trk activity (e.g. kinase activity). In some embodiments, invention methods may involve administering to the subject suffering from or at risk of a disease or condition related to Trk an effective amount of any one or more compound(s) of Formula I or a composition comprising any one or more compound(s) of Formula I. In one embodiment, the disease related to Trk is selected from the group consisting of malignancies, including, but not limited to, prostate cancer, small cell lung cancer, non-small cell lung cancer, Wilms tumors, mesoblastic nephroma, infantile fibrosarcoma, neuroblastoma, brain cancer, squamous cell cancer, bladder cancer, gastric cancer, pancreatic cancer, breast cancer, head and neck cancer, esophageal cancer, colorectal cancer, renal cancer, hepatocellular cancer, ovarian cancer, gynecological cancer, thyroid cancer, cervical cancer, ewings tumor, tumors of the central and peripheral nervous system, melanoma, multiple myeloma, acute myelogenous leukemia, and myeloid leukemia; neuropathies, including, but not limited to, stroke, multiple sclerosis, Parkinson's disease, Alzheimer's disease, transverse myelitis, and encephalitis; pain, including, but not limited to, chronic pain, acute pain, inflammatory pain, neuropathic pain, and pain associated with cancer, surgery, or bone fracture; bone-related diseases, including, but not limited to, metastatic bone disease, treatment-induced bone loss, osteoporosis, rheumatoid arthritis, ankylosing spondylitis, Paget's disease, and periodontal disease; other diseases, including, but not limited to, asthma, arthritis, diabetic retinopathy, macular degeneration, psoriasis, acute and chronic inflammation, Kaposi's sarcoma, haemangioma, acute and chronic nephropathies, atheroma, atherosclerosis, arterial restenosis, fibrosarcoma, osteosarcoma, panic disorder, and infectious disease (e.g. Typanosoma cruzi infection (Chagas disease)).

In aspects and embodiments involving treatment or prophylaxis of a disease or condition, methods may involve administering an effective amount of any one or more compound(s) of Formula I or a composition comprising any one or more compound(s) of Formula I to a subject in need thereof suffering from or at risk of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, global ischemia, ulcerative colitis, Crohn's disease, immune thrombocytopenic purpura, atherosclerosis, systemic lupus erythematosus, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In aspects and embodiments involving treatment or prophylaxis of a disease or condition, methods may involve administering an effective amount of any one or more compound(s) of Formula I or a composition comprising any one or more compound(s) of Formula I to a subject in need thereof suffering from or at risk of a disease or condition selected from the group consisting of rheumatoid arthritis, osteoarthritis, osteoporosis, peri-prosthetic osteolysis, multiple sclerosis, Alzheimer's disease, Parkinson's disease, global ischemia, renal hypertrophy, acute myeloid leukemia, melanoma, multiple myeloma, breast cancer, prostate cancer, pancreatic cancer, glioblastoma, neurofibromatosis, brain metastases, and gastrointestinal stromal tumors.

In aspects and embodiments involving treatment or prophylaxis of a disease or condition, methods may involve administering an effective amount of any one or more Kit inhibitor(s) of Formula I or a composition comprising any one or more Kit inhibitor(s) of Formula I to a subject in need thereof suffering from or at risk of a disease or condition selected from the group consisting of rheumatoid arthritis, gastrointestinal stromal tumors, melanoma and neurofibromatosis.

In aspects and embodiments involving treatment or prophylaxis of a disease or condition, methods may involve administering an effective amount of any one or more Fms selective inhibitor(s) of Formula I or a composition comprising any one or more Fms selective inhibitor(s) of Formula I to a subject in need thereof suffering from or at risk of a disease or condition selected from the group consisting of multiple sclerosis, Alzheimer's disease, Parkinson's disease, global ischemia, rheumatoid arthritis, osteoarthritis, osteoporosis, peri-prosthetic osteolysis, glomerulonephritis, interstitial nephritis, Lupus nephritis, diabetic nephropathy, and renal hypertrophy.

In aspects and embodiments involving treatment or prophylaxis of a disease or condition, methods may involve administering an effective amount of any one or more Fms selective inhibitor(s) of Formula I or a composition comprising any one or more Fms selective inhibitor(s) of Formula I to a subject in need thereof suffering from or at risk of a disease or condition selected from the group consisting of multiple sclerosis, Alzheimer's disease, Parkinson's disease, and global ischemia, wherein the one or more Fms selective inhibitor(s) does effectively cross the blood brain barrier.

In aspects and embodiments involving treatment or prophylaxis of a disease or condition, methods may involve administering an effective amount of any one or more Fms selective inhibitor(s) of Formula I or a composition comprising any one or more Fms selective inhibitor(s) of Formula I to a subject in need thereof suffering from or at risk of a disease or condition selected from the group consisting of rheumatoid arthritis, osteoarthritis, osteoporosis, peri-prosthetic osteolysis, glomerulonephritis, interstitial nephritis, Lupus nephritis, diabetic nephropathy, and renal hypertrophy, wherein the one or more Fms selective inhibitor(s) does not effectively cross the blood brain barrier.

In aspects and embodiments involving treatment or prophylaxis of a disease or condition, methods may involve administering an effective amount of any one or more dual Fms/Kit inhibitor(s) of Formula I or a composition comprising any one or more dual Fms/Kit inhibitor(s) of Formula I to a subject in need thereof suffering from or at risk of a disease or condition selected from the group consisting of breast cancer, prostate cancer, multiple myeloma, melanoma, acute myeloid leukemia, glioblastoma, brain metastases, neurofibromatosis, gastrointestinal stromal tumors, rheumatoid arthritis, and multiple sclerosis.

In aspects and embodiments involving treatment or prophylaxis of a disease or condition, methods may involve administering an effective amount of any one or more dual Fms/Flt-3 inhibitor(s) of Formula I or a composition comprising any one or more dual Fms/Flt-3 inhibitor(s) of Formula I to a subject in need thereof suffering from or at risk of a disease or condition selected from the group consisting of breast cancer, prostate cancer, multiple myeloma, melanoma, acute myeloid leukemia, glioblastoma, brain metastases, neurofibromatosis, gastrointestinal stromal tumors, rheumatoid arthritis, and multiple sclerosis, preferably wherein the disease is acute myeloid leukemia.

In aspects and embodiments involving treatment or prophylaxis of a disease or condition, methods may involve administering an effective amount of any one or more dual Fms/Trk inhibitor(s) of Formula I or a composition comprising any one or more dual Fms/Trk inhibitor(s) of Formula I to a subject in need thereof suffering from or at risk of a disease or condition selected from the group consisting of pancreatic cancer, prostate cancer, and multiple myeloma.

In a seventy-third aspect, any one or more compound(s) of Formula I can be used in the preparation of a medicament for the treatment of a disease or condition related to Kit selected from the group consisting of malignancies, including, but not limited to, mast cell tumors, small cell lung cancer, non-small cell lung cancer (NSCLC), testicular cancer, pancreatic cancer, breast cancer, prostate cancer, merkel cell carcinoma, carcinomas of the female genital tract, sarcomas of neuroectodermal origin, colorectal carcinoma, carcinoma in situ, gastrointestinal stromal tumors (GISTs), multiple myeloma, tumor angiogenesis, brain metastases, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

In a seventy-fourth aspect, any one or more compound(s) of Formula I can be used in the preparation of a medicament for the treatment of a disease or condition related to Fms selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, glioma, other tumors of the central nervous system, brain metasteses, osteolytic bone metastases, metastasis of tumors to other tissues, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); global ischemia, and surgical indications, including but not limited to (cardiopulmonary) bypass surgery, vascular surgery, and vascular grafts.

In a seventy-fifth aspect, any one or more compound(s) of Formula I can be used in the preparation of a medicament for the treatment of a disease or condition related to Flt-3 selected from the group consisting of malignancies, including, but not limited to, glioma, glioblastoma, brain metastases, lung cancer, breast cancer, colorectal cancer, prostate cancer, gastric cancer, esophageal cancer, pancreatic cancer, ovarian cancer, non-Hodgkin's lymphoma, Hodgkin's lymphoma, multiple myeloma, acute lymphocytic leukemia, acute myeloid leukemia, acute myeloid leukemia with trilineage myelodysplasia, acute promyelocytic leukemia, chronic lymphocytic leukemia, chronic myeloid leukemia, chronic neutrophilic leukemia, acute undifferentiated leukemia, anaplastic large-cell lymphoma, prolymphocyte leukemia, juvenile myelomonocyctic leukemia, adult T-cell acute lymphocytic leukemia, T-cell type acute lymphocytic leukemia, B-cell type acute lymphocytic leukemia, mixed lineage leukemia, multiple myeloma, chronic myelocytic leukemia, acute lymphoblastic leukemia, acute myeloblastic leukemia, chronic myelomonocytic leukemia; other diseases including psoriasis, atopic dermatitis, axonal degeneration, acute transverse myelitis, amyotrophic lateral sclerosis, infantile spinal muscular atrophy, juvenile spinal muscular atrophy, Creutzfeldt-Jakob disease, subacute sclerosing panencephalitis, organ rejection, bone marrow transplant rejection, non-myeloablative bone marrow transplant rejection, ankylosing spondylitis, aplastic anemia, Behcet's disease, graft-versus-host disease, Graves' disease, autoimmune hemolytic anemia, Wegener's granulomatosis, hyper IgE syndrome, idiopathic thrombocytopenia purpura, Myasthenia gravis, type 1 diabetes mellitus, rheumatoid arthritis, Crohn's disease, multiple sclerosis, systemic lupus erythematosus, myelodysplastic syndrome, thrombocythemia, essential thrombocytosis, angiogenic myeloid metaplasia, myelofibrosis, myelofibrosis with myeloid metaplasia, chronic idiopathic myelofibrosis, polycythemia vera, anemia, leukopenia, neutropenia, thrombocytopenia, granulocytopenia, and pancytopenia.

In a seventy-sixth aspect, any one or more compound(s) of Formula I can be used in the preparation of a medicament for the treatment of a disease or condition related to Trk selected from the group consisting of malignancies, including, but not limited to, prostate cancer, small cell lung cancer, non-small cell lung cancer, Wilms tumors, mesoblastic nephroma, infantile fibrosarcoma, neuroblastoma, brain cancer, squamous cell cancer, bladder cancer, gastric cancer, pancreatic cancer, breast cancer, head and neck cancer, esophageal cancer, colorectal cancer, renal cancer, hepatocellular cancer, ovarian cancer, gynecological cancer, thyroid cancer, cervical cancer, ewings tumor, tumors of the central and peripheral nervous system, melanoma, multiple myeloma, acute myelogenous leukemia, and myeloid leukemia; neuropathies, including, but not limited to, stroke, multiple sclerosis, Parkinson's disease, Alzheimer's disease, transverse myelitis, and encephalitis; pain, including, but not limited to, chronic pain, acute pain, inflammatory pain, neuropathic pain, and pain associated with cancer, surgery, or bone fracture; bone-related diseases, including, but not limited to, metastatic bone disease, treatment-induced bone loss, osteoporosis, rheumatoid arthritis, ankylosing spondylitis, Paget's disease, and periodontal disease; other diseases, including, but not limited to, asthma, arthritis, diabetic retinopathy, macular degeneration, psoriasis, acute and chronic inflammation, Kaposi's sarcoma, haemangioma, acute and chronic nephropathies, atheroma, atherosclerosis, arterial restenosis, fibrosarcoma, osteosarcoma, panic disorder, and infectious disease (e.g. Typanosoma cruzi infection (Chagas disease)).

In a seventy-seventh aspect, any one or more compound(s) of Formula I can be used in the preparation of a medicament for the treatment of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, global ischemia, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In a seventy-eighth aspect, any one or more compound(s) of Formula I can be used in the preparation of a medicament for the treatment of a disease or condition selected from the group consisting of rheumatoid arthritis, osteoarthritis, osteoporosis, peri-prosthetic osteolysis, multiple sclerosis, Alzheimer's disease, Parkinson's disease, global ischemia, renal hypertrophy, acute myeloid leukemia, melanoma, multiple myeloma, breast cancer, prostate cancer, pancreatic cancer, glioblastoma, neurofibromatosis, brain metastases, and gastrointestinal stromal tumors.

In a seventy-ninth aspect, one or more compounds as described herein that are Kit inhibitors can be used in the preparation of a medicament for the treatment of rheumatoid arthritis, gastrointestinal stromal tumors, melanoma or neurofibromatosis.

In an eightieth aspect, one or more compounds as described herein that are Fms selective inhibitors can be used in the preparation of a medicament for the treatment of multiple sclerosis, Alzheimer's disease, Parkinson's disease, global ischemia, rheumatoid arthritis, osteoarthritis, osteoporosis, peri-prosthetic osteolysis, glomerulonephritis, interstitial nephritis, Lupus nephritis, diabetic nephropathy, or renal hypertrophy.

In an eighty-first aspect, one or more compounds as described herein that are Fms selective inhibitors that effectively cross the blood brain barrier can be used in the preparation of a medicament for the treatment of multiple sclerosis, glioblastoma, Alzheimer's disease, Parkinson's disease, or global ischemia.

In an eighty-second aspect, one or more compounds as described herein that are Fms selective inhibitors that do not effectively cross the blood brain barrier can be used in the preparation of a medicament for the treatment of rheumatoid arthritis, osteoarthritis, osteoporosis, peri-prosthetic osteolysis, glomerulonephritis, interstitial nephritis, Lupus nephritis, diabetic nephropathy, or renal hypertrophy.

In an eighty-third aspect, one or more compounds as described herein that are dual Fms/Kit inhibitors can be used in the preparation of a medicament for the treatment of breast cancer, prostate cancer, multiple myeloma, melanoma, acute myeloid leukemia, glioblastoma, brain metastases, neurofibromatosis, gastrointestinal stromal tumors, rheumatoid arthritis, or multiple sclerosis.

In an eighty-fourth aspect, one or more compounds as described herein that are dual Fms/Flt-3 inhibitors can be used in the preparation of a medicament for the treatment of breast cancer, prostate cancer, multiple myeloma, melanoma, acute myeloid leukemia, glioblastoma, brain metastases, neurofibromatosis, gastrointestinal stromal tumors, rheumatoid arthritis, or multiple sclerosis, preferably wherein the disease is acute myeloid leukemia.

In an eighty-fifth aspect, one or more compounds as described herein that are dual Fms/Trk inhibitors can be used in the preparation of a medicament for the treatment of pancreatic cancer, prostate cancer, and multiple myeloma.

In an eighty-sixth aspect, there are provided compounds of Formula I for the treatment of a disease or condition related to Kit selected from the group consisting of malignancies, including, but not limited to, mast cell tumors, small cell lung cancer, non-small cell lung cancer (NSCLC), testicular cancer, pancreatic cancer, breast cancer, prostate cancer, merkel cell carcinoma, carcinomas of the female genital tract, sarcomas of neuroectodermal origin, colorectal carcinoma, carcinoma in situ, gastrointestinal stromal tumors (GISTs), multiple myeloma, tumor angiogenesis, brain metastases, glioblastoma, astrocytoma, neuroblastoma, neurofibromatosis (including Schwann cell neoplasia associated with neurofibromatosis), acute myeloid leukemia, acute lymphocytic leukemia, chronic myeloid leukemia, mastocytosis, melanoma, and canine mast cell tumors; cardiovascular disease, including but not limited to atherosclerosis, cardiomyopathy, heart failure, pulmonary arterial hypertension and pulmonary fibrosis; inflammatory and autoimmune indications, including, but not limited to, allergy, anaphylaxis, asthma, rheumatoid arthritis, allergic rhinitis, multiple sclerosis, inflammatory bowel disease, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

In an eighty-seventh aspect there are provided compounds of Formula I for the treatment of a disease or condition related to Fms selected from the group consisting of inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel disease, ulcerative colitis, Crohn's disease, systemic lupus erythematosis (SLE), immune thrombocytopenic purpura (ITP), myelopreparation for autologous transplantation, transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the nervous system, including, but not limited to, demyelinating disorders (e.g. multiple sclerosis, Charcot Marie Tooth syndrome), amyotrophic lateral sclerosis (ALS), myasthenia gravis, chronic demyelinating polyneuropathy, other demyelinating disorders, stroke, Alzheimer's disease and Parkinson's disease; pain, including, but not limited to, chronic pain, acute pain, inflammatory pain, neuropathic pain, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumors, (e.g. giant cell tumor of bone, giant cell tumor of tendon sheath (TGCT)), pigmented villonodular synovitis (PVNS), tumor angiogenesis, melanoma, glioblastoma multiforme, glioma, other tumors of the central nervous system, brain metasteses, osteolytic bone metastases, metastasis of tumors to other tissues, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); global ischemia, and surgical indications, including but not limited to (cardiopulmonary) bypass surgery, vascular surgery, and vascular grafts.

In an eighty-eighth aspect, there are provided compounds of Formula I for the treatment of a disease or condition related to Flt-3 selected from the group consisting of malignancies, including, but not limited to, glioma, glioblastoma, brain metastases, lung cancer, breast cancer, colorectal cancer, prostate cancer, gastric cancer, esophageal cancer, pancreatic cancer, ovarian cancer, non-Hodgkin's lymphoma, Hodgkin's lymphoma, multiple myeloma, acute lymphocytic leukemia, acute myeloid leukemia, acute myeloid leukemia with trilineage myelodysplasia, acute promyelocytic leukemia, chronic lymphocytic leukemia, chronic myeloid leukemia, chronic neutrophilic leukemia, acute undifferentiated leukemia, anaplastic large-cell lymphoma, prolymphocyte leukemia, juvenile myelomonocytic leukemia, adult T-cell acute lymphocytic leukemia, T-cell type acute lymphocytic leukemia, B-cell type acute lymphocytic leukemia, mixed lineage leukemia, multiple myeloma, chronic myelocytic leukemia, acute lymphoblastic leukemia, acute myeloblastic leukemia, chronic myelomonocytic leukemia; other diseases including psoriasis, atopic dermatitis, axonal degeneration, acute transverse myelitis, amyotrophic lateral sclerosis, infantile spinal muscular atrophy, juvenile spinal muscular atrophy, Creutzfeldt-Jakob disease, subacute sclerosing panencephalitis, organ rejection, bone marrow transplant rejection, non-myeloablative bone marrow transplant rejection, ankylosing spondylitis, aplastic anemia, Behcet's disease, graft-versus-host disease, Graves' disease, autoimmune hemolytic anemia, Wegener's granulomatosis, hyper IgE syndrome, idiopathic thrombocytopenia purpura, Myasthenia gravis, type 1 diabetes mellitus, rheumatoid arthritis, Crohn's disease, multiple sclerosis, systemic lupus erythematosus, myelodysplastic syndrome, thrombocythemia, essential thrombocytosis, angiogenic myeloid metaplasia, myelofibrosis, myelofibrosis with myeloid metaplasia, chronic idiopathic myelofibrosis, polycythemia vera, anemia, leukopenia, neutropenia, thrombocytopenia, granulocytopenia, and pancytopenia.

In an eighty-ninth aspect, there are provided compounds of Formula I for the treatment of a disease or condition related to Trk selected from the group consisting of malignancies, including, but not limited to, prostate cancer, small cell lung cancer, non-small cell lung cancer, Wilms tumors, mesoblastic nephroma, infantile fibrosarcoma, neuroblastoma, brain cancer, squamous cell cancer, bladder cancer, gastric cancer, pancreatic cancer, breast cancer, head and neck cancer, esophageal cancer, colorectal cancer, renal cancer, hepatocellular cancer, ovarian cancer, gynecological cancer, thyroid cancer, cervical cancer, ewings tumor, tumors of the central and peripheral nervous system, melanoma, multiple myeloma, acute myelogenous leukemia, and myeloid leukemia; neuropathies, including, but not limited to, stroke, multiple sclerosis, Parkinson's disease, Alzheimer's disease, transverse myelitis, and encephalitis; pain, including, but not limited to, chronic pain, acute pain, inflammatory pain, neuropathic pain, and pain associated with cancer, surgery, or bone fracture; bone-related diseases, including, but not limited to, metastatic bone disease, treatment-induced bone loss, osteoporosis, rheumatoid arthritis, ankylosing spondylitis, Paget's disease, and periodontal disease; other diseases, including, but not limited to, asthma, arthritis, diabetic retinopathy, macular degeneration, psoriasis, acute and chronic inflammation, Kaposi's sarcoma, haemangioma, acute and chronic nephropathies, atheroma, atherosclerosis, arterial restenosis, fibrosarcoma, osteosarcoma, panic disorder, and infectious disease (e.g. Typanosoma cruzi infection (Chagas disease)).

In a ninetieth aspect, there are provided compounds of Formula I for the treatment of a disease or condition selected from the group consisting of rheumatoid arthritis, osteoarthritis, osteoporosis, peri-prosthetic osteolysis, systemic sclerosis, demyelinating disorders, multiple sclerosis, Charcot Marie Tooth syndrome, amyotrophic lateral sclerosis, Alzheimer's disease, Parkinson's disease, global ischemia, ulcerative colitis, Crohn's disease, immune thrombocytopenic purpura, atherosclerosis, systemic lupus erythematosis, myelopreparation for autologous transplantation, transplant rejection, glomerulonephritis, interstitial nephritis, Lupus nephritis, tubular necrosis, diabetic nephropathy, renal hypertrophy, type I diabetes, acute pain, inflammatory pain, neuropathic pain, acute myeloid leukemia, melanoma, multiple myeloma, breast cancer, prostate cancer, pancreatic cancer, lung cancer, ovarian cancer, gliomas, glioblastomas, neurofibromatosis, osteolytic bone metastases, brain metastases, gastrointestinal stromal tumors, and giant cell tumors.

In a ninety-first aspect, there are provided compounds of Formula I for the treatment of a disease or condition selected from the group consisting of rheumatoid arthritis, osteoarthritis, osteoporosis, peri-prosthetic osteolysis, multiple sclerosis, Alzheimer's disease, Parkinson's disease, global ischemia, renal hypertrophy, acute myeloid leukemia, melanoma, multiple myeloma, breast cancer, prostate cancer, pancreatic cancer, glioblastoma, neurofibromatosis, brain metastases, and gastrointestinal stromal tumors.

In a ninety-second aspect, there are provided compounds as described herein that are Kit inhibitors for the treatment of a disease or condition selected from the group consisting of rheumatoid arthritis, gastrointestinal stromal tumors, melanoma and neurofibromatosis.

In a ninety-third aspect, there are provided compounds as described herein that are Fms selective inhibitors for the treatment of a disease or condition selected from the group consisting of multiple sclerosis, Alzheimer's disease, Parkinson's disease, global ischemia, rheumatoid arthritis, osteoarthritis, osteoporosis, peri-prosthetic osteolysis, glomerulonephritis, interstitial nephritis, Lupus nephritis, diabetic nephropathy, and renal hypertrophy.

In a ninety-fourth aspect, there are provided compounds as described herein that are Fms selective inhibitors that effectively cross the blood brain barrier for the treatment of a disease or condition selected from the group consisting of multiple sclerosis, glioblastoma, Alzheimer's disease, Parkinson's disease, and global ischemia.

In a ninety-fifth aspect, there are provided compounds as described herein that are Fms selective inhibitors that do not effectively cross the blood brain barrier for the treatment of a disease or condition selected from the group consisting of rheumatoid arthritis, osteoarthritis, osteoporosis, peri-prosthetic osteolysis, glomerulonephritis, interstitial nephritis, Lupus nephritis, diabetic nephropathy, and renal hypertrophy.

In a ninety-sixth aspect, there are provided compounds as described herein that are dual Fms/Kit inhibitors for the treatment of a disease or condition selected from the group consisting of breast cancer, prostate cancer, multiple myeloma, melanoma, acute myeloid leukemia, glioblastoma, brain metastases, neurofibromatosis, gastrointestinal stromal tumors, rheumatoid arthritis, and multiple sclerosis.

In a ninety-seventh aspect, there are provided compounds as described herein that are dual Fms/Flt-3 inhibitors for the treatment of a disease or condition selected from the group consisting of breast cancer, prostate cancer, multiple myeloma, melanoma, acute myeloid leukemia, glioblastoma, brain metastases, neurofibromatosis, gastrointestinal stromal tumors, rheumatoid arthritis, and multiple sclerosis, preferably wherein the disease is acute myeloid leukemia.

In a ninety-eighth aspect, there are provided compounds as described herein that are dual Fms/Trk inhibitors for the treatment of a disease or condition selected from the group consisting of pancreatic cancer, prostate cancer, and multiple myeloma.

In a ninety-nineth aspect, the invention provide a compound of Formula II:

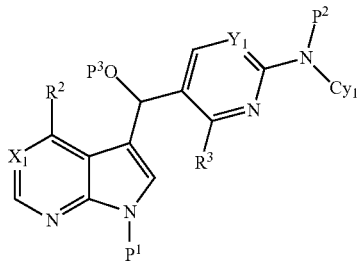
(II)

wherein $P^1$ and $P^2$ are each independently H or an amino protecting group. $P^3$ is H or a hydroxyl protecting group or a labile group. In one embodiment, $P^1$ and $P^2$ are each independently amino protecting group. In one embodiment, $P^3$ is H. All the other variables $X_1$, $R^2$, $R^3$, $Y_1$ and $Cy_1$ are as defined in any of the embodiments of Formula I described herein.

In a 100$^{th}$ aspect, the invention provides a compound of Formula IIa:

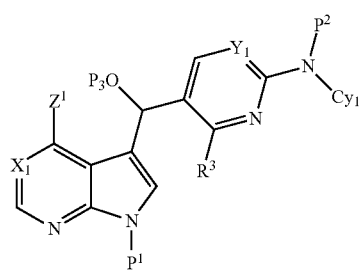
IIa wherein $P^1$ and $P^2$ are each independently H or an amino protecting group. $P^3$ is H or a hydroxyl protecting group or a labile group. $Z^1$ is Br, $C^1$ or $R^2$, wherein $R^2$ is as defined in any of the embodiments of formula I descried herein. In one embodiment, $Z^1$ is Cl or Br. In one embodiment, $P^1$ and $P^2$ are each independently amino protecting group. In one embodiment, $P^3$ is H. All the other variables $X_1$, $R^3$, $Y_1$ and $Cy_1$ are as defined in any of the embodiments of Formula I described herein.

In a 101$^{st}$ aspect, the invention provides a method of preparing a compound of Formula I. The method includes contacting a compound of Formula II with an agent under conditions sufficient to form a compound of Formula I. The agent can be an oxidizing or a reducing agent. Examples of the oxidizing agent include, but are not limited to, Dess-Martin periodinane (DMP). Examples of the reducing agents include, but are not limited to, trialkylsilane. In some embodiments, the method is provided to prepare any of the compounds set forth in Tables 1 or 2, or any of compounds of Formula I or any compounds as described herein.

In a 102$^{nd}$ aspect, the invention provides a method of preparing a compound of Formulas II or IIa. The method includes contacting a compound of Formula III:

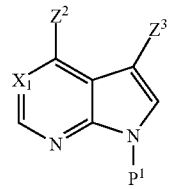
III with a compound of Formula IV:

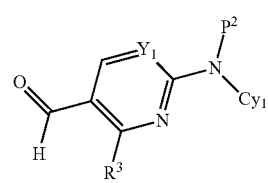
IV under conditions sufficient to form a compound of Formula II or IIa, wherein $Z^2$ is Br, $C^1$ or $R^2$ as defined in any of the embodiments described herein; $Z^3$ is iodo, a leaving group or a labile group; $P^1$ and $P^2$ are each independently an amino protecting group. In one embodiment, $Z^2$ is Cl or Br and $Z^3$ is I. In another embodiment, $Z^2$ is $R^2$. In some embodiments, $Z^3$ is iodo, methanesulfonyloxy, p-toluenesulfonyloxy, trifluoromethanesulfonyloxy. All the other variables $X_1$, $R^3$, $Y_1$ and $Cy_1$ are as defined in any of the embodiments of Formula I described herein. In some embodiments, the method is provided to prepare any of the compounds set forth in Tables 1 or 2, or any of compounds of Formula I or any of the compounds as described herein. In some embodiments, a compound of Formula IV is an aldehyde selected from those set forth in Tables 3, 4, 5 and/or 6. In some embodiments, compounds of Formula III is a pyrrolo[2,3-b]pyridine compound selected from those set forth in Tables 4, 5 and/or 6. In some embodiments, compounds of formula IV is a pyrrolo[2,3-b]pyrimidine selected from those set forth in Table 5.

Any one or more of compounds of Formula I demonstrate desirable inhibitory activity on one or more of Fms, Kit, Flt3 and Trk kinases, including desirable activity profiles as described herein with selectivity relative to other kinases. Compounds of Formula I further demonstrate one or more desirable properties, including enhanced pharmacokinetic properties, favorable solubility, favorable lack of Cyp inhibition, and the like.

Additional aspects and embodiments will be apparent from the following Detailed Description of the Invention and from the claims.

DETAILED DESCRIPTION OF THE INVENTION

As used herein the following definitions apply unless clearly indicated otherwise:

It is noted here that as used in this specification and the appended claims, the singular forms "a," "an," and "the" include plural reference unless the context clearly dictates otherwise.

All atoms designated within a Formula described herein, either within a structure provided, or within the definitions of variables related to the structure, is intended to include any isotope thereof, unless clearly indicated to the contrary. It is understood that for any given atom, the isotopes may be present essentially in ratios according to their natural occurrence, or one or more particular atoms may be enhanced with respect to one or more isotopes using synthetic methods known to one skilled in the art. Thus hydrogen includes for example $^1H$, $^2H$, $^3H$; carbon includes for example $^{11}C$, $^{12}C$, $^{13}C$, $^{14}C$; oxygen includes for example $^{16}O$, $^{17}O$, $^{18}O$; nitrogen includes for example $^{13}N$, $^{14}N$, $^{15}N$; sulfur includes for example $^{32}S$, $^{33}S$, $^{34}S$, $^{35}S$, $^{36}S$, $^{37}S$, $^{38}S$; fluoro includes for example $^{17}F$, $^{18}F$, $^{19}F$; chloro includes for example $^{35}Cl$, $^{36}Cl$, $^{37}Cl$, $^{38}Cl$, $^{39}Cl$; and the like.

"Halogen" refer to all halogens, that is, chloro (Cl), fluoro (F), bromo (Br), or iodo (I).

"Haloalkyl," is meant to include alkyl substituted by one to seven halogen atoms. Haloalkyl includes monohaloalkyl and polyhaloalkyl. For example, the term "$C_{1-6}$ haloalkyl" is meant to include trifluoromethyl, difluoromethyl, 2,2,2-trifluoroethyl, 4-chlorobutyl, 3-bromopropyl, and the like.

"Hydroxyl" or "hydroxy" refer to the group —OH.

"Thiol" refers to the group —SH.

"Lower alkyl" alone or in combination means an alkane-derived radical containing from 1 to 6 carbon atoms (unless otherwise specified) that includes a straight chain alkyl or branched alkyl. The straight chain or branched lower alkyl group is chemically feasible and attached at any available point to provide a stable compound. In many embodiments, a lower alkyl is a straight or branched alkyl group containing from 1-6, 1-4, 1-3, or 1-2, carbon atoms, such as methyl, ethyl, propyl, isopropyl, butyl, t-butyl, and the like. In some instances, the option of the number of carbon atoms in a lower alkyl is specified, for example, $C_{1-3}$ alkyl refers to lower alkyl having 1, 2 or 3 carbon atoms. A "substituted lower alkyl" denotes lower alkyl that is independently substituted, unless indicated otherwise, with one or more, preferably 1, 2, 3, 4, 5 or 6, also 1, 2, or 3 substituents, as described herein, attached at any available atom to provide a stable compound. For example "fluoro substituted lower alkyl" denotes a lower alkyl group substituted with one or more fluoro atoms, such as perfluoroalkyl, where preferably the lower alkyl is substituted with 1, 2, 3, 4, 5 or 6 fluoro atoms, also 1, 2, or 3 fluoro atoms. It is understood that substitutions are chemically feasible and attached at any available atom to provide a stable compound.

"Lower alkoxy" denotes the group —$OR^a$, where $R^a$ is lower alkyl. In some instances, the option of the number of carbon atoms in the lower alkyl is specified, for example, $C_{1-3}$ alkoxy refers to lower alkoxy having 1, 2 or 3 carbon atoms. "Substituted lower alkoxy" denotes lower alkoxy in which $R^z$ is lower alkyl substituted with one or more substituents as indicated herein, for example, in the description of compounds of Formula I, including descriptions of substituted cycloalkyl, phenyl and heteroaryl, attached at any available atom to provide a stable compound. Preferably, substitution of lower alkoxy is with 1, 2, 3, 4, 5 or 6 substituents, also 1, 2, or 3 substituents. For example "fluoro substituted lower alkoxy" denotes lower alkoxy in which the lower alkyl is substituted with one or more fluoro atoms, where preferably the lower alkoxy is substituted with 1, 2, 3, 4, 5 or 6 fluoro atoms, also 1, 2, or 3 fluoro atoms. It is understood that substitutions on alkoxy are chemically feasible and attached at any available atom to provide a stable compound.

"Lower alkylthio" denotes the group —$SR^b$, where $R^b$ is lower alkyl. In some instances, the option of the number of carbon atoms in the lower alkyl is specified, for example, $C_{1-3}$ alkylthio refers to lower alkylthio having 1, 2 or 3 carbon atoms. "Substituted lower alkylthio" denotes lower alkylthio in which $R^z$ is lower alkyl substituted with one or more substituents as indicated herein, for example, in the description of compounds of Formula I, including descriptions of substituted cycloalkyl, phenyl and heteroaryl, attached at any available atom to provide a stable compound. Preferably, substitution of lower alkylthio is with 1, 2, 3, 4, 5 or 6 substituents, also 1, 2, or 3 substituents. For example "fluoro substituted lower alkylthio" denotes lower alkylthio in which the lower alkyl is substituted with one or more fluoro atoms, where preferably the lower alkylthio is substituted with 1, 2, 3, 4, 5 or 6 fluoro atoms, also 1, 2, or 3 fluoro atoms. It is understood that substitutions on alkylthio are chemically feasible and attached at any available atom to provide a stable compound.

"Lower alkylsulfonyl" denotes the group —$S(O)_2R^c$, where $R^c$ is lower alkyl. In some instances, the option of the number of carbon atoms in the lower alkyl is specified, for example, $C_{1-3}$ alkylsulfonyl refers to lower alkylsulfonyl having 1, 2 or 3 carbon atoms. "Substituted lower alkylsulfonyl" denotes lower alkysulfonyl in which $R^z$ is lower alkyl substituted with one or more substituents as indicated herein, for example, in the description of compounds of Formula I, including descriptions of substituted cycloalkyl, phenyl and heteroaryl, attached at any available atom to provide a stable compound. Preferably, substitution of lower alkylsulfonyl is with 1, 2, 3, 4, 5 or 6 substituents, also 1, 2, or 3 substituents. For example "fluoro substituted lower alkylsulfonyl" denotes lower alkylsulfonyl in which the lower alkyl is substituted with one or more fluoro atoms, where preferably the lower alkylsulfonyl is substituted with 1, 2, 3, 4, 5 or 6 fluoro atoms, also 1, 2, or 3 fluoro atoms. It is understood that substitutions on alkylsulfonyl are chemically feasible and attached at any available atom to provide a stable compound.

"Cycloalkyl" refers to saturated or unsaturated, non-aromatic monocyclic carbon ring systems of 3-8, more preferably 3-6, ring members per ring, such as cyclopropyl, cyclopentyl, cyclohexyl, and the like. In some instances, the option of the number of carbon atoms in the cycloalkyl is specified, for example, $C_{1-3}$ cycloalkyl refers to cycloalkyl having 1, 2 or 3 carbon atoms. A "substituted cycloalkyl" is a cycloalkyl that is independently substituted, unless indicated otherwise, with one or more, preferably 1, 2, 3, 4 or 5, also 1, 2, or 3 substituents, as described herein, attached at any available atom to provide a stable compound. It is understood that substitutions are chemically feasible and attached at any available atom to provide a stable compound.

"Cycloalkylalkyl" refers to an -(alkylene)-cycloalkyl group where alkylene as defined herein has the indicated number of carbon atoms or if unspecified having six or fewer, preferably four or fewer main chain carbon atoms; and cycloalkyl is as defined herein has the indicated number of carbon atoms. $C_{3-8}$cycloalkylalkyl is meant to have 3 to 8 ring carbon atoms. Exemplary cycloalkylalkyl include, e.g., cyclopropylmethylene, cyclobutylethylene, cyclobutylmethylene, and the like.

The term "alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —$CH_2$—, ethylene —$CH_2CH_2$—, propylene —$CH_2CH_2CH_2$—, and isopropylene —$CH(CH_3)CH_2$—, —$CH_2CH(CH_3)$—, —$CH_2$—$(CH_2)_2CH_2$—, —$CH_2$—$CH(CH_3)CH_2$—, —$CH_2$—$C(CH_3)_2$—, —$CH_2$—$CH_2CH(CH_3)$—. Typically, an alkyl (or alkylene) group will have from 1 to 24 carbon atoms, with those groups having 10 or fewer, 8 or fewer, or 6 or fewer carbon atoms being preferred in the present invention. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms or 4 or fewer main chain carbon atoms.

"Aryl" by itself or as part of another substituent refers to a monocyclic, bicyclic or polycyclic polyunsaturated aromatic hydrocarbon moiety containing 6 to 14 ring carbon atoms. Non-limiting examples of unsubstituted aryl groups include phenyl, 1-naphthyl, 2-naphthyl and 4-biphenyl. Exemplary aryl group, such as phenyl or naphthyl, which may be optionally fused with a cycloalkyl of preferably 5-7, more preferably 5-6, ring members.

"Arylalkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, and the like.

A "substituted phenyl" is a phenyl ring that is independently substituted, unless indicated otherwise, with one or more, preferably 1, 2, 3, 4 or 5, also 1, 2, or 3 substituents, as described herein, attached at any available atom to provide a stable compound. It is understood that substitutions are chemically feasible and attached at any available atom to provide a stable compound.

"Heteroaryl" by itself or as part of another substituent refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. "5 or 6 membered heteroaryl" alone or in combination refers to a monocyclic aromatic ring structure containing 5 or 6 ring atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is provided. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzothienyl, quinolyl, isoquinolyl, indazolyl, pteridinyl and thiadiazolyl, and the like. A "substituted heteroaryl" is a heteroaryl that is independently substituted, unless indicated otherwise, with one or more, preferably 1, 2, 3, 4 or 5, also 1, 2, or 3 substituents, as described herein, attached at any available atom to provide a stable compound. It is understood that substitutions are chemically feasible and attached at any available atom to provide a stable compound.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein. Examples of heteroarylalkyl include 2-pyridylmethyl, 2-thiazolylethyl, and the like.

"Heterocycloalkyl" refers to a saturated or unsaturated non-aromatic cycloalkyl group that contains from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system of 3 to 12, preferably 4 to 10 ring atoms, more preferably 5 to 8 ring atoms in which one to five ring atoms are heteroatoms selected from —N═, —N—, —O—, —S—, —S(O)—, or —S(O)$_2$— and further wherein one or two ring atoms are optionally replaced by a —C(O)— group. The heterocycloalkyl can also be a heterocyclic alkyl ring fused with a cycloalkyl, an aryl or a heteroaryl ring. Non limiting examples of heterocycloalkyl groups include pyrrolidinyl, piperidinyl, imidazolidinyl, pyrazolidinyl, butyrolactam moiety, valerolactam moiety, imidazolidinone moiety, hydantoin, dioxolane moiety, phthalimide moiety, piperidine, 1,4-dioxane moiety, morpholinyl, thiomorpholinyl, thiomorpholinyl-S-oxide, thiomorpholinyl-S,S-oxide, piperazinyl, pyranyl, pyridine moiety, 3-pyrrolinyl, thiopyranyl, pyrone moiety, tetrahydrofuranyl, tetrahydrothiophenyl, quinuclidinyl, and the like. A heterocycloalkyl group can be attached to the remainder of the molecule through a ring carbon or a heteroatom.

"Heterocycloalkylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein. Examples of heterocycloalkylalkyl include 2-pyridylmethyl, 2-thiazolylethyl, and the like.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, *Tetrahedron* 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, $CH_2$═$CHCH_2$—, and the like, groups of the formula —C(O)R', wherein R' is, for example, methyl, phenyl, trifluoromethyl, and the like, groups of the formula —$SO_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000). Representative hydroxyl protecting groups include, but are not limited to, acetyl, benzoyl, dimethoxytrityl, methoxyethyoxymethyl, methoxymethyl, p-methoxybenzyl, tetrahydropyranyl, methylthiomethyl, trityl, t-butyldimethylsilyloxymethyl and trialkylsilyl, such as TMS, TIPS and the like.

As used herein, "Leaving group" or "Labile group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present invention.

Certain compounds of the present invention can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention As used herein, the term "Fms and Kit related disease or condition" refers to a disease or condition in which the biological function of a Fms protein kinase, including any mutation thereof, a Kit protein kinase, including any mutation thereof, or both a Fms and Kit protein kinase, including any mutations thereof, affects the development, course, and/or symptoms of the disease or condition, and/or in which modulation of the Fms and/or Kit protein kinase alters the development, course, and/or symptoms of the disease or condition. A Fms and/or Kit related disease or condition includes a disease or condition for which modulation provides a therapeutic benefit, e.g. wherein treatment with a Fms and/or Kit protein kinase inhibitor, preferably a dual Fms/Kit inhibitor, including one or more compound(s) described herein, provides a therapeutic benefit to the subject suffering from or at risk of the disease or condition.

As used herein, the term "Fms related disease or condition" and the like refers to a disease or condition in which the biological function of a Fms protein kinase, including any mutations thereof, affects the development, course, and/or symptoms of the disease or condition, and/or in which modulation of the Fms protein kinase alters the development, course, and/or symptoms of the disease or condition. The Fms related disease or condition includes a disease or condition for which Fms inhibition provides a therapeutic benefit, e.g. wherein treatment with a Fms inhibitor, preferably a Fms selective inhibitor including one or more compound(s) described herein, provides a therapeutic benefit to the subject suffering from or at risk of the disease or condition.

As used herein, the terms "Kit related disease or condition" and the like refers to a disease or condition in which the biological function of a Kit protein kinase, including any mutations thereof, affects the development, course, and/or symptoms of the disease or condition, and/or in which modulation of the Kit protein kinase alters the development, course, and/or symptoms of the disease or condition. The Kit related disease or condition includes a disease or condition for which Kit inhibition provides a therapeutic benefit, e.g. wherein treatment with a Kit inhibitor, including one or more compound(s) described herein, provides a therapeutic benefit to the subject suffering from or at risk of the disease or condition.

As used herein, the term "dual Fms/Kit inhibitor" refers to a compound that inhibits both Fms and Kit protein kinases, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and having an $IC_{50}$ of less than 500 nm, less than 100 nM, less than 50 nM, less than 20 nM, less than 10 nM, less than 5 nM, or less than 1 nM as determined in a comparable generally accepted Kit kinase activity assay, wherein the activity is approximately equipotent on each. Compounds are considered approximately equipotent if the ratio of $IC_{50}$ for Kit kinase activity divided by the $IC_{50}$ for Fms kinase activity is in the range of 20 to 0.05, also 10 to 0.1, also 5 to 0.2. Such compounds are effective in treating a disease or condition that is either or both of a Fms related and Kit related disease or condition. Such compounds are preferably, but not necessarily, selective with respect to other protein kinases, i.e. when compared to another protein kinase, the $IC_{50}$ for the other kinase divided by the $IC_{50}$ for Fms kinase (and/or Kit kinase) is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a dual Fms/Kit inhibitor may be used to treat any Fms related disease or condition, the dual inhibition of Fms and Kit provides beneficial effects in treating certain diseases or conditions, including, but not limited to, breast cancer, prostate cancer, multiple myeloma, melanoma, acute myeloid leukemia, glioblastoma, brain metastases, neurofibromatosis, gastrointestinal stromal tumors, rheumatoid arthritis, or multiple sclerosis.

As used herein, the term "dual Fms/Flt-3 inhibitor" refers to a compound that inhibits both Fms and Flt-3 protein kinases, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and having an $IC_{50}$ of less than 500 nm, less than 100 nM, less than 50 nM, less than 20 nM, less than 10 nM, less than 5 nM, or less than 1 nM as determined in a comparable generally accepted Flt-3 kinase activity assay, wherein the activity is approximately equipotent on each. Compounds are considered approximately equipotent if the ratio of $IC_{50}$ for Flt-3 kinase activity divided by the $IC_{50}$ for Fms kinase activity is in the range of 20 to 0.05, also 10 to 0.1, also 5 to 0.2. Such compounds are effective in treating a disease or condition that is either or both of a Fms related and Flt-3 related disease or condition. Such compounds are preferably, but not necessarily, selective with respect to other protein kinases, i.e. when compared to another protein kinase, the $IC_{50}$ for the other kinase divided by the $IC_{50}$ for Fms kinase (and/or Flt3 kinase) is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a dual Fms/Flt-3 inhibitor may be used to treat any Fms related mediated disease or condition, the dual inhibition of Fms and Flt-3 provides beneficial effects in treating certain diseases or conditions, including, but not limited to, breast cancer, prostate cancer, multiple myeloma, melanoma, acute myeloid leukemia, glioblastoma, brain metastases, neurofibromatosis, gastrointestinal stromal tumors, rheumatoid arthritis, or multiple sclerosis.

As used herein, the term "dual Fms/Trk inhibitor" refers to a compound that inhibits both Fms and Trk protein kinases, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and having an $IC_{50}$ of less than 500 nm, less than 100 nM, less than 50 nM, less than 20 nM, less than 10 nM, less than 5 nM, or less than 1 nM as determined in a comparable generally accepted Trk kinase activity assay (i.e. any one or more of TrkA, TrkB and TrkC), wherein the activity is approximately equipotent on each. Compounds are considered approximately equipotent if the ratio of $IC_{50}$ for Trk kinase activity (i.e. at least one of TrkA, TrkB and TrkC) divided by the $IC_{50}$ for Fms kinase activity is in the range of 20 to 0.05, also 10 to 0.1, also 5 to 0.2. Such compounds are effective in treating a disease or condition that is either or both of a Fms related and Trk related disease or condition. Such compounds are preferably, but not necessarily, selective with respect to other protein kinases, i.e. when compared to another protein kinase, the $IC_{50}$ for the other kinase divided by the $IC_{50}$ for Fms kinase (and/or Trk kinase) is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a dual Fms/Trk inhibitor may be used to treat any Fms related mediated disease or condition, the dual inhibition of Fms and Trk provides beneficial effects in treating certain diseases or conditions, including, but not limited to, pancreatic cancer, prostate cancer, and multiple myeloma.

As used herein, the term "Fms selective inhibitor" refers to a compound that selectively inhibits Fms kinase relative to Kit kinase, i.e. a compound having an $IC_{50}$ of less than 500 nm, less than 100 nM, less than 50 nM, less than 20 nM, less than 10 nM, less than 5 nM, or less than 1 nM as determined in a generally accepted Fms kinase activity assay and when determined in a comparable generally accepted Kit kinase activity assay will have a ratio of $IC_{50}$ for Kit kinase divided by the $IC_{50}$ for Fms kinase of >20, also >30, also >40, also >50, also >60, also >70, also >80, also >90, also >100. Such compounds are effective in treating a disease or condition that is Fms protein kinase mediated, without effecting Kit protein kinase. Such compounds are preferably, but not necessarily, selective with respect to other protein kinases, i.e. when compared to another protein kinase, the $IC_{50}$ for the other kinase divided by the $IC_{50}$ for Fms kinase is >20, also >30, also >40, also >50, also >60, also >70, also >80, also >90, also >100. Preferably, the compounds are selective relative to other protein kinases including, but not limited to, CSK, Insulin receptor kinase, AMPK, PDGFR or VEGFR. While it is understood that a Fms selective inhibitor may be used to treat any Fms related disease or condition, the Fms selectivity provides beneficial effects in treating certain diseases or conditions, including, but not limited to, multiple sclerosis, Alzheimer's disease, Parkinson's disease, global ischemia, rheumatoid arthritis, osteoarthritis, osteoporosis, peri-prosthetic osteolysis, glomerulonephritis, interstitial nephritis, Lupus nephritis, diabetic nephropathy, or renal hypertrophy.

As used herein, the term "blood brain barrier" refers to the physical barrier in the circulation system that prevents many substances, including certain small molecule drugs, from entering into the central nervous system (CNS). Drugs which are intended to interact with molecular targets in the CNS must cross the blood brain barrier to reach their intended targets. Conversely, peripherally acting agents should not cross the blood brain barrier so as to avoid any CNS related side effects. The ability of a compound to penetrate the blood brain barrier is expressed as the blood brain barrier permeability or the ratio of the steady-state concentrations of the compound in the brain and in the blood. The experimental blood brain barrier permeability can be measured by in vivo methods. Various methods can be employed for measuring the fraction of compound transported from the blood to brain tissue, including brain blood partitioning, brain perfusion, brain uptake index, and intracerebral microdialysis. However, these in vivo methods are laborious and low-throughput in nature. In practice, in silico computational methods are often used to predict the blood brain barrier permeability prior to in vivo confirmation. Most of the blood brain barrier models that have been built so far are based on the assumption that the majority of the compounds are transported across the blood brain barrier by passive diffusion. Of all the physicochemical properties, polar surface area (PSA) shows the best correlation with the blood brain barrier permeability for passively diffused compounds. Empirical evidence suggests that compounds having a polar surface area of 100 or greater typically have a low probability of crossing the blood brain barrier. Polar surface area is readily calculated from the compound structure using a published algorithm (Ertl et al., J. Med. Chem. 2000, 43:3714-3717). While it is understood that a Fms selective inhibitor may be used to treat any Fms related disease or condition, compounds that effectively cross the blood brain barrier provide beneficial effects in treating certain diseases or conditions, including, but not limited to, multiple sclerosis, Alzheimer's disease, Parkinson's disease, and global ischemia, while compounds that do not effectively cross the blood brain barrier provide beneficial effects in treating certain diseases or conditions, including, but not limited to, rheumatoid arthritis, osteoarthritis, osteoporosis, peri-prosthetic osteolysis, glomerulonephritis, interstitial nephritis, Lupus nephritis, diabetic nephropathy, or renal hypertrophy.

As used herein, the terms "treat", "treating", "therapy", "therapies", and like terms refer to the administration of material, e.g., any one or more compound(s) as described herein in an amount effective to prevent, alleviate, or ameliorate one or more symptoms of a disease or condition, i.e., indication, and/or to prolong the survival of the subject being treated.

As used herein, the term "solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

As used herein, the term "substantially crystalline" material embraces material which has greater than about 90% crystallinity; and "crystalline" material embraces material which has greater than about 98% crystallinity.

As used herein, the term "substantially amorphous" material embraces material which has no more than about 10% crystallinity; and "amorphous" material embraces material which has no more than about 2% crystallinity.

As used herein, the term "semi-crystalline" material embraces material which is greater than 10% crystallinity, but no greater than 90% crystallinity; preferably "semi-crystalline" material embraces material which is greater than 20% crystallinity, but no greater than 80% crystallinity. In one aspect of the present invention, a mixture of solid forms of a compound may be prepared, for example, a mixture of amorphous and crystalline solid forms, e.g. to provide a "semi-crystalline" solid form. Such a "semi-crystalline" solid form may be prepared by methods known in the art, for example by mixing an amorphous solid form with a crystalline solid form in the desired ratio. In some instances, a compound mixed with acid or base forms an amorphous complex; a semi-crystalline solid can be prepared employing an amount of compound component in excess of the stoichiometry of the compound and acid or base in the amorphous complex, thereby resulting in an amount of the amorphous complex that is based on the stoichiometry thereof, with excess compound in a crystalline form. The amount of excess compound used in the preparation of the complex can be adjusted to provide the desired ratio of amorphous complex to crystalline compound in the resulting mixture of solid forms. For example, where the amorphous complex of acid or base and compound has a 1:1 stoichiometry, preparing said complex with a 2:1 mole ratio of compound to acid or base will result in a solid form of 50% amorphous complex and 50% crystalline compound. Such a mixture of solid forms may be beneficial as a drug product, for example, by providing an amorphous component having improved biopharmaceutical properties along with the crystalline component. The amorphous component would be more readily bioavailable while the crystalline component would have a delayed bioavailablity. Such a mixture may provide both rapid and extended exposure to the active compound.

As used herein, the term "complex" refers to a combination of a pharmaceutically active compound and an additional molecular species that forms or produces a new chemical species in a solid form. In some instances, the complex may be a salt, i.e. where the additional molecular species provides an acid/base counter ion to an acid/base group of the compound resulting in an acid:base interaction that forms a typical salt. While such salt forms are typically substantially crystalline, they can also be partially crystalline, substantially amorphous, or amorphous forms. In some instances, the additional molecular species, in combination with the pharmaceutically active compound, forms a non-salt co-crystal, i.e. the compound and molecular species do not interact by way of a typical acid:base interaction, but still form a substantially crystalline structure. Co-crystals may also be formed from a salt of the compound and an additional molecular species. In some instances, the complex is a substantially amorphous complex, which may contain salt-like acid:base interactions that do not form typical salt crystals, but instead form a substantially amorphous solid, i.e. a solid whose X-ray powder diffraction pattern exhibits no sharp peaks (e.g. exhibits an amorphous halo).

As used herein, the term "stoichiometry" refers to the molar ratio of two or more reactants that combine to form a complex, for example, the molar ratio of acid or base to compound that form an amorphous complex. For example, a 1:1 mixture of acid or base with compound (i.e. 1 mole acid or base per mole of compound) resulting in an amorphous solid form has a 1:1 stoichiometry.

As used herein, the term "composition" refers to a pharmaceutical preparation suitable for administration to an intended animal subject for therapeutic purposes that contains at least one pharmaceutically active compound, including any solid form thereof. The composition may include at least one pharmaceutically acceptable component to provide an improved formulation of the compound, such as a suitable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectibles.

In the present context, the term "therapeutically effective" or "effective amount" indicates that the materials or amount of material is effective to prevent, alleviate, or ameliorate one or more symptoms of a disease or medical condition, and/or to prolong the survival of the subject being treated.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the invention, the term "synthesizing" and like terms means chemical synthesis from one or more precursor materials.

By "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal chord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gall bladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

Kinase Targets and Indications of the Invention

Protein kinases play key roles in propagating biochemical signals in diverse biological pathways. More than 500 kinases have been described, and specific kinases have been implicated in a wide range of diseases or conditions (i.e., indications), including for example without limitation, cancer, cardiovascular disease, inflammatory disease, neurological disease, and other diseases. As such, kinases represent important control points for small molecule therapeutic intervention. Specific target protein kinases contemplated by the present invention are described in the art, including, without limitation, protein kinases as described in U.S. patent application Ser. No. 11/473,347 (see also, PCT publication WO2007002433), the disclosure of which is hereby incorporated by reference with respect to such kinase targets, as well as the following:

Fms: Target kinase Fms (i.e., feline McDonough sarcoma) is a member of the family of genes originally isolated from the Susan McDonough strain of feline sarcoma viruses. Fms is a transmembrane tyrosine kinase of 108.0 kDa coded by chromosome 5q33.2-q33.3 (symbol: CSF1R). The structure of the transmembrane receptor Fms comprises two Ig-like domains, a IgC2-like domain, two additional Ig-like domains, a TM domain, and the TK domain.

Fms is the receptor for the macrophage colony-stimulating factor (M-CSF), and is crucial for the growth and differentiation of the monocyte-macrophage lineage. Upon binding of M-CSF to the extracellular domain of Fms, the receptor dimerizes and trans-autophosphorylates cytoplasmic tyrosine residues.

M-CSF, first described by Robinson and co-workers (Blood. 1969, 33:396-9), is a cytokine that controls the production, differentiation, and function of macrophages. M-CSF stimulates differentiation of progenitor cells to mature monocytes, and prolongs the survival of monocytes. Furthermore, M-CSF enhances cytotoxicity, superoxide production, phagocytosis, chemotaxis, and secondary cytokine production of additional factors in monocytes and macrophages. Examples of such additional factors include granulocyte colony stimulating factor (G-CSF), interleukin-6 (IL-6), and interleukin-8 (IL-8). M-CSF stimulates hematopoiesis, promotes differentiation and proliferation of osteoclast progenitor cells, and has profound effects on lipid metabolism. Furthermore, M-CSF is important in pregnancy. Physiologically, large amounts of M-CSF are produced in the placenta, and M-CSF is believed to play an essential role in trophoblast differentiation (Motoyoshi, Int J Hematol. 1998, 67:109-22). The elevated serum M-CSF levels of early pregnancy may participate in the immunologic mechanisms responsible for the maintenance of the pregnancy (Flanagan & Lader, Curr Opin Hematol. 1998, 5:181-5).

Aberrant expression and/or activation of Fms has been implicated in acute myeloid leukemia, AML (Ridge et al, Proc. Nat. Acad. Sci., 1990, 87:1377-1380). Mutations at codon 301 are believed to lead to neoplastic transformation by ligand independence and constitutive tyrosine kinase activity of the receptor. The tyrosine residue at codon 969 has been shown to be involved in a negative regulatory activity, which is disrupted by amino acid substitutions. Accordingly, Fms mutations are most prevalent (20%) in chronic myelomonocytic leukemia and AML type M4 (23%), both of which are characterized by monocytic differentiation.

A condition related to AML is chronic myeloid leukemia (CML). During the myeloid blast crisis (BC) of CML, non-random additional chromosome abnormalities occur in over 80% of patients. However, these cytogenetic changes have been reported to precede the clinical signs of CML-BC by several months to years suggesting that other biological events may participate in the multistep process of acute transformation of CML. The autocrine production of growth factors has been shown to occur in several hematological malignancies and particularly in AML. Specchia et al [Br J Haematol. 1992 March; 80(3):310-6] have demonstrated that IL-1 beta gene is expressed in almost all cases of CML in myeloid blast crisis, and that a high proportion of cases showed constitutive expression of the M-CSF gene. Many of the same patients in the Specchia et al study demonstrated simultaneous co-expression of Fms. After exposure of leukemic cells to phorbol myristate acetate (PMA), release of M-CSF protein was documented in three of five patients studied; however, no significant interleukin-3 (IL-3), granulocyte-macrophage colony-stimulating factor (GM-CSF) or granulocyte colony-stimulating factor (G-CSF), was detected in these patients. This demonstrates that different patterns of growth factors secretion exist in AML and CML, and that distinct molecular events are likely involved in the control of leukemic proliferation.

The observation that production of M-CSF, the major macrophage growth factor, is increased in tissues during inflammation (Le Meur et al, J. Leukocyte Biology. 2002; 72:530-537) provides a role for Fms in certain diseases. For example, COPD is characterized by airflow limitation that is not fully reversible. The airflow limitation is usually progressive and associated with an abnormal inflammatory response of the lungs to noxious particles or gases. The chronic inflammation of COPD is observed through the airways, parenchyma, and pulmonary vasculature. The inflammatory cell population consists of neutrophils, macrophages, and T lymphocytes, along with eosinophils in some patients. Macrophages are postulated to play an orchestrating role in COPD inflammation by releasing mediators such as TNF-a, IL-8 and LTB4, which are capable of damaging lung structures and/or sustaining neutrophilic inflammation.

Further, M-CSF/fms signaling is critical to osteoclast formation and survival of osteoclast precursors. For example, estrogen loss in menopause results in increased M-CSF and thus increased osteoclast number and bone resorption which leads to increased risk of fracture and osteoporosis. Accordingly, blockage of this signal is a target for the inhibition of bone resorption (Teitelbaum, Science. 2000; 289:1504; Rohan, Science. 2000; 289:1508).

Atherosclerosis, an inflammatory disease of the vessel walls, is associated with significant morbidity and mortality. A beneficial effect for Fms inhibition in the treatment and prevention of atherosclerosis depends on several observations (Libby, Nature. 2002; 420:868-874). First, monocytes resident in the arterial intima increase expression of scavenger receptors and internalize modified lipoproteins. The resulting lipid-laden macrophages develop into foam cells characteristic of the atherosclerotic lesion. Macrophages in atheroma secrete cytokines and growth factors involved in lesion progression. Additionally, macrophages replicate within the intima. Through Fms, M-CSF activates the transition from monocyte to lipid-laden macrophage and augments expression of scavenger receptor A. Indeed, atherosclerotic plaques over-express M-CSF which is critical for atherosclerotic progression. Mice deficient in M-CSF have been found to experience less severe atherosclerosis than mice with normal M-CSF (Rajavashisth, et. al., J. Clin. Invest. 1998; 101: 2702-2710; Qiao, et. al., Am. J. Path. 1997; 150:1687-1699). Accordingly, inhibitors of Fms disrupt M-CSF signaling, compromising monocyte to macrophage foam cell progression, macrophage survival and replication, and cytokine signaling that participates in lesion progression.

The role of M-CSF and Fms in emphysema appears to involve the regulation of elastin metabolism through control of matrix metalloproteins. M-CSF has a role in the modulation of the accumulation and function of alveolar macrophages (AMs) in vivo (Shibata et al, Blood 2001, 98: pp. 2845-2852). Osteopetrotic (Op/Op) mice have no detectable M-CSF and show variable tissue-specific reductions in macrophage numbers. Accordingly, it was hypothesized that AMs would be decreased in number and have altered function in Op/Op mice because of the absence of M-CSF. Shibata et al found that lung macrophages identified in lung sections were decreased in number in 20-day-old Op/Op mice but not Op/Op mice older than 4 months compared with findings in age-matched littermate controls. The numbers of AMs recovered by bronchoalveolar lavage (BAL) were also reduced in young but not adult Op/Op mice compared with controls. Importantly, AMs of Op/Op mice spontaneously release higher levels of matrix metalloproteinases (MMPs) than AMs of controls. Consistent with an increased release of MMP, Op/Op mice have abnormal elastin deposition and spontaneously develop emphysema in the absence of molecular or cellular evidence of lung inflammation. Accordingly, the modulation of metalloelastase activity in macrophages by M-CSF may control the degradation of elastin fibers in lungs or blood vessels.

Metastatic cancer cells cause bone destruction, with associated fracture, pain, deformation, and hypercalcaemia, due to production of osteoclasticogenic factors including M-CSF by tumor cells (Clohisy et al, Clin. Orthop. 2000, 373: 104-14). Binding of M-CSF to the Fms product stimulates formation of osteoclasts and osteolytic activity (Kodama et al, J. Exp. Med. 1991, 173: 269-72; Feng et al, Endocrinology 2002, 143: 4868-74). Accordingly, inhibition of osteoclast activity at the level of Fms offers a compelling target for amelioration of bone metastasis.

Nephritis is inflammation of the kidneys. It may be caused for example by a bacterial infection of the kidneys or exposure to a toxin. However, nephritis more commonly develops from an abnormal immune reaction, which can occur, for example, when an antibody attacks either the kidney itself or an antigen attached to kidney cells, or when an antigen-antibody complex formed elsewhere in the body attachs to cells in the kidney. Some types of nephritis involve infiltration of kidney tissues by white blood cells and deposits of antibodies. In other types of nephritis, inflammation may consist of tissue swelling or scarring without white blood cells or antibodies. Furthermore, nephritis can occur anywhere in the kidneys. With respect to the glomeruli, progressive damage to glomeruli causes urine production to fall and metabolic waste products to build up in the blood. When damage to glomeruli is severe, inflammatory cells and injured glomerular cells accumulate, compressing the capillaries within the glomerulus and interfering with filtration. Scarring may develop, impairing kidney function and reducing urine production. In some cases, microthrombi may form in the small blood vessels, further decreasing kidney function. Less commonly, nephritis involves the tubulointerstitial tissues; such inflammation is called tubulointerstitial nephritis. When inflammation damages the tubules and the tubulointerstitial tissues, the kidneys may become unable to concentrate urine, eliminate (excrete) metabolic waste products from the body, or balance the excretion of sodium and other electrolytes, such as potassium. When the tubules and tubulointerstitial tissues are damaged, kidney failure often develops. Accordingly, inhibition of Fms offers a target for therapeutic intervention in nephritis due to the modulation of the inflammatory response comprising the etiology of the disease.

Lupus nephritis, i.e., renal involvement in systemic lupus erythematosus (SLE), is a common disease manifestation with a poor prognosis. At least three potentially overlapping, immuno-pathogenic mechanisms for lupus nephritis are supported by experimental data. First, circulating immune complexes consisting chiefly of DNA and anti-DNA are deposited in the kidney. Resulting complement activation and chemotaxis of neutrophils leads to a local inflammatory process. Second, in situ formation of antigen and antibody complexes may similarly lead to complement activation and leucocyte mediated injury. Third, antibodies against specific cellular targets may produce renal injury. An additional mechanism is observed in SLE patients with the antiphospholipid antibody syndrome. Glomerular thrombosis can result from the hypercoagulability that accompanies antibodies directed against negatively charged phospholipid-protein complexes (e.g. biologic false positive VDRL, anticardiolipin antibodies, and lupus anticoagulant). Mesangial lupus nephritis is accompanied by normal diagnostic findings or with a mild degree of proteinuria but typically absence of hypertension or abnormal urinary sediment. Focal and diffuse proliferative lupus glomerulonephritis are often associated with the worst prognosis for renal survival and can be accompanied by nephrotic syndrome, significant hypertension and abnormal urine sediment. Membranous lupus nephritis often presents with proteinuria, moderate to high grade, but usually normal urinary sediment in the absence of hypertension. Mesangial lupus nephropathy is generally associated with an excellent prognosis, whereas proliferative lupus nephropathy, especially diffuse variant, is often characterized by hypertension, red cell casts and significant deterioration of renal function. Nephrotic syndrome in the absence of hypertension, active urinary sediment or significant hypocomplementemia suggest the membranous variant of lupus nephropathy. Membranous nephropathy generally is associated with a good prognosis and relative preservation of renal function. However, in the presence of persistent nephrotic range proteinuria, membranous lupus nephropathy can, in fact, lead to loss of renal function and end stage renal disease (ESRD). Accordingly, inhibition of Fms offers a target for therapeutic intervention in lupus due to the modulation of the inflammatory response comprising the etiology of the disease.

Macrophage accumulation is a prominent feature in many forms of glomerulonephritis. Local proliferation of macrophages within the kidney has been described in human and experimental glomerulonephritis and may have an important role in augmenting the inflammatory response. Isbel et al (Nephrol Dial Transplant 2001, 16: 1638-1647) examined the relationship between local macrophage proliferation and renal expression of M-CSF. Glomerular and tubulointerstitial M-CSF expression was found to be up-regulated in human glomerulonephritis, being most prominent in proliferative forms of disease. Because this correlates with local macrophage proliferation, it suggests that increased renal M-CSF production plays an important role in regulating local macrophage proliferation in human glomerulonephritis. In a model of renal inflammation (UUO—unilateral ureteric obstruction) anti-Fms antibody treatment reduced macrophage accumulation (Le Meur et. al., J Leukocyte Biology, 2002, 72: 530-537). Accordingly, inhibition of Fms offers a target for therapeutic intervention in glomerulonephritis.

Insulin resistance and obesity are hallmarks of type II diabetes and a strong correlation exists between insulin resistance and abdominal visceral fat accumulation (Bjorntrop, Diabetes Metab. Res. Rev., 1999, 15: 427-441). Current evidence indicates that macrophages accumulating in adipose tissue release TNF-a and other factors that cause adipocyte changes (hypertrophy, lipolysis, reduced insulin sensitivity) and also promote insulin resistance in surrounding tissues. Therefore, macrophage accumulation in type 2 diabetes is important for disease progression. Accordingly, inhibition of Fms has potential in preventing the development of insulin resistance and hyperglycemia.

Similarly, the observation that production of M-CSF, the major macrophage growth factor, is increased in tissues during inflammation points out a role for Fms in diseases, such as for example inflammatory diseases. More particularly, because elevated levels of M-CSF are found in the disease state, modulation of the activity of Fms can ameliorate disease associated with increased levels of M-CSF.

Fms inhibitors may be useful in treating inflammatory and autoimmune indications, including, but not limited to, rheumatoid arthritis, osteoarthritis, psoriatic arthritis, psoriasis, dermatitis, ankylosing spondylitis, polymyositis, dermatomyositis, systemic sclerosis, juvenile idiopathic arthritis, polymyalgia rheumatica, Sjogren's disease, Langerhan's cell histiocytosis (LCH), Still's disease, inflammatory bowel syndrome, ulcerative colitis, Crohn's disease, systemic lupus erythematosis (SLE), transplant rejection, chronic obstructive pulmonary disease (COPD), emphysema, Kawasaki's Disease, hemophagocytic syndrome (macrophage activation syndrome), multicentric reticulohistiocytosis, and atherosclerosis; metabolic disorders, including, but not limited to, Type I diabetes, Type II diabetes, insulin resistance, hyperglycemia, obesity, and lipolysis; disorders of bone structure, mineralization and bone formation and resorption, including, but not limited to, osteoporosis, osteodystrophy, increased risk of fracture, Paget's disease, hypercalcemia, infection-mediated osteolysis (e.g. osteomyelitis), and peri-prosthetic or wear-debris-mediated osteolysis; kidney and genitourinary diseases, including, but not limited to, endometriosis, nephritis (e.g. glomerulonephritis, interstitial nephritis, Lupus nephritis), tubular necrosis, diabetes-associated renal complications (e.g. diabetic nephropathy), and renal hypertrophy; disorders of the central nervous system, including, but not limited to, multiple sclerosis, amyotrophic lateral sclerosis (ALS), myasthenia gravis, chronic demyelinating polyneuropathy, other demyelinating disorders, stroke, Alzheimer's disease and Parkinson's disease; inflammatory and chronic pain, including, but not limited to, bone pain; malignancies, including, but not limited to, multiple myeloma, acute myeloid leukemia (AML), chronic myeloid leukemia (CML), lung cancer, pancreatic cancer, prostate cancer, breast cancer, ovarian cancer, neuroblastoma, sarcoma, osteosarcoma, giant cell tumor of bone, giant cell tumor of tendon sheath (TGCT), pigmented villonodular synovitis (PVNS), tumor angiogenesis, melanoma, glioblastoma multiforme, glioma, other tumors of the central nervous system, metastasis of tumors to other tissues, and other chronic myeloproliferative diseases such as myelofibrosis; vasculitis, including but not limited to collagen vascular disease, polyarteritis nodosa, Behcet's disease, sarcoidosis, familiar Mediterranean fever, Churg-Strauss vasculitis, temporal arteritis, giant cell arteritis, Takayasu's arteritis; ophthalmic indications, including but not limited to uveitis, scleritis, retinitis, age related macular degeneration, choroidal neovascularization, diabetic retinopathy; inherited disorders, including but not limited to cherubism, neurofibromatosis; infectious disease indications, including but not limited to infections associated with human immunodeficiency virus, hepatitis B virus, hepatitis C virus, human granulocytic anaplasmosis; lysosomal storage disorders, including but not limited to Gaucher's disease, Fabry's disease, Niemann-Pick disease; gastrointestinal indications, including but not limited to liver cirrhosis; pulmonary indications, including but not limited to pulmonary fibrosis, acute lung injury (e.g. ventilator-induced, smoke- or toxin-induced); and surgical indications, including but not limited to (cardiopulmonary) bypass surgery, vascular surgery, and vascular grafts.

Kit: Target kinase Kit (i.e., feline Hardy-Zuckerman 4 sarcoma viral oncogene) is a 109.9 kDa transmembrane tyrosine kinase encoded by chromosome 4q12 (symbol: KIT). Receptor protein tyrosine kinases (RPTKs) regulate key signal transduction cascades that control cellular growth and proliferation. The Stem Cell Factor (SCF) receptor Kit is a type III transmembrane RPTK that includes five extracellular immunoglobulin (IG) domains, a single transmembrane domain, and a split cytoplasmic kinase domain separated by a kinase insert segment. Kit plays an important role in the development of melanocytes, mast, germ, and hematopoietic cells.

Stem Cell Factor (SCF) is a protein encoded by the 51 locus, and has also been called kit ligand (KL) and mast cell growth factor (MGF), based on the biological properties used to identify it (reviewed in Tsujimura, Pathol Int 1996, 46:933-938; Loveland, et al., J. Endocrinol 1997, 153:337-344; Vliagoftis, et al., Clin Immunol 1997, 100:435-440; Broudy, Blood 1997, 90:1345-1364; Pignon, Hermatol Cell Ther 1997, 39:114-116; and Lyman, et al., Blood 1998, 91:1101-1134.). Herein the abbreviation SCF refers to the ligand for Kit.

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate Kit. For example, in the skin, SCF is predominantly expressed by fibroblasts, keratinocytes, and endothelial cells, which modulate the activity of melanocytes and mast cells expressing Kit. In bone, marrow stromal cells express SCF and regulate hematopoiesis of Kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with Kit on germ cells.

According to OMIM, signaling from Kit is essential for primordial germ cell growth both in vivo and in vitro. Many downstream effectors of the KIT signaling pathway have been identified in other cell types, but how these molecules control primordial germ cell survival and proliferation are unknown. Determination of the KIT effectors acting in primordial germ cells has been hampered by the lack of effective methods to manipulate easily gene expression in these cells. De Miguel et al. (2002) overcame this problem by testing the efficacy of retroviral-mediated gene transfer for manipulating gene expression in mammalian germ cells. They found that primordial germ cells can successfully be infected with a variety of types of retroviruses. They used this method to demonstrate an important role of the AKT1 in regulating primordial germ cell growth (OMIM MIM Number: 164920: Apr. 17, 2006).

Aberrant expression and/or activation of Kit has been implicated in a variety of pathologic states. For example, evidence for a contribution of Kit to neoplastic pathology includes its association with leukemias and mast cell tumors, small cell lung cancer, testicular cancer, and some cancers of the gastrointestinal tract and central nervous system. In addition, Kit has been implicated in playing a role in carcinogenesis of the female genital tract sarcomas of neuroectodermal origin, and Schwann cell neoplasia associated with neurofibromatosis. It was found that mast cells are involved in modifying the tumor microenvironment and enhancing tumor growth (Yang et al., J Clin Invest. 2003, 112:1851-1861; Viskochil, J Clin Invest. 2003, 112:1791-1793).

Kit inhibitors may be useful in treating malignancies, including, but not limited to, mast cell tumors, small cell lung cancer, non-small cell lung cancer (NSCLC), testicular cancer, pancreatic cancer, breast cancer, merkel cell carcinoma, carcinomas of the female genital tract, sarcomas of neuroectodermal origin, colorectal carcinoma, carcinoma in situ, gastrointestinal stromal tumors (GISTs), tumor angiogenesis, glioblastoma, astrocytoma, neuroblastoma, Schwann cell neoplasia associated with neurofibromatosis, neurofibromatosis not associated with Schwann cell neoplasia, acute myelocytic leukemia, acute lymphocytic leukemia, chronic myelogenous leukemia, mastocytosis, melanoma, and canine mast cell tumors; cardiovascular disease, including but not limited to atherosclerosis, cardiomyopathy, heart failure, pulmonary hypertension; inflammatory and autoimmune indications, including, but not limited to, allergy, anaphylaxis, asthma, rheumatoid arthritis, allergic rhinitis, multiple sclerosis, inflammatory bowel syndrome, transplant rejection, hypereosinophilia, urticaria and dermatitis; gastrointestinal indications, including but not limited to gastroesophageal reflux disease (GERD), esophagitis, and gastrointestinal tract ulcers; ophthalmic indications, including but not limited to uveitis and retinitis; and neurologic indications, including but not limited to migraine.

Flt3: Target kinase Flt3 (i.e., Fms-like tyrosine kinase 3) is a transmembrane tyrosine kinase of 112.8 kDa encoded by chromosome 13q12 (symbol: FLT3). According to OMIM, Rosnet et al. (Genomics 1991, 9: 380-385) isolated a novel member of the class 3 receptors discussed above. They demonstrated that this gene of the tyrosine kinase family, called FLT3, has strong sequence similarities with other members of the group. Lymphohematopoietic stem cells serve as a reservoir for virtually all blood cells but make up only approximately 0.01% of human or murine marrow cells. The ability to isolate and expand this population has clinical applications in bone marrow transplantations for cancer and genetic diseases. Small et al. (Proc. Nat. Acad. Sci. 1994, 91: 459-463) cloned the cDNA for stem cell tyrosine kinase 1, the human homolog of murine Flk2/Flt3, from a CD34+ hematopoietic stem cell-enriched library. The cDNA encoded a protein of 993 amino acids with 85% identity and 92% similarity to the murine homolog. STK1, which is identical to FLT3, is a member of the type III receptor tyrosine kinase family that includes KIT, FMS, and platelet-derived growth factor receptor. STK1 expression in human blood and marrow is restricted to CD34+ cells, a population greatly enriched by stem/progenitor cells. Antisense oligonucleotides directed against STK1 sequences inhibited hematopoietic colony formation, most strongly in long-term bone marrow cultures. The data suggested that STK1 may function as a growth factor receptor on hematopoietic stem and/or progenitor cells (OMIM MIM Number: 136351: Mar. 3, 2005).

Levis et al., state that Internal tandem duplication (ITD) mutations of the receptor tyrosine kinase FLT3 have been found in 20% to 30% of patients with acute myeloid leukemia (AML). These mutations constitutively activate the receptor and appear to be associated with a poor prognosis. In their study, dose-response cytotoxic assays were performed with AG1295, a tyrosine kinase inhibitor active against FLT3, on primary blasts from patients with AML, and they found that AG1295 was specifically cytotoxic to AML blasts harboring FLT3/ITD mutations. They suggest that these mutations contribute to the leukemic process and that the FLT3 receptor represents a therapeutic target in AML (Levis et al., Blood 2001, 98:885-887). An Flt3 inhibitor may be useful in treating acute myeloid leukemia, myelodysplastic syndrome, acute lymphoblastic leukemia.

TrkA: Target kinase TrkA (i.e., neurotrophic tyrosine kinase, receptor, type 1) is a 140 kDa tyrosine kinase encoded by chromosome 1q21-q22 (symbol: NTRK1). TrkA inhibitors may be useful in treating pain (e.g. chronic pain, neuropathic pain), cancer (e.g. prostate cancer, lung cancer, myeloid leukemia, pancreatic cancer), allergic disorders (e.g. asthma), arthritis, diabetic retinopathy, macular degeneration and psoriasis.

TrkA is a plasma member receptor composed of an extracellular domain (responsible for high affinity binding to nerve growth factor, NGF), a transmembrane segment and an intracellular protein tyrosine kinase domain (responsible to transmit the NGF signal to initiate and coordinate neuronal responses). NGF binding induces TrkA clustering on the membrane and activates the kinase. The kinase initiates a cascade of protein phosphorylation events through multiple pathways including SHC/Ras/MAPK, PI3K and PLCg1. A TrkA kinase inhibitor would not be expected to prevent NGF/TrkA binding, but could prevent down-stream signal transduction.

Nerve Growth Factor (NGF) is produced by a number of tissues and inflammatory cells during tissue injury and host immune response. It initiates and maintains hypersensitivity to incoming stimulus (hyperalgesia) and the perception of non-noxious stimuli (allodynia). Through its high-affinity receptor TrkA, NGF increases the excitation state of sensory neurons leading to the central nervous system (peripheral sensitization), and increases transmitter release from the dorsal spinal cord (central sensitization). In clinical trials, a single NGF subcutaneous injection generated local hyperalgesia persisting up to 7 weeks. At doses above 0.1 microgram/kg, NGF caused muscle pain that varied from mild to moderate, primarily in the bulbar and truncal musculature. Intravenous NGF produced earlier and more pronounced systemic effects (Petty et al, 1994, Ann Neurol. 36: 244-6). Conversely, TrkA kinase inhibitors could be used to treat diseases of enhanced states of nociception.

In Complete Freund's Adjuvant (CFA)-induced hind-paw inflammation, spinal nerve ligation and streptozoticin-induced neuropathic pain models, a single intraperitoneal injection of anti-NGF reversed established tactile allodynia from day 3 to day 7 following treatment. In the mouse CCI model, anti-NGF reversed tactile allodynia when administered 2 weeks after surgery. Repeated administration of this antibody to CCI mice for 3 weeks produced a sustained reversal of tactile allodynia (Wild et al, 2007, J. Pharmacol. Exp. Ther. 322:282-287).

Prostate tumors that have metastasized to bone frequently induce bone pain which can be difficult to fully control as it seems to be driven simultaneously by inflammatory, neuropathic, and tumorigenic mechanisms. Anti-NGF produced a significant reduction in both early and late stage bone cancer pain-related behaviors. This therapy did not influence tumor-induced bone remodeling, osteoblast proliferation, osteoclastogenesis, tumor growth, or markers of sensory or sympathetic innervation in the skin or bone. All nerve fibers that innervate the bone express TrkA and p'75, and these are the receptors through which NGF sensitizes and/or activates nociceptors (Halvorson et al, 2005, Cancer Res. 65:9426-35).

In patients with mild asthma due to exposure to cat allergen, NGF expression was strongly induced in epithelial cells, fibroblasts, blood vessels, and a few infiltrating cells. TrkA mRNA and protein levels in bronchial biopsies were increased significantly after allergen exposure in infiltrating mast cells before the onset of symptoms (Kassel et al, 2001, Clin Exp Allergy 31:1432-40).

The late phase reaction in asthma following allergen provocation is dominated by an influx of activated eosinophils into the bronchial lumen, which correlates with the release of eosinophilic products into the airways to increase disease severity. The viability and activation of eosinophils from patients with mild asthma were significantly enhanced after NGF stimulation. Addition of neutralizing anti-NGF antibodies ex vivo abrogated the effects (Nassentein et al, 2003, J Exp Med 198:455-467). TrkA kinase inhibitors could decrease this paracrine loop between the respiratory tract and infiltrating mast cells as well as endobronchial eosinophils, and thus be useful for the treatment of asthma and other allergic disorders.

TrkB: Target kinase TrkB (i.e., neurotrophic tyrosine kinase, receptor, type 2) is a 145 kDa tyrosine kinase encoded by chromosome 9q22.1 (symbol: NTRK2). TrkB inhibitors may be useful in treating various cancers and their metastases (e.g. prostate cancer, lung cancer, Wilms tumors, neuroblastoma, and pancreatic cancer), and various neuropathies (e.g. stroke, multiple sclerosis, transverse myelitis, and encephalitis).

In clinical trials with recombinant BDNF, paresthesia was developed at the site of subcutaneous injection (Coulie et al, 2000, Gastroenterology 119:41-50). Intrathecal infusion of BDNF in humans also induced paresthesia and warmth as side effects (Ochs et al, 2000, Amyotroph Lateral Scler Other Motor Neuron Disord. 1:201-6). Chronic paresthesia is often a symptom of an underlying neurological disease or traumatic nerve damage. Paresthesia can be caused by disorders affecting the central nervous system, such as stroke and transient ischemic attacks (mini-strokes), multiple sclerosis, transverse myelitis, and encephalitis. Since BDNF binds to TrkB specifically with high affinity these neuropath effects are mediated through TrkB signaling. Thus Trkb kinase inhibitors could be used to treat certain patients with neuropathy.

BDNF is known to act at the synapses between primary sensory and spinal dorsal horn neurons to affect pain transmission during inflammation. The primary afferent is the only source of BDNF in the spinal cord, and it is up-regulated in the dorsal root ganglion (DRG) by peripheral NGF a few days after inflammation, and is transported and released into the superficial dorsal horn in an activity-dependent manner. TrkB expression in the dorsal horn also increases for a few days after inflammation. These findings suggest that BDNF may act during the restricted period in the early phase of inflammation. Through TrkB, BDNF activates two distinct channels: (1) transient receptor potential canonicals (TRPC3), which produces a slow response by opening of a non-selective cation channel; and (2) Na+ channel, which mediates a rapid depolarization in the hippocampus. These channels have been strongly associated with inflammatory pain. Anti-BDNF significantly increased the withdrawal threshold in CFA-treated rats, a model of inflammatory pain. Since the swelling at the site of CFA injection was not affected by antiserum, the residual component might be due to peripheral sensitization (Matayoshi et al, 2005, J Physiol. 569:685-95).

In patients with neuroblastomas, co-expression of TrkB and BDNF, co-expression of TrkB with N-Myc amplification, and expression of truncated TrkB are found to be associated with poorer clinical outcome (Nakagawara et al, 1994, Mol Cell Biol. 14:759-767). Co-expression of TrkB with its ligand BDNF could generate a positive feedback loop through autocrine and paracrine loops. Also TrkB truncations found in these tumors generate activated forms of the intracellular protein tyrosine kinase. The constitutively active TrkB signals through multiple pathways to promote cancer initiation, progression and metastasis. These truncated TrkB kinases were also found in hepatocellular carcinoma (Yang et al, 2005, Cancer. Res 65:219-225). Thus TrkB inhibitors could be used to treat a sub-population of cancer patients with an activated TrkB pathway.

In patients with pancreatic cancer, TrkB expression is correlated with perineural invasion, positive retroperitoneal margin, and shorter latency to development of liver metastasis (Sclabas et al, 2005, Clin. Cancer. Res V11:440-449). Mechanistically, TrkB activates the PI3K pathway to suppress anoikis (apoptosis resulting from loss of cell-matrix interactions) which is one of the physiological barriers to metastasis. TrkB kinase inhibition could break down resistance to anoikis of metastasizing tumors (Douma et al, 2004, Nature 430: 1034-9). Therefore, TrkB inhibitors could have utility in a broad range of tumor types.

TrkC: Target kinase TrkC (i.e., neurotrophic tyrosine kinase, receptor, type 3) is a 145 kDa tyrosine kinase encoded by chromosome 15q25 (symbol: NTRK3). TrkC inhibitors may be useful in treating pain (e.g. chronic pain, neuropathic pain), cancer (e.g. lung cancer, breast cancer, pancreatic cancer, mesoblastic nephroma, infantile fibrosarcoma, neuroblastoma, gastric cancer), and panic disorder.

Involvement of TrkC in the molecular and cellular changes underlying panic attacks and opiate dependence has been indicated (Gallego et al., Front Behav. Neurosci., 2010, 3:60). TrkC expression in mechanosecnsory neurons suggests a role for TrkC inhibition in treatment of pain (J Comp. Neurol., 2008, 511(4):543-56.

TrkC is also involved in a variety of cancers, for example neuroblastoma (J. Clin. Invest., 2010, 120(3):850-8), mesoblastic nephroma, infantile fibrosarcoma, and secretory breast cancer, where ETV6-NTRK3 gene fusion is present (Pediatr. Radiol. 2009, 39(10):1066-74; J. Clin. Pathol. 2009, 62(7):604-12) and cancers involving mutations in TrkC, such as lung cancer, gastric cancer, and pancreatic cancer (Marchetti et al., Hum. Mutat. 2008, 29(5):609-16; Kubo et al., Carcinogenesis, 2009, 30(11):1857-64); and Kubo et al., Pancreas, 2009, 38(7):e200-6).

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

Additional alternative assays can employ binding determinations. For example, this sort of assay can be formatted either in a fluorescence resonance energy transfer (FRET) format, or using an AlphaScreen (amplified luminescent proximity homogeneous assay) format by varying the donor and acceptor reagents that are attached to streptavidin or the phosphor-specific antibody.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, *Advanced Organic Chemistry; Reactions, Mechanisms and Structure*, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, invention compounds may exist in a number of different forms or derivatives, all within the scope of the present invention. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the invention also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the 1H-pyrrolo[2,3-b]pyridine ring or the 7-position of the 7H-pyrrolo[2,3-d]pyrimidine of compounds of Formula I, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalitites, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application Ser. No. 10/656,838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016; Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present invention may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond, or on carbon atoms of a cycloalkyl. All such single stereoisomers, racemates and mixtures thereof are intended to be within the scope of the present invention. Unless specified to the contrary, all such steroisomeric forms are included within the formulae provided herein.

In some embodiments, a chiral compound of the present invention is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds of Formula I can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the invention may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see *Remington's Pharmaceutical Sciences*, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present invention and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the invention are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the invention with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitiates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

Formulations and Administration

The methods and compounds will typically be used in therapy for human subjects. However, they may also be used to treat similar or identical indications in other animal subjects. Compounds of Formula I or any of the subformulas as described herein, or any of the compounds disclosed in any of the embodiments and examples, and pharmaceutically acceptable salts or solvates thereof can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, di-fatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, hypromellose, and the like.

In some embodiments, oral administration may be used. Pharmaceutical preparations for oral use can be formulated into conventional oral dosage forms such as capsules, tablets, and liquid preparations such as syrups, elixirs, and concentrated drops. Compounds of Formula I may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethyl-cellulose, sodium carboxymethylcellulose (CMC), and/or polyvinylpyrrolidone (PVP: povidone); oily excipients, including vegetable and animal oils, such as sunflower oil, olive oil, or codliver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations. Also provided are dragee cores with suitable coatings. For this purpose, concentrated sugar solutions may be used, which may optionally contain, for example, gum arabic, talc, polyvinylpyrrolidone, carbopol gel, polyethylene glycol, and/or titanium dioxide, lacquer solutions, and suitable organic solvents or solvent mixtures.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the invention (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds of Formula I for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use.

In some embodiments, transmucosal, topical or transdermal administration may be used. In such formulations of compounds of Formula I, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds of Formula I for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds of Formula I may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds of Formula I may also be used in combination with other inhaled therapies, for example corticosteroids such as fluticasone proprionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds of Formula I may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the invention or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound of Formula I, or at the same time as a compound of Formula I. Use in combination also includes use with a therapy or medical procedure that is administered once or infrequently, such as surgery, along with a compound of Formula I administered within a short time or longer time before or after the other therapy or procedure. In some embodiments, the present invention provides for delivery of a compound of Formula I and one or more other drug therapeutics delivered by a different route of administration or by the same route of administration. The use in combination for any route of administration includes delivery of a compound of Formula I and one or more other drug therapeutics delivered by the same route of administration together in any formulation, including formulations where the two compounds are chemically linked in such a way that they maintain their therapeutic activity when administered. In one aspect, the other drug therapy may be co-administered with a compound of Formula I. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound of Formula I and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

EXAMPLES

Examples related to the present invention are described below. In most cases, alternative techniques can be used. The examples are intended to be illustrative and are not limiting or restrictive to the scope of the invention. For example, where additional compounds are prepared following a protocol of a Scheme for a particular compound, it is understood that conditions may vary, for example, any of the solvents, reaction times, reagents, temperatures, work up conditions, or other reaction parameters may be varied employing alternate solvents, reagents, reaction times, temperatures, work up conditions, and the like, as are readily available to one skilled in the art. In some examples, the mass spectrometry result indicated for a compound may have more than one value due to the isotope distribution of an atom in the molecule, such as a compound having a bromo or chloro substituent.

Unless specifically indicated otherwise, the Formula enumeration and R group enumeration used in the following examples is not related to such enumeration in other sections of this application. The reagents and solvents used in these examples can be readily substituted with appropriate alternatives as are known in the art and isolation of products is readily achieved by methods known in the art, including, but not limited to, extraction, crystallization, and chromatographic methods.

Ring numbering for the 1H-pyrrolo[2,3-b]pyridine in the following Examples is as follows:

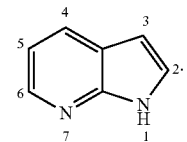

Ring numbering for the 7H-pyrrolo[2,3-d]pyrimidine in the following Examples is as follows:

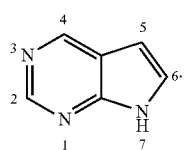

Example 1

Synthesis of 5-chloro-3-iodo-1-triisopropylsilanyl-1H-pyrrolo[2,3-b]pyridine 4

5-Chloro-3-iodo-1-triisopropylsilanyl-1H-pyrrolo[2,3-b]pyridine 4 is prepared in two steps from 5-chloro-1H-pyrrolo[2,3-b]pyridine 1 as shown in Scheme 1.

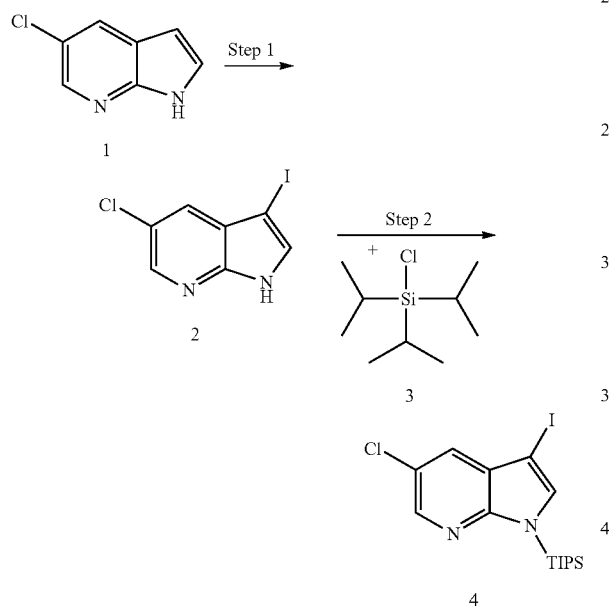

Step 1—Preparation of 5-chloro-3-iodo-1H-pyrrolo[2,3-b]pyridine (2)

To a solution of 5-chloro-1H-pyrrolo[2,3-b]pyridine (1, 15.00 g, 98.31 mmol) in 300 mL of dichloromethane under an atmosphere or nitrogen, pyridine (7.951 mL, 98.31 mmol) and iodine monochloride (110 mL, 1.0 M in dichloromethane, 110 mmol) are added slowly over 20 minutes. The reaction is stirred at room temperature for 2 hours, then quenched with 100 mL of 1 M aqueous sodium thiosulfate pentahydrate. The layers are separated, solids collected from the aqueous layer by filtration and combined with the organic layer. The aqueous layer is extracted with ethyl acetate, and the organic layers are combined and washed with brine, then concentrated under vacuum. The resulting solid is washed with 20% ethyl acetate in hexane to provide the desired compound.

Step 2—Preparation of 5-chloro-3-iodo-1-triisopropylsilanyl-1H-pyrrolo[2,3-b]pyridine (4)

To 5-chloro-3-iodo-1H-pyrrolo[2,3-b]pyridine (2, 16.50 g, 59.25 mmol) in 250.0 mL of N,N-dimethylformamide, sodium hydride (3.10 g, 77.5 mmol) is added. The reaction is stirred at room temperature for 90 minutes, then triisopropylsilyl chloride (3, 13.00 mL, 61.36 mmol) is added slowly. The reaction is stirred at room temperature overnight, then poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (4, 10.0 g).

Example 2

Synthesis of 3-iodo-5-methyl-1H-pyrrolo[2,3-b]pyridine 7

3-Iodo-5-methyl-1H-pyrrolo[2,3-b]pyridine 7 is prepared in two steps from 5-bromo-1-triisopropylsilanyl-1H-pyrrolo[2,3-b]pyridine 5 as shown in Scheme 2.

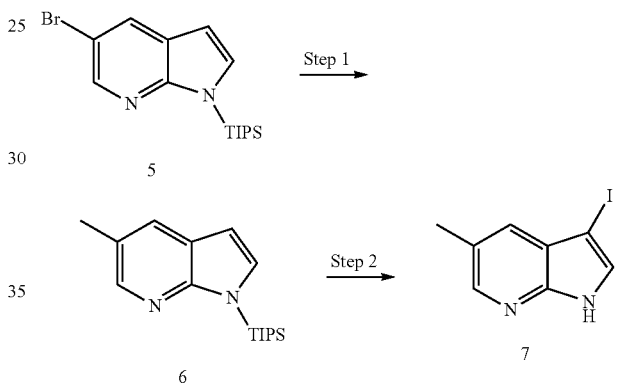

Step 1—Preparation of 5-methyl-1-triisopropylsilanyl-1H-pyrrolo[2,3-b]pyridine (6)

In a round bottom flask, [1,1'-bis(diphenylphosphino)ferrocene]dichloropalladium(II) 1:1 complex with dichloromethane (0.04 g, 0.05 mmol) is combined with 10 mL of toluene under an atmosphere of nitrogen, and 5-bromo-1-triisopropylsilanyl-1H-pyrrolo[2,3-b]pyridine (5, 0.3 g, 0.8 mmol) in 1 mL of toluene is added dropwise. The reaction is stirred at 60° C. for 1 hour, then at 90° C. for 30 minutes. The reaction is cooled to room temperature, an ice/water solution of 0.1 N citric acid at pH 4 is added, and the mixture extracted with ethyl acetate. The organic layer is washed with brine, de-colored with charcoal, filtered through celite and the filtrate dried over sodium sulfate. The sodium sulfate is removed by filtration and the filtrate concentrated under vacuum to provide the desired compound (6, 218 mg).

Step 2—Preparation of 3-iodo-5-methyl-1H-pyrrolo[2,3-b]pyridine (7)

To a solution of 5-methyl-1-triisopropylsilanyl-1H-pyrrolo[2,3-b]pyridine (6, 1 g, 2.0 mmol) in 10 mL of tetrahydrofuran, iodine (0.43 g, 1.7 mmol) in 5 mL of tetrahydrofuran is added. The reaction is stirred at room temperature overnight, then quenched with 20 mL of 1M aqueous sodium thiosulfate and extracted with ethyl acetate. The organic layers are combined and washed with water and brine, dried over sodium sulfate, filtered and the filtrate concentrated under vacuum. The resulting material is purified by silica gel column chromatography, eluting with ethyl acetate and hexanes. Appropriate fractions are combined and concentrated under vacuum to provide the desired compound as a white solid (7, 20 mg). MS (ESI) [M+H$^+$]$^+$=258.70.

Example 3

Synthesis of 3-iodo-5-methyl-1-triisopropylsilanyl-1H-pyrrolo[2,3-b]pyridine 8

3-Iodo-5-methyl-1-triisopropylsilanyl-1H-pyrrolo[2,3-b]pyridine 8 is prepared in one step from 5-methyl-1-triisopropylsilanyl-1H-pyrrolo[2,3-b]pyridine 6 as shown in Scheme 3.

Scheme 3

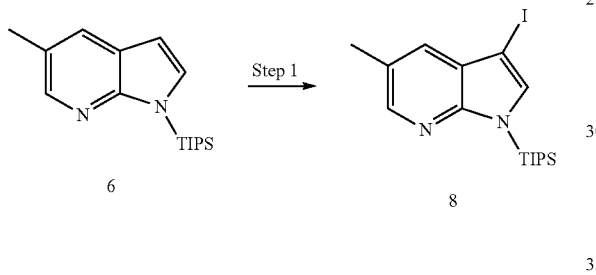

Step 1—Preparation of 3-iodo-5-methyl-1-triisopropylsilanyl-1H-pyrrolo[2,3-b]pyridine (8)

5-Methyl-1-triisopropylsilanyl-1H-pyrrolo[2,3-b]pyridine (6, 1.1 g, 3.8 mmol) and 10 mL of dichloromethane are combined in a round bottom flask and stirred for 10 minutes. A slurry of N-iodosuccinimide (1.0 g, 4.6 mmol) in 5 mL of dichloromethane is added and stirred at room temperature overnight. The reaction is quenched with sodium thiosulfate (20 mL, 1M in water) and the aqueous layer is extracted with ethyl acetate. The combined organic layer is washed with water and brine, dried with sodium sulfate, filtered and the filtrate concentrated under vacuum. The resulting material is purified by silica gel column chromatography, eluting with ethyl acetate and hexanes. Appropriate fractions are combined and concentrated under vacuum to provide the desired compound as a light yellow oil (8, 1.2 g, 75%). MS (ESI) [M+H$^+$]$^+$=415.08.

Example 4

Synthesis of 4-ethoxy-5-iodo-7-triisopropylsilanyl-7H-pyrrolo[2,3-d]pyrimidine 13

4-Ethoxy-5-iodo-7-triisopropylsilanyl-7H-pyrrolo[2,3-d]pyrimidine 13 is prepared in three steps from 4-chloro-7H-pyrrolo[2,3-d]pyrimidine 9 as shown in Scheme 4.

Scheme 4

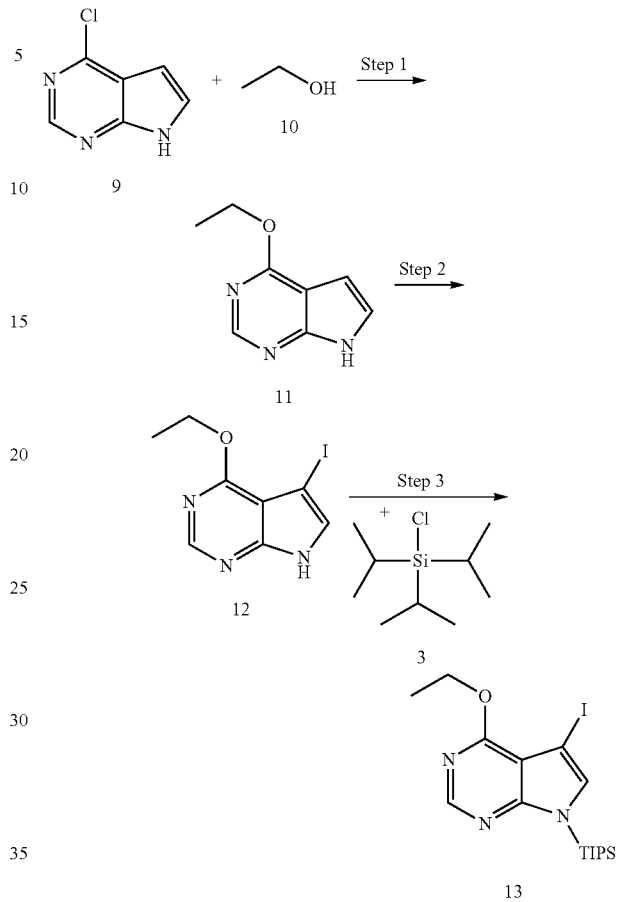

Step 1—Preparation of 4-ethoxy-7H-pyrrolo[2,3-d]pyrimidine (11)

4-Chloro-7H-pyrrolo[2,3-d]pyrimidine (9, 300 mg, 1.95 mmol) is combined with 3.00 mL of ethanol (10, 51.4 mmol), then potassium hydroxide (0.226 g, 4.03 mmol) is added. The reaction is heated at 120° C. for 3 hours in a microwave, then extracted with ethyl acetate and aqueous saturated ammonium chloride. The organic layer is washed with brine, dried with magnesium sulfate, filtered and the filtrate concentrated under vacuum. The resulting material is recrystallized from methanol to provide the desired compound (11, 213 mg). MS (ESI) [M+H$^+$]$^+$=164.9.

Step 2—Preparation of 4-ethoxy-5-iodo-7H-pyrrolo[2,3-d]pyrimidine (12)

To 4-ethoxy-7H-pyrrolo[2,3-d]pyrimidine (11, 1.60 g, 9.8 mmol) in 50.0 mL of dichloromethane, N,N-dimethylformamide (2.0 mL, 26 mmol) and N-iodosuccinimide (2.40 g, 10.7 mmol) are added and the reaction stirred at room temperature for 2 hours. The reaction is poured into water and extracted with ethyl acetate. The organic layer is dried with sodium sulfate, filtered and the filtrate concentrated under vacuum to provide the desired compound (12, 2.70 g).

Step 3—Preparation of 4-ethoxy-5-iodo-7-triisopropylsilanyl-7H-pyrrolo[2,3-d]pyrimidine (13)

To 4-ethoxy-5-iodo-7H-pyrrolo[2,3-d]pyrimidine (12, 2.70 g, 9.34 mmol) in 60.0 mL of tetrahydrofuran under an atmosphere of nitrogen, sodium hydride (411.0 mg, 10.27 mmol) is added. The reaction is stirred at room temperature for 20 minutes, then triisopropylsilyl chloride (3, 2.177 mL, 10.27 mmol) is added. The reaction is stirred at room temperature for 2 hours, then poured into water and extracted with ethyl acetate. The organic layer is dried over sodium sulfate, filtered and the filtrate concentrated under vacuum. The resulting material is purified by silica gel column chromatography, eluting with 5-100% ethyl acetate in hexane. Appropriate fractions are combined and concentrated under vacuum to provide the desired compound (13, 3.90 g).

5-Iodo-4-methoxy-7-triisopropylsilanyl-7H-pyrrolo[2,3-d]pyrimidine 14

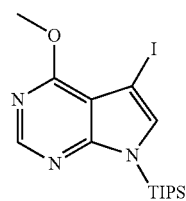

is prepared similarly to the protocol of Scheme 4, replacing ethanol with methanol in step 1.

5-Iodo-4-methyl-7-triisopropylsilanyl-7H-pyrrolo[2,3-d]pyrimidine 16

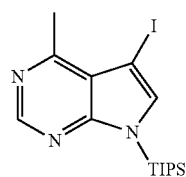

is prepared similarly to the protocol of Scheme 4, where step 1 is replaced by the following step 1a:

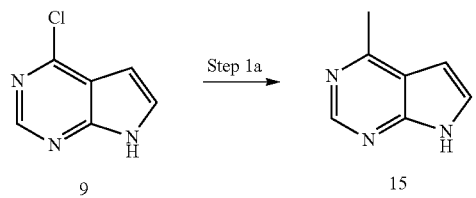

Step 1a—Preparation of
4-methyl-7H-pyrrolo[2,3-d]pyrimidine (15)

To 4-chloro-7H-pyrrolo[2,3-d]pyrimidine (9, 5.03 g, 32.8 mmol) in 100 mL of toluene, [1,1'-bis(diphenylphosphino)ferrocene]dichloropalladium(II) 1:1 complex with dichloromethane (0.627 g, 0.328 mmol) is added under an atmosphere of nitrogen. After stirring for 10 minutes, methylmagnesium bromide (62.9 mL, 3.00 M in ether, 189 mmol) is added slowly. The reaction is heated at 55° C. overnight, then cooled to −70 to −80° C. and quenched by adding ammonium chloride dropwise. Then 1N hydrochloric acid is added and the pH is adjusted to 7-8 with the addition of saturated sodium bicarbonate. This is extracted 3× with ethyl acetate. The combined organic layer is washed with saturated ammonium chloride and brine, then dried with magnesium sulfate, filtered and the filtrate concentrated under vacuum. The resulting material is purified by silica gel column chromatography, eluting with ethyl acetate and dichloromethane, then methanol and dichloromethane. Appropriate fractions are combined and concentrated under vacuum to provide the desired compound as a tan solid (15). MS (ESI) [M+H$^+$]$^+$=134. This is reacted similarly to steps 2 and 3 of Scheme 4 to provide the desired compound 16.

4-Cyclopropyl-5-iodo-7-triisopropylsilanyl-7H-pyrrolo[2,3-d]pyrimidine 19

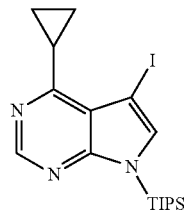

is prepared similarly to the protocol of Scheme 4, where step 1 is replaced by the following step 1b:

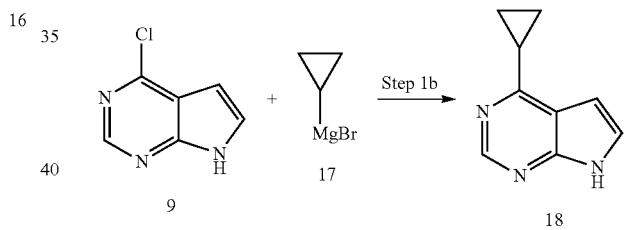

Step 1b—Preparation of
4-cyclopropyl-7H-pyrrolo[2,3-d]pyrimidine (18)

4-Chloro-7H-pyrrolo[2,3-d]pyrimidine (9, 0.452 g, 2.94 mmol), cyclopropylmagnesium bromide (17, 31.4 mL, 0.50 M in tetrahydrofuran, 15.7 mmol), and [1,1'-bis(diphenylphosphino)ferrocene]dichloropalladium(II) 1:1 complex with dichloromethane (0.240 g, 0.294 mmol) are combined with 15.4 mL of toluene. The reaction is heated at 60° C. overnight, then quenched with 1 M aqueous hydrochloric acid to pH 4 and filtered through a bed of celite. The layers of the filtrate are separated and the aqueous layer extracted with ethyl acetate. The combined organic layers are washed with brine, dried over sodium sulfate, filtered and the filtrate concentrated under vacuum. The resulting material is purified by silica gel column chromatography, eluting with ethyl acetate and hexane. Appropriate fractions are combined and concentrated under vacuum to provide the desired compound (18, 0.465 g). MS (ESI) [M+H$^+$]$^+$=160.1. This is reacted similarly to steps 2 and 3 of Scheme 4 to provide the desired compound 19.

153

Cyclopropyl-(5-iodo-7H-pyrrolo[2,3-d]pyrimidin-4-yl)-amine 22

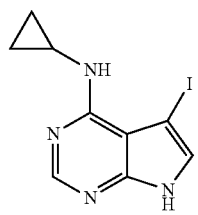

22 is prepared similarly to the protocol of scheme 4, steps 1 and 2, where step 1 is replaced by the following step 1c:

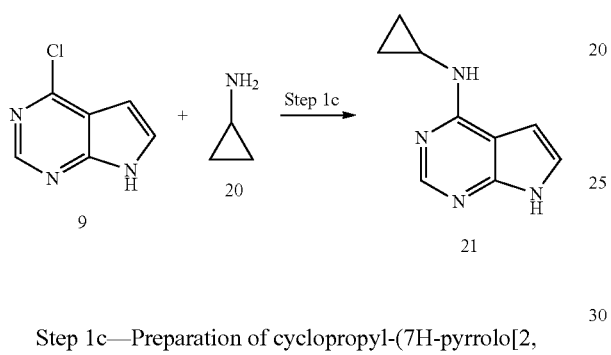

Step 1c—Preparation of cyclopropyl-(7H-pyrrolo[2, 3-d]pyrimidin-4-yl)-amine (21)

4-Chloro-7H-pyrrolo[2,3-d]pyrimidine (9, 1.06 g, 6.90 mmol) is dissolved in cyclopropylamine (20, 2.42 mL, 34.5 mmol) and heated to reflux overnight. The reaction mixture is cooled and poured into water, then extracted with ethyl acetate. The organic layer is washed with brine, dried over sodium sulfate, filtered and the filtrate concentrated under vacuum. The resulting material is purified by silica gel column chromatography, eluting with ethyl acetate and dichloromethane. Appropriate fractions are combined and concentrated under vacuum to provide the desired compound (21, 337 mg). MS (ESI) $[M+H^+]^+ = 174.9$. This is reacted similarly to step 2 of Scheme 4 to provide the desired compound 22.

Example 5

Synthesis of 7-benzenesulfonyl-5-iodo-4-(2-methoxy-ethoxy)-7H-pyrrolo[2,3-d]pyrimidine 27

7-Benzenesulfonyl-5-iodo-4-(2-methoxy-ethoxy)-7H-pyrrolo[2,3-d]pyrimidine 27 is prepared in three steps from 4-chloro-7H-pyrrolo[2,3-d]pyrimidine 9 as shown in Scheme 5.

Scheme 5

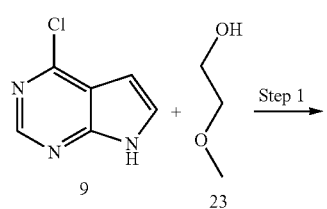

154

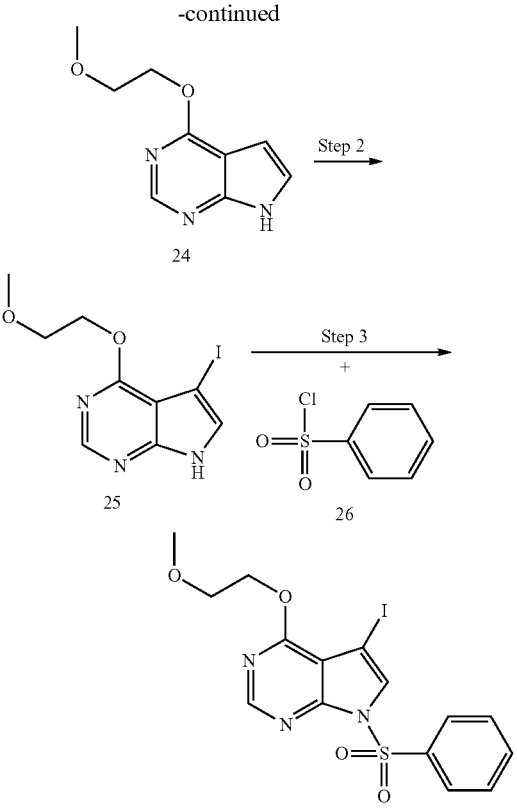

Step 1—Preparation of 4-(2-methoxy-ethoxy)-7H-pyrrolo[2,3-d]pyrimidine (24)

To 4-Chloro-7H-pyrrolo[2,3-d]pyrimidine (9, 5.00 g, 32.6 mmol) in 12.5 mL of 2-methoxy-ethanol (23, 158 mmol), potassium hydroxide (3.3 g, 59 mmol) is added. The reaction is heated at 100° C. overnight, then poured into water and extracted with ethyl acetate. The organic layer is dried with sodium sulfate, filtered and the filtrate concentrated under vacuum to provide the desired compound (24, 5.70 g).

Step 2—Preparation of 5-iodo-4-(2-methoxy-ethoxy)-7H-pyrrolo[2,3-d]pyrimidine (25)

To 4-(2-methoxy-ethoxy)-7H-pyrrolo[2,3-d]pyrimidine (24, 5.70 g, 29.5 mmol) in 150.0 mL of dichloromethane, N,N-dimethylformamide (6.0 mL, 78 mmol) and N-iodosuccinimide (7.22 g, 32.1 mmol) are added and the reaction stirred at room temperature for 2 hours. The reaction is poured into water and extracted with ethyl acetate. The organic layer is dried with sodium sulfate, filtered and the filtrate concentrated under vacuum. The resulting material is washed with ethyl acetate and hexane to provide the desired compound (25, 6.75 g).

Step 3—Preparation of 7-benzenesulfonyl-5-iodo-4-(2-methoxy-ethoxy)-7H-pyrrolo[2,3-d]pyrimidine (27)

To 5-iodo-4-(2-methoxy-ethoxy)-7H-pyrrolo[2,3-d]pyrimidine (25, 3.67 g, 11.5 mmol) in 60.0 mL of tetrahydrofuran under an atmosphere of nitrogen, sodium hydride (506.0 mg, 12.65 mmol) is added. The reaction is stirred at room temperature for 20 minutes, then benzenesulfonyl chloride (26, 1.614 mL, 12.65 mmol) is added. The reaction is stirred at room temperature for 30 minutes, then poured into water and extracted with ethyl acetate. The organic layer is dried over sodium sulfate, filtered and the filtrate concentrated under vacuum. The resulting material is purified by silica gel column chromatography, eluting with 15-100% ethyl acetate in hexane. Appropriate fractions are combined and concentrated under vacuum to provide the desired compound (27, 4.50 g). MS (ESI) [M+H$^+$]$^+$=460.0.

1-Benzenesulfonyl-5-chloro-3-iodo-1H-pyrrolo[2,3-b]pyridine 28, 1-benzenesulfonyl-3-iodo-5-methyl-1H-pyrrolo[2,3-b]pyridine 29, and 7-benzenesulfonyl-4-chloro-5-iodo-7H-pyrrolo[2,3-d]pyrimidine 30,

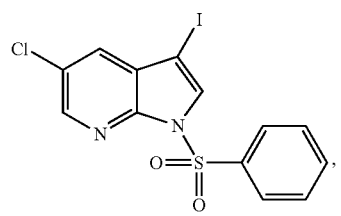

28

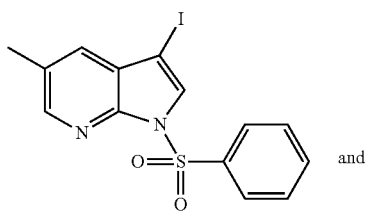

29

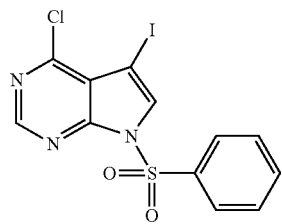

30 are prepared following the protocol of scheme 5 step 3 or steps 2 and 3, replacing 5-iodo-4-(2-methoxy-ethoxy)-7H-pyrrolo[2,3-d]pyrimidine 25 with 5-chloro-3-iodo-1H-pyrrolo[2,3-b]pyridine 2 and 3-iodo-5-methyl-1H-pyrrolo[2,3-b]pyridine 7, respectively in step 3, or by reacting 4-chloro-7H-pyrrolo[2,3-d]pyrimidine 9 directly in step 2.

7-Benzenesulfonyl-5-iodo-4-methyl-7H-pyrrolo[2,3-d]pyrimidine 31 and 7-benzenesulfonyl-4-cyclopropyl-5-iodo-7H-pyrrolo[2,3-d]pyrimidine 32,

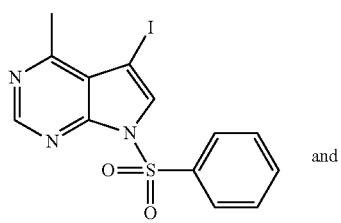

31

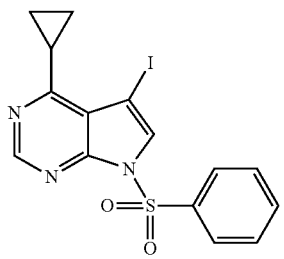

32 are prepared following the protocol of scheme 5 steps 2 and 3, replacing 4-(2-methoxy-ethoxy)-7H-pyrrolo[2,3-d]pyrimidine 24 with 4-methyl-7H-pyrrolo[2,3-d]pyrimidine 15 and 4-cyclopropyl-7H-pyrrolo[2,3-d]pyrimidine 18, respectively, in step 2.

4-Cyclopropyl-5-iodo-7-(toluene-4-sulfonyl)-7H-pyrrolo[2,3-d]pyrimidine 33,

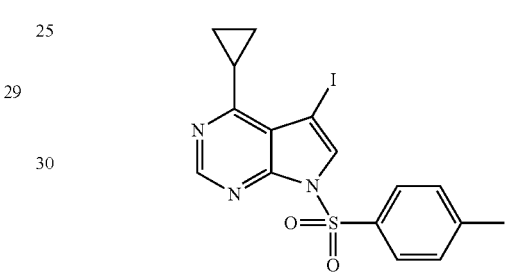

33 is synthesized similarly to compound 32, where 4-methyl-benzenesulfonyl chloride is used in place of benzenesulfonyl chloride 26 in step 3 of Scheme 5.

Example 6

Synthesis of 1-benzenesulfonyl-5-chloro-3-(2-methanesulfonyl-pyrimidin-5-ylmethyl)-1H-pyrrolo[2,3-b]pyridine 37

1-benzenesulfonyl-5-chloro-3-(2-methanesulfonyl-pyrimidin-5-ylmethyl)-1H-pyrrolo[2,3-b]pyridine 37 is prepared in three steps from 1-benzenesulfonyl-5-chloro-3-iodo-1H-pyrrolo[2,3-b]pyridine 28 and 2-methylsulfanyl-pyrimidine-5-carbaldehyde 34 as shown in Scheme 6.

Scheme 6

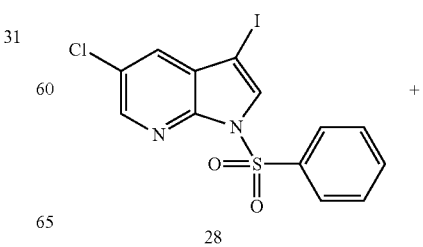

28

+

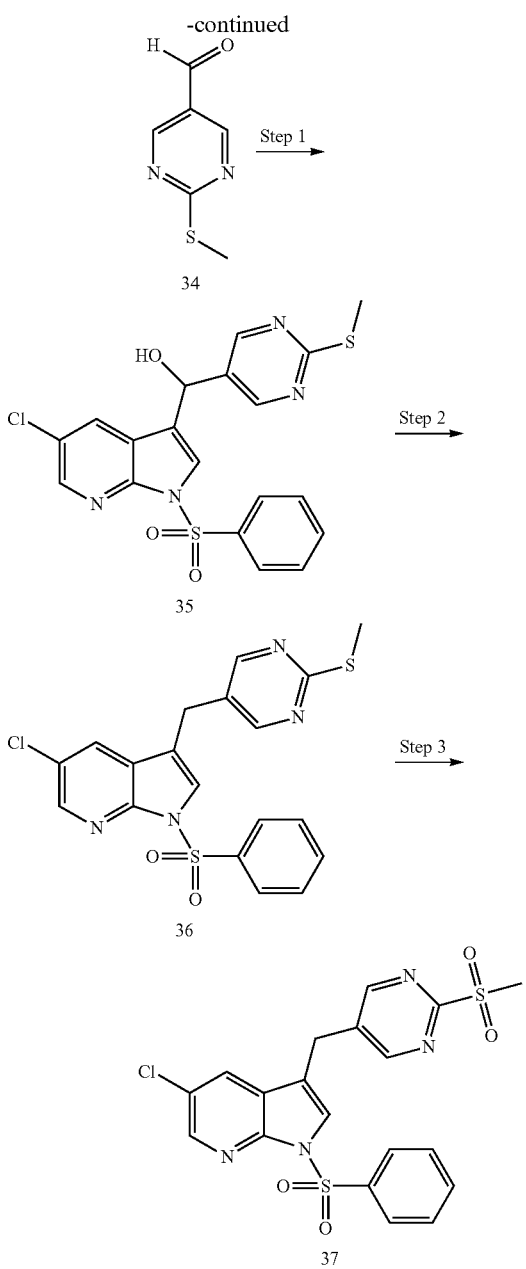

raphy eluting with 40-100% ethyl acetate in hexane. Appropriate fractions are combined and the solvents removed under vacuum to provide the desired compound as an off-white solid (35, 4.0 g). MS (ESI) [M+H$^+$]$^+$=447.2.

Step 2—Preparation of 1-benzenesulfonyl-5-chloro-3-(2-methylsulfanyl-pyrimidin-5-ylmethyl)-1H-pyrrolo[2,3-b]pyridine (36)

To (1-benzenesulfonyl-5-chloro-1H-pyrrolo[2,3-b]pyridin-3-yl)-(2-methylsulfanyl-pyrimidin-5-yl)-methanol (35, 4.70 g, 10.5 mmol) in 120.0 mL of acetonitrile, triethylsilane (22.0 mL, 138 mmol) and trifluoroacetic acid (11.0 mL, 143 mmol) are added. The reaction is stirred at 80° C. for 3 hours, then concentrated under vacuum, mixed with aqueous potassium carbonate and extracted with ethyl acetate. The organic layer is dried over sodium sulfate, filtered and the filtrate concentrated under vacuum. The resulting material is purified by silica gel column chromatography eluting with 20-100% ethyl acetate in hexane. Appropriate fractions are combined and solvents removed under vacuum to provide the desired compound (36, 2.90 g).

Step 3—Preparation of 1-benzenesulfonyl-5-chloro-3-(2-methanesulfonyl-pyrimidin-5-ylmethyl)-1H-pyrrolo[2,3-b]pyridine (37)

To 1-benzenesulfonyl-5-chloro-3-(2-methylsulfanyl-pyrimidin-5-ylmethyl)-1H-pyrrolo[2,3-b]pyridine (36, 4.40 g, 10.2 mmol) in 100.0 mL of dichloromethane, meta-chloroperoxybenzoic acid (max. 77%, 4.90 g, 21.9 mmol) is added at 0° C. The reaction is stirred at 0° C. for 40 minutes, then poured into water and extracted with ethyl acetate. The organic layer is dried over sodium sulfate, filtered, and the filtrate is concentrated under vacuum. The resulting material is purified by silica gel column chromatography eluting with 20% ethyl acetate in hexane. Appropriate fractions are combined and solvents removed under vacuum to provide the desired compound (37, 3.76 g). MS (ESI) [M+H$^+$]$^+$=463.0.

1-Benzenesulfonyl-3-(2-methanesulfonyl-pyrimidin-5-ylmethyl)-5-methyl-1H-pyrrolo[2,3-b]pyridine 38

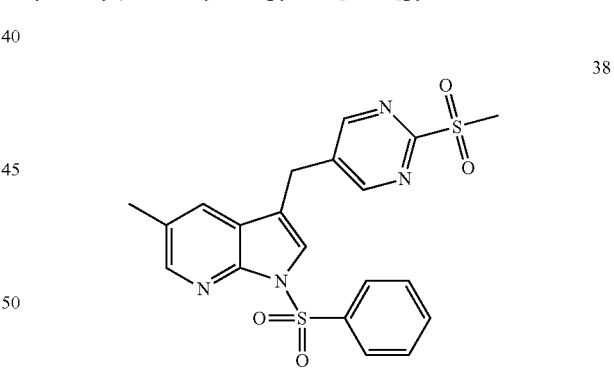

Step 1—Preparation of (1-benzenesulfonyl-5-chloro-1H-pyrrolo[2,3-b]pyridin-3-yl)-(2-methylsulfanyl-pyrimidin-5-yl)-methanol (35)

To a solution of 1-benzenesulfonyl-5-chloro-3-iodo-1H-pyrrolo[2,3-b]pyridine (28, 8.40 g, 20.1 mmol) in 96.3 mL of tetrahydrofuran at −40° C. under nitrogen, isopropylmagnesium chloride (10.1 mL, 2.0 M in tetrahydrofuran, 20.3 mmol) is added slowly. The reaction is allowed to warm to 5° C. over 60 minutes, then cooled to −40° C., followed by addition of 2-methylsulfanyl-pyrimidine-5-carbaldehyde (34, 2.50 g, 16.2 mmol) in 15.0 mL of tetrahydrofuran. The reaction is allowed to warm to 10° C. over 2 hours, then poured into aqueous ammonium chloride and extracted with ethyl acetate. The organic layer is dried over sodium sulfate, filtered and the filtrate is concentrated under vacuum. The resulting material is purified by silica gel column chromatogis prepared following the protocol of Scheme 6, replacing 1-benzenesulfonyl-5-chloro-3-iodo-1H-pyrrolo[2,3-b]pyridine 28 with 1-benzenesulfonyl-3-iodo-5-methyl-1H-pyrrolo[2,3-b]pyridine 29 in step 1.

Example 7

Synthesis of 6-fluoro-5-(5-methyl-1H-pyrrolo[2,3-b]pyridin-3-ylmethyl)-pyridin-2-ylamine 49

6-fluoro-5-(5-methyl-1H-pyrrolo[2,3-b]pyridin-3-ylmethyl)-pyridin-2-ylamine 49 is prepared in seven steps from 2,6-difluoro-pyridine 39 and 4-methoxy-benzylamine 40 as shown in Scheme 7.

Scheme 7

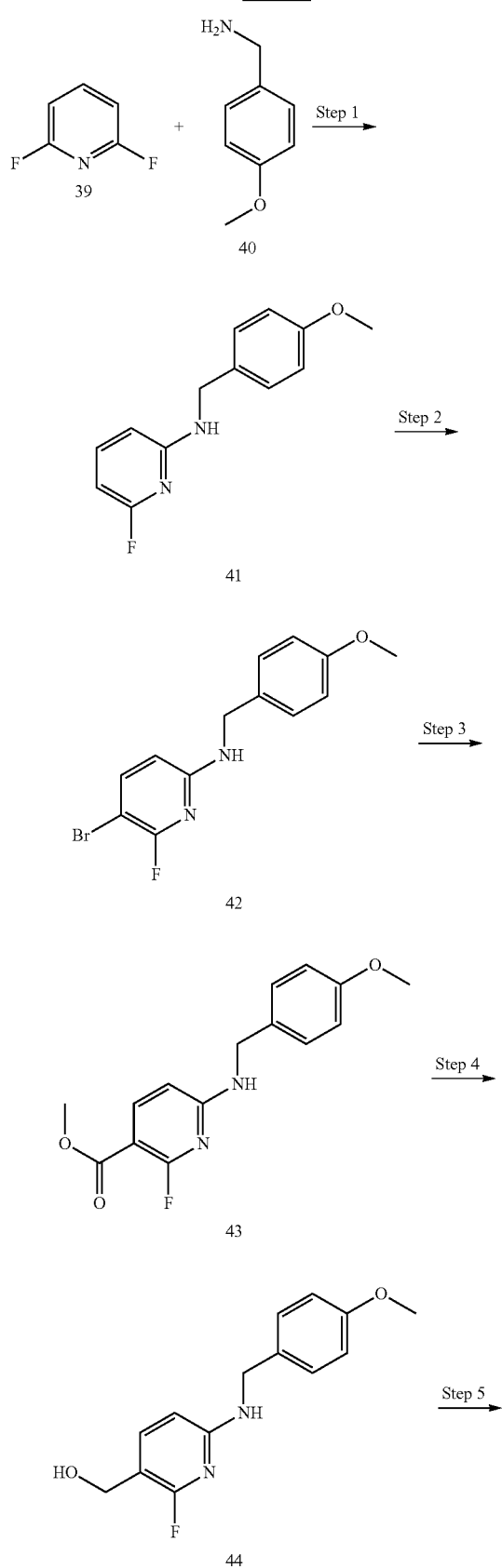

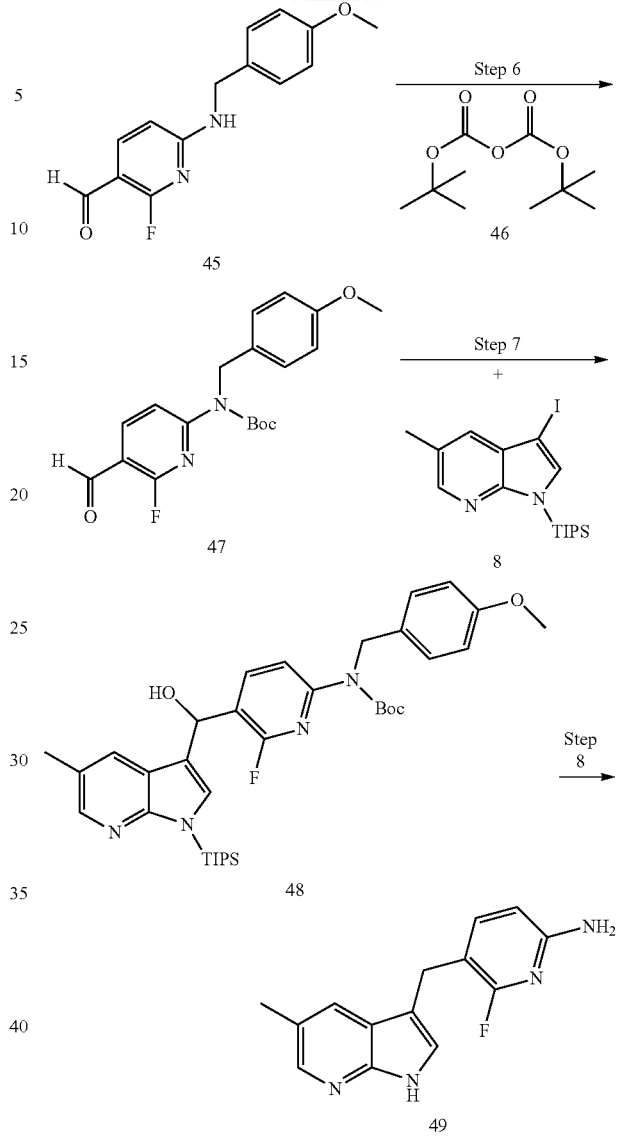

Step 1—Preparation of (6-fluoro-pyridin-2-yl)-(4-methoxy-benzyl)-amine (41)

To 2,6-difluoro-pyridine (39, 100 g, 869 mmol) in 500 mL of N-methylpyrrolidinone, 4-methoxy-benzylamine (40, 136 mL, 1.043 mol) and N,N-diisopropylethylamine (304 mL, 1.738 mol) are added. The reaction is stirred at 90° C. overnight, then poured into 8 L of water. The resulting precipitate is collected by filtration and washed with water, then taken up in ethyl acetate and washed with water. The organic layer is dried over sodium sulfate, filtered and the filtrate concentrated under vacuum. The resulting material is triturated with heptane and collected by filtration to provide the desired compound (41, 151 g, 650 mmol, 74.8% yield).

Step 2—Preparation of (5-bromo-6-fluoro-pyridin-2-yl)-(4-methoxy-benzyl)-amine (42)

To (6-fluoro-pyridin-2-yl)-(4-methoxy-benzyl)-amine (41, 151 g, 650 mmol) in 4 L of acetonitrile under an atmosphere of nitrogen, N-bromosuccinimide (116 g, 650 mmol) is added in portions. After reacting for 2 hours, the solvent is removed under vacuum and the residue is taken up in ethyl acetate, then poured into aqueous sodium thiosulfate. The organic layer is washed with warm water, dried over sodium sulfate, filtered and the filtrate concentrated under vacuum. The resulting material is crystallized from heptane to provide the desired compound (42, 172 g, 553 mmol, 85% yield).

Step 3—Preparation of 2-fluoro-6-(4-methoxy-benzylamino)-nicotinic acid methyl ester (43)

To (5-bromo-6-fluoro-pyridin-2-yl)-(4-methoxy-benzyl)-amine (42, 85 g, 273 mmol) in 1.5 L of methanol in a 2 L Parr flask, triethylamine (77 mL, 546 mmol) and [1,1'-bis(diphenylphosphino)ferrocene]dichloropalladium(II) (5.80 g, 7.10 mmol) are added. The reaction is heated at 100° C. under 100 psi of carbon monoxide overnight. The reaction is cooled and filtered through celite and the filtrate is concentrated under vacuum. The resulting material is dissolved in dichloromethane and passed through a plug of silica gel, eluting with ethyl acetate. The solvent is removed under vacuum to provide the desired compound as a peach colored solid (43, 70 g, 241 mmol, 88% yield).

Step 4—Preparation of [2-fluoro-6-(4-methoxy-benzylamino)-pyridin-3-yl]-methanol (44)

To 2-fluoro-6-(4-methoxy-benzylamino)-nicotinic acid methyl ester (43, 70 g, 241 mmol) in 350 mL of tetrahydrofuran, lithium aluminum hydride (362 mL, 1 M in tetrahydrofuran, 362 mmol) is added dropwise while cooling. The reaction is stirred at room temperature for 2 hours, then quenched with dropwise addition of 14 mL of water, 14 mL of 15% aqueous sodium hydroxide, and 42 mL of water, sequentially. Then 500 mL of methyl tert-butyl ether is added and solids are removed by filtration. The filtrate is concentrated under vacuum and the resulting solid is dissolved in dichloromethane, passed through a plug of silica gel and eluted with 50-100% ethyl acetate in heptane. The solvent is removed under vacuum to provide the desired compound as an off-white solid (44, 63 g, 240 mmol, 100% yield).

Step 5—Preparation of 2-fluoro-6-(4-methoxy-benzylamino)-pyridine-3-carbaldehyde (45)

To [2-fluoro-6-(4-methoxy-benzylamino)-pyridin-3-yl]-methanol (44, 63 g, 240 mmol) in 1.25 L of ethyl acetate, manganese(IV) oxide (210 g, 2.416 mol) is added. The reaction is stirred overnight at room temperature, then filtered through celite and the celite rinsed with ethyl acetate. The combined filtrates are concentrated under vacuum and the resulting solid is triturated with heptane and collected by filtration to provide the desired compound as a white solid (45, 62 g, 238 mmol, 99% yield).

Step 6—Preparation of (6-fluoro-5-formyl-pyridin-2-yl)-(4-methoxy-benzyl)-carbamic acid tert-butyl ester (47)

2-Fluoro-6-(4-methoxy-benzylamino)-pyridine-3-carbaldehyde (45, 62 g, 238 mmol), 600 mL of tert-butyl alcohol, di-tert-butyldicarbonate (46, 83 mL, 357 mmol) and dimethylaminopyridine (2.91 g, 23.82 mmol) are combined in a round bottom flask. The reaction is stirred at 30° C. overnight and then concentrated under vacuum. The resulting material is purified by silica gel column chromatography, eluting with 0-20% ethyl acetate in hexane. Appropriate fractions are combined and the solvents removed under vacuum to provide the desired compound (47, 54 g, 150 mmol, 62.9% yield).

Step 7—Preparation of {6-fluoro-5-[hydroxy-(5-methyl-1-triisopropylsilanyl-1H-pyrrolo[2,3-b]pyridin-3-yl)-methyl]-pyridin-2-yl}-(4-methoxy-benzyl)-carbamic acid tert-butyl ester (48)

To 3-iodo-5-methyl-1-triisopropylsilanyl-1H-pyrrolo[2,3-b]pyridine (8, 40 g, 97.0 mmol) in 400 mL of tetrahydrofuran under an atmosphere of nitrogen at −20° C., isopropylmagnesium chloride (54.8 mL, 2 M in tetrahydrofuran, 110 mmol) is added and the reaction allowed to warm to 0° C. over 30 minutes. The reaction is cooled to −40° C. and (6-fluoro-5-formyl-pyridin-2-yl)-(4-methoxy-benzyl)-carbamic acid tert-butyl ester (47, 15.81 g, 43.9 mmol) in tetrahydrofuran is added. The reaction is allowed to warm to 0° C. over an hour, then quenched with brine and extracted with ethyl acetate. The organic layer is dried over sodium sulfate, filtered and the filtrate concentrated under vacuum. The resulting material is purified by silica gel column chromatography, eluting with 0-40% ethyl acetate in hexane. Appropriate fractions are combined and the solvents removed under vacuum to provide the desired compound (48, 21 g, 32.4 mmol, 73.8% yield).

Step 8—Preparation of 6-fluoro-5-(5-methyl-1H-pyrrolo[2,3-b]pyridin-3-ylmethyl)-pyridin-2-ylamine (49)

To {6-fluoro-5-[hydroxy-(5-methyl-1-triisopropylsilanyl-1H-pyrrolo[2,3-b]pyridin-3-yl)-methyl]-pyridin-2-yl}-(4-methoxy-benzyl)-carbamic acid tert-butyl ester (48, 21 g, 32.4 mmol) in 500 mL of acetonitrile, triethylsilane (51.7 mL, 324 mmol) and trifluoroacetic acid (24.93 mL, 324 mmol) are added. The reaction is stirred at 50° C. for several hours, then concentrated under vacuum, and the residue is taken up in 250 mL of dichloromethane and 250 mL of trifluoroacetic acid is added. The mixture is stirred at reflux for several hours, then concentrated under vacuum. The residue is taken up in ethyl acetate and poured into aqueous potassium carbonate. The organic layer is separated, concentrated under vacuum and purified by silica gel column chromatography, eluting with 0-5% methanol in dichloromethane. Appropriate fractions are combined and the solvents removed under vacuum to provide the desired compound (49, 5.2 g, 20.29 mmol, 62.7% yield).

5-(5-Chloro-1H-pyrrolo[2,3-b]pyridin-3-ylmethyl)-6-fluoro-pyridin-2-ylamine 50

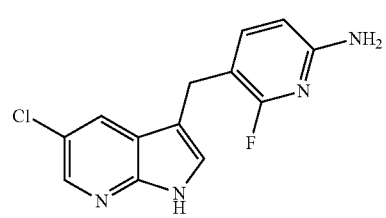

is prepared following the protocol of Scheme 7, replacing 3-iodo-5-methyl-1-triisopropylsilanyl-1H-pyrrolo[2,3-b]pyridine 8 with 5-chloro-3-iodo-1-triisopropylsilanyl-1H-pyrrolo[2,3-b]pyridine 4 in step 7.

Example 8

Synthesis of Aldehyde Reagents

Aldehyde reagents that are used in making compounds are prepared according to the following protocols. In these reactions, the unprotected aldehyde isolated after step 5, or the subsequently Boc-protected aldehyde may be used in preparation of compounds.

(6-ethoxy-pyridin-3-yl)-(6-fluoro-5-formyl-pyridin-2-yl)-carbamic acid tert-butyl ester 57 is prepared in six steps from 2,6-difluoro-pyridine 39 as shown in Scheme 8.

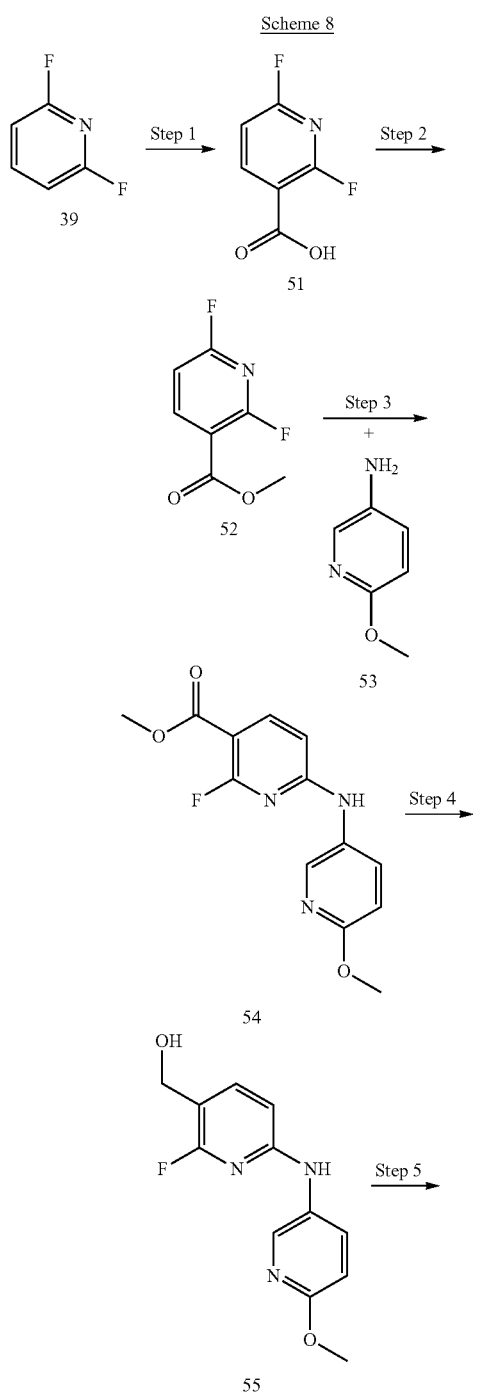

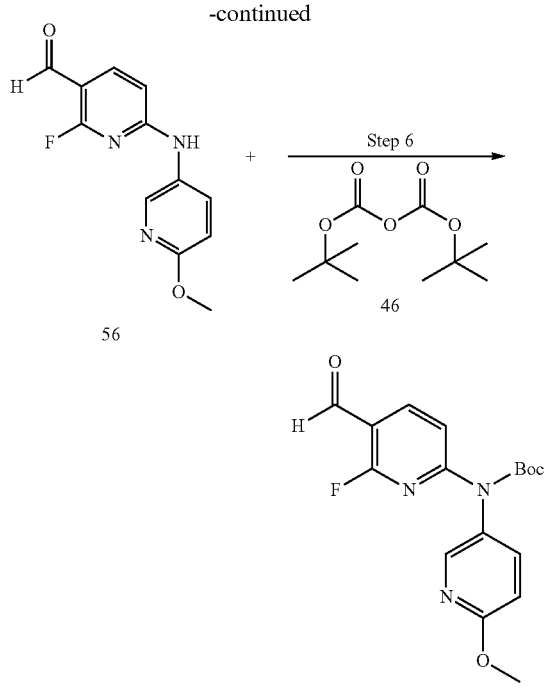

Step 1—Preparation of 2,6-difluoro-nicotinic acid (51)

In a round bottom flask, to 2,6-difluoro-pyridine (39, 7.10 g, 61.7 mmol) in 150.0 mL of tetrahydrofuran under an atmosphere of nitrogen at −78° C., n-butyllithium (26.0 mL, 2.50 M in hexane, 65.0 mmol) is slowly added. After 30 minutes, 3.0 g of dry ice is added and an hour later the reaction is allowed to warm to room temperature. The reaction is poured into water, extracted with ethyl acetate and the aqueous layer is adjusted to pH 4-5 with 1 N hydrochloric acid. This is extracted with ethyl acetate and the organic layer is dried over sodium sulfate, filtered and the filtrate concentrated under vacuum to provide the desired compound (51, 5.6 g).

Step 2—Preparation of 2,6-difluoro-nicotinic acid methyl ester (52)

In a round bottom flask, 2,6-difluoro-nicotinic acid (51, 5.60 g, 35.2 mmol), 60.0 mL of methanol and sulfuric acid (1.0 mL, 19.0 mmol) are combined and heated to reflux overnight. The reaction is poured into water, adjusted to pH around 9 with 1M aqueous potassium carbonate, and extracted with ethyl acetate. The organic layer is dried over sodium sulfate, filtered and the filtrate concentrated under vacuum to provide the desired compound as a yellow oil (52, 3.5 g).

Step 3—Preparation of 2-fluoro-6-(6-methoxy-pyridin-3-ylamino)-nicotinic acid methyl ester (54)

To a round bottom flask, 2,6-difluoro-nicotinic acid methyl ester (52, 2.00 g, 11.6 mmol) is combined with 20.0 mL of N,N-dimethylformamide under an atmosphere of nitrogen at −40° C. To this, 5-amino-2-methoxypyridine (53, 1.55 g, 12.5 mmol) and triethylamine (5.0 mL, 36.0 mmol) are added and the reaction stirred at −40° C., then warmed to room temperature and reacted overnight. The reaction is then heated to 50° C. over the weekend, then at 70° C. for 3 hours. The reaction is poured into water and extracted with ethyl acetate. The organic layer is dried over sodium sulfate, filtered and the filtrate concentrated under vacuum. The resulting material is purified by silica gel column chromatography eluting with 20-100% ethyl acetate in hexane. Appropriate fractions are combined and concentrated under vacuum to provide the desired compound (54, 1.20 g).

Step 4—Preparation of [2-fluoro-6-(6-methoxy-pyridin-3-ylamino)-pyridin-3-yl]-methanol (55)

To 2-fluoro-6-(6-methoxy-pyridin-3-ylamino)-nicotinic acid methyl ester (54, 1.20 g, 4.33 mmol) in 50.0 mL of tetrahydrofuran, lithium tetrahydroaluminate (8.66 mL, 1.00 M in tetrahydrofuran, 8.66 mmol) is added and the reaction is stirred at room temperature for 3 hours. Sodium sulfate decahydrate (5 g) is added and after 1 hour, the reaction is filtered and the filtrate concentrated under vacuum. The resulting material is purified by silica gel column chromatography eluting with 20-100% ethyl acetate in hexane. Appropriate fractions are combined and concentrated under vacuum to provide the desired compound (55, 700 mg). MS (ESI) [M+H$^+$]$^+$=250.1.

Step 5—Preparation of 2-fluoro-6-(6-methoxy-pyridin-3-ylamino)-pyridine-3-carbaldehyde (56)

To [2-fluoro-6-(6-methoxy-pyridin-3-ylamino)-pyridin-3-yl]-methanol (55, 0.700 g, 2.81 mmol) in 20.0 mL of tetrahydrofuran, Dess-Martin periodinane (1.44 g, 3.40 mmol) is added and the reaction stirred at room temperature for 30 minutes. The reaction is poured into aqueous potassium carbonate and extracted with ethyl acetate. The organic layer is dried over sodium sulfate, filtered and the filtrate concentrated under vacuum. The resulting material is purified by silica gel column chromatography eluting with 20-100% ethyl acetate in hexane. Appropriate fractions are combined and concentrated under vacuum to provide the desired compound (56, 450 mg). MS (ESI) [M+H$^+$]$^+$=248.0.

Step 6—Preparation of (6-fluoro-5-formyl-pyridin-2-yl)-(6-methoxy-pyridin-3-yl)-carbamic acid tert-butyl ester (57)

To 2-fluoro-6-(6-methoxy-pyridin-3-ylamino)-pyridine-3-carbaldehyde (56, 2.21 g, 8.94 mmol) in 50 mL of tetrahydrofuran, di-tert-butyldicarbonate (46, 2.82 g, 12.9 mmol) and 4-dimethylaminopyridine (0.30 g, 2.4 mmol) are added and the reaction stirred at room temperature overnight. The reaction is concentrated under vacuum and the resulting material is purified by silica gel column chromatography eluting with 20-100% ethyl acetate in hexane. Appropriate fractions are combined and concentrated under vacuum to provide the desired compound (57, 1.39 g).

Additional aldehydes are prepared similarly to the protocol of scheme 8, as shown in the following table, replacing 5-amino-2-methoxypyridine 53 with a suitable amine compound in step 3. While the table indicates the Boc-protected aldehyde, the non-Boc protected aldehyde may be isolated after step 5.

TABLE 3

| Step 3 amine compound | Final aldehyde |
|---|---|

Example 9

Synthesis of [5-(5-chloro-1H-pyrrolo[2,3-b]pyridin-3-ylmethyl)-pyrimidin-2-yl]-cyclohexyl-amine P-3001

[5-(5-Chloro-1H-pyrrolo[2,3-b]pyridin-3-ylmethyl)-pyrimidin-2-yl]-cyclohexyl-amine P-3001 is prepared in one step from 1-benzenesulfonyl-5-chloro-3-(2-methanesulfonyl-pyrimidin-5-ylmethyl)-1H-pyrrolo[2,3-b]pyridine 37 and cyclohexanamine 62 as shown in Scheme 9.

Scheme 9

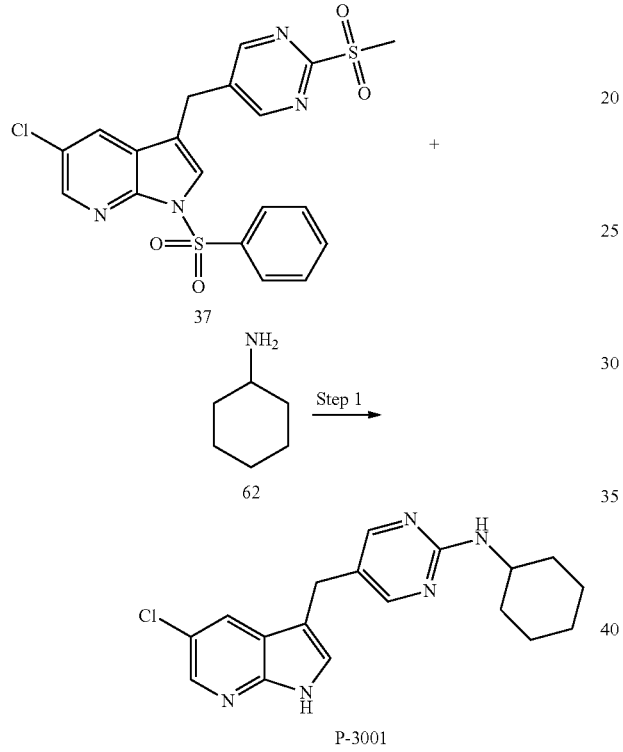

Step 1—Preparation of [5-(5-chloro-1H-pyrrolo[2,3-b]pyridin-3-ylmethyl)-pyrimidin-2-yl]-cyclohexyl-amine (P-3001)

In a microwave vial, to 1-benzenesulfonyl-5-chloro-3-(2-methanesulfonyl-pyrimidin-5-ylmethyl)-1H-pyrrolo[2,3-b]pyridine (37, 60 mg, 0.13 mmol) in 1.0 mL of N-methylpyrrolidinone, cyclohexanamine (62, 0.20 g, 2.0 mmol) is added. The reaction is heated at 155° C. for 25 minutes in a microwave, then potassium hydroxide (1.0 mL, 1.00 M in water, 1.0 mmol) is added and the reaction heated at 95° C. for 15 minutes in a microwave. The reaction is poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are collected and concentrated under vacuum to provide the desired compound (P-3001, 11.4 mg). MS (ESI) [M+H$^+$]$^+$=341.9.

[5-(5-Chloro-1H-pyrrolo[2,3-b]pyridin-3-ylmethyl)-pyrimidin-2-yl]-(4-methyl-cyclohexyl)-amine P-3009 was prepared similarly to Scheme 9, replacing step 1 with the following steps 1a and 2

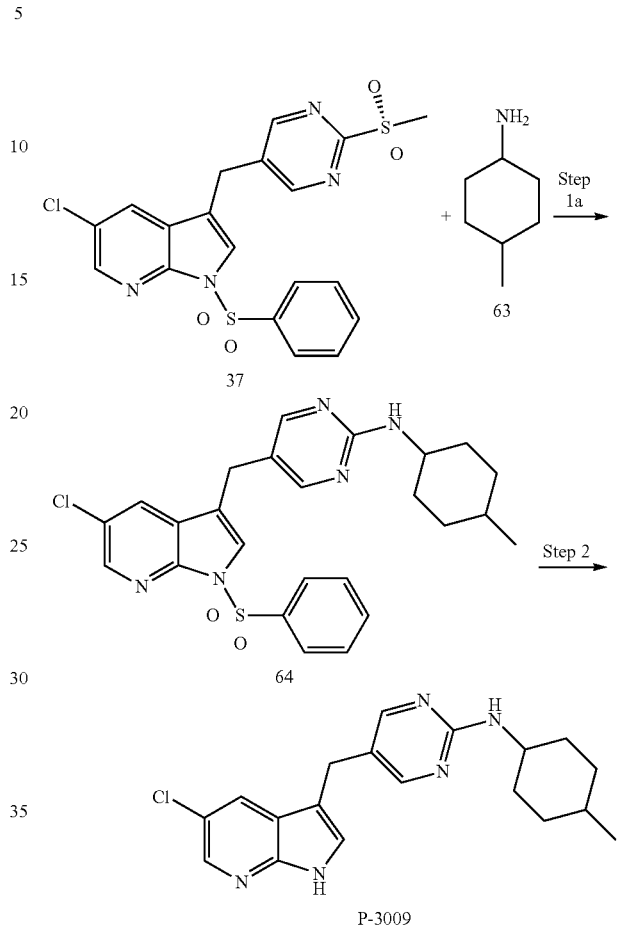

Step 1a—Preparation of [5-(1-benzenesulfonyl-5-chloro-1H-pyrrolo[2,3-b]pyridin-3-ylmethyl)-pyrimidin-2-yl]-(4-methyl-cyclohexyl)-amine (64)

In a microwave vial, to 1-benzenesulfonyl-5-chloro-3-(2-methanesulfonyl-pyrimidin-5-ylmethyl)-1H-pyrrolo[2,3-b]pyridine (37, 0.140 g, 0.302 mmol) in 2.0 mL of N-methylpyrrolidinone, 4-methylcyclohexylamine (63, 0.30 g, 2.6 mmol) is added. The reaction is heated at 160° C. for 20 minutes in a microwave, then poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (64, 0.120 g). MS (ESI) [M+H$^+$]$^+$=496.4.

Step 2—Preparation of [5-(5-chloro-1H-pyrrolo[2,3-b]pyridin-3-ylmethyl)-pyrimidin-2-yl]-(4-methyl-cyclohexyl)-amine (P-3009)

To [5-(1-benzenesulfonyl-5-chloro-1H-pyrrolo[2,3-b]pyridin-3-ylmethyl)-pyrimidin-2-yl]-(4-methyl-cyclohexyl)- amine (64, 0.120 g, 0.242 mmol) in 5.0 mL of tetrahydrofuran, tetrabutylammonium fluoride trihydrate (0.20 g, 0.63 mmol) is added. The reaction is stirred at room temperature overnight, then poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are collected and concentrated under vacuum to provide the desired compound (P-3009, 1.4 mg). MS (ESI) [M+H⁺]⁺=355.95.

Additional compounds are prepared following the protocol of Scheme 9. Compounds are made substituting cyclohexanamine 62 with a suitable amine and optionally substituting 1-benzenesulfonyl-5-chloro-3-(2-methanesulfonyl-pyrimidin-5-ylmethyl)-1H-pyrrolo[2,3-b]pyridine 37 with 1-benzenesulfonyl-3-(2-methanesulfonyl-pyrimidin-5-ylmethyl)-5-methyl-1H-pyrrolo[2,3-b]pyridine 38.

The following compounds are made using this procedure:
[5-(5-Chloro-1H-pyrrolo[2,3-b]pyridin-3-ylmethyl)-pyrimidin-2-yl]-cyclopentyl-amine (P-3003),
[5-(5-Chloro-1H-pyrrolo[2,3-b]pyridin-3-ylmethyl)-pyrimidin-2-yl]-4,4-difluoro-cyclohexyl)-amine (P-3004),
[5-(5-Chloro-1H-pyrrolo[2,3-b]pyridin-3-ylmethyl)-pyrimidin-2-yl]-cyclopropyl-amine (P-3005),
[5-(5-Chloro-1H-pyrrolo[2,3-b]pyridin-3-ylmethyl)-pyrimidin-2-yl]-cycloheptyl-amine (P-3006),
[5-(5-Chloro-1H-pyrrolo[2,3-b]pyridin-3-ylmethyl)-pyrimidin-2-yl]-cyclobutyl-amine (P-3007),
(4-Fluoro-phenyl)-[5-(5-methyl-1H-pyrrolo[2,3-b]pyridin-3-ylmethyl)-pyrimidin-2-yl]-amine (P-3010),
(4-Chloro-phenyl)-[5-(5-chloro-1H-pyrrolo[2,3-b]pyridin-3-ylmethyl)-pyrimidin-2-yl]-amine (P-3011),
[5-(5-Chloro-1H-pyrrolo[2,3-b]pyridin-3-ylmethyl)-pyrimidin-2-yl]-(4-fluoro-phenyl)-amine (P-3012),
[5-(5-Chloro-1H-pyrrolo[2,3-b]pyridin-3-ylmethyl)-pyrimidin-2-yl]-(2-fluoro-phenyl)-amine (P-3014),
(2-Chloro-phenyl)-[5-(5-chloro-1H-pyrrolo[2,3-b]pyridin-3-ylmethyl)-pyrimidin-2-yl]-amine (P-3015),
[5-(5-Chloro-1H-pyrrolo[2,3-b]pyridin-3-ylmethyl)-pyrimidin-2-yl]-(2-methoxy-phenyl)-amine (P-3016),
[5-(5-Chloro-1H-pyrrolo[2,3-b]pyridin-3-ylmethyl)-pyrimidin-2-yl]-(3-fluoro-phenyl)-amine (P-3017),
[5-(5-Methyl-1H-pyrrolo[2,3-b]pyridin-3-ylmethyl)-pyrimidin-2-yl]-(6-trifluoromethyl-pyridin-3-yl)-amine (P-3018),
(6-Methoxy-pyridin-3-yl)-[5-(5-methyl-1H-pyrrolo[2,3-b]pyridin-3-ylmethyl)-pyrimidin-2-yl]-amine (P-3020),
(4-Methoxy-phenyl)-[5-(5-methyl-1H-pyrrolo[2,3-b]pyridin-3-ylmethyl)-pyrimidin-2-yl]-amine (P-3021),
(4-Fluoro-3-methoxy-phenyl)-[5-(5-methyl-1H-pyrrolo[2,3-b]pyridin-3-ylmethyl)-pyrimidin-2-yl]-amine (P-3022),
(3-Fluoro-4-methoxy-phenyl)-[5-(5-methyl-1H-pyrrolo[2,3-b]pyridin-3-ylmethyl)-pyrimidin-2-yl]-amine (P-3023),
[5-(5-Methyl-1H-pyrrolo[2,3-b]pyridin-3-ylmethyl)-pyrimidin-2-yl]-(4-propoxy-phenyl)-amine (P-3024),
(4-Ethyl-phenyl)-[5-(5-methyl-1H-pyrrolo[2,3-b]pyridin-3-ylmethyl)-pyrimidin-2-yl]-amine (P-3025),
(4-Ethoxy-phenyl)-[5-(5-methyl-1H-pyrrolo[2,3-b]pyridin-3-ylmethyl)-pyrimidin-2-yl]-amine (P-3026),
(6-Ethoxy-pyridin-3-yl)-[5-(5-methyl-1H-pyrrolo[2,3-b]pyridin-3-ylmethyl)-pyrimidin-2-yl]-amine (P-3027),
[5-(4-Fluoro-phenyl)-2H-pyrazol-3-yl]-[5-(5-methyl-1H-pyrrolo[2,3-b]pyridin-3-ylmethyl)-pyrimidin-2-yl]-amine (P-3028),
(5-tert-Butyl-2H-pyrazol-3-yl)-[5-(5-methyl-1H-pyrrolo[2,3-b]pyridin-3-ylmethyl)-pyrimidin-2-yl]-amine (P-3029),
(4-tert-Butyl-phenyl)-[5-(5-methyl-1H-pyrrolo[2,3-b]pyridin-3-ylmethyl)-pyrimidin-2-yl]-amine amine (P-3030),
1,1,1,3,3,3-Hexafluoro-2-{4-[5-(5-methyl-1H-pyrrolo[2,3-b]pyridin-3-ylmethyl)-pyrimidin-2-ylamino]-phenyl}-propan-2-ol (P-3031),
(5-Cyclopropyl-2H-pyrazol-3-yl)-[5-(5-methyl-1H-pyrrolo[2,3-b]pyridin-3-ylmethyl)-pyrimidin-2-yl]-amine (P-3032),
[5-(5-Methyl-1H-pyrrolo[2,3-b]pyridin-3-ylmethyl)-pyrimidin-2-yl]-(4-methylsulfanyl-phenyl)-amine (P-3033),
(1-Ethyl-1H-pyrazol-3-yl)-[5-(5-methyl-1H-pyrrolo[2,3-b]pyridin-3-ylmethyl)-pyrimidin-2-yl]-amine (P-3035),
(1-Ethyl-1H-pyrazol-4-yl)-[5-(5-methyl-1H-pyrrolo[2,3-b]pyridin-3-ylmethyl)-pyrimidin-2-yl]-amine (P-3036),
[5-(5-Methyl-1H-pyrrolo[2,3-b]pyridin-3-ylmethyl)-pyrimidin-2-yl]-(5-trifluoromethyl-2H-pyrazol-3-yl)-amine (P-3037), and
(5-Isopropoxy-2H-pyrazol-3-yl)-[5-(5-methyl-1H-pyrrolo[2,3-b]pyridin-3-ylmethyl)-pyrimidin-2-yl]-amine (P-3038).

The following table indicates the 2-methanesulfonyl-pyrimidin-5-ylmethyl)-1H-pyrrolo[2,3-b]pyridine (column 2) and amine compound (column 3) used in step 1 to afford the desired compound (column 4). The compound number is provided in column 1, and the observed mass is in column 5

TABLE 4

| Comp. number | pyrrolo[2,3-b]pyridine | Amine structure | Compound structure | MS (ESI) [M + H⁺]⁺ |
|---|---|---|---|---|
| P-3003 | 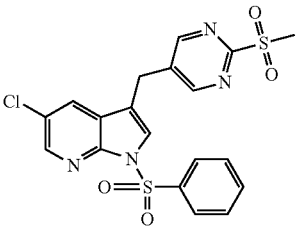 [SMILES: CS(=O)(=O)c1ncc(Cc2cn(S(=O)(=O)c3ccccc3)c3ncc(Cl)cc23)cn1] |  | 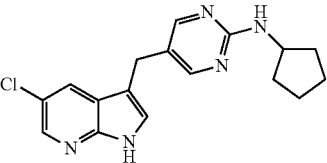 [SMILES: Clc1cnc2[nH]cc(Cc3cnc(NC4CCCC4)nc3)c2c1] | 328.0 |

TABLE 4-continued

| Comp. number | pyrrolo[2,3-b]pyridine | Amine structure | Compound structure | MS (ESI) [M + H⁺]⁺ |
|---|---|---|---|---|
| P-3004 | | | 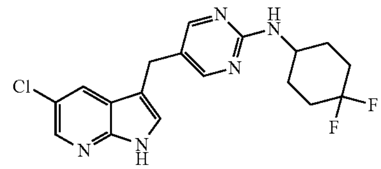 [SMILES: FC1(F)CCC(Nc2ncc(Cc3c[nH]c4ncc(Cl)cc34)cn2)CC1] | 377.9 |
| P-3005 | | | 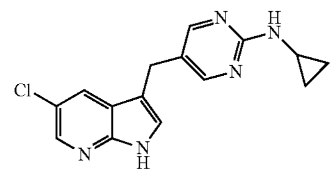 [SMILES: Clc1cnc2[nH]cc(Cc3cnc(NC4CC4)nc3)c2c1] | 300.0 |
| P-3006 | | | 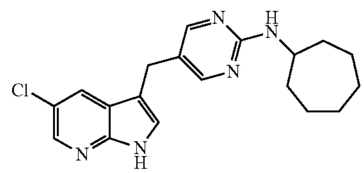 [SMILES: Clc1cnc2[nH]cc(Cc3cnc(NC4CCCCCC4)nc3)c2c1] | 356.3 |
| P-3007 | | | 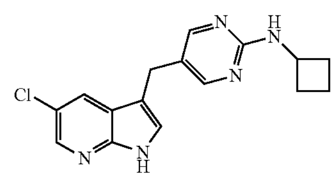 [SMILES: Clc1cnc2[nH]cc(Cc3cnc(NC4CCC4)nc3)c2c1] | 314.2 |
| P-3010 | | | 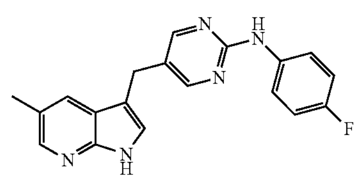 [SMILES: Cc1cnc2[nH]cc(Cc3cnc(Nc4ccc(F)cc4)nc3)c2c1] | 334.1 |
| P-3011 | | | 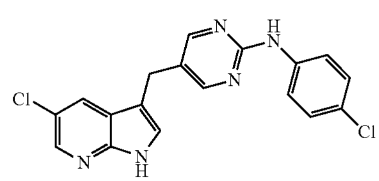 [SMILES: Clc1ccc(Nc2ncc(Cc3c[nH]c4ncc(Cl)cc34)cn2)cc1] | 370.8 |

TABLE 4-continued

| Comp. number | pyrrolo[2,3-b]pyridine | Amine structure | Compound structure | MS (ESI) [M + H⁺]⁺ |
|---|---|---|---|---|
| P-3012 | | | 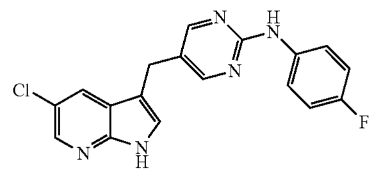 [SMILES: Fc1ccc(Nc2ncc(Cc3c[nH]c4ncc(Cl)cc34)cn2)cc1] | 354.0 |
| P-3014 | | | 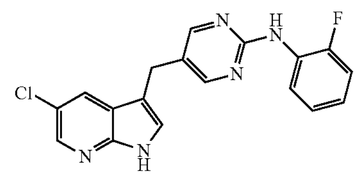 [SMILES: Fc1ccccc1Nc1ncc(Cc2c[nH]c3ncc(Cl)cc23)cn1] | 353.9 |
| P-3015 | | | 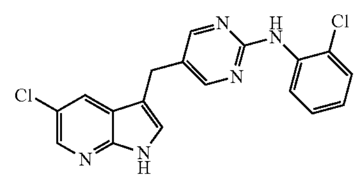 | 369.9 |
| P-3016 | | | 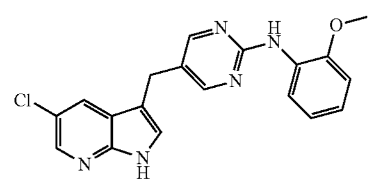 [SMILES: COc1ccccc1Nc1ncc(Cc2c[nH]c3ncc(Cl)cc23)cn1] | 365.9 |
| P-3017 | | | 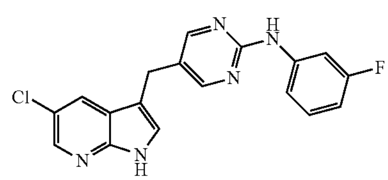 [SMILES: Fc1cccc(Nc2ncc(Cc3c[nH]c4ncc(Cl)cc34)cn2)c1] | 353.9 |
| P-3018 | | | 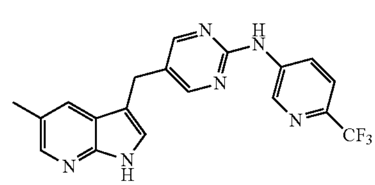 [SMILES: Cc1cnc2[nH]cc(Cc3cnc(Nc4ccc(C(F)(F)F)nc4)nc3)c2c1] | 384.9 |

TABLE 4-continued

| Comp. number | pyrrolo[2,3-b]pyridine | Amine structure | Compound structure | MS (ESI) [M + H+]+ |
|---|---|---|---|---|
| P-3020 | | | 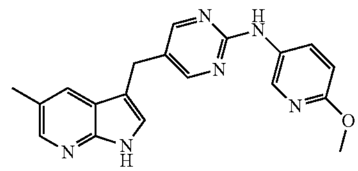 [SMILES: COc1ccc(Nc2ncc(Cc3c[nH]c4ncc(C)cc34)cn2)cn1] | 347.1 |
| P-3021 | | | 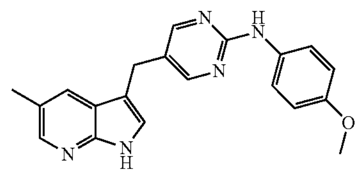 [SMILES: COc1ccc(Nc2ncc(Cc3c[nH]c4ncc(C)cc34)cn2)cc1] | 346.2 |
| P-3022 | | | 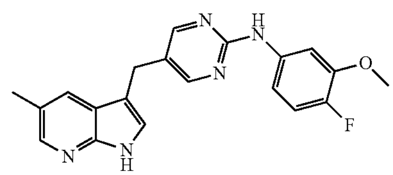 | 363.9 |
| P-3023 | | | 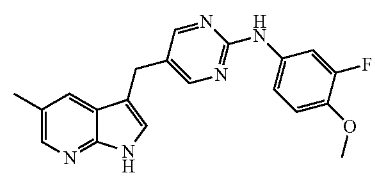 [SMILES: COc1ccc(Nc2ncc(Cc3c[nH]c4ncc(C)cc34)cn2)cc1F] | 363.9 |
| P-3024 | | | 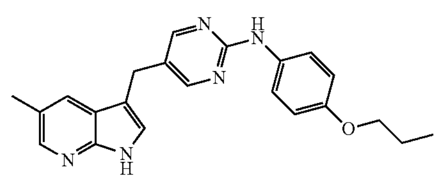 [SMILES: CCCOc1ccc(Nc2ncc(Cc3c[nH]c4ncc(C)cc34)cn2)cc1] | 374.0 |
| P-3025 | | | 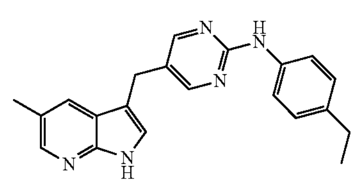 [SMILES: CCc1ccc(Nc2ncc(Cc3c[nH]c4ncc(C)cc34)cn2)cc1] | 344.0 |

TABLE 4-continued

| Comp. number | pyrrolo[2,3-b]pyridine | Amine structure | Compound structure | MS (ESI) [M + H⁺]⁺ |
|---|---|---|---|---|
| P-3026 | | | 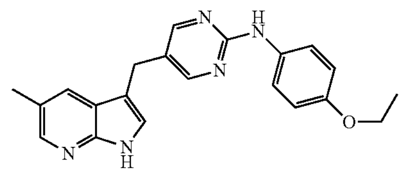 [SMILES: CCOc1ccc(Nc2ncc(Cc3c[nH]c4ncc(C)cc34)cn2)cc1] | 360.0 |
| P-3027 | | | 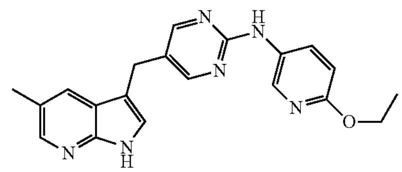 [SMILES: CCOc1ccc(Nc2ncc(Cc3c[nH]c4ncc(C)cc34)cn2)cn1] | 501.3 |
| P-3028 | | | 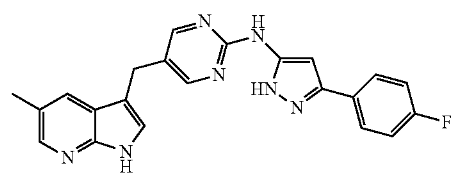 [SMILES: Cc1cnc2[nH]cc(Cc3cnc(Nc4cc(-c5ccc(F)cc5)n[nH]4)nc3)c2c1] | 399.9 |
| P-3029 | | | 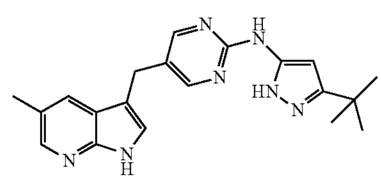 [SMILES: Cc1cnc2[nH]cc(Cc3cnc(Nc4cc(C(C)(C)C)n[nH]4)nc3)c2c1] | 362.0 |
| P-3030 | | | 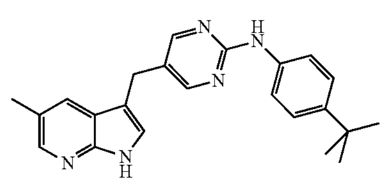 [SMILES: Cc1cnc2[nH]cc(Cc3cnc(Nc4ccc(C(C)(C)C)cc4)nc3)c2c1] | 372.0 |
| P-3031 | | | 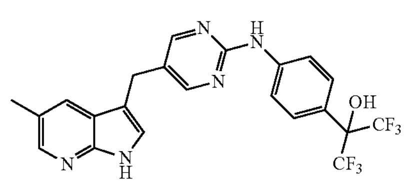 [SMILES: Cc1cnc2[nH]cc(Cc3cnc(Nc4ccc(C(O)(C(F)(F)F)C(F)(F)F)cc4)nc3)c2c1] | 482.3 |

TABLE 4-continued

| Comp. number | pyrrolo[2,3-b]pyridine | Amine structure | Compound structure | MS (ESI) [M + H⁺]⁺ |
|---|---|---|---|---|
| P-3032 | | | 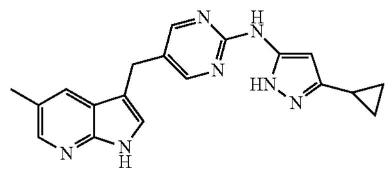 [SMILES: Cc1cnc2[nH]cc(Cc3cnc(Nc4cc(C5CC5)n[nH]4)nc3)c2c1] | 346.0 |
| P-3033 | | | 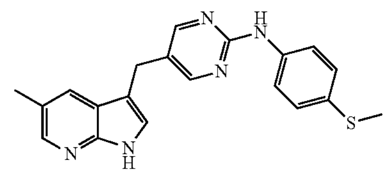 | 362.1 |
| P-3035 | | | 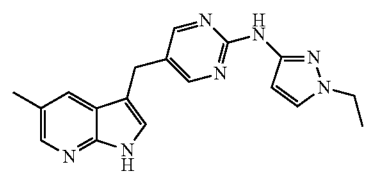 [SMILES: CCn1ccc(Nc2ncc(Cc3c[nH]c4ncc(C)cc34)cn2)n1] | 334.2 |
| P-3036 | | | 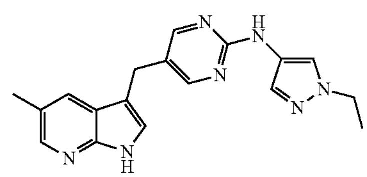 [SMILES: CCn1cc(Nc2ncc(Cc3c[nH]c4ncc(C)cc34)cn2)cn1] | 333.9 |
| P-3037 | | | 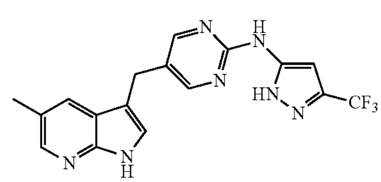 [SMILES: Cc1cnc2[nH]cc(Cc3cnc(Nc4cc(C(F)(F)F)n[nH]4)nc3)c2c1] | 374.0 |
| P-3038 | | | 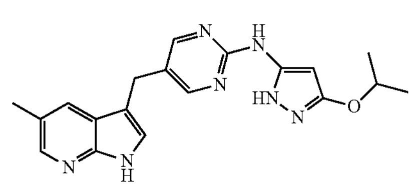 [SMILES: Cc1cnc2[nH]cc(Cc3cnc(Nc4cc(OC(C)C)n[nH]4)nc3)c2c1] | 363.9 |

(4-Methanesulfonyl-phenyl)-[5-(5-methyl-1H-pyrrolo[2,3-b]pyridin-3-ylmethyl)-pyrimidin-2-yl]-amine P-3034

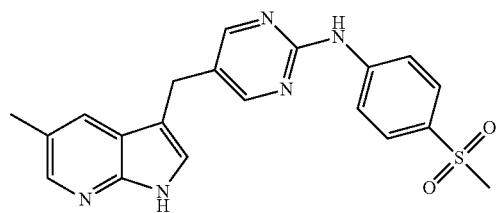

P-3034 is prepared by oxidizing the product of Scheme 9 step 1a in the preparation of [5-(5-methyl-1H-pyrrolo[2,3-b]pyridin-3-ylmethyl)-pyrimidin-2-yl]-(4-methylsulfanyl-phenyl)-amine (P-3033), prior to reaction of step 2, according to the following step 1b:

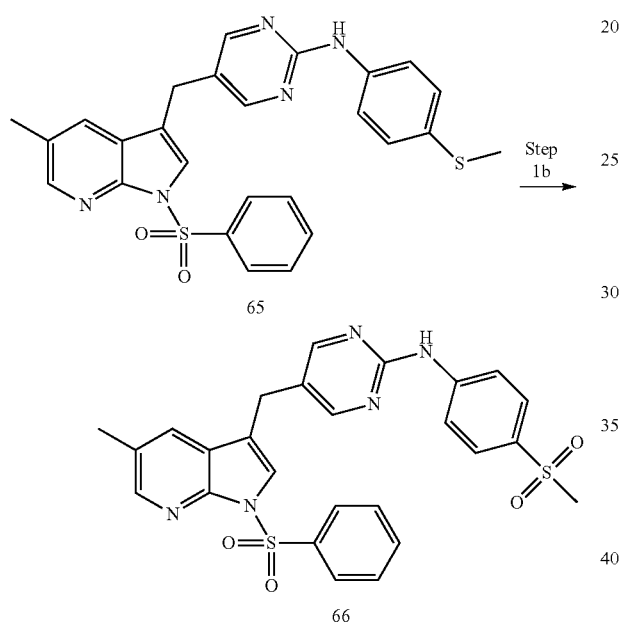

Step 1b—Preparation of [5-(1-benzenesulfonyl-5-methyl-1H-pyrrolo[2,3-b]pyridin-3-ylmethyl)-pyrimidin-2-yl]-(4-methanesulfonyl-phenyl)-amine (66)

To [5-(1-benzenesulfonyl-5-methyl-1H-pyrrolo[2,3-b]pyridin-3-ylmethyl)-pyrimidin-2-yl]-(4-methylsulfanyl-phenyl)-amine (65, 80 mg, 0.16 mmol) in 10.0 mL of dichloromethane, meta-chloroperoxybenzoic acid (78.6 mg, 0.351 mmol) is added at 0° C. The reaction is stirred at room temperature for 30 minutes, then concentrated under vacuum to provide [5-(1-benzenesulfonyl-5-methyl-1H-pyrrolo[2,3-b]pyridin-3-ylmethyl)-pyrimidin-2-yl]-(4-methanesulfonyl-phenyl)-amine 66, which is reacted according to Scheme 9 step 2 to provide the desired compound (P-3034, 30.7 mg). MS (ESI) [M+H$^+$]$^+$=393.9.

Example 10

Synthesis of cyclohexyl-[6-fluoro-5-(5-methyl-1H-pyrrolo[2,3-b]pyridin-3-ylmethyl)-pyridin-2-yl]-amine P-3008

Cyclohexyl-[6-fluoro-5-(5-methyl-1H-pyrrolo[2,3-b]pyridin-3-ylmethyl)-pyridin-2-yl]-amine P-3008 is prepared in one step from 6-fluoro-5-(5-methyl-1H-pyrrolo[2,3-b]pyridin-3-ylmethyl)-pyridin-2-ylamine 49 and cyclohexanone 67 as shown in Scheme 10.

Scheme 10

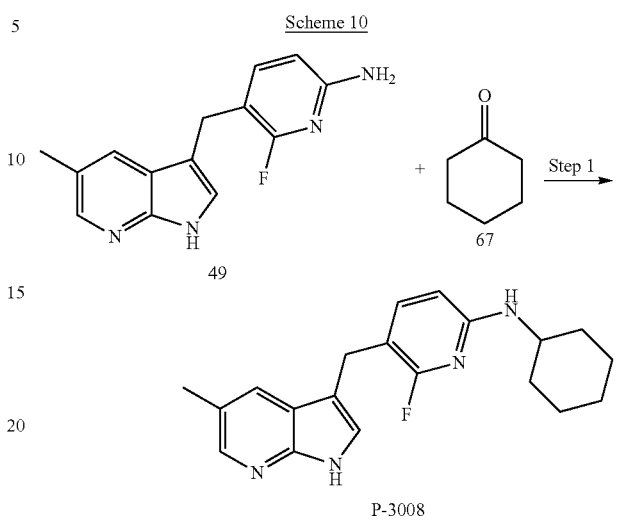

Step 1—Preparation of cyclohexyl-[6-fluoro-5-(5-methyl-1H-pyrrolo[2,3-b]pyridin-3-ylmethyl)-pyridin-2-yl]-amine (P-3008)

To 6-fluoro-5-(5-methyl-1H-pyrrolo[2,3-b]pyridin-3-ylmethyl)-pyridin-2-ylamine (49, 100 mg, 0.39 mmol) and cyclohexanone (67, 0.0465 mL, 0.449 mmol) in 3.00 mL of acetonitrile, triethylsilane (0.400 mL, 2.50 mmol) and trifluoroacetic acid (0.300 mL, 3.89 mmol) were added. The reaction was stirred at 80° C. overnight, then extracting with ethyl acetate and 1N aqueous sodium bicarbonate. The organic layer was washed with brine, dried with magnesium sulfate, filtered and the filtrate concentrated under vacuum. The resulting material was purified by silica gel column chromatography, eluting with 0-60% ethyl acetate in hexane. Appropriate fractions were combined and concentrated under vacuum to provide the desired compound (P-3008, 115 mg). MS (ESI) [M+H$^+$]$^+$=339.0.

[5-(5-Chloro-1H-pyrrolo[2,3-b]pyridin-3-ylmethyl)-6-fluoro-pyridin-2-yl]-(4,4-difluoro-cyclohexyl)-amine P-3013

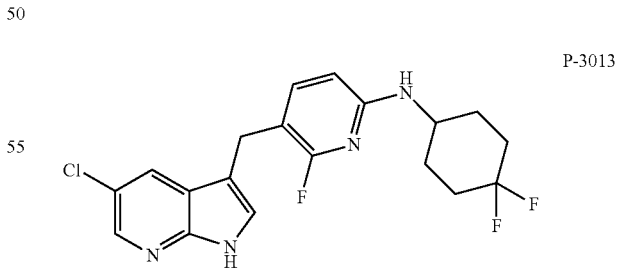

is prepared following the protocol of Scheme 10, replacing 6-fluoro-5-(5-methyl-1H-pyrrolo[2,3-b]pyridin-3-ylmethyl)-pyridin-2-ylamine 49 with 5-(5-chloro-1H-pyrrolo[2,3-b]pyridin-3-ylmethyl)-6-fluoro-pyridin-2-ylamine 50 and replacing cyclohexanone 67 with 4,4-difluoro-cyclohexanone. MS (ESI) [M+H$^+$]$^+$=394.9 and 396.9.

Example 11

Synthesis of [6-fluoro-5-(5-methyl-1H-pyrrolo[2,3-b]pyridin-3-ylmethyl)-pyridin-2-yl]-(6-methoxy-pyridin-3-yl)-amine P-3019

[6-Fluoro-5-(5-methyl-1H-pyrrolo[2,3-b]pyridin-3-ylmethyl)-pyridin-2-yl]-(6-methoxy-pyridin-3-yl)-amine P-3019 is prepared in two steps from 3-iodo-5-methyl-1-triisopropylsilanyl-1H-pyrrolo[2,3-b]pyridine 8 and 2-fluoro-6-(6-methoxy-pyridin-3-ylamino)-pyridine-3-carbaldehyde 56 as shown in Scheme 11.

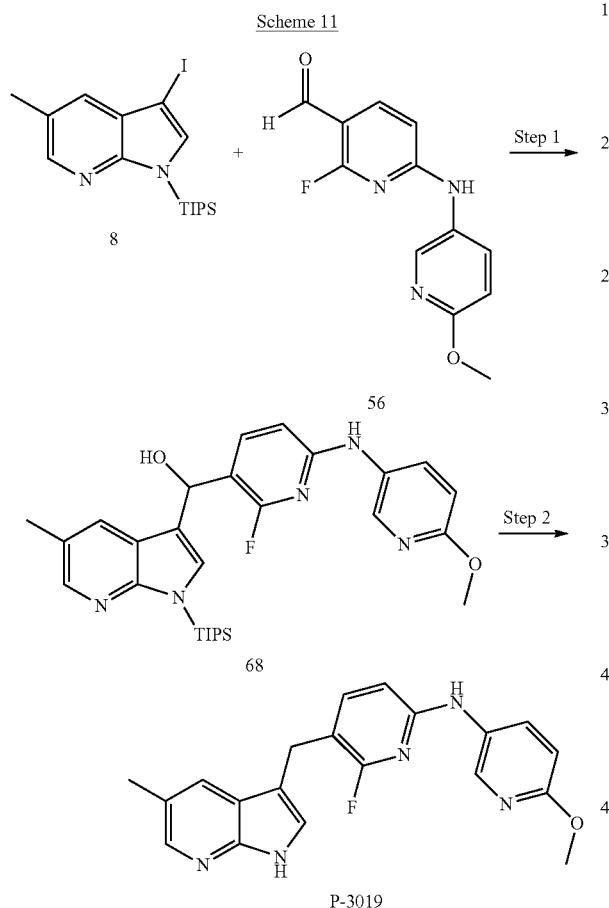

Step 6—Preparation of [2-fluoro-6-(6-methoxy-pyridin-3-ylamino)-pyridin-3-yl]-(5-methyl-1-triisopropylsilanyl-1H-pyrrolo[2,3-b]pyridin-3-yl)-methanol (68)

To a solution of 3-iodo-5-methyl-1-triisopropylsilanyl-1H-pyrrolo[2,3-b]pyridine (8, 1.02 g, 2.461 mmol) in 6.0 mL of tetrahydrofuran at −50° C. under nitrogen, isopropylmagnesium chloride (1.23 mL, 2.00 M in tetrahydrofuran, 2.46 mmol) is added slowly. The reaction is allowed to warm to 5° C. over 70 minutes, then cooled to −45° C., followed by addition of 2-fluoro-6-(6-methoxy-pyridin-3-ylamino)-pyridine-3-carbaldehyde (56, 0.165 g, 0.667 mmol) in 2.0 mL of tetrahydrofuran. The reaction is allowed to warm to room temperature over an hour, then poured into water and extracted with ethyl acetate. The organic layer is dried over sodium sulfate, filtered and the filtrate concentrated under vacuum. The resulting material is purified by silica gel column chromatography eluting with 20-100% ethyl acetate in hexane. Appropriate fractions are combined and concentrated under vacuum to provide the desired compound (68, 330 mg). MS (ESI) [M+H$^+$]$^+$=536.2.

Step 7—Preparation of [6-fluoro-5-(5-methyl-1H-pyrrolo[2,3-b]pyridin-3-ylmethyl)-pyridin-2-yl]-(6-methoxy-pyridin-3-yl)-amine (P-3019)

To [2-fluoro-6-(6-methoxy-pyridin-3-ylamino)-pyridin-3-yl]-(5-methyl-1-triisopropylsilanyl-1H-pyrrolo[2,3-b]pyridin-3-yl)-methanol (68, 0.220 g, 0.411 mmol) in 20.0 mL of 1,2-dichloroethane, triethylsilane (2.0 mL, 12 mmol) and trifluoroacetic acid (1.0 mL, 13 mmol) are added and the reaction stirred at 80° C. for 3 hours. The reaction is poured into water and extracted with ethyl acetate. The organic layer is dried over sodium sulfate, filtered and the filtrate concentrated under vacuum. The resulting material is purified by silica gel column chromatography eluting with 20-100% ethyl acetate in hexane. Appropriate fractions are combined and concentrated under vacuum to provide the desired compound (P-3019, 105.1 mg). MS (ESI) [M+H$^+$]$^+$=364.2.

[6-Fluoro-5-(4-methoxy-7H-pyrrolo[2,3-d]pyrimidin-5-ylmethyl)-pyridin-2-yl]-(6-methoxy-pyridin-3-yl)-amine P-4001 and [6-Fluoro-5-(4-methyl-7H-pyrrolo[2,3-d]pyrimidin-5-ylmethyl)-pyridin-2-yl]-(6-methoxy-pyridin-3-yl)-amine P-4002 are prepared similarly to the protocol of Scheme 11, replacing 3-iodo-5-methyl-1-triisopropylsilanyl-1H-pyrrolo[2,3-b]pyridine 8 with 5-iodo-4-methoxy-7-triisopropylsilanyl-7H-pyrrolo[2,3-d]pyrimidine 14 and 5-iodo-4-methyl-7-triisopropylsilanyl-7H-pyrrolo[2,3-d]pyrimidine 16, respectively in step 1.

Example 12

Synthesis of (6-ethoxy-pyridin-3-yl)-[6-fluoro-5-(5-methyl-1H-pyrrolo[2,3-b]pyridin-3-ylmethyl)-pyridin-2-yl]-amine P-3039 or [6-(6-ethoxy-pyridin-3-ylamino)-2-fluoro-pyridin-3-yl]-(5-methyl-1H-pyrrolo[2,3-b]pyridin-3-yl)-methanone P-3045

(6-Ethoxy-pyridin-3-yl)-[6-fluoro-5-(5-methyl-1H-pyrrolo[2,3-b]pyridin-3-ylmethyl)-pyridin-2-yl]-amine P-3039 or [6-(6-ethoxy-pyridin-3-ylamino)-2-fluoro-pyridin-3-yl]-(5-methyl-1H-pyrrolo[2,3-b]pyridin-3-yl)-methanone P-3045 are prepared in two steps or three steps from 3-iodo-5-methyl-1-triisopropylsilanyl-1H-pyrrolo[2,3-b]pyridine 8, and (6-ethoxy-pyridin-3-yl)-(6-fluoro-5-formyl-pyridin-2-yl)-carbamic acid tert-butyl ester 69 as shown in Scheme 12.

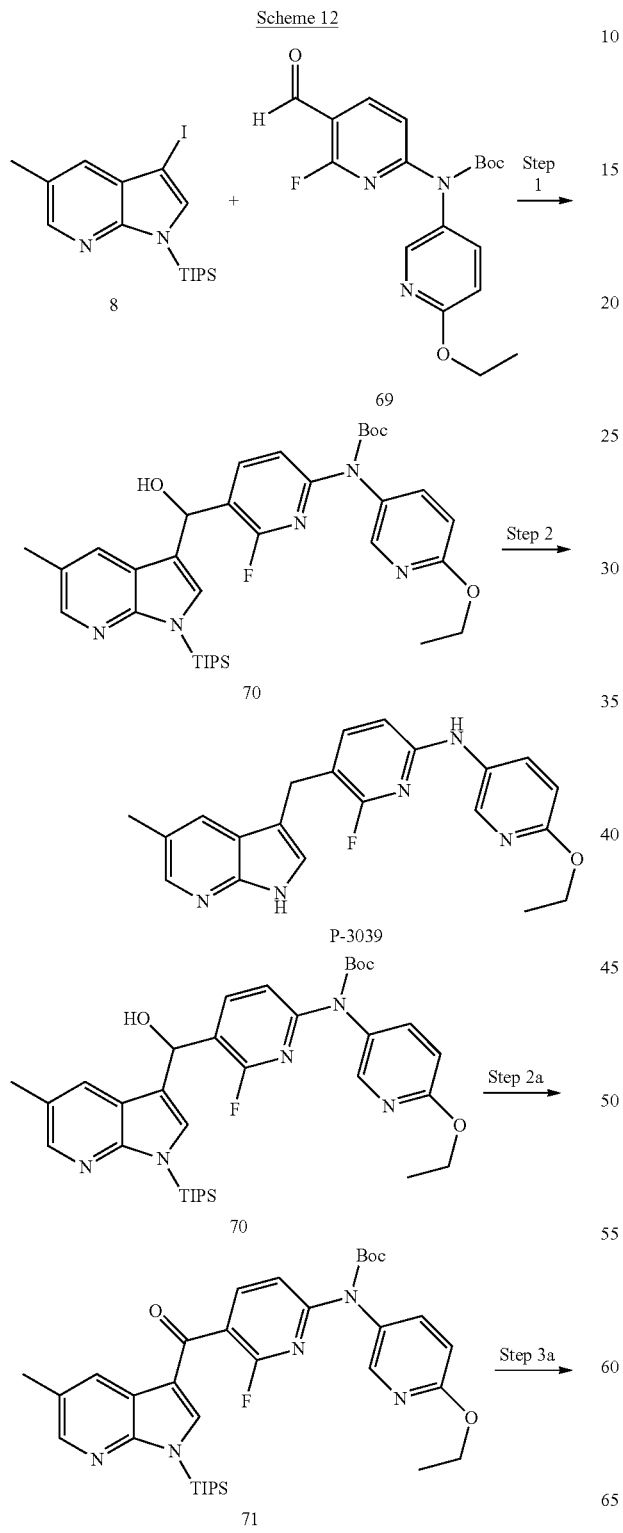

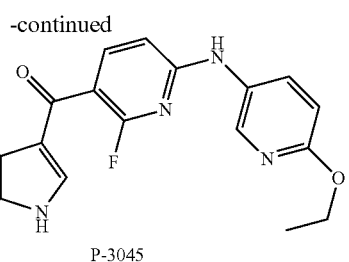

P-3045

Step 1—Preparation of (6-Ethoxy-pyridin-3-yl)-{6-fluoro-5-[hydroxy-(5-methyl-1-triisopropylsilanyl-1H-pyrrolo[2,3-b]pyridin-3-yl)-methyl]-pyridin-2-yl}-carbamic acid tert-butyl ester (70)

To a solution of 3-iodo-5-methyl-1-triisopropylsilanyl-1H-pyrrolo[2,3-b]pyridine (8, 0.43 g, 1.0 mmol) in 5 mL of tetrahydrofuran at −40° C. under nitrogen, isopropylmagnesium chloride (0.51 mL, 2.00 M in tetrahydrofuran, 1.0 mmol) is added slowly. The reaction is allowed to warm to −5° C. over 60 minutes, then cooled to −45° C., followed by addition of (6-ethoxy-pyridin-3-yl)-(6-fluoro-5-formyl-pyridin-2-yl)-carbamic acid tert-butyl ester (69, 0.06 g, 0.2 mmol) in 2.0 mL of tetrahydrofuran. The reaction is allowed to warm to room temperature over 2 hours, then poured into water and extracted with ethyl acetate. The organic layer is dried over sodium sulfate, filtered and the filtrate concentrated under vacuum. The resulting material is purified by silica gel column chromatography eluting with 20-100% ethyl acetate in hexane. Appropriate fractions are combined and concentrated under vacuum to provide the desired compound (70, 108.1 mg).

Step 2—Preparation of (6-ethoxy-pyridin-3-yl)-[6-fluoro-5-(5-methyl-1H-pyrrolo[2,3-b]pyridin-3-ylmethyl)-pyridin-2-yl]-amine (P-3039)

To (6-ethoxy-pyridin-3-yl)-{6-fluoro-5-[hydroxy-(5-methyl-1-triisopropylsilanyl-1H-pyrrolo[2,3-b]pyridin-3-yl)-methyl]-pyridin-2-yl}-carbamic acid tert-butyl ester (70, 108.1 mg, 0.166 mmol) in 4.54 mL of 1,2-dichloroethane, triethylsilane (0.454 mL, 2.84 mmol) and trifluoroacetic acid (0.27 mL, 3.5 mmol) are added and the reaction stirred at 80° C. for 4 hours. The reaction is poured into aqueous potassium carbonate and extracted with ethyl acetate. The organic layer is dried over sodium sulfate, filtered and the filtrate concentrated under vacuum. The resulting material is purified by silica gel column chromatography eluting with 25-100% ethyl acetate in hexane. Appropriate fractions are combined and concentrated under vacuum to provide the desired compound (P-3039), which is further purified by additional chromatography.

Step 2a—Preparation of (6-ethoxy-pyridin-3-yl)-[6-fluoro-5-(5-methyl-1-triisopropylsilanyl-1H-pyrrolo[2,3-b]pyridine-3-carbonyl)-pyridin-2-yl]-carbamic acid tert-butyl ester (71)

(6-Ethoxy-pyridin-3-yl)-{6-fluoro-5-[hydroxy-(5-methyl-1-triisopropylsilanyl-1H-pyrrolo[2,3-b]pyridin-3-yl)-methyl]-pyridin-2-yl}-carbamic acid tert-butyl ester (70, 0.400 g, 0.616 mmol) is alternatively dissolved in 11.8 mL of dichloromethane, and Dess-Martin periodinane (0.100 g, 0.236 mmol) is added. The reaction is stirred at room temperature for 30 minutes, then concentrated under vacuum. The resulting material is purified by silica gel column chromatography, eluting with 20-100% ethyl acetate in hexane. Appropriate fraction are combined and concentrated under vacuum to provide the desired compound (71, 0.200 g).

Step 3a—Preparation of [6-(6-ethoxy-pyridin-3-ylamino)-2-fluoro-pyridin-3-yl]-(5-methyl-1H-pyrrolo[2,3-b]pyridin-3-yl)-methanone (P-3045)

To (6-ethoxy-pyridin-3-yl)-[6-fluoro-5-(5-methyl-1-triisopropylsilanyl-1H-pyrrolo[2,3-b]pyridine-3-carbonyl)-pyridin-2-yl]-carbamic acid tert-butyl ester (71, 0.200 g, 0.309 mmol) in 10 mL of 1,2-dichloroethane, trifluoroacetic acid (0.80 mL, 10.0 mmol) is added. The reaction is stirred at 80° C. for 2 hours, then poured into aqueous potassium carbonate and extracted with ethyl acetate. The organic layer is dried over sodium sulfate, filtered and the filtrate concentrated under vacuum. The resulting material is purified by silica gel column chromatography, eluting with 2-15% methanol in dichloromethane. Appropriate fractions are combined and concentrated under vacuum to provide the desired compound (P-3045, 60.7 mg). MS (ESI) [M+H$^+$]$^+$=391.9.

Additional compounds are prepared following the protocol of Scheme 12. Compounds are made substituting either of 3-iodo-5-methyl-1-triisopropylsilanyl-1H-pyrrolo[2,3-b]pyridine 8 with a suitable TIPS-protected 1H-pyrrolo[2,3-b]pyridine or 7H-pyrrolo[2,3-d]pyrimidine and (6-ethoxy-pyridin-3-yl)-(6-fluoro-5-formyl-pyridin-2-yl)-carbamic acid tert-butyl ester 69 with a suitable Boc-protected aldehyde in step 1. The following compounds are made using this procedure:
[6-Fluoro-5-(5-methyl-1H-pyrrolo[2,3-b]pyridin-3-ylmethyl)-pyridin-2-yl]-(6-methoxy-pyridin-3-yl)-amine (P-3019),
[2-Fluoro-6-(6-methoxy-pyridin-3-ylamino)-pyridin-3-yl]-(5-methyl-1H-pyrrolo[2,3-b]pyridin-3-yl)-methanone (P-3040),
[6-Fluoro-5-(5-methyl-1H-pyrrolo[2,3-b]pyridin-3-ylmethyl)-pyridin-2-yl]-(6-methyl-pyridin-3-yl)-amine (P-3041),
[5-(5-Chloro-1H-pyrrolo[2,3-b]pyridin-3-ylmethyl)-6-fluoro-pyridin-2-yl]-(6-methyl-pyridin-3-yl)-amine (P-3042),
[2-Fluoro-6-(6-methyl-pyridin-3-ylamino)-pyridin-3-yl]-(5-methyl-1H-pyrrolo[2,3-b]pyridin-3-yl)-methanone (P-3043),
(5-Chloro-1H-pyrrolo[2,3-b]pyridin-3-yl)-[2-fluoro-6-(6-methyl-pyridin-3-ylamino)-pyridin-3-yl]-methanone (P-3044),
(6-Ethyl-pyridin-3-yl)-[6-fluoro-5-(5-methyl-1H-pyrrolo[2,3-b]pyridin-3-ylmethyl)-pyridin-2-yl]-amine (P-3048),
[6-(6-Ethyl-pyridin-3-ylamino)-2-fluoro-pyridin-3-yl]-(5-methyl-1H-pyrrolo[2,3-b]pyridin-3-yl)-methanone (P-3049),
(6-Chloro-pyridin-3-yl)-[6-fluoro-5-(4-methoxy-7H-pyrrolo[2,3-d]pyrimidin-5-ylmethyl)-pyridin-2-yl]-amine (P-4003),
(6-Ethoxy-pyridin-3-yl)-[6-fluoro-5-(4-methoxy-7H-pyrrolo[2,3-d]pyrimidin-5-ylmethyl)-pyridin-2-yl]-amine (P-4005),
(6-Ethoxy-pyridin-3-yl)-[6-fluoro-5-(4-methyl-7H-pyrrolo[2,3-d]pyrimidin-5-ylmethyl)-pyridin-2-yl]-amine (P-4006),
(6-Ethyl-pyridin-3-yl)-[6-fluoro-5-(4-methoxy-7H-pyrrolo[2,3-d]pyrimidin-5-ylmethyl)-pyridin-2-yl]-amine (P-4007),
(6-Ethyl-pyridin-3-yl)-[6-fluoro-5-(4-methyl-7H-pyrrolo[2,3-d]pyrimidin-5-ylmethyl)-pyridin-2-yl]-amine (P-4009),
[6-Fluoro-5-(4-methoxy-7H-pyrrolo[2,3-d]pyrimidin-5-ylmethyl)-pyridin-2-yl]-(6-methyl-pyridin-3-yl)-amine (P-4010),
(1-Ethyl-1H-pyrazol-4-yl)-[6-fluoro-5-(4-methoxy-7H-pyrrolo[2,3-d]pyrimidin-5-ylmethyl)-pyridin-2-yl]-amine (P-4011),
[5-(4-Ethoxy-7H-pyrrolo[2,3-d]pyrimidin-5-ylmethyl)-6-fluoro-pyridin-2-yl]-(1-ethyl-1H-pyrazol-4-yl)-amine (P-4012),
(1-Ethyl-1H-pyrazol-4-yl)-[6-fluoro-5-(4-methyl-7H-pyrrolo[2,3-d]pyrimidin-5-ylmethyl)-pyridin-2-yl]-amine (P-4013),
[5-(4-Ethoxy-7H-pyrrolo[2,3-d]pyrimidin-5-ylmethyl)-6-fluoro-pyridin-2-yl]-(6-methyl-pyridin-3-yl)-amine (P-4017),
[5-(4-Ethoxy-7H-pyrrolo[2,3-d]pyrimidin-5-ylmethyl)-6-fluoro-pyridin-2-yl]-(6-methoxy-pyridin-3-yl)-amine (P-4018),
(6-Bromo-pyridin-3-yl)-[5-(4-ethoxy-7H-pyrrolo[2,3-d]pyrimidin-5-ylmethyl)-6-fluoro-pyridin-2-yl]-amine (P-4020), The following table indicates the TIPS-protected 1H-pyrrolo[2,3-b]pyridine (column 2) and Boc-protected aldehyde compound (column 3) used in step 1 to afford the desired compound (column 4). The compound number is provided in column 1, and the observed mass is in column 5

TABLE 5

| Comp. number | pyrrolo[2,3-b]pyridine or pyrrolo[2,3-d]pyrimidine | Aldehyde | Compound structure | MS (ESI) [M + H$^+$]$^+$ |
| --- | --- | --- | --- | --- |
| P-3019 | | | 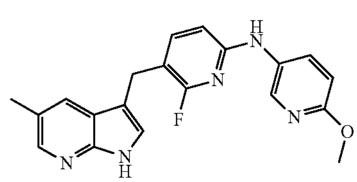 [SMILES: COc1ccc(Nc2ccc(Cc3c[nH]c4ncc(C)cc34)c(F)n2)cn1] | 363.9 |

TABLE 5-continued

| Comp. number | pyrrolo[2,3-b]pyridine or pyrrolo[2,3-d]pyrimidine | Aldehyde | Compound structure | MS (ESI) [M + H⁺]⁺ |
|---|---|---|---|---|
| P-3040 | | | 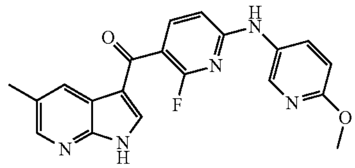 [SMILES: COc1ccc(Nc2ccc(C(=O)c3c[nH]c4ncc(C)cc34)c(F)n2)cn1] | 378.0 |
| P-3041 | | | 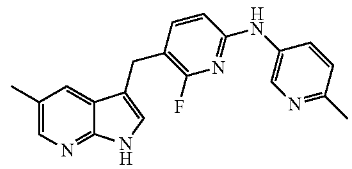 | 347.8 |
| P-3043 | | | 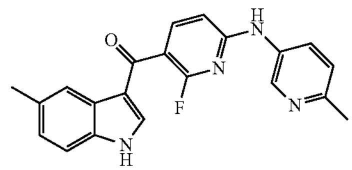 | 361.9 |
| P-3042 | | | 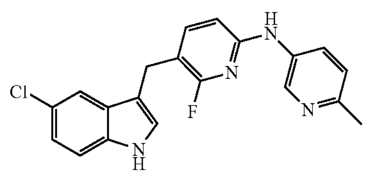 [SMILES: Cc1ccc(Nc2ccc(Cc3c[nH]c4ccc(Cl)cc34)c(F)n2)cn1] | 367.9 |
| P-3044 | | | 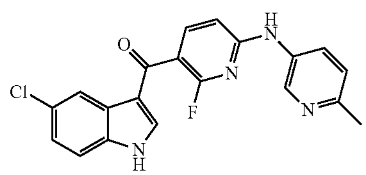 [SMILES: Cc1ccc(Nc2ccc(C(=O)c3c[nH]c4ccc(Cl)cc34)c(F)n2)cn1] | 382.0 |
| P-3048 | | | 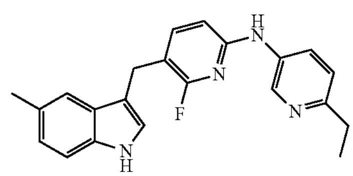 [SMILES: CCc1ccc(Nc2ccc(Cc3c[nH]c4ccc(C)cc34)c(F)n2)cn1] | 362.0 |
| P-3049 | | | 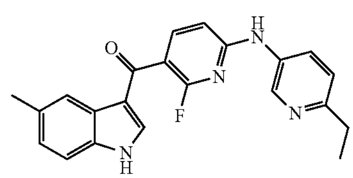 [SMILES: CCc1ccc(Nc2ccc(C(=O)c3c[nH]c4ccc(C)cc34)c(F)n2)cn1] | 376.1 |
| P-4003 | | | 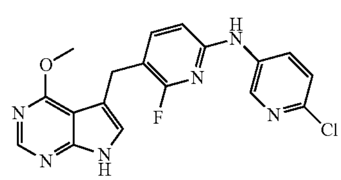 [SMILES: COc1ncnc2[nH]cc(Cc3ccc(Nc4ccc(Cl)nc4)nc3F)c12] | 385.0 |

TABLE 5-continued

| Comp. number | pyrrolo[2,3-b]pyridine or pyrrolo[2,3-d]pyrimidine | Aldehyde | Compound structure | MS (ESI) [M + H+]+ |
|---|---|---|---|---|
| P-4005 | | | 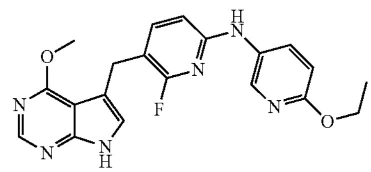 [SMILES: CCOc1ccc(Nc2ccc(Cc3c[nH]c4ncnc(OC)c34)c(F)n2)cn1] | 394.95 |
| P-4024 | | | 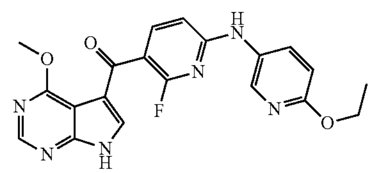 [SMILES: CCOc1ccc(Nc2ccc(C(=O)c3c[nH]c4ncnc(OC)c34)c(F)n2)cn1] | 409.2 |
| P-4006 | | | 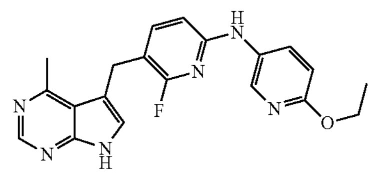 [SMILES: CCOc1ccc(Nc2ccc(Cc3c[nH]c4ncnc(C)c34)c(F)n2)cn1] | 378.95 |
| P-4007 | | | 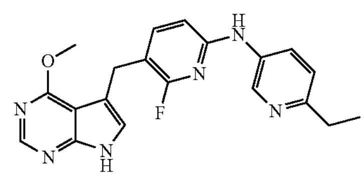 [SMILES: CCc1ccc(Nc2ccc(Cc3c[nH]c4ncnc(OC)c34)c(F)n2)cn1] | 379.0 |
| P-4009 | | | 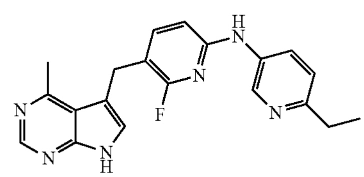 [SMILES: CCc1ccc(Nc2ccc(Cc3c[nH]c4ncnc(C)c34)c(F)n2)cn1] | 379.0 |
| P-4010 | | | 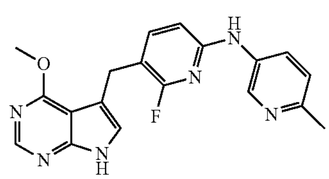 [SMILES: COc1ncnc2[nH]cc(Cc3ccc(Nc4ccc(C)nc4)nc3F)c12] | 365.0 |
| P-4011 | | | 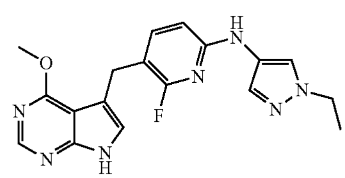 [SMILES: CCn1cc(Nc2ccc(Cc3c[nH]c4ncnc(OC)c34)c(F)n2)cn1] | 367.9 |
| P-4012 | | | 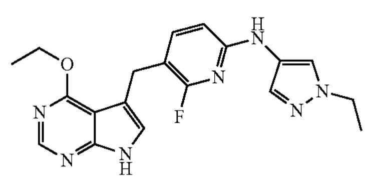 [SMILES: CCOc1ncnc2[nH]cc(Cc3ccc(Nc4cnn(CC)c4)nc3F)c12] | 382.1 |

TABLE 5-continued
| Comp. number | pyrrolo[2,3-b]pyridine or pyrrolo[2,3-d]pyrimidine | Aldehyde | Compound structure | MS (ESI) [M + H+]+ |
|---|---|---|---|---|
| P-4013 | | | 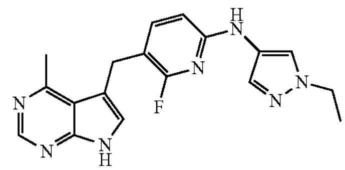 [SMILES: CCn1cc(Nc2ccc(Cc3c[nH]c4ncnc(C)c34)c(F)n2)cn1] | 351.9 |
| P-4017 | | | 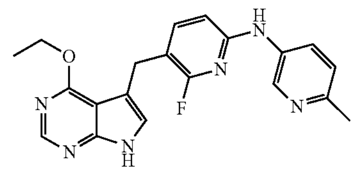 [SMILES: CCOc1ncnc2[nH]cc(Cc3ccc(Nc4ccc(C)nc4)nc3F)c12] | 379.0 |
| P-4018 | | | 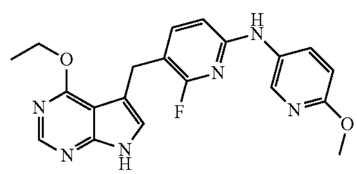 [SMILES: CCOc1ncnc2[nH]cc(Cc3ccc(Nc4ccc(OC)nc4)nc3F)c12] | 394.8 |
| P-4025 | | | 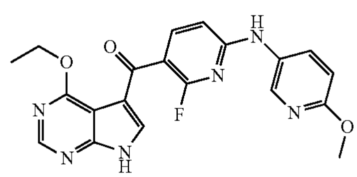 [SMILES: CCOc1ncnc2[nH]cc(C(=O)c3ccc(Nc4ccc(OC)nc4)nc3F)c12] | 409.2 |
| P-4020 | | | 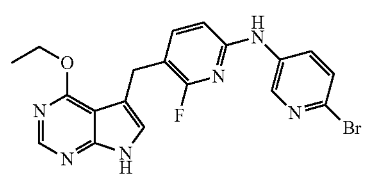 [SMILES: CCOc1ncnc2[nH]cc(Cc3ccc(Nc4ccc(Br)nc4)nc3F)c12] | 442.9 444.9 |
(6-Cyclopropyl-pyridin-3-yl)-[6-fluoro-5-(4-methoxy-7H-pyrrolo[2,3-d]pyrimidin-5-ylmethyl)-pyridin-2-yl]-amine P-4004
is prepared from the intermediate isolated after step 1 in the preparation of P-4003 according to the following steps 1b and 2b.
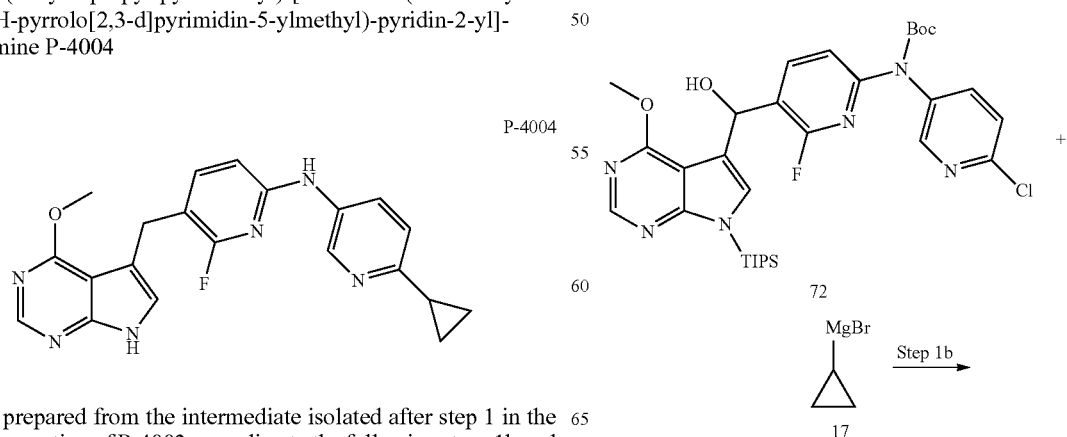

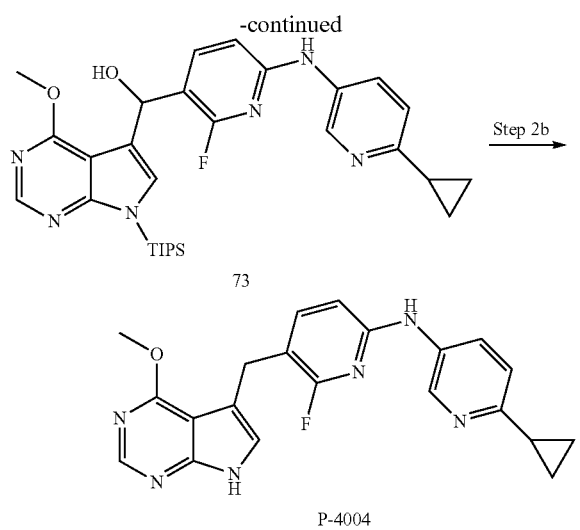

73

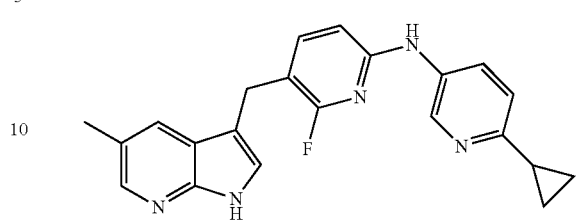

P-4004

Step 1b—Preparation of [6-(6-cyclopropyl-pyridin-3-ylamino)-2-fluoro-pyridin-3-yl]-(4-methoxy-7-triisopropylsilanyl-7H-pyrrolo[2,3-d]pyrimidin-5-yl)-methanol (73)

To (6-chloro-pyridin-3-yl)-{6-fluoro-5-[hydroxy-(4-methoxy-7-triisopropylsilanyl-7H-pyrrolo[2,3-d]pyrimidin-5-yl)-methyl]-pyridin-2-yl}-carbamic acid tert-butyl ester (72, 105 mg, 0.160 mmol) in 3.8 mL of toluene, [1,1'-bis(diphenylphosphino)ferrocene]dichloropalladium(II) 1:1 complex with dichloromethane (13.0 mg, 0.016 mmol) is added under an atmosphere of nitrogen. The reaction is stirred for 5 minutes, then cyclopropylmagnesium bromide (17, 1.60 mL, 1.0 M in tetrahydrofuran, 1.60 mmol) is added slowly. The reaction is heated at 65° C. for 5 hours, then poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (73, 70 mg). MS (ESI) [M+H$^+$]$^+$=563.6.

Step 2b—Preparation of (6-cyclopropyl-pyridin-3-yl)-[6-fluoro-5-(4-methoxy-7H-pyrrolo[2,3-d]pyrimidin-5-ylmethyl)-pyridin-2-yl]-amine (P-4004)

To [6-(6-cyclopropyl-pyridin-3-ylamino)-2-fluoro-pyridin-3-yl]-(4-methoxy-7-triisopropylsilanyl-7H-pyrrolo[2,3-d]pyrimidin-5-yl)-methanol (73, 70 mg, 0.12 mmol) in 10.0 mL of 1,2-dichloroethane, triethylsilane (1.00 mL, 6.26 mmol) and trifluoroacetic acid (0.60 mL, 7.8 mmol) are added and the reaction stirred at 80° C. for 4 hours. The reaction is poured into aqueous potassium carbonate and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (P-4004, 11.8 mg). MS (ESI) [M+H$^+$]$^+$=390.9.

(6-Cyclopropyl-pyridin-3-yl)-[6-fluoro-5-(5-methyl-1H-pyrrolo[2,3-b]pyridin-3-ylmethyl)-pyridin-2-yl]-amine P-3050

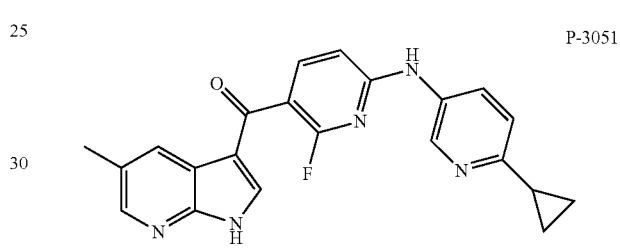

P-3050 is prepared similarly to the protocol of Scheme 12, step 1, followed by steps 1b and 2b, where (6-ethoxy-pyridin-3-yl)-(6-fluoro-5-formyl-pyridin-2-yl)-carbamic acid tert-butyl ester 69 is replaced with (6-chloro-pyridin-3-yl)-(6-fluoro-5-formyl-pyridin-2-yl)-carbamic acid tert-butyl ester in step 1. MS (ESI) [M+H$^+$]$^+$=374.2.

[6-(6-Cyclopropyl-pyridin-3-ylamino)-2-fluoro-pyridin-3-yl]-(5-methyl-1H-pyrrolo[2,3-b]pyridin-3-yl)-methanone P-3051

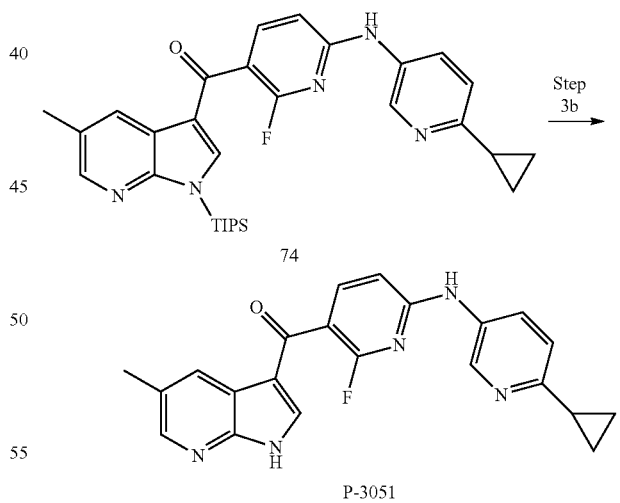

is similarly prepared from the intermediate formed from step 1b in the preparation of P-3050, reacting similarly to step 2a of Scheme 12, and then according to the following step 3b.

Step 3b—Preparation of [6-(6-cyclopropyl-pyridin-3-ylamino)-2-fluoro-pyridin-3-yl]-(5-methyl-1H-pyrrolo[2,3-b]pyridin-3-yl)-methanone (P-3051)

To [6-(6-cyclopropyl-pyridin-3-ylamino)-2-fluoro-pyridin-3-yl]-(5-methyl-1-triisopropylsilanyl-1H-pyrrolo[2,3-b]pyridin-3-yl)-methanone (74, 134 mg, 0.25 mmol) in 10 mL of tetrahydrofuran, tetrabutylammonium fluoride, trihydrate (85.53 mg, 0.27 mmol) is added and the reaction stirred at room temperature for 30 minutes. Water is added and the mixture is extracted with ethyl acetate. The organic layer is washed with water and brine, dried with magnesium sulfate, filtered and the filtrate concentrated under vacuum. The resulting material is purified by silica gel column chromatography, eluting with ethyl acetate in hexane. Appropriate fractions are combined and concentrated under vacuum to provide the desired compound (P-3051, 82 mg). MS (ESI) [M+H$^+$]$^+$=388.0.

[6-(6-Cyclopropyl-pyridin-3-ylamino)-2-fluoro-pyridin-3-yl]-(1H-pyrrolo[2,3-b]pyridin-3-yl)-methanone P-3052 and (6-Cyclopropyl-pyridin-3-yl)-[6-fluoro-5-(1H-pyrrolo[2,3-b]pyridin-3-ylmethyl)-pyridin-2-yl]-amine P-3053

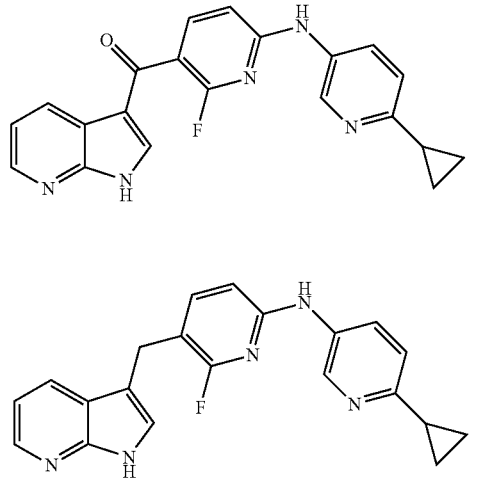

P-3052 and

P-3053 were prepared similarly to the protocols used for P-3051 and P-3052, respectively, where 3-iodo-1-triisopropylsilanyl-1H-pyrrolo[2,3-b]pyridine (prepared similarly to the protocol of Scheme 1, replacing 5-chloro-1H-pyrrolo[2,3-b]pyridine 1 with 1H-pyrrolo[2,3-b]pyridine in step 1) was used in place of 3-iodo-5-methyl-1-triisopropylsilanyl-1H-pyrrolo[2,3-b]pyridine 8 in step 1. P-3052 MS (ESI) [M+H$^+$]$^+$=374.0. P-3053 MS (ESI) [M+H$^+$]$^+$=359.9.

[5-(4-Ethoxy-7H-pyrrolo[2,3-d]pyrimidin-5-ylmethyl)-6-fluoro-pyridin-2-yl]-pyridin-3-yl-amine P-4021

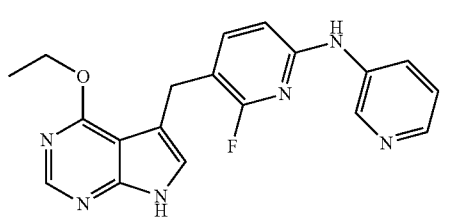

P-4021 is prepared from (6-bromo-pyridin-3-yl)-[5-(4-ethoxy-7H-pyrrolo[2,3-d]pyrimidin-5-ylmethyl)-6-fluoro-pyridin-2-yl]-amine P-4020 according to the following step 3c.

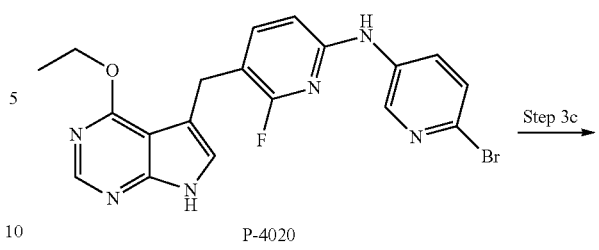

P-4020

Step 3b—Preparation of [5-(4-ethoxy-7H-pyrrolo[2,3-d]pyrimidin-5-ylmethyl)-6-fluoro-pyridin-2-yl]-pyridin-3-yl-amine (P-4021)

To (6-bromo-pyridin-3-yl)-[5-(4-ethoxy-7H-pyrrolo[2,3-d]pyrimidin-5-ylmethyl)-6-fluoro-pyridin-2-yl]-amine (P-4020, 0.040 g, 0.090 mmol) in 5.0 mL of tetrahydrofuran under nitrogen at −78° C., tert-butyllithium (0.531 mL, 1.70 M in hexane, 0.903 mmol) is added. The reaction is stirred at −78° C. for 30 minutes, then poured into water and extracted with ethyl acetate. The organic layer is dried over sodium sulfate, filtered and the filtrate concentrated under vacuum. The resulting material is purified with silica gel column chromatography, eluting with 20-100% ethyl acetate in hexane. Appropriate fractions are combined and concentrated under vacuum to provide the desired compound (P-4021, 25.7 mg). MS (ESI) [M+H$^+$]$^+$=364.9.

Example 13

Synthesis of [5-(4-cyclopropyl-7H-pyrrolo[2,3-d]pyrimidin-5-ylmethyl)-6-fluoro-pyridin-2-yl]-(6-methoxy-pyridin-3-yl)-amine P-4023 or (4-cyclopropyl-7H-pyrrolo[2,3-d]pyrimidin-5-yl)-[2-fluoro-6-(6-methoxy-pyridin-3-ylamino)-pyridin-3-yl]-methanone P-4022

[5-(4-Cyclopropyl-7H-pyrrolo[2,3-d]pyrimidin-5-ylmethyl)-6-fluoro-pyridin-2-yl]-(6-methoxy-pyridin-3-yl)-amine P-4023 or 4-cyclopropyl-7H-pyrrolo[2,3-d]pyrimidin-5-yl)-[2-fluoro-6-(6-methoxy-pyridin-3-ylamino)-pyridin-3-yl]-methanone P-4022 are prepared in three steps or four steps from 7-benzenesulfonyl-4-cyclopropyl-5-iodo-7H-pyrrolo[2,3-d]pyrimidine 32 and (6-fluoro-5-formyl-pyridin-2-yl)-(6-methoxy-pyridin-3-yl)-carbamic acid tert-butyl ester 57 as shown in Scheme 13.

Scheme 13

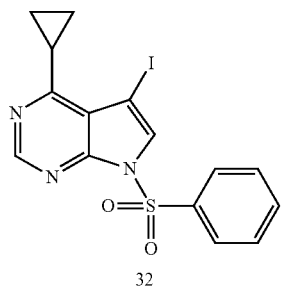

32

+

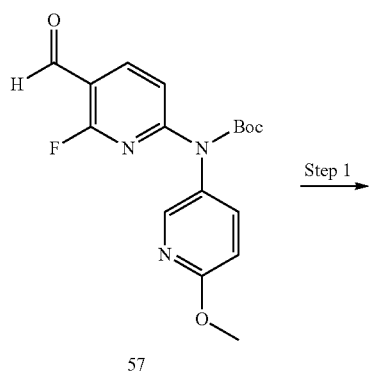

57

Step 1 →

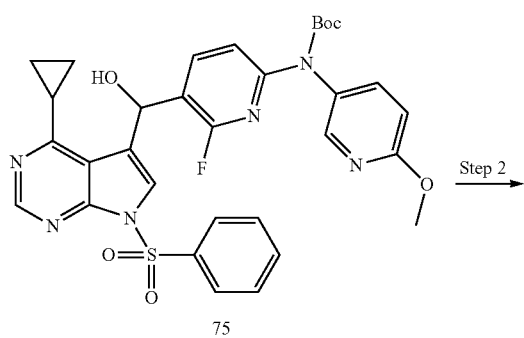

75

Step 2 →

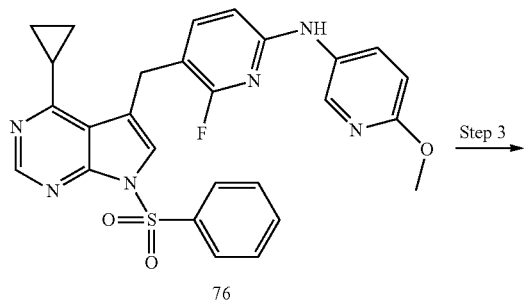

76

Step 3 →

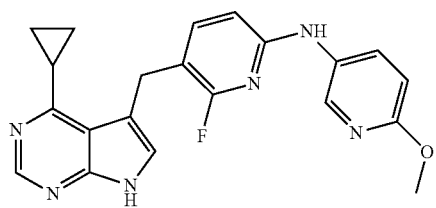

P-4023

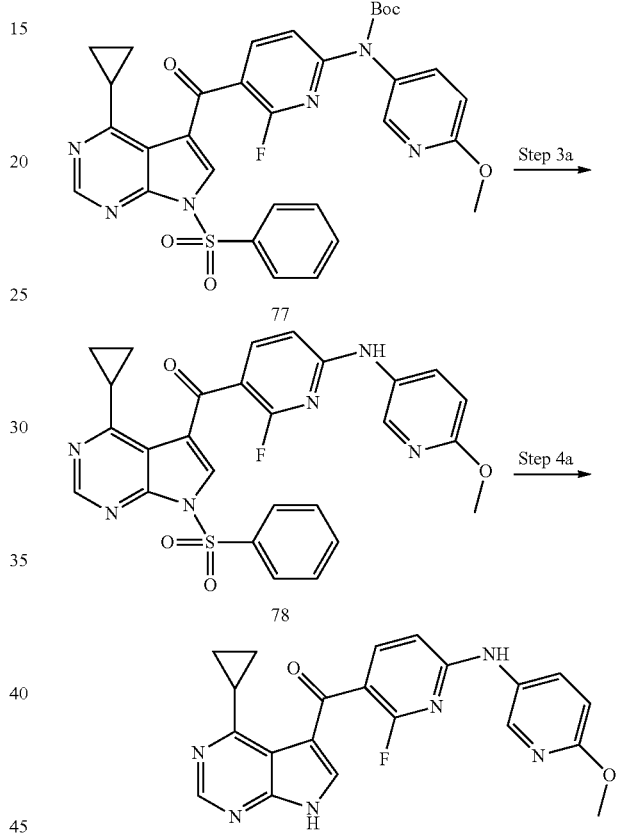

Step 1—Preparation of {5-[(7-benzenesulfonyl-4-cyclopropyl-7H-pyrrolo[2,3-d]pyrimidin-5-yl)-hydroxy-methyl]-6-fluoro-pyridin-2-yl}-(6-methoxy-pyridin-3-yl)-carbamic acid tert-butyl ester (75)

To a solution of 7-benzenesulfonyl-4-cyclopropyl-5-iodo-7H-pyrrolo[2,3-d]pyrimidine (32, 0.760 g, 1.79 mmol) in 5.43 mL of tetrahydrofuran at −40° C. under nitrogen, isopropylmagnesium chloride (0.892 mL, 2.0 M in tetrahydrofuran, 1.78 mmol) is added slowly. The reaction is allowed to warm to −5° C. over 75 minutes, then cooled to −45° C. and (6-fluoro-5-formyl-pyridin-2-yl)-(6-methoxy-pyridin-3-yl)-carbamic acid tert-butyl ester (57, 0.38 g, 1.1 mmol) in 2.0 mL of tetrahydrofuran is added. The reaction is allowed to warm to room temperature over 2 hours, then poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (75, 0.64 g). MS (ESI) [M+H$^+$]$^+$=647.2.

Step 2—Preparation of [5-(7-Benzenesulfonyl-4-cyclopropyl-7H-pyrrolo[2,3-d]pyrimidin-5-ylmethyl)-6-fluoro-pyridin-2-yl]-(6-methoxy-pyridin-3-yl)-amine (76)

To {5-[(7-benzenesulfonyl-4-cyclopropyl-7H-pyrrolo[2,3-d]pyrimidin-5-yl)-hydroxy-methyl]-6-fluoro-pyridin-2-yl}-(6-methoxy-pyridin-3-yl)-carbamic acid tert-butyl ester (75, 0.290 g, 0.448 mmol) in 9.93 mL of 1,2-dichloroethane, triethylsilane (0.31 mL, 2.0 mmol) and trifluoroacetic acid (0.16 mL, 2.0 mmol) are added and the reaction stirred at 80° C. for 4 hours. The reaction is poured into aqueous potassium carbonate and extracted with ethyl acetate. The organic layer is dried with sodium sulfate, filtered and the filtrate concentrated under vacuum to provide the desired compound (76, 170 mg). MS (ESI) [M+H$^+$]$^+$=530.9.

Step 3—Preparation of [5-(4-cyclopropyl-7H-pyrrolo[2,3-d]pyrimidin-5-ylmethyl)-6-fluoro-pyridin-2-yl]-(6-methoxy-pyridin-3-yl)-amine (P-4023)

To [5-(7-benzenesulfonyl-4-cyclopropyl-7H-pyrrolo[2,3-d]pyrimidin-5-ylmethyl)-6-fluoro-pyridin-2-yl]-(6-methoxy-pyridin-3-yl)-amine (76, 0.170 g, 0.320 mmol) in 10.0 mL of tetrahydrofuran, tetrabutylammonium fluoride, trihydrate (0.174 g, 0.551 mmol) is added and the reaction is stirred at room temperature overnight. The reaction is poured into water and extracted with ethyl acetate. The organic layer is dried with sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (P-4023, 100.4 mg). MS (ESI) [M+H$^+$]$^+$=390.8.

Step 2a—Preparation of [5-(7-benzenesulfonyl-4-cyclopropyl-7H-pyrrolo[2,3-d]pyrimidine-5-carbonyl)-6-fluoro-pyridin-2-yl]-(6-methoxy-pyridin-3-yl)-carbamic acid tert-butyl ester (77)

{5-[(7-Benzenesulfonyl-4-cyclopropyl-7H-pyrrolo[2,3-d]pyrimidin-5-yl)-hydroxy-methyl]-6-fluoro-pyridin-2-yl}-(6-methoxy-pyridin-3-yl)-carbamic acid tert-butyl ester (75, 0.350 g, 0.541 mmol) is alternatively dissolved in 10.0 mL of dichloromethane, and Dess-Martin periodinane (0.211 g, 0.498 mmol) is added. The reaction is stirred at room temperature for 30 minutes, then concentrated under vacuum. The resulting material is purified by silica gel column chromatography, eluting with 10-100% ethyl acetate in hexane. Appropriate fraction are combined and concentrated under vacuum to provide the desired compound (77, 340 mg). MS (ESI) [M+H$^+$]$^+$=645.4.

Step 3a—Preparation of (7-benzenesulfonyl-4-cyclopropyl-7H-pyrrolo[2,3-d]pyrimidin-5-yl)-[2-fluoro-6-(6-methoxy-pyridin-3-ylamino)-pyridin-3-yl]-methanone (78)

To [5-(7-benzenesulfonyl-4-cyclopropyl-7H-pyrrolo[2,3-d]pyrimidine-5-carbonyl)-6-fluoro-pyridin-2-yl]-(6-methoxy-pyridin-3-yl)-carbamic acid tert-butyl ester (77, 0.340 g, 0.527 mmol) in 10 mL of 1,2-dichloroethane, trifluoroacetic acid (0.80 mL, 10.4 mmol) is added. The reaction is stirred at 80° C. for 45 minutes, then poured into aqueous potassium carbonate and extracted with ethyl acetate. The organic layer is dried over sodium sulfate, filtered and the filtrate concentrated under vacuum to provide the desired compound (78, 235 mg). MS (ESI) [M+H$^+$]$^+$=545.4.

Step 4a—Preparation of (4-cyclopropyl-7H-pyrrolo[2,3-d]pyrimidin-5-yl)-[2-fluoro-6-(6-methoxy-pyridin-3-ylamino)-pyridin-3-yl]-methanone (P-4022)

To (7-benzenesulfonyl-4-cyclopropyl-7H-pyrrolo[2,3-d]pyrimidin-5-yl)-[2-fluoro-6-(6-methoxy-pyridin-3-ylamino)-pyridin-3-yl]-methanone (78, 0.235 g, 0.432 mmol) in 10.0 mL of tetrahydrofuran, tetrabutylammonium fluoride, trihydrate (0.174 g, 0.551 mmol) is added. The reaction is stirred at room temperature overnight, then poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fraction are combined and concentrated under vacuum to provide the desired compound (P-4022, 104.5 mg). MS (ESI) [M+H$^+$]$^+$=405.0.

Additional compounds are prepared following the protocol of Scheme 13. 4-Cyclopropyl-5-iodo-7-(toluene-4-sulfonyl)-7H-pyrrolo[2,3-d]pyrimidine 33 may be used in place of 7-benzenesulfonyl-4-cyclopropyl-5-iodo-7H-pyrrolo[2,3-d]pyrimidine 32. Compounds are made substituting either of 7-benzenesulfonyl-4-cyclopropyl-5-iodo-7H-pyrrolo[2,3-d]pyrimidine 32 with a suitable benzenesulfonyl or 4-methybenzenesulfonyl-protected 7H-pyrrolo[2,3-d]pyrimidine or 1H-pyrrolo[2,3-b]pyridine and (6-ethoxy-pyridin-3-yl)-(6-fluoro-5-formyl-pyridin-2-yl)-carbamic acid tert-butyl ester 57 with a suitable Boc-protected aldehyde in step 1. In some instances, a non-Boc protected aldehyde is used as indicated in the following table (with no step 3a in this case). The following compounds are made using this procedure:

(6-Ethoxy-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4008), (1-Ethyl-1H-pyrazol-4-yl)-{6-fluoro-5-[4-(2-methoxy-ethoxy)-7H-pyrrolo[2,3-d]pyrimidin-5-ylmethyl]-pyridin-2-yl}-amine (P-4014), {6-Fluoro-5-[4-(2-methoxy-ethoxy)-7H-pyrrolo[2,3-d]pyrimidin-5-ylmethyl]-pyridin-2-yl}-(6-methyl-pyridin-3-yl)-amine (P-4015), (6-Ethyl-pyridin-3-yl)-{6-fluoro-5-[4-(2-methoxy-ethoxy)-7H-pyrrolo[2,3-d]pyrimidin-5-ylmethyl]-pyridin-2-yl}-amine (P-4016), {6-Fluoro-5-[4-(2-methoxy-ethoxy)-7H-pyrrolo[2,3-d]pyrimidin-5-ylmethyl]-pyridin-2-yl}-(6-methoxy-pyridin-3-yl)-amine (P-4019),

[5-(4-Cyclopropyl-7H-pyrrolo[2,3-d]pyrimidin-5-ylmethyl)-6-fluoro-pyridin-2-yl]-(6-ethoxy-pyridin-3-yl)-amine (P-4026), (4-Cyclopropyl-7H-pyrrolo[2,3-d]pyrimidin-5-yl)-[6-(6-ethoxy-pyridin-3-ylamino)-2-fluoro-pyridin-3-yl]-methanone (P-4027),

[5-(4-Cyclopropyl-7H-pyrrolo[2,3-d]pyrimidin-5-ylmethyl)-6-fluoro-pyridin-2-yl]-(6-ethyl-pyridin-3-yl)-amine (P-4028), (4-Cyclopropyl-7H-pyrrolo[2,3-d]pyrimidin-5-yl)-[6-(6-ethyl-pyridin-3-ylamino)-2-fluoro-pyridin-3-yl]-methanone (P-4029),

[5-(4-Cyclopropyl-7H-pyrrolo[2,3-d]pyrimidin-5-ylm-ethyl)-6-fluoro-pyridin-2-yl]-(6-methyl-pyridin-3-yl)-amine (P-4030), (4-Cyclopropyl-7H-pyrrolo[2,3-d]pyrimidin-5-yl)-[2-fluoro-6-(6-methyl-pyridin-3-ylamino)-pyridin-3-yl]-methanone (P-4031),

[6-(6-Ethoxy-pyridin-3-ylamino)-2-fluoro-pyridin-3-yl]-(4-methyl-7H-pyrrolo[2,3-d]pyrimidin-5-yl)-methanone (P-4032),

[5-(4-Cyclopropyl-7H-pyrrolo[2,3-d]pyrimidin-5-ylm-ethyl)-6-fluoro-pyridin-2-yl]-(1-ethyl-1H-pyrazol-4-yl)-amine (P-4036), (4-Cyclopropyl-7H-pyrrolo[2,3-d]pyrimidin-5-yl)-[6-(1-ethyl-1H-pyrazol-4-ylamino)-2-fluoro-pyridin-3-yl]-methanone (P-4037),

[5-(4-Cyclopropyl-7H-pyrrolo[2,3-d]pyrimidin-5-ylm-ethyl)-6-fluoro-pyridin-2-yl]-(5-methyl-pyridin-3-yl)-amine (P-4038), (4-Cyclopropyl-7H-pyrrolo[2,3-d]pyrimidin-5-yl)-[2-fluoro-6-(5-methyl-pyridin-3-ylamino)-pyridin-3-yl]-methanone (P-4039), The following table indicates the Benzenesulfonyl-protected 1H-pyrrolo[2,3-b]pyridine (column 2) and Boc-protected aldehyde compound (column 3) used in step 1 to afford the desired compound (column 4). The compound number is provided in column 1, and the observed mass is in column 5

TABLE 6

| Comp. number | pyrrolo[2,3-b]pyridine | Aldehyde | Compound structure | MS (ESI) [M + H⁺]⁺ |
|---|---|---|---|---|
| P-4008 | | | 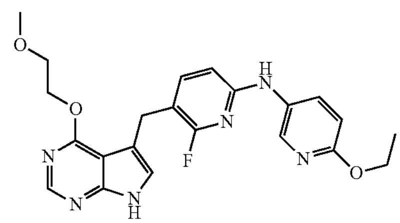 [SMILES: CCOc1ccc(Nc2ccc(Cc3c[nH]c4ncnc(OCCOC)c34)c(F)n2)cn1] | 439.0 |
| P-4014 | | | 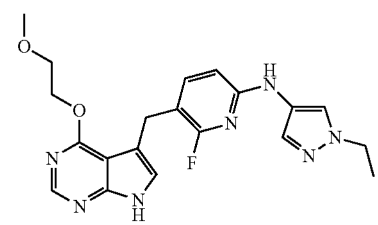 [SMILES: CCn1cc(Nc2ccc(Cc3c[nH]c4ncnc(OCCOC)c34)c(F)n2)cn1] | 412.0 |
| P-4015 | | | 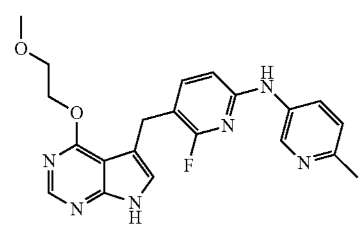 [SMILES: COCCOc1ncnc2[nH]cc(Cc3ccc(Nc4ccc(C)nc4)nc3F)c12] | 409.0 |
| P-4016 | | | 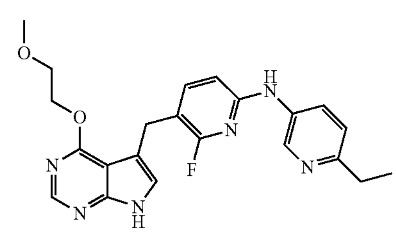 [SMILES: CCc1ccc(Nc2ccc(Cc3c[nH]c4ncnc(OCCOC)c34)c(F)n2)cn1] | 423.0 |

TABLE 6-continued

| Comp. number | pyrrolo[2,3-b]pyridine | Aldehyde | Compound structure | MS (ESI) [M + H+]+ |
|---|---|---|---|---|
| P-4019 | | | 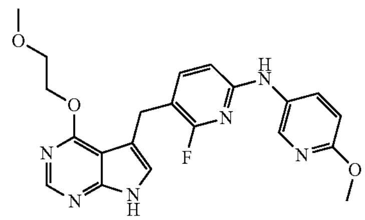 [SMILES: COCCOc1ncnc2[nH]cc(Cc3ccc(Nc4ccc(OC)nc4)nc3F)c12] | 424.9 |
| P-4026 | | | 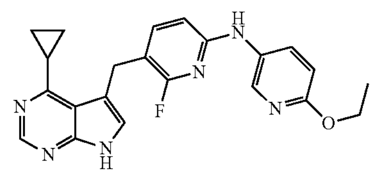 [SMILES: CCOc1ccc(Nc2ccc(Cc3c[nH]c4ncnc(C5CC5)c34)c(F)n2)cn1] | 404.9 |
| P-4027 | | | 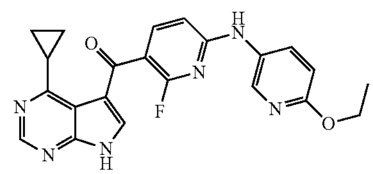 [SMILES: CCOc1ccc(Nc2ccc(C(=O)c3c[nH]c4ncnc(C5CC5)c34)c(F)n2)cn1] | 418.8 |
| P-4028 | | | 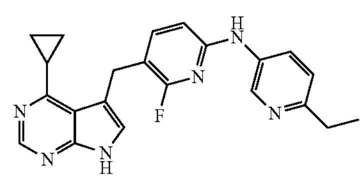 [SMILES: CCc1ccc(Nc2ccc(Cc3c[nH]c4ncnc(C5CC5)c34)c(F)n2)cn1] | 389.0 |
| P-4029 | | | 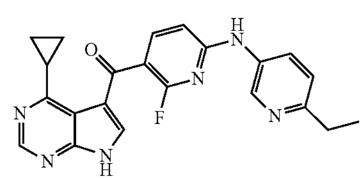 [SMILES: CCc1ccc(Nc2ccc(C(=O)c3c[nH]c4ncnc(C5CC5)c34)c(F)n2)cn1] | 402.9 |
| P-4030 | | | 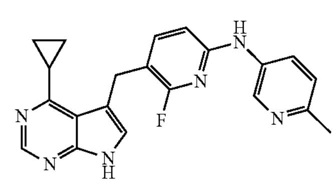 [SMILES: Cc1ccc(Nc2ccc(Cc3c[nH]c4ncnc(C5CC5)c34)c(F)n2)cn1] | 375.0 |
| P-4031 | | | 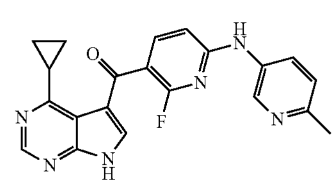 [SMILES: Cc1ccc(Nc2ccc(C(=O)c3c[nH]c4ncnc(C5CC5)c34)c(F)n2)cn1] | 388.9 |

TABLE 6-continued

| Comp. number | pyrrolo[2,3-b]pyridine | Aldehyde | Compound structure | MS (ESI) [M + H⁺]⁺ |
|---|---|---|---|---|
| P-4032 | | | 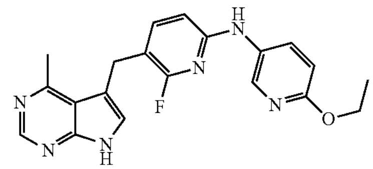 [SMILES: CCOc1ccc(Nc2ccc(Cc3c[nH]c4ncnc(C)c34)c(F)n2)cn1] | 393.1 |
| P-4036 | | | 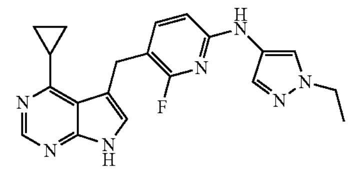 [SMILES: CCn1cc(Nc2ccc(Cc3c[nH]c4ncnc(C5CC5)c34)c(F)n2)cn1] | 378.0 |
| P-4037 | | | 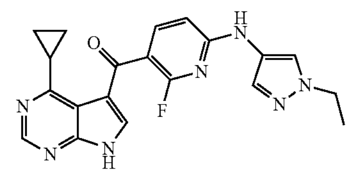 [SMILES: CCn1cc(Nc2ccc(C(=O)c3c[nH]c4ncnc(C5CC5)c34)c(F)n2)cn1] | 392.0 |
| P-4038 | | | 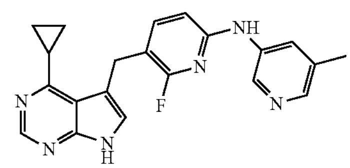 [SMILES: Cc1cncc(Nc2ccc(Cc3c[nH]c4ncnc(C5CC5)c34)c(F)n2)c1] | 375.1 |
| P-4039 | | | 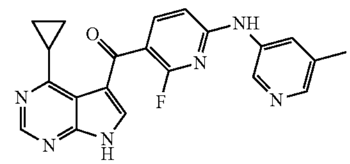 [SMILES: Cc1cncc(Nc2ccc(C(=O)c3c[nH]c4ncnc(C5CC5)c34)c(F)n2)c1] | 389.1 |
| P-4042 | | | 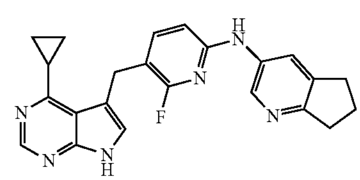 [SMILES: Fc1nc(Nc2cnc3c(c2)CCC3)ccc1Cc1c[nH]c2ncnc(C3CC3)c12] | |
| P-4043 | | | 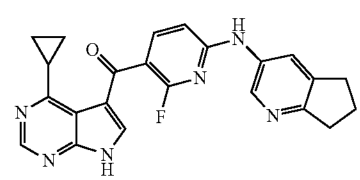 [SMILES: O=C(c1ccc(Nc2cnc3c(c2)CCC3)nc1F)c1c[nH]c2ncnc(C3CC3)c12] | |

Example 14

Synthesis of [6-(6-cyclopropyl-pyridin-3-ylamino)-2-fluoro-pyridin-3-yl]-(4-cyclopropyl-7H-pyrrolo[2,3-d]pyrimidin-5-yl)-methanone P-4040 and (6-cyclopropyl-pyridin-3-yl)-[5-(4-cyclopropyl-7H-pyrrolo[2,3-d]pyrimidin-5-ylmethyl)-6-fluoro-pyridin-2-yl]-amine P-4041

[6-(6-Cyclopropyl-pyridin-3-ylamino)-2-fluoro-pyridin-3-yl]-(4-cyclopropyl-7H-pyrrolo[2,3-d]pyrimidin-5-yl)-methanone P-4040 and (6-cyclopropyl-pyridin-3-yl)-[5-(4-cyclopropyl-7H-pyrrolo[2,3-d]pyrimidin-5-ylmethyl)-6-fluoro-pyridin-2-yl]-amine P-4041 are prepared in three steps from 4-cyclopropyl-5-iodo-7-triisopropylsilanyl-7H-pyrrolo[2,3-d]pyrimidine 19 and (6-chloro-pyridin-3-yl)-(6-fluoro-5-formyl-pyridin-2-yl)-carbamic acid tert-butyl ester 80 as shown in Scheme 14.

Scheme 14

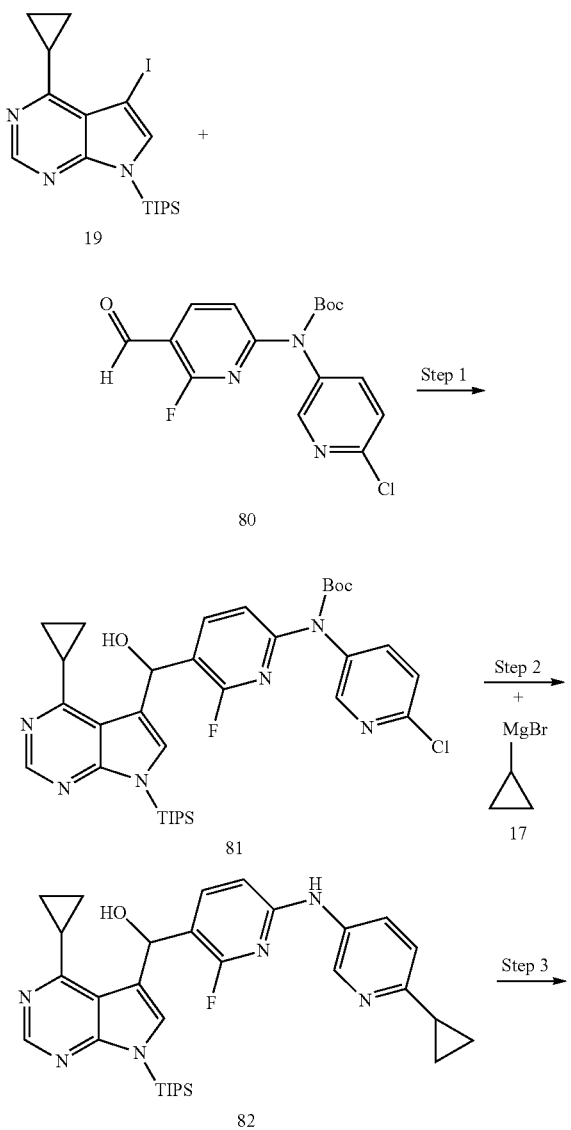

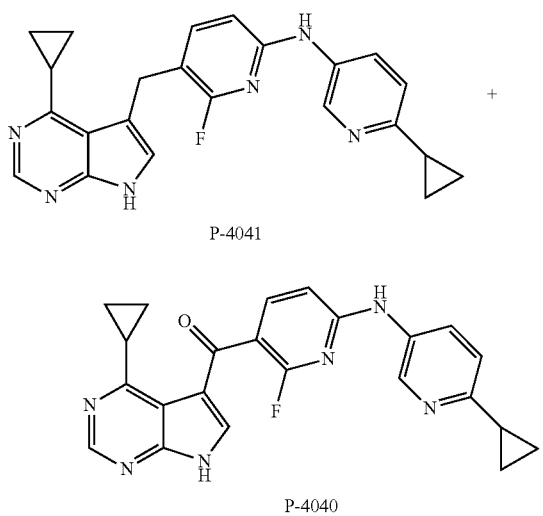

Step 1—Preparation of (6-chloro-pyridin-3-yl)-{5-[(4-cyclopropyl-7-triisopropylsilanyl-7H-pyrrolo[2,3-d]pyrimidin-5-yl)-hydroxy-methyl]-6-fluoro-pyridin-2-yl}-carbamic acid tert-butyl ester (81)

To 4-cyclopropyl-5-iodo-7-triisopropylsilanyl-7H-pyrrolo[2,3-d]pyrimidine (19, 0.72 g, 1.64 mmol) in 6.0 mL of tetrahydrofuran at −40° C. under nitrogen, isopropylmagnesium chloride (0.82 mL, 2.01 M in tetrahydrofuran, 1.65 mmol) is added slowly. The reaction is allowed to warm to −5° C. in 75 minutes, then cooled to −45° C. and (6-chloro-pyridin-3-yl)-(6-fluoro-5-formyl-pyridin-2-yl)-carbamic acid tert-butyl ester (80, 0.48 g, 1.38 mmol) in 5.0 mL is added. The reaction is allowed to warm to room temperature in 2 hours, then poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (81, 0.51 g). MS (ESI) $[M+H^+]^+$=667.2).

Step 2—Preparation of [6-(6-cyclopropyl-pyridin-3-ylamino)-2-fluoro-pyridin-3-yl]-(4-cyclopropyl-7-triisopropylsilanyl-7H-pyrrolo[2,3-d]pyrimidin-5-yl)-methanol (82)

To (6-chloro-pyridin-3-yl)-{5-[(4-cyclopropyl-7-triisopropylsilanyl-7H-pyrrolo[2,3-d]pyrimidin-5-yl)-hydroxymethyl]-6-fluoro-pyridin-2-yl}-carbamic acid tert-butyl ester (81, 0.51 g, 0.77 mmol) in 12 mL of toluene, [1,1'-bis(diphenylphosphino) ferrocene]dichloropalladium(II) (0.13 g, 0.17 mmol) is added under nitrogen and the reaction stirred for 5 minutes. Cyclopropylmagnesium bromide (17, 15.29 mL, 0.50 M in tetrahydrofuran, 7.65 mmol) is added slowly and the reaction is heated at 65° C. for 2 hours. The reaction is poured into water and extracted with ethyl acetate. The organic layer is dried over sodium sulfate, filtered and the filtrate concentrated under vacuum. The resulting material is purified by silica gel column chromatography, eluting with 20-100% ethyl acetate in hexane. Appropriate fractions are combined and concentrated under vacuum to provide the desired compound (82, 400 mg).

Step 3—Preparation of [6-(6-cyclopropyl-pyridin-3-ylamino)-2-fluoro-pyridin-3-yl]-(4-cyclopropyl-7H-pyrrolo[2,3-d]pyrimidin-5-yl)-methanone (P-4040) and (6-cyclopropyl-pyridin-3-yl)-[5-(4-cyclopropyl-7H-pyrrolo[2,3-d]pyrimidin-5-ylmethyl)-6-fluoro-pyridin-2-yl]-amine (P-4041)

To [6-(6-cyclopropyl-pyridin-3-ylamino)-2-fluoro-pyridin-3-yl]-(4-cyclopropyl-7-triisopropylsilanyl-7H-pyrrolo[2,3-d]pyrimidin-5-yl)-methanol (82, 400 mg, 0.7 mmol) in 30 mL of dichloromethane, triethylsilane (2.6 mL, 16.28 mmol) and trifluoroacetic acid (1.5 mL, 15.13 mmol) are added, and the reaction is stirred at 80° C. for 3 hours. The reaction is poured into aqueous potassium carbonate and extracted with ethyl acetate. The organic layer is washed with brine, dried over sodium sulfate, filtered and the filtrate concentrated under vacuum. The resulting material is purified by silica gel column chromatography, eluting with 20-100% ethyl acetate in hexane to give a mixture of compounds P-4040 and P-4041. These are separated by preparative HPLC to provide the isolated compounds (P-4040, 3.0 mg, MS (ESI) [M+H$^+$]$^+$=414.9), (P-4041, 37.9 mg, MS (ESI) [M+H$^+$]$^+$=401.0).

(6-Cyclopropyl-pyridin-3-yl)-[6-fluoro-5-(4-methyl-7H-pyrrolo[2,3-d]pyrimidin-5-ylmethyl)-pyridin-2-yl]-amine P-4044 and [6-(6-cyclopropyl-pyridin-3-ylamino)-2-fluoro-pyridin-3-yl]-(4-methyl-7H-pyrrolo[2,3-d]pyrimidin-5-yl)-methanone P-4045

P-4044

P-4045

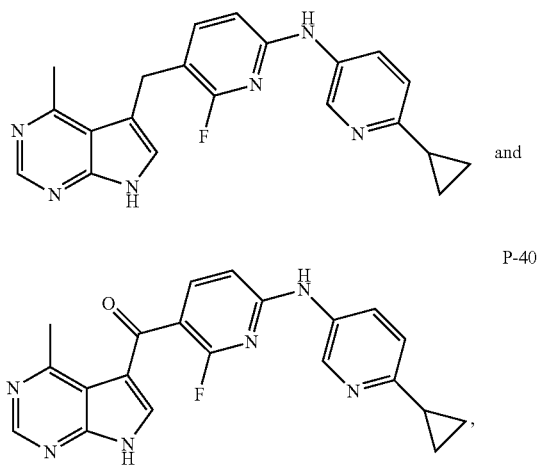

are prepared similarly to Scheme 14, where 4-cyclopropyl-5-iodo-7-triisopropylsilanyl-7H-pyrrolo[2,3-d]pyrimidine 19, is replaced in step 1 with 5-iodo-4-methyl-7H-pyrrolo[2,3-d]pyrimidine (prepared similarly to Scheme 4 steps 1 and 2). P-4044, 2.5 mg, MS (ESI) [M+H$^+$]$^+$375.0. P-4045, 5.3 mg, MS (ESI) [M+H$^+$]$^+$=388.9.

Example 15

Synthesis of [2-fluoro-6-[(6-methyl-3-pyridyl)amino]-3-pyridyl]-[4-(methylamino)-7H-pyrrolo[2,3-d]pyrimidin-5-yl]methanone (P-4115)

Scheme 15

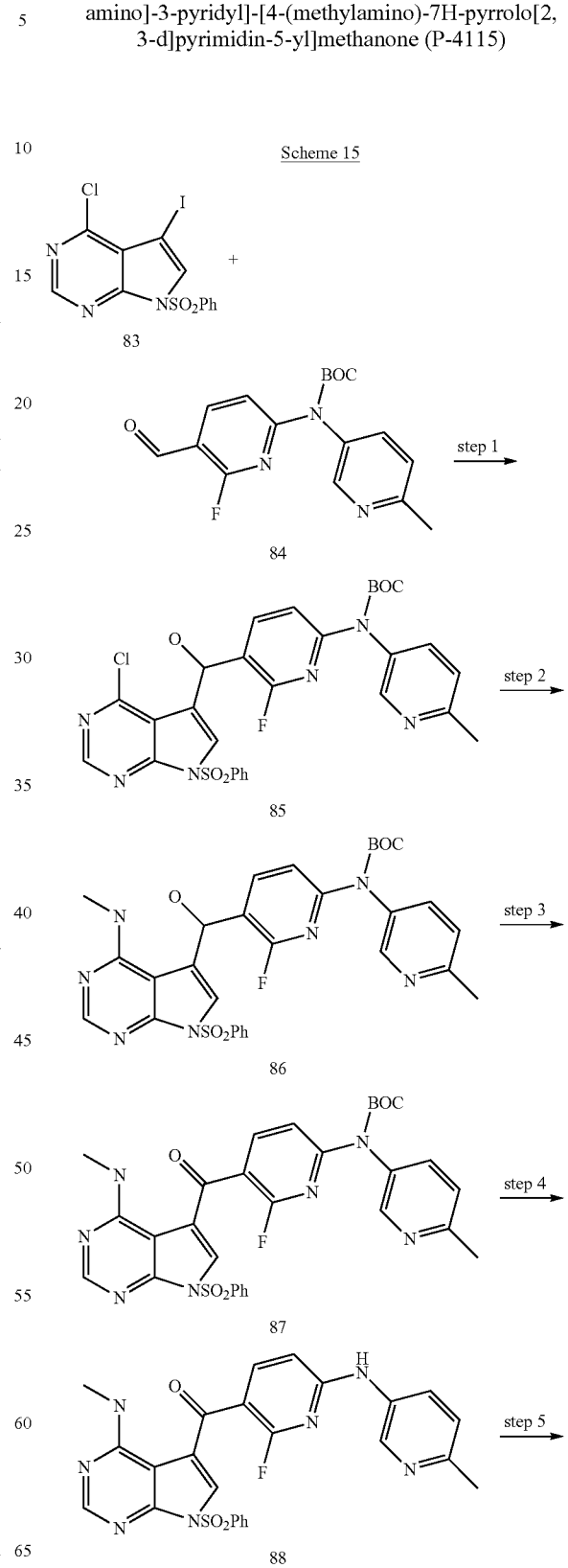

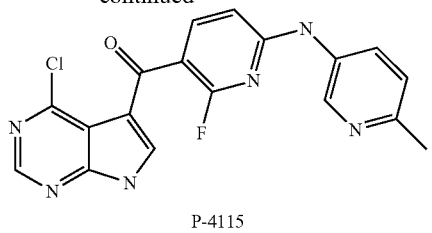

P-4115

Step 1—Preparation of tert-butyl N-[5-[[7-(benzenesulfonyl)-4-chloro-pyrrolo[2,3-d]pyrimidin-5-yl]-hydroxy-methyl]-6-fluoro-2-pyridyl]-N-(6-methyl-3-pyridyl)carbamate 85

To a solution of 7-(benzenesulfonyl)-4-chloro-5-iodo-pyrrolo[2,3-d]pyrimidine (1, 0.43 g, 1.01 mmol) in Tetrahydrofuran (5 mL) at −30° C. under nitrogen was added 2.0 M Isopropylmagnesium Chloride in Tetrahydrofuran (0.5 ml) slowly. The reaction was allowed to warm to −5° C. in 75 minutes. Then, the reaction was cooled to −45° C., followed by adding tert-butyl N-(6-fluoro-5-formyl-2-pyridyl)-N-(6-methyl-3-pyridyl)carbamate (84, 0.24 g, 0.72 mmol) in THF (3.0 mL). The reaction was allowed to warm to room temperature in around 2 hours. The reaction was poured in to water, extracted with ethyl acetate. The organic layer was dried over anhydrous sodium sulfate, and filtered. The filtrate was concentrated, purified with silica gel column chromatography eluting with 20%-100% ethyl acetate in hexane to give product (85, 0.41 g, 90.6%). MS (ESI) [M+H+]+=625.0.

Step 2—Preparation of tert-butyl N-[5-[[7-(benzenesulfonyl)-4-methylamino-pyrrolo[2,3-d]pyrimidin-5-yl]-hydroxy-methyl]-6-fluoro-2-pyridyl]-N-(6-methyl-3-pyridyl)carbamate 86

To tert-butyl N-[5-[[7-(benzenesulfonyl)-4-chloro-pyrrolo[2,3-d]pyrimidin-5-yl]-hydroxy-methyl]-6-fluoro-2-pyridyl]-N-(6-methyl-3-pyridyl)carbamate (85, 75 mg, 0.12 mmol) in Isopropyl alcohol (0.80 mL) was added 2M methylamine in THF (0.6 ml). The resulting solution was stirred at 40° C. for 6 hours. The reaction was concentrated to give product (86, 70 mg, 94.2%). MS (ESI) [M+H+]+=620.

Step 3—Preparation of tert-butyl N-[5-[7-(benzenesulfonyl)-4-methylamino-pyrrolo[2,3-d]pyrimidine-5-carbonyl]-6-fluoro-2-pyridyl]-N-(6-methyl-3-pyridyl)carbamate 87

To tert-butyl N-[5-[[7-(benzenesulfonyl)-4-methylamino-pyrrolo[2,3-d]pyrimidin-5-yl]-hydroxy-methyl]-6-fluoro-2-pyridyl]-N-(6-methyl-3-pyridyl)carbamate (86, 0.07 g, 0.11 mmol) in DCM (10 mL) was added DMP (0.06 g, 0.14 mmol). The reaction was stirred at room temperature for 20 minutes. The reaction was concentrated, and purified with silica gel column chromatography eluting with 20% to 100% ethyl acetate in hexane to give product (87, 0.065 g, 93.6%).

Step 4—Preparation of [7-(benzenesulfonyl)-4-methylamino-pyrrolo[2,3-d]pyrimidin-5-yl]-[2-fluoro-6-[(6-methyl-3-pyridyl)amino]-3-pyridyl]methanone; 2,2,2-trifluoroacetic acid 88

To tert-butyl N-[5-[7-(benzenesulfonyl)-4-methylamino-pyrrolo[2,3-d]pyrimidine-5-carbonyl]-6-fluoro-2-pyridyl]-N-(6-methyl-3-pyridyl)carbamate (87, 65 mg, 0.11 mmol) in dichloroethane (10 mL) was added TFA (0.65 ml, 8.75 mmol). The reaction was heated 80° C. for 1 hour. The reaction was concentrated to give crude product (CF3COOH salt) around (88, 0.080 g, 86.4%). MS (ESI) [M+H+]+=518. MS is the free base product.

Step 5—Preparation of [2-fluoro-6-[(6-methyl-3-pyridyl)amino]-3-pyridyl]-(4-methylamino-7H-pyrrolo[2,3-d]pyrimidin-5-yl)methanone P-4115

To [7-(benzenesulfonyl)-4-methylamino-pyrrolo[2,3-d]pyrimidin-5-yl]-[2-fluoro-6-[(6-methyl-3-pyridyl)amino]-3-pyridyl]methanone; 2,2,2-trifluoroacetic acid (88, 80 mg, 0.09 mmol) in Methanol (6 ml) was added KOH (0.1 g, 1.78 mmol). The reaction was stirred at room temperature for 1 hour. The reaction mixture was concentrated and purified with silica gel column chromatography eluting with 2% to 25% methanol in methylene chloride to give product (P-4115, 9.6 mg, 27.3%). MS (ESI) [M+H+]+=377.9.

Table 2 below provides compounds prepared according to the synthetic protocols set forth in Schemes 14 and 15. The structures were characterized by mass spectroscopy and $^1$H and $^{13}$C NMR spectroscopies.

TABLE 2

| No. | Compound Structure | MS (ESI) [M + H+]+ |
|---|---|---|
| P-4046 | 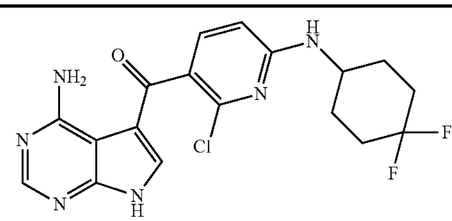 | 407.2 |
| P-4047 | 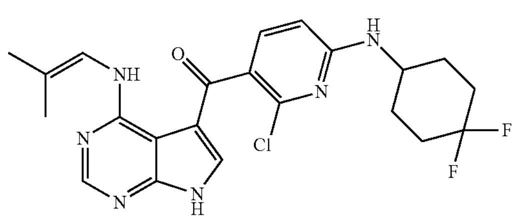 [SMILES: CC(C)=CNc1ncnc2[nH]cc(C(=O)c3ccc(NC4CCC(F)(F)CC4)nc3Cl)c12] | 461.3 |

TABLE 2-continued
| No. | Compound Structure | MS (ESI) [M + H⁺]⁺ |
|---|---|---|
| P-4048 | 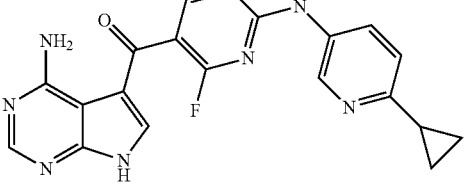 | 390.1 |
| P-4049 | 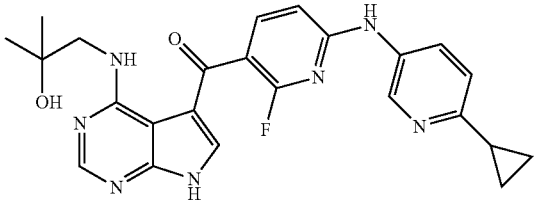 [SMILES: CC(C)(O)CNc1ncnc2[nH]cc(C(=O)c3ccc(Nc4ccc(C5CC5)nc4)nc3F)c12] | 462.1 |
| P-4050 | 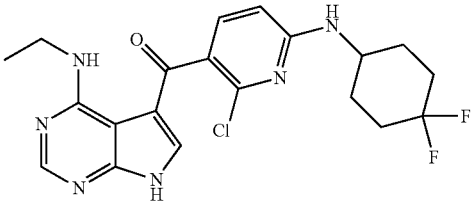 [SMILES: CCNc1ncnc2[nH]cc(C(=O)c3ccc(NC4CCC(F)(F)CC4)nc3Cl)c12] | 435.0 |
| P-4051 | 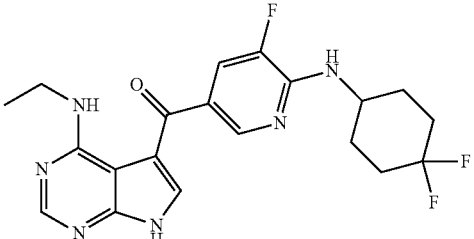 | 419.0 |
| P-4052 | 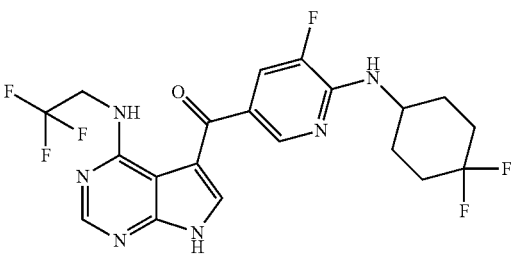 [SMILES: O=C(c1cnc(NC2CCC(F)(F)CC2)c(F)c1)c1c[nH]c2ncnc(NCC(F)(F)F)c12] | 472.95 |
| P-4053 | 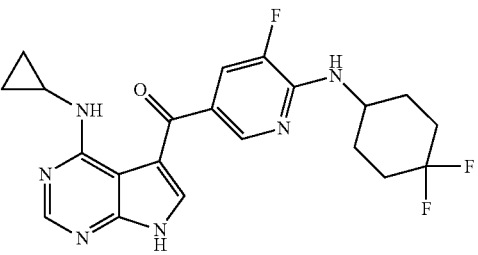 [SMILES: O=C(c1cnc(NC2CCC(F)(F)CC2)c(F)c1)c1c[nH]c2ncnc(NC3CC3)c12] | 431.0 |

TABLE 2-continued

| No. | Compound Structure | MS (ESI) [M + H$^+$]$^+$ |
|---|---|---|
| P-4054 | 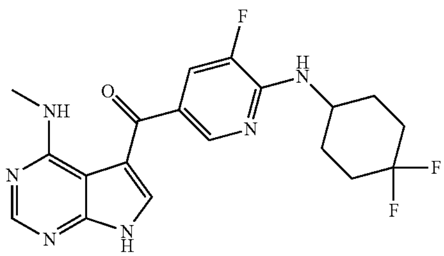 [SMILES: CNc1ncnc2[nH]cc(C(=O)c3cnc(NC4CCC(F)(F)CC4)c(F)c3)c12] | 405.0 |
| P-4055 | 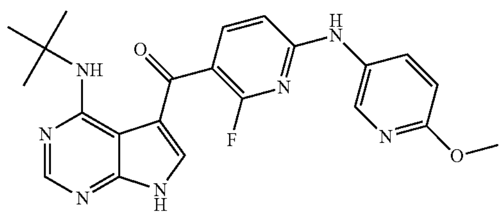 [SMILES: COc1ccc(Nc2ccc(C(=O)c3c[nH]c4ncnc(NC(C)(C)C)c34)c(F)n2)cn1] | 436.5 |
| P-4056 | 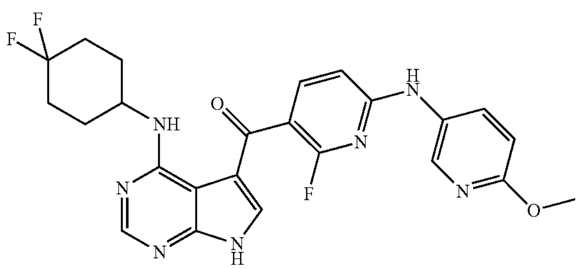 [SMILES: COc1ccc(Nc2ccc(C(=O)c3c[nH]c4ncnc(NC5CCC(F)(F)CC5)c34)c(F)n2)cn1] | 498.5 |
| P-4057 | 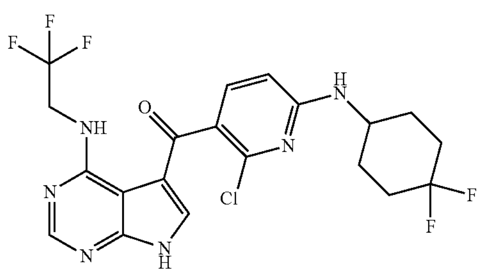 [SMILES: O=C(c1ccc(NC2CCC(F)(F)CC2)nc1Cl)c1c[nH]c2ncnc(NCC(F)(F)F)c12] | 489.0 |
| P-4058 | 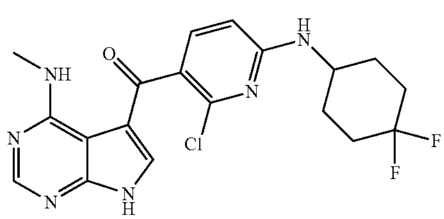 [SMILES: CNc1ncnc2[nH]cc(C(=O)c3ccc(NC4CCC(F)(F)CC4)nc3Cl)c12] | 420.9 |
| P-4059 | 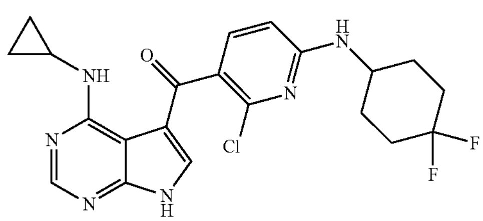 [SMILES: O=C(c1ccc(NC2CCC(F)(F)CC2)nc1Cl)c1c[nH]c2ncnc(NC3CC3)c12] | 447.1 |

TABLE 2-continued

| No. | Compound Structure | MS (ESI) [M + H⁺]⁺ |
|---|---|---|
| P-4060 | 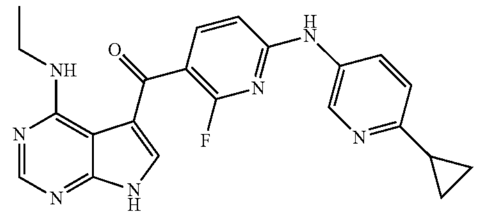 [SMILES: CCNc1ncnc2[nH]cc(C(=O)c3ccc(Nc4ccc(C5CC5)nc4)nc3F)c12] | 418.0 |
| P-4061 | 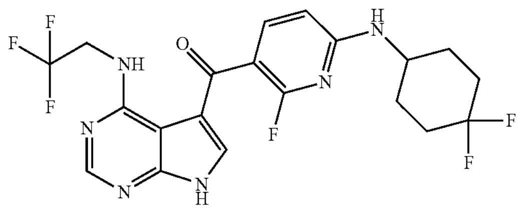 [SMILES: O=C(c1ccc(NC2CCC(F)(F)CC2)nc1F)c1c[nH]c2ncnc(NCC(F)(F)F)c12] | 473.0 |
| P-4062 | 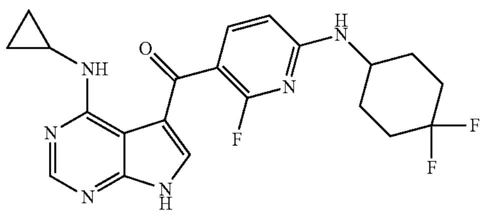 [SMILES: O=C(c1ccc(NC2CCC(F)(F)CC2)nc1F)c1c[nH]c2ncnc(NC3CC3)c12] | 431.1 |
| P-4063 | 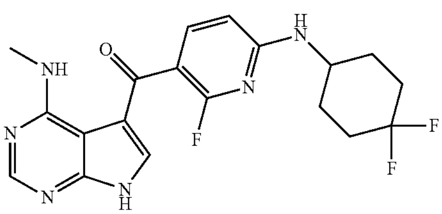 [SMILES: CNc1ncnc2[nH]cc(C(=O)c3ccc(NC4CCC(F)(F)CC4)nc3F)c12] | 405.0 |
| P-4064 | 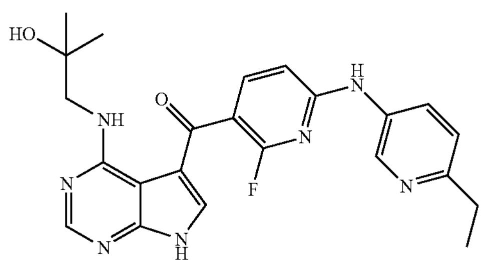 [SMILES: CCc1ccc(Nc2ccc(C(=O)c3c[nH]c4ncnc(NCC(C)(C)O)c34)c(F)n2)cn1] | 445.0 |
| P-4065 | 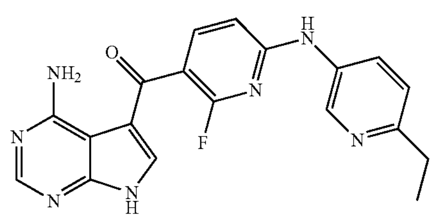 [SMILES: CCc1ccc(Nc2ccc(C(=O)c3c[nH]c4ncnc(N)c34)c(F)n2)cn1] | 377.9 |
| P-4066 | 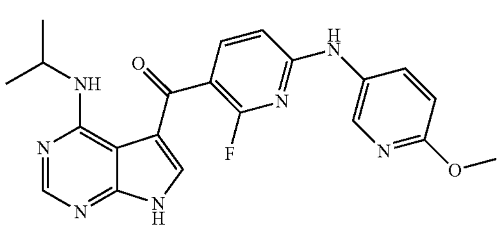 [SMILES: COc1ccc(Nc2ccc(C(=O)c3c[nH]c4ncnc(NC(C)C)c34)c(F)n2)cn1] | 422.0 |

TABLE 2-continued
| No. | Compound Structure | MS (ESI) [M + H⁺]⁺ |
|---|---|---|
| P-4067 | 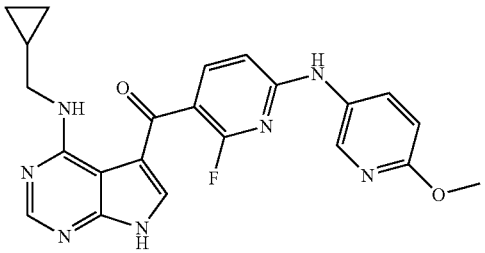 [SMILES: COc1ccc(Nc2ccc(C(=O)c3c[nH]c4ncnc(NCC5CC5)c34)c(F)n2)cn1] | 434.5 |
| P-4068 | 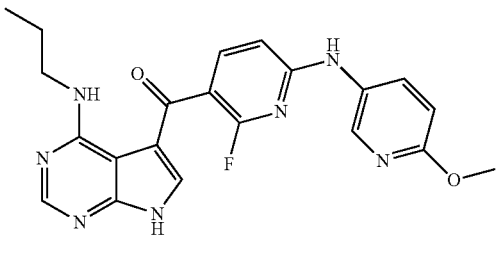 [SMILES: CCCNc1ncnc2[nH]cc(C(=O)c3ccc(Nc4ccc(OC)nc4)nc3F)c12] | 422.0 |
| P-4069 | 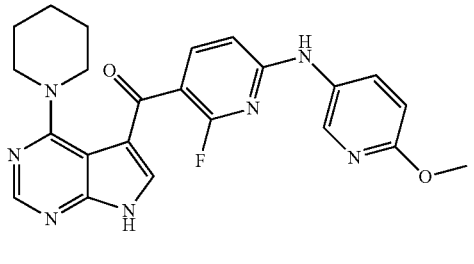 [SMILES: COc1ccc(Nc2ccc(C(=O)c3c[nH]c4ncnc(N5CCCCC5)c34)c(F)n2)cn1] | 449.5 |
| P-4070 | 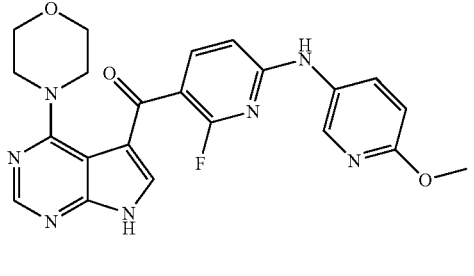 [SMILES: COc1ccc(Nc2ccc(C(=O)c3c[nH]c4ncnc(N5CCOCC5)c34)c(F)n2)cn1] | 450.0 |
| P-4071 | 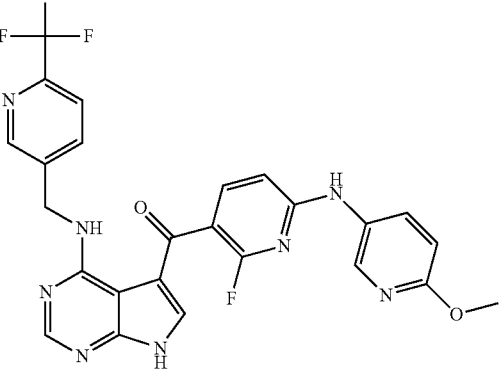 | 539.5 |

TABLE 2-continued
| No. | Compound Structure | MS (ESI) [M + H+]+ |
|---|---|---|
| P-4072 | 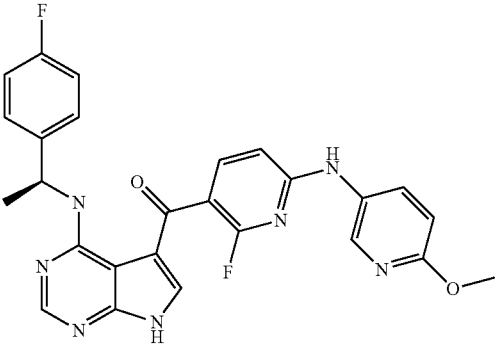 [SMILES: COc1ccc(Nc2ccc(C(=O)c3c[nH]c4ncnc(N[C@@H](C)c5ccc(F)cc5)c34)c(F)n2)cn1] | 502.5 |
| P-4073 | 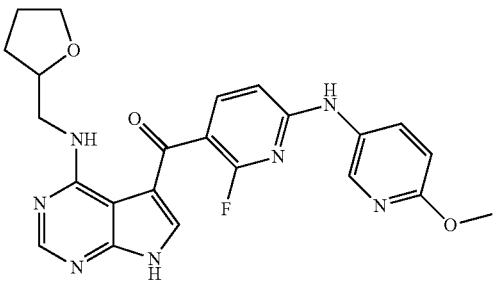 [SMILES: COc1ccc(Nc2ccc(C(=O)c3c[nH]c4ncnc(NCC5CCCO5)c34)c(F)n2)cn1] | 464.0 |
| P-4074 | 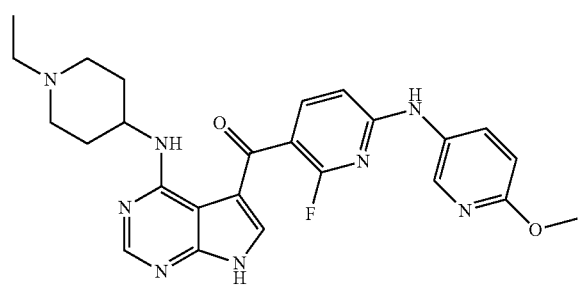 [SMILES: CCN1CCC(Nc2ncnc3[nH]cc(C(=O)c4ccc(Nc5ccc(OC)nc5)nc4F)c23)CC1] | 491.5 |
| P-4075 | 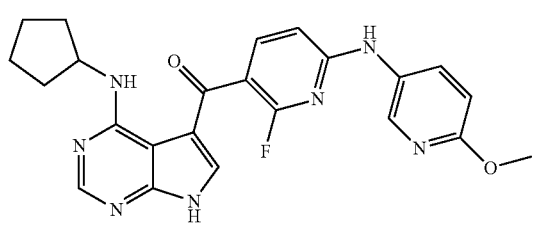 [SMILES: COc1ccc(Nc2ccc(C(=O)c3c[nH]c4ncnc(NC5CCCC5)c34)c(F)n2)cn1] | 448.0 |
| P-4076 | 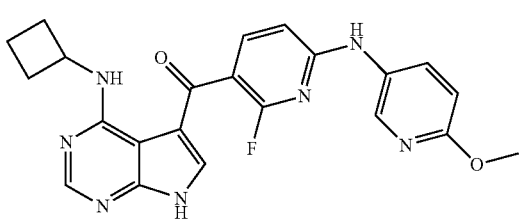 [SMILES: COc1ccc(Nc2ccc(C(=O)c3c[nH]c4ncnc(NC5CCC5)c34)c(F)n2)cn1] | 434.5 |
| P-4077 | 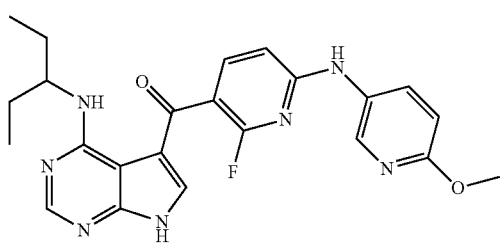 [SMILES: CCC(CC)Nc1ncnc2[nH]cc(C(=O)c3ccc(Nc4ccc(OC)nc4)nc3F)c12] | 450.0 |

TABLE 2-continued

| No. | Compound Structure | MS (ESI) [M + H⁺]⁺ |
|---|---|---|
| P-4078 | 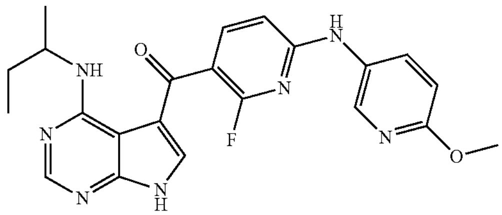 [SMILES: CCC(C)Nc1ncnc2[nH]cc(C(=O)c3ccc(Nc4ccc(OC)nc4)nc3F)c12] | 436.5 |
| P-4079 | 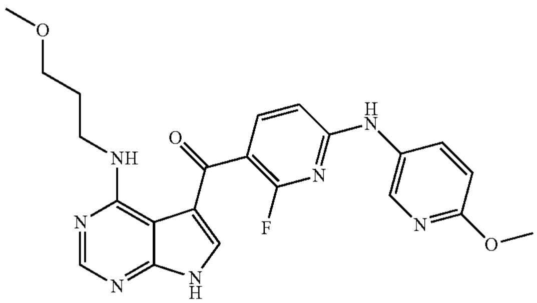 | 452.0 |
| P-4080 | 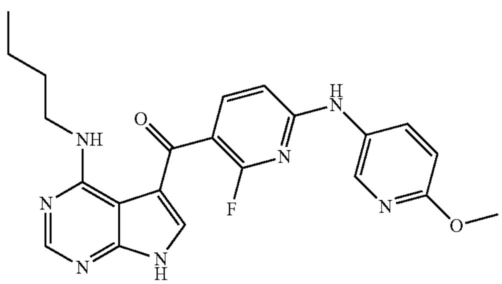 [SMILES: CCCCNc1ncnc2[nH]cc(C(=O)c3ccc(Nc4ccc(OC)nc4)nc3F)c12] | 436.5 |
| P-4081 | 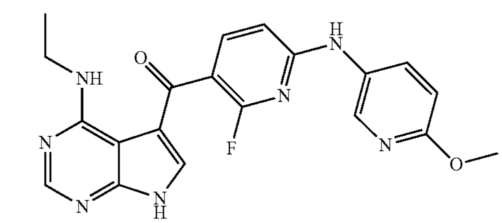 [SMILES: CCNc1ncnc2[nH]cc(C(=O)c3ccc(Nc4ccc(OC)nc4)nc3F)c12] | 408.5 |
| P-4082 | 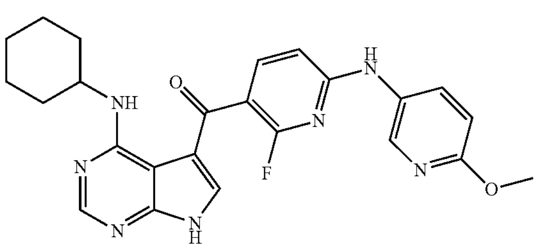 [SMILES: COc1ccc(Nc2ccc(C(=O)c3c[nH]c4ncnc(NC5CCCCC5)c34)c(F)n2)cn1] | 462.5 |
| P-4083 | 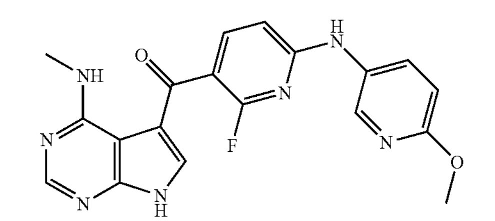 [SMILES: CNc1ncnc2[nH]cc(C(=O)c3ccc(Nc4ccc(OC)nc4)nc3F)c12] | 394.5 |

TABLE 2-continued

| No. | Compound Structure | MS (ESI) [M + H+]+ |
|---|---|---|
| P-4084 | 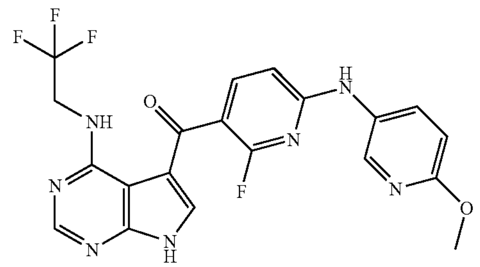 [SMILES: COc1ccc(Nc2ccc(C(=O)c3c[nH]c4ncnc(NCC(F)(F)F)c34)c(F)n2)cn1] | 462.5 |
| P-4085 | 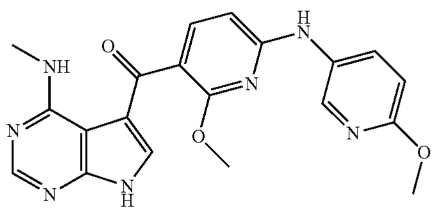 | 406.0 |
| P-4086 | 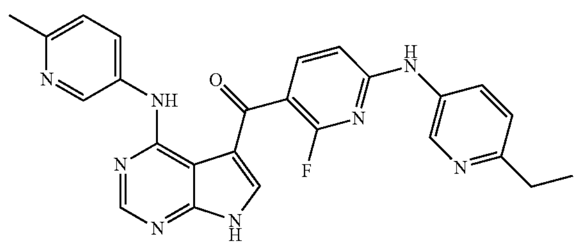 [SMILES: CCc1ccc(Nc2ccc(C(=O)c3c[nH]c4ncnc(Nc5ccc(C)nc5)c34)c(F)n2)cn1] | 469.5 |
| P-4087 | 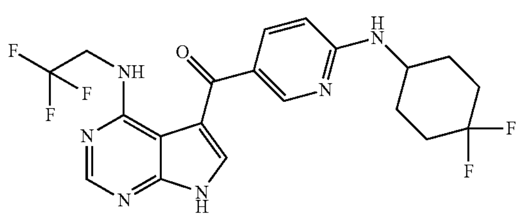 [SMILES: O=C(c1ccc(NC2CCC(F)(F)CC2)nc1)c1c[nH]c2ncnc(NCC(F)(F)F)c12] | 455.2 |
| P-4088 | 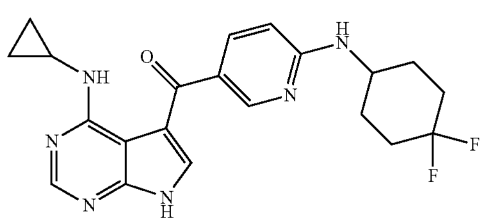 [SMILES: O=C(c1ccc(NC2CCC(F)(F)CC2)nc1)c1c[nH]c2ncnc(NC3CC3)c12] | 413.2 |
| P-4089 | 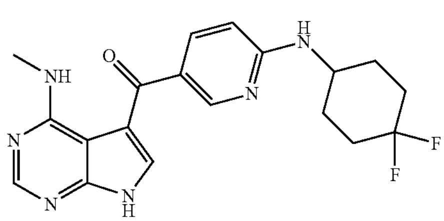 [SMILES: CNc1ncnc2[nH]cc(C(=O)c3ccc(NC4CCC(F)(F)CC4)nc3)c12] | 387.2 |
| P-4090 | 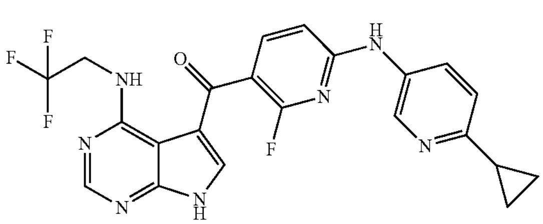 [SMILES: O=C(c1ccc(Nc2ccc(C3CC3)nc2)nc1F)c1c[nH]c2ncnc(NCC(F)(F)F)c12] | 470.2 |

TABLE 2-continued
| No. | Compound Structure | MS (ESI) [M + H⁺]⁺ |
|---|---|---|
| P-4091 | 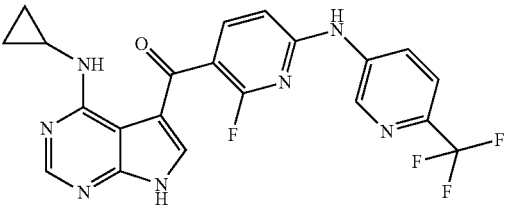 [SMILES: O=C(c1ccc(Nc2ccc(C(F)(F)F)nc2)nc1F)c1c[nH]c2ncnc(NC3CC3)c12] | 458.0 |
| P-4092 | 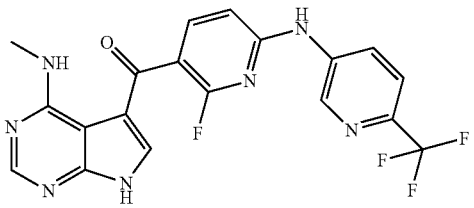 [SMILES: CNc1ncnc2[nH]cc(C(=O)c3ccc(Nc4ccc(C(F)(F)F)nc4)nc3F)c12] | 432.0 |
| P-4093 | 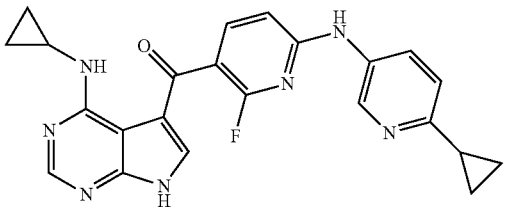 [SMILES: O=C(c1ccc(Nc2ccc(C3CC3)nc2)nc1F)c1c[nH]c2ncnc(NC3CC3)c12] | 429.9 |
| P-4094 | 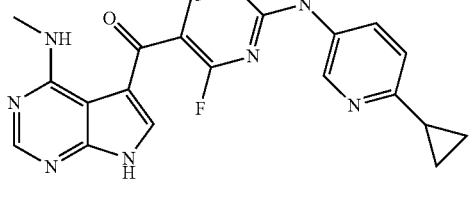 | 403.9 |
| P-4095 | 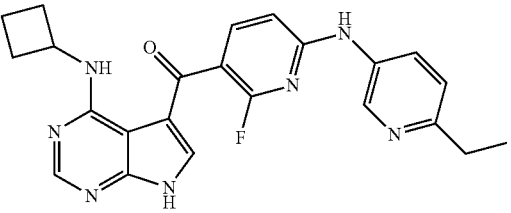 [SMILES: CCc1ccc(Nc2ccc(C(=O)c3c[nH]c4ncnc(NC5CCC5)c34)c(F)n2)cn1] | 432.5 |
| P-4096 | 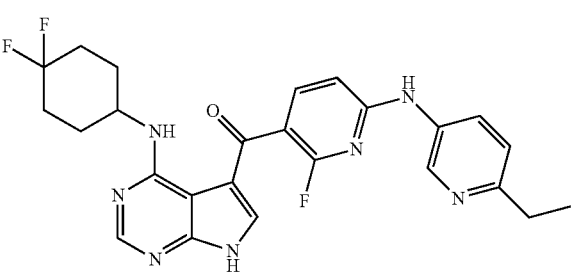 [SMILES: CCc1ccc(Nc2ccc(C(=O)c3c[nH]c4ncnc(NC5CCC(F)(F)CC5)c34)c(F)n2)cn1] | 496.5 |

TABLE 2-continued
| No. | Compound Structure | MS (ESI) [M + H+]+ |
|---|---|---|
| P-4097 | 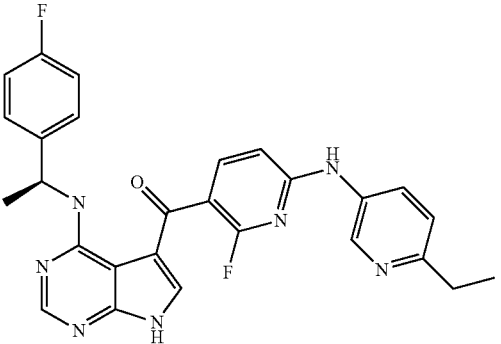 | 500.5 |
| P-4098 | 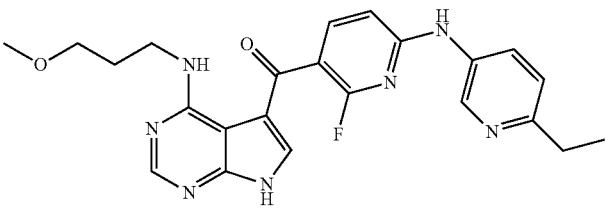 [SMILES: CCc1ccc(Nc2ccc(C(=O)c3c[nH]c4ncnc(NCCCOC)c34)c(F)n2)cn1] | 450.0 |
| P-4099 | 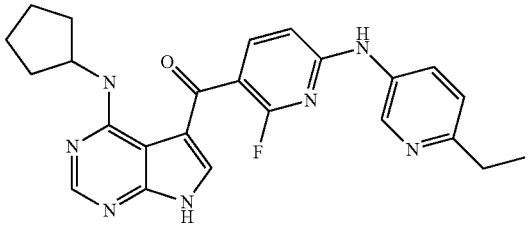 [SMILES: CCc1ccc(Nc2ccc(C(=O)c3c[nH]c4ncnc(NC5CCCC5)c34)c(F)n2)cn1] | 446.5 |
| P-4100 | 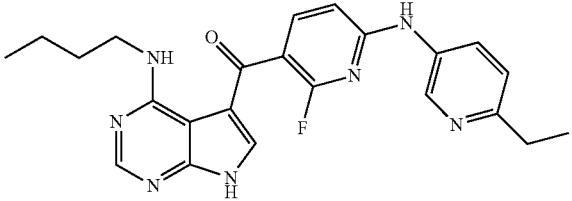 [SMILES: CCCCNc1ncnc2[nH]cc(C(=O)c3ccc(Nc4ccc(CC)nc4)nc3F)c12] | 434.5 |
| P-4101 | 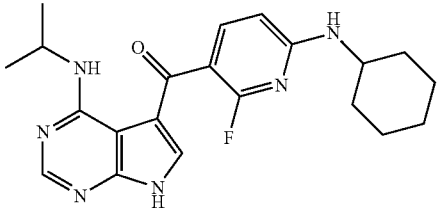 [SMILES: CC(C)Nc1ncnc2[nH]cc(C(=O)c3ccc(NC4CCCCC4)nc3F)c12] | 397.5 |
| P-4102 | 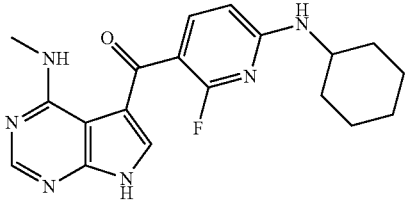 [SMILES: CNc1ncnc2[nH]cc(C(=O)c3ccc(NC4CCCCC4)nc3F)c12] | 369.1 |

TABLE 2-continued
| No. | Compound Structure | MS (ESI) [M + H+]+ |
|---|---|---|
| P-4103 | 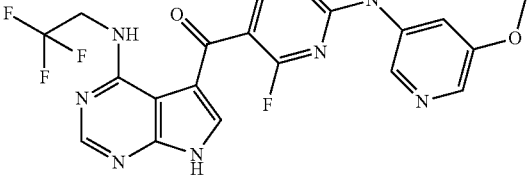 | 462.1 |
| P-4104 | 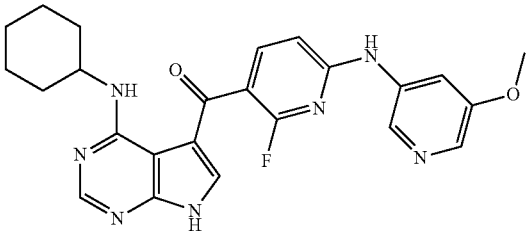 [SMILES: COc1cncc(Nc2ccc(C(=O)c3c[nH]c4ncnc(NC5CCCCC5)c34)c(F)n2)c1] | 462.1 |
| P-4105 | 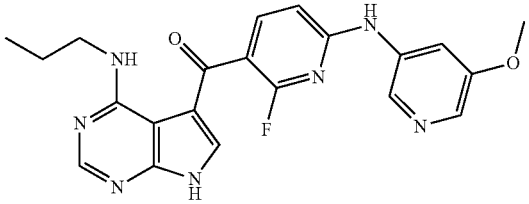 [SMILES: CCCNc1ncnc2[nH]cc(C(=O)c3ccc(Nc4cncc(OC)c4)nc3F)c12] | 422.0 |
| P-4106 | 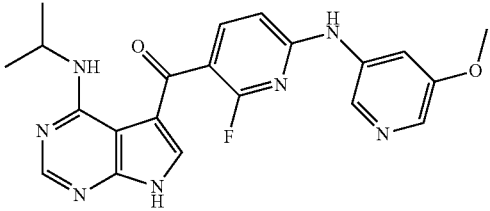 [SMILES: COc1cncc(Nc2ccc(C(=O)c3c[nH]c4ncnc(NC(C)C)c34)c(F)n2)c1] | 422.2 |
| P-4107 | 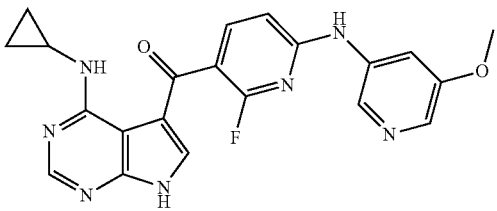 [SMILES: COc1cncc(Nc2ccc(C(=O)c3c[nH]c4ncnc(NC5CC5)c34)c(F)n2)c1] | 420.2 |
| P-4108 | 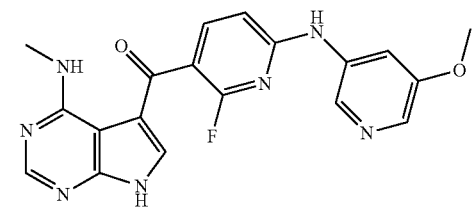 [SMILES: CNc1ncnc2[nH]cc(C(=O)c3ccc(Nc4cncc(OC)c4)nc3F)c12] | 393.9 |
| P-4109 | 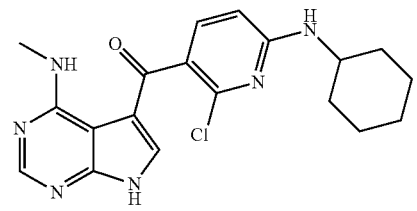 [SMILES: CNc1ncnc2[nH]cc(C(=O)c3ccc(NC4CCCCC4)nc3Cl)c12] | 412.9 |

TABLE 2-continued

| No. | Compound Structure | MS (ESI) [M + H+]+ |
|---|---|---|
| P-4110 | 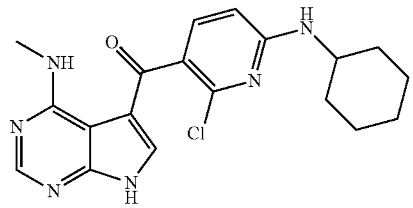 [SMILES: CNc1ncnc2[nH]cc(C(=O)c3ccc(NC4CCCCC4)nc3Cl)c12] | 384.9 |
| P-4111 | 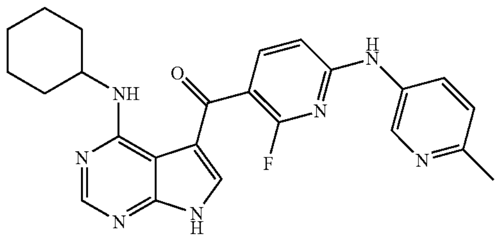 [SMILES: Cc1ccc(Nc2ccc(C(=O)c3c[nH]c4ncnc(NC5CCCCC5)c34)c(F)n2)cn1] | 446.1 |
| P-4112 | 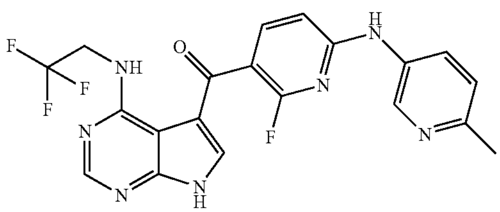 [SMILES: Cc1ccc(Nc2ccc(C(=O)c3c[nH]c4ncnc(NCC(F)(F)F)c34)c(F)n2)cn1] | 446.0 |
| P-4113 | 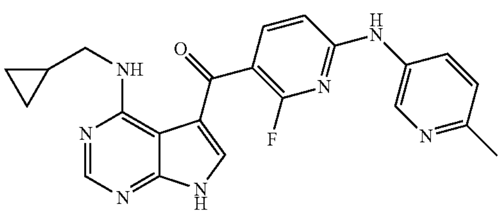 [SMILES: Cc1ccc(Nc2ccc(C(=O)c3c[nH]c4ncnc(NCC5CC5)c34)c(F)n2)cn1] | 418.1 |
| P-4114 | 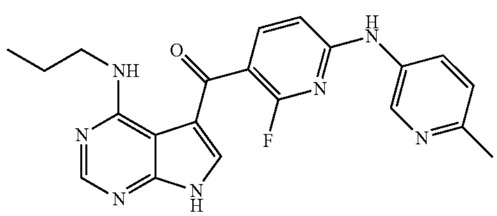 [SMILES: CCCNc1ncnc2[nH]cc(C(=O)c3ccc(Nc4ccc(C)nc4)nc3F)c12] | 406.0 |
| P-4115 | 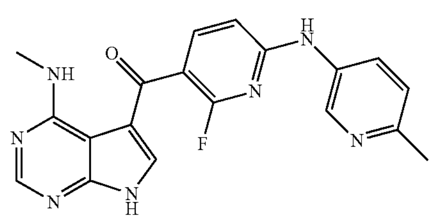 [SMILES: CNc1ncnc2[nH]cc(C(=O)c3ccc(Nc4ccc(C)nc4)nc3F)c12] | 377.9 |
| P-4116 | 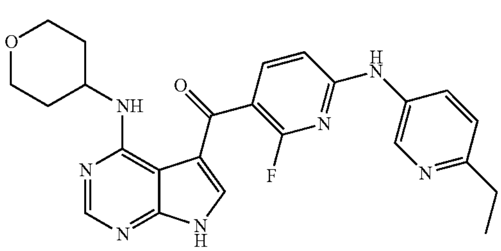 [SMILES: CCc1ccc(Nc2ccc(C(=O)c3c[nH]c4ncnc(NC5CCOCC5)c34)c(F)n2)cn1] | 462.1 |

TABLE 2-continued

| No. | Compound Structure | MS (ESI) [M + H+]+ |
|---|---|---|
| P-4117 | 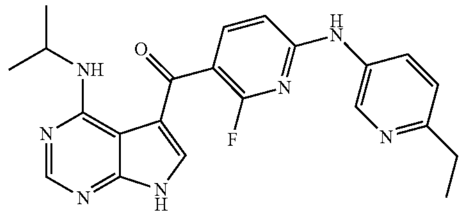 [SMILES: CCc1ccc(Nc2ccc(C(=O)c3c[nH]c4ncnc(NC(C)C)c34)c(F)n2)cn1] | 420.0 |
| P-4118 | 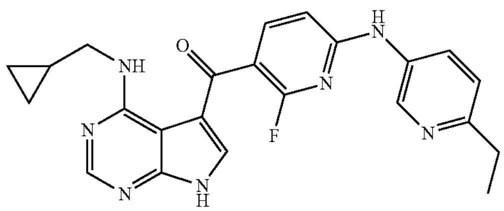 [SMILES: CCc1ccc(Nc2ccc(C(=O)c3c[nH]c4ncnc(NCC5CC5)c34)c(F)n2)cn1] | 432.2 |
| P-4119 | 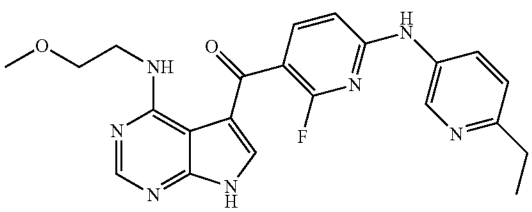 [SMILES: CCc1ccc(Nc2ccc(C(=O)c3c[nH]c4ncnc(NCCOC)c34)c(F)n2)cn1] | 436.1 |
| P-4120 | 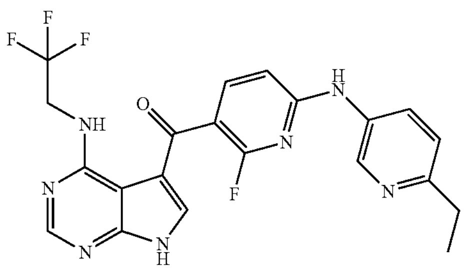 [SMILES: CCc1ccc(Nc2ccc(C(=O)c3c[nH]c4ncnc(NCC(F)(F)F)c34)c(F)n2)cn1] | 460.1 |
| P-4121 | 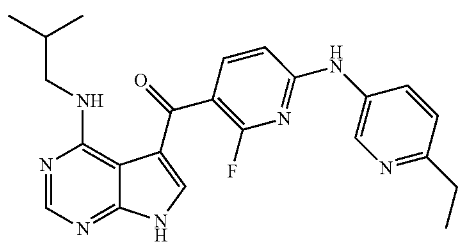 [SMILES: CCc1ccc(Nc2ccc(C(=O)c3c[nH]c4ncnc(NCC(C)C)c34)c(F)n2)cn1] | 434.1 |
| P-4122 | 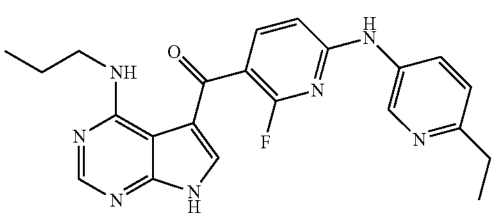 [SMILES: CCCNc1ncnc2[nH]cc(C(=O)c3ccc(Nc4ccc(CC)nc4)nc3F)c12] | 420.0 |
| P-4123 | 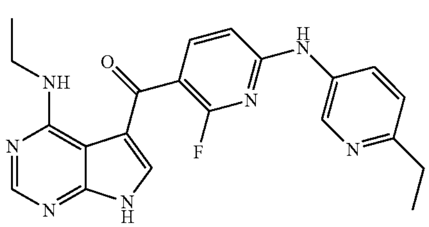 [SMILES: CCNc1ncnc2[nH]cc(C(=O)c3ccc(Nc4ccc(CC)nc4)nc3F)c12] | 406.5 |

TABLE 2-continued

| No. | Compound Structure | MS (ESI) [M + H⁺]⁺ |
|---|---|---|
| P-4124 | 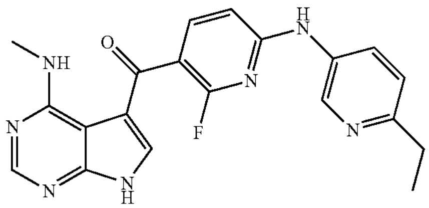 [SMILES: CCc1ccc(Nc2ccc(C(=O)c3c[nH]c4ncnc(NC)c34)c(F)n2)cn1] | 391.9 |
| P-4125 | 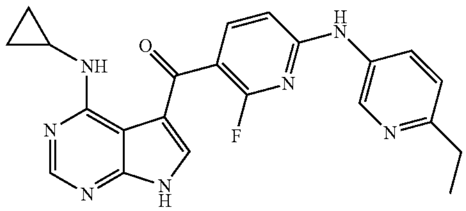 [SMILES: CCc1ccc(Nc2ccc(C(=O)c3c[nH]c4ncnc(NC5CC5)c34)c(F)n2)cn1] | 418.0 |
| P-4126 | 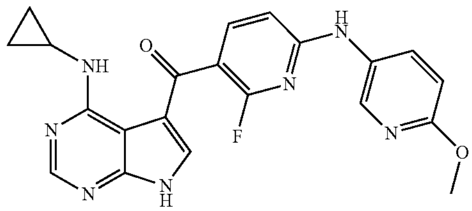 [SMILES: COc1ccc(Nc2ccc(C(=O)c3c[nH]c4ncnc(NC5CC5)c34)c(F)n2)cn1] | 420.0 |
| P-4127 | 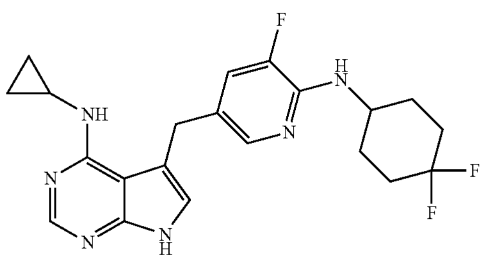 [SMILES: Fc1cc(Cc2c[nH]c3ncnc(NC4CC4)c23)cnc1NC1CCC(F)(F)CC1] | 417.0 |
| P-4128 | 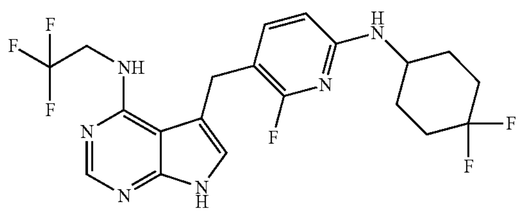 [SMILES: Fc1nc(NC2CCC(F)(F)CC2)ccc1Cc1c[nH]c2ncnc(NCC(F)(F)F)c12] | 459.0 |
| P-4129 | 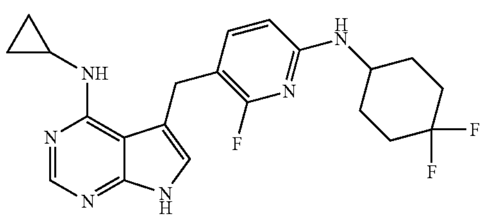 [SMILES: Fc1nc(NC2CCC(F)(F)CC2)ccc1Cc1c[nH]c2ncnc(NC3CC3)c12] | 417.0 |
| P-4130 | 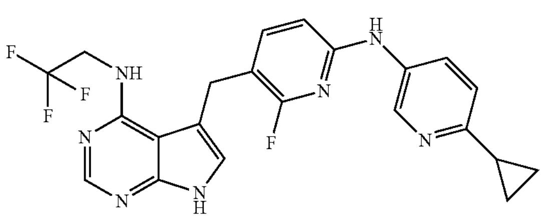 [SMILES: Fc1nc(Nc2ccc(C3CC3)nc2)ccc1Cc1c[nH]c2ncnc(NCC(F)(F)F)c12] | 458.0 |

TABLE 2-continued

| No. | Compound Structure | MS (ESI) [M + H⁺]⁺ |
|---|---|---|
| P-4131 | 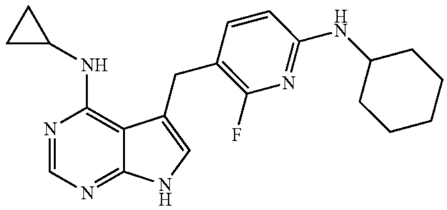 [SMILES: Fc1nc(NC2CCCCC2)ccc1Cc1c[nH]c2ncnc(NC3CC3)c12] | 379.0 |
| P-4132 | 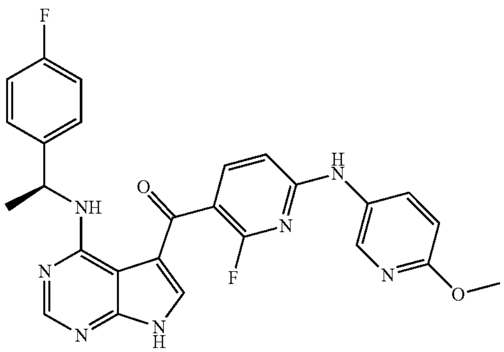 [SMILES: COc1ccc(Nc2ccc(C(=O)c3c[nH]c4ncnc(N[C@@H](C)c5ccc(F)cc5)c34)c(F)n2)cn1] | 502.5 |
| P-4133 | 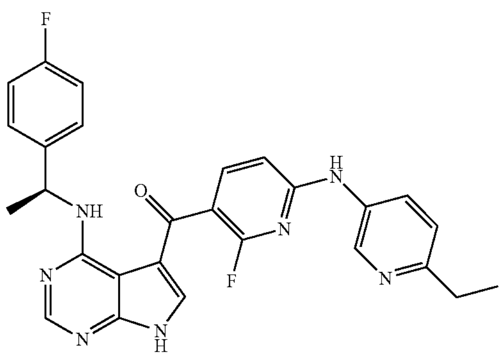 [SMILES: CCc1ccc(Nc2ccc(C(=O)c3c[nH]c4ncnc(N[C@@H](C)c5ccc(F)cc5)c34)c(F)n2)cn1] | 500.5 |

The compounds set forth in Table 7 below are prepared according to the synthetic protocols set forth in Schemes 14 and 15. The structures are characterized by mass spectroscopy and $^1$H and $^{13}$C NMR spectroscopies.

TABLE 7

| No | Name | Structure |
|---|---|---|
| P-4134 | [2-fluoro-6-[(4-fluorocyclohexyl)amino]-3-pyridyl]-[4-(methylamino)-7H-pyrrolo[2,3-d]pyrimidin-5-yl]methanone | 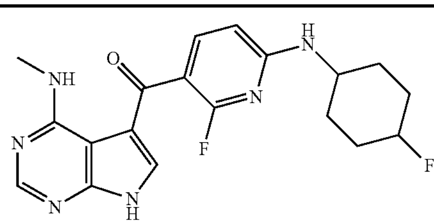 |
| P-4135 | [4-(ethylamino)-7H-pyrrolo[2,3-d]pyrimidin-5-yl]-[2-fluoro-6-[(4-fluorocyclohexyl)amino]-3-pyridyl]methanone | 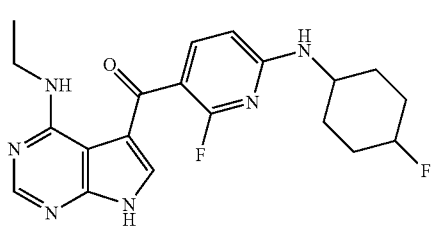 [SMILES: CCNc1ncnc2[nH]cc(C(=O)c3ccc(NC4CCC(F)CC4)nc3F)c12] |

TABLE 7-continued

| No | Name | Structure |
|---|---|---|
| P-4136 | [2-fluoro-6-[(4-fluorocyclohexyl)amino]-3-pyridyl]-[4-(isopropylamino)-7H-pyrrolo[2,3-d]pyrimidin-5-yl]methanone | 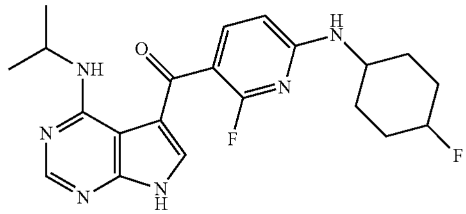 [SMILES: CC(C)Nc1ncnc2[nH]cc(C(=O)c3ccc(NC4CCC(F)CC4)nc3F)c12] |
| P-4137 | [4-(cyclopropylamino)-7H-pyrrolo[2,3-d]pyrimidin-5-yl]-[2-fluoro-6-[(4-fluorocyclohexyl)amino]-3-pyridyl]methanone | 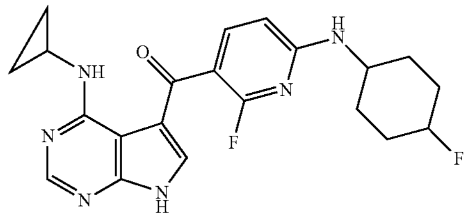 [SMILES: O=C(c1ccc(NC2CCC(F)CC2)nc1F)c1c[nH]c2ncnc(NC3CC3)c12] |
| P-4138 | [2-fluoro-6-[(4-fluorocyclohexyl)amino]-3-pyridyl]-[4-(2,2,2-trifluoroethylamino)-7H-pyrrolo[2,3-d]pyrimidin-5-yl]methanone | 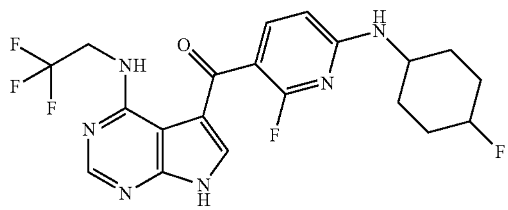 [SMILES: O=C(c1ccc(NC2CCC(F)CC2)nc1F)c1c[nH]c2ncnc(NCC(F)(F)F)c12] |
| P-4139 | [4-[[(1R)-1-cyclopropylethyl]amino]-7H-pyrrolo[2,3-d]pyrimidin-5-yl]-[2-fluoro-6-[(4-fluorocyclohexyl)amino]-3-pyridyl]methanone | 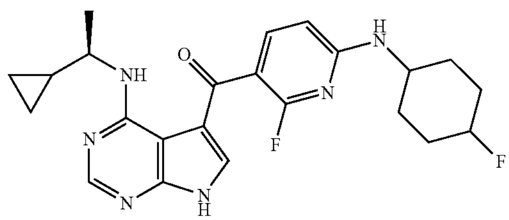 [SMILES: C[C@@H](Nc1ncnc2[nH]cc(C(=O)c3ccc(NC4CCC(F)CC4)nc3F)c12)C1CC1] |
| P-4140 | [4-[[(1S)-1-cyclopropylethyl]amino]-7H-pyrrolo[2,3-d]pyrimidin-5-yl]-[2-fluoro-6-[(4-fluorocyclohexyl)amino]-3-pyridyl]methanone | 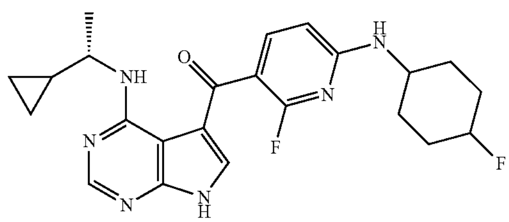 [SMILES: C[C@H](Nc1ncnc2[nH]cc(C(=O)c3ccc(NC4CCC(F)CC4)nc3F)c12)C1CC1] |
| P-4141 | [2-fluoro-6-[(4-fluorocyclohexyl)amino]-3-pyridyl]-[4-(methoxymethylamino)-7H-pyrrolo[2,3-d]pyrimidin-5-yl]methanone | 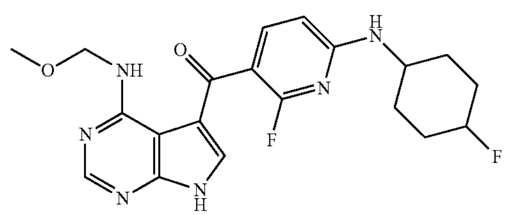 [SMILES: COCNc1ncnc2[nH]cc(C(=O)c3ccc(NC4CCC(F)CC4)nc3F)c12] |
| P-4142 | [2-fluoro-6-[(4-fluorocyclohexyl)amino]-3-pyridyl]-[4-(3-methoxypropylamino)-7H-pyrrolo[2,3-d]pyrimidin-5-yl]methanone | 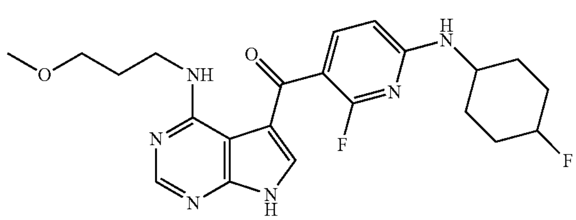 [SMILES: COCCCNc1ncnc2[nH]cc(C(=O)c3ccc(NC4CCC(F)CC4)nc3F)c12] |

| No | Name | Structure |
|---|---|---|
| P-4143 | [2-fluoro-6-[(4-fluorocyclohexyl)amino]-3-pyridyl]-[4-(tetrahydropyran-4-ylamino)-7H-pyrrolo[2,3-d]pyrimidin-5-yl]methanone | 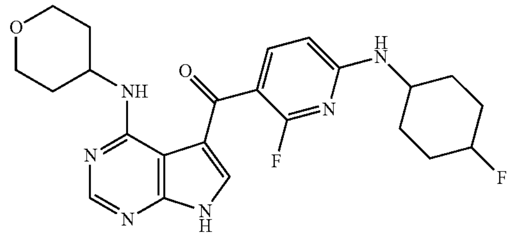 [SMILES: O=C(c1ccc(NC2CCC(F)CC2)nc1F)c1c[nH]c2ncnc(NC3CCOCC3)c12] |
| P-4144 | [4-(cyclobutylamino)-7H-pyrrolo[2,3-d]pyrimidin-5-yl]-[2-fluoro-6-[(4-fluorocyclohexyl)amino]-3-pyridyl]methanone | 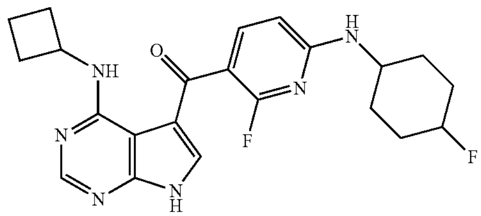 [SMILES: O=C(c1ccc(NC2CCC(F)CC2)nc1F)c1c[nH]c2ncnc(NC3CCC3)c12] |
| P-4145 | [6-[(3,3-difluorocyclobutyl)amino]-2-fluoro-3-pyridyl]-[4-(methylamino)-7H-pyrrolo[2,3-d]pyrimidin-5-yl]methanone | 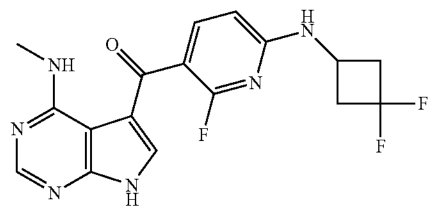 [SMILES: CNc1ncnc2[nH]cc(C(=O)c3ccc(NC4CC(F)(F)C4)nc3F)c12] |
| P-4146 | [6-[(3,3-difluorocyclobutyl)amino]-2-fluoro-3-pyridyl]-[4-(ethylamino)-7H-pyrrolo[2,3-d]pyrimidin-5-yl]methanone | 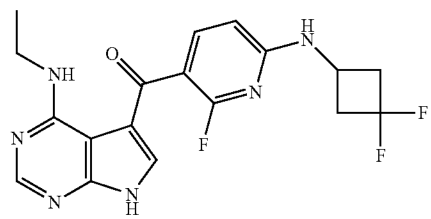 [SMILES: CCNc1ncnc2[nH]cc(C(=O)c3ccc(NC4CC(F)(F)C4)nc3F)c12] |
| P-4147 | [6-[(3,3-difluorocyclobutyl)amino]-2-fluoro-3-pyridyl]-[4-(propylamino)-7H-pyrrolo[2,3-d]pyrimidin-5-yl]methanone | 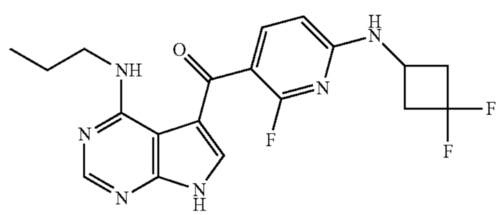 |
| P-4148 | [6-[(3,3-difluorocyclobutyl)amino]-2-fluoro-3-pyridyl]-[4-(isopropylamino)-7H-pyrrolo[2,3-d]pyrimidin-5-yl]methanone | 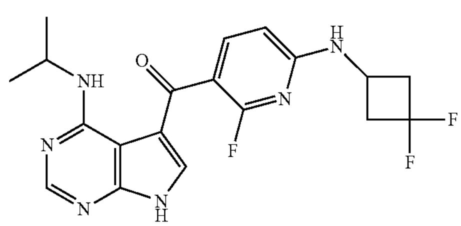 [SMILES: CC(C)Nc1ncnc2[nH]cc(C(=O)c3ccc(NC4CC(F)(F)C4)nc3F)c12] |
| P-4149 | [6-[(3,3-difluorocyclobutyl)amino]-2-fluoro-3-pyridyl]-[4-(2,2,2-trifluoroethylamino)-7H-pyrrolo[2,3-d]pyrimidin-5-yl]methanone | 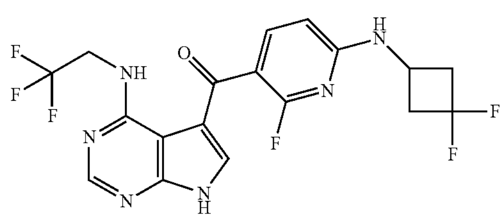 [SMILES: O=C(c1ccc(NC2CC(F)(F)C2)nc1F)c1c[nH]c2ncnc(NCC(F)(F)F)c12] |

TABLE 7-continued

| No | Name | Structure |
|---|---|---|
| P-4150 | [4-[[(1R)-1-cyclopropylethyl]amino]-7H-pyrrolo[2,3-d]pyrimidin-5-yl]-[6-[(3,3-difluorocyclobutyl)amino]-2-fluoro-3-pyridyl]methanone | 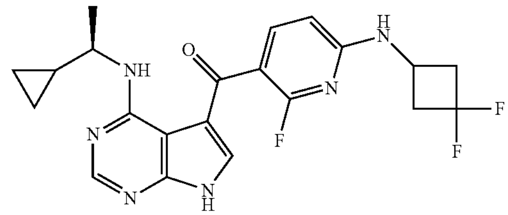 [SMILES: C[C@@H](Nc1ncnc2[nH]cc(C(=O)c3ccc(NC4CC(F)(F)C4)nc3F)c12)C1CC1] |
| P-4151 | [4-[[(1S)-1-cyclopropylethyl]amino]-7H-pyrrolo[2,3-d]pyrimidin-5-yl]-[6-[(3,3-difluorocyclobutyl)amino]-2-fluoro-3-pyridyl]methanone | 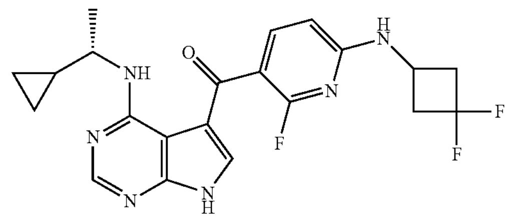 [SMILES: C[C@H](Nc1ncnc2[nH]cc(C(=O)c3ccc(NC4CC(F)(F)C4)nc3F)c12)C1CC1] |
| P-4152 | [6-[(3,3-difluorocyclobutyl)amino]-2-fluoro-3-pyridyl]-[4-(methoxymethylamino)-7H-pyrrolo[2,3-d]pyrimidin-5-yl]methanone | 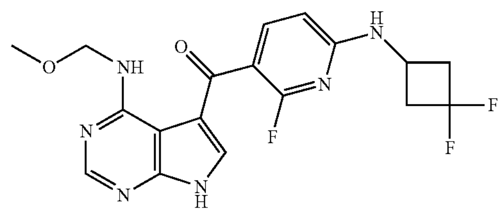 [SMILES: COCNc1ncnc2[nH]cc(C(=O)c3ccc(NC4CC(F)(F)C4)nc3F)c12] |
| P-4153 | [6-[(3,3-15difluorocyclobutyl)amino]-2-fluoro-3-pyridyl]-[4-(tetrahydropyran-4-ylamino)-7H-pyrrolo[2,3-d]pyrimidin-5-yl]methanone | 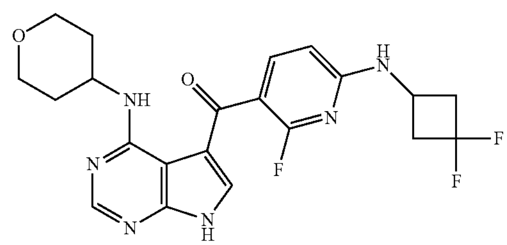 [SMILES: O=C(c1ccc(NC2CC(F)(F)C2)nc1F)c1c[nH]c2ncnc(NC3CCOCC3)c12] |
| P-4154 | [4-(cyclobutylamino)-7H-pyrrolo[2,3-d]pyrimidin-5-yl]-[6-[(3,3-difluorocyclobutyl)amino]-2-fluoro-3-pyridyl]methanone | 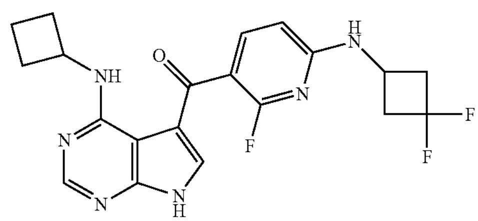 [SMILES: O=C(c1ccc(NC2CC(F)(F)C2)nc1F)c1c[nH]c2ncnc(NC3CCC3)c12] |
| P-4155 | [6-[(3,3-difluorocyclobutyl)amino]-2-fluoro-3-pyridyl]-[4-(3-methoxypropylamino)-7H-pyrrolo[2,3-d]pyrimidin-5-yl]methanone | 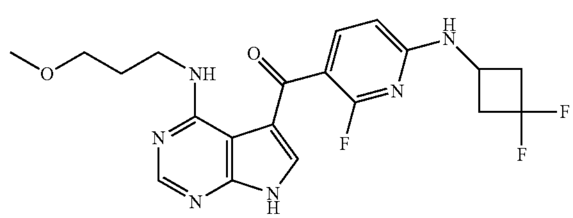 [SMILES: COCCCNc1ncnc2[nH]cc(C(=O)c3ccc(NC4CC(F)(F)C4)nc3F)c12] |
| P-4156 | [6-[(4,4-difluorocyclohexyl)amino]-2-fluoro-3-pyridyl]-[4-(3-methoxypropylamino)-7H-pyrrolo[2,3-d]pyrimidin-5-yl]methanone | 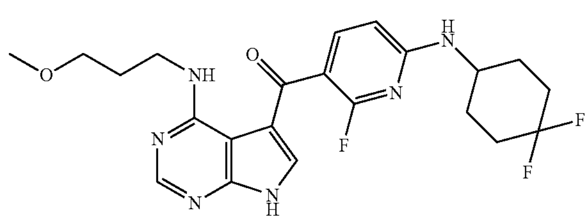 [SMILES: COCCCNc1ncnc2[nH]cc(C(=O)c3ccc(NC4CCC(F)(F)CC4)nc3F)c12] |

TABLE 7-continued

| No | Name | Structure |
|---|---|---|
| P-4157 | [6-[(4,4-difluorocyclohexyl)amino]-2-fluoro-3-pyridyl]-[4-(2-methoxyethylamino)-7H-pyrrolo[2,3-d]pyrimidin-5-yl]methanone | 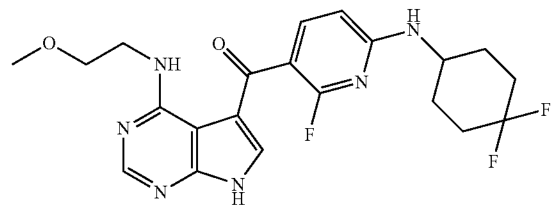 [SMILES: COCCNc1ncnc2[nH]cc(C(=O)c3ccc(NC4CCC(F)(F)CC4)nc3F)c12] |
| P-4158 | [4-(cyclobutylamino)-7H-pyrrolo[2,3-d]pyrimidin-5-yl]-[6-[(4,4-difluorocyclohexyl)amino]-2-fluoro-3-pyridyl]methanone | 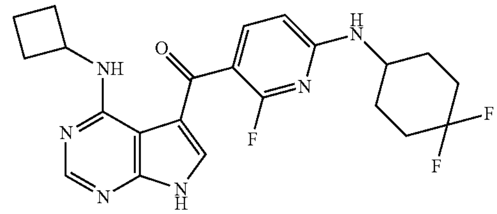 [SMILES: O=C(c1ccc(NC2CCC(F)(F)CC2)nc1F)c1c[nH]c2ncnc(NC3CCC3)c12] |
| P-4159 | [6-[(4,4-difluorocyclohexyl)amino]-2-fluoro-3-pyridyl]-[4-(tetrahydropyran-4-ylamino)-7H-pyrrolo[2,3-d]pyrimidin-5-yl]methanone | 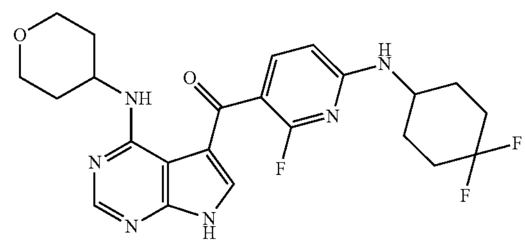 [SMILES: O=C(c1ccc(NC2CCC(F)(F)CC2)nc1F)c1c[nH]c2ncnc(NC3CCOCC3)c12] |
| P-4160 | [4-[[(1R)-1-cyclopropylethyl]amino]-7H-pyrrolo[2,3-d]pyrimidin-5-yl]-[6-[(4,4-difluorocyclohexyl)amino]-2-fluoro-3-pyridyl]methanone | 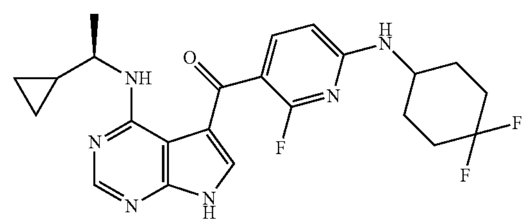 [SMILES: C[C@@H](Nc1ncnc2[nH]cc(C(=O)c3ccc(NC4CCC(F)(F)CC4)nc3F)c12)C1CC1] |
| P-4161 | [4-[[(1S)-1-cyclopropylethyl]amino]-7H-pyrrolo[2,3-d]pyrimidin-5-yl]-[6-[(4,4-difluorocyclohexyl)amino]-2-fluoro-3-pyridyl]methanone | 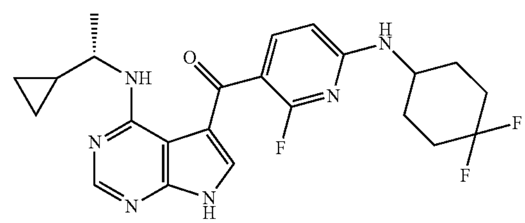 [SMILES: C[C@H](Nc1ncnc2[nH]cc(C(=O)c3ccc(NC4CCC(F)(F)CC4)nc3F)c12)C1CC1] |
| P-4162 | [6-[(4,4-difluorocyclohexyl)amino]-2-fluoro-3-pyridyl]-[4-(ethylamino)-7H-pyrrolo[2,3-d]pyrimidin-5-yl]methanone | 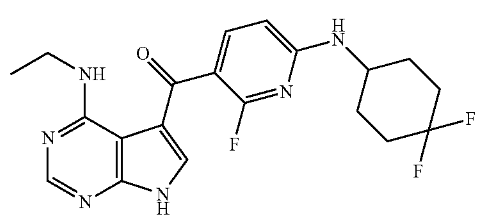 [SMILES: CCNc1ncnc2[nH]cc(C(=O)c3ccc(NC4CCC(F)(F)CC4)nc3F)c12] |
| P-4163 | [4-(cyclobutylamino)-7H-pyrrolo[2,3-d]pyrimidin-5-yl]-[6-[(4,4-difluorocyclohexyl)amino]-5-fluoro-3-pyridyl]methanone | 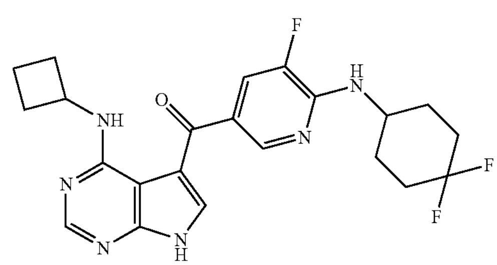 [SMILES: O=C(c1cnc(NC2CCC(F)(F)CC2)c(F)c1)c1c[nH]c2ncnc(NC3CCC3)c12] |

TABLE 7-continued

| No | Name | Structure |
|---|---|---|
| P-4164 | [6-[(4,4-difluorocyclohexyl)amino]-5-fluoro-3-pyridyl]-[4-(methoxymethylamino)-7H-pyrrolo[2,3-d]pyrimidin-5-yl]methanone | 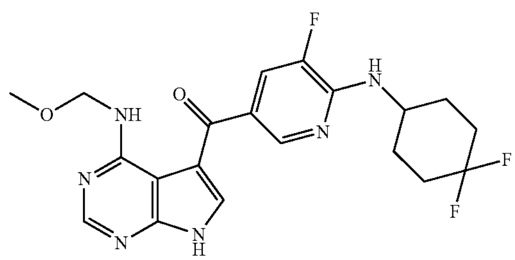 [SMILES: COCNc1ncnc2[nH]cc(C(=O)c3cnc(NC4CCC(F)(F)CC4)c(F)c3)c12] |
| P-4165 | [6-[(4,4-difluorocyclohexyl)amino]-5-fluoro-3-pyridyl]-[4-(3-methoxypropylamino)-7H-pyrrolo[2,3-cl]pyrimidin-5-yl]methanone | 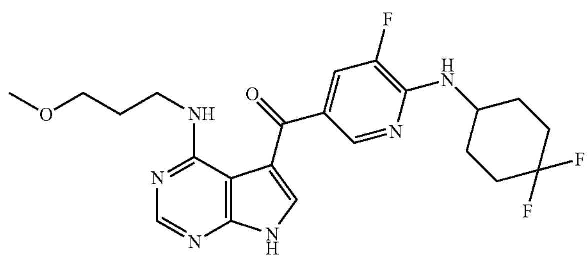 [SMILES: COCCCNc1ncnc2[nH]cc(C(=O)c3cnc(NC4CCC(F)(F)CC4)c(F)c3)c12] |
| P-4166 | [6-[(4,4-difluorocyclohexyl)amino]-5-fluoro-3-pyridyl]-[4-(tetrahydropyran-4-ylamino)-7H-pyrrolo[2,3 d]pyrimidin-5-yl]methanone | 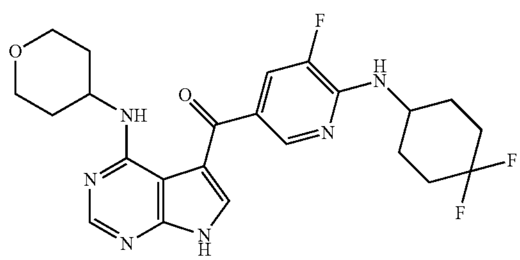 [SMILES: O=C(c1cnc(NC2CCC(F)(F)CC2)c(F)c1)c1c[nH]c2ncnc(NC3CCOCC3)c12] |
| P-4167 | [4-[[(1R)-1-cyclopropylethyl]amino]-7H-pyrrolo[2,3-d]pyrimidin-5-yl]-[6-[(4,4-difluorocyclohexyl)amino]-5-fluoro-3-pyridyl]methanone | 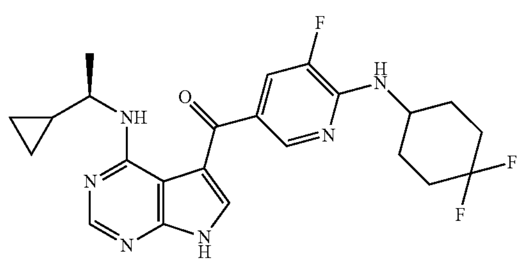 [SMILES: C[C@@H](Nc1ncnc2[nH]cc(C(=O)c3cnc(NC4CCC(F)(F)CC4)c(F)c3)c12)C1CC1] |
| P-4168 | [4-[[(1S)-1-cyclopropylethyl]amino]-7H-pyrrolo[2,3-d]pyrimidin-5-yl]-[6-[(4,4-difluorocyclohexyl)amino]-5-fluoro-3-pyridyl]methanone | 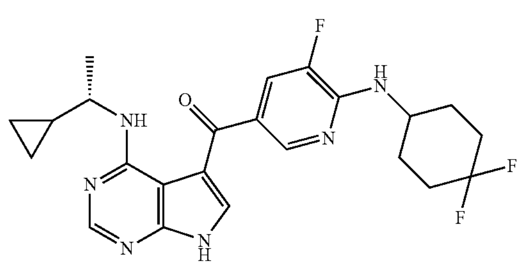 [SMILES: C[C@H](Nc1ncnc2[nH]cc(C(=O)c3cnc(NC4CCC(F)(F)CC4)c(F)c3)c12)C1CC1] |
| P-4169 | [6-[(6-cyclopropyl-3-pyridyl)amino]-2-fluoro-3-pyridyl]-[4-[[(1S)-1-methylpropyl]amino]-7H-pyrrolo[2,3-d]pyrimidin-5-yl]methanone | 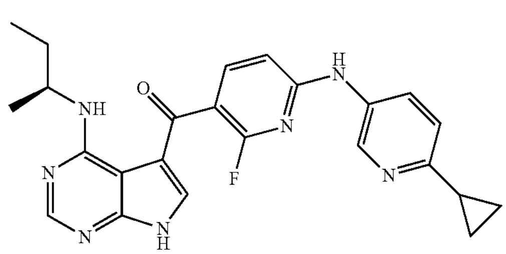 [SMILES: CC[C@H](C)Nc1ncnc2[nH]cc(C(=O)c3ccc(Nc4ccc(C5CC5)nc4)nc3F)c12] |

TABLE 7-continued

| No | Name | Structure |
|---|---|---|
| P-4170 | [6-[(6-cyclopropyl-3-pyridyl)amino]-2-fluoro-3-pyridyl]-[4-[(3-hydroxy-1-methyl-propyl)amino]-7H-pyrrolo[2,3-d]pyrimidin-5-yl]methanone | 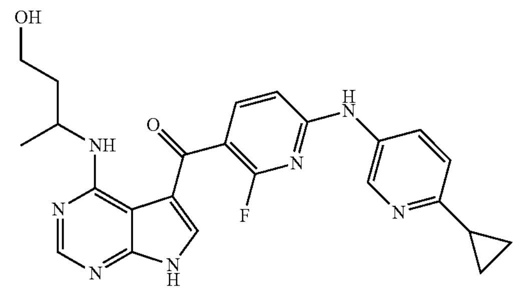 [SMILES: CC(CCO)Nc1ncnc2[nH]cc(C(=O)c3ccc(Nc4ccc(C5CC5)nc4)nc3F)c12] |
| P-4171 | [6-[(6-cyclopropyl-3-pyridyl)amino]-2-fluoro-3-pyridyl]-[4-[[(1R)-1-(hydroxymethyl)propyl]amino]-7H-pyrrolo[2,3-d]pyrimidin-5-yl]methanone | 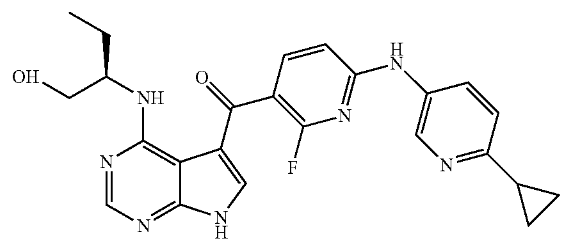 [SMILES: CC[C@H](CO)Nc1ncnc2[nH]cc(C(=O)c3ccc(Nc4ccc(C5CC5)nc4)nc3F)c12] |
| P-4172 | 4-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-2-one | 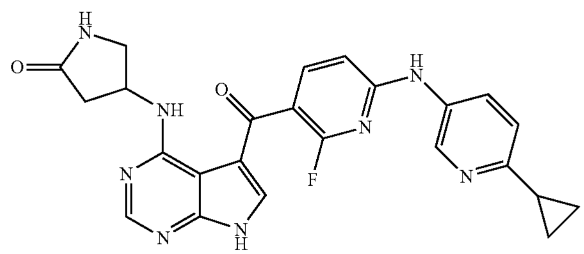 [SMILES: O=C1CC(Nc2ncnc3[nH]cc(C(=O)c4ccc(Nc5ccc(C6CC6)nc5)nc4F)c23)CN1] |
| P-4173 | [6-[(6-cyclopropyl-3-pyridyl)amino]-2-fluoro-3-pyridyl]-[4-[[(1R)-2-hydroxy-1-methyl-ethyl]amino]-7H-pyrrolo[2,3-d]pyrimidin-5-yl]methanone | 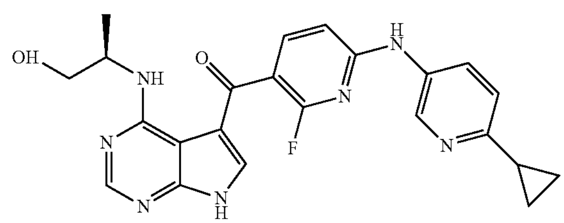 [SMILES: C[C@H](CO)Nc1ncnc2[nH]cc(C(=O)c3ccc(Nc4ccc(C5CC5)nc4)nc3F)c12] |
| P-4174 | [6-[(6-cyclopropyl-3-pyridyl)amino]-2-fluoro-3-pyridyl]-[4-[[(1R,3R)-3-hydroxycyclohexyl]amino]-7H-pyrrolo[2,3-d]pyrimidin-5-yl]methanone | 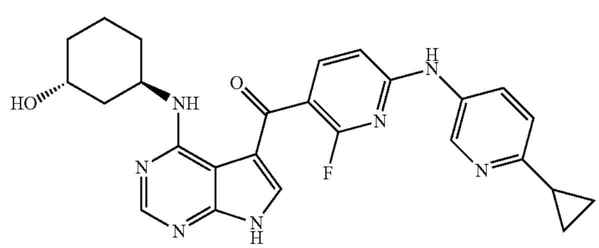 [SMILES: O=C(c1ccc(Nc2ccc(C3CC3)nc2)nc1F)c1c[nH]c2ncnc(N[C@@H]3CCC[C@@H](O)C3)c12] |
| P-4175 | [6-[(6-cyclopropyl-3-pyridyl)amino]-2-fluoro-3-pyridyl]-[4-[[(1R,2R)-2-hydroxycyclopentyl]amino]-7H-pyrrolo[2,3-d]pyrimidin-5-yl]methanone | 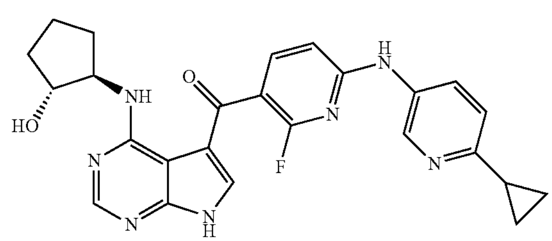 [SMILES: O=C(c1ccc(Nc2ccc(C3CC3)nc2)nc1F)c1c[nH]c2ncnc(N[C@@H]3CCC[C@H]3O)c12] |

TABLE 7-continued

| No | Name | Structure |
|---|---|---|
| P-4176 | 1-[3-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-1-yl]ethanone | 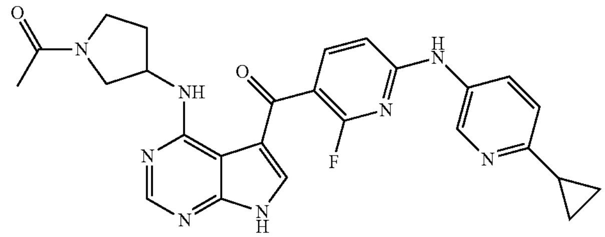 [SMILES: CC(=O)N1CCC(Nc2ncnc3[nH]cc(C(=O)c4ccc(Nc5ccc(C6CC6)nc5)nc4F)c23)C1] |
| P-4177 | (2R)-2-[[5-[6-[(6-cyclopropyl-3-pyridyl)amino]-2-fluoro-pyridine-3-carbonyl]-7H-pyrrolo[2,3-d]pyrimidin-4-yl]amino]cyclohexanone | 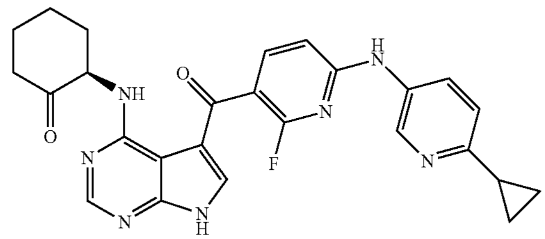 [SMILES: O=C(c1ccc(Nc2ccc(C3CC3)nc2)nc1F)c1c[nH]c2ncnc(N[C@@H]3CCCCC3=O)c12] |
| P-4178 | [6-[(6-cyclopropyl-3-pyridyl)amino]-2-fluoro-3-pyridyl]-[4-[(1,1-dioxothiolan-3-yl)amino]-7H-pyrrolo[2,3-d]pyrimidin-5-yl]methanone | 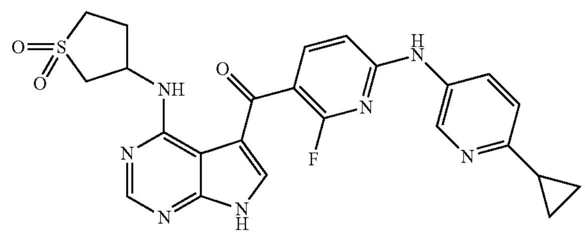 [SMILES: O=C(c1ccc(Nc2ccc(C3CC3)nc2)nc1F)c1c[nH]c2ncnc(NC3CCS(=O)(=O)C3)c12] |
| P-4179 | [6-[(6-cyclopropyl-3-pyridyl)amino]-2-fluoro-3-pyridyl]-[4-[[(1R,2R)-2-hydroxycyclohexyl]amino]-7H-pyrrolo[2,3-d]pyrimidin-5-yl]methanone | 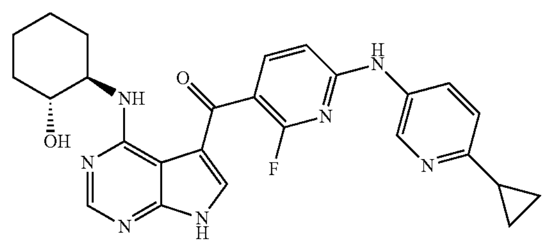 [SMILES: O=C(c1ccc(Nc2ccc(C3CC3)nc2)nc1F)c1c[nH]c2ncnc(N[C@@H]3CCCC[C@H]3O)c12] |
| P-4180 | [6-[(6-cyclopropyl-3-pyridyl)amino]-2-fluoro-3-pyridyl]-[4-[[(1R)-2-methoxy-1-methyl-ethyl]amino]-7H-pyrrolo[2,3-d]pyrimidin-5-yl]methanone | 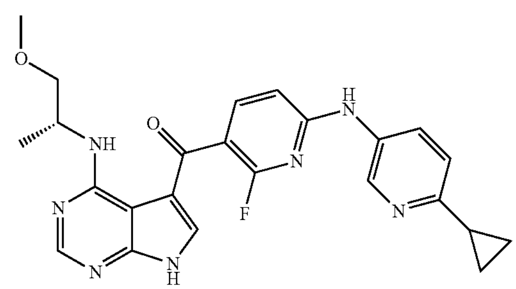 [SMILES: COC[C@@H](C)Nc1ncnc2[nH]cc(C(=O)c3ccc(Nc4ccc(C5CC5)nc4)nc3F)c12] |
| P-4181 | 4-[[5-[6-[(6-cyclopropyl-3-pyridyl)amino]-2-fluoro-pyridine-3-carbonyl]-7H-pyrrolo[2,3-d]pyrimidin-4-yl]amino]piperidin-2-one | 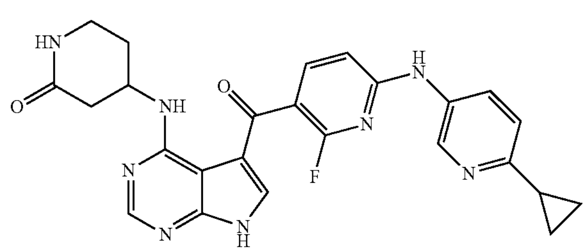 [SMILES: O=C1CC(Nc2ncnc3[nH]cc(C(=O)c4ccc(Nc5ccc(C6CC6)nc5)nc4F)c23)CCN1] |

TABLE 7-continued

| No | Name | Structure |
|---|---|---|
| P-4182 | [6-[(6-cyclopropyl-3-pyridyl)amino]-2-fluoro-3-pyridyl]-[4-[[(1R)-2,2,2-trifluoro-1-methyl-ethyl]amino]-7H-pyrrolo[2,3-d]pyrimidin-5-yl]methanone | 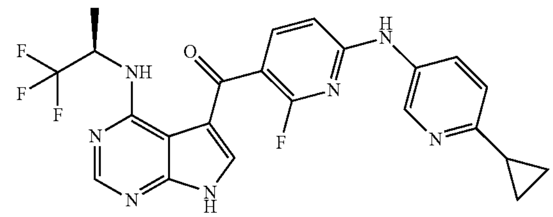 [SMILES: C[C@@H](Nc1ncnc2[nH]cc(C(=O)c3ccc(Nc4ccc(C5CC5)nc4)nc3F)c12)C(F)(F)F] |
| P-4183 | 4-[[5-[6-[(6-cyclopropyl-3-pyridyl)amino]-2-fluoro-pyridine-3-carbonyl]-7H-pyrrolo[2,3-d]pyrimidin-4-yl]amino]-1-methyl-piperidin-2-one | 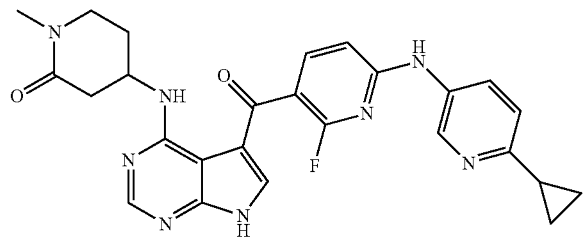 [SMILES: CN1CCC(Nc2ncnc3[nH]cc(C(=O)c4ccc(Nc5ccc(C6CC6)nc5)nc4F)c23)CC1=O] |
| P-4184 | [6-[(6-cyclopropyl-3-pyridyl)amino]-2-fluoro-3-pyridyl]-[4-[(1,1-dioxothian-3-yl)amino]-7H-pyrrolo[2,3-d]pyrimidin-5-yl]methanone | 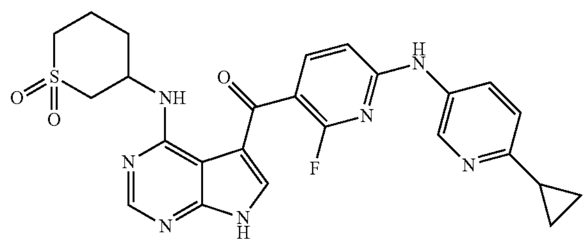 [SMILES: O=C(c1ccc(Nc2ccc(C3CC3)nc2)nc1F)c1c[nH]c2ncnc(NC3CCCS(=O)(=O)C3)c12] |
| P-4185 | 1-cyclopropyl-4-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-2-one | 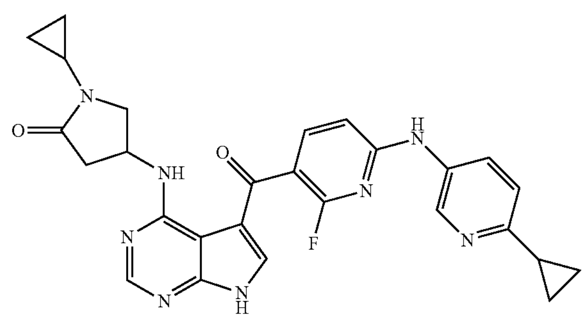 [SMILES: O=C(c1ccc(Nc2ccc(C3CC3)nc2)nc1F)c1c[nH]c2ncnc(NC3CC(=O)N(C4CC4)C3)c12] |
| P-4186 | [6-[(4,4-difluorocyclohexyl)amino]-2-fluoro-3-pyridyl]-[4-[[(1S)-1-methylpropyl]amino]-7H-pyrrolo[2,3-d]pyrimidin-5-yl]methanone | 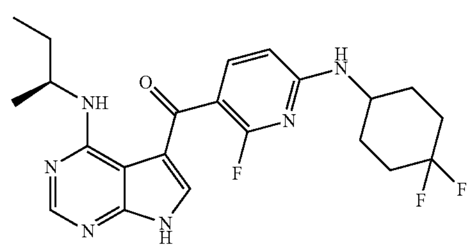 [SMILES: CC[C@H](C)Nc1ncnc2[nH]cc(C(=O)c3ccc(NC4CCC(F)(F)CC4)nc3F)c12] |
| P-4187 | [6-[(4,4-difluorocyclohexyl)amino]-2-fluoro-3-pyridyl]-[4-[(3-hydroxy-1-methyl-propyl)amino]-7H-pyrrolo[2,3-d]pyrimidin-5-yl]methanone | 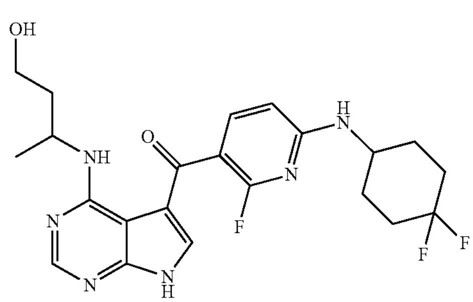 [SMILES: CC(CCO)Nc1ncnc2[nH]cc(C(=O)c3ccc(NC4CCC(F)(F)CC4)nc3F)c12] |

TABLE 7-continued

| No | Name | Structure |
|---|---|---|
| P-4188 | [6-[(4,4-difluorocyclohexyl)amino]-2-fluoro-3-pyridyl]-[4-[[(1R)-1-(hydroxymethyl)propyl]amino]-7H-pyrrolo[2,3-d]pyrimidin-5-yl]methanone | 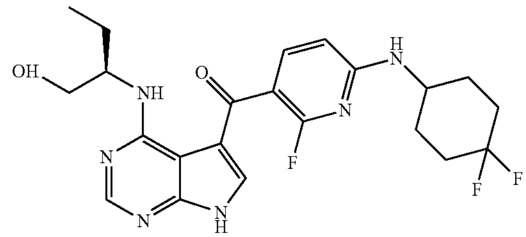 [SMILES: CC[C@H](CO)Nc1ncnc2[nH]cc(C(=O)c3ccc(NC4CCC(F)(F)CC4)nc3F)c12] |
| P-4189 | 4-[[5-[6-[(4,4-difluorocyclohexyl)amino]-2-fluoro-pyridine-3-carbonyl]-7H-pyrrolo[2,3-d]pyrimidin-4-yl]amino]pyrrolidin-2-one | 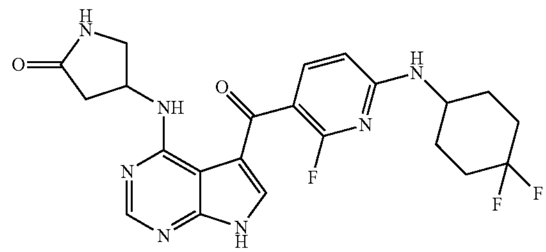 [SMILES: O=C1CC(Nc2ncnc3[nH]cc(C(=O)c4ccc(NC5CCC(F)(F)CC5)nc4F)c23)CN1] |
| P-4190 | [6-[(4,4-difluorocyclohexyl)amino]-2-fluoro-3-pyridyl]-[4-[[(1R)-2-hydroxy-1-methyl-ethyl]amino]-7H-pyrrolo[2,3-d]pyrimidin-5-yl]methanone | 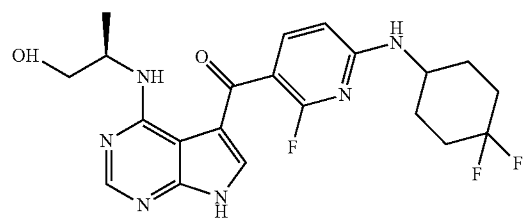 [SMILES: C[C@H](CO)Nc1ncnc2[nH]cc(C(=O)c3ccc(NC4CCC(F)(F)CC4)nc3F)c12] |
| P-4191 | [6-[(4,4-difluorocyclohexyl)amino]-2-fluoro-3-pyridyl]-[4-[[(1R,3R)-3-hydroxycyclohexyl]amino]-7H-pyrrolo[2,3-d]pyrimidin-5-yl]methanone | 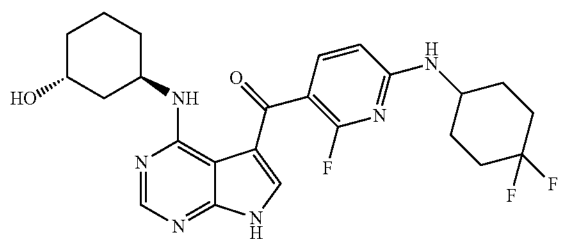 [SMILES: O=C(c1ccc(NC2CCC(F)(F)CC2)nc1F)c1c[nH]c2ncnc(N[C@@H]3CCC[C@@H](O)C3)c12] |
| P-4192 | [6-[(4,4-difluorocyclohexyl)amino]-2-fluoro-3-pyridyl]-[4-[[(1R,2R)-2-hydroxycyclopentyl]amino]-7H-pyrrolo[2,3-d]pyrimidin-5-yl]methanone | 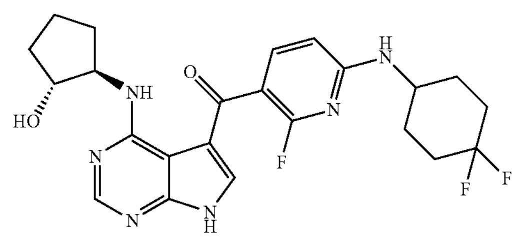 [SMILES: O=C(c1ccc(NC2CCC(F)(F)CC2)nc1F)c1c[nH]c2ncnc(N[C@@H]3CCC[C@H]3O)c12] |
| P-4193 | 1-[3-[[5-[6-[(4,4-difluorocyclohexyl)amino]-2-fluoro-pyridine-3-carbonyl]-7H-pyrrolo[2,3-d]pyrimidin-4-yl]amino]pyrrolidin-1-yl]ethanone | 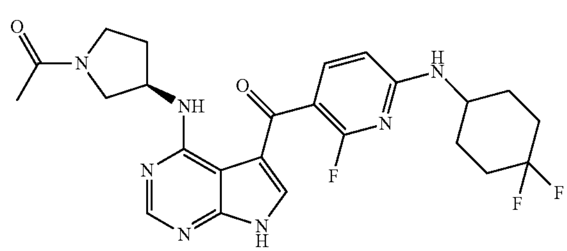 [SMILES: CC(=O)N1CC[C@@H](Nc2ncnc3[nH]cc(C(=O)c4ccc(NC5CCC(F)(F)CC5)nc4F)c23)C1] |

TABLE 7-continued

| No | Name |
|---|---|
| P-4194 | (2R)-2-[[5-[6-[(4,4-difluorocyclohexyl)amino]-2-fluoro-pyridine-3-carbonyl]-7H-pyrrolo[2,3-d]pyrimidin-4-yl]amino]cyclohexanone |
| P-4195 | [6-[(4,4-difluorocyclohexyl)amino]-2-fluoro-3-pyridyl]-[4-[(1,1-dioxothiolan-3-yl)amino]-7H-pyrrolo[2,3-d]pyrimidin-5-yl]methanone |
| P-4196 | [6-[(4,4-difluorocyclohexyl)amino]-2-fluoro-3-pyridyl]-[4-[[(1R,2R)-2-hydroxycyclohexyl]amino]-7H-pyrrolo[2,3-d]pyrimidin-5-yl]methanone |
| P-4197 | [6-[(4,4-difluorocyclohexyl)amino]-2-fluoro-3-pyridyl]-[4-[[(1R)-2-methoxy-1-methyl-ethyl]amino]-7H-pyrrolo[2,3-d]pyrimidin-5-yl]methanone |
| P-4198 | 4-[[5-[6-[(4,4-difluorocyclohexyl)amino]-2-fluoro-pyridine-3-carbonyl]-7H-pyrrolo[2,3-d]pyrimidin-4-yl]amino]piperidin-2-one |
| P-4199 | [6-[(4,4-difluorocyclohexyl)amino]-2-fluoro-3-pyridyl]-[4-[[(1R)-2,2,2-trifluoro-1-methyl-ethyl]amino]-7H-pyrrolo[2,3-d]pyrimidin-5-yl]methanone |

TABLE 7-continued

| No | Name | Structure |
|---|---|---|
| P-4200 | 4-[[5-[6-[(4,4-difluorocyclohexyl)amino]-2-fluoro-pyridine-3-carbonyl]-7H-pyrrolo[2,3-d]pyrimidin-4-yl]amino]-1-methyl-piperidin-2-one | 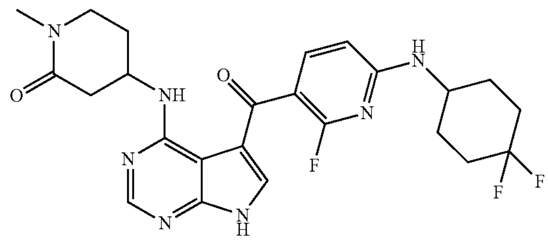 [SMILES: CN1CCC(Nc2ncnc3[nH]cc(C(=O)c4ccc(NC5CCC(F)(F)CC5)nc4F)c23)CC1=O] |
| P-4201 | [6-[(4,4-difluorocyclohexyl)amino]-2-fluoro-3-pyridyl]-[4-[(1,1-dioxothian-3-yl)amino]-7H-pyrrolo[2,3-d]pyrimidin-5-yl]methanone | 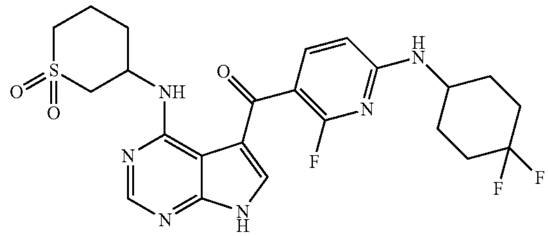 [SMILES: O=C(c1ccc(NC2CCC(F)(F)CC2)nc1F)c1c[nH]c2ncnc(NC3CCCS(=O)(=O)C3)c12] |
| P-4202 | 1-cyclopropyl-4-[[5-[6-[(4,4-difluorocyclohexyl)amino]-2-fluoro-pyridine-3-carbonyl]-7H-pyrrolo[2,3-d]pyrimidin-4-yl]amino]pyrrolidin-2-one | 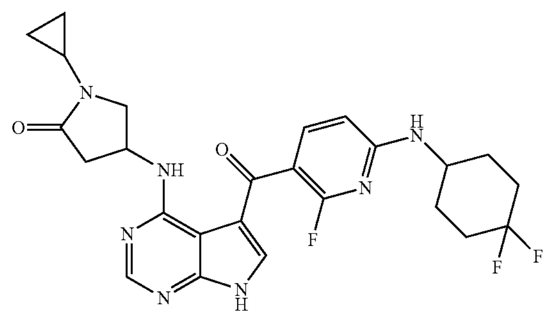 [SMILES: O=C(c1ccc(NC2CCC(F)(F)CC2)nc1F)c1c[nH]c2ncnc(NC3CC(=O)N(C4CC4)C3)c12] |

Example 16

Compound Properties

While the inhibitory activity of the compounds on any of Fms, Kit, Flt-3, TrkA, TrkB and TrkC kinase is important to their activity in treating of disease, the compounds described herein show favorable properties that provide advantages as a pharmaceutical as well. In some instances, Fms selectivity relative to Kit and other kinases provides preferred activity for treating certain diseases, such as rheumatoid arthritis, Alzheimer's disease, Parkinson's disease, osteoarthritis, glomerulonephritis, interstitial nephritis, Lupus nephritis, tubular necrosis, diabetic nephropathy, or renal hypertrophy. In some instances, Fms selectivity of compounds in combination with the compounds inability to cross the blood brain barrier provides preferred activity for treating certain diseases, such as osteoarthritis, glomerulonephritis, interstitial nephritis, Lupus nephritis, tubular necrosis, diabetic nephropathy, or renal hypertrophy. In some instances, Fms selectivity of compounds in combination with the compounds ability to effectively cross the blood brain barrier provides preferred activity for treating certain diseases, such as rheumatoid arthritis, Alzheimer's disease, or Parkinson's disease. In some instances, dual Fms/Kit activity provides preferred activity for treating certain diseases, such as breast cancer, prostate cancer, multiple myeloma, melanoma, acute myeloid leukemia, brain metastases, neurofibromatosis, gastrointestinal stromal tumors, rheumatoid arthritis, or multiple sclerosis. In some instances, dual Fms/Flt-3 activity provides preferred activity for treating certain diseases, such as acute myeloid leukemia. In addition to demonstrating kinase inhibitory activity against Fms, Kit, Flt-3 or at least both Fms and Kit or at least both Fms and Flt-3 in both biochemical and cell based assays, compounds have improved solubility, improved pharmacokinetic properties, and low Cyp inhibition. The compounds are assessed in the following assays or similar assays available to one skilled in the art.

Assays for biochemical and cell based activity are known in the art, for example, U.S. Patent Application Publication Number 2009/0076046, the disclosure of which is hereby incorporated by reference as it relates to such assays. For example, in one assay the biochemical activity $IC_{50}$ values are determined with respect to inhibition of c-Kit kinase activity, where inhibition of phosphorylation of a peptide substrate is measured as a function of compound concentration. Compounds to be tested are dissolved in DMSO to a concentration of 20 mM. These are diluted 30 μL into 120 μL of DMSO (4 mM) and 1 μL is added to an assay plate. These are then serially diluted 1:2 (50 μL to 100 μL DMSO) for a total of 8 points. Plates are prepared such that each kinase reaction is 20 μL in 1× kinase buffer (25 mM HEPES, pH 7.5, 2 mM $MgCl_2$, 2 mM $MnCl_2$, 0.01% Tween-20, 1 mM DTT, 0.01% BSA), 5% DMSO and 100 μM ATP. Substrate is 30 nM biotin-(E4Y) 10 (Millipore). C-kit kinase (obtained from Millipore (#14-559) or is prepared as described in U.S. Patent Application Publication Number 2009/0076046, the disclosure of which is hereby incorporated by reference as it relates to this assay) is at 0.75 ng per sample. After incubation of the kinase reaction for 1 hour at room temperature, 5 μL of donor beads (Streptavidin coated beads (Perkin Elmer Life Science) final concentration 10 µg/mL) in stop buffer (25 mM Hepes pH 7.5, 100 mM EDTA, 0.01% BSA) is added, the sample is mixed and incubated for 20 minutes at room temperature before adding 5 µL of acceptor beads (PY20 coated beads (Perkin Elmer Life Science) final concentration 10 µg/mL) in stop buffer. The samples are incubated for 60 minutes at room temperature and the signal per well is read on Envision reader. Phosphorylated substrate results in binding of the PY20 antibody and association of the donor and acceptor beads such that signal correlates with kinase activity. The signal vs. compound concentration is used to determine the $IC_{50}$.

In one assay the biochemical activity $IC_{50}$ values are determined with respect to inhibition of Fms kinase activity, where inhibition of phosphorylation of a peptide substrate is measured as a function of compound concentration. Compounds to be tested, dissolved in DMSO (1 µL), are added to a white 384-well plate (Costar #3705). Working stocks of Fms kinase (Invitrogen #PV3249), biotin-$(E4Y)_{10}$ substrate (Upstate Biotech, Cat#12-440), and ATP (Sigma, Cat#A-3377) are prepared in 25 mM Hepes pH 7.5, 0.5 mM $MgCl_2$, 2 mM $MnCl_2$, 2 mM DTT, 0.01% BSA, and 0.01% Tween-20. All components are added to the 384-well plate for a final concentration of 1 ng/well Fms, 30 nM biotin-$(E4Y)_{10}$ (Upstate Biotechnology) and 100 µM ATP in a volume of 20 µL. Each sample is at 5% DMSO. The plate is then incubated for 20 minutes at 30° C. Just before use, working stocks of donor and acceptor beads from the AlphaScreen PY20 Detection Kit (PerkinElmer, Cat#676601M) are prepared in 25 mM Hepes pH 7.5, pH 7.4, 100 mM EDTA, 0.01% BSA. To stop the reaction, the plate is uncovered in the dark and 5 µL of Donor Beads solution (Streptavidin beads) is added to each well. The plate is incubated at room temperature for 20 minutes. Five microliters of Acceptor Beads solution (PY20 coated beads) are then added to each well. The final concentration of each bead is 10 µg/mL. The plates are incubated at room temperature for 60 minutes. Fluorescence signal is recorded on the Envision reader. Phosphorylated substrate results in binding of the PY20 antibody and association of the donor and acceptor beads such that signal correlates with kinase activity. The signal vs. compound concentration is used to determine the $IC_{50}$.

In one assay the biochemical activity $IC_{50}$ values are determined with respect to inhibition of Flt-3 kinase activity, where inhibition of phosphorylation of a peptide substrate is measured as a function of compound concentration. Compounds to be tested, dissolved in DMSO (1 µL), are added to a white 384-well plate (Costar #3705). Working stocks of Flt-3 kinase (Invitrogen), biotin-$(E4Y)_{10}$ substrate (Upstate Biotech, Cat#12-440), and ATP (Sigma, Cat#A-3377) are prepared in 25 mM Hepes pH 7.5, 5 mM $MgCl_2$, 5 mM $MnCl_2$, 1 mM DTT, and 0.01% Tween-20. All components are added to the 384-well plate for a final concentration of 1 ng/well Flt-3, 30 nM biotin-$(E4Y)_{10}$ and 100 µM ATP in a volume of 20 µL. Each sample is at 5% DMSO. The plate is then incubated for 1 hour at room temperature. Just before use, working stocks of donor and acceptor beads from the AlphaScreen PY20 Detection Kit (PerkinElmer, Cat#676601M) are prepared in 25 mM Hepes pH 7.5, pH 7.4, 100 mM EDTA. 0.3% BSA. To stop the reaction, the plate is uncovered in the dark and 5 µL of Donor Beads solution (Streptavidin beads) is added to each well. The plate is incubated at room temperature for 20 minutes. Five microliters of Acceptor Beads solution (PY20 coated beads) are then added to each well. The final concentration of each bead is 10 µg/mL. The plates are incubated at room temperature for 60 minutes. Fluorescence signal is recorded on the Envision reader. Phosphorylated substrate results in binding of the PY20 antibody and association of the donor and acceptor beads such that signal correlates with kinase activity. The signal vs. compound concentration is used to determine the $IC_{50}$.

In one assay the biochemical activity $IC_{50}$ values are determined with respect to inhibition of TrkA kinase activity, where inhibition of phosphorylation of a peptide substrate is measured as a function of compound concentration. Compounds to be tested, dissolved in DMSO (1 µL), are added to a white 384-well plate (Costar #3705). Working stocks of TrkA kinase (UBI), biotin-$(E4Y)_{10}$ substrate (Upstate Biotech, Cat#12-440), and ATP (Sigma, Cat#A-3377) are prepared in 25 mM Hepes pH 7.5, 10 mM $MnCl_2$, 1 mM DTT, 0.01% BSA, and 0.01% Tween-20. All components are added to the 384-well plate for a final concentration of 1 ng/well TrkA, 30 nM biotin-$(E4Y)_{10}$ and 100 µM ATP in a volume of 20 µL. Each sample is at 5% DMSO. The plate is shaken for 1 minute at 1200 rpm, spun for 1 minute at 1000 rpm, then incubated for 40 minutes at room temperature. Just before use, working stocks of donor and acceptor beads from the AlphaScreen PY20 Detection Kit (PerkinElmer, Cat#676601M) are prepared in 25 mM Hepes pH 7.5, 100 mM EDTA. 0.01% BSA. Donor Beads solution (Streptavidin beads) is added (5 µL) to each well to final bead concentration of 10 µg/mL. The plate is incubated at room temperature for 20 minutes. Acceptor Beads solution (PY20 coated beads) are then added to each well (5 µL) to a final concentration of bead at 10 µg/mL. The plates are incubated at room temperature for 60 minutes. Fluorescence signal is recorded on the Envision reader. Phosphorylated substrate results in binding of the PY20 antibody and association of the donor and acceptor beads such that signal correlates with kinase activity. The signal vs. compound concentration is used to determine the $IC_{50}$. Similar assays are used for TrkB and Trk C kinase.

Compounds are assessed in a variety of cell based assays. For example BaF3 cells engineered with any of BCR-FMS, BCR-KIT, BCR-FLT3, BCR-NTRK1, BCR-NTRK2, and BCR-NTRK3, are used in cell proliferation assays to assess inhibitory activity of Fms, Kit, Flt-3, TrkA, TrkB, and TrkC, respectively. An MV-4-11 (leukemia) cell proliferation assay is used to assess inhibitory activity in Flt-3, and SKNSH (human neuroblastoma) cell proliferation assay is used to assess efficacy of Fms/Trk inhibitors. Additional cells may be assayed similarly to assess the efficacy of Fms/Trk inhibitors, such as MiaPaCa (human pancreatic cancer) and Capan-1 (human pancreatic carcinoma) cells. Reagent and assay conditions are as follows:

BaF3 cells:
    Maintained in RPMI containing 10% FBS, 1% PenStrep, 1% NEAA, and 1% L-Glutamine, supplemented with 1 mg/mL G418 and 5% WEHI-CM (or recombinant murine IL-3).
    Confluent cells are split 1:50 to 1:100 every 3-4 days.
MV-4-11 cells:
    Maintained in Iscove's Modified Dulbecco's Medium containing 10% FBS.
    Confluent cells are split 1:4 every 3-4 days.
    SKNSH cells: RPMI containing 10% FBS.
On day 1, cells are counted, then centrifuged in a conical tube for 5 minutes at 1000 rpm. The supernatant is removed and cells are re-suspended as follows:
    BaF3: resuspend in growth media +1 mg/mL G418 (without WEHFIL-3) to $2\times10^5$ cells/mL.
    MV-4-11: resuspend in growth media to $5\times10^5$ cells/mL.
    SKNSH: resuspend in growth media to $2\times10^4$ cells/mL.

The cells are plated (50 μL, 150 μL for SKNSH cells) in each well of a 96-well dish (Corning 3610) and incubated at 37° C. in 5% $CO_2$ overnight, cells plated to a final concentration of cells as follows:
  BaF3: 10,000 cells per well.
  MV-4-11: 25,000 cells per well.
  SKNSH: 3,000 cells per well.
On day 2, compound at a maximum concentration of 5 mM is serially diluted 1:3 for a total of 8 point titration with DMSO as a control. A 1 μL aliquot of each dilution point is added to 249 μL growth media and 50 μL is added to a well containing cells, providing 10 μM compound for the maximum concentration point. The cells are incubated for 3 days at 37° C. in 5% $CO_2$. For SKNSH cells, a 0.75 μL aliquot of appropriate dilution in DMSO is added to 150 μL of cells.
On day 5, ATPlite 1 step Luminescence Assay System (Perkin Elmer #6016739) is brought to room temperature along with the cell cultures. ATPlite is added to each well as follows:
  BaF3: 25 μL per well.
  MV-4-11: 40 μL per well.
  SKNSH: 20 μL per well.
The cells are incubated at room temperature for 10 minutes, then luminescence is read on Safire reader. The measured luminescence correlates directly with cell number, such that the reading as a function of compound concentration is used to determine the $IC_{50}$ value.

Further, an osteoclast differentiation assay is used to assess the efficacy of Fms inhibitors for treating bone disease such as osteoarthritis. On day 0, Osteoclast Medium BulletKit (Lonza catalog #PT-8001, containing Media, FBS, L-Glutamine, PenStrep, RANKL, and M-CSF) media is thawed and the FBS, L-glutamine and PenStrep from the kit is added to 100 mL of Osteoclast Precursor Basal medium to provide the Osteoclast Precursor Growth Medium (OPGM). This is warmed to 37° C. Osteoclast precursor cells (Lonza catalog #2T-110) frozen in cryovial are warmed to 37° C. and transferred to a 50 mL conical tube. The cryovial is rinsed with OPGM and added dropwise to the conical tube of cells with swirling, then the volume is adjusted to 20-30 mL with addition of OPGM. The cells are centrifuged at 200×g for 15 minutes at room temperature and all but approximately 3 mL of supernatant is removed to a new conical tube. The cells are suspended in the remaining supernatant and the volume is adjusted to 10-15 mL with OPGM added dropwise with swirling. The cells are centrifuged at 200×g for 15 minutes at room temperature and all but approximately 1 mL of supernatant is removed. The cells are resuspended in the remaining supernatant, counted, and the volume adjusted with an appropriate amount of OPGM to provide approximately $1\times10^5$ cells/mL. A 0.1 mL aliquot of cells is added to each well of a 96-well plate. Compound to be tested is prepared in DMSO for plating at a high concentration of 2.5 mM, with 8 point 1:3 serial dilutions. A 1 μL aliquot of each compound dilution is added to a 96 well v-bottom polypropylene plate and 0.124 mL of OPGM is added to the compound. Then 50 μL at of the compound in OPGM is added to the osteoclast precursor cells in 96-well plate (providing highest test concentration of 5 μM). RANKL (2 μg) from the BulletKit is reconstituted in 1 mL of OPGM, then vortexed and centrifuged briefly. A 792 μL at aliquot of RANKL is added to 6 mL of OPGM and 50 μL at is added to low control wells. Then 76.6 μL M-CSF (10 μg/mL) from the BulletKit is added to the remaining 5.8 mL of OPGM/RANKL solution (4×RANKL/M-CSF/OPGM). A 50 μL at aliquot of this is added to the remaining wells, and the remainder is stored at 4° C. for later use. The plate is incubated at 37° C. for 6 days, then the remaining OPGM/RANKL/M-CSF solution is warmed to 37° C. The remaining approximately 198 μL is combined with 6 mL of OPGM. The media is aspirated from the osteoclast wells and 100 μL of RANKL/OPGM is added to the low controls. The remaining RANKL/OPGM is combined with the approximately 18.5 μL of remaining M-CSF. The remaining 4×RANKL/M-CSF/OPGM from day 0 is diluted to 1× and combined with the freshly prepared solution. A 0.1 mL aliquot of this is added to each osteoclast well and incubated for 37° C. for 1 day. The Acid Phosphatase kit (Cayman Chemical catalog #10008051) is warmed to room temperature. The assay buffer is diluted 5 mL with 45 mL of water. For each plate, two substrate tablets are dissolved in 4.5 mL of the assay buffer, mixing by vortex to break up the tablet. Stop solution is diluted 12 mL with 36 mL of water. In a tissue culture hood, 20 μL of each osteoclast well supernatant is transferred to a 96 well plate. A 30 μL aliquot of the substrate solution is added to each well and incubated at 37° C. for 20 minutes, then added 100 μL stop solution to each well. The absorbance of each well is read at 405 nM on Safire plate reader. The absorbance reading is plotted vs. concentration to provide the $IC_{50}$ for each compound.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition at or below the threshold of the highest concentration tested does not necessarily indicate that the compound has no inhibitory activity on the cells, only that under the conditions tested, no inhibition is observed. Results for compounds that are tested and show substantially no inhibition below the highest tested concentration are represented as "-" in the tables below. In some instances, the compounds were not tested in all of the assays, or assay results were not valid, as indicated by NA in the tables below.

The following table indicates the Fms, Kit, Flt3, TrkA, and TrkC biochemical inhibitory activity for the exemplary compounds indicated:

| Compound number | Biochemical Inhibition $IC_{50}$ (μM) | | | | |
| --- | --- | --- | --- | --- | --- |
| | Fms | Kit | Flt3 | TrkA | TrkC |
| P-3001 | <0.1 | <1 | NA | NA | NA |
| P-3003 | <1 | >1 | NA | NA | NA |
| P-3004 | <0.01 | <1 | >1 | NA | NA |
| P-3005 | <1 | >1 | NA | NA | NA |
| P-3006 | <0.01 | <1 | NA | NA | NA |
| P-3007 | <1 | >1 | NA | NA | NA |
| P-3008 | <0.1 | <1 | NA | NA | NA |
| P-3009 | <0.1 | NA | NA | NA | NA |
| P-3010 | <0.01 | <0.1 | <0.1 | <1 | NA |
| P-3011 | <0.01 | <0.01 | <0.01 | >1 | NA |
| P-3012 | <0.01 | <0.01 | <0.1 | >1 | NA |
| P-3013 | <0.01 | <1 | >1 | NA | NA |
| P-3014 | <0.01 | <0.1 | <1 | >1 | NA |
| P-3015 | <0.01 | <1 | <0.1 | >1 | NA |

| Compound number | Biochemical Inhibition IC$_{50}$ (μM) | | | | |
|---|---|---|---|---|---|
| | Fms | Kit | Flt3 | TrkA | TrkC |
| P-3016 | <0.1 | <0.1 | <0.1 | >1 | NA |
| P-3017 | <0.1 | <1 | <0.1 | >1 | NA |
| P-3018 | <0.01 | <0.01 | <0.01 | <1 | NA |
| P-3019 | <0.01 | <1 | <1 | <0.1 | <0.1 |
| P-3020 | <0.01 | <0.01 | <0.01 | <0.1 | <1 |
| P-3021 | <0.01 | <0.01 | <0.01 | <0.1 | <1 |
| P-3022 | <0.1 | <0.1 | <0.1 | <1 | <1 |
| P-3023 | <0.1 | <0.1 | NA | NA | NA |
| P-3024 | <0.1 | <0.01 | <0.01 | <1 | >1 |
| P-3025 | <0.1 | <0.01 | <0.01 | <0.1 | <0.01 |
| P-3026 | <0.01 | <0.01 | <0.1 | >1 | <0.1 |
| P-3027 | <0.01 | <0.01 | <0.01 | <1 | <0.1 |
| P-3028 | >1 | <1 | NA | <0.1 | <0.1 |
| P-3029 | <0.1 | <1 | NA | <1 | <1 |
| P-3030 | <0.1 | <0.1 | NA | <0.01 | <0.01 |
| P-3031 | <1 | <0.1 | NA | <0.1 | <0.1 |
| P-3032 | >1 | <1 | NA | >1 | >1 |
| P-3033 | <0.1 | <0.01 | NA | <0.01 | <0.1 |
| P-3034 | <0.1 | <0.1 | NA | <1 | <1 |
| P-3035 | <1 | <0.1 | <0.1 | <1 | <1 |
| P-3036 | <0.01 | <0.1 | <0.1 | <1 | <1 |
| P-3037 | >1 | <1 | NA | NA | NA |
| P-3038 | <1 | <1 | NA | NA | NA |
| P-3039 | <0.01 | <0.1 | <0.1 | <0.1 | NA |
| P-3040 | <0.1 | >1 | <0.1 | <0.01 | NA |
| P-3041 | <0.01 | <1 | <1 | <1 | NA |
| P-3042 | <0.01 | <0.1 | <1 | <0.1 | NA |
| P-3043 | <0.01 | <1 | <1 | <1 | NA |
| P-3044 | <0.01 | <1 | <1 | <0.1 | NA |
| P-3045 | <0.01 | <1 | <0.1 | <0.01 | NA |
| P-3048 | <0.01 | <0.1 | NA | <0.01 | NA |
| P-3049 | <0.01 | <0.1 | NA | <0.01 | NA |
| P-3050 | <0.1 | <0.1 | NA | <0.1 | NA |
| P-3051 | <0.01 | <0.1 | NA | <0.01 | NA |
| P-3052 | <0.1 | <0.1 | NA | <0.01 | NA |
| P-3053 | <0.01 | <0.1 | NA | <0.1 | NA |
| P-4001 | <0.01 | <1 | <1 | <0.1 | <0.01 |
| P-4002 | <0.1 | <1 | NA | <0.1 | <1 |
| P-4003 | <0.1 | <1 | <1 | <1 | NA |
| P-4004 | <0.1 | <0.1 | <0.01 | <0.1 | NA |
| P-4005 | <0.01 | <0.1 | <0.1 | <0.1 | NA |
| P-4006 | <0.01 | <0.1 | <0.1 | <0.1 | NA |
| P-4007 | <0.01 | <0.1 | <0.1 | <0.01 | NA |
| P-4008 | <0.01 | <1 | <0.1 | <0.01 | NA |
| P-4009 | <0.01 | <0.1 | <0.1 | <0.01 | NA |
| P-4010 | <0.01 | <1 | <1 | <1 | NA |
| P-4011 | <0.01 | <1 | <1 | <1 | NA |
| P-4012 | <0.01 | <1 | <1 | <0.1 | NA |
| P-4013 | <0.01 | <1 | >1 | <1 | NA |
| P-4014 | <0.01 | <0.1 | <1 | >1 | NA |
| P-4015 | <0.1 | <0.1 | >1 | >1 | NA |
| P-4016 | <0.01 | <0.1 | <0.01 | <0.01 | NA |
| P-4017 | <0.01 | <0.1 | <0.1 | <0.1 | NA |
| P-4018 | <0.01 | <0.1 | <0.1 | <0.1 | NA |
| P-4019 | <0.01 | <1 | <0.1 | <0.1 | NA |
| P-4020 | <0.01 | <0.1 | <0.1 | <0.01 | NA |
| P-4021 | <0.1 | <1 | >1 | <1 | NA |
| P-4022 | <0.1 | <1 | <0.1 | <0.01 | NA |
| P-4023 | <0.01 | <1 | <1 | <0.1 | NA |
| P-4024 | <1 | <1 | <0.1 | <0.1 | NA |
| P-4025 | <1 | >1 | <1 | <0.1 | NA |
| P-4026 | <0.01 | <1 | <0.1 | <0.01 | NA |
| P-4027 | <0.1 | <0.1 | <0.01 | <0.01 | NA |
| P-4028 | <0.01 | <0.1 | <0.1 | <0.01 | NA |
| P-4029 | <0.01 | <0.1 | <0.01 | <0.01 | NA |
| P-4030 | <0.01 | <1 | <1 | <0.1 | NA |
| P-4031 | <0.1 | <0.1 | <0.1 | <0.1 | NA |
| P-4032 | <0.1 | <0.1 | <0.1 | <0.1 | NA |
| P-4036 | <0.01 | <1 | >1 | <0.1 | NA |
| P-4037 | <0.1 | <1 | <1 | <0.1 | NA |
| P-4038 | <0.1 | <1 | NA | <0.1 | NA |
| P-4039 | <1 | <1 | NA | <0.1 | NA |
| P-4040 | <0.1 | <0.1 | NA | <0.01 | NA |
| P-4041 | <0.1 | <0.1 | NA | <0.01 | NA |
| P-4046 | <0.1 | <1 | NA | <1 | NA |
| P-4047 | >1 | >1 | NA | >1 | NA |
| P-4048 | <0.01 | <0.01 | NA | <0.01 | NA |
| P-4049 | <0.01 | <1 | NA | <0.01 | NA |
| P-4050 | <1 | <1 | NA | <1 | NA |
| P-4051 | <1 | <1 | NA | <0.01 | NA |
| P-4052 | <1 | >1 | NA | <1 | NA |
| P-4053 | <0.01 | <1 | NA | <0.01 | NA |
| P-4054 | <0.01 | >1 | NA | <0.1 | NA |
| P-4055 | <0.1 | <1 | NA | NA | NA |
| P-4056 | <0.1 | <0.1 | NA | NA | NA |
| P-4057 | <0.1 | >1 | NA | <1 | NA |
| P-4058 | <0.1 | >1 | NA | <1 | NA |
| P-4059 | <0.1 | <1 | NA | <0.1 | NA |
| P-4060 | <0.01 | <0.1 | NA | <0.01 | NA |
| P-4061 | <0.1 | >1 | NA | <0.1 | NA |
| P-4062 | <0.01 | <0.1 | NA | <0.01 | NA |
| P-4063 | <0.01 | <1 | NA | <0.01 | NA |
| P-4064 | <0.01 | <0.1 | NA | <0.01 | NA |
| P-4065 | <0.01 | <0.1 | NA | <0.01 | NA |
| P-4066 | <0.01 | <0.1 | NA | <0.01 | NA |
| P-4067 | <0.01 | <1 | NA | <0.01 | NA |
| P-4068 | <0.01 | <0.1 | NA | <0.01 | NA |
| P-4069 | <1 | >1 | NA | <0.1 | NA |
| P-4070 | >1 | >1 | NA | >1 | NA |
| P-4071 | <1 | >1 | NA | <0.01 | NA |
| P-4072 | <0.1 | >1 | NA | <0.1 | NA |
| P-4073 | <0.1 | <1 | NA | <0.01 | NA |
| P-4074 | <0.1 | <1 | NA | <0.01 | NA |
| P-4075 | <0.01 | <1 | NA | <0.01 | NA |
| P-4076 | <0.01 | <0.1 | NA | <0.01 | NA |
| P-4077 | <0.1 | <1 | NA | <0.01 | NA |
| P-4078 | <0.01 | <1 | NA | <0.01 | NA |
| P-4079 | <0.01 | <0.1 | NA | <0.01 | NA |
| P-4080 | <0.01 | <1 | NA | <0.01 | NA |
| P-4081 | <0.01 | <0.1 | NA | <0.01 | NA |
| P-4082 | <0.1 | <1 | NA | <0.01 | NA |
| P-4083 | <0.01 | <0.1 | NA | <0.01 | NA |
| P-4084 | <0.01 | <0.1 | NA | <0.01 | NA |
| P-4085 | <0.01 | <0.1 | NA | <0.01 | NA |
| P-4086 | <1 | <1 | NA | <0.1 | NA |
| P-4087 | <0.1 | <0.1 | NA | <0.01 | NA |
| P-4088 | <0.1 | <1 | NA | <0.01 | NA |
| P-4089 | <0.1 | <0.1 | NA | <0.1 | NA |
| P-4090 | <0.1 | <1 | NA | <0.1 | NA |
| P-4091 | <0.1 | <0.1 | NA | <0.01 | NA |
| P-4092 | <0.01 | <0.1 | NA | <0.01 | NA |
| P-4093 | <0.01 | <0.1 | NA | <0.01 | NA |
| P-4094 | <0.01 | <0.01 | NA | <0.01 | NA |
| P-4095 | <0.01 | <0.1 | NA | <0.01 | NA |
| P-4096 | <0.1 | <1 | NA | <0.1 | NA |
| P-4097 | <1 | <1 | NA | <0.1 | NA |
| P-4098 | <0.01 | <0.1 | NA | <0.01 | NA |
| P-4099 | <0.1 | <0.1 | NA | <0.1 | NA |
| P-4100 | <0.1 | <0.1 | NA | <0.1 | NA |
| P-4101 | <0.1 | <1 | NA | <0.1 | NA |
| P-4102 | <0.1 | <1 | NA | <0.1 | NA |
| P-4103 | <1 | <1 | NA | <0.1 | NA |
| P-4104 | <1 | <1 | NA | <0.1 | NA |
| P-4105 | <0.1 | >1 | NA | <0.1 | NA |
| P-4106 | <0.1 | <1 | NA | <0.01 | NA |
| P-4107 | <0.1 | <0.1 | NA | <0.01 | NA |
| P-4108 | <0.1 | <1 | NA | <0.1 | NA |
| P-4109 | <0.1 | <1 | NA | <0.1 | NA |
| P-4110 | <0.1 | <1 | NA | <1 | NA |
| P-4111 | <0.1 | <1 | NA | <0.1 | NA |
| P-4112 | <0.1 | <1 | NA | <0.1 | NA |
| P-4113 | <0.01 | <0.1 | NA | <0.01 | NA |
| P-4114 | <0.01 | <0.1 | NA | <0.01 | NA |
| P-4115 | <0.01 | <0.1 | NA | <0.01 | NA |
| P-4116 | <0.1 | <0.1 | NA | <0.01 | NA |
| P-4117 | <0.01 | <0.1 | NA | <0.01 | NA |
| P-4118 | <0.1 | <0.1 | NA | <0.01 | NA |
| P-4119 | <0.01 | <0.01 | NA | <0.01 | NA |
| P-4120 | <0.1 | <0.1 | NA | <0.1 | NA |
| P-4121 | <0.1 | <0.01 | NA | <0.1 | NA |

| Compound | Biochemical Inhibition IC$_{50}$ (μM) | | | | |
|---|---|---|---|---|---|
| number | Fms | Kit | Flt3 | TrkA | TrkC |
| P-4122 | <0.01 | <0.01 | NA | <0.01 | NA |
| P-4123 | <0.01 | <0.01 | NA | <0.01 | NA |
| P-4124 | <0.01 | <0.01 | NA | <0.01 | NA |
| P-4125 | <0.1 | <0.1 | NA | <0.01 | NA |
| P-4126 | <0.01 | <0.1 | NA | <0.01 | NA |
| P-4127 | <0.1 | <1 | NA | <0.1 | NA |
| P-4128 | <0.1 | >1 | NA | <1 | NA |
| P-4129 | <0.1 | <1 | NA | <1 | NA |
| P-4130 | <0.01 | <1 | NA | <0.01 | NA |

The following table indicates the inhibition of cell proliferation for BCR-FMS, BCR-KIT, BCR-FLT3, BCR-NTRK1, BCR-NTRK2 and BCR-NTRK3 BaF3 cells, MV-4-11 cells and SKNSH cells for the exemplary compounds indicated:

| Comp. | Inhibition of Cell Proliferation IC$_{50}$ (μM) | | | | | | |
|---|---|---|---|---|---|---|---|
| | BCR/BaF3 | | | | | | |
| number | Fms | Kit | TrkA | TrkB | TrkC | MV-4-11 | SKNSH |
| P-3001 | <0.1 | >1 | — | — | — | NA | NA |
| P-3003 | <1 | >1 | NA | NA | NA | NA | NA |
| P-3004 | <0.1 | >1 | <10 | <10 | <10 | <10 | NA |
| P-3005 | <1 | >1 | — | — | — | NA | NA |
| P-3006 | <1 | >1 | <20 | — | — | NA | NA |
| P-3007 | <1 | — | — | — | — | NA | NA |
| P-3008 | <0.1 | >1 | NA | NA | NA | NA | NA |
| P-3009 | <1 | >1 | — | — | — | NA | NA |
| P-3010 | <0.1 | <1 | — | — | — | NA | NA |
| P-3011 | <0.1 | <0.1 | <1 | <1 | <0.1 | NA | NA |
| P-3012 | <0.1 | <1 | <1 | <1 | <1 | NA | NA |
| P-3013 | <0.1 | >1 | — | — | — | <10 | NA |
| P-3014 | <0.1 | >1 | — | — | — | NA | NA |
| P-3015 | <1 | >1 | — | — | — | NA | NA |
| P-3016 | <1 | >1 | — | — | — | NA | NA |
| P-3017 | <1 | >1 | — | — | — | NA | NA |
| P-3018 | <0.1 | <0.1 | <1 | <0.1 | <0.1 | <0.01 | NA |
| P-3019 | <0.01 | <1 | <0.1 | <0.1 | <0.1 | <1 | <10 |
| P-3020 | <0.01 | <0.1 | <0.1 | <0.1 | <0.1 | <0.1 | <1 |
| P-3021 | <0.01 | <0.1 | <1 | <0.1 | <0.1 | NA | <1 |
| P-3022 | <0.1 | <0.1 | <1 | <1 | <1 | NA | NA |
| P-3023 | <0.1 | <0.1 | <1 | <1 | <1 | <0.1 | NA |
| P-3024 | <0.01 | <0.1 | <1 | <1 | <0.1 | NA | <1 |
| P-3025 | <0.01 | <0.01 | <0.01 | <0.01 | <0.01 | NA | <1 |
| P-3026 | <0.01 | <0.1 | <0.1 | <0.1 | <0.1 | NA | — |
| P-3027 | <0.01 | <0.1 | <0.1 | <1 | <0.1 | <0.01 | — |
| P-3028 | <1 | <0.1 | <0.1 | <1 | <0.1 | NA | <20 |
| P-3029 | <0.1 | <1 | >1 | >1 | <1 | NA | — |
| P-3030 | <0.01 | <0.01 | <0.01 | <0.01 | <0.01 | NA | <0.1 |
| P-3031 | <0.01 | <0.01 | <0.01 | <0.01 | <0.01 | NA | <0.1 |
| P-3032 | <1 | <1 | <1 | >1 | <1 | NA | <1 |
| P-3033 | <0.01 | <0.01 | <0.1 | <0.1 | <0.1 | NA | <1 |
| P-3034 | <0.01 | <0.1 | <1 | <1 | <0.1 | NA | <1 |
| P-3035 | <0.1 | <1 | <1 | <1 | <0.1 | <1 | <1 |
| P-3036 | <0.01 | <0.1 | <1 | <1 | <1 | <0.1 | <20 |
| P-3037 | >1 | >1 | >1 | — | >1 | NA | — |
| P-3038 | <1 | <1 | <1 | >1 | <1 | >1 | — |
| P-3039 | <0.01 | <1 | <1 | <1 | <0.1 | <1 | >1 |
| P-3040 | <0.1 | >1 | <0.1 | <0.01 | <0.01 | NA | >1 |
| P-3041 | <0.01 | <1 | <1 | <1 | <0.1 | NA | >1 |
| P-3042 | <0.1 | <1 | <1 | <1 | <0.1 | NA | >1 |
| P-3043 | <0.1 | <1 | <0.1 | <0.1 | <0.1 | NA | <1 |
| P-3044 | <0.1 | <1 | <1 | <1 | <0.1 | NA | >1 |
| P-3045 | <0.1 | <1 | <0.1 | <0.01 | <0.1 | NA | — |
| P-3048 | <0.01 | <0.1 | <0.1 | NA | NA | NA | NA |
| P-3049 | <0.01 | <0.1 | <0.01 | NA | NA | NA | NA |
| P-3050 | <0.1 | <1 | <0.1 | NA | NA | NA | NA |
| P-3051 | <0.1 | <1 | <0.1 | NA | NA | NA | NA |
| P-3052 | <0.1 | NA | <0.1 | NA | <0.01 | NA | NA |
| P-3053 | <0.01 | NA | <0.1 | NA | <0.01 | NA | NA |

| Comp. | Inhibition of Cell Proliferation IC$_{50}$ (μM) | | | | | | |
|---|---|---|---|---|---|---|---|
| | BCR/BaF3 | | | | | | |
| number | Fms | Kit | TrkA | TrkB | TrkC | MV-4-11 | SKNSH |
| P-4001 | <0.01 | <1 | <0.1 | <0.1 | <0.01 | <1 | <1 |
| P-4002 | <0.1 | <1 | <1 | <1 | <0.1 | NA | <0.1 |
| P-4003 | <0.1 | <1 | <1 | <1 | <0.1 | <1 | >1 |
| P-4004 | <0.01 | <0.1 | <0.01 | <0.01 | <0.01 | <1 | <1 |
| P-4005 | <0.01 | <0.1 | <0.1 | <0.01 | <0.01 | <1 | <1 |
| P-4006 | <0.01 | <0.1 | <0.1 | <0.01 | <0.01 | <0.1 | <0.1 |
| P-4007 | <0.01 | <1 | <0.01 | <0.1 | <0.01 | <1 | <1 |
| P-4008 | <0.01 | <1 | <0.1 | <0.1 | <0.1 | <0.1 | >1 |
| P-4009 | <0.01 | <1 | <0.1 | <0.01 | <0.01 | <0.1 | <0.1 |
| P-4010 | <0.01 | <1 | <1 | <0.1 | <0.1 | <1 | <1 |
| P-4011 | <0.01 | >1 | <1 | <1 | <1 | <1 | >1 |
| P-4012 | <0.01 | <1 | <1 | <0.1 | <0.1 | <1 | >1 |
| P-4013 | <0.01 | <1 | <1 | <1 | <1 | <1 | >1 |
| P-4014 | <0.1 | >1 | <1 | <1 | <1 | <1 | >10 |
| P-4015 | <0.01 | >1 | <1 | <1 | <0.1 | <1 | >1 |
| P-4016 | <0.01 | <0.1 | <0.1 | <0.1 | <0.1 | <0.1 | >1 |
| P-4017 | <0.01 | <1 | <1 | <1 | <0.1 | <1 | <1 |
| P-4018 | <0.01 | <1 | <0.1 | <0.1 | <0.01 | <1 | <1 |
| P-4019 | <0.01 | <1 | <1 | <0.1 | <0.1 | <1 | >1 |
| P-4020 | <1 | <1 | <1 | <0.1 | <0.1 | NA | <1 |
| P-4021 | <1 | >1 | >1 | <1 | <1 | NA | <1 |
| P-4022 | <0.1 | <1 | <0.01 | <0.01 | <0.01 | NA | <1 |
| P-4023 | <0.01 | <1 | <0.1 | <0.1 | <0.01 | NA | <1 |
| P-4024 | <0.1 | <1 | <0.1 | <0.1 | <0.1 | NA | >1 |
| P-4025 | <0.1 | >1 | <0.1 | <0.1 | <0.1 | NA | >1 |
| P-4026 | <0.01 | <1 | <0.1 | <0.01 | <0.01 | NA | NA |
| P-4027 | <0.1 | <1 | <0.1 | <0.01 | <0.01 | NA | NA |
| P-4028 | <0.01 | <1 | <0.01 | <0.01 | <0.01 | NA | NA |
| P-4029 | <0.1 | <0.1 | <0.01 | <0.01 | <0.01 | NA | NA |
| P-4030 | <0.01 | <1 | <1 | <0.1 | <0.1 | NA | NA |
| P-4031 | <0.1 | <1 | <0.1 | <0.01 | <0.01 | NA | NA |
| P-4032 | <0.1 | <1 | <0.1 | <0.1 | <0.1 | NA | NA |
| P-4036 | <0.1 | <1 | <1 | <0.1 | <0.1 | NA | NA |
| P-4037 | <0.1 | <0.1 | <0.1 | NA | NA | NA | NA |
| P-4038 | <0.1 | <1 | <1 | <1 | <0.1 | NA | NA |
| P-4039 | <0.1 | <1 | <0.1 | <0.1 | <0.1 | NA | NA |
| P-4040 | <0.1 | <0.1 | <0.1 | <0.01 | <0.01 | NA | NA |
| P-4041 | <0.01 | <0.1 | <0.01 | <0.01 | <0.01 | NA | NA |
| P-4046 | <0.1 | <1 | <1 | <1 | <1 | NA | <10 |
| P-4047 | >1 | >1 | >1 | >1 | >1 | NA | NA |
| P-4048 | <0.01 | <1 | <1 | <0.01 | <0.01 | NA | <1 |
| P-4049 | <1 | <1 | <1 | <1 | <1 | NA | <1 |
| P-4050 | <1 | >1 | <1 | <1 | <1 | NA | <1 |
| P-4051 | <1 | >1 | <1 | <0.01 | <0.01 | NA | <1 |
| P-4052 | <1 | >1 | <1 | <1 | <0.01 | NA | >1 |
| P-4053 | <1 | <1 | <0.01 | <0.01 | <0.01 | NA | <1 |
| P-4054 | <1 | <1 | <1 | <1 | <0.01 | NA | <10 |
| P-4055 | <1 | >1 | <1 | <0.01 | <0.01 | NA | <1 |
| P-4056 | <1 | >1 | <1 | <0.01 | <0.01 | NA | <1 |
| P-4057 | <1 | >1 | >1 | >1 | <1 | NA | <10 |
| P-4058 | <0.1 | <1 | <1 | <1 | <0.1 | NA | <10 |
| P-4059 | <0.01 | >1 | <1 | <0.1 | <0.1 | NA | <1 |
| P-4060 | <0.01 | <0.1 | <0.1 | <0.01 | <0.01 | NA | <0.1 |
| P-4061 | <0.1 | >1 | <0.1 | <0.1 | <0.1 | NA | NA |
| P-4062 | <0.1 | <1 | <0.01 | <0.01 | <0.01 | NA | <1 |
| P-4063 | <0.1 | <0.1 | <0.01 | <0.1 | <0.01 | NA | <1 |
| P-4064 | <0.1 | <1 | <0.1 | <0.01 | <0.01 | NA | NA |
| P-4065 | <0.1 | <0.1 | <0.1 | <0.01 | <0.01 | NA | <1 |
| P-4066 | <0.01 | <0.01 | <0.01 | <0.01 | <0.01 | NA | NA |
| P-4067 | <0.01 | <0.1 | <0.01 | <0.01 | <0.01 | NA | NA |
| P-4068 | <0.01 | <0.1 | <0.01 | <0.01 | <0.01 | NA | NA |
| P-4069 | >1 | >1 | >1 | >1 | >1 | NA | NA |
| P-4070 | >1 | >1 | >1 | >1 | >1 | NA | NA |
| P-4071 | <0.1 | <0.1 | <0.1 | <0.1 | <0.01 | NA | NA |
| P-4072 | <0.1 | <1 | <0.01 | <0.01 | <0.01 | NA | NA |
| P-4073 | <0.1 | <1 | <0.1 | <0.01 | <0.01 | NA | NA |
| P-4074 | <1 | <1 | <0.1 | <0.1 | <0.01 | NA | NA |
| P-4075 | <0.01 | <0.1 | <0.01 | <0.01 | <0.01 | NA | NA |
| P-4076 | <0.1 | <0.1 | <0.01 | <0.01 | <0.01 | NA | NA |
| P-4077 | <0.01 | <0.1 | <0.01 | <0.01 | <0.01 | NA | NA |
| P-4078 | <0.01 | <0.1 | <0.01 | <0.01 | <0.01 | NA | NA |
| P-4079 | <0.1 | <0.1 | <0.01 | <0.01 | <0.01 | NA | NA |
| P-4080 | <0.1 | <0.1 | <0.01 | <0.01 | <0.01 | NA | NA |

-continued

Inhibition of Cell Proliferation IC$_{50}$ (μM)

| Comp. number | BCR/BaF3 | | | | | MV-4-11 | SKNSH |
|---|---|---|---|---|---|---|---|
| | Fms | Kit | TrkA | TrkB | TrkC | | |
| P-4081 | <0.01 | <0.1 | <0.01 | <0.01 | <0.01 | NA | NA |
| P-4082 | <0.01 | <0.1 | <0.01 | <0.01 | <0.01 | NA | NA |
| P-4083 | <0.1 | <0.1 | <0.01 | <0.01 | <0.01 | NA | NA |
| P-4084 | <0.01 | <1 | <0.1 | <0.01 | <0.01 | NA | <10 |
| P-4085 | <1 | >1 | <1 | NA | <0.1 | NA | NA |
| P-4086 | NA | NA | <0.01 | NA | NA | NA | NA |
| P-4087 | <1 | >1 | <1 | <0.1 | <0.01 | NA | NA |
| P-4088 | <0.1 | <1 | <0.1 | <0.1 | <0.01 | NA | NA |
| P-4089 | <0.1 | <1 | <1 | <0.1 | <0.01 | NA | <10 |
| P-4090 | <0.1 | <1 | <0.1 | <0.01 | <0.01 | NA | <1 |
| P-4091 | <0.01 | <0.1 | <0.01 | <0.01 | <0.01 | NA | <0.1 |
| P-4092 | <0.01 | <0.1 | <0.01 | <0.01 | <0.01 | NA | <1 |
| P-4093 | <0.01 | <0.1 | <0.01 | <0.01 | <0.01 | NA | NA |
| P-4094 | <0.1 | <0.1 | <0.01 | <0.01 | <0.01 | NA | <1 |
| P-4095 | <0.01 | <0.1 | <0.01 | <0.01 | <0.01 | NA | <1 |
| P-4096 | <0.01 | <1 | <0.01 | <0.01 | NA | NA | <10 |
| P-4097 | <0.1 | <1 | <0.1 | <0.1 | NA | NA | <10 |
| P-4098 | <0.1 | <0.1 | <0.01 | <0.01 | NA | NA | <10 |
| P-4099 | <0.01 | <0.1 | <0.01 | <0.01 | NA | NA | <1 |
| P-4100 | <0.1 | <1 | <0.01 | <0.01 | NA | NA | <1 |
| P-4101 | <0.01 | <1 | <0.1 | <0.01 | NA | NA | <1 |
| P-4102 | <0.01 | <1 | <1 | <0.1 | NA | NA | <1 |
| P-4103 | <0.1 | >1 | <1 | >1 | >1 | NA | >1 |
| P-4104 | <0.1 | >1 | <0.1 | <0.1 | <0.1 | NA | <1 |
| P-4105 | <0.1 | >1 | <0.1 | <1 | <1 | NA | <10 |
| P-4106 | <0.1 | <1 | <0.1 | <0.1 | <0.01 | NA | <1 |
| P-4107 | <0.1 | <1 | <0.1 | <0.1 | <0.01 | NA | <1 |
| P-4108 | <0.1 | >1 | <1 | <1 | <0.1 | NA | >1 |
| P-4109 | <0.1 | <1 | <1 | <1 | NA | NA | <10 |
| P-4110 | <0.1 | <1 | >1 | >1 | NA | NA | <10 |
| P-4111 | <0.1 | <1 | <0.01 | <0.01 | <0.01 | NA | NA |
| P-4112 | <0.1 | >1 | <0.1 | <0.1 | <0.01 | NA | <10 |
| P-4113 | <0.01 | <1 | <0.1 | NA | NA | NA | NA |
| P-4114 | <0.01 | <1 | <0.01 | NA | NA | NA | NA |
| P-4115 | <0.01 | <1 | <0.1 | <0.1 | <0.01 | NA | NA |
| P-4116 | <0.01 | <0.1 | <0.01 | <0.01 | <0.01 | NA | NA |
| P-4117 | <0.01 | <0.1 | <0.01 | <0.01 | <0.01 | NA | NA |
| P-4118 | <0.01 | <0.1 | <0.01 | <0.01 | <0.01 | NA | NA |
| P-4119 | <0.01 | <0.1 | <0.01 | <0.01 | <0.01 | NA | NA |
| P-4120 | <0.1 | <1 | <0.01 | <0.01 | <0.01 | NA | <1 |
| P-4121 | <0.01 | <0.1 | <0.01 | <0.01 | <0.01 | NA | NA |
| P-4122 | <0.01 | <0.1 | <0.01 | <0.01 | <0.01 | NA | NA |
| P-4123 | <0.01 | <0.1 | <0.01 | <0.01 | <0.01 | NA | <0.1 |
| P-4124 | <0.01 | <0.1 | <0.01 | <0.01 | <0.01 | NA | <1 |
| P-4125 | <0.01 | <0.1 | <0.01 | <0.01 | <0.01 | NA | NA |
| P-4126 | <0.01 | <0.1 | <0.01 | <0.01 | <0.01 | NA | <0.1 |
| P-4127 | <0.01 | <0.1 | <1 | <0.1 | <0.1 | NA | <10 |
| P-4128 | <0.1 | <1 | <1 | <0.1 | <0.1 | NA | >1 |
| P-4129 | <0.1 | <1 | <1 | <0.1 | <0.1 | NA | >10 |
| P-4130 | <0.01 | >1 | <0.1 | <0.01 | <0.01 | NA | <10 |

Compounds P-3001, P-3004, P-3006, P-3008, P-3013, P-3019, P-3027, P-3036, P-3039, P-3040, P-3041, P-3042, P-3043, P-3044, P-3045, P-4001, P-4004, P-4005, P-4006, P-4007, P-4008, P-4009, P-4010, P-4011, P-4012, P-4013, P-4014, P-4015, P-4016, P-4017, P-4022, P-4023, P-4024, P-4025, and P-4026 to P-4130 were assessed and showed activity in the osteoclast differentiation assay, where compounds P-3004, P-3006, P-3008, P-3019, P-3027, P-3036, P-3039, P-3041, P-3042, P-4001, P-4004, P-4005, P-4006, P-4007, P-4008, P-4009, P-4010, P-4011, P-4012, P-4013, P-4014, P-4015, P-4016, and P-4023 demonstrated an IC$_{50}$ below 0.1 μM in this assay.

Compounds also demonstrate in vivo activity in a splenomegaly mouse model, where BaF3 cell growth in the spleens of nude mice may show inhibition with compound treatment. BaF3 cells are engineered with any of BCR-FMS, BCR-TRK1 or BCR-TRK2 to assess in vivo inhibitory effects of Fms, TrkA or TrkB inhibition, respectively. BaF3 cells are maintained in growth media (RPMI containing 10% FBS, 1% PenStrep, 1% NEAA, and 1% L-Glutamine, supplemented with 5% murine IL-3 and 1 mg/mL G418). Four days prior to start, 2×10$^6$ cells are inoculated into a T150 vented flask using the growth media and incubated at 37° C. in 5% CO$_2$ for three days. One day prior to start, cells are collected by centrifugation and are suspended in growth media without IL-3. On the day of cell implant, the cells are collected by centrifugation, rinsed 3×20 mL with RPMI, then are suspended in 5.4 mL of media and counted, then adjusted with additional RPMI as needed to give 5×10$^7$ cells/mL. On day 1, female nu/nu mice at 5-6 weeks of age are injected intravenously with BaF3 cells injected injecting 0.1 mL (5×10$^6$) cells in the tail vein (mice without cell injected are included as control group). Compound stocks in dimethylsulfoxide are stored at room temperature protected from light. Stocks are diluted prior to dosing, diluting 22 μL of compound stock into 858 μL of diluent (or 50 μL into 1950 μL) to provide vehicle of 1.0% Polysorbate 80, 0.5% hydroxypropyl methyl cellulose, with final dimethylsulfoxide at 2.5% in all dosing suspensions and vehicle control. Dosing suspension is prepared prior to use, mixing by inversion and sonication in a water bath to make a uniform suspension. On days 10-18, mice are treated with vehicle only or the desired level of compound in vehicle, ~0.2 mL per 25 gm mouse, once a day by oral gavage, or in some instances, twice per day. On day 18, mice are administered a final dose and two hours later a plasma sample is taken. At four hours following the final dose, mice are sacrificed, an additional plasma sample is collected and mouse spleens are removed and weighed. The average spleen weight of vehicle control group mice is compared to the average spleen weight of the test compound mice. Percent spleen growth inhibition is calculated as 100×[(spleen weight vehicle control-spleen weight test compound)/spleen weight vehicle control]. In some instances, the compounds were not tested in all of the assays as indicated by NA in the table below.

The following table provides data indicating the percent spleen growth inhibition for exemplary compounds indicated (dosed once per day at 10 mg per kg unless indicated otherwise) in the splenomegaly mouse model:

| Comp. number | % spleen growth inhibition | | |
|---|---|---|---|
| | Fms | TrkA | TrkB |
| P-3004 | 43 | NA | NA |
| P-3010 | 47 | NA | NA |
| P-3013 | 48 | NA | NA |
| P-3019 | 40 | NA | 14 |
| P-3027 | 42 | NA | 2 |
| P-3045 | 11 | NA | NA |
| P-4004 | 36 | 16 | 41 |
| P-4004* | 70 | 40 | 91 |
| P-4005 | 65 | 25 | 35 |
| P-4006 | 55 | NA | 21 |
| P-4007 | 28 | NA | 19 |
| P-4012 | 24 | NA | NA |
| P-4022 | 42 | NA | 33 |
| P-4026 | 41 | NA | NA |
| P-4027 | −1.4 | NA | NA |
| P-4028 | 86 | NA | 88 |
| P-4029 | 66 | NA | NA |
| P-4030 | 58 | NA | 50 |
| P-4031 | 29 | NA | NA |
| P-4053 | 69 | NA | NA |
| P-4090# | 38 | NA | NA |
| P-4084 | 6.2 | NA | NA |
| P-4062 | 76 | NA | NA |
| P-4061 | 48 | NA | NA |
| P-4112 | 9.5 | NA | NA |
| P-4110 | 30 | NA | NA |

| Comp. | % spleen growth inhibition | | |
|---|---|---|---|
| number | Fms | TrkA | TrkB |
| P-4124 | 20 | NA | NA |
| P-4120 | 37 | NA | NA |
| P-4123# | 14 | NA | NA |
| P-4130 | 70 | NA | NA |
| P-4128 | 15 | NA | NA |

*Dosed at 30 mg/kg.
Dosed at 5 mg/kg.

As an indication of relative solubility, the turbidity of compounds in aqueous solutions is assessed. To assess possible compound properties in different physiological compartments, such as stomach, intestine, and blood, a series of aqueous buffers with varying pH is used. Thus each compound is diluted into four different physiologically relevant buffers and solution turbidity is measured by spectrophotometry. The concentration of compound that demonstrates turbidity by forming enough insoluble suspension to raise the average optical density above 0.01 at three wavelengths (490, 535, and 650 nm) is used to define the limit of the compound solubility in that buffer.

Compounds are dissolved at a concentration of 25 mM in dimethyl sulfoxide, then serially diluted 1:1 into a 96 well plate, diluting 10 times in pure dimethyl sulfoxide, with the final well of each row a dimethyl sulfoxide blank. In an assay plate, 99 μL of appropriate buffer is added to each well, and 1 μL of each sample dilution is added to the buffer, achieving a range of final total concentrations in aqueous solutions having different pH. The buffers used are Simulated Gastric Fluid (SGF-pH 1.5) 0.5M NaCl, pH 1.5; Simulated Intestinal fluid (SIF-pH 4.5 and pH 6.8) 0.05M $NaH_2PO_4$, pH 4.5 and 6.8; and Hepes Buffer (HEPES-pH 7.4) 10 mM HEPES, 150 mM NaCl, pH 7.4. Control compounds pyrene, estriol and propranolol HCl are also assessed. Plates are spun and then mixed for 1 minute, and the absorbance is read using a Tecan Safire II to read wavelengths in the visible range (490, 535, and 650 nm) at four locations per well, reflecting the degree of turbidity present. The average optical density for each wavelength in each well is graphed vs. compound concentration, and the concentration at which the curve crosses a threshold O.D. of 0.01 for each wavelength is reported as the endpoint turbidity assay result. The average of the three wavelengths is used to compare turbidity of compounds. Compounds are considered to have low solubility if the threshold concentration is <31.3 μM, moderate solubility if the threshold concentration is 31.3 μM to 250 μM, and high solubility if the threshold concentration is >250 μm.

The following table indicates the relative solubility (L=low, M=moderate, H=high) based on turbidity threshold concentration at each pH for exemplary compounds according to the invention as indicated:

| Compound | turbidity threshold (L, M, H) | | | |
|---|---|---|---|---|
| number | 1.4 | 4.5 | 6.8 | 7.4 |
| P-3001 | H | L | L | L |
| P-3004 | H | L | L | L |
| P-3010 | H | L | L | M |
| P-3011 | L | L | L | L |
| P-3012 | M | M | M | M |
| P-3013 | L | L | L | L |
| P-3014 | H | M | M | M |
| P-3018 | H | M | M | M |
| P-3019 | H | L | L | L |
| P-3039 | H | M | M | M |
| P-3040 | M | M | M | M |
| P-3043 | M | M | M | M |
| P-3044 | L | L | L | M |
| P-3045 | M | M | M | L |
| P-4001 | M | M | M | M |
| P-4002 | H | M | M | M |
| P-4003 | M | M | M | M |
| P-4004 | M | M | L | L |
| P-4005 | M | L | L | L |
| P-4006 | H | L | L | L |
| P-4007 | M | L | L | L |
| P-4008 | M | M | M | M |
| P-4009 | H | M | L | L |
| P-4010 | H | M | L | L |
| P-4011 | M | M | M | M |
| P-4012 | M | L | L | L |
| P-4013 | H | M | M | M |
| P-4014 | M | M | M | M |
| P-4015 | M | M | M | M |
| P-4016 | M | H | M | M |
| P-4017 | M | M | M | L |
| P-4018 | M | L | L | L |
| P-4019 | M | L | L | L |
| P-4022 | H | M | L | L |
| P-4023 | H | M | L | L |
| P-4024 | M | L | M | M |
| P-4025 | M | L | L | L |
| P-4036 | H | M | L | L |
| P-4037 | H | M | M | M |
| P-4048 | H | M | M | M |
| P-4049 | H | L | L | L |
| P-4050 | H | L | L | L |
| P-4051 | H | M | M | L |
| P-4052 | L | L | L | L |
| P-4053 | H | M | M | M |
| P-4054 | H | M | M | M |
| P-4055 | M | M | L | L |
| P-4056 | M | M | M | L |
| P-4057 | L | L | L | M |
| P-4058 | M | L | L | L |
| P-4059 | M | L | L | L |
| P-4060 | H | M | M | M |
| P-4061 | M | L | M | M |
| P-4062 | H | L | M | L |
| P-4063 | M | M | M | M |
| P-4064 | H | M | L | L |
| P-4065 | H | M | M | M |
| P-4066 | M | L | L | M |
| P-4067 | H | M | M | M |
| P-4068 | H | M | M | M |
| P-4069 | M | L | M | M |
| P-4070 | H | M | M | M |
| P-4071 | M | M | M | M |
| P-4072 | M | L | L | L |
| P-4073 | M | L | L | L |
| P-4074 | H | M | M | M |
| P-4075 | M | L | L | L |
| P-4076 | M | M | M | M |
| P-4077 | M | L | L | L |
| P-4078 | M | L | L | L |
| P-4079 | H | M | M | M |
| P-4080 | M | M | H | M |
| P-4081 | H | M | H | M |
| P-4082 | M | L | L | L |
| P-4083 | M | M | M | H |
| P-4084 | M | M | M | H |
| P-4087 | H | M | M | M |
| P-4088 | H | M | M | M |
| P-4089 | H | M | M | M |
| P-4090 | M | M | M | M |
| P-4091 | H | M | M | M |
| P-4092 | M | M | M | M |
| P-4093 | H | L | L | L |

-continued

| Compound | turbidity threshold (L, M, H) | | | |
|---|---|---|---|---|
| number | 1.4 | 4.5 | 6.8 | 7.4 |
| P-4094 | H | L | M | M |
| P-4095 | M | M | M | M |
| P-4096 | H | L | L | L |
| P-4097 | M | L | L | L |
| P-4098 | H | L | M | M |
| P-4099 | H | L | L | L |
| P-4100 | H | M | M | M |
| P-4101 | M | L | L | L |
| P-4102 | H | M | M | M |
| P-4103 | L | M | M | M |
| P-4104 | M | L | L | L |
| P-4105 | M | M | M | M |
| P-4106 | M | M | L | M |
| P-4107 | M | M | M | M |
| P-4108 | H | M | M | M |
| P-4109 | L | L | L | L |
| P-4110 | M | L | L | L |
| P-4111 | H | L | L | L |
| P-4112 | M | M | M | H |
| P-4114 | H | L | L | L |
| P-4115 | H | M | M | M |
| P-4116 | H | M | M | M |
| P-4117 | H | L | L | L |
| P-4118 | H | M | M | L |
| P-4119 | H | M | M | L |
| P-4120 | L | M | M | M |
| P-4121 | H | H | H | H |
| P-4122 | H | L | M | L |
| P-4123 | H | L | L | L |
| P-4124 | M | L | L | M |
| P-4125 | H | L | L | L |
| P-4127 | H | M | M | M |
| P-4128 | H | M | M | M |
| P-4129 | H | M | M | M |
| P-4130 | H | M | M | M |

CYP (Cytochrome P450) enzymes are the major drug metabolizing enzymes present in the liver. The inhibition of CYP enzyme activity ($IC_{50}$) for each of CYP1A2, CYP2C19, CYP2C9, CYP2D6, CYP3A4(BFC) and CYP3A4(BQ) is determined for compounds, where inhibition of metabolism of a known substrate leads to a decrease in the fluorescence of the metabolized product. The fluorescence of the product is monitored as a function of compound concentration.

Compounds are dissolved in DMSO to a concentration of 100 mM. These are diluted 1 μL into 82 μL of acetonitrile. An 11 μL aliquot of this solution is then added to 204 μL of cofactor mix (1.3% NADPH Regeneration system Solution A, 1.04% NADPH Regeneration system Solution B from BD Biosciences, 5% acetonitrile and 0.05% DMSO). These are then serially diluted 1:1 (160 μL to 160 μL co-factor mix) for a total of 10 points. A 10 μL aliquot of this final mixture is dispensed into 384 well assay plates and incubated for 10 minutes at 37° C. Enzyme and substrate mix (10 μL; 0.5 pmol CYP1A2/5 μM CEC; 1.0 pmol CYP2C9/75 μM MFC; 0.5 pmol CYP2C19/25 μM CEC; 1.5 pmol CYP2D6/1.5 μM AMMC; 1.0 pmol CYP3A4/50 μM BFC; or 1.0 pmol CYP3A4/40 μM BQ) is added to these assay plates. Assay plates are incubated at 37° C. (CYP1A2-15 min; CYP2C9-45 min; CYP2C19, 2D6 and 3A4-30 min) and read in a Tecan Safire 2 plate reader (CYP1A2, 2C19 and 3A4 409 ex/460 em; CYP2C9 and 2D6 409 ex/530 em). The signal versus compound concentration is used to determine the $IC_{50}$. The enzymes and substrates for this assay are obtained from BD Biosciences. While other factors are involved in determining CYP effects in vivo, compounds preferably have $IC_{50}$ values of >5 μM, more preferably $IC_{50}$ values of >10 μM.

The following table indicates the Cyp inhibition for exemplary compounds according to the invention as indicated:

| Compound | Cyp $IC_{50}$ (μM) | | | | | |
|---|---|---|---|---|---|---|
| number | 1A2 | 2C19 | 2C9 | 2D6 | 3A4(BFC) | 3A4(BQ) |
| P-3001 | >10 | >10 | >10 | >10 | >10 | >10 |
| P-3004 | >10 | 5-10 | >10 | >10 | >10 | >10 |
| P-3006 | >10 | >10 | >10 | >10 | >10 | NA |
| P-3008 | >10 | <5 | 5-10 | >10 | 5-10 | NA |
| P-3009 | >10 | <5 | >10 | >10 | 5-10 | NA |
| P-3010 | >10 | >10 | >10 | >10 | >10 | >10 |
| P-3011 | >10 | >10 | >10 | >10 | >10 | >10 |
| P-3012 | >10 | >10 | >10 | >10 | >10 | >10 |
| P-3013 | 5-10 | <5 | >10 | >10 | >10 | >10 |
| P-3018 | >10 | >10 | >10 | >10 | <5 | >10 |
| P-3019 | >10 | <5 | >10 | >10 | >10 | >10 |
| P-3039 | >10 | >10 | >10 | >10 | >10 | NA |
| P-3040 | >10 | >10 | >10 | >10 | >10 | >10 |
| P-3041 | >10 | >10 | >10 | >10 | 5-10 | >10 |
| P-3043 | >10 | >10 | >10 | >10 | >10 | >10 |
| P-3044 | >10 | >10 | >10 | >10 | >10 | >10 |
| P-3048 | >10 | <5 | >10 | >10 | >10 | >10 |
| P-3049 | >10 | >10 | >10 | >10 | >10 | >10 |
| P-3050 | >10 | >10 | >10 | >10 | >10 | >10 |
| P-3051 | >10 | >10 | >10 | >10 | >10 | >10 |
| P-3052 | >10 | 5-10 | 5-10 | >10 | >10 | >10 |
| P-3053 | >10 | >10 | >10 | >10 | >10 | >10 |
| P-4001 | >10 | <5 | >10 | >10 | >10 | NA |
| P-4002 | >10 | >10 | >10 | >10 | >10 | >10 |
| P-4003 | >10 | >10 | >10 | >10 | >10 | >10 |
| P-4004 | >10 | >10 | >10 | >10 | >10 | >10 |
| P-4005 | >10 | >10 | >10 | >10 | >10 | >10 |
| P-4006 | >10 | >10 | >10 | >10 | >10 | >10 |
| P-4007 | >10 | >10 | >10 | >10 | >10 | >10 |
| P-4008 | >10 | >10 | >10 | >10 | 5-10 | >10 |
| P-4009 | >10 | 5-10 | >10 | >10 | >10 | >10 |
| P-4010 | >10 | >10 | >10 | >10 | >10 | >10 |
| P-4011 | >10 | >10 | 5-10 | >10 | 5-10 | >10 |
| P-4012 | >10 | >10 | >10 | >10 | >10 | >10 |
| P-4013 | >10 | >10 | <5 | >10 | >10 | >10 |
| P-4014 | >10 | >10 | 5-10 | <5 | 5-10 | >10 |
| P-4015 | >10 | >10 | >10 | >10 | >10 | >10 |
| P-4016 | >10 | >10 | >10 | >10 | >10 | >10 |
| P-4017 | >10 | >10 | >10 | >10 | >10 | >10 |
| P-4018 | >10 | <5 | >10 | >10 | 5-10 | >10 |
| P-4019 | >10 | 5-10 | >10 | >10 | 5-10 | >10 |
| P-4022 | >10 | 5-10 | >10 | 5-10 | 5-10 | >10 |
| P-4023 | >10 | <5 | >10 | 5-10 | <5 | >10 |
| P-4024 | >10 | >10 | >10 | >10 | <5 | >10 |
| P-4025 | >10 | 5-10 | >10 | >10 | <5 | >10 |
| P-4028 | >10 | 5-10 | 5-10 | >10 | >10 | >10 |
| P-4029 | >10 | >10 | >10 | >10 | >10 | >10 |
| P-4030 | >10 | 5-10 | >10 | >10 | >10 | >10 |
| P-4031 | >10 | >10 | >10 | <5 | >10 | >10 |
| P-4036 | 5-10 | 5-10 | 5-10 | >10 | 5-10 | 5-10 |
| P-4037 | >10 | >10 | 5-10 | >10 | 5-10 | 5-10 |
| P-4041 | 5-10 | <5 | 5-10 | >10 | >10 | 5-10 |
| P-4047 | >10 | >10 | >10 | >10 | >10 | >10 |
| P-4048 | >10 | >10 | >10 | >10 | >10 | >10 |
| P-4049 | >10 | 5-10 | 5-10 | >10 | >10 | >10 |
| P-4050 | >10 | >10 | >10 | >10 | >10 | >10 |
| P-4051 | >10 | >10 | >10 | >10 | >10 | >10 |
| P-4052 | >10 | >10 | >10 | >10 | >10 | >10 |
| P-4053 | >10 | >10 | >10 | >10 | >10 | >10 |
| P-4054 | >10 | >10 | >10 | >10 | >10 | >10 |
| P-4055 | <10 | <10 | >10 | >10 | >10 | >10 |
| P-4056 | >10 | 5-20 | >10 | >10 | >10 | >10 |
| P-4057 | >10 | >10 | >10 | >10 | >10 | >10 |
| P-4058 | >10 | >10 | >10 | >10 | >10 | >10 |
| P-4059 | >10 | >10 | 5-10 | >10 | >10 | >10 |
| P-4060 | >10 | >10 | >10 | >10 | >10 | >10 |
| P-4061 | >10 | >10 | >10 | >10 | >10 | >10 |
| P-4062 | >10 | >10 | >10 | >10 | >10 | >10 |
| P-4063 | >10 | >10 | >10 | >10 | >10 | >10 |
| P-4064 | >10 | >10 | >10 | >10 | >10 | >10 |
| P-4065 | >10 | >10 | >10 | >10 | >10 | >10 |
| P-4066 | >10 | >10 | >10 | >10 | >10 | 5-10 |
| P-4067 | >10 | 5-10 | >10 | >10 | >10 | >10 |

-continued

| Compound number | Cyp IC$_{50}$ (μM) | | | | | |
|---|---|---|---|---|---|---|
| | 1A2 | 2C19 | 2C9 | 2D6 | 3A4(BFC) | 3A4(BQ) |
| P-4068 | >10 | >10 | >10 | >10 | >10 | >10 |
| P-4069 | >10 | 5-10 | >10 | >10 | 5-10 | >10 |
| P-4070 | >10 | >10 | >10 | >10 | >10 | >10 |
| P-4071 | >10 | >10 | >10 | >10 | >10 | >10 |
| P-4072 | >10 | <10 | 5-10 | 5-10 | >10 | >10 |
| P-4073 | >10 | 5-10 | >10 | >10 | >10 | >10 |
| P-4074 | >10 | 5-10 | >10 | >10 | >10 | >10 |
| P-4075 | >10 | 5-10 | >10 | >10 | >10 | >10 |
| P-4076 | >10 | 5-10 | >10 | >10 | >10 | >5 |
| P-4077 | 5-10 | 5-10 | >10 | >10 | >10 | >10 |
| P-4078 | 5-10 | >10 | >10 | >10 | >10 | >10 |
| P-4079 | >10 | 5-10 | >10 | >10 | >10 | >10 |
| P-4080 | >10 | >10 | >10 | >10 | >10 | >10 |
| P-4081 | >10 | >10 | >10 | >10 | >10 | >10 |
| P-4082 | >10 | >10 | >10 | >10 | >10 | 5-10 |
| P-4083 | >10 | >10 | >10 | >10 | >10 | >10 |
| P-4084 | >10 | 5-10 | >10 | >10 | >10 | >10 |
| P-4087 | >10 | >10 | >10 | >10 | >10 | >10 |
| P-4088 | >10 | >10 | >10 | >10 | >10 | >10 |
| P-4089 | >10 | >10 | >10 | >10 | >10 | >10 |
| P-4090 | >10 | >10 | >10 | >10 | >10 | >10 |
| P-4091 | >10 | >10 | >10 | >10 | >10 | >10 |
| P-4092 | <5 | <5 | <5 | <5 | >10 | >10 |
| P-4093 | >10 | >10 | >10 | >10 | >10 | >10 |
| P-4094 | <5 | <5 | <5 | <5 | >10 | >10 |
| P-4095 | >10 | >10 | >10 | >10 | >10 | >10 |
| P-4096 | <5 | <5 | <5 | <5 | >10 | 5-10 |
| P-4097 | <5 | <5 | <5 | <5 | >10 | >10 |
| P-4098 | <5 | <5 | <5 | <5 | >10 | >10 |
| P-4099 | <5 | <5 | <5 | <5 | >10 | <5 |
| P-4100 | <5 | <5 | <5 | <5 | >10 | >10 |
| P-4101 | >10 | 5-10 | 5-10 | >10 | >10 | >10 |
| P-4102 | <5 | <5 | <5 | <5 | >10 | >10 |
| P-4103 | <5 | >10 | >10 | >10 | >10 | >10 |
| P-4104 | >10 | 5-10 | >10 | >10 | >10 | >10 |
| P-4105 | >10 | >10 | >10 | >10 | >10 | >10 |
| P-4106 | <5 | <5 | <5 | <5 | >10 | >10 |
| P-4107 | <5 | <5 | <5 | <5 | >10 | >10 |
| P-4108 | <5 | <5 | <5 | <5 | >10 | >10 |
| P-4109 | >10 | 5-10 | 5-10 | >10 | >10 | >10 |
| P-4110 | <5 | <5 | <5 | <5 | >10 | >10 |
| P-4111 | >10 | 5-10 | 5-10 | >10 | >10 | 5-10 |
| P-4112 | <5 | <5 | <5 | <5 | >10 | >10 |
| P-4113 | >10 | >10 | >10 | >10 | >10 | >10 |
| P-4114 | >10 | >10 | >10 | >10 | >10 | >10 |
| P-4115 | <5 | <5 | <5 | <5 | >10 | >10 |
| P-4116 | >10 | >10 | >10 | >10 | >10 | >10 |
| P-4117 | 5-10 | >10 | 5-10 | >10 | >10 | >10 |
| P-4118 | >10 | >10 | >10 | >10 | >10 | >10 |
| P-4119 | >10 | >10 | >10 | >10 | >10 | >10 |
| P-4120 | <5 | <5 | <5 | <5 | >10 | >10 |
| P-4121 | >10 | 5-10 | >10 | >10 | >10 | >10 |
| P-4122 | >10 | >10 | 5-10 | >10 | >10 | >10 |
| P-4123 | >10 | >10 | >10 | >10 | >10 | >10 |
| P-4124 | <5 | <5 | <5 | <5 | >10 | >10 |
| P-4125 | >10 | >10 | >10 | >5 | >10 | >10 |
| P-4126 | <5 | >10 | >10 | >10 | <10 | 5-10 |
| P-4127 | >10 | 5-10 | >10 | >10 | <5 | <5 |
| P-4128 | >10 | >10 | >10 | >10 | >10 | >10 |
| P-4129 | >10 | >10 | 5-10 | 5-10 | <5 | <5 |
| P-4130 | >10 | <5 | >10 | >10 | <5 | >10 |

Pharmacokinetic properties of compounds (including any solid forms or formulations thereof) are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present invention preferably show improved pharmacokinetic properties relative to previously described compounds, i.e. they have substantially higher values for one or more of AUC, Cmax and half-life relative to previously described compounds.

Analysis of penetration of compound into the brain can be assessed similarly. Each compound is prepared as a 100 mg/mL stock solution in dimethyl sulfoxide, as well as control compounds atenolol at 100 mg/mL and antipyrine at 50 mg/mL. In a cassette format, up to three test compounds, along with atenolol and antipyrine, are combined, 180 μL each, and added to 17.1 mL of 1% methylcellulose. The compounds are in a suspension that is administered in a single dose (10 mL per kg body weight) to 2 groups of CD rats (8-9 weeks, n=3 per group) by oral gavage, an additional group of rats dosed with vehicle only. One group of compound treated rats is sacrificed at 2 hours post dosing, the other group at 6 hours. Plasma is collected in Li-heparin and the brains are collected, cut into right and left hemispheres, weighed and flash frozen. Brain homogenate (30%) and plasma samples are assessed by equilibrium dialysis using a 96 well equilibrium dialysis apparatus with a 5K MW cut off membrane (The Nest Group, Inc.) as per the vendor's protocol with the samples on one side of the dialysis membrane and an equal volume of 1×PBS on the other side. The apparatus is incubated overnight at 37° C. on a plate rotator (The Nest Group, Inc.). The compound concentrations on both sides are analyzed by LC/MS/MS to calculate the mass balance recovery. The concentration in the PBS side is calculated using a standard curve generated for each compound. The PBS concentration is the free compound concentration, while the side with the biological sample provides the concentration in plasma or brain.

Example 17

Efficacy of Compounds in Combination with Standard-of-Care Chemotherapeutic Agents in Four Human Cancer Cell Lines Compounds of the invention, such as compounds of Formula I, in combination with a standard chemotherapeutic agent, such as 5-fluorouracil, carboplatin, dacarbazine, gefitinib, oxaliplatin, paclitaxel, SN-38, temozolomide, or vinblastine, can be assessed for their effectiveness in killing human tumor cells. Such assays are known in the art, for example, as described in U.S. patent application Ser. No. 11/473,347, the disclosure of which are hereby incorporated by reference with respect to such assays.

All patents and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. Thus, for an embodiment of the invention using one of the terms, the invention also includes another embodiment wherein one of these terms is replaced with another of these terms. In each embodiment, the terms have their established meaning. Thus, for example, one embodiment may encompass a method "comprising" a series of steps, another embodiment would encompass a method "consisting essentially of" the same steps, and a third embodiment would encompass a method "consisting of" the same steps. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any 2 different values as the endpoints of a range. Such ranges are also within the scope of the described invention.

Thus, additional embodiments are within the scope of the invention and within the following claims.

What is claimed is:

1. A compound having the chemical structure of Formula I,

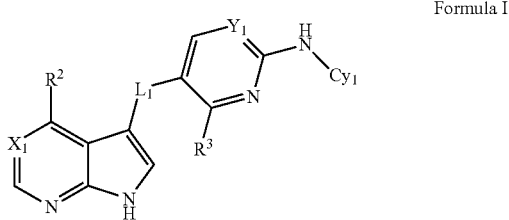

Formula I or a salt, a solvate, a tautomer or a stereoisomer thereof, wherein:

$X_1$ is N;
$Y_1$ is —N= and $R^3$ is hydrogen; or $Y_1$ is —C(H)= and $R^3$ is fluoro or chloro;
$L_1$ is —C(H$_2$)— or —C(O)—;
$Cy_1$ is cycloalkyl optionally substituted with one or more $R^4$, phenyl optionally substituted with one or more $R^5$, or 5 or 6 membered heteroaryl optionally substituted on an available carbon atom with one or more $R^6$ and optionally substituted on an available nitrogen atom with $R^7$;
$R^2$ is selected from the group consisting of hydrogen, cycloalkyl, lower alkyl optionally substituted with one or more $R^8$, —N($R^{9a}$)($R^{9b}$), and —O—$R^9$;
each $R^4$ is independently selected from the group consisting of fluoro, —OH, lower alkyl optionally substituted with one or more fluoro, and lower alkoxy optionally substituted with one or more fluoro;
each $R^5$ is independently selected from the group consisting of fluoro, chloro, —O—$R^{10}$, —S—$R^{11}$, —S(O$_2$)—$R^{12}$, and lower alkyl optionally substituted with one or more $R^{13}$;
each $R^6$ is independently selected from the group consisting of fluoro, chloro, bromo, cycloalkyl, lower alkyl optionally substituted with one or more fluoro, and lower alkoxy optionally substituted with one or more fluoro; or two $R^6$ bound to adjacent carbon atoms of the heteroaryl ring form a fused cycloalkyl ring;
$R^7$ is cycloalkyl, lower alkoxy or lower alkyl optionally substituted with one or more fluoro;
$R^8$ is fluoro or lower alkoxy optionally substituted with one or more fluoro;
$R^{9a}$ is H and $R^{9b}$ is selected from the group consisting of (i) H, lower alkyl, lower alkyl substituted with one or more fluoro, lower alkyl substituted with lower alkoxy or lower alkyl substituted with hydroxyl and (ii) cycloalkyl, cycloalkylalkyl, heterocycloalkyl, heterocycloalkylalkyl, arylalkyl, heteroarylalkyl, each of which is optionally substituted with one to three members selected from lower alkyl, haloalkyl, lower alkoxy or fluoro; or
$R^{9a}$ and $R^{9b}$ together with the nitrogen to which they are attached form a 5- or 6-membered ring having from 0 to 1 additional heteroatom selected from O, N or S, each of which is optionally substituted with one to three members selected from lower alkyl, haloalkyl, lower alkoxy or fluoro;
$R^9$ is lower alkyl, lower alkyl substituted with one or more fluoro, or lower alkyl substituted with lower alkoxy;
each $R^{10}$, $R^{11}$ and $R^{12}$ are independently lower alkyl optionally substituted with one or more fluoro; and
each $R^{13}$ is independently selected from the group consisting of fluoro, —OH, and lower alkoxy optionally substituted with one or more fluoro.

2. The compound of claim 1, wherein $L_1$ is CH$_2$, $Y_1$ is CH and $R^3$ is F, or a salt, a solvate, a tautomer or a stereoisomer thereof.

3. The compound of claim 1, wherein $L_1$ is CH$_2$, $Y_1$ is N and $R^3$ is H, or a salt, a solvate, a tautomer or a stereoisomer thereof.

4. The compound of claim 1, wherein $L_1$ is —C(=O)—, $Y_1$ is CH and $R^3$ is F, or a salt, a solvate, a tautomer or a stereoisomer thereof.

5. The compound of claim 1, wherein $L_1$ is —C(=O)—, $Y_1$ is N and $R^3$ is H, or a salt, a solvate, a tautomer or a stereoisomer thereof.

6. The compound of claim 1, wherein $R^2$ is —N($R^{9a}$)($R^{9b}$), or a salt, a solvate, a tautomer or a stereoisomer thereof.

7. The compound of claim 1, wherein $Cy_1$ is cycloalkyl optionally substituted with one or more $R^4$, or a salt, a solvate, a tautomer or a stereoisomer thereof.

8. The compound of claim 7, wherein $Cy_1$ is cyclopropyl, cyclobutyl, cyclopentyl, cyclohexyl, cyclopentyl, each of which is optionally substituted with from 1 to 3 $R^4$, or a salt, a solvate, a tautomer or a stereoisomer thereof.

9. The compound of claim 1, wherein $Cy_1$ is phenyl optionally substituted with one or more $R^5$, or a salt, a solvate, a tautomer or a stereoisomer thereof.

10. The compound of claim 1, wherein $Cy_1$ is 5 or 6-membered heteroaryl optionally substituted on an available carbon atom with one or more $R^6$ and optionally substituted on an available nitrogen atom with $R^7$, or a salt, a solvate, a tautomer or a stereoisomer thereof.

11. The compound of claim 10, wherein $Cy_1$ is 3-pyridyl, 2-pyrrolyl, 3-pyrrolyl or 4-pyrazolyl, optionally substituted on an available carbon atom with from 1 to 3 $R^6$ and optionally substituted on an available nitrogen atom with $R^7$, or a salt, a solvate, a tautomer or a stereoisomer thereof.

12. The compound of claim 10, wherein each $R^6$ is independently selected from the group consisting of fluoro, chloro, bromo, lower alkyl optionally substituted with from one to three fluoro, and lower alkoxy optionally substituted with one to three fluoro; or two $R^6$ bound to adjacent carbon atoms of the heteroaryl ring form a fused cycloalkyl ring, or a salt, a solvate, a tautomer or a stereoisomer thereof.

13. The compound of claim 1, wherein $R^{9a}$ is H and $R^{9b}$ is selected from H, lower alkyl, lower alkyl substituted with hydroxy, lower alkyl substituted with lower alkoxy, lower alkyl substituted with 1 to 3 fluoro groups, cycloalkyl optionally substituted with lower alkyl or one to three fluoro, cycloalkylalkyl optionally substituted with lower alkyl or one to three fluoro substituents, heterocycloalkyl optionally substituted with lower heterocycloalkylalkyl, arylalkyl optionally substituted with from 1 to 3 members selected from lower alkyl, fluoro or haloalkyl and heteroarylalkyl optionally substituted with from one to three members selected from alkyl, fluoro or haloalkyl.

14. The compound of claim 13, wherein $R^{9a}$ is H and $R^{9b}$ is selected from (i) H, methyl, ethyl, t-butyl, propyl, isopropyl, 2-butyl, n-butyl, 2-hydroxy-2-methylpropyl, 2-methoxyethyl, 3-methoxypropyl, 2,2,2-trifluoroethyl, or 4-methoxybutyl and (ii) cyclopropyl, cyclobutyl, cyclopentyl, cyclohexyl, cyclopropylmethyl, cyclobutylmethyl, cyclopentylmethyl, cyclohexylmethyl, benzyl, 1-methylbenzyl, 4,4-difluorocyclohexyl, 2-tetrahydrofuranylmethyl, 4-piperidinyl, each of which is optionally substituted with from 1 to 3 members selected from lower alkyl, fluoro or $CF_3$, or a salt, a solvate, a tautomer or a stereoisomer thereof.

15. The compound of claim 1, wherein —$N(R^{9a})(R^{9b})$ is 1-piperidinyl, 4-morpholinyl, 1-piperazinyl 1-pyrrolidinyl, each of which is optionally substituted with one to three members selected from lower alkyl, haloalkyl, lower alkoxy or fluoro, or a salt, a solvate, a tautomer, or a stereoisomer thereof.

16. A compound selected from:
[6-Fluoro-5-(4-methoxy-7H-pyrrolo[2,3-d]pyrimidin-5-ylmethyl)-pyridin-2-yl]-(6-methoxy-pyridin-3-yl)-amine (P-4001),
[6-Fluoro-5-(4-methyl-7H-pyrrolo[2,3-d]pyrimidin-5-ylmethyl)-pyridin-2-yl]-(6-methoxy-pyridin-3-yl)-amine (P-4002),
(6-Chloro-pyridin-3-yl)-[6-fluoro-5-(4-methoxy-7H-pyrrolo[2,3-d]pyrimidin-5-ylmethyl)-pyridin-2-yl]-amine (P-4003),
(6-Cyclopropyl-pyridin-3-yl)-[6-fluoro-5-(4-methoxy-7H-pyrrolo[2,3-d]pyrimidin-5-ylmethyl)-pyridin-2-yl]-amine (P-4004),
(6-Ethoxy-pyridin-3-yl)-[6-fluoro-5-(4-methoxy-7H-pyrrolo-[2,3-d]pyrimidin-5-ylmethyl)-pyridin-2-yl]-amine (P-4005),
(6-Ethoxy-pyridin-3-yl)-[6-fluoro-5-(4-methyl-7H-pyrrolo[2,3-d]pyrimidin-5-ylmethyl)-pyridin-2-yl]amine (P-4006),
(6-Ethyl-pyridin-3-yl)-[6-fluoro-5-(4-methoxy-7H-pyrrolo[2,3-d]pyrimidin-5-ylmethyl)-pyridin-2-yl]-amine (P-4007),
(6-Ethoxy-pyridin-3-yl)-{6-fluoro-5-[4-(2-methoxyethoxy)-7H-pyrrolo[2,3-d]pyrimidin-5-ylmethyl]-pyridin-2-yl}-amine (P-4008),
(6-Ethyl-pyridin-3-yl)-[6-fluoro-5-(4-methyl-7H-pyrrolo[2,3-d]pyrimidin-5-ylmethyl)-pyridin-2-yl]-amine (P-4009),
[6-Fluoro-5-(4-methoxy-7H-pyrrolo[2,3-d]pyrimidin-5-ylmethyl)-pyridin-2-yl]-(6-methyl-pyridin-3-yl)-amine (P-4010),
(1-Ethyl-1H-pyrazol-4-yl)-[6-fluoro-5-(4-methoxy-7H-pyrrolo[2,3-d]pyrimidin-5-ylmethyl)-pyridin-2-yl]-amine (P-4011),
[5-Ethoxy-7H-pyrrolo[2,3-d]pyrimidin-5-ylmethyl)-6-fluoro-pyridin-2-yl]-(1 ethyl-1H-pyrazol-4-yl)-amine (P-4012),
(1-Ethyl-1H-pyrazol-4-yl)-[6-fluoro-5-(4-methyl-7H-pyrrolo[2,3-d]pyrimidin-5-ylmethyl)-pyridin-2-yl]-amine (P-4013),
(1-Ethyl-1H-pyrazol-4-yl)-{6-fluoro-5-[4-(2-methoxyethoxy)-7H-pyrrolo[2,3-d]pyrimidin-5-ylmethyl]-pyridin-2-yl}-amine (P-4014),
{6-Fluoro-5-[4-(2-methoxy-ethoxy)-7H-pyrrolo[2,3-d]pyrimidin-5-ylmethyl]-pyridin-2-yl}-(6-methyl-pyridin-3-yl)-amine (P-4015),
(6-Ethyl-pyridin-3-yl)-{6-fluoro-5-[4-(2-methoxyethoxy)-7H-pyrrolo[2,3-d]pyrimidin-5-ylmethyl]-pyridin-2-yl}-amine (P-4016),
[5-(4-Ethoxy-7H-pyrrolo[2,3-d]pyrimidin-5-ylmethyl)-6-fluoro-pyridin-2-yl]-(6-methyl-pyridin-3-yl)-amine (P-4017),
[5-(4-Ethoxy-7H-pyrrolo[2,3d]pyrimidin-5-ylmethyl)-6-fluoro-pyridin-2-yl]-(6-methoxy-pyridin-3-yl)-amine (P-4018),
{6-Fluoro-5-[4-(2-methoxy-ethoxy)-7H-pyrrolo[2,3-d]pyrimidin-5-ylmethyl]-pyridin-2-yl}-(6-methoxy-pyridin-3-yl)-amine (P-4019),
(6-Bromo-pyridin-3-yl)-[5-(4-ethoxy-7H-pyrrolo[2,3-d]pyrimidin-5-ylmethyl)-6-fluoro-pyridin-2-yl]-amine (P-4020),
[5-(4-Ethoxy-7H-pyrrolo[2,3-d]pyrimidin-5-ylmethyl)-6-fluoro-pyridin-2-yl]-pyridin-3-yl-amine (P-4021),
(4-Cyclopropyl-7H-pyrrolo[2,3-d]pyrimidin-5-yl)-[2-fluoro-6-(6-methoxy-pyridin-3-ylamino)-pyridin-3-yl]-methanone (P-4022),
[5-(4-Cyclopropyl-7H-pyrrolo[2,3-d]pyrimidin-5-ylmethyl)-6-fluoro-pyridin-2-yl]-(6-methoxy-pyridin-3-yl)-amine (P-4023),
[6-(6-Ethoxy-pyridin-3-ylamino)-2-fluoro-pyridin-3-yl]-(4-methoxy-pyrrolo[2,3-d]pyrimidin-5-yl)-methanone (P-4024),
(4-Ethoxy-7H-pyrrolo[2,3-d]pyrimidin-5-yl)-[2-fluoro-6-(6-methoxy-pyridin-3-ylamino)-pyridin-3-yl]-methanone (P-4025),

[5-(4-Cyclopropyl-7H-pyrrolo[2,3-d]pyrimidin-5-ylmethyl)-6-fluoro-pyridin-2-yl]-(6-ethoxy-pyridin-3-yl)-amine (P-4026), (4-Cyclopropyl-7H-pyrrolo[2,3-d]pyrimidin-5-yl)-[6-(6-ethoxy-pyridin-3-ylamino)-2-fluoro-pyridin-3-yl]-methanone (P-4027),

[5-(4-Cyclopropyl-7H-pyrrolo[2,3-d]pyrimidin-5-ylmethyl)-6-fluoro-pyridin-2-yl]-(6-ethyl-pyridin-3-yl)-amine (P-4028), (4-Cyclopropyl-7H-pyrrolo[2,3-d]pyrimidin-5-yl)-[6-(6-ethyl-pyridin-3-ylamino)-2-fluoro-pyridin-3-yl]-methanone (P-4029),

[5-(4-Cyclopropyl-7H-pyrrolo[2,3-d]pyrimidin-5-ylmethyl)-6-fluoro-pyridin-2-yl]-(6-methyl-pyridin-3-yl)-amine (P-4030), (4-Cyclopropyl-7H-pyrrolo[2,3-d]pyrimidin-5-yl)-[2-fluoro-6-(6-methyl-pyridin-3-ylamino)-pyridin-3-yl]-methanone (P-4031),

[6-(6-Ethoxy-pyridin-3-ylamino)-2-fluoro-pyridin-3-yl]-(4-methyl-7H-pyrrolo[2,3-d]pyrimidin-5-yl)-methanone (P-4032),

[5-(4-Cyclopropyl-7H-pyrrolo[2,3-d]pyrimidin-5-ylmethyl)-6-fluoro-pyridin-2-yl]-(1-ethyl-1H-pyrazol-4-yl)-amine (P-4036), (4-Cyclopropyl-7H-pyrrolo[2,3-d]pyrimidin-5-yl)-[6-(1-ethyl-1H-pyrazol-4-ylamino)-2-fluoro-pyridin-3-yl]-methanone (P-4037),

[5-(4-Cyclopropyl-7H-pyrrolo[2,3-d]pyrimidin-5-ylmethyl)-6-fluoro-pyridin-2-yl]-(5-methyl-pyridin-3-yl)-amine (P-4038), (4-Cyclopropyl-7H-pyrrolo[2,3-d]pyrimidin-5-yl)-[2-fluoro-6-(5-methyl-pyridin-3-ylamino)-pyridin-3-yl]-methanone (P-4039),

[6-(6-Cyclopropyl-7H-pyridin-3-ylamino)-2-fluoro-pyridin-3-yl]-(4-cyclopropyl-7H-pyrrolo[2,3-d]pyrimidin-5-yl)-methanone (P-4040), (6-Cyclopropyl-pyridin-3-yl)-[5-(4-cyclopropyl-7H-pyrrolo[2,3-d]pyrimidin-5-ylmethyl)-6-fluoro-pyridin-2-yl]-amine (P-4041),

[5-(4-Cyclopropyl-7H-pyrrolo[2,3-d]pyrimidin-5-ylmethyl)-6-fluoro-pyridin-2-yl]-(6,7-dihydro-5H-[1]pyrindin-3-yl)-amine (P-4042), (4-Cyclopropyl-7H-pyrrolo[2,3-d]pyrimidin-5-yl)-[6-(6,7-dihydro-5H-[1]pyrindin-3-ylamino)-2-fluoro-pyridin-3-yl]-methanone (P-4043), (6-Cyclopropyl-pyridin-3-yl)-[6-fluoro-5-(4-methyl-7H-pyrrolo[2,3-d]pyrimidin-5-ylmethyl)-pyridin-2-yl]-amine (P-4044),

[6-(6-Cyclopropyl-pyridin-3-ylamino)-2-fluoro-pyridin-3-yl]-(4-methyl-7H-pyrrolo[2,3-d]pyrimidin-5-yl)-methanone (P-4045), (4-amino-7H-pyrrolo[2,3-d]pyrimidin-5-yl)-[2-chloro-6-[(4,4-difluorocyclohexyl)amino]-3-pyridyl]methanone (P-4046),

[2-chloro-6-[(4,4-difluorocyclohexyl)amino]-3 pyridyl]-[4-(2-methylprop-1-enylamino)-7H-pyrrolo[2,3-d]pyrimidin-5-yl]methanone (P-4047), (4-amino-7H-pyrrolo[2,3-d]pyrimidin-5-yl)-[6-[(6-cyclopropyl-3-pyridyl)amino]-2-fluoro-3-pyridyl]methanone (P-4048),

[6-[(6-cyclopropyl-3-pyridyl)amino]-2-fluoro 3 pyridyl]-[4-[(2-hydroxy-2-methyl-propyl)amino]-7H pyrrolo[2,3-d]pyrimidin-5-yl]methanone (P-4049),

[2-chloro-6-[(4,4-difluorocyclohexyl)amino]-3-pyridyl]-[4-(ethylamino)-7H-pyrrolo[2,3-d]pyrimidin-5-yl]methanone (P-4050),

[6-[(4,4-difluorocyclohexyl)amino]-5-fluoro-3-pyridyl]-[4-(ethylamino)-7H-pyrrolo[2,3-d]pyrimidin-5-yl]methanone (P-4051),

[6-[(4,4-difluorocyclohexyl)amino]-5-fluoro-3-pyridyl]-[4-(2,2,2-trifluoroethylamino)-7H-pyrrolo[2,3-d]pyrimidin-5-yl]methanone (P-4052),

[4-(cyclopropylamino)-7H-pyrrolo[2,3-d]pyrimidin-5-yl]-[6-[(4,4-difluorocyclohexyl)amino]-5-fluoro-3-pyridyl]methanone (P-4053),

[6-[(4,4-difluorocyclohexyl)amino]-5-fluoro-3-pyridyl]-[4-(methylamino)-7H-pyrrolo[2,3-d]pyrimidin-5-yl]methanone (P-4054),

[4-(tert-butylamino)-7H-pyrrolo[2,3-d]pyrimidin-5-yl]-[2-fluoro-6-[(6-methoxy-3-pyridyl)amino]-3-pyridyl]methanone (P-4055),

[4-[(4,4-difluorocyclohexyl)amino]-7H-pyrrolo[2,3-d]pyrimidin-5-yl]-[2-fluoro-6-[(6-methoxy-3-pyridyl)amino]-3-pyridyl]methanone (P-4056),

[2-chloro-6-[(4,4-difluorocyclohexyl)amino]-3-pyridyl]-[4-(2,2,2-trifluoroethylamino)-7H-pyrrolo[2,3-d]pyrimidin-5-yl]methanone (P-4057),

[2-chloro-6-[(4,4-difluorocyclohexyl)amino]-3-pyridyl]-[4-(methylamino)-7H-pyrrolo[2,3-d]pyrimidin-5-yl]methanone (P-4058),

[2-chloro-6-[(4,4-difluorocyclohexyl)amino]-3-pyridyl]-[4-(cyclopropylamino)-7H-pyrrolo[2,3-d]pyrimidin-5-yl]methanone (P-4059),

[6-[(6-cyclopropyl-3-pyridyl)amino]-2-fluoro-3-pyridyl]-[4-(ethylamino)-7H-pyrrolo[2,3-d]pyrimidin-5-yl]methanone (P-4060),

[6-[(4,4-difluorocyclohexyl)amino]-2-fluoro-3-pyridyl]-[4-(2,2,2-trifluoroethylamino)-7H-pyrrolo[2,3-d]pyrimidin-5-yl]methanone (P-4061),

[4-(cyclopropylamino)-7H-pyrrolo[2,3-d]pyrimidin-5-yl]-[6-[(4,4-difluorocyclohexyl)amino]-2-fluoro-3 pyridyl]methanone (P-4062),

[6-[(4,4-difluorocyclohexyl)amino]-2-fluoro-3-pyridyl]-[4-(methylamino)-7H-pyrrolo[2,3-d]pyrimidin-5-yl]methanone (P-4063),

[6-[(6-ethyl-3-pyridyl)amino]-2-fluoro-3-pyridyl]-[4-[(2-hydroxy-2-methyl-propyl)amino]-7H-pyrrolo[2,3-d]pyrimidin-5-yl]methanone (P-4064), (4-amino-7H-pyrrolo[2,3-d]pyrimidin-5-yl)-[6-[(6-ethyl-3-pyridyl)amino]-2-fluoro-3-pyridyl]methanone (P-4065),

[2-fluoro-6-[(6-methoxy-3-pyridyl)amino]-3-pyridyl]-[4-(isopropylamino)-7H-pyrrolo[2,3-d]pyrimidin-5-yl]methanone (P-4066),

[4-(cyclopropylmethylamino)-7H-pyrrolo[2,3-d]pyrimidin-5-yl]-[2-fluoro-6-[(6-methoxy-3-pyridyl)amino]-3 pyridyl]methanone (P-4067),

[2-fluoro-6-[(6-methoxy-3-pyridyl)amino]-3-pyridyl]-[4-(propylamino)-7H-pyrrolo[2,3-d]pyrimidin-5-yl]methanone (P-4068),

[2-fluoro-6-[(6-methoxy-3-pyridyl)amino]-3-pyridyl]-[4-(1-piperidyl)-7H-pyrrolo[2,3-d]pyrimidin-5-yl]methanone (P-4069),

[2-fluoro-6-[(6-methoxy-3-pyridyl)amino]-3-pyridyl]-(4-morpholino-7H-pyrrolo[2,3-d]pyrimidin-5-yl)methanone (P-4070),

[2-fluoro-6-[(6-methoxy-3-pyridyl)amino]-3-pyridyl]-[4-[[6-(trifluoromethyl)-3-pyridyl]methylamino]-7H-pyrrolo[2,3-d]pyrimidin-5-yl]methanone (P-4071),

[2-fluoro-6-[(6-methoxy-3 pyridyl)amino]-3-pyridyl]-[4-[[(1S)-1-(4-fluorophenyl)ethyl]amino]-7H-pyrrolo[2,3-d]pyrimidin-5-yl]methanone (P-4072),

[2-fluoro-6-[(6-methoxy-3-pyridyl)amino]-3-pyridyl]-[4-(tetrahydrofuran-2-ylmethylamino)-7H-pyrrolo[2,3-d]pyrimidin-5-yl]methanone (P-4073),

[4-[(1-ethyl-4-piperidyl)amino]-7H-pyrrolo[2,3-d]pyrimidin-5-yl]-[2-fluoro-6-[(6-methoxy-3-pyridyl)amino]-3-pyridyl]methanone (P-4074),

[4-(cyclopentylamino)-7H-pyrrolo[2,3-d]pyrimidin-5-yl]-[2-fluoro-6-[(6-methoxy-3-pyridyl)amino]-3-pyridyl]methanone (P-4075),

[4-(cyclobutylamino)-7H-pyrrolo[2,3-d]pyrimidin-5-yl]-[2-fluoro-6-[(6-methoxy-3-pyridyl)amino]-3-pyridyl]methanone (P-4076),

[4-(1-ethylpropylamino)-7H-pyrrolo[2,3-d]pyrimidin-5-yl]-[2-fluoro-6-[(6-methoxy-3-pyridyl)amino]-3-pyridyl]methanone (P-4077),

[2-fluoro-6-[(6-methoxy-3-pyridyl)amino]-3-pyridyl]-[4-(sec-butylamino)-7H-pyrrolo[2,3-d]pyrimidin-5-yl]methanone (P-4078),

[2-fluoro-6-[(6-methoxy-3-pyridyl)amino]-3-pyridyl]-[4-(3-methoxypropylamino)-7H-pyrrolo[2,3-d]pyrimidin-5-yl]methanone (P-4079),

[4-(butylamino)-7H-pyrrolo[2,3-d]pyrimidin-5-yl]-[2-fluoro-6-[(6-methoxy-3-pyridyl)amino]-3-pyridyl]methanone (P-4080),

[4-(ethylamino)-7H-pyrrolo[2,3-d]pyrimidin-5-yl]-[2-fluoro-6-[(6-methoxy-3-pyridyl)amino]-3-pyridyl]methanone (P-4081),

[4-(cyclohexylamino)-7H-pyrrolo[2,3-d]pyrimidin-5 yl]-[2-fluoro-6-[(6-methoxy-3-pyridyl)amino]-3-pyridyl]methanone (P-4082),

[2-fluoro-6-[(6-methoxy-3-pyridyl)amino]-3-pyridyl]-[4-(methylamino)-7H-pyrrolo[2,3-d]pyrimidin-5-yl]methanone (P-4083),

[2-fluoro-6-[(6-methoxy-3-pyridyl)amino]-3-pyridyl]-[4-(2,2,2-trifluoroethylamino)-7H-pyrrolo[2,3-d]pyrimidin-5-yl]methanone (P-4084),

[2-methoxy-6-[(6-methoxy-3-pyridyl)amino]-3-pyridyl]-[4-(methylamino)-7H-pyrrolo[2,3-d]pyrimidin-5-yl]methanone (P-4085),

[6-[(6-ethyl-3-pyridyl)amino]-2-fluoro-3 pyridyl]-[4-[(6-methyl-3-pyridyl)amino]-7H-pyrrolo[2,3-d]pyrimidin-5-yl]methanone (P-4086),

[6-[(4,4-difluorocyclohexyl)amino]-3-pyridyl]-[4-(2,2,2-trifluoroethylamino)-7H-pyrrolo[2,3-d]pyrimidin-5-yl]methanone (P-4087),

[4-(cyclopropylamino)-7H-pyrrolo[2,3-d]pyrimidin-5-yl]-[6-[(4,4-difluorocyclohexyl)amino]-3-pyridyl]methanone (P-4088),

[6-[(4,4-difluorocyclohexyl)amino]-3-pyridyl]-[4-(methylamino)-7H-pyrrolo[2,3-d]pyrimidin-5-yl]methanone (P-4089),

[6-[(6-cyclopropyl-3-pyridyl)amino]-2-fluoro-3-pyridyl]-[4-(2,2,2-trifluoroethylamino)-7H-pyrrolo[2,3-d]pyrimidin-5-yl]methanone (P-4090),

[4-(cyclopropylamino)-7H-pyrrolo[2,3-d]pyrimidin-5-yl]-[2-fluoro-6-[[6-(trifluoromethyl)-3-pyridyl]amino]-3-pyridyl]methanone (P-4091),

[2-fluoro-6-[[6-(trifluoromethyl)-3-pyridyl]amino]-3 pyridyl]-[4-(methylamino)-7H-pyrrolo[2,3-d]pyrimidin-5-yl]methanone (P-4092),

[4-(cyclopropylamino)-7H-pyrrolo[2,3-d]pyrimidin-5-yl]-[6-[(6-cyclopropyl-3-pyridyl)amino]-2-fluoro-3-pyridyl]methanone (P-4093),

[6-[(6-cyclopropyl-3-pyridyl)amino]-2-fluoro-3-pyridyl]-[4-(methylamino)-7H-pyrrolo[2,3-d]pyrimidin-5-yl]methanone (P-4094),

[4-(cyclobutylamino)-7H-pyrrolo[2,3-d]pyrimidin-5-yl]-[6-[(6-ethyl-3-pyridyl)amino]-2-fluoro-3-pyridyl]methanone (P-4095),

[4-[(4,4-difluorocyclohexyl)amino]-7H-pyrrolo[2,3-d]pyrimidin-5-yl]-[6-[(6-ethyl-3-pyridyl)amino]-2-fluoro-3-pyridyl]methanone (P-4096),

[6-[(6-ethyl-3-pyridyl)amino]-2-fluoro-3-pyridyl]-[4-[[(1S)-1-(4-fluorophenyl)ethyl]amino]-7H-pyrrolo[2,3-d]pyrimidin-5-yl]methanone (P-4097),

[6-[(6-ethyl-3-pyridyl)amino]-2-fluoro-3-pyridyl]-[4-(3-methoxypropylamino)-7H-pyrrolo[2,3-d]pyrimidin-5-yl]methanone (P-4098),

[4-(cyclopentylamino)-7H-pyrrolo[2,3-d]pyrimidin-5-yl]-[6-[(6-ethyl-3-pyridyl)amino]-2-fluoro-3-pyridyl]methanone (P-4099),

[4-(butylamino)-7H-pyrrolo[2,3-d]pyrimidin-5-yl]-[6-[(6-ethyl-3-pyridyl)amino]-2-fluoro-3-pyridyl]methanone (P-4100),

[6-(cyclohexylamino)-2-fluoro-3-pyridyl]-[4-(isopropylamino)-7H-pyrrolo[2,3-d]pyrimidin-5-yl]methanone (P-4101),

[6-(cyclohexylamino)-2-fluoro-3-pyridyl]-[4-(methylamino)-7H-pyrrolo[2,3-d]pyrimidin-5-yl]methanone (P-4102),

[2-fluoro-6-[(5-methoxy-3-pyridyl)amino]-3-pyridyl]-[4-(2,2,2-trifluoroethylamino)-7H-pyrrolo[2,3-d]pyrimidin-5-yl]methanone (P-4103),

[4-(cyclohexylamino)-7H-pyrrolo[2,3-d]pyrimidin-5-yl]-[2-fluoro-6-[(5-methoxy-3-pyridyl)amino]-3-pyridyl]methanone (P-4104),

[2-fluoro-6-[(5-methoxy-3-pyridyl)amino]-3-pyridyl]-[4-(propylamino)-7H-pyrrolo[2,3-d]pyrimidin-5-yl]methanone (P-4105),

[2-fluoro-6-[(5-methoxy-3-pyridyl)amino]-3-pyridyl]-[4-(isopropylamino)-7H-pyrrolo[2,3-d]pyrimidin-5-yl]methanone (P-4106),

[4-(cyclopropylamino)-7H-pyrrolo[2,3-d]pyrimidin-5-yl]-[2-fluoro-6-[(5-methoxy-3-pyridyl)amino]-3-pyridyl]methanone (P-4107),

[2-fluoro-6-[(5-methoxy-3-pyridyl)amino]-3-pyridyl]-[4-(methylamino)-7H-pyrrolo[2,3-d]pyrimidin-5-yl]methanone (P-4108),

[2-chloro-6-(cyclohexylamino)-3-pyridyl]-[4-(isopropylamino)-7H-pyrrolo[2,3-d]pyrimidin-5-yl]methanone (P-4109),

[2-chloro-6-(cyclohexylamino)-3-pyridyl]-[4-(methylamino)-7H-pyrrolo[2,3-d]pyrimidin-5-yl]methanone (P-4110),

[4-(cyclohexylamino)-7H-pyrrolo[2,3-d]pyrimidin-5-yl]-[2-fluoro-6-[(6-methyl-3-pyridyl)amino]-3-pyridyl]methanone (P-4111),

[2-fluoro-6-[(6-methyl-3-pyridyl)amino]-3-pyridyl]-[4-(2,2,2-trifluoroethylamino)-7H-pyrrolo[2,3-d]pyrimidin-5-yl]methanone (P-4112),

[4-(cyclopropylmethylamino)-7H-pyrrolo[2,3-d]pyrimidin-5-yl]-[2-fluoro-6-[(6-methyl-3-pyridyl)amino]-3-pyridyl]methanone (P-4113),

[2-fluoro-6-[(6-methyl-3-pyridyl)amino]-3-pyridyl]-[4-propylamino)-7H-pyrrolo[2,3-d]pyrimidin-5-yl]methanone (P-4114),

[2-fluoro-6-[(6-methyl-3-pyridyl)amino]-3-pyridyl]-[4-(methylamino)-7H-pyrrolo[2,3-d]pyrimidin-5-yl]methanone (P-4115),

[6-[(6-ethyl-3-pyridyl)amino]-2-fluoro-3-pyridyl]-[4-(tetrahydropyran-4-ylamino)-7H-pyrrolo[2,3-d]pyrimidin-5-yl]methanone (P-4116),

[6-[(6-ethyl-3-pyridyl)amino]-2-fluoro-3-pyridyl]-[4-(isopropylamino)-7H-pyrrolo[2,3-d]pyrimidin-5-yl]methanone (P-4117),

[4-(cyclopropylmethylamino)-7H-pyrrolo[2,3-d]pyrimidin-5-yl]-[6-[(6-ethyl-3-pyridyl)amino]-2-fluoro-3-pyridyl]methanone (P-4118),

[6-[(6-ethyl-3-pyridyl)amino]-2-fluoro-3-pyridyl]-[4-(2-methoxyethylamino)-7H-pyrrolo[2,3-d]pyrimidin-5-yl]methanone (P-4119),

[6-[(6-ethyl-3-pyridyl)amino]-2-fluoro-3-pyridyl]-[4-(2,2,2-trifluoroethylamino)-7H-pyrrolo[2,3-d]pyrimidin-5-yl]methanone (P-4120),

[6-[(6-ethyl-3 pyridyl)amino]-2-fluoro-3-pyridyl]-[4-(isobutylamino)-7H-pyrrolo[2,3-d]pyrimidin-5-yl]methanone (P-4121),

[6-[(6-ethyl-3-pyridyl)amino]-2-fluoro-3-pyridyl]-[4-(propylamino)-7H-pyrrolo[2,3-d]pyrimidin-5-yl]methanone (P-4122),

[4-(ethylamino)-7H-pyrrolo[2,3-d]pyrimidin-5-yl]-[6-[(6-ethyl-3-pyridyl)amino]-2-fluoro-3-pyridyl]methanone (P-4123),

[6-[(6-ethyl-3-pyridyl)amino]-2-fluoro-3-pyridyl]-[4-(methylamino)-7H-pyrrolo[2,3-d]pyrimidin-5-yl]methanone (P-4124),

[4-(cyclopropylamino)-7H-pyrrolo[2,3-d]pyrimidin-5-yl]-[6-[(6-ethyl-3-pyridyl)amino]-2-fluoro-3-pyridyl]methanone (P-4125),

[4-(cyclopropylamino)-7H-pyrrolo[2,3-d]pyrimidin-5-yl]-[2-fluoro-6-[6-methoxy-3-pyridyl)amino]-3-pyridyl]methanone (P-4126), N-cyclopropyl-5-[[6-[(4,4-difluorocyclohexyl)amino]-5-fluoro-3-pyridyl]methyl]-7H-pyrrolo[2,3-d]pyrimidin-4-amine (P-4127), 5-[[6-[(4,4-difluorocyclohexyl)amino]-2-fluoro-3-pyridyl]methyl]-N-(2,2,2-trifluoroethyl)-7H-pyrrolo[2,3-d]pyrimidin-4-amine (P-4128), N-cyclopropyl-5-[[6-[(4,4-difluorocyclohexyl)amino]-2-fluoro-3-pyridyl]methyl]-7H-pyrrolo[2,3-d]pyrimidin-4-amine (P-4129), 5-[[6-[(6-cyclopropyl-3-pyridyl)amino]-2-fluoro-3-pyridyl]methyl]-N-(2,2,2-trifluoroethyl)-7H-pyrrolo[2,3-d]pyrimidin-4-amine (P-4130), 5-[[6-(cyclohexylamino)-2-fluoro-3-pyridyl]methyl]-N-cyclopropyl-7H-pyrrolo[2,3-d]pyrimidin-4-amine (P-4131),

[2-fluoro-6-[(6-methoxy-3-pyridyl)amino]-3-pyridyl]-[4-[[(1R)-1-(4-fluorophenyl)ethyl]amino]-7H-pyrrolo[2,3-d]pyrimidin-5-yl]methanone (P-4132),

[6-[(6-ethyl-3-pyridyl)amino]-2-fluoro-3-pyridyl]-[4-[[(1R)-1-(4-fluorophenyl)ethyl]amino]-7H-pyrrolo[2,3-d]pyrimidin-5-yl]methanone (P-4133),

[2-fluoro-6-[(4-fluorocyclohexyl)amino]-3-pyridyl]-[4-(methylamino)-7H-pyrrolo[2,3-d]pyrimidin-5-yl]methanone (P-4134),

[4-(ethylamino)-7H-pyrrolo[2,3-d]pyrimidin-5-yl]-[2-fluoro-6-[(4-fluorocyclohexyl)amino]-3-pyridyl]methanone (P-4135),

[2-fluoro-6-[(4-fluorocyclohexyl)amino]-3-pyridyl]-[4-(isopropylamino)-7H-pyrrolo[2,3-d]pyrimidin-5-yl]methanone (P-4136),

[4-(cyclopropylamino)-7H-pyrrolo[2,3-d]pyrimidin-5-yl]-[2-fluoro-6-[(4-fluorocyclohexyl)amino]-3-pyridyl]methanone (P-4137),

[2-fluoro-6-[4-fluorocyclohexyl)amino]-3-pyridyl]-[4-(2,2,2-trifluoroethylamino)-7H-pyrrolo[2,3-d]pyrimidin-5-yl]methanone (P-4138),

[4-[[(1R)-1-cyclopropylethyl]amino]-7H-pyrrolo[2,3-d]pyrimidin-5-yl]-[2-fluoro-6-[(4-fluorocyclohexyl)amino]-3-pyridyl]methanone (P-4139),

[4-[[(1S)-1-cyclopropylethyl]amino]-7H-pyrrolo[2,3-d]pyrimidin-5-yl]-[2-fluoro-6-[(4-fluorocyclohexyl)amino]-3-pyridyl]methanone (P-4140),

[2-fluoro-6-[(4-fluorocyclohexyl)amino]-3-pyridyl]-[4-(methoxymethylamino)-7H-pyrrolo[2,3-d]pyrimidin-5-yl]methanone (P-4141),

[2-fluoro-6-[(4-fluorocyclohexyl)amino]-3-pyridyl]-[4-(3-methoxypropylamino)-7H-pyrrolo[2,3-d]pyrimidin-5-yl]methanone (P-4142),

[2-fluoro-6-[(4-fluorocyclohexyl)amino]-3-pyridyl]-[4-(tetrahydropyran-4-ylamino)-7H-pyrrolo[2,3-d]pyrimidin-5-yl]methanone (P-4143),

[4-(cyclobutylamino)-7H-pyrrolo[2,3-d]pyrimidin-5-yl]-[2-fluoro-6-[(4-fluorocyclohexyl)amino]-3-pyridyl]methanone (P-4144),

[6-[(3,3-difluorocyclobutyl)amino]-2-fluoro-3-pyridyl]-[4-(methylamino)-7H-pyrrolo[2,3-d]pyrimidin-5-yl]methanone (P-4145),

[6-[(3,3-difluorocyclobutyl)amino]-2-fluoro-3-pyridyl]-[4-(ethylamino)-7H-pyrrolo[2,3-d]pyrimidin-5-yl]methanone (P-4146),

[6-[(3,3-difluorocyclobutyl)amino]-2-fluoro-3-pyridyl]-[4-(propylamino)-7H-pyrrolo[2,3-d]pyrimidin-5-yl]methanone (P-4147),

[6-[(3,3-difluorocyclobutyl)amino]-2-fluoro-3-pyridyl]-[4-(isopropylamino)-7H-pyrrolo[2,3-d]pyrimidin-5-yl]methanone (P-4148),

[6-[(3,3-difluorocyclobutyl)amino]-2-fluoro-3-pyridyl]-[4-(2,2,2-trifluoroethylamino)-7H-pyrrolo[2,3-d]pyrimidin-5-yl]methanone (P-4149),

[4-[[(1R)-1-cyclopropylethyl]amino]-7H-pyrrolo[2,3-d]pyrimidin-5-yl]-[6-[(3,3-difluorocyclobutyl)amino]-2-fluoro-3-pyridyl]methanone (P-4150),

[4-[[(1S)-1-cyclopropylethyl]amino]-7H-pyrrolo[2,3-d]pyrimidin-5-yl]-[6-[(3,3-difluorocyclobutyl)amino]-2-fluoro-3-pyridyl]methanone (P-4151),

[6-[(3,3-difluorocyclobutyl)amino]-2-fluoro-3-pyridyl]-[4-(methoxymethylamino)-7H-pyrrolo[2,3-d]pyrimidin-5-yl]methanone (P-4152),

[6-[(3,3-15difluorocyclobutyl)amino]-2-fluoro-3-pyridyl]-[4-(tetrahydropyran-4-ylamino)-7H-pyrrolo[2,3-d]pyrimidin-5-yl]methanone (P-4153),

[4-(cyclobutylamino)-7H-pyrrolo[2,3-d]pyrimidin-5-yl]-[6-[(3,3-difluorocyclobutyl)amino]-2-fluoro-3-pyridyl]methanone (P-4154),

[6-[(3,3-difluorocyclobutyl)amino]-2-fluoro-3-pyridyl]-[4-(3-methoxypropylamino)-7H-pyrrolo[2,3-d]pyrimidin-5-yl]methanone (P-4155),

[6-[(4,4-difluorocyclohexyl)amino]-2-fluoro-3-pyridyl]-[4-(3-methoxypropylamino)-7H-pyrrolo[2,3-d]pyrimidin-5-yl]methanone (P-4156),

[6-[(4,4-difluorocyclohexyl)amino]-2-fluoro-3-pyridyl]-[4-(2-methoxyethylamino)-7H-pyrrolo[2,3-d]pyrimidin-5-yl]methanone (P-4157),

[4-(cyclobutylamino)-7H pyrrolo[2,3-d]pyrimidin-5-yl]-[6-[(4,4-difluorocyclohexyl)amino]-2-fluoro-3-pyridyl]methanone (P-4158),

[6-[(4,4-difluorocyclohexyl)amino]-2-fluoro-3-pyridyl]-[4-(tetrahydropyran-4-ylamino)-7H-pyrrolo[2,3-d]pyrimidin-5-yl]methanone (P-4159),

[4-[[(1R)-1-cyclopropylethyl]amino]-7H-pyrrolo[2,3-d]pyrimidin-5-yl]-[6-[(4,4-difluorocyclohexyl)amino]-2-fluoro-3-pyridyl]methanone (P-4160),

[4-[[(1S)-1-cyclopropylethyl]amino]-7H-pyrrolo[2,3-d]pyrimidin-5-yl]-[6-[(4,4-difluorocyclohexyl)amino]-2-fluoro-3-pyridyl]methanone (P-4161),

[6-[(4,4-difluorocyclohexyl)amino]-2-fluoro-3-pyridyl]-[4-(ethylamino)-7H-pyrrolo[2,3-d]pyrimidin-5-yl]methanone (P-4162),

[4-(cyclobutylamino)-7H-pyrrolo[2,3-d]pyrimidin-5-yl]-[6-[(4,4-difluorocyclohexyl)amino]-5-fluoro-3-pyridyl]methanone (P-4163),

[6-[(4,4-difluorocyclohexyl)amino]-5-fluoro-3-pyridyl]-[4-(methoxymethylamino)-7H-pyrrolo[2,3-d]pyrimidin-5-yl]methanone (P-4164),

[6-[(4,4-difluorocyclohexyl)amino]-5-fluoro-3-pyridyl]-[4-(3-methoxypropylamino)-7H-pyrrolo[2,3-d]pyrimidin-5-yl]methanone (P-4165),

[6-[(4,4-difluorocyclohexyl)amino]-5-fluoro-3-pyridyl]-[4-(tetrahydropyran-4-ylamino)-7H-pyrrolo[2,3-d]pyrimidin-5-yl]methanone (P-4166),

[4-[[(1R)-1-cyclopropylethyl]amino]-7H-pyrrolo[2,3-d]pyrimidin-5-yl]-[6-[(4,4-difluorocyclohexyl)amino]-5-fluoro-3-pyridyl]methanone (P-4167),

[4-[[(1S)-1-cyclopropylethyl]amino]-7H-pyrrolo[2,3-d]pyrimidin-5-yl]-[6-[(4,4-difluorocyclohexyl)amino]-5-fluoro-3-pyridyl]methanone (P-4168),

[6-[(6-cyclopropyl-3-pyridyl)amino]-2-fluoro-3-pyridyl]-[4-[[(1S)-1-methylpropyl]amino]-7H-pyrrolo[2,3-d]pyrimidin-5-yl]methanone (P-4169),

[6-[(6-cyclopropyl-3 pyridyl)amino]-2-fluoro-3-pyridyl]-[4-[(3-hydroxy-1-methyl-propyl)amino]-7H-pyrrolo[2,3-d]pyrimidin-5-yl]methanone (P-4170),

[6-[(6-cyclopropyl-3-pyridyl)amino]-2-fluoro-3-pyridyl]-[4-[[(1R)-1-(hydroxymethyl)propyl]-amino]-7H-pyrrolo[2,3-d]pyrimidin-5-yl]methanone (P-4171), 4-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-2-one (P-4172),

[6-[(6-cyclopropyl-3-pyridyl)amino]-2-fluoro-3-pyridyl]-[4-[[(1R)-2-hydroxy-1-methyl-ethyl]amino]-7H-pyrrolo[2,3-d]pyrimidin-5-yl]methanone (P-4173),

[6-[(6-cyclopropyl-3-pyridyl)amino]-2-fluoro-3-pyridyl]-[4-[[(1R,3R)-3-hydroxycyclohexyl]amino]-7H-pyrrolo[2,3-d]pyrimidin-5-yl]methanone (P-4174),

[6-[(6-cyclopropyl-3-pyridyl)amino]-2-fluoro-3-pyridyl]-[4-[[(1R,2R)-2-hydroxycyclopentyl]amino]-7H-pyrrolo[2,3-d]pyrimidin-5-yl]methanone (P-4175), 1-[3-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-1-yl]ethanone (P-4176), (2R)-2-[[5-[6-[(6-cyclopropyl-3-pyridyl)amino]-2-fluoro-pyridine-3-carbonyl]-7H-pyrrolo[2,3-d]pyrimidin-4-yl]amino]cyclohexanone (P-4177),

[6-[(6-cyclopropyl-3-pyridyl)amino]-2-fluoro-3-pyridyl]-[4-[(1,1-dioxothiolan-3-yl)amino]-7H-pyrrolo[2,3-d]pyrimidin-5-yl]methanone (P-4178),

[6-[(6-cyclopropyl-3-pyridyl)amino]-2-fluoro-3-pyridyl]-[4-[[(1R,2R)-2-hydroxycyclohexyl]amino]-7H-pyrrolo[2,3-d]pyrimidin-5-yl]methanone (P-4179),

[6-[(6-cyclopropyl-3-pyridyl)amino]-2-fluoro-3 pyridyl]-[4-[[(1R)-2-methoxy-1-methyl-ethyl]amino]-7H-pyrrolo[2,3-d]pyrimidin-5-yl]methanone (P-4180), 4-[[5-[6-[(6-cyclopropyl-3-pyridyl)amino]-2-fluoro-pyridine-3-carbonyl]-7H-pyrrolo[2,3-d]pyrimidin-4-yl]amino]piperidin-2-one (P-4181),

[6-[(6-cyclopropyl-3-pyridyl)amino]-2-fluoro-3-pyridyl]-[4-[[(1R)-2,2,2-trifluoro-1-methyl-ethyl]amino]-7H-pyrrolo[2,3-d]pyrimidin-5-yl]methanone (P-4182), 4-[[5-[6-[(6-cyclopropyl-3-pyridyl)amino]-2-fluoro-pyridine-3-carbonyl]-7H-pyrrolo[2,3-d]pyrimidin-4-yl]amino]-1-methyl-piperidin-2-one (P-4183),

[6-[(6-cyclopropyl-3-pyridyl)amino]-2-fluoro-3-pyridyl]-[4-[(1,1-dioxothian-3-yl)amino]-7H-pyrrolo[2,3-d]pyrimidin-5-yl]methanone (P-4184), 1-cyclopropyl-4-[[5-[6-[(6-cyclopropyl-3-pyridyl)amino]-2-fluoro-pyridine-3-carbonyl]-7H-pyrrolo[2,3-d]pyrimidin-4-yl]amino]pyrrolidin-2-one (P-4185),

[6-[(4,4-difluorocyclohexyl)amino]-2-fluoro-3-pyridyl]-[4-[[(1S)-1-methylpropyl]amino]-7H-pyrrolo[2,3-d]pyrimidin-5-yl]methanone (P-4186),

[6-[(4,4-difluorocyclohexyl)amino]-2-fluoro-3-pyridyl-[4-[(3-hydroxy-1-methyl-propyl)amino]-7H-pyrrolo[2,3-d]pyrimidin-5-yl]methanone (P-4187), 6-[(4,4-difluorocyclohexyl)amino]-2-fluoro-3-pyridyl]-[4-[[(1R)-1-(hydroxymethyl)propyl]amino]-7H-pyrrolo[2,3-d]pyrimidin-5-yl]methanone (P-4188), 4-[[5-[6-[(4,4-difluorocyclohexyl)amino]-2-fluoro-pyridine-3-carbonyl]-7H-pyrrolo[2,3-d]pyrimidin-4-yl]amino]pyrrolidin-2-one (P-4189),

[6-[(4,4-difluorocyclohexyl)amino]-2-fluoro-3-pyridyl]-[4-[[(1R)-2-hydroxy-1-methyl-ethyl]amino]-7H-pyrrolo[2,3-d]pyrimidin-5-yl]methanone (P-4190),

[6-[(4,4-difluorocyclohexyl)amino]-2-fluoro-3-pyridyl]-[4-[[(1R,3R)-3-hydroxycyclohexyl]amino]-7H-pyrrolo[2,3-d]pyrimidin-5-yl]methanone (P-4191),

[6-[(4,4-difluorocyclohexyl)amino]-2-fluoro-3-pyridyl]-[4-[[(1R,2R)-2-hydroxycyclopentyl]amino]-7H-pyrrolo[2,3-d]pyrimidin-5-yl]methanone (P-4192), 1-[3-[[5-[6-[(4,4-difluorocyclohexyl)amino]-2-fluoro-pyridine-3-carbonyl]-7H-pyrrolo[2,3-d]pyrimidin-4-yl]amino]pyrrolidin-1-yl]ethanone (P-4193), (2R)-2-[[5-[6-[(4,4-difluorocyclohexyl)amino]-2-fluoro-pyridine-3-carbonyl]-7H-pyrrolo[2,3-d]pyrimidin-4-yl]amino]cyclohexanone (P-4194),

[6-[(4,4-difluorocyclohexyl)amino]-2-fluoro-3-pyridyl]-[4-[(1,1-dioxothiolan-3-yl)amino]-7H-pyrrolo[2,3-d]pyrimidin-5-yl]methanone (P-4195),

[6-[(4,4-difluorocyclohexyl)amino]-2-fluoro-3-pyridyl]-[4-[[(1R,2R)-2-hydroxycyclohexyl]amino]-7H-pyrrolo[2,3-d]pyrimidin-5-yl]methanone (P-4196),

[6-[(4,4-difluorocyclohexyl)amino]-2-fluoro-3-pyridyl]-[4-[[(1R)-2-methoxy-1-methyl-ethyl]amino]-7H-pyrrolo[2,3-d]pyrimidin-5-yl]methanone (P-4197), 4-[[5-[6-[(4,4-difluorocyclohexyl)amino]-2-fluoro-pyridine-3-carbonyl]-7H-pyrrolo[2,3-d]pyrimidin-4-yl]amino]piperidin-2-one (P-4198),

[6-[(4,4-difluorocyclohexyl)amino]-2-fluoro-3-pyridyl]-[4-[[(1R)-2,2,2-trifluoro-1-methyl-ethyl]amino]-7H-pyrrolo[2,3-d]pyrimidin-5-yl]methanone (P-4199), 4-[[5-[6-[(4,4-difluorocyclohexyl)amino]-2-fluoro-pyridine-3-carbonyl]-7H-pyrrolo[2,3-d]pyrimidin-4-yl]amino]-1-methyl-piperidin-2-one (P-4200),

[6-[(4,4-difluorocyclohexyl)amino]-2-fluoro-3-pyridyl]-[4-[(1,1-dioxothian-3-yl)amino]-7H-pyrrolo[2,3-d]pyrimidin-5-yl]methanone (P-4201), and 1-cyclopropyl-4-[[5-[6-[(4,4-difluorocyclohexyl)amino]-2-fluoro-pyridine-3-carbonyl]-7H-pyrrolo[2,3-d]pyrimidin-4-yl]amino]pyrrolidin-2-one (P-4202);

or a salt, a solvate, a tautomer, or a stereoisomer thereof.

17. A composition comprising a compound according to claim 1, or a salt, a solvate, a tautomer, or a stereoisomer thereof; and a pharmaceutically acceptable carrier.

18. A composition comprising a compound of claim 1, or a salt, a solvate, a tautomer or a stereoisomer thereof, a pharmaceutically acceptable carrier and a chemotherapeutic agent.

19. A kit comprising a compound according to claim 1, or a salt, a solvate, a tautomer or a stereoisomer thereof.

20. A method for preparing a compound of Formula I according to claim 1, said method comprising:
contacting a compound of Formula (II):

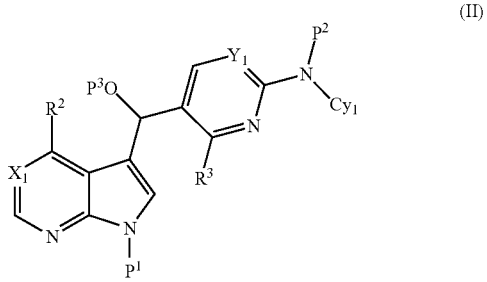

with an oxidizing a rent or a reducing agent under conditions sufficient to prepare the compound of Formula (I), wherein $P^1$ and $P^2$ are each independently an amino protecting group and $P^3$ is H or a protecting group.

21. A method for preparing a compound of Formula II according to claim 20, said method comprising:
contacting a compound of Formula (III):

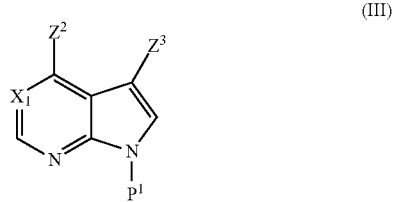

with a compound of Formula IV:

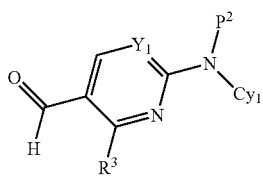

under conditions sufficient to form a compound of Formula (II), wherein $Z^2$ is Cl, Br or $R^2$ and $Z^3$ is iodo or a leaving group.

22. A composition comprising a compound according to claim 16, or a salt, a solvate, a tautomer, or a stereoisomer thereof; and a pharmaceutically acceptable carrier.

23. The method of claim 20, wherein the oxidizing agent is Dess-Martin periodinane or the reducing agent is trialkylsilane.

24. The compound of claim 23, wherein the compound is [6-[(4,4-difluorocyclohexyl)amino]-5-fluoro-3-pyridyl]-[4-(2,2,2-trifluoroethylamino)-7H-pyrrolo[2,3-d]pyrimidin-5-yl]methanone (P-4052), or a salt, a solvate, a tautomer, or a stereoisomer thereof.

25. The compound of claim 23, wherein the compound is [4-(cyclopropylamino)-7H -pyrrolo[2,3-d]pyrimidin-5-yl]-[6-[(4,4-difluorocyclohexyl)amino]-5-fluoro-3-pyridyl] methanone (P-4053), or a salt, a solvate, a tautomer, or a stereoisomer thereof.

26. The compound of claim 1, wherein the compound is [6-[(6-cyclopropyl-3-pyridyl)amino]-2-fluoro-3-pyridyl]-[4-(ethylamino)-7H-pyrrolo[2,3-d]pyrimidin-5-yl]methanone (P-4060), or a salt, a solvate, a tautomer, or a stereoisomer thereof.

27. The compound of claim 1, wherein the compound is [6-[(4,4-difluorocyclohexyl)amino]-2-fluoro-3-pyridyl]-[4-(2,2,2-trifluoroethylamino)-7H-pyrrolo[2,3-d]pyrimidin-5-yl]methanone (P-4061), or a salt, a solvate, a tautomer, or a stereoisomer thereof.

28. The compound of claim 1, wherein the compound is [4-(cyclopropylamino)-7H -pyrrolo[2,3-d]pyrimidin-5-yl]-[6-[(4,4-difluorocyclohexyl)amino]-2-fluoro-3-pyridyl] methanone (P-4062), or a salt, a solvate, a tautomer, or a stereoisomer thereof.

29. The compound of claim 1, wherein the compound is [4-(ethylamino)-7H-pyrrolo[2,3-d]pyrimidin-5-yl]-[2-fluoro-6-[(6-methoxy-3-pyridyl)amino]-3-pyridyl]methanone (P-4081), or a salt, a solvate, a tautomer, or a stereoisomer thereof.

30. The compound of claim 1, wherein the compound is [2-fluoro-6-[(6-methoxy-3-pyridyl)amino]-3-pyridyl]-[4-(2,2,2-trifluoroethylamino)-7H-pyrrolo[2,3-d]pyrimidin-5-yl] methanone (P-4084), or a salt, a solvate, a tautomer, or a stereoisomer thereof.

31. The compound of claim 1, wherein the compound is [6-[(4,4-difluorocyclohexyl)amino]-3-pyridyl]-[4-(2,2,2-trifluoroethylamino)-7H-pyrrolo[2,3-d]pyrimidin-5-yl]methanone (P-4087), or a salt, a solvate, a tautomer, or a stereoisomer thereof.

32. The compound of claim 1, wherein the compound is [4-(cyclopropylamino)-7H-pyrrolo[2,3-d]pyrimidin-5-yl]-[6-[(4,4-difluorocyclohexyl)amino]-3-pyridyl]methanone (P-4088), or a salt, a solvate, a tautomer, or a stereoisomer thereof.

33. The compound of claim 1, wherein the compound is [6-[(6-cyclopropyl-3-pyridyl)amino]-2-fluoro-3-pyridyl]-[4-(2,2,2-trifluoroethylamino)-7H-pyrrolo[2,3-d]pyrimidin-5-yl]methanone (P-4090), or a salt, a solvate, a tautomer, or a stereoisomer thereof.

34. The compound of claim 1, wherein the compound is [4-(cyclopropylamino)-7H -pyrrolo[2,3-d]pyrimidin-5-yl]-[2-fluoro-6-[[6-(trifluoromethyl)-3-pyridyl]amino]-3-pyridyl]methanone (P-4091), or a salt, a solvate, a tautomer, or a stereoisomer thereof.

35. The compound of claim 1, wherein the compound is [2-fluoro-6[[6-(trifluoromethyl)-3-pyridyl]amino]-3-pyridyl]-[4-(methylamino)-7H -pyrrolo[2,3-d]pyrimidin-5-yl] methanone (P-4092), or a salt, a solvate, a tautomer, or a stereoisomer thereof.

36. The compound of claim 1, wherein the compound is [4-(cyclopropylamino)-7H -pyrrolo[2,3-d]pyrimidin-5-yl]-[6-[(6-cyclopropyl-3-pyridyl)amino]-2-fluoro-3-pyridyl] methanone (P-4093), or a salt, a solvate, a tautomer, or a stereoisomer thereof.

37. The compound of claim 1, wherein the compound is [4-(cyclobutylamino)-7H -pyrrolo[2,3-d]pyrimidin-5-yl]-[6-[(6-ethyl-3-pyridyl)amino]-2-fluoro-3-pyridyl]methanone (P-4095), or a salt, a solvate, a tautomer, or a stereoisomer thereof.

38. The compound of claim 1, wherein the compound is [6[(6-ethyl-3-pyridyl)amino]-2-fluoro-3-pyridyl]-[4-(3- methoxypropylamino)-7H-pyrrolo[2,3-d]pyrimidin-5-yl]methanone (P-4098), or a salt, a solvate, a tautomer, or a stereoisomer thereof.

39. The compound of claim 1, wherein the compound is [2-fluoro-6-[(6-methyl-3-pyridyl)amino]-3-pyridyl]-[4-(2,2,2-trifluoroethylamino)-7H-pyrrolo[2,3-d]pyrimidin-5-yl]methanone (P-4112), or a salt, a solvate, a tautomer, or a stereoisomer thereof.

40. The compound of claim 1, wherein the compound is [4-(cyclopropylmethylamino) -7H-pyrrolo[2,3-d]pyrimidin-5-yl]-[6-[(6-ethyl-3-pyridyl)amino]-2fluoro-3-pyridyl]methanone (P-4118), or a salt, a solvate, a tautomer, or a stereoisomer thereof.

41. The compound of claim 1, wherein the compound is [6[(6-ethyl-3-pyridyl)amino]-2-fluoro-3-pyridyl]-[4-(2,2,2-trifluoroethylamino)-7H-pyrrolo[2,3-d]pyrimidin-5-yl]methanone (P-4120), or a salt, a solvate, a tautomer, or a stereoisomer thereof.

42. The compound of claim 1, wherein the compound is [6-[(6-ethyl-3-pyridyl)amino]-2-fluoro-3-pyridyl]-[4-(isobutylamino)-7H-pyrrolo[2,3-d]pyrimidin-5-yl]methanone (P-4121), or a salt, a solvate, a tautomer, or a stereoisomer thereof.

43. The compound of claim 1, wherein the compound is [4-(ethylamino)-7H-pyrrolo[2,3-d]pyrimidin-5-yl]-[6-[(6-ethyl-3-pyridyl)amino]-2-fluoro-3-pyridyl]methanone (P-4123), or a salt, a solvate, a tautomer, or a stereoisomer thereof.

44. The compound of claim 1, wherein the compound is [4-(cyclopropylamino)-7H -pyrrolo[2,3-d]pyrimidin-5-yl]-[6-[(6-ethyl-3-pyridyl)amino]-2-fluoro-3-pyridyl]methanone (P-4125), or a salt, a solvate, a tautomer, or a stereoisomer thereof.

45. The compound of claim 1, wherein the compound is [4-(cyclopropylamino)-7H -pyrrolo[2,3-d]pyrimidin-5-yl]-[2-fluoro-6-[(6-methoxy-3-pyridyl)amino]-3-pyridyl]methanone (P-4126), or a salt, a solvate, a tautomer, or a stereoisomer thereof.

46. The compound of claim 1, wherein the compound is N-cyclopropyl-5-[[6-[(4,4-difluorocyclohexyl)amino]-2-fluoro-3 -pyridyl]methyl]-7H-pyrrolo[2,3-d]pyrimidin-4-amine (P-4129), or a salt, a solvate, a tautomer, or a stereoisomer thereof.

* * * * *